US007456255B2

(12) United States Patent
Strittmatter et al.

(10) Patent No.: US 7,456,255 B2
(45) Date of Patent: Nov. 25, 2008

(54) NOGO RECEPTOR HOMOLOGS THAT DECREASE INHIBITION OF AXONAL ELONGATION

(75) Inventors: Stephen Strittmatter, Guilford, CT (US); Richard L. Cate, Cohasset, MA (US); Dinah W. Y. Sah, Boston, MA (US)

(73) Assignees: Yale University, New Haven, CT (US); Biogen Idec MA Inc., Cambridge, MA (US)

( * ) Notice: Subject to any disclaimer, the term of this patent is extended or adjusted under 35 U.S.C. 154(b) by 0 days.

(21) Appl. No.: 11/544,013

(22) Filed: Oct. 6, 2006

(65) Prior Publication Data

US 2007/0104713 A1 May 10, 2007

Related U.S. Application Data

(60) Division of application No. 10/735,256, filed on Dec. 12, 2003, now Pat. No. 7,173,118, which is a continuation of application No. 09/972,546, filed on Oct. 6, 2001, now abandoned.

(60) Provisional application No. 60/238,361, filed on Oct. 6, 2000.

(51) Int. Cl.
*C07K 14/00* (2006.01)
*C07K 17/00* (2006.01)
*C07K 1/00* (2006.01)

(52) U.S. Cl. ...................................... 530/350; 530/324

(58) Field of Classification Search ........................ None
See application file for complete search history.

(56) References Cited

U.S. PATENT DOCUMENTS

| | | | | |
|---|---|---|---|---|
| 5,250,414 | A | 10/1993 | Schwab et al. | |
| 5,684,133 | A | 11/1997 | Schwab et al. | |
| 5,858,708 | A | 1/1999 | Bandman et al. | |
| 6,025,333 | A | 2/2000 | Schwab et al. | |
| 6,475,753 | B1 * | 11/2002 | Ruben et al. | 435/69.1 |
| 6,806,351 | B2 * | 10/2004 | Ruben et al. | 530/350 |
| 7,119,165 | B2 | 10/2006 | Strittmatter | |
| 2002/0025554 | A1 | 2/2002 | Khodadoust | |
| 2003/0124704 | A1 | 7/2003 | Strittmattter et al. | |
| 2005/0048520 | A1 | 3/2005 | Strittmatter et al. | |
| 2005/0221420 | A1 | 10/2005 | Barske et al. | |
| 2005/0271655 | A1 | 12/2005 | Lee et al. | |

FOREIGN PATENT DOCUMENTS

| | | |
|---|---|---|
| WO | WO 98/06841 | 2/1998 |
| WO | WO 99/46281 | 9/1999 |
| WO | WO 99/66041 | 12/1999 |
| WO | WO 00/05364 | 2/2000 |
| WO | WO 00/31235 | 6/2000 |
| WO | WO 00/32221 | 6/2000 |
| WO | WO 00/37638 | 6/2000 |
| WO | WO 00/53756 | 9/2000 |
| WO | WO 00/53758 | 9/2000 |
| WO | WO 00/58473 | 10/2000 |
| WO | WO 00/70050 | 11/2000 |
| WO | WO0070050 | * 11/2000 |
| WO | WO 00/73452 | 12/2000 |
| WO | WO 01/09162 | 2/2001 |
| WO | WO 01/51520 | 7/2001 |
| WO | WO0175067 | * 10/2001 |
| WO | WO 03/018631 | 3/2003 |
| WO | WO 03/035687 A1 | 5/2003 |

OTHER PUBLICATIONS

Burgess et al. J of Cell Biol. 1990. 111:2129-2138.*
Bowie et al. Science, 1990, 247:1306-1310.*
Pawson et al. 2003, Science 300:445-452.*
Andrade, M., et al., "Protein Repeats: Structures, Functions, and Evolution," *J. Struct. Biol.* 134:117-131, Academic Press (May-Jun. 2002).
Bandtlow, C., et al., "NI-35/250/Nogo-A: A Neurite Growth Inhibitor Restricting Structural Plasticity and Regeneration of Nerve Fibers in the Adult Vertebrate CNS," *Glia 29*:175-181, Wiley-Liss (Jan. 2000).
Bork, P., "Powers and Pitfalls in Sequence Analysis: The 70% Hurdle," *Genome Res.* 10:398-400, Cold Spring Harbor Laboratory Press (Apr. 2000).
Bork, P. and Bairoch A., "Go hunting in sequence databases but watch out for the traps," *Trends Genet.* 12:425-427, Elsevier Trends Journals (1996).
Brenner, S., "Errors in genome annotation," *Trends Genet.* 15: 132-133, Elsevier Trends Journals (Apr. 1999).
Chen, M., et al., "Nogo-A is a myelin-associated neurite outgrowth inhibitor and an antigen for monoclonal antibody IN-1," *Nature* 403:434-439, Nature Publishing Group (Jan. 2000).
Doerks, T., et al., "Protein annotation: detective work for function prediction," *Trends Genet.* 14:248-250, Elsevier Trends Journals (1998).
Domeniconi, M., et al., "Myelin-Associated Glycoprotein Interacts with the Nogo66 Receptor to Inhibit Neurite Outgrowth," *Neuron 35*:283-290, Cell Press (Jul. 2002).
Fournier, A., et al., "Identification of a receptor mediating Nogo-66 inhibition of axonal regeneration," *Nature 409*:341-346, Nature Publishing Group (Jan. 2001).
GrandPré, T., et al., "Identification of the Nogo inhibitor of axon regeneration as a Reticulon protein," *Nature 403*:439-444, Nature Publishing Group (Jan. 2000).
GrandPré, T., et al., "Nogo-66 receptor antagonist peptide promotes axonal regeneration," *Nature 417*:547-551, Nature Publishing Group (May 2002).

(Continued)

*Primary Examiner*—Christine J Saoud
*Assistant Examiner*—Chang-Yu Wang
(74) *Attorney, Agent, or Firm*—Sterne, Kessler, Goldstein & Fox P.L.L.C.

(57) ABSTRACT

The invention relates generally to genes that encode proteins that inhibit axonal growth. The invention relates specifically to genes encoding NgR protein homologs in humans and mice. The invention also includes compositions and methods for modulating the expression and activity of Nogo and the NgR proteins. Specifically, the invention includes peptides, proteins and antibodies that block Nogo-mediated inhibition of axonal extension. The compositions and methods of the invention are useful in the treatment of cranial or cerebral trauma, spinal cord injury, stroke or a demyelinating disease.

16 Claims, 6 Drawing Sheets

OTHER PUBLICATIONS

Gustafsson, J.-A., "New insights in oetrogen receptor (ER) research—the ERβ," *Eur. J. Cancer 36*:S13-S23, Elsevier Science Ltd. (Sep. 2000).
Huber, A., et al., "Nogo-A, a Potent Inhibitor of Neurite Outgrowth and Regeneration," *Biol. Chem.* 381:407-419, Walter D. Gruyter (May-Jun. 2000).
Hunt, D., et al., "Nogo Receptor mRNA Expression in Intact and Regenerating CNS Neurons," *Molec. Cell. Neurosci.* 20:537-552, Academic Press (Aug. 2002).
Kobe, B. and Kajava, A., "The leucine-rich repeat as a protein recognition motif," *Curr. Opin. Structural Biol.* 11:725-732, Current Biology (Dec. 2001).
Li, C., et al., "The Genetic Defect in Two Well-Studied Cases of Bernard-Soulier Syndrome: A Point Mutation in the Fifth Leucine-Rich Repeat of Platelet Glycoprotein Ibα," *Blood 86*:3805-3814, American Society of Hematology (1995).
Li, M., et al., "Effect of soluble Nogo reeceptor treatment on functional and histological outcome after spinal cord injury in the rat," Biosis Database, Accession No. PREV200400194121, Abstract No. 80.22, *Presented at the 33rd Annual Meeting of the Society of Neuroscience*, New Orleans, LA (Nov. 8-12, 2003).
Li, W., et al., "A Neutralizing Anti-Nogo66 Receptor Monoclonal Antibody Reverses Inhibition of Neurite Outgrowth by Central Nervous System Myelin," *J. Biol. Chem.* 42:43780-43788, The American Society for Biochemistry and Molecular Biology, Inc. (Oct. 2004).
Li, W., et al., "Neutralization of NGR1 May Be Sufficient to Promote Rat DRG Neurite Outgrowth in the Presence of CNS Myeline," SFN 2003 Abstract Viewer & Itinerary Planner, Program No. 678.3, *Presented at the 33rd Annual Meeting of the Society of Neuroscience*, New Orleans, LA (Nov. 8-12, 2003).
Merkler, D., et al., "Locomotor Recovery in Spinal Cord-Injured Rats Treated with an Antibody Neutralizing the Myelin-Associated Neurite Growth Inhibitor Nogo-A," *J. Neurosci.* 21:3665-3673, Society for Neuroscience (May 2001).
Ngo, J., et al., "Computational Complexity, Protein Structure Prediction, and the Levinthal Paradox," in *The Protein Folding Problem and Tertiary Structure Prediction*, K.M. Merz and S.M. LeGrand, eds, Springer Verlag, New York, NY, pp. 433-506 (1994).
Nykjaer, A., et al., "p75NTR—live or let die," *Curr. Opin. Neurobiol.* 15:49-57, Current Biology (Feb. 2005).
Oertle, T., et al., "Nogo-A Inhibits Neurite Outgrowth and Cell Spreading with Three Discrete Regions," *J. Neurosci.* 23:5393-5406, Society for Neuroscience (Jul. 2003).
Oudega, M., et al., "Neutralizing Antibodies Against Neurtie Growth Inhibitor NI-35/250 Do Not Promote Regeneration of Sensory Axons in the Adult Rat Spinal Cord," *Neuroscience* 100:873-883, Elsevier Science (Oct. 2000).
Pignot, V., et al., "Characterization of two novel proteins, NgRH1 and NgRH2, structurally and biochemically homologous to the Nogo-66 receptor," *J. Neurochem.* 85:717-728, Blackwell Science (May 2003).
Prinjha, R., et al., "Inhibitor of neurite outgrowth in humans," *Nature 403*:383-384, Nature Publishing Group (Jan. 2000).
Raineteau, O., et al., "Sprouting and regeneration after pyramidotomy and blockade of the myelin-associated neurite growth inhibitors N1 35/250 in adult rats," *Eur. J. Neurosci.* 11:1486-1490, Blackwell Science (Apr. 1999).
Raineteau, O., et al., "Functional switch between motor tracts in the presence of the mAb IN-1 in the adult rat," *Proc. Natl. Acad. Sci. U.S.A.* 98:6929-6934, National Academy of Sciences (Jun. 2001).
Skolnick, J. and Fetrow, J., "From genes to protein structure and function: novel applications of computational approaches in the genomic era," *Trends Biotechnol.* 18:34-39, Elsevier Science Publishers (Jan. 2000).
Smith, T. and Zhang, X., "The challenges of genome sequence annotation or The devil is in the details,"*Nat. Biotechnol.* 15:1222-1223, Nature America Publishing (1997).
Spillman, A., et al., Identification and Characterization of a Bovine Neurite Growth Inhibitor (bNI-220), *J. Biol. Chem.* 273:19283-19293, American Society for Biochemistry and Molecular Biology (1998).
Tatagiba, M., et al., "Regeneration of Injured Axons in the Adult Mammalian Central Nervous System," *Neurosurgery* 40:541-547, Lippincott Williams & Wilkins (1997).
Thallmair, M., et al., "Neurite growth inhibitors restrict plasticity and functional recovery following corticospinal tract lesions," *Nat. Neurosci.* 1:124-131, Nature Publishing Group (1998).
Wang, X., et al., "Localization of Nogo-A and Nogo-66 Receptor Proteins at Sites of Axon-Myelin and Synaptic Contact," *J. Neurosci.* 22:5505-5515, Society for Neuroscience (Jul. 2002).
Wells, J., "Additivity of Mutational Effects in Proteins," *Biochemistry* 29:8509-8517, American Chemical Society (1990).
Z'Graggen, W., et al., "Functional Recovery and Enhanced Corticofugal Plasticity After Unilateral Pyramidal Tract Lesion and Blockade of Myelin-Associated Neurite Growth Inhibitors in Adult Rats," *J. Neurosci.* 18:4744-4757, Society for Neuroscience (1998).
Database EMBL, Accession No. AC013606, Birren, B., et al., 39 pages (Nov. 1999).
Database EMBL, Accession No. AC021768, Birren, B., et al., 74 pages (Jan. 2000).
Database EMBL, Accession No. AC006549, Hu, P., et al., 46 pages (Feb. 1999).
International Search Report for International Application No. PCT/US2005/002535, European Patent Office, Netherlands, mailed Oct. 24, 2005.
International Search Report for International Application No. PCT/US05/35719, ISA/US, Alexandria, VA, mailed Apr. 13, 2006.
Communication pursuant to Article 96(2) EPC for European Application No. 01 979 595.4, mailed May 17, 2005, European Patent Office, The Netherlands.
Office Action for U.S. Appl. No. 10/735,256, Strittmatter et al., mailed Sep. 29, 2005.
Office Action for U.S. Appl. No. 10/735,256, Strittmatter et al., mailed Mar. 14, 2006.
Office Action for U.S. Appl. No. 10/735,256, Strittamtter et al., mailed May 16, 2006.

* cited by examiner

FIG. 1A

```
                1                                                          50
NOGO-R2         ~~~~~~MLPG LRRLLQAPAS AC...LLLML LA..LPLAAP SCPMLCTCYS
NOGO-R3         MSWQSGTTVT QSPVQAAQVS GCCVELLLLL LAGELPLGG. GCPRDCVCYP
NOGO-R1         ~~~~~~~~~~ ~~~~~MKRAS AGGSRLLAWV LWLQAWQVAA PCPGACVCYN
Consensus       ~~~~~~~~~~ ---------S -----LL--- L--------- -CP--C-CY-

                51                                                        100
NOGO-R2         SP.PTVSCQA NNFSSVPLSL PPSTQRLFLQ NNLIRTLRPG TFGS..NLLT
NOGO-R3         AP.MTVSCQA HNFAAIPEGI PEDSERIFLQ NNRITFLQQG HFSP..AMVT
NOGO-R1         EPKVTTSCPQ QGLQAVPVGI PAASQRIFLH GNRISHVPAA SFRACRNLTI
Consensus       -P--T-SC-- ------P--- P----R-FL- -N-I------ -F--------

                101                                                       150
NOGO-R2         LWLFSNNLST IYPGTFRHLQ ALEELDLGDN RHLRSLEPDT FQGLERLQSL
NOGO-R3         LWIYSNNITF IAPNTFEGFV HLEELDLGDN RQLRTLAPET FQGLVKLHAL
NOGO-R1         LWLHSNVLAR IDAAAFTGLA LLEQLDLSDN AQLRSVDPAT FHGLGRLHTL
Consensus       LW--SN---- I----F---- -LE-LDL-DN --LR---P-T F-GL--L--L

                151                                                       200
NOGO-R2         HLYRCQLSSL PGNIFRGLVS LQYLYLQENS LLHLQDDLFA DLANLSHLFL
NOGO-R3         YLYKCGLSAL PAGIFGGLHS LQYLYLQDNH IEYLQDDIFV DLVNLSHLFL
NOGO-R1         HLDRCGLQEL GPGLFRGLAA LQYLYLQDNA LQALPDDTFR DLGNLTHLFL
Consensus       -L--C-L--L ----F-GL-- LQYLYLQ-N- ---L-DD-F- DL-NL-HLFL

                201                                                       250
NOGO-R2         HGNRLRLLTE HVFRGLGSLD RLLLHGNRLQ GVHRAAFRGL SRLTILYLFN
NOGO-R3         HGNKLWSLGQ GIFRGLVNLD RLLLHENQLQ WVHHKAFHDL HRLTTLFLFN
NOGO-R1         HGNRISSVPE RAFRGLHSLD RLLLHQNRVA HVHPHAFRDL GRLMTLYLFA
Consensus       HGN------- --FRGL--LD RLLLH-N--- -VH--AF--L -RL--L-LF-
```

FIG. 1B

```
                251                                                      300
NOGO-R2         NSLASLPGEA LADLPSLEFL RLNANPWACD CRARPLWAWF QRARVSSSDV
NOGO-R3         NSLTELQGDC LAPLVALEFL RLNGNAWDCG CRARSLWEWL RRFRGSSSAV
NOGO-R1         NNLSALPTEA LAPLRALQYL RLNDNPWVCD CRARPLWAWL QKFRGSSSEV
Consensus       N-L--L---- LA-L--L--L RLN-N-W-C- CRAR-LW-W- ---R-SSS-V

                301                                                      350
NOGO-R2         TCATPPERQG RDLRALREAD FQAC...P.P AAPTRPCSRA ..........
NOGO-R3         PCATPELRQG QDLKLLRVED FRNC...TGP VSPHQIKSHT ..........
NOGO-R1         PCSLPQRLAG RDLKRLAAND LQGCAVATGP YHPIWTGRAT DEEPLGLPKC
Consensus       -C--P----G -DL--L---D ---C-----P --P------- ----------

                351                                                      400
NOGO-R2         .......RGN ..SSSNH.LY G.VAE..... AGAPPADPS. ..TLYRDLPA
NOGO-R3         ..LTTSDRAA ..RKEHHPSH G.ASRDKGHP HGHPPGSRSG YKKAGKNCTS
NOGO-R1         CQPDAADKAS VLEPGRPASA GNALKGRVPP GDSPPGNGSG PRHI.NDSPF
Consensus       ---------- ---------- G--------- ---PP---S- ----------

                401                                                      450
NOGO-R2         EDSRGR.... QGGDAPTE.D DYWGGY.... ......GGED QRGEQMCPGA
NOGO-R3         HRNRNQISKV SSGKELTELQ DYAPDYQHKF SFDIMPTARP KRKGKCARRT
NOGO-R1         GTLPGSAEPP LTAVRPEGSE P..PGFPTSG PRRRPGCSRK NRTRSHCRLG
Consensus       ---------- ---------- ---------- ---------- -R--------

                451                                           491
NOGO-R2         ACQAPPDSRG PALSAGLPSP LLCLLLLVPH HL~~~~~~~~ ~
NOGO-R3         PIRAPSGVQQ ASSGTALGAP LLAWILGLAV TLR~~~~~~~ ~
NOGO-R1         QAGSGGGGTG DSEGSGALPS LTCSLTPLGL ALVLWTVLGP C
Consensus       ---------- ---------- L--------- -L~~~~~~~~ ~
```

FIG. 3

```
                  1                                                     50
  Human NOGO-R1   ~~~~~~~~~~ ~~~~MKRASA GGSRLLAWVL WLQAWQVAAP CPGACVCYNE
 Murine NOGO-R1   ~~~~~~~~~~ ~~~~MKRASS GGSRLLAWVL WLQAWRVATP CPGACVCYNE
 Murine NOGO-R3   MSWQSGTTVT QSPVQAAQVS GCCVELLLLL LAGELPLGGG CPRDCVCYPA
  Human NOGO-R3   ~~~~~~~~~~ ~~~~~~~~~~ ~~~~~~~~~~ ~~~~~~~~~~ ~~~~~~~~~~
  Human NOGO-R2   ~~~~~~~~~~ MLPGLRRLLQ APASACLLLM LLALPLAAPS CPMLCTCYSS
      Consensus   ~~~~~~~~~~ ~~~~------ ---------- ---------- CP--C-CY--

                      LRR NT                        LRR 1
                  51                                                   100
  Human NOGO-R1   PKVTTSCPQQ GLQAVPVGIP AASQRIFLHG NRISHVPAAS FRACRNLTIL
 Murine NOGO-R1   PKVTTSCPQQ GLQAVPTGIP ASSQRIFLHG NRISHVPAAS FQSCRNLTIL
 Murine NOGO-R3   P.MTVSCQAH NFAAIPEGIP EDSERIFLQN NRITFLQQGH FSP..AMVTL
  Human NOGO-R3   ~~~~~~~~~~ ~~~~~~EGIP VDSERVFLQN NRIGLLQPGH FSP..AMVTL
  Human NOGO-R2   P.PTVSCQAN NFSSVPLSLP PSTQRLFLQN NLIRTLRPGT FGS..NLLTL
      Consensus   P--T-SC--- -----P---P ----R-FL-- N-I------- F---------L

                       LRR 2                        LRR 3
                  101                                                  150
  Human NOGO-R1   WLHSNVLARI DAAAFTGLAL LEQLDLSDNA QLRSVDPATF HGLGRLHTLH
 Murine NOGO-R1   WLHSNALARI DAAAFTGLTL LEQLDLSDNA QLHVVDPTTF HGLGHLHTLH
 Murine NOGO-R3   WIYSNNITFI APNTFEGFVH LEELDLGDNR QLRTLAPETF QGLVKLHALY
  Human NOGO-R3   WIYSNNITYI HPSTFEGFVH LEELDLGDNR QLRTLAPETF QGLVKLHALY
  Human NOGO-R2   WLFSNNLSTI YPGTFRHLQA LEELDLGDNR HLRSLEPDTF QGLERLQSLH
      Consensus   W--SN----I ----F----- LE-LDL-DN- -L----P-TF -GL--L--L-

                       LRR 4                        LRR 5
                  151                                                  200
  Human NOGO-R1   LDRCGLQELG PGLFRGLAAL QYLYLQDNAL QALPDDTFRD LGNLTHLFLH
 Murine NOGO-R1   LDRCGLRELG PGLFRGLAAL QYLYLQDNNL QALPDNTFRD LGNLTHLFLH
 Murine NOGO-R3   LYKCGLSALP AGIFGGLHSL QYLYLQDNHI EYLQDDIFVD LVNLSHLFLH
  Human NOGO-R3   LYKCGLSALP AGVFGGLHSL QYLYLQDNHI EYLQDDIFVD LVNLSHLFLH
  Human NOGO-R2   LYRCQLSSLP GNIFRGLVSL QYLYLQENSL LHLQDDLFAD LANLSHLFLH
      Consensus   L--C-L--L- ---F-GL--L QYLYLQ-N-- --L-D--F-D L-NL-HLFLH
                     •
```

FIG. 3, cont.

| | 201 LRR 6 | | LRR 7 | | 250 |
|---|---|---|---|---|---|
| Human NOGO-R1 | GNRISSVPER | AFRGLHSLDR | LLLHQNRVAH | VHPHAFRDLG | RLMTLYLFAN |
| Murine NOGO-R1 | GNRIPSVPEH | AFRGLHSLDR | LLLHQNHVAR | VHPHAFRDLG | RLMTLYLFAN |
| Murine NOGO-R3 | GNKLWSLGQG | IFRGLVNLDR | LLLHENQLQW | VHHKAFHDLH | RLTTLFLFNN |
| Human NOGO-R3 | GNKLWSLGPG | TFRGLVNLDR | LLLHENQLQW | VHHKAFHDLR | RLTTLFLFNN |
| Human NOGO-R2 | GNRLRLLTEH | VFRGLGSLDR | LLLHGNRLQG | VHRAAFRGLS | RLTILYLFNN |
| Consensus | GN-------- | -FRGL--LDR | LLLH-N---- | VH--AF--L- | RL--L-LF-N |

| | 251 LRR 8 | | | LRR CT | 300 |
|---|---|---|---|---|---|
| Human NOGO-R1 | NLSALPTEAL | APLRALQYLR | LNDNPWVCDC | RARPLWAWLQ | KFRGSSSEVP |
| Murine NOGO-R1 | NLSMLPAEVL | MPLRSLQYLR | LNDNPWVCDC | RARPLWAWLQ | KFRGSSSEVP |
| Murine NOGO-R3 | SLTELQGDCL | APLVALEFLR | LNGNAWDCGC | RARSLWEWLR | RFRGSSSAVP |
| Human NOGO-R3 | SLSELQGECL | APLGALEFLR | LNGNPWDCGC | RARSLWEWLQ | RFRGSSSAVP |
| Human NOGO-R2 | SLASLPGEAL | ADLPSLEFLR | LNANPWACDC | RARPLWAWFQ | RARVSSSDVT |
| Consensus | -L--L----L | --L--L--LR | LN-N-W-C-C | RAR-LW-W-- | --R-SSS-V- |

| | 301 | | | | 350 |
|---|---|---|---|---|---|
| Human NOGO-R1 | CSLPQRLAGR | DLKRLAANDL | QGCAVATGPY | HPIWTGRATD | EEPLGLPKCC |
| Murine NOGO-R1 | CNLPQRLADR | DLKRLAASDL | EGCAVASGPF | RPIQTSQLTD | EELLSLPKCC |
| Murine NOGO-R3 | CATPELRQGQ | DLKLLRVEDF | RNCTGPVSP. | HQIKSHTLTT | SDRAARKEHH |
| Human NOGO-R3 | CVSPGLRHGQ | DLKLLRAEDF | RNCTGPASP. | HQIKSHTLTT | TDRAARKEHH |
| Human NOGO-R2 | CATPPERQGR | DLRALREADF | QACP.PAAP. | TRPGSRA... | ..RGNSSSNH |
| Consensus | C--P------ | DL--L---D- | --C-----P- | ---------- | ---------- |

| | 351 | | | | 400 |
|---|---|---|---|---|---|
| Human NOGO-R1 | QPDAADKASV | LEPGRPASAG | NALKGRVPPG | DSPPGNGSGP | RHINDSPFGT |
| Murine NOGO-R1 | QPDAADKASV | LEPGRPASAG | NALKGRVPPG | DTPPGNGSGP | RHINDSPFGT |
| Murine NOGO-R3 | PSHGASRDKG | HPHGHPPGSR | SGYK...... | .KAGKNCTSH | RNRNQISKVS |
| Human NOGO-R3 | SPHGPTRSKG | HPH....GPR | PGHR...... | .KPGKNCTNP | RNRNQISKAG |
| Human NOGO-R2 | .LYGVA.EAG | AP...PADPS | TLYR...... | .DLPA..... | ....EDSRGR |
| Consensus | ---------- | ---------- | ---------- | ---------- | ---------- |

FIG. 3, cont.

```
                 401                                                    450
  Human NOGO-R1  LPGSAEPPLT AVRPEGSEPP GF...PTSGP RRRPGCSRKN RTRSHCRLGQ
 Murine NOGO-R1  LPSSAEPPLT ALRPGGSEPP GL...PTTGP RRRPGCSRKN RTRSHCRLGQ
 Murine NOGO-R3  .SGKELTELQ DYAPDYQHKF SFDIMPTARP KRKGKCARRT PIRAPSGVQQ
  Human NOGO-R3  .AGKQAPELP DYAPDYQHKF SFDIMPTARP KRKGKCARRT PIRAPSGVQQ
  Human NOGO-R2  .QGGDAPTED DYWGGY.... ......GGED QRGEQMCPGA ACQAPPD...
      Consensus  ---------- ---------- ---------- -R-------- ----------

                 451                Putative GPI Signals     490
  Human NOGO-R1  AGSGGGGTGD SEGSGALPSL TCSLTPLGLA LVLWTVLGPC
 Murine NOGO-R1  AGSGASGTGD AEGSGALPAL ACSLAPLGLA LVLWTVLGPC
 Murine NOGO-R3  .......... ..ASSGTALG APLLAWILGL AVTLR~~~~~
  Human NOGO-R3  .......... ..ASSASSLG ASLLAWTLGL AVTLR~~~~~
  Human NOGO-R2  .......... ..SRGPALSA GLPS PLLCL LLLVPHHL~~
      Consensus  ---------- ---------- ---------- ----------
```

NOGO RECEPTOR HOMOLOGS THAT DECREASE INHIBITION OF AXONAL ELONGATION

This application is a divisional of U.S. application Ser. No. 10/735,256, filed Dec. 12, 2003, which is a continuation of U.S. application Ser. No. 09/972,546, filed Oct. 6, 2001, now abandoned, which claims benefit under 35 U.S.C. § 119(e) to U.S. Provisional Application No. 60/238,361, filed Oct. 6, 2000, all of which are incorporated by reference herein.

REFERENCE TO A SEQUENCE LISTING SUBMITTED ON A COMPACT DISC

This application includes a "Sequence Listing," which is provided as an electronic document on two identical copies of a compact disc (CD-R). These identical copies of the compact disc contain the file "sequence listing ascii.txt" (512 kilobytes, created on Dec. 20, 2006), which is hereby incorporated by reference in its entirety.

FIELD OF THE INVENTION

The invention relates to neurology and molecular biology. More particularly, the invention relates to CNS neurons and axonal growth

BACKGROUND

Among the mechanisms through which the cells of an organism communicate with each other and obtain information and stimuli from their environment is through cell membrane receptor molecules expressed on the cell surface. Many such receptors have been identified, characterized, and sometimes classified into major receptor superfamilies based on structural motifs and signal transduction features. The receptors are a first essential link for translating an extracellular signal into a cellular physiological response.

Receptors on neurons are particularly important in the development of the nervous system during embryogenesis. The neurons form connections with target cells during development through axonal extension of the neurons toward the target cells in a receptor-mediated process. Axons and dendrites have a specialized region of their distal tips known as the growth cone. Growth cones enable the neuron to sense the local environment through a receptor-mediated process and direct the movement of the axon or dendrite of the neuron toward the neuron's target cell. This process is known as elongation. Growth cones can be sensitive to several guidance cues, for example, surface adhesiveness, growth factors, neurotransmitters and electric fields. The guidance of growth at the cone depends on various classes of adhesion molecules, intercellular signals, as well as factors that stimulate and inhibit growth cones.

Interestingly, damaged neurons do not elongate in the central nervous system (CNS) following injury due to trauma or disease, whereas axons in the peripheral nervous system (PNS) regenerate readily. The fact that damaged CNS neurons fail to elongate is not due to an intrinsic property of CNS axons, but rather due to the CNS environment that is not permissive for axonal elongation. Classical grafting experiments by Aguayo and colleagues (e.g., Richardson et al., (1980) *Nature* 284, 264-265) demonstrated that CNS axons can in fact elongate over substantial distances within peripheral nerve grafts, and that CNS myelin inhibits CNS axon elongation. Therefore, given the appropriate environment, CNS axons can regenerate, implying that CNS axonal injury can potentially be addressed by appropriate manipulation of the CNS environment.

The absence of axon regeneration following injury can be attributed to the presence of axon growth inhibitors. These inhibitors are predominantly associated with myelin and constitute an important barrier to regeneration. Axon growth inhibitors are present in CNS-derived myelin and the plasma membrane of oligodendrocytes that synthesize myelin in the CNS (Schwab et al., (1993) *Annu. Rev. Neurosci.* 16, 565-595). Myelin-associated inhibitors appear to be a primary contributor to the failure of CNS axon regeneration in vivo after an interruption of axonal continuity, whereas other non-myelin associated axon growth inhibitors in the CNS may play a lesser role. These inhibitors block axonal regeneration following neuronal injury due to trauma, stroke or viral infection.

Numerous myelin-derived axon growth inhibitors have been characterized (see, for review, David et al., (1999) WO995394547; Bandman et al., (1999) U.S. Pat. No. 5,858, 708; Schwab, (1996) *Neurochem. Res.* 21, 755-761); Several components of CNS white matter, NI35, NI250 (Nogo) and Myelin-associated glycoprotein (MAG), which have inhibitory activity for axonal extension, have been described as well (Schwab et al., (1990) WO9005191; Schwab et al., (1997) U.S. Pat. No. 5,684,133). In particular, Nogo is a 250 kDa myelin-associated axon growth inhibitor that was originally characterized based on the effects of the purified protein in vitro and monoclonal antibodies that neutralize the protein's activity (Schwab (1990) *Exp. Neurol.* 109, 2-5). The Nogo cDNA was first identified through random analysis of brain cDNA and had no suggested function (Nagase et al., (1998) *DNA Res.* 5, 355-364). The identification of this Nogo cDNA as the cDNA encoding the 250 kDa myelin-associated axon growth inhibitor was discovered only recently (GrandPre et al., (2000) *Nature* 403, 439-444; Chen et al., (2000) *Nature* 403, 434-439; Prinjha at al., (2000) *Nature* 403, 383-384).

Importantly, Nogo has been shown to be the primary component of CNS myelin responsible for inhibiting axonal elongation and regeneration. Nogo's selective expression by oligodendrocytes and not by Schwann cells (the cells that myelinate P.S. axons) is consistent with the inhibitory effects of CNS myelin, in contrast to P.S. myelin (GrandPre et al., (2000) *Nature* 403, 434-439). In culture, Nogo inhibits axonal elongation and causes growth cone collapse (Spillmann et al., (1998) *J. Biol. Chem.* 272, 19283-19293). Antibodies (e.g., IN-1) against Nogo have been shown to block most of the inhibitory action of CNS myelin on neurite growth in vitro (Spillmann et al., (1998) *J. Biol. Chem.* 272: 19283-19293). These experiments indicate that Nogo is the main component of CNS myelin responsible for inhibition of axonal elongation in culture. Furthermore, in vivo, the IN-1 antibody has been shown to enhance axonal regeneration after spinal cord injury, resulting in recovery of behaviors such as contact placing and stride length (Schnell and Schwab (1990) *Nature* 343, 269-272; Bregman et al., (1995) *Nature* 378, 498-501). Thus, there is substantial evidence that Nogo is a disease-relevant molecular target. Agents that interfere with the binding of Nogo to its receptor would be expected to improve axonal regeneration in clinical states in which axons have been damaged, and improve patient outcome.

Modulation of Nogo has been described as a means for treatment of regeneration for neurons damaged by trauma, infarction and degenerative disorders of the CNS (Schwab et al., (1994) WO9417831; Tatagiba et al., (1997) *Neurosurgery* 40, 541-546) as well as malignant tumors in the CNS such as glioblastoma (Schwab et al, (1993) U.S. Pat. No. 5,250,414); Schwab et al., (2000) U.S. Pat. No. 6,025,333).

Antibodies which recognize Nogo have been suggested to be useful in the diagnosis and treatment of nerve damage resulting from trauma, infarction and degenerative disorders of the CNS (Schnell & Schwab, (1990) *Nature* 343, 269-272; Schwab et al., (1997) U.S. Pat. No. 5,684,133). For CNS axons, there is a correlation between the presence of myelin and the inhibition of axon regeneration over long distances (Savio and Schwab (1990) *Proc. Natl. Acad. Sci.* 87, 4130-4133; Keirstead et al., (1992) *Proc. Natl. Acad. Sci.* 89, 11664-11668). After Nogo is blocked by antibodies, neurons can again extend across lesions caused by nerve damage (Schnell and Schwab (1990) *Nature* 343, 269-272).

SUMMARY OF THE INVENTION

Genes encoding homologs (NgR2 and NgR3) of a Nogo receptor (NGR1) in mice and humans have been discovered. Various domains in the polypeptides encoded by the NgR2 and NgR3 genes have been identified and compared to domains in mouse and human NGR1 polypeptides. This comparison has led to identification of a consensus sequence (NgR consensus sequence) that characterizes a family of proteins (NgR family). Based on these and other discoveries, the invention features molecules and methods for modulating axonal growth in CNS neurons.

The invention provides a polypeptide that contains a polypeptide containing a tryptophan rich LRRCT domain consisting of the amino acid sequence:

[SEQ ID NO: 19]

$N\ X_1\ W\ X_2\ C\ X_3\ C\ R\ A\ R\ X_4\ L\ W\ X_5\ W\ X_6\ X_7\ X_8\ X_9\ R$ $X_{10}\ S\ S\ S\ X_{11}\ V\ X_{12}\ C\ X_{13}\ X_{14}\ P\ X_{15}\ X_{16}\ X_{17}\ X_{18}$ $X_{19}\ X_{20}\ D\ L\ X_{21}\ X_{22}\ L\ X_{23}\ X_{24}\ X_{25}\ D\ X_{26}\ X_{27}\ X_{28}\ C$ wherein X is any protein amino acid or a gap, and the polypeptide does not include amino acid sequence from residue 260 to 309 of SEQ ID NO: 5 (human NGR1) or SEQ ID NO:17 (mouse NgR1).

Preferably, X17 and X23 are (independently) arginine or lysine. In some embodiments, the amino acid sequence of the LRRCT domain is residues 261-310 of SEQ ID NO:2, or residues 261-310 of SEQ ID NO: 2 with up to 10 conservative amino acid substitutions. In some embodiments, the polypeptide contains the following NTLRRCT amino acid sequence:

[SEQ ID NO: 18]

$C\ P\ X_1\ X_2\ C\ X_3\ C\ Y\ X_4\ X_5\ P\ X_6\ X_7\ T\ X_8\ S\ C\ X_9\ X_{10}$ $X_{11}\ X_{12}\ X_{13}\ X_{14}\ X_{15}\ X_{16}\ P\ X_{17}\ X_{18}\ X_{19}\ P\ X_{20}\ X_{21}$ $X_{22}\ X_{23}\ R\ X_{24}\ F\ L\ X_{25}\ X_{26}\ N\ X_{27}\ I\ X_{28}\ X_{29}\ X_{30}\ X_{31}$ $X_{32}\ X_{33}\ X_{34}\ F\ X_{35}\ X_{36}\ X_{37}\ X_{38}\ X_{39}\ X_{40}\ X_{41}\ X_{42}\ L\ W$ $X_{43}\ X_{44}\ N\ X_{45}\ X_{46}\ X_{47}\ X_{48}\ I\ X_{49}\ X_{50}\ X_{51}\ X_{52}\ F\ X_{53}$ $X_{54}\ X_{55}\ X_{56}\ X_{55}\ L\ E\ X_{58}\ L\ D\ L\ X_{59}\ D\ N\ X_{60}\ X_{61}\ L$ $X_{62}\ X_{63}\ X_{64}\ X_{65}\ P\ X_{66}\ T\ F\ X_{67}\ G\ L\ X_{68}\ X_{69}\ L\ X_{70}$ $X_{71}\ L\ X_{72}\ L\ X_{73}\ X_{74}\ C\ X_{75}\ L\ X_{76}\ X_{77}\ L\ X_{78}\ X_{79}\ X_{80}$ $X_{81}\ F\ X_{82}\ G\ L\ X_{83}\ X_{84}\ L\ Q\ Y\ L\ Y\ L\ Q\ X_{85}\ N\ X_{86}\ X_{87}$ $X_{88}\ X_{89}\ L\ X_{90}\ D\ X_{91}\ X_{92}\ F\ X_{93}\ D\ L\ X_{94}\ N\ L\ X_{95}\ H\ L$

-continued $F\ L\ H\ G\ N\ X_{96}\ X_{97}\ X_{98}\ X_{99}\ X_{100}\ X_{101}\ X_{102}\ X_{103}\ X_{104}$ $F\ R\ G\ L\ X_{105}\ X_{106}\ L\ D\ R\ L\ L\ L\ H\ X_{107}\ N\ X_{108}\ X_{109}$ $X_{110}\ X_{111}\ V\ H\ X_{112}\ X_{113}\ A\ F\ X_{114}\ X_{115}\ L\ X_{116}\ R\ L$ $X_{117}\ X_{118}\ L\ X_{119}\ L\ F\ X_{120}\ N\ X_{121}\ L\ X_{122}\ X_{123}\ L$ $X_{124}\ X_{125}\ X_{126}\ X_{127}\ L\ X_{128}\ X_{129}\ L\ X_{130}\ X_{131}\ L\ X_{132}$ $X_{133}\ L\ R\ L\ N\ X_{134}\ N\ X_{135}\ W\ X_{136}\ C\ X_{137}\ C\ R\ X_{138}\ R$ $X_{139}\ L\ W\ X_{140}\ W\ X_{141}\ X_{142}\ X_{143}\ X_{144}\ R\ X_{145}\ S\ S\ S$ $X_{146}\ V\ X_{147}\ C\ X_{148}\ X_{149}\ P\ X_{150}\ X_{151}\ X_{152}\ X_{153}\ X_{154}$ $X_{155}\ D\ L\ X_{156}\ X_{157}\ L\ X_{158}\ X_{159}\ X_{160}\ D\ X_{161}\ X_{162}$ $X_{163}\ C$ wherein X is any amino acid residue or a gap and wherein the polypeptide is not the polypeptide of SEQ ID NO: 5 (human NgR1) or SEQ ID NO:17 (mouse NgR1). For example, $X_6$, $X_{37}$ and $X_{38}$ may represent a gap. Specific examples of polypeptides of the invention are SEQ ID NO: 2 (human NgR2), SEQ ID NO: 4 (mouse NgR3), and SEQ ID NO:14 (human NgR3). In some embodiments, the polypeptide contains: (a) a NTLRRCT domain, and (b) less than a complete CTS domain, provided that a partial CTS domain, if present, consists of no more than the first 39 amino acids of the CTS domain. While the polypeptide may contain a functional GPI domain, a functional GPI domain may be absent, e.g., when a soluble polypeptide is desired. A polypeptide of the invention optionally includes an amino acid sequence of a heterologous polypeptide, e.g., an Fc portion of an antibody.

The invention also provides a nucleic acid encoding an above-described polypeptide; a vector containing the nucleic acid, which nucleic acid may be operably linked to an expression control sequence; and a transformed host cell containing the vector. A method of producing a polypeptide of the invention is also provided. The method includes introducing a nucleic acid encoding the above-described polypeptide into a host cell, culturing the cell under conditions suitable for expression of the polypeptide, and recovering the polypeptide.

The invention also provides an antisense molecule whose nucleotide sequence is complementary to a nucleotide sequence encoding a polypeptide selected from the group consisting of: a polypeptide consisting of residues 311-395 of SEQ ID NO: 2, a polypeptide consisting of residues 256-396 of SEQ ID NO:14 and a polypeptide consisting of residues 321-438 of SEQ ID NO: 4, wherein the nucleic acid is from 8 to 100 nucleotides in length, e.g., about 20, 30, 40, 50, 60, 70, 80 or 90 nucleotides. The invention also provides a nucleic acid encoding such an antisense molecule.

The invention also provides an antibody that binds to an above-described polypeptide. Polypeptides or antibodies of the invention can be formulated into pharmaceutical compositions containing the polypeptide or antibody and a pharmaceutically acceptable carrier.

The invention also provides a method for decreasing inhibition of axonal growth of a CNS neuron. The method includes the step of contacting the neuron with an effective amount of a polypeptide or antibody of the invention. The invention also provides a method for treating a central nervous system disease, disorder or injury. The method includes administering to a mammal, e.g., a human, an effective amount of a polypeptide or antibody of the invention. Exemplary diseases, disorders and injuries that may be treated using molecules and methods of the invention include, but are not limited to, cerebral injury, spinal cord injury, stroke, demyelinating diseases, e.g., multiple sclerosis, monophasic demyelination, encephalomyelitis, multifocal leukoencephalopathy, panencephalitis, Marchiafava-Bignami disease, Spongy degeneration, Alexander's disease, Canavan's disease, metachromatic leukodystrophy and Krabbe's disease.

The invention also provides a method for identifying a molecule that binds a polypeptide of the invention. The method includes the steps of: (a) providing a polypeptide of the invention; (b) contacting the polypeptide with the candidate molecule; and (c) detecting binding of the candidate molecule to the polypeptide.

Unless otherwise defined, all technical and scientific terms used herein have the same meaning as commonly understood by one of ordinary skill in the art to which the invention belongs. In case of conflict, the present application, including definitions, will control. All publications, patent and other references mentioned herein are incorporated by reference.

The materials, methods and examples presented below are illustrative only, and not intended to be limiting. Other features and advantages of the invention will be apparent from the detail description and from the claims.

BRIEF DESCRIPTION OF THE FIGURES

FIG. 1A-1B shows an alignment of NgR2 (SEQ ID NO:2) and NgR3 (SEQ ID NO:4) with the known NgR, NgR1 (SEQ ID NO:5) and the Consensus Sequence (SEQ ID NO:6).

FIG. 3. An alignment of the amino acid sequences of human NGR1, murine NGR1, murine NgR3, human NgR3 and human NgR2. Numbering begins with amino acid #1 of murine NgR3. The consensus sequence is listed below. The LRR NT domain is indicated by a shaded box; domains LLR 1, LLR 3, LLR 5, and LLR 7 are indicated by open boxes; LLR 2, LLR 4, LLR 6 and LLR 8 are indicated by shaded boxes; and the LLR CT domain is indicated by a shaded box. Amino acids in bold in LLR 8 indicate a conserved glycosylation sites. A dot indicates conserved cystine residue in LRR4. Box at C terminus indicates putative GPI signals.

DETAILED DESCRIPTION OF THE INVENTION

Figure 2:
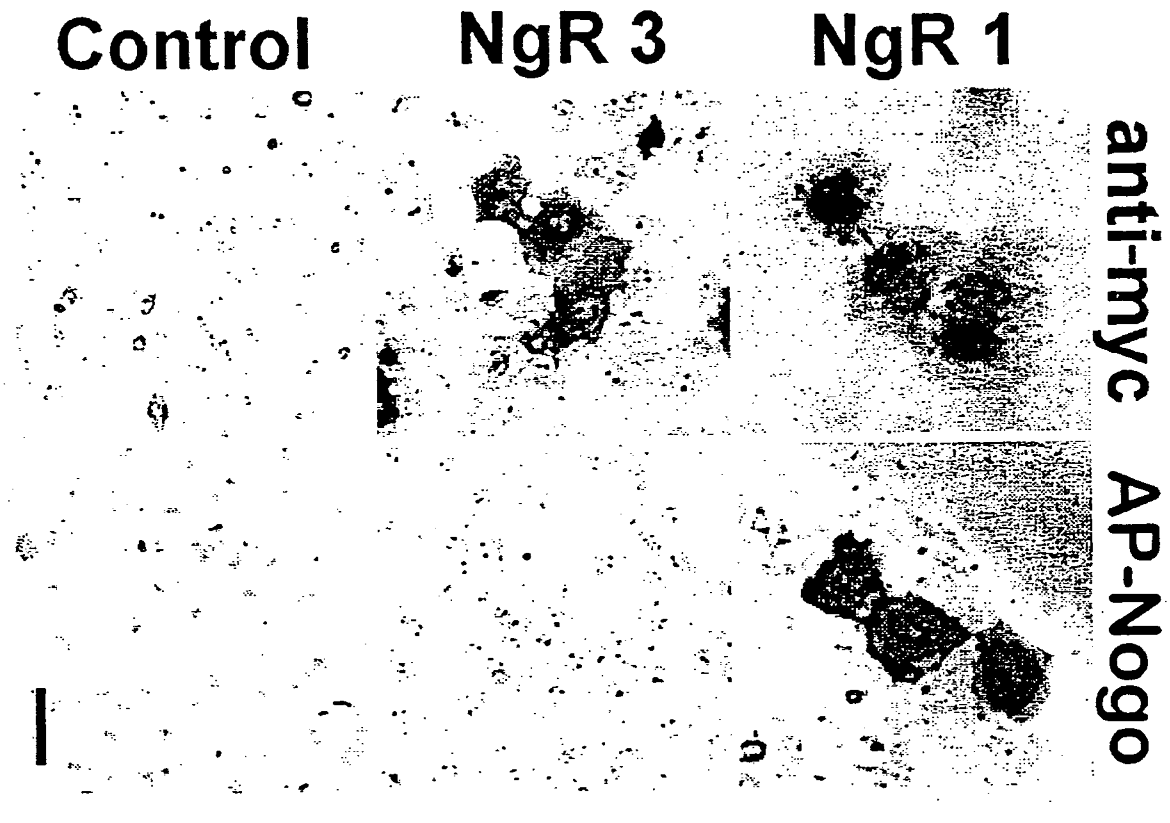
FIG. 2. mNgR3 does not bind hNogoA(1055-1120). COS-7 cells were transfected with vectors encoding myc-NgR1 or myc-NgR3, fixed, and stained with anti-myc antibodies or AP-hNogoA(1055-1120).

The present invention provides purified and isolated polynucleotides (e.g., DNA sequences and RNA transcripts, both sense and complementary antisense strands, both single- and double-stranded, including splice variants thereof) encoding NgR homologs, referred to herein as NgR. Unless indicated otherwise, as used herein, the abbreviation in lower case (NgR) refers to a gene, cDNA, RNA or nucleic acid sequence, whereas the upper case version (Ng) refers to a protein, polypeptide, peptide, oligopeptide, or amino acid sequence. Specific proteins are designated by number, e.g., "NgR2" is a human NgR homolog, "NgR3" is a murine-derived NgR homolog, and "NgR1" is the known NgR identified by Dr. Stephen Strittmatter. Known NgRs are herein referred to as "NgRs." DNA polynucleotides of the invention include genomic DNA, cDNA and DNA that has been chemically synthesized in whole or in part.

Standard reference works setting forth the general principles of recombinant DNA technology known to those of skill in the art include Ausubel et al., Current Protocols in Molecular Biology, John Wiley & Sons, New York (1998); Sambrook et al., Molecular Cloning: A Laboratory Manual, 2d Ed., Cold Spring Harbor Laboratory Press, Plainview, N.Y. (1989); Kaufman et al., Eds., Handbook of Molecular and Cellular Methods in Biology and Medicine, CRC Press, Boca Raton (1995); McPherson, Ed., Directed Mutagenesis: A Practical Approach, IRL Press, Oxford (1991).

As used herein, the term "axon" refers to a long cellular protrusion from a neuron, whereby action potentials are conducted, either to or from the cell body.

As used herein, the term "axonal growth" refers to an extension of the long process or axon, originating at the cell body and proceeded by the growth cone.

As used herein, the term "central nervous system disorder" refers to any pathological state associated with abnormal function of the central nervous system (CNS). The term includes, but is not limited to, altered CNS function resulting from physical trauma to cerebral tissue, viral infection, autoimmune mechanisms and genetic mutation.

As used herein, the term "demyelinating disease" refers to a pathological disorder characterized by the degradation of the myelin sheath of the oligodendrocyte cell membrane.

As used herein, the term "growth cone" refers to a specialized region at the tip of a growing neurite that is responsible for sensing the local environment and moving the axon toward its appropriate synaptic target cell.

As used herein, the term "growth cone movement" refers to the extension or collapse of the growth cone toward a neuron's target cell.

As used herein, the term "neurite" refers to a process growing out of a neuron. As it is sometimes difficult to distinguish a dendrite from in axon in culture, the term "neurite" is used for both.

As used herein, the term "oligodendrocyte" refers to a neuroglial cell of the CNS whose function is to myelinate CNS axons.

"Synthesized" as used herein and understood in the art, refers to polynucleotides produced by purely chemical, as opposed to enzymatic, methods. "Wholly" synthesized DNA sequences are therefore produced entirely by chemical means, and "partially" synthesized DNAs embrace those wherein only portions of the resulting DNA were produced by chemical means. By the term "region" is meant a physically contiguous portion of the primary structure of a biomolecule. In the case of proteins, a region is defined by a contiguous portion of the amino acid sequence of that protein. The term "domain" is herein defined as referring to a structural part of a biomolecule that contributes to a known or suspected function of the biomolecule. Domains may be co-extensive with regions or portions thereof, domains may also incorporate a portion of a biomolecule that is distinct from a particular region, in addition to all or part of that region. Examples of NgR protein domains include, but are not limited to, the signal peptide, extracellular (i.e., N-terminal) domain, and leucine-rich repeat domains.

As used herein, the term "activity" refers to a variety of measurable indicia suggesting or revealing binding, either direct or indirect; affecting a response, i.e., having a measurable affect in response to some exposure or stimulus, including, for example, the affinity of a compound for directly binding a polypeptide or polynucleotide of the invention, or, for example, measurement of amounts of upstream or downstream proteins or other similar functions after some stimulus or event. Such activities may be measured by assays such as competitive inhibition of NGR1 binding to Nogo assays wherein, for example, unlabeled, soluble NgR2 is added to an assay system in increasing concentrations to inhibit the binding of Nogo to NGR1 expressed on the surface of CHO cells. As another example, one may assess the ability of neurons to extend across lesions caused by nerve damage (as in Schnell and Schwab (1990) *Nature* 343, 269-272) following inhibition of Nogo by various forms of NgR2 and/or NgR3 as a biological indicator of NgR function.

As used herein, the term "antibody" is meant to refer to complete, intact antibodies, and Fab, Fab', F(ab)2, and other fragments thereof. Complete, intact antibodies include monoclonal antibodies such as murine monoclonal antibodies, chimeric antibodies, anti-idiotypic antibodies, anti-anti-idiotypic antibodies, and humanized antibodies.

As used herein, the term "binding" means the physical or chemical interaction between two proteins or compounds or associated proteins or compounds or combinations thereof. Binding includes ionic, non-ionic, hydrogen bonds, Van der Waals, hydrophobic interactions, etc. The physical interaction, the binding, can be either direct or indirect, indirect being through or due to the effects of another protein or compound. Direct binding refers to interactions that do not take place through or due to the effect of another protein or compound but instead are without other substantial chemical intermediates.

As used herein, the term "compound" means any identifiable chemical or molecule, including, but not limited to, small molecules, peptides, proteins, sugars, nucleotides or nucleic acids, and such compound can be natural or synthetic.

As used herein, the term "complementary" refers to Watson-Crick basepairing between nucleotide units of a nucleic acid molecule.

As used herein, the term "contacting" means bringing together, either directly or indirectly, a compound into physical proximity to a polypeptide or polynucleotide of the invention. The polypeptide or polynucleotide can be in any number of buffers, salts, solutions etc. Contacting includes, for example, placing the compound into a beaker, microtiter plate, cell culture flask, or a microarray, such as a gene chip, or the like, which contains the nucleic acid molecule, or polypeptide encoding the NgR or fragment thereof.

As used herein, the phrase "homologous nucleotide sequence," or "homologous amino acid sequence," or variations thereof, refers to sequences characterized by an identity at the nucleotide level, or a homology at the amino acid level, of at least the specified percentage. Homologous nucleotide sequences include those sequences coding for isoforms of proteins. Such isoforms can be expressed in different tissues of the same organism as a result of, for example, alternative splicing of RNA. Alternatively, isoforms can be encoded by different genes. Homologous nucleotide sequences include nucleotide sequences encoding for a protein of a species other than humans, including, but not limited to, mammals. Homologous nucleotide sequences also include, but are not limited to, naturally occurring allelic variations and mutations of the nucleotide sequences set forth herein. A homologous nucleotide sequence does not, however, include the nucleotide sequence encoding NgR1. Homologous amino acid sequences include those amino acid sequences which contain conservative amino acid substitutions and which polypeptides have the same binding and/or activity. A homologous amino acid sequence does not, however, include the amino acid sequence encoding other known NgRs. Percent homology can be determined by, for example, the Gap program (Wisconsin Sequence Analysis Package, Version 8 for Unix, Genetics Computer Group, University Research Park, Madison Wis.), using the default settings, which uses the algorithm of Smith and Waterman (Adv. Appl. Math., 1981, 2, 482-489, which is incorporated herein by reference in its entirety).

As used herein, the term "isolated" nucleic acid molecule-refers to a nucleic acid molecule (DNA or RNA) that is substantially free of nucleic acids encoding other proteins with which it is associated in nature, i.e., a nucleic acid that has been removed from its native environment. Examples of isolated nucleic acid molecules include, but are not limited to, recombinant DNA molecules contained in a vector, recombinant DNA molecules maintained in a heterologous host cell, partially or substantially purified nucleic acid molecules, and synthetic DNA or RNA molecules. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated NgR nucleic acid molecule can contain less than about 50 kb, 25 kb, 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material or culture medium when produced by recombinant techniques, or of chemical precursors or other chemicals when chemically synthesized.

As used herein, the term "heterologous" refers to a nucleotide or amino acid sequence that is a different, or non-corresponding sequence, or a sequence derived from a different species. For example, a mouse NgR nucleotide or amino acid sequence is heterologous to a human NgR nucleotide or amino acid sequence, and a human NgR nucleic or amino acid sequence is heterologous to a human immunoglobulin nucleotide or amino acid sequence.

As used herein, a "soluble NgR polypeptide" is a NgR polypeptide that does not anchor itself in a membrane. Such soluble polypeptides include, for example, NgR2 and NgR3 polypeptides that lack a sufficient portion of their GPI anchor signal to anchor the polypeptide or are modified such that the GPI anchor signal is not adequate to result in replacement of the peptide with a GPI anchor. In preferred embodiments, up to 5, 10, 20 or 25 amino acids are removed from the C-terminus of NgR2 or NgR3 to make the respective proteins soluble. As used herein soluble NgR polypeptides include full-length or truncated (e.g., with internal deletions) NgR.

Soluble NgR polypeptides may include the entire NgR protein up to the putative GPI signal sequence (e.g., amino acid 1 to about amino acid 395 of NgR2, and from amino acid 1 to about amino acid 438 of NgR3). In other embodiments, the signal peptide of the proteins may be removed or truncated (e.g., all or part of the signal sequence of NgR2, which spans amino acid 1 to about amino acid 30 of SEQ ID NO:2, may be removed; all or part of the signal sequence of NgR3, which spans amino acid 1 to about amino acid 40 of SEQ ID NO:4, may be removed). In some embodiments, the mature NgR2 (SEQ ID NO 8) and the mature NgR3 (SEQ ID NO:9) are used.

Soluble NgR polypeptides include at least one of the putative ligand-binding portions of NgR, including the first cysteine-rich region (SEQ ID NO:10, the leucine repeat region (SEQ ID NO:12) and the second cysteine-rich region (SEQ ID NO:11). In some embodiments, soluble NgR polypeptides consist of amino acid 1 through about amino acid 395 of SEQ ID NO:2, or amino acid 1 through about amino acid 438 of SEQ ID NO:4.

In other embodiments, the soluble NgR polypeptides are fusion proteins that contain amino acids 30 through about amino acid 395 of mature NgR2 or amino acid 40 through about amino acid 438 of NgR3, the C-terminal 10 amino acids of a human IgG1 hinge region containing the two cysteine residues thought to participate in interchain disulfide bonding, and the CH2 and CH3 regions of a human IgG1 heavy chain constant domain. This type of recombinant protein is designed to modulate inhibition of axonal elongation through inhibition of the Nogo ligand binding to NgR1, or by inhibiting the ligand of the NgR from interacting with cell surface NgR. The NgR portion of the fusion binds to the Nogo ligand and the IgG1 portion binds to the FcγRI (macrophage) and FcγIII (NK cells and neutrophils) receptors.

The production of the soluble polypeptides useful in this invention may be achieved by a variety of methods known in the art. For example, the polypeptides may be derived from intact transmembrane NgR molecules by proteolysis using specific endopeptidases in combination with exopeptidases, Edman degradation, or both. The intact NgR molecule, in turn, may be purified from its natural source using conventional methods. Alternatively, the intact NgR may be produced by known recombinant DNA techniques using cDNAs, expression vectors and well-known techniques for recombinant gene expression.

Preferably, the soluble polypeptides useful in the present invention are produced directly, thus eliminating the need for an entire NgR as a starting material. This may be achieved by conventional chemical synthesis techniques or by well-known recombinant DNA techniques wherein only those DNA sequences which encode the desired peptides are expressed in transformed hosts. For example, a gene which encodes the desired soluble NgR polypeptide may be synthesized by chemical means using an oligonucleotide synthesizer. Such oligonucleotides are designed based on the amino acid sequence of the desired soluble NgR polypeptide. Specific DNA sequences coding for the desired peptide also can be derived from the full-length DNA sequence by isolation of specific restriction endonuclease fragments or by PCR synthesis of the specified region from cDNA.

A nucleic acid molecule of the present invention, e.g., a nucleic acid molecule having the nucleotide sequence of SEQ ID NOs:1, 3 or a complement of either of these nucleotide sequences, can be isolated using standard molecular biology techniques and the sequence information provided herein. Using all or a portion of the nucleic acid sequences of SEQ ID NOs:1 or 3 as a hybridization probe, NgR nucleic acid sequences can be isolated using standard hybridization and cloning techniques (e.g. as described in Sambrook et al., eds., Molecular Cloning: A Laboratory Manual 2$^{nd}$ Ed., Cold Spring Harbor Laboratory Press, Cold Spring Harbor, N.Y., 1989; and Ausubel, et al., eds., Current Protocols in Molecular Biology, John Wiley & Sons, New York, N.Y., 1993).

A nucleic acid of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to NgR nucleotide sequences can be prepared by standard synthetic techniques, e.g., using an automated DNA synthesizer.

As used herein, the terms "modulates" or "modifies" means an increase or decrease in the amount, quality, or effect of a particular activity or protein.

As used herein, the term "oligonucleotide" refers to a series of linked nucleotide residues which has a sufficient number of bases to be used in a polymerase chain reaction (PCR). This short sequence is based on (or designed from) a genomic or cDNA sequence and is used to amplify, confirm or reveal the presence of an identical, similar or complementary DNA or RNA in a particular cell or tissue. Oligonucleotides comprise portions of a DNA sequence having at least about 10 nucleotides and as many as about 50 nucleotides, preferably about 15 to 30 nucleotides. They are chemically synthesized and may be used as probes.

As used herein, the term "probe" refers to nucleic acid sequences of variable length, preferably between at least about 10 and as many as about 6,000 nucleotides, depending on use. They are used in the detection of identical, similar or complementary nucleic acid sequences. Longer length probes are usually obtained from a natural or recombinant source, are highly specific and much slower to hybridize than oligomers. They may be single- or double-stranded and carefully designed to have specificity in PCR, hybridization membrane-based, or ELISA-like technologies.

The term "preventing" refers to decreasing the probability that an organism contracts or develops an abnormal condition.

The term "treating" refers to having a therapeutic effect and at least partially alleviating or abrogating an abnormal condition in the organism.

The term "therapeutic effect" refers to the inhibition or activation factors causing or contributing to the abnormal condition. A therapeutic effect relieves to some extent one or more of the symptoms of the abnormal condition. In reference to the treatment of abnormal conditions, a therapeutic effect can refer to one or more of the following: (a) an increase in the proliferation, growth, and/or differentiation of cells; (b) inhibition (i.e., slowing or stopping) of cell death; (c) inhibition of degeneration; (d) relieving to some extent one or more of the symptoms associated with the abnormal condition; and (e) enhancing the function of the affected population of cells. Compounds demonstrating efficacy against abnormal conditions can be identified as described herein.

The term "abnormal condition" refers to a function in the cells or tissues of an organism that deviates from their normal functions in that organism. An abnormal condition can relate to cell proliferation, cell differentiation, cell signaling, or cell survival. An abnormal condition may also include obesity, diabetic complications such as retinal degeneration, and irregularities in glucose uptake and metabolism, and fatty acid uptake and metabolism.

Abnormal cell proliferative conditions, for example, include cancers such as fibrotic and mesangial disorders, abnormal angiogenesis and vasculogenesis, wound healing, psoriasis, diabetes mellitus and inflammation.

Abnormal differentiation conditions include, for example, neurodegenerative disorders, slow wound healing rates and slow tissue grafting healing rates.

Abnormal cell signaling conditions include, for example, psychiatric disorders involving excess neurotransmitter activity.

Abnormal cell survival conditions may also relate to conditions in which programmed cell death (apoptosis) pathways are activated or abrogated. A number of protein kinases are associated with the apoptosis pathways. Aberrations in the function of any one of the protein kinases could lead to cell immortality or premature cell death.

The term "administering" relates to a method of incorporating a compound into cells or tissues of an organism. The abnormal condition can be prevented or treated when the cells or tissues of the organism exist within the organism or outside of the organism. Cells existing outside the organism can be maintained or grown in cell culture dishes. For cells harbored within the organism, many techniques exist in the art to administer compounds, including (but not limited to) oral, parenteral, dermal, injection, and aerosol applications. For cells outside of the organism, multiple techniques exist in the art to administer the compounds, including (but not limited to) cell microinjection techniques, transformation techniques and carrier techniques.

The abnormal condition can also be prevented or treated by administering a compound to a group of cells having an aberration in a signal transduction pathway to an organism. The effect of administering a compound on organism function can then be monitored. The organism is preferably a mouse, rat, rabbit, guinea pig or goat, more preferably a monkey or ape, and most preferably a human.

By "amplification" it is meant increased numbers of DNA or RNA in a cell compared with normal cells. "Amplification" as it refers to RNA can be the detectable presence of RNA in cells, since in some normal cells there is no basal expression of RNA. In other normal cells, a basal level of expression exists, therefore in these cases amplification is the detection of at least 1-2-fold, and preferably more, compared to the basal level.

The amino acid sequences are presented in the amino to carboxy direction, from left to right. The amino and carboxy groups are not presented in the sequence. The nucleotide sequences are presented by single strand only, in the 5' to 3' direction, from left to right. Nucleotides and amino acids are represented in the manner recommended by the IUPAC-IUB Biochemical Nomenclature Commission or (for amino acids) by three letters code.

Nucleic Acids

Genomic DNA of the invention comprises the protein-coding region for a polypeptide of the invention and is also intended to include allelic variants thereof. It is widely understood that, for many genes, genomic DNA is transcribed into RNA transcripts that undergo one or more splicing events wherein intron (i.e., non-coding regions) of the transcripts are removed, or "spliced out." RNA transcripts that can be spliced by alternative mechanisms, and therefore be subject to removal of different RNA sequences but still encode a NgR polypeptide, are referred to in the art as splice variants which are embraced by the invention. Splice variants comprehended by the invention therefore are encoded by the same original genomic DNA sequences but arise from distinct mRNA transcripts. Allelic variants are modified forms of a wild-type gene sequence, the modification resulting from recombination during chromosomal segregation or exposure to conditions which give rise to genetic mutation. Allelic variants, like wild-type genes, are naturally occurring sequences (as opposed to non-naturally occurring variants arising from in vitro manipulation).

The invention also comprehends cDNA that is obtained through reverse transcription of an RNA polynucleotide encoding NgR (conventionally followed by second-strand synthesis of a complementary strand to provide a double-stranded DNA).

Preferred DNA sequences encoding a human NgR polypeptide is set out in SEQ ID NOs:1 and 13. A preferred DNA of the invention comprises a double stranded molecule comprising the coding molecule (i.e., the "coding strand") along with the complementary molecule (the "non-coding strand" or "complement") having a sequence unambiguously deducible from the coding strand according to Watson-Crick base-pairing rules for DNA. Also preferred are other polynucleotides encoding NgR polypeptides, as shown in SEQ ID NO:3, which comprises murine NgR homolog, NgR3.

Also preferred are nucleotide sequences that encode at least a portion of a NgR polypeptide that has at least one biological function of a NgR. More preferred are nucleotide sequences that encode a portion of N that encodes at least the mature NgR without the hydrophobic C-terminal GPI signal; Also preferred are nucleotide sequences that encode the portion of NgR that encodes at least the ligand-binding region of NgR.

The invention further embraces other species, preferably mammalian, homologs of the human NgR DNA. Species homologs, sometimes referred to as "orthologs," in general, share at least 35%, at least 40%, at least 45%, at least 50%, at least 60%, at least 65%, at least 70%, at least 75%, at least 80%, at least 85%, at least 90%, at least 95%, at least 98%, or at least 99% homology with human DNA of the invention. Generally, percent sequence "homology" with respect to polynucleotides of the invention may be calculated as the percentage of nucleotide bases in the candidate sequence that are identical to nucleotides in the NgR sequences set forth in SEQ ID NOs:1, 3 or 13, after aligning the sequences and introducing gaps, if necessary, to achieve the maximum percent sequence identity.

The polynucleotide sequence information provided by the invention makes possible large-scale expression of the encoded polypeptide by techniques well known and routinely practiced in the art. Polynucleotides of the invention also permit identification and isolation of polynucleotides encoding related NgR polypeptides, such as human allelic variants and species homologs, by well-known techniques including Southern and/or Northern hybridization, and polymerase chain reaction (PCR). Examples of related polynucleotides include human and non-human genomic sequences, including allelic variants, as well as polynucleotides encoding polypeptides homologous to NgR and structurally related polypeptides sharing one or more biological, immunological, and/or physical properties of NgR. Non-human species genes encoding proteins homologous to NgR can also be identified by Southern and/or PCR analysis and are useful in animal models for NgR disorders. Knowledge of the sequence of a human NgR DNA also makes possible through use of Southern hybridization or polymerase chain reaction (PCR) the identification of genomic DNA sequences encoding NgR expression control regulatory sequences such as promoters, operators, enhancers, repressors, and the like. Polynucleotides of the invention are also useful in hybridization assays to detect the capacity of cells to express NgR. Polynucleotides of the invention may also provide a basis for diagnostic methods useful for identifying a genetic alteration(s) in a NgR locus that underlies a disease state or states, which information is useful both for diagnosis and for selection of therapeutic strategies.

The disclosure herein of a full-length polynucleotide encoding a NgR polypeptide makes readily available to the worker of ordinary skill in the art every possible fragment of the full-length polynucleotide. The invention, therefore, provides fragments of NgR-encoding polynucleotides comprising at least 6, and preferably at least 14, 16, 18, 20, 25, 50, or 75 consecutive nucleotides of a polynucleotide encoding NgR. Preferably, fragments of polynucleotides of the invention comprise sequences unique to the NgR-encoding polynucleotide sequence, and therefore hybridize under highly stringent or moderately stringent conditions only (i.e., "specifically") to polynucleotides encoding NgR (or fragments thereof). Polynucleotide fragments of genomic sequences of the invention comprise not only sequences unique to the coding region, but also include fragments of the full-length sequence derived from introns, regulatory regions, and/or other non-translated sequences. Sequences unique to polynucleotides of the invention are recognizable through sequence comparison to other known polynucleotides, and can be identified through use of alignment programs routinely utilized in the art, e.g., those made available in public sequence databases. Such sequences also are recognizable from Southern hybridization analyses to determine the number of fragments of genomic DNA to which a polynucleotide will hybridize. Polynucleotides of the invention can be labeled in a manner that permits their detection, including radioactive, fluorescent and enzymatic labeling.

Fragments of polynucleotides are particularly-useful as probes for detection of full-length or fragment of NgR polynucleotides. One or more polynucleotides can be included in kits that are used to detect the presence of a polynucleotide encoding NgR, or used to detect variations in a polynucleotide sequence encoding NgR.

The invention also embraces DNAs encoding NgR polypeptides that hybridize under moderately stringent or high stringency conditions to the noncoding strand, or complement, of the polynucleotide in any of SEQ ID NOs:1 or 3.

Stringent conditions are known to those skilled in the art and can be found in Current Protocols in Molecular Biology, John Wiley & Sons, N.Y. (1989), 6.3.1?6.3.6. Preferably, the conditions are such that sequences at least about 65%, 70%, 75%, 85%, 90%, 95%, 98% or 99% homologous to each other typically remain hybridized to each other. A non-limiting example of stringent hybridization conditions is hybridization in a high salt buffer comprising 6×SSC, 50 mM Tris-HCl (pH 7.5), 1 mM EDTA, 0.02% PVP, 0.02% Ficoll, 0.02% BSA and 500 mg/ml denatured salmon sperm DNA at 65° C. This hybridization is followed by one or more washes in 0.2×SSC, 0.01% BSA at 50° C. An isolated nucleic acid molecule of the invention that hybridizes under stringent conditions to the sequence of SEQ ID NOs:1 or 3 corresponds to a naturally occurring nucleic acid molecule. As used herein, a "naturally-occurring" nucleic acid molecule refers to an RNA or DNA molecule having a nucleotide sequence that occurs in nature (e.g., encodes a natural protein). As used herein, "stringent hybridization conditions" means: 42° C. in a hybridization solution comprising 50% formamide, 1% SDS, 1 M NaCl, 10% (wt/vol) dextran sulfate, and washing twice for 30 minutes at 60° C. in a wash solution comprising 0.1×SSC and 1% SDS.

Vectors

Another aspect of the present invention is directed to vectors, or recombinant expression vectors, comprising any of the nucleic acid molecules described above. Vectors are used herein either to amplify DNA or RNA encoding NgR and/or to express DNA which encodes NgR. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), that serve equivalent functions.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: (1) to increase expression of recombinant protein; (2) to increase the solubility of the recombinant protein; and (3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson (1988) *Gene* 67, 31-40), pMAL (New England Biolabs, Beverly, Mass.) and pRIT5 (Pharmacia, Piscataway, N.J.) that fuse glutathione-S-transferase (GST), maltose E binding protein, or protein A, respectively, to the target recombinant protein.

Examples of suitable inducible non-fusion *E. coli* expression vectors include pTrc (Amrann et al., (1988) *Gene* 69, 301-315) and pET 11d (Studier et al., Gene Expression Technology: Methods in Enzymology 185, Academic Press, San Diego, Calif. (1990) 60-89).

One strategy to maximize recombinant protein expression in *E. coli* is to express the protein in host bacteria with an impaired capacity to proteolytically cleave the recombinant protein. See, Gottesman, Gene Expression Technology: Methods in Enzymology 185, Academic Press, San Diego, Calif. (1990) 119-128. Another strategy is to alter the nucleic acid sequence of the nucleic acid to be inserted into an expression vector so that the individual codons for each amino acid are those preferentially utilized in *E. coli* (Wada et al., (1992) *Nucleic Acids Res.* 20, 2111-2118). Such alteration of nucleic acid sequences of the invention can be carried out by standard DNA synthesis techniques.

In another embodiment, the NgR expression vector is a yeast expression vector. Examples of vectors for expression in yeast *S. cerevisiae* include pYepSec1 (Baldari, et al., (1987) *EMBO J.* 6, 229-234), pMFa (Kujan and Herskowitz (1982) *Cell* 30, 933-943), pJRY88 (Schultz et al., (1987) *Gene* 54, 113-123), pYES2 (Invitrogen Corporation, San Diego, Calif.), and picZ (InVitrogen Corp, San Diego, Calif.).

Alternatively, NgR can be expressed in insect cells using baculovirus expression vectors. Baculovirus vectors available for expression of proteins in cultured insect cells (e.g., SF9 cells) include the pAc series (Smith et al., (1983) *Mol. Cell. Biol.* 3, 2156-2165) and the pVL series (Lucklow and Summers (1989) *Virology* 170, 31-39).

In yet another embodiment, a nucleic acid of the invention is expressed in mammalian cells using a mammalian expression vector. Examples of mammalian expression vectors include pCDM8 (Seed (1987) *Nature* 329, 840) and pMT2PC (Kaufman et al. (1987) *EMBO J.* 6, 187-195). When used in mammalian cells, the expression vector's control functions are often provided by viral regulatory elements. For example, commonly used promoters are derived from polyoma, adenovirus 2, cytomegalovirus and Simian Virus 40. For other suitable expression systems for both prokaryotic and eukaryotic cells. See, e.g., Chapters 16 and 17 of Sambrook et al., (Eds.) MOLECULAR CLONING: A LABORATORY MANUAL. $2^{nd}$ Ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev.* 1, 268-277), lymphoid-specific promoters (Calame and Eaton (1988) *Adv. Immunol.* 43, 235-275), in particular promoters of T cell receptors (Winoto and Baltimore (1989) *EMBO J.* 8, 729-733) and immunoglobulins (Banerji et al. (1983) *Cell* 33, 729-740; Queen and Baltimore (1983) *Cell* 33, 741-748), neuron-specific promoters (e.g., the neurofilament promoter; Byrne and Ruddle (1989) *Proc. Natl. Acad. Sci. USA* 86, 5473-5477), pancreas-specific promoters (Edlund et al. (1985) *Science* 230, 912-916), and mammary gland-specific promoters (e.g., milk whey promoter; U.S. Pat. No. 4,873,316 and European Application Publication No. 264,166). Developmentally-regulated promoters are also encompassed, e.g., the murine hox promoters (Kessel and Gruss (1990) *Science* 249, 374-379) and the α-fetoprotein promoter (Campes and Tilghman (1989) *Genes Dev.* 3, 537-546).

The invention further provides a recombinant expression vector comprising a DNA molecule of the invention cloned into the expression vector in an antisense orientation. That is, the DNA molecule is operatively linked to a regulatory sequence in a manner that allows for expression (by transcription of the DNA molecule) of an RNA molecule that is antisense NgR mRNA. Regulatory sequences operatively linked to a nucleic acid cloned in the antisense orientation can be chosen that direct the continuous expression of the antisense RNA molecule in a variety of cell types, for instance viral promoters and/or enhancers, or regulatory sequences can be chosen that direct constitutive, tissue-specific or cell-type-specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub et al., *Antisense RNA as a molecular tool for genetic analysis*, REVIEWS—TRENDS IN GENETICS, Vol. 1(1) 1986.

Preferred vectors include, but are not limited to, plasmids, phages, cosmids, episomes, viral particles or viruses and integratable DNA fragments (i.e., fragments integratable into the host genome by homologous recombination). Preferred viral particles include, but are not limited to, adenoviruses, baculoviruses, parvoviruses, herpesviruses, poxviruses, adeno-associated viruses, Semliki Forest viruses, vaccinia viruses and retroviruses. Preferred expression vectors include, but are not limited to, pcDNA3 (Invitrogen) and pSVL (Pharmacia Biotech). Other expression vectors include, but are not limited to, pSPORT™ vectors, pGEMT™ vectors (Promega), pPROEXvectors™ (LTI, Bethesda, Md.), Bluescript™ vectors (Stratagene), pQET™ vectors (Qiagen), pSE420™ (Invitrogen) and pYES2™(Invitrogen).

Preferred expression vectors are replicable DNA constructs in which a DNA sequence encoding NgR is operably linked or connected to suitable control sequences capable of effecting the expression of the NgR in a suitable host. DNA regions are operably linked or connected when they are functionally related to each other. For example, a promoter is operably linked or connected to a coding sequence if it controls the transcription of the sequence. Amplification vectors do not require expression control domains, but rather need only the ability to replicate in a host, usually conferred by an origin of replication, and a selection gene to facilitate recognition of transformants. The need for control sequences in the expression vector will vary depending upon the host selected and the transformation method chosen. Generally, control sequences include, but are not limited to a transcriptional promoter, enhancers, an optional operator sequence to control transcription, polyadenylation signals, a sequence encoding suitable mRNA ribosomal binding and sequences which control the termination of transcription and translation. Such regulatory sequences are described, for example, in Goeddel, GENE EXPRESSION TECHNOLOGY: METHODS IN ENZYMOLOGY 185, Academic Press, San Diego, Calif. (1996). Regulatory sequences include those that direct constitutive expression of a nucleotide sequence in many types of host cell and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., NgR proteins, mutant forms of NgR, fusion proteins, etc.).

Preferred vectors preferably contain a promoter that is recognized by the host organism. The promoter sequences of the present invention may be prokaryotic, eukaryotic or viral. Examples of suitable prokaryotic sequences include the PR and PL promoters of bacteriophage lambda (THE BACTERIOPHAGE LAMBDA, Hershey, A. D. (Ed.), Cold Spring Harbor Laboratory Press, Cold Spring Harbor, N.Y. (1973), which is incorporated herein by reference in its entirety; LAMBDA II, Hendrix, R. W. (Ed.), Cold Spring Harbor Laboratory Press, Cold Spring Harbor, N.Y. (1980), which is incorporated herein by reference in its entirety); the trp, recA, heat shock, and lacZ promoters of *E. coli* and the SV40 early promoter (Benoist et al., (1981) *Nature* 290, 304-310, which is incorporated herein by reference in its entirety). Additional promoters include, but are not limited to, mouse mammary tumor virus, long terminal repeat of human immunodeficiency virus, maloney virus, cytomegalovirus immediate early promoter, Epstein Barr virus, Rous sarcoma virus, human actin, human myosin, human hemoglobin, human muscle creatine and human metallothionein.

Additional regulatory sequences can also be included in preferred vectors. Preferred examples of suitable regulatory sequences are represented by the Shine-Dalgarno sequence of the replicase gene of the phage MS-2 and of the gene cII of bacteriophage lambda. The Shine-Dalgarno sequence may be directly followed by DNA encoding NgR and result in the expression of the mature Ng protein.

Moreover, suitable expression vectors can include an appropriate marker that allows the screening of the transformed host cells. The transformation of the selected host is carried out using any one of the various techniques well known to the expert in the art and described in Sambrook et al., supra.

An origin of replication can also be provided either by construction of the vector to include an exogenous origin or may be provided by the host cell chromosomal replication mechanism. If the vector is integrated into the host cell chromosome, the latter may be sufficient. Alternatively, rather than using vectors which contain viral origins of replication, one skilled in the art can transform mammalian cells by the method of co-transformation with a selectable marker and NgR DNA. An example of a suitable marker is dihydrofolate reductase (DHFR) or thymidine kinase (see, U.S. Pat. No. 4,399,216).

Nucleotide sequences encoding NgR may be recombined with vector DNA in accordance with conventional techniques, including blunt-ended or staggered-ended termini for ligation, restriction enzyme digestion to provide appropriate termini, filling in of cohesive ends as appropriate, alkaline phosphatase treatment to avoid undesirable joining and ligation with appropriate ligases. Techniques for such manipulation are disclosed by Sambrook et al., supra and are well known in the art. Methods for construction of mammalian expression vectors are disclosed in, for example, Okayama et al., (1983) *Mol. Cell. Biol.* 3:280, Cosman et al. (1986) *Mol. Immunol.* 23:935, Cosman et al., (1984) *Nature* 312:768, EP-A-0367566, and WO 91/18982, each of which is incorporated herein by reference in its entirety.

Host Cells and Transformed Host Cells

According to another aspect of the invention, host cells are provided, including prokaryotic and eukaryotic cells, comprising a polynucleotide of the invention (or vector of the invention) in a manner that permits expression of the encoded NgR polypeptide. Preferably, the cell produces little or no endogenous NgR polypeptide. Polynucleotides of the invention may be introduced into the host cell as part of a circular plasmid, or as linear DNA comprising an isolated protein coding region or a viral vector. Methods for introducing DNA into the host cell that are well known and routinely practiced in the art include transformation, transfection, electroporation, nuclear injection, or fusion with carriers such as liposomes, micelles, ghost cells and protoplasts. Expression systems of the invention include bacterial, yeast, fungal, plant, insect, invertebrate, vertebrate and mammalian cells systems.

Host cells of the invention are a valuable source of immunogen for development of antibodies specifically immunoreactive with NgR. Host cells of the invention are also useful in methods for the large-scale production of NgR polypeptides wherein the cells are grown in a suitable culture medium and the desired polypeptide products are isolated from the cells, or from the medium in which the cells are grown, by purification methods known in the art, e.g., conventional chromatographic methods including immunoaffinity chromatography, receptor affinity chromatography, hydrophobic interaction chromatography, lectin affinity chromatography, size exclusion filtration, cation or anion exchange chromatography, high pressure liquid chromatography (HPLC), reverse phase HPLC, and the like. Still other methods of purification include those methods wherein the desired protein is expressed and purified as a fusion protein having a specific tag, label or chelating moiety that is recognized by a specific binding partner or agent. The purified protein can be cleaved to yield the desired protein, or can be left as an intact fusion protein. Cleavage of the fusion component may produce a form of the desired protein having additional amino acid residues as a result of the cleavage process.

Knowledge of NgR DNA sequences allows for modification of cells to permit, or increase, expression of endogenous NgR. Cells can be modified (e.g., by homologous recombination) to provide increased expression by replacing, in whole or in part, the naturally occurring NgR promoter with all or part of a heterologous promoter so that the cells express NgR at higher levels. The heterologous promoter is inserted in such a manner that it is operatively linked to endogenous NgR encoding sequences. (See, for example, PCT International Publication No. WO 94/12650, PCT International Publication No. WO 92/20808, and PCT International Publication No. WO 91/09955.) It is also contemplated that, in addition to heterologous promoter DNA, amplifiable marker DNA (e.g., ada, dhfr, and the multifunctional CAD gene which encodes carbamoyl phosphate synthase, aspartate transcarbamylase, and dihydroorotase) and/or intron DNA may be inserted along with the heterologous promoter DNA If linked to the NgR coding sequence, amplification of the marker DNA by standard selection methods results in co-amplification of the NgR coding sequences in the cells.

The DNA sequence information provided by the present invention also makes possible the development (e.g., by homologous recombination or "knock-out" strategies; see Capecchi, *Science* 244:1288-1292 (1989)) of animals that fail to express functional NgR or that express a variant of NgR. Such animals (especially small laboratory animals such as rats, rabbits and mice) are useful as models for studying the in vivo activities of NgR and modulators of NgR.

Suitable host cells for expression of the polypeptides of the invention include, but are not limited to, prokaryotes, yeast, and eukaryotes. If a prokaryotic expression vector is employed, then the appropriate host cell would be any prokaryotic cell capable of expressing the cloned sequences. Suitable prokaryotic cells include, but are not limited to, bacteria of the genera *Escherichia, Bacillus, Salmonella, Pseudomonas, Streptomyces* and *Staphylococcus.*

If a eukaryotic expression vector is employed, then the appropriate host cell would be any eukaryotic cell capable of expressing the cloned sequence. Preferably, eukaryotic cells are cells of higher eukaryotes. Suitable eukaryotic cells include, but are not limited to, non-human mammalian tissue culture cells and human tissue culture cells. Preferred host cells include, but are not limited to, insect cells, HeLa cells, Chinese hamster ovary cells (CHO cells), African green monkey kidney cells (COS cells), human 293 cells, and murine 3T3 fibroblasts. Propagation of such cells in cell culture has become a routine procedure (see, Tissue Culture, Academic Press, Kruse and Patterson, Eds. (1973), which is incorporated herein by reference in its entirety).

In addition, a yeast cell may be employed as a host cell. Preferred yeast cells include, but are not limited to, the genera *Saccharomyces, Pichia* and *Kluveromyces*. Preferred yeast hosts are *S. cerevisiae* and *P. pastoris*. Preferred yeast vectors can contain an origin of replication sequence from a 2T yeast plasmid, an autonomously replication sequence (ARS), a promoter region, sequences for polyadenylation, sequences for transcription termination and a selectable marker gene. Shuttle vectors for replication in both yeast and *E. coli* are also included herein.

Alternatively, insect cells may be used as host cells. In a preferred embodiment, the polypeptides of the invention are expressed using a baculovirus expression system (see, Luckow et al., *Bio/Technology,* 1988, 6, 47; BACULOVIRUS EXPRESSION VECTORS: A LABORATORY MANUAL, O'Rielly et al. (Eds.), W.H. Freeman and Company, New York, 1992; and U.S. Pat. No. 4,879,236, each of which is incorporated herein by reference in its entirety). In addition, the MAXBAC™ complete baculovirus expression system (Invitrogen) can, for example, be used for production in insect cells.

Suitable host cells are discussed further in Goeddel, GENE EXPRESSION TECHNOLOGY: METHODS IN ENZYMOLOGY 185, Academic Press, San Diego, Calif. (1990). Alternatively, the recombinant expression vector can be transcribed and translated in vitro, for example using T7 promoter regulatory sequences and T7 polymerase.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (MOLECULAR CLONING: A LABORATORY MANUAL. 2nd ed., Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Various selectable markers include those that confer resistance to drugs, such as G418, hygromycin, dihydrofolate reductase (DHFR) and methotrexate. Nucleic acid encoding a selectable marker can be introduced into a host cell on the same vector as that encoding NgR or can be introduced on a separate vector. Cells stably transfected with the introduced nucleic acid can be identified by drug selection (e.g., cells that have incorporated the selectable marker gene will survive, while the other cells die).

In a preferred embodiment, the polypeptides of the invention, including forms of NgR2 and NgR3, soluble forms of NgR, chimeric NgR polypeptides, NgR/Ig fusions and fragments and variations of each of the above are expressed in Chinese Hamster Ovary (CHO) cells.

In order to introduce the DNA fragment coding for the NgR protein or polypeptide into the CHO cell to express the recombinant NgR protein or polypeptide, it is necessary to construct the expression vector.

The vectors for CHO expression include, but are not limited to, pA1-11, pXT1, pRc/CMV, pRc/RSV and pcDNAINeo. The promoter is not specifically limited provided it effectively promotes expression in CHO cells. Examples of suitable promoters are: SRα, SV40, LTR, CMV, and HSV-TK. Of these, CMV and Srα promoters are preferred.

In addition to the above-mentioned promoters, the expression vectors may contain enhancers, splicing signals, polyadenylation signals, selectable markers and an SV40 replication origin. Suitable selectable markers include, but are not limited to the dihydrofolate reductase (DHFR) gene which provides resistance to methotrexate (MTX), the ampicillin resistance gene, and the neomycin resistance gene.

Examples of the expression vectors each containing the DNA coding for NgR, portions, fragments and soluble constructs thereof include the vector (such as one described above), into which the promoter is operably linked (preferably upstream) to the nucleotide sequence encoding the desired NgR construct; a polyadenylation signal downstream from the nucleotide sequence encoding the NgR construct; and, preferably, the vector includes an operable DHFR gene. Preferably, the ampicillin resistant gene is also operably contained in the vector.

CHO cell lacking the DHFR gene (Urlaub, G. et al., (1980) *Proc. Natl. Acad. Sci. USA* 77, 4216-4220) and CHO-K1 (*Proc. Natl. Acad. Sci. USA* 60, 1275 (1968)) are suitable for use.

The NgR expression vectors prepared as above are introduced into CHO cells by any known method, including, but not limited to the calcium phosphate method (Graham and van der Eb (1973) *Virol.* 52, 456-467) and electroporation (Nuemann et al. (1982) *EMBO J.* 1, 841-845).

Transformants carrying the expression vectors are selected based on the above-mentioned selectable markers. Repeated clonal selection of the transformants using the selectable markers allows selection of stable cell lines having high expression of the NgR constructs. Increased MTX concentrations in the selection medium allows gene amplification and greater expression of the desired protein. The CHO cell containing the recombinant NgR can be produced by cultivating the CHO cells containing the NR expression vectors constitutively expressing the NgR constructs.

Media used in cultivating CHO cells includes DMEM medium supplemented with about 0.5 to 20% fetal calf serum, DMEM medium and RPMI1640 medium. The pH of the medium is preferably about 6 to 8. Cultivation is preferably at about 30 to 40° C. for about 15 to 72 hours with aeration.

A host cell of the invention, such as a prokaryotic or eukaryotic host cell in culture, can be used to produce (i.e., express) NgR protein. Accordingly, the invention further provides methods for producing NgR protein using the host cells of the invention. In one embodiment, the method comprises culturing the host cell of invention (into which a recombinant expression vector encoding NgR has been introduced) in a suitable medium such that NgR protein is produced. In another embodiment, the method further comprises isolating NgR from the medium or the host cell.

In situations where the NgR polypeptide will be found primarily intracellularly, intracellular material (including inclusion bodies for Gram-negative bacteria) can be extracted from the host cell using any standard technique known to one of ordinary skill in the art. Such methods would encompass, by way of example and not by way of limitation, lysing the host cells to release the contents of the periplasm/cytoplasm by French press, homogenization and/or sonication followed by centrifugation.

If the NgR polypeptide has formed inclusion bodies in the cytosol, such inclusion bodies may frequently bind to the inner and/or outer cellular membranes. Upon centrifugation, the inclusion bodies will be found primarily in the pellet material. The pellet material can then be treated at pH extremes or with one or more chaotropic agents such as a detergent, guanidine, guanidine derivatives, urea, or urea derivatives in the presence of a reducing agent such as dithiothreitol at alkaline pH or tris-carboxyethyl phosphine at acid pH to release, break apart and solubilize the inclusion bodies. Once solubilized, NgR polypeptide can be analyzed using gel electrophoresis, immunoprecipitation or the like. Various methods of isolating the NgR polypeptide would be apparent to one of ordinary skill in the art, for example, isolation may be accomplished using standard methods such as those set forth below and in Marston et al (1990) *Meth. Enzymol.* 182, 264-275 (incorporated by reference herein in its entirety).

If isolated NgR polypeptide is not biologically active following the isolation procedure employed, various methods for "refolding" or converting the polypeptide to its tertiary structure and generating disulfide linkages, can be used to restore biological activity. Methods known to one of ordinary skill in the art include adjusting the pH of the solubilized polypeptide to a pH usually above 7 and in the presence of a particular concentration of a chaotrope. The selection of chaotrope is very similar to the choices used for inclusion body solubilization but usually at a lower concentration and is not necessarily the same chaotrope as used for the solubilization. It may be required to employ a reducing agent or the reducing agent plus its oxidized form in a specific ratio, to generate a particular redox potential allowing for disulfide shuffling to occur in the formation of the protein's cysteine bridge(s). Some of the commonly used redox couples include cysteine/cystamine, glutathione (GSH)/dithiobis GSH, cupric chloride, dithiothreitol (DTT)/dithiane DTT, 2-mercaptoethanol (b(ME)/dithio-b(ME). To increase the efficiency of the refolding, it may be necessary to employ a cosolvent, such as glycerol, polyethylene glycol of various molecular weights and arginine.

Transgenic Animals

The host cells of the invention can also be used to produce non-human transgenic animals. For example, in one embodiment, a host cell of the invention is a fertilized oocyte or an embryonic stem cell into which NgR-coding sequences have been introduced. Such host cells can then be used to create non-human transgenic animals in which exogenous NgR sequences have been introduced into their genome or homologous recombinant animals in which endogenous NgR sequences have been altered. Such animals are useful for studying the function and/or activity of NgR and for identifying and/or evaluating modulators of NgR activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, etc. A transgene is exogenous DNA that is integrated into the genome of a cell from which a transgenic animal develops and that remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous NgR gene has been altered by homologous recombination between the endogenous gene and an exogenous DNA molecule introduced into a cell of the animal, e.g., an embryonic cell of the animal, prior to development of the animal.

A transgenic animal of the invention can be created by introducing NgR-encoding nucleic acid into the male pronuclei of a fertilized oocyte, e.g., by microinjection, retroviral infection, and allowing the oocyte to develop in a pseudopregnant female foster animal. The human NgR DNA sequence of SEQ ID NOs:1 or 3 can be introduced as a transgene into the genome of a non-human animal. Alternatively, a nonhuman homolog of the human NgR gene, such as a mouse NgR gene, can be isolated based on hybridization to the human NgR cDNA (described further above) and used as a transgene. Intronic sequences and polyadenylation signals can also be included in the transgene to increase the efficiency of expression of the transgene. A tissue-specific regulatory sequence(s) can be operably linked to the NgR transgene to direct expression of NgR protein to particular cells. Methods for generating transgenic animals via embryo manipulation and microinjection, particularly animals such as mice, have become conventional in the art and are described, for example, in U.S. Pat. Nos. 4,736,866; 4,870,009; and 4,873,191; and Hogan 1986, in Manipulating the Mouse Embryo, Cold Spring Harbor Laboratory Press, Cold Spring Harbor, N.Y. Similar methods are used for production of other transgenic animals. A transgenic founder animal can be identified based upon the presence of the NgR transgene in its genome and/or expression of NgR mRNA in tissues or cells of the animals. A transgenic founder animal can then be used to breed additional animals carrying the transgene. Moreover, transgenic animals carrying a transgene encoding NgR can further be bred to other transgenic animals carrying other transgenes.

To create a homologous recombinant animal, a vector is prepared which contains at least a portion of a NgR gene into which a deletion, addition or substitution has been introduced to thereby alter, e.g., functionally disrupt, the NgR gene. The NgR gene can be a human gene (e.g., SEQ ID NOs:1 or 13), but more preferably, is a non-human homolog of a human NgR gene. For example, a mouse homolog of human NgR gene of SEQ ID NOs:1 or 13 can be used to construct a homologous recombination vector suitable for altering an endogenous NgR gene in the mouse genome. In one embodiment, the vector is designed such that, upon homologous recombination, the endogenous NgR gene is functionally disrupted (i.e., no longer encodes a functional protein; also referred to as a "knock out" vector).

Alternatively, the vector can be designed such that, upon homologous recombination, the endogenous NgR gene is mutated or otherwise altered but still encodes functional protein (e.g., the upstream regulatory region can be altered to thereby alter the expression of the endogenous NgR protein). In the homologous recombination vector, the altered portion of the NgR gene is flanked at its 5' and 3' ends by additional nucleic acid of the NgR gene to allow for homologous recombination to occur between the exogenous NgR gene carried by the vector and an endogenous NgR gene in an embryonic stem cell. The additional flanking NgR nucleic acid is of sufficient length for successful homologous recombination with the endogenous gene. Typically, several kilobases of flanking DNA (both at the 5' and 3' ends) are included in the vector. See e.g., Thomas et al. (1987) *Cell* 51:503 for a description of homologous recombination vectors. The vector is introduced into an embryonic stem cell line (e.g., by electroporation) and cells in which the introduced NgR gene has homologously recombined with the endogenous NgR gene are selected (see e.g., Li et al. (1992) *Cell* 69:915).

The selected cells are then injected into a blastocyst of an animal (e.g., a mouse) to form aggregation chimeras. See e.g., Bradley 1987, In: Teratocarcinomas and Embryonic Stem Cells: A Practical Approach, Robertson, ed. IRL, Oxford, pp. 113-152. A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley (1991) *Curr. Opin. Biotechnol.* 2:823-829; PCT International Publication Nos.: WO 90/11354; WO 91/01140; WO 92/0968; and WO 93/04169.

In another embodiment, transgenic non-humans animals can be produced that contain selected systems that allow for regulated expression of the transgene. One example of such a system is the cre/loxP recombinase system of bacteriophage P1. For a description of the cre/loxP recombinase system, see, e.g., Lakso et al. (1992) *Proc. Natl. Acad. Sci. USA* 89:6232-6236. Another example of a recombinase system is the FLP recombinase system of *Saccharomyces cerevisiae* (O'Gorman et al. (1991) *Science* 251:1351-1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut et al. (1997) *Nature* 385:810-813. In brief, a cell, e.g., a somatic cell, from the transgenic animal can be isolated and induced to exit the growth cycle and enter $G_0$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyte and then transferred to pseudopregnant female foster animal. The offspring borne of this female foster animal will be a clone of the animal from which the cell, e.g., the somatic cell, is isolated.

Antisense

Also provided by the invention are antisense polynucleotides that recognize and hybridize to NgR polynucleotides. Full-length and fragment antisense polynucleotides are provided. Fragment antisense molecules of the invention include (i) those that specifically recognize and hybridize to NgR RNA (as determined by sequence comparison of DNA encoding NgR to DNA encoding other known molecules). Identification of sequences unique to NgR encoding polynucleotides can be deduced through use of any publicly available sequence database, and/or through use of commercially available sequence comparison programs. After identification of the desired sequences, isolation through restriction digestion or amplification using any of the various polymerase chain reaction techniques well known in the art can be performed. Antisense polynucleotides are particularly relevant to regulating expression of NgR by those cells expressing NgR mRNA.

Antisense oligonucleotides, or fragments of a nucleotide sequence set forth in SEQ ID NO:1, 3, 13 or sequences complementary or homologous thereto, derived from the nucleotide sequences of the present invention encoding NgR are useful as diagnostic tools for probing gene expression in various tissues. For example, tissue can be probed in situ with oligonucleotide probes carrying detectable groups by conventional autoradiography techniques to investigate native expression of this enzyme or pathological conditions relating thereto. In specific aspects, antisense nucleic acid molecules are provided that comprise a sequence complementary to at least about 10, 25, 50, 100, 250 or 500 nucleotides or an entire NgR coding strand, or to only a portion thereof. Nucleic acid molecules encoding fragments, homologs, derivatives and analogs of a NgR protein of SEQ ID NO:2, 4 or 14 or antisense nucleic acids complementary to a NgR nucleic acid sequence of SEQ ID NOs:1, 3 or 13 are additionally provided.

In one embodiment, an antisense nucleic acid molecule is antisense to a "coding region" of the coding strand of a nucleotide sequence encoding NgR. The term "coding region" refers to the region of the nucleotide sequence comprising codons which are translated into amino acid residues (e.g., the protein coding region of human NgR corresponds to the coding region SEQ ID NO:1, 3 or 13). In another embodiment, the antisense nucleic acid molecule is antisense to a "noncoding region" of the coding strand of a nucleotide sequence encoding NgR. The term "noncoding region" refers to 5' and 3' sequences which flank the coding region that are not translated into amino acids (i.e., also referred to as 5' and 3' untranslated regions).

Antisense oligonucleotides are preferably directed to regulatory regions of a nucleotide sequence of SEQ ID NO:1, 3, 13 or mRNA corresponding thereto, including, but not limited to, the initiation codon, TATA box, enhancer sequences, and the like. Given the coding strand sequences encoding NgR disclosed herein (e.g., SEQ ID NO:1, 3 or 13), antisense nucleic acids of the invention can be designed according to the rules of Watson and Crick or Hoogsteen base pairing. The antisense nucleic acid molecule can be complementary to the entire coding region of NgR mRNA, but more preferably is an oligonucleotide that is antisense to only a portion of the coding or noncoding region of NgR mRNA For example, the antisense oligonucleotide can be complementary to the region surrounding the translation start site of NgR mRNA. An antisense oligonucleotide can be, for example, about 5, 10, 15, 20, 25, 30, 35, 40, 45 or 50 nucleotides in length. An antisense nucleic acid of the invention can be constructed using chemical synthesis or enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used.

Examples of modified nucleotides that can be used to generate the antisense nucleic acid include: 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention (preferably oligonucleotides of 10 to 20 nucleotides in length) are typically administered to a subject or generated in situ such that they hybridize with or bind to cellular mRNA and/or genomic DNA encoding a NgR protein to thereby inhibit expression of the protein, e.g., by inhibiting transcription and/or translation. Suppression of NgR expression at either the transcriptional or translational level is useful to generate cellular or animal models for diseases/conditions characterized by aberrant NgR expression. The hybridization can be by conventional nucleotide complementarity to form a stable duplex, or, for example, in the case of an antisense nucleic acid molecule that binds to DNA duplexes, through specific interactions in the major groove of the double helix.

Phosphorothioate and methylphosphonate antisense oligonucleotides are specifically contemplated for therapeutic use by the invention. The antisense oligonucleotides may be further modified by adding poly-L-lysine, transferrin polylysine or cholesterol moieties at their 5' end.

An example of a route of administration of antisense nucleic acid molecules of the invention includes direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies that bind to cell surface receptors or antigens. The antisense nucleic acid molecules can also be delivered to cells using the vectors described herein. To achieve sufficient intracellular concentrations of antisense molecules, vector constructs in which the antisense nucleic acid molecule is placed under the control of a strong pol II or pol III promoter are preferred.

In yet another embodiment, the antisense nucleic acid molecule of the invention is an $\alpha$-anomeric nucleic acid molecule. An $\alpha$-anomeric nucleic acid molecule forms specific double-stranded hybrids with complementary RNA in which, contrary to the usual $\beta$-units, the strands run parallel to each other (Gaultier et al., (1987) *Nucleic Acids Res.* 15, 6625-6641). The antisense nucleic acid molecule can also comprise a 2'-o-methylribonucleotide (Inoue et al., (1987) *Nucleic Acids Res.* 15, 6131-6148) or a chimeric RNA-DNA analogue (Inoue et al., (1987) *FEBS Lett.* 215, 327-330).

The NgR sequences taught in the present invention facilitate the design of novel transcription factors for modulating NgR expression in native cells and animals, and cells transformed or transfected with NgR polynucleotides. For example, the $Cys_2$-$His_2$ zinc finger proteins, which bind DNA via their zinc finger domains, have been shown to be amenable to structural changes that lead to the recognition of different target sequences. These artificial zinc finger proteins recognize specific target sites with high affinity and low dissociation constants, and are able to act as gene switches to modulate gene expression. Knowledge of the particular NgR target sequence of the present invention facilitates the engineering of zinc finger proteins specific for the target sequence using known methods such as a combination of structure-based modeling and screening of phage display libraries (Segal et al., (1999) *Proc. Natl. Acad. Sci. USA* 96, 2758-2763; Liu et al., (1997) *Proc. Natl. Acad. Sci. USA* 94, 5525-5530; Greisman et al. (1997) *Science* 275, 657-661; Choo et al., (1997) *J. Mol. Biol.* 273, 525-532). Each zinc finger domain usually recognizes three or more base pairs. Since a recognition sequence of 18 base pairs is generally sufficient in length to render it unique in any known genome, a zinc finger protein consisting of 6 tandem repeats of zinc fingers would be expected to ensure specificity for a particular sequence (Segal et al., (1999), above). The artificial zinc finger repeats, designed based on the promoter of NgR sequences, are fused to activation or repression domains to promote or suppress NgR expression (Liu et al., (1997), above). The promoter of NgR may be obtained by standard methods known to one of ordinary skill in the art with the disclosure contained herein and knowledge of the NgR sequence. Alternatively, the zinc finger domains can be fused to the TATA box-binding factor (TBP) with varying lengths of linker region between the zinc finger peptide and the TBP to create either transcriptional activators or repressors (Kim et al., (1997) *Proc. Natl. Acad. Sci. USA* 94, 3616-3620. Such proteins and polynucleotides that encode them, have utility for modulating NgR expression in vivo in both native cells, animals and humans; and/or cells transfected with NgR-encoding sequences. The novel transcription factor can be delivered to the target cells by transfecting constructs that express the transcription factor (gene therapy), or by introducing the protein. Engineered zinc finger proteins can also be designed to bind RNA sequences for use in therapeutics as alternatives to antisense or catalytic RNA methods (McColl et al., (1997) *Proc. Natl. Acad. Sci. USA* 96, 9521-9526); Wu et al., (1995) *Proc. Natl. Acad. Sci. USA* 92, 344-348). The present invention contemplates methods of designing such transcription factors based on the gene sequence of the invention, as well as customized zinc finger proteins, that are useful to modulate NgR expression in cells (native or transformed) whose genetic complement includes these sequences.

Ribozymes and PNA Moieties

In still another embodiment, an antisense nucleic acid of the invention is a ribozyme. Ribozymes are catalytic RNA molecules with ribonuclease activity that are capable of cleaving a single-stranded nucleic acid, such as an mRNA, to which they have a complementary region. Thus, ribozymes (e.g., hammerhead ribozymes, described in Haselhoff and Gerlach (1988) *Nature* 334, 585-591) can be used to catalytically cleave NgR mRNA transcripts to thereby inhibit translation of NgR mRNA. A ribozyme having specificity for a NgR-encoding nucleic acid can be designed based upon the nucleotide sequence of a NgR DNA disclosed herein (i.e., SEQ ID NOs:1, 3 or 13). For example, a derivative of a Tetrahymena L-19 IVS RNA can be constructed in which the nucleotide sequence of the active site is complementary to the nucleotide sequence to be cleaved in a NgR-encoding mRNA. See, e.g., Cech et al. U.S. Pat. No. 4,987,071; and Cech et al. U.S. Pat. No. 5,116,742. Alternatively, NgR mRNA can be used to select a catalytic RNA having a specific ribonuclease activity from a pool of RNA molecules. See, e.g., Bartel et al., (1993) *Science* 261, 1411-1418.

Alternatively, NgR gene expression can be inhibited by targeting nucleotide sequences complementary to the regulatory region of the NgR (e.g., the NgR promoter and/or enhancers) to form triple helical structures that prevent transcription of the NgR gene in target cells. See generally, Helene (1991) *Anticancer Drug Des.* 6: 569-584; Helene et al., (1992) *Ann. N.Y. Acad. Sci.* 660:27-36; and Maher (1992) *BioEssays* 14, 807-815.

In various embodiments, the nucleic acids of NgR can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids (see Hyrup et al., (1996) *Bioorg. Med. Chem. Lett.* 4, 5-23). As used herein, the terms “peptide nucleic acids” or “PNAs” refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al., (1996) above; Perry-O’Keefe et al., (1996) *Proc. Natl. Acad. Sci. USA* 93, 14670-14675.

PNAs of NgR can be used in therapeutic and diagnostic applications. For example, PNAs can be used as antisense or antigene agents for sequence-specific modulation of gene expression by, e.g., inducing transcription or translation arrest or inhibiting replication. PNAs of NgR can also be used, e.g., in the analysis of single base pair mutations in a gene by, e.g., PNA directed PCR clamping; as artificial restriction enzymes when used in combination with other enzymes, e.g., S1 nucleases (Hyrup (1996), above); or as probes or primers for DNA sequence and hybridization (Hyrup et al., (1996), above; Perry-O'Keefe (1996), above).

In another embodiment, PNAs of NgR can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras of NgR can be generated that may combine the advantageous properties of PNA and DNA. Such chimeras allow DNA recognition enzymes, e.g., RNase H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup (1996), above). The synthesis of PNA-DNA chimeras can be performed as described in Hyrup (1996), above and Finn et al. (1996) *Nucleic Acids Res.* 24, 3357-3363. For example, a DNA chain can be synthesized on a solid support using standard phosphoramidite coupling chemistry, and modified nucleoside analogs, e.g., 5'-(4-methoxytrityl)amino-5'-deoxy-thymidine phosphoramidite, can be used between the PNA and the 5' end of DNA (Mag et al. (1989) *Nucleic Acids Res.* 17, 973-988). PNA monomers are then coupled in a stepwise manner to produce a chimeric molecule with a 5' PNA segment and a 3' DNA segment (Finn et al. (1996), above). Alternatively, chimeric molecules can be synthesized with a 5' DNA segment and a 3' PNA segment. See, Petersen et al. (1975) *Bioorg. Med. Chem. Lett.* 5:1119-1124.

In other embodiments, the oligonucleotide may include other appended groups such as peptides (e.g., for targeting host cell receptors in vivo), or agents facilitating transport across the cell membrane (see Letsinger et al., (1989) *Proc. Natl. Acad. Sci. USA* 86, 6553-6556; Lemaitre et al., (1987) *Proc. Natl. Acad. Sci. USA* 84, 648-652; PCT Publication No. WO 88/09810) or the blood-brain barrier (see, e.g., PCT Publication No. WO 89/10134). In addition, oligonucleotides can be modified with hybridization triggered cleavage agents (see, e.g., Krol et al., (1988) *Biotechniques* 6, 958-976) or intercalating agents (see, e.g., Zon (1988) *Pharm. Res.* 5, 539-549). To this end, the oligonucleotide may be conjugated to another molecule, e.g., a peptide, a hybridization triggered cross-linking agent, a transport agent, a hybridization-triggered cleavage agent, etc.

Automated sequencing methods can be used to obtain or verify the nucleotide sequence of NgR. The NgR nucleotide sequences of the present invention are believed to be 100% accurate. However, as is known in the art, nucleotide sequence obtained by automated methods may contain some errors. Nucleotide sequences determined by automation are typically at least about 90%, more typically at least about 95% to at least about 99.9% identical to the actual nucleotide sequence of a given nucleic acid molecule. The actual sequence may be more precisely determined using manual sequencing methods, which are well known in the art. An error in a sequence which results in an insertion or deletion of one or more nucleotides may result in a frame shift in translation such that the predicted amino acid sequence will differ from that which would be predicted from the actual nucleotide sequence of the nucleic acid molecule, starting at the point of the mutation.

Polypeptides

The invention also provides purified and isolated mammalian NgR polypeptides encoded by a polynucleotide of the invention. Presently preferred is a human NgR polypeptide comprising the amino acid sequence set forth in SEQ ID NO:2 or SEQ ID NO:14. Another preferred embodiment is a mouse NgR polypeptide comprising the amino acid sequence of NgR3, as set forth in SEQ ID NO:4.

One aspect of the invention pertains to isolated NgR proteins, and biologically active portions thereof, or derivatives, fragments, analogs or homologs thereof. Also provided are polypeptide fragments suitable for use as immunogens to raise anti-NgR antibodies. Preferably, fragments of NgR proteins comprise at least one biological activity of NgR. In one embodiment, native NgR proteins can be isolated from cells or tissue sources by an appropriate purification scheme using standard protein purification techniques. In another embodiment, NgR proteins are produced by recombinant DNA techniques. Alternative to recombinant expression, a NgR protein or polypeptide can be synthesized chemically using standard peptide synthesis techniques.

The invention also embraces polypeptides that have at least 99%, at least 95%, at least 90%, at least 85%, at least 80%, at least 75%, at least 70%, at least 65%, at least 60%, at least 55%, at least 50% or at least 45% identity and/or homology to the preferred polypeptide of the invention. In addition, the invention embraces polypeptides having the consensus sequence shown in SEQ ID NO:6, shown in Table 5) excluding the previously characterized NgR ("NgR1"), and polypeptides comprising at least about 90% of the consensus sequence.

The term "percentage of sequence identity" is calculated by comparing two optimally aligned sequences over that region of comparison, determining the number of positions at which the identical nucleic acid base (e.g., A, T, C, G, U, or I, in the case of nucleic acids) occurs in both sequences to yield the number of matched positions, dividing the number of matched positions by the total number of positions in the region of comparison (i.e., the window size), and multiplying the result by 100 to yield the percentage of sequence identity. The term "substantial identity" as used herein denotes a characteristic of a polynucleotide sequence, wherein the polynucleotide comprises a sequence that has at least 80 percent sequence identity, preferably at least 85 percent identity and often 90 to 95 percent sequence identity, more usually at least 99 percent sequence identity as compared to a reference sequence over a comparison region.

In one aspect, percent homology is calculated as the percentage of amino acid residues in the smaller of two sequences which align with identical amino acid residue in the sequence being compared, when four gaps in a length of 100 amino acids may be introduced to maximize alignment (Dayhoff, in Atlas of Protein Sequence and Structure, Vol. 5, p. 124, National Biochemical Research Foundation, Washington, D.C. (1972), incorporated herein by reference).

A determination of homology or identity is typically made by a computer homology program known in the art. An exemplary program is the Gap program (Wisconsin Sequence Analysis Package, Version 8 for UNIX, Genetics Computer Group, University Research Park, Madison, Wis.) using the default settings, which uses the algorithm of Smith and Waterman (*Adv. Appl. Math,* 1981, 2, 482-489, which in incorporated herein by reference in its entirety). Employing the GAP software provided in the GCG program package, (see Needleman and Wunsch (1970) *J. Mol. Biol.* 48, 443-453) the following settings for nucleic acid sequence comparison may be used: GAP creation penalty of 5.0 and GAP extension penalty of 0.3, the coding region of the analogous nucleic acid sequences referred to above exhibits a degree of identity preferably of at least 70%, 75%, 80%, 85%, 90%, 95%, 98%, or 99%, with the CDS (encoding) part of the DNA sequence shown in SEQ ID NOs:1, 3 or 13. BestFit was originally written for Version 1.0 by Paul Haeberli from a careful reading of the papers by Needleman and Wunsch (1970), above, and Smith and Waterman (1981), above. The following Bestfit settings for nucleic acid sequence comparison may be used: GAP creation penalty of 8.0 and GAP extension penalty of 2, the coding region of the analogous nucleic acid sequences referred to above exhibits a degree of identity preferably of at least 70%, 75%, 80%, 85%, 90%, 95%, 98% or 99%, with the CDS (encoding) part of the amino acid sequence shown in SEQ ID NOs:2, 4 or 14.

Alternatively, homology may be determined by hybridization analysis wherein a nucleic acid sequence is hybridized to the complement of a sequence encoding the aforementioned proteins under stringent, moderately stringent, or low stringent conditions. See e.g. Ausubel, et al., (Eds.) Current Protocols in Molecular Biology, John Wiley & Sons, New York, N.Y., 1993; and below.

Polypeptides of the invention may be isolated from natural cell sources or may be chemically synthesized, but are preferably produced by recombinant procedures involving host cells of the invention.

An "isolated" or "purified" protein or biologically active portion thereof is substantially free of cellular material or other contaminating proteins from the cell or tissue source from which the NgR protein is derived, or substantially free from chemical precursors or other chemicals when chemically synthesized. The language "substantially free of cellular material" includes preparations of NgR protein in which the protein is separated from cellular components of the cells from which it is isolated or recombinantly produced. In one embodiment, the language "substantially free of cellular material" includes preparations of NgR protein having less than about 30% (by dry weight) of non-NgR protein (also referred to herein as a "contaminating protein"), more preferably less than about 20% of non-NgR protein, still more preferably less than about 10% of non-NgR protein, and most preferably less than about 5% non-NgR protein. When the NgR protein or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of NgR protein in which the protein is separated from chemical precursors or other chemicals that are involved in the synthesis of the protein. In one embodiment, the language "substantially free of chemical precursors or other chemicals" includes preparations of NGR protein having less than about 30% (by dry weight) of chemical precursors or non-NgR chemicals, more preferably less than about 20% chemical precursors or non-NgR chemicals, still more preferably less than about 10% chemical precursors or non-NgR chemicals, and most preferably less than about 5% chemical precursors or non-NgR chemicals.

Biologically active portions of a NgR protein include peptides comprising amino acid sequences sufficiently homologous to or derived from the amino acid sequence of the NgR protein, e.g., the amino acid sequence shown in SEQ ID NO:2, 4 or 14 that include fewer amino acids than the full length NgR proteins, and exhibit at least one activity of a NgR protein. Typically, biologically active portions comprise a domain or motif with at least one activity of the NgR protein. A biologically active portion of a NGR protein can be a polypeptide which is, for example, 10, 25, 50, 100 or more amino acids in length.

A biologically active portion of a NgR protein of the present invention may contain at least one of the features that is conserved between the NgR proteins (e.g., a conserved cysteine as the N-terminus of the mature protein, four conserved cysteines in the N-terminus before a leucine-rich region, four conserved cysteines C-terminal with respect to a leucine repeat region, eight leucine-rich repeats, and a hydrophobic C-terminus). An alternative biologically active portion of a NgR protein may contain at least two of the above-identified domains. Another biologically active portion of a NgR protein may contain at least three of the above-identified domains. Yet another biologically active portion of a NgR protein of the present invention may contain at least four of the above-identified domains.

Moreover, other biologically active portions, in which other regions of the protein are deleted, can be prepared by recombinant techniques and evaluated for one or more of the functional activities of a native NgR protein.

In an embodiment, the NgR protein has an amino acid sequence shown in SEQ ID NO:2, 4 or 14. In other embodiments, the NgR protein is substantially homologous to SEQ ID NO:2, 4 or 14 and retains the functional activity of the protein of SEQ ID NO:2, 4 or 14, yet differs in amino acid sequence due to natural allelic variation or mutagenesis, as described in detail below.

Accordingly, in another embodiment, the NgR protein is a protein that comprises an amino acid sequence at least about 45% homologous to the amino acid sequence of SEQ ID NO:2 or SEQ ID NO:4 or SEQ ID NO:14 and retains the functional activity of the NgR proteins of SEQ ID NO:2, 4 or 14.

Use of mammalian host cells is expected to provide for such post-translational modifications (e.g., glycosylation, truncation, lipidation and phosphorylation) as may be needed to confer optimal biological activity on recombinant expression products of the invention. Glycosylated and non-glycosylated forms of NgR polypeptides are embraced by the invention.

The invention also embraces variant (or analog) NgR polypeptides. In one example, insertion variants are provided wherein one or more amino acid residues supplement a NgR amino acid sequence. Insertions may be located at either or both termini of the protein, or may be positioned within internal regions of the NgR amino acid sequence. Insertional variants with additional residues at either or both termini can include, for example, fusion proteins and proteins including amino acid tags or labels.

Insertion variants include NgR polypeptides wherein one or more amino acid residues are added to a NgR acid sequence or to a biologically active fragment thereof.

Variant products of the invention also include mature NgR products, i.e., NgR products wherein leader or signal sequences are removed, with additional amino terminal residues. The additional amino terminal residues may be derived from another protein, or may include one or more residues that are not identifiable as being derived from specific proteins. NgR products with an additional methionine residue at position −1 ($Met^{-1}$-NgR) are contemplated, as are variants with additional methionine and lysine residues at positions −2 and −1 ($Met^{-2}$-$Lys^{-1}$-NgR). Variants of NgR with additional Met, Met-Lys, Lys residues (or one or more basic residues in general) are particularly useful for enhanced recombinant protein production in bacterial host cells.

Polypeptide Variants

The invention also embraces NgR variants having additional amino acid residues which result from use of specific expression systems.

As used herein, a NgR "chimeric protein" or "fusion protein" comprises a NgR polypeptide operatively linked to a non-NgR polypeptide. A "NgR polypeptide" refers to a polypeptide having an amino acid sequence corresponding to NgR, whereas a "non-NgR polypeptide" refers to a polypeptide having an amino acid sequence corresponding to a protein that is not homologous to the NgR protein, e.g., a protein that is different from the NgR protein and that is derived from the same or a different organism. Within a NgR fusion protein the NgR polypeptide can correspond to all or a portion of a NgR protein. In one embodiment, a NgR fusion protein comprises at least one biologically active portion of a NgR protein. In another embodiment, a NgR fusion protein comprises at least two biologically active portions of a NgR protein. In yet another embodiment, a NgR fusion protein comprises at least three biologically active portions of a NgR protein. Within the fusion protein, the term "operatively linked" is intended to indicate that the NgR polypeptide and the non-NgR polypeptide are fused in-frame to each other. The non-NgR polypeptide can be fused to the N-terminus or C-terminus of the NgR polypeptide.

For example, in one embodiment a NgR fusion protein comprises a NgR domain operably linked to the extracellular domain of a second protein. Such fusion proteins can be further utilized in screening assays for compounds which modulate NgR activity (such assays are described in detail below).

For example, use of commercially available vectors that express a desired polypeptide as part of a glutathione-S-transferase (GST) fusion product provides the desired polypeptide having an additional glycine residue at position −1 after cleavage of the GST component from the desired polypeptide.

In another embodiment, the fusion protein is a NgR protein containing a heterologous signal sequence at its N-terminus. For example, the native NgR signal sequence (i.e., amino acids 1-30 of SEQ ID NO:2 and amino acids 1-40 of SEQ ID NO:4) can be removed and replaced with a signal sequence from another protein. In certain host cells (e.g., mammalian host cells), expression and/or secretion NgR can be increased through use of a heterologous signal sequence.

In yet another embodiment, the fusion protein is a NgR-immunoglobulin fusion protein in which the NgR sequences comprising one or more domains are fused to sequences derived from a member of the immunoglobulin protein family. The NgR-immunoglobulin fusion proteins of the invention can be incorporated into pharmaceutical compositions and administered to a subject to inhibit an interaction between NgR ligand and a NgR protein on the surface of a cell, to thereby suppress NgR-mediated signal transduction in vivo. NgR-immunoglobulin fusion proteins can be used to affect the bioavailability of a NgR cognate ligand. Inhibition of the NgR ligand/NgR interaction may be useful therapeutically for both the treatment of proliferative and differentiative disorders, as well as modulating (e.g., promoting or inhibiting) cell survival. Moreover, the NgR-immunoglobulin fusion proteins of the invention can be used as immunogens to produce anti-NgR antibodies in a subject, to purify NgR ligands, and in screening assays to identify molecules that inhibit the interaction of NgR with NgR ligand.

A NgR chimeric or fusion protein of the invention can be produced by standard recombinant DNA techniques. For example, DNA fragments coding for the different polypeptide sequences are ligated together in-frame in accordance with conventional techniques, e.g., by employing blunt-ended or stagger-ended termini for ligation, restriction enzyme digestion to provide for appropriate termini, filling in of cohesive ends as appropriate, alkaline phosphatase treatment to avoid undesirable joining and enzymatic ligation. In another embodiment, the fusion gene can be synthesized by conventional techniques including automated DNA synthesizers. Alternatively, PCR amplification of gene fragments can be carried out using anchor primers that give rise to complementary overhangs between two consecutive gene fragments that can subsequently be annealed and reamplified to generate a chimeric gene sequence (see, for example, Ausubel et al. (Eds.) CURRENT PROTOCOLS IN MOLECULAR BIOLOGY, John Wiley & Sons, 1992). Moreover, many expression vectors are commercially available that already encode a fusion moiety (e.g., a GST polypeptide). A NgR-encoding nucleic acid can be cloned into such an expression vector such that the fusion moiety is linked in-frame to the NgR protein.

Variants resulting from expression in other vector systems are also contemplated.

Insertional variants also include fusion proteins wherein the amino terminus and/or the carboxy terminus of NgR is/are fused to another polypeptide.

In another aspect, the invention provides deletion variants wherein one or more amino acid residues in a NgR polypeptide are removed. Deletions can be effected at one or both termini of the NgR polypeptide, or with removal of one or more non-terminal amino acid residues of NgR. Deletion variants, therefore, include all fragments of a NgR polypeptide.

The invention also embraces polypeptide fragments of the sequence set forth in SEQ ID NO:2, 4 or 14 wherein the fragments maintain biological (e.g., ligand binding and/or intracellular signaling) immunological properties of a NgR polypeptide. Fragments comprising at least 4, 5, 10, 15, 20, 25, 30, 35, or 40 consecutive amino acids of SEQ ID NO:2, 4 or 14 are contemplated by the invention. Preferred polypeptide fragments display antigenic properties unique to, or specific for, human NgR and its allelic and species homologs. Fragments of the invention having the desired biological and immunological properties can be prepared by any of the methods well known and routinely practiced in the art.

In still another aspect, the invention provides substitution variants of NgR polypeptides. Substitution variants include those polypeptides wherein one or more amino acid residues of a NgR polypeptide are removed and replaced with alternative residues. In one aspect, the substitutions are conservative in nature; however, the invention embraces substitutions that are also non-conservative. Conservative substitutions for this purpose may be defined as set out in Tables 2, 3, or 4 below.

TABLE 1

| $X_{aa}$# (based on a NTLRRCT domain) | Column I (R1, R2, R3) | Column II (R2 + R3 only) |
|---|---|---|
| $X_1$ | G, R, M | |
| $X_2$ | A, D, C | |
| $X_3$ | V, T | |
| $X_4$ | N, P, S | |
| $X_5$ | E, A, S | |

TABLE 1-continued

| $X_{aa}$# (based on a NTLRRCT domain) | Column I (R1, R2, R3) | Column II (R2 + R3 only) |
|---|---|---|
| $X_6$ | nothing, K | nothing |
| $X_7$ | V, M, P | |
| $X_8$ | T, V | V |
| $X_9$ | Q, P | Q |
| $X_{10}$ | Q, A | Q |
| $X_{11}$ | Q, H, N | |
| $X_{12}$ | G, N | N |
| $X_{13}$ | L, F | F |
| $X_{14}$ | Q, A, S | |
| $X_{15}$ | A, S | |
| $X_{16}$ | V, I | |
| $X_{17}$ | V, T, E, L | |
| $X_{18}$ | S, G | |
| $X_{19}$ | L, I | |
| $X_{20}$ | A, E, V, P | |
| $X_{21}$ | A, S, D | |
| $X_{22}$ | S, T | |
| $X_{23}$ | Q, E | |
| $X_{24}$ | IVL | |
| $X_{25}$ | Q, H | Q |
| $X_{26}$ | N, G | N |
| $X_{27}$ | R, L | |
| $X_{28}$ | T, G, R, S | |
| $X_{29}$ | F, L, T, H | |
| $X_{30}$ | L, V | L |
| $X_{31}$ | Q, R, P | |
| $X_{32}$ | Q, P, A | P |
| $X_{33}$ | G, A | G |
| $X_{34}$ | H, T, S | |
| $X_{35}$ | S, G, R | |
| $X_{36}$ | P, S, A | |
| $X_{37}$ | C, nothing | nothing |
| $X_{38}$ | R, nothing | nothing |
| $X_{39}$ | A, N | |
| $X_{40}$ | M, L | |
| $X_{41}$ | V, L, T | |
| $X_{42}$ | T, I | T |
| $X_{43}$ | L, I | |
| $X_{44}$ | Y, F, H | |
| $X_{45}$ | N, V | N |
| $X_{46}$ | I, L | |
| $X_{47}$ | T, S, A | |
| $X_{48}$ | F, Y, T, R | |
| $X_{49}$ | A, H, Y, D | |
| $X_{50}$ | P, A | P |
| $X_{51}$ | N, S, G, A | |
| $X_{52}$ | T, A | T |
| $X_{53}$ | E, R, T | |
| $X_{54}$ | G, H | |
| $X_{55}$ | F, L | |
| $X_{56}$ | V, Q, H | |
| $X_{57}$ | H, A, L | |
| $X_{58}$ | E, Q | E |
| $X_{59}$ | G, S | G |
| $X_{60}$ | R, A | R |
| $X_{61}$ | Q, H | Q |
| $X_{62}$ | R, H | H |
| $X_{63}$ | T, S | |
| $X_{64}$ | L, V | L |
| $X_{65}$ | A, E, D | |
| $X_{66}$ | E, D, A | |
| $X_{67}$ | Q, H | Q |
| $X_{68}$ | V, E, G | |
| $X_{69}$ | K, R | |
| $X_{70}$ | H, Q | |
| $X_{71}$ | A, S, T | |
| $X_{72}$ | Y, H | |
| $X_{73}$ | Y, D | Y |
| $X_{74}$ | K, R | |
| $X_{75}$ | G, Q | |
| $X_{76}$ | S, Q | S |
| $X_{77}$ | A, S, E | |
| $X_{78}$ | P, G | P |
| $X_{79}$ | A, G, P | |
| $X_{80}$ | G, N | |

TABLE 1-continued

| $X_{aa}$# (based on a NTLRRCT domain) | Column I (R1, R2, R3) | Column II (R2 + R3 only) |
|---|---|---|
| $X_{81}$ | I, V, L | |
| $X_{82}$ | G, R | |
| $X_{83}$ | H, V, A | |
| $X_{84}$ | S, A | S |
| $X_{85}$ | D, E | |
| $X_{86}$ | H, S, A | |
| $X_{87}$ | I, L | |
| $X_{88}$ | E, L, Q | |
| $X_{89}$ | Y, H, A | |
| $X_{90}$ | Q, P | Q |
| $X_{91}$ | D, N | |
| $X_{92}$ | I, L, T | |
| $X_{93}$ | V, A, R | |
| $X_{94}$ | V, A, G | |
| $X_{95}$ | S, T | S |
| $X_{96}$ | K, R | |
| $X_{97}$ | L, I | L |
| $X_{98}$ | W, R, S | |
| $X_{99}$ | S, L | |
| $X_{100}$ | L, V | L |
| $X_{101}$ | G, T, P | |
| $X_{102}$ | Q, P, E | |
| $X_{103}$ | G, H, R | |
| $X_{104}$ | I, T, V, A | |
| $X_{105}$ | V, G, H | |
| $X_{106}$ | N, S | |
| $X_{107}$ | E, G, Q | |
| $X_{108}$ | Q, R | |
| $X_{109}$ | L, V | |
| $X_{110}$ | Q, A | |
| $X_{111}$ | W, G, H | |
| $X_{112}$ | H, R, P | |
| $X_{113}$ | K, A, H | |
| $X_{114}$ | H, R | |
| $X_{115}$ | D, G | |
| $X_{116}$ | H, R, S, G | |
| $X_{117}$ | T, M | |
| $X_{118}$ | T, I | |
| $X_{119}$ | F, Y | |
| $X_{120}$ | N, A | |
| $X_{121}$ | S, N | |
| $X_{122}$ | T, A, S | |
| $X_{123}$ | E, S, A | |
| $X_{124}$ | Q, P | |
| $X_{125}$ | G, T | |
| $X_{126}$ | D, E | D |
| $X_{127}$ | C, A | |
| $X_{128}$ | P, D | |
| $X_{129}$ | V, G, P, R | |
| $X_{130}$ | A, S | |
| $X_{131}$ | E, Q | Q |
| $X_{132}$ | F, Y | F |
| $X_{133}$ | G, A, D | |
| $X_{134}$ | A, P | |
| $X_{135}$ | D, A, V | |
| $X_{136}$ | G, D | |
| $X_{137}$ | A, E | |
| $X_{138}$ | S, P | |
| $X_{139}$ | E, A | |
| $X_{140}$ | L, F | |
| $X_{141}$ | R, Q | |
| $X_{142}$ | R, K | R |
| $X_{143}$ | R, K | R |
| $X_{144}$ | F, A | |
| $X_{145}$ | G, V | |
| $X_{146}$ | A, D, E | |
| $X_{147}$ | T, P | |
| $X_{148}$ | A, V, S | |
| $X_{149}$ | T, S, L | |
| $X_{150}$ | E, G, P, Q | |
| $X_{151}$ | L, E, R | |
| $X_{152}$ | R, L | R |
| $X_{153}$ | G, D | |
| $X_{154}$ | Q, H, A | |
| $X_{155}$ | Q, R | |

TABLE 1-continued

| $X_{aa}$# (based on a NTLRRCT domain) | Column I (R1, R2, R3) | Column II (R2 + R3 only) |
|---|---|---|
| $X_{156}$ | K, R | |
| $X_{157}$ | L, A, R | |
| $X_{158}$ | R, A | R |
| $X_{159}$ | V, A, E | |
| $X_{160}$ | E, A, N | |
| $X_{161}$ | F, L | F |
| $X_{162}$ | R, Q | |
| $X_{163}$ | N, A, G | |

Variant polypeptides include those wherein conservative substitutions have been introduced by modification of polynucleotides encoding polypeptides of the invention. Amino acids can be classified according to physical properties and contribution to secondary and tertiary protein structure. A conservative substitution is recognized in the art as a substitution of one amino acid for another amino acid that has similar properties. Exemplary conservative substitutions are set out in Table 2 (from WO 97/09433, page 10, published Mar. 13, 1997 (PCT/GB96/02197, filed Sep. 6, 1996), immediately below.

TABLE 2

Conservative Substitutions I

| SIDE CHAIN CHARACTERISTIC | AMINO ACID |
|---|---|
| Aliphatic | |
| Non-polar | G A P |
| | I L V |
| Polar - uncharged | C S T M |
| | N Q |
| Polar - charged | D E |
| | K R |
| Aromatic | H F W Y |
| Other | N Q D E |

Alternatively, conservative amino acids can be grouped as described in Lehninger, [BIOCHEMISTRY, Second Edition; Worth Publishers, Inc. NY, N.Y. (1975), pp. 71-77] as set out in Table 3, immediately below.

TABLE 3

Conservative Substitutions II

| SIDE CHAIN CHARACTERISTIC | AMINO ACID |
|---|---|
| Non-polar (hydrophobic) | |
| A. Aliphatic: | A L I V P |
| B. Aromatic: | F W |
| C. Sulfur-containing: | M |
| D. Boderline: | G |
| Uncharged-polar | |
| A. Hydroxyl: | S T Y |
| B. Amides: | N Q |
| C. Sylfhydryl: | C |
| D. Boderline: | G |
| Positively Charged (Basic): | K R H |
| Negatively Charged (Acidic): | D E |

As still another alternative, exemplary conservative substitutions are set out in Table 4, below.

TABLE 4

Conservative Substitutions III

| Original Residue | Exemplary Substitution |
|---|---|
| Ala (A) | Val, Leu, Ile |
| Arg (R) | Lys, Gln, Asn |
| Asn (N) | Gln, His, Lys, Arg |
| Asp (D) | Glu |
| Cys (C) | Ser |
| Gln (Q) | Asn |
| Glu (E) | Asp |
| His (H) | Asn, Gln, Lys, Arg |
| Ile (I) | Leu, Val, Met, Ala, Phe, |
| Leu (L) | Ile, Val, Met, Ala, Phe |
| Lys (K) | Arg, Gln, Asn |
| Met (M) | Leu, Phe, Ile |
| Phe (F) | Leu, Val, Ile, Ala |
| Pro (P) | Gly |
| Ser (S) | Thr |
| Thr (T) | Ser |
| Trp (W) | Tyr |
| Tyr (Y) | Trp, Phe, Thr, Ser |
| Val (V) | Ile, Leu, Met, Phe, Ala |

In addition, amino acid residues that are conserved among family members of the NgR proteins of the present invention, as indicated by the alignment presented herein, are also predicted to be particularly unamenable to alteration For example, NgR proteins of the present invention can contain at least one domain that is a typically conserved region in NgRs. Examples of these conserved domains include, e.g., leucine-rich repeat domain Amino acid residues that are not conserved or are only semi-conserved among members of the NgR proteins may be readily amenable to alteration.

Full-length NgRs have an LRR region characterized by the amino acid consensus sequence shown in SEQ ID NO:19. At least some full-length NgRs also include a CT signaling (CTS) domain and a GPI domain.

The NgR domain designations used herein are defined as follows:

| Domain | hNgR1 SEQ ID: 5 | mNgR1 SEQ ID NO: 17 | hNgR2 SEQ ID: 2 | hNgR3 SEQ ID: 14 | mNgR3 SEQ ID: 4 |
|---|---|---|---|---|---|
| Signal Seq. | 1-26 | 1-26 | 1-30 | — | 1-40 |
| LRRNT | 27-56 | 27-56 | 31-59 | — | 41-69 |
| LRR1 | 57-81 | 57-81 | 60-82 | 5-27 | 70-92 |
| LRR2 | 82-105 | 82-105 | 83-106 | 28-51 | 93-106 |
| LRR3 | 106-130 | 106-130 | 107-131 | 52-76 | 106-141 |
| LRR4 | 131-154 | 131-154 | 132-155 | 77-100 | 142-165 |
| LRR5 | 155-178 | 155-178 | 156-179 | 101-124 | 166-189 |
| LRR6 | 179-202 | 179-202 | 180-203 | 125-148 | 190-213 |
| LRR7 | 203-226 | 203-226 | 204-227 | 149-172 | 214-237 |
| LRR8 | 227-250 | 227-250 | 228-251 | 173-196 | 238-261 |
| LRRCT | 260-309 | 260-309 | 261-310 | 206-255 | 271-320 |
| CTS (CT Signaling) | 310-445 | 310-445 | 311-395 | 256-396 | 321-438 |
| GPI | 446-473 | 456-473 | 396-420 | 370-392 | 439-462 |

In some embodiments of the invention, the above domains are modified. Modification can be in a manner that preserves domain functionality. Modification can include addition, deletion or substitution of certain amino acids. Exemplary modifications include conservative amino acid substitutions. Preferably such substitutions number 20 or fewer per 100 residues. More preferably, such substitutions number 10 or fewer per 100 residues. Further exemplary modifications include addition of flanking sequences of up to five amino acids at the N terminus and/or C terminus of one or more of the domains.

In some embodiments, the isolated nucleic acid molecule encodes a polypeptide at least about 70%, 80%, 90%, 95%, 98%, and most preferably at least about 99% homologous to SEQ ID NO:2, 4 or 14.

Mutations can be introduced into SEQ ID NOS:1, 3 or 13 by standard techniques, e.g., site-directed mutagenesis and PCR-mediated mutagenesis. Conservative amino acid substitutions can be made at one or more amino acid residues predicted to be non-essential. Alternatively, mutations can be introduced randomly along a NgR coding sequence. This can be accomplished, e.g., by saturation mutagenesis. The resulting mutants can be screened for NgR biological activity. Biological activities of NgR may include but are not limited to: (1) protein:protein interactions, e.g., with other NgRs or other cell-surface proteins involved in Nogo-related signaling; (2) complex formation with a NgR ligand; (3) binding to an anti-NgR antibody.

It should be understood that the definition of polypeptides of the invention is intended to include polypeptides bearing modifications other than insertion, deletion, or substitution of amino acid residues. By way of example, the modifications may be covalent in nature, and include for example, chemical bonding with polymers, lipids, other organic and inorganic moieties. Such derivatives may be prepared to increase circulating half-life of a polypeptide, or may be designed to improve the targeting capacity of the polypeptide for desired cells, tissues or organs Similarly, the invention further embraces NgR polypeptides that have been covalently modified to include one or more water-soluble polymer attachments such as polyethylene glycol, polyoxyethylene glycol or polypropylene glycol. Variants that display ligand binding properties of native NgR and are expressed at higher levels, as well as variants that provide for constitutively active receptors, are particularly useful in assays of the invention; the variants are also useful in providing cellular, tissue and animal models of diseases/conditions characterized by aberrant NgR activity.

Chemically modified NgR polypeptide compositions in which the NgR polypeptide is linked to a polymer are included within the scope of the present invention. The polymer may be water soluble to prevent precipitation of the protein in an aqueous environment, such as a physiological environment. Suitable water-soluble polymers may be selected from the group consisting of, for example, polyethylene glycol (PEG), monomethoxypolyethylene glycol, dextran, cellulose, or other carbohydrate based polymers, poly-(N-vinyl pyrrolidone) polyethylene glycol, polypropylene glycol homopolymers, a polypropylene oxide/ethylene oxide copolymer polyoxyethylated polyols (e.g. glycerol) and polyvinyl alcohol. The selected polymer is usually modified to have a single reactive group, such as an active ester for acylation or an aldehyde for alkylation, so that the degree of polymerization may be controlled. Polymers may be of any molecular weight, and may be branched or unbranched, and mixtures of such polymers may also be used. When the chemically modified NgR polymer is destined for therapeutic use, pharmaceutically acceptable polymers will be selected for use.

When the polymer is to be modified by an acylation reaction, the polymer should have a single reactive ester group. Alternatively, if the polymer is to be modified by reductive alkylation, the polymer should have a single reactive aldehyde group. A preferred reactive aldehyde is polyethylene glycol propionaldehyde, which is water stable, or mono Cl—ClO alkoxy or aryloxy derivatives thereof (see U.S. Pat. No. 5,252,714, incorporated by reference herein in its entirety).

Pegylation of NgR polypeptides may be carried out by any of the pegylation reactions known in the art, as described, for example, in the following references: *Focus on Growth Factors* 3, 4-10 (1992); EP 0 154 316; and EP 0 401 384 (each of which is incorporated by reference herein in its entirety). Preferably, the pegylation is carried out via an acylation reaction or an alkylation reaction with a reactive polyethylene glycol molecule (or an analogous reactive water-soluble polymer). A preferred water-soluble polymer for pegylation of polypeptides such as NgR is polyethylene glycol (PEG). As used herein, "polyethylene glycol" is meant to encompass any of the forms of PEG that have been used to derivatize other proteins, such as mono (Cl—ClO) alkoxy- or aryloxy-polyethylene glycol.

Chemical derivatization of NgR polypeptides may be performed under any suitable conditions used to react a biologically active substance with an activated polymer molecule. Methods for preparing pegylated NgR polypeptides will generally comprise the steps of (a) reacting the polypeptide with polyethylene glycol, such as a reactive ester or aldehyde derivative of PEG, under conditions whereby NgR polypeptide becomes attached to one or more PEG groups, and (b) obtaining the reaction products. It will be apparent to one of ordinary skill in the art to select the optimal reaction conditions or the acylation reactions based on known parameters and the desired result.

Pegylated and other polymer:NgR polypeptides may generally be used to treat conditions that may be alleviated or modulated by administration of the NgR polypeptides described herein. However, the chemically-derivatized polymer:NgR polypeptide molecules disclosed herein may have additional activities, enhanced or reduced biological activity, or other characteristics, such as increased or decreased half-life, as compared to the nonderivatized molecules. The NgR polypeptides, fragments thereof, variants and derivatives, may be employed alone, together, or in combination with other pharmaceutical compositions. The cytokines, growth factors, antibiotics, antiinflammatories and/or chemotherapeutic agents as is appropriate for the indication being treated.

The present invention provides compositions comprising purified polypeptides of the invention. Preferred compositions comprise, in addition to the polypeptide of the invention, a pharmaceutically acceptable (i.e., sterile and non-toxic) liquid, semisolid, or solid diluent that serves as a pharmaceutical vehicle, excipient or medium. Any diluent known in the art may be used; Exemplary diluents include, but are not limited to, water, saline solutions, polyoxyethylene sorbitan monolaurate, magnesium stearate, methyl- and propylhydroxybenzoate, talc, alginates, starches, lactose, sucrose, dextrose, sorbitol, mannitol, glycerol, calcium phosphate, mineral oil and cocoa butter.

Variants that display ligand binding properties of native NgR and are expressed at higher levels, as well as variants that provide for constitutively active receptors, are particularly useful in assays of the invention; the variants are also useful in assays of the invention and in providing cellular, tissue and animal models of diseases/conditions characterized by aberrant NgR activity.

With the knowledge of the nucleotide sequence information disclosed in the present invention, one skilled in the art can identify and obtain nucleotide sequences which encode NgR from different sources (i.e., different tissues or different organisms) through a variety of means well known to the skilled artisan and as disclosed by, for example, Sambrook et al., MOLECULAR CLONING: A LABORATORY MANUAL, Second Edition, Cold Spring Harbor Press, Cold Spring Harbor, N.Y. (1989), which is incorporated herein by reference in its entirety.

For example, DNA that encodes NgR may be obtained by screening of mRNA, cDNA, or genomic DNA with oligonucleotide probes generated from the NgR gene sequence information provided herein. Probes may be labeled with a detectable group, such as a fluorescent group, a radioactive atom or a chemiluminescent group in accordance with procedures known to the skilled artisan and used in conventional hybridization assays, as described by, for example, Sambrook et al. (1989) above.

A nucleic acid molecule comprising any of the NgR nucleotide sequences described above can alternatively be synthesized by use of the polymerase chain reaction (PCR) procedure, with the PCR oligonucleotide primers produced from the nucleotide sequences provided herein. See U.S. Pat. No. 4,683,195 to Mullis et al. and U.S. Pat. No. 4,683,202 to Mullis. The PCR reaction provides a method for selectively increasing the concentration of a particular nucleic acid sequence even when that sequence has not been previously purified and is present only in a single copy in a particular sample. The method can be used to amplify either single- or double-stranded DNA. The essence of the method involves the use of two oligonucleotide probes to serve as primers for the template-dependent, polymerase-mediated replication of a desired nucleic acid molecule.

A wide variety of alternative cloning and in vitro amplification methodologies are well known to those skilled in the art. Examples of these techniques are found in, for example, Berger et al., *Guide to Molecular Cloning Techniques*, METHODS IN ENZYMOLOGY 152 Academic Press, San Diego, Calif., which is incorporated herein by reference in its entirety.

The nucleic acid molecules of the present invention, and fragments derived therefrom, are useful for screening for restriction fragment length polymorphism (RFLP) associated with certain disorders, as well as for genetic mapping.

Antibodies

Also comprehended by the present invention are antibodies (e.g., monoclonal and polyclonal antibodies, single chain antibodies, chimeric antibodies, bifunctional/bispecific antibodies, humanized antibodies, human antibodies, and complementary determining region (CDR)-grafted antibodies, including compounds which include CDR sequences which specifically recognize a polypeptide of the invention) specific for NgR or fragments thereof. Preferred antibodies of the invention are human antibodies which are produced and identified according to methods described in WO93/11236, published Jun. 20, 1993, which is incorporated herein by reference in its entirety. Antibody fragments, including Fab, Fab', F(ab')$_2$, and F$_v$, are also provided by the invention. The term "specific for," when used to describe antibodies of the invention, indicates that the variable regions of the antibodies of the invention recognize and bind NgR polypeptides exclusively (i.e., are able to distinguish NgR polypeptides from other known NgR polypeptides by virtue of measurable differences in binding affinity, despite the possible existence of localized sequence identity, homology, or similarity between NgR and such polypeptides).

The antigenic peptide of NgR comprises at least 8 amino acid residues of the amino acid sequence shown in SEQ ID NO:2, 4 or 14 and encompasses an epitope of NgR such that an antibody raised against the peptide forms a specific immune complex with NgR. Preferably, the antigenic peptide comprises at least 10 amino acid residues, more preferably at least 15 amino acid residues, even more preferably at least 20 amino acid residues, and most preferably at least 30 amino acid residues. Preferred epitopes encompassed by the antigenic peptide are regions of NgR that are located on the surface of the protein, e.g., hydrophilic regions.

It will be understood that specific antibodies may also interact with other proteins (for example, *S. aureus* protein A or other antibodies in ELISA techniques) through interactions with sequences outside the variable region of the antibodies, and, in particular, in the constant region of the molecule. Screening assays to determine binding specificity of an antibody of the invention are well known and routinely practiced in the art. For a comprehensive discussion of such assays, see Harlow et al. in ANTIBODIES: A LABORATORY MANUAL, Cold Spring Harbor Laboratory Press; Cold Spring Harbor, N.Y. (1988), Chapter 6. Antibodies that recognize and bind fragments of the NgR polypeptides of the invention are also contemplated, provided that the antibodies are specific for NgR polypeptides. Antibodies of the invention can be produced using any method well known and routinely practiced in the art.

For the production of polyclonal antibodies, various suitable host animals (e.g., rabbit, goat, mouse or other mammal) may be immunized by injection with the native protein, or a synthetic variant thereof, or a derivative of the foregoing. An appropriate immunogenic preparation can contain, for example, recombinantly expressed NgR protein or a chemically synthesized NgR polypeptide. The preparation can further include an adjuvant. Various adjuvants used to increase the immunological response include, but are not limited to, Freund's (complete and incomplete), mineral gels (e.g., aluminum hydroxide), surface active substances (e.g., lysolecithin, pluronic polyols, polyanions, peptides, oil emulsions, dinitrophenol, etc.), human adjuvants such as Bacille Calmette-Guerin and *Corynebacterium parvum* or similar immunostimulatory agents. If desired, the antibody molecules directed against NgR can be isolated from the mammal (e.g., from the blood) and further purified by well known techniques, such as protein A chromatography to obtain the IgG fraction.

The term "monoclonal antibody" or "monoclonal antibody composition," as used herein, refers to a population of antibody molecules that contain only one species of an antigen binding site capable of immunoreacting with a particular epitope of NgR. A monoclonal antibody composition thus typically displays a single binding affinity for a particular NgR protein with which it immunoreacts. For preparation of monoclonal antibodies directed towards a particular NgR protein, or derivatives, fragments, analogs or homologs thereof, any technique that provides for the production of antibody molecules by continuous cell fine culture may be utilized. Such techniques include, but are not limited to, the hybridoma technique (see Kohler and Milstein (1975) *Nature* 256, 495-497); the trioma technique; the human B-cell hybridoma technique (see Kozbor et al., (1983) *Immunol. Today* 4, 72) and the EBV hybridoma technique to produce human monoclonal antibodies (see Cole et al., (1985) in MONOCLONAL ANTIBODIES AND CANCER THERAPY, Alan R. Liss, Inc., pp. 77-96). Human monoclonal antibodies may be utilized in the practice of the present invention and may be produced by using human hybridomas (see Cote et al., (1983) *Proc. Natl. Acad. Sci. USA* 80, 2026-2030) or by transforming human B-cells with Epstein Barr Virus in vitro (see Cole et al., (1985), above).

According to the invention, techniques can be adapted for the production of single-chain antibodies specific to a NgR protein (see e.g., U.S. Pat. No. 4,946,778). In addition, methods can be adapted for the construction of Fab expression libraries (see e.g., Huse et al., (1989) *Science* 246, 1275-1281) to allow rapid and effective identification of monoclonal $F_{ab}$ fragments with the desired specificity for a NgR protein or derivatives, fragments, analogs or homologs thereof. Non-human antibodies can be "humanized" by techniques well known in the art. See e.g., U.S. Pat. No. 5,225,539. In one method, the non-human CDRs are inserted into a human antibody or consensus antibody framework sequence. Further changes can then be introduced into the antibody framework to modulate affinity or immunogenicity. Antibody fragments that contain the idiotypes to a NgR protein may be produced by techniques known in the art including, but not limited to: (i) an $F(ab')_2$ fragment produced by pepsin digestion of an antibody molecule; (ii) an Fab fragment generated by reducing the disulfide bridges of an $F(ab)_2$ fragment; (iii) an Fab fragment generated by the treatment of the antibody molecule with papain and a reducing agent and (iv) $F_v$ fragments.

Additionally, recombinant anti-NgR antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in PCT International Application No. PCT/US86/02269; European Patent Application No. 184,187; European Patent Application No. 171,496; European Patent Application No. 173,494; PCT International Publication No. WO 86/01533; U.S. Pat. No. 4,816,567; European Patent Application No. 125,023; Better et al., (1988) *Science* 240, 1041-1043; Liu et al., (1987) *Proc. Natl. Acad. Sci. USA* 84, 3439-3443; Liu et al., (1987) *J. Immunol.* 139, 3521-3526; Sun et al., (1987) *Proc. Natl. Acad. Sci. USA* 84, 214-218; Nishimura et al., (1987) *Cancer Res.* 47, 999-1005; Wood et al., (1985) *Nature* 314, 446-449; Shaw et al., (1988) *J. Natl. Cancer Inst.* 80, 1553-1559); Morrison (1985) *Science* 229, 1202-1207; Oi et al., (1986) *BioTechniques* 4, 214; U.S. Pat. No. 5,225,539; Jones et al., (1986) *Nature* 321, 552-525; Verhoeyan et al., (1988) *Science* 239, 1534; and Beidler et al., (1988) *J. Immunol* 141, 4053-4060.

In a preferred embodiment of the invention a portion of a NgR is joined to an Fc portion of an antibody to form a NgR/Fc fusion protein. Preferably, the Ig fusion protein is soluble. The NgR/Fc fusion protein may be formed by recombinant techniques as described above. In one embodiment, a portion of a NgR including the entire amino acid sequence of NgR except the C-terminal hydrophobic region is fused to an Fc portion of an antibody. In preferred embodiments, the NgR is a human NgR and the Fc is also human. More preferably, the human Fc portion is derived from an IgG antibody. In other embodiments, the N-terminal signal sequence is omitted. Such antibodies are useful in binding Nogo to prevent Nogo signaling through the NgR.

In one embodiment, methods for the screening of antibodies that possess the desired specificity include, but are not limited to, enzyme-linked immunosorbent assay (ELISA) and other immunologically-mediated techniques known within the art. In a specific embodiment, selection of antibodies that are specific to a particular domain of a NgR protein is facilitated by generation of hybridomas that bind to the fragment of a NgR protein possessing such a domain. Antibodies that are specific for one or more domains within a NgR protein, e.g., domains spanning the above-identified conserved regions of NgRs, or derivatives, fragments analogs or homologs thereof, are also provided herein.

Anti-NgR antibodies may be used in methods known within the art relating to the localization and/or quantitation of a NgR protein (e.g., for use in measuring levels of the NgR protein within appropriate physiological samples, for use in diagnostic methods, for use in imaging the protein, and the like). In a given embodiment, antibodies for NgR proteins, or derivatives, fragments analogs or homologs thereof, that contain the antibody derived binding domain, are utilized as pharmacologically-active compounds [hereinafter "Therapeutics"].

An anti-NgR antibody (e.g., monoclonal antibody) can be used to isolate NgR by standard techniques, such as affinity chromatography or immunoprecipitation. An anti-NgR antibody can facilitate the purification of natural NgR from cells and of recombinantly produced NgR expressed in host cells. Moreover, an anti-NgR antibody can be used to detect NgR protein (e.g., in a cellular lysate or cell supernatant) in order to evaluate the abundance and pattern of expression of the NgR protein. Anti-NgR antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin and aequorin, and examples of suitable radioactive material include $^{125}I$, $^{131}I$, $^{35}S$ or $^{3}H$.

Another aspect of the present invention is directed to methods of inducing an immune response in a mammal against a polypeptide of the invention by administering to the mammal an amount of the polypeptide sufficient to induce an immune response. The amount will be dependent on the animal species, size of the animal, and the like but can be determined by those skilled in the art.

Another aspect of the invention is directed to anti-idiotypic antibodies and anti-anti-idiotypic antibodies. An anti-idiotypic antibody is an antibody that recognizes determinants of another antibody (a target antibody). Generally, the anti-idiotypic antibody recognizes determinants of the antigen-binding site of the target antibody. Typically, the target antibody is a monoclonal antibody. An anti-idiotypic antibody is generally prepared by immunizing an animal (particularly, mice) of the same species and genetic type as the source of the target monoclonal antibody, with the target monoclonal antibody. The immunized animal mounts an immune response to the idiotypic determinants of the target monoclonal antibody and produces antibodies against the idiotypic determinants of the target monoclonal antibody. Antibody-producing cells, such as splenic cells, of the immunized animal may be used to generate anti-idiotypic monoclonal antibodies. Furthermore, an anti-idiotypic antibody may also be used to immunize animals to produce anti-anti-idiotypic antibodies. These immunized animals may be used to generate anti-anti-idiotypic monoclonal antibodies using standard techniques. The anti-anti-idiotypic antibodies may bind to the same epitope as the original, target monoclonal antibody used to prepare the anti-idiotypic antibody. The anti-anti-idiotypic antibodies represent other monoclonal antibodies with the same antigen specificity as the original target monoclonal antibody.

If the binding of the anti-idiotypic antibody with the target antibody is inhibited by the relevant antigen of the target antibody, and if the anti-idiotypic antibody induces an antibody response with the same specificity as the target antibody, it mimics the antigen of the target antibody. Such an anti-idiotypic antibody is an "internal image anti-idiotype" and is capable of inducing an antibody response as if it were the original antigen. (Bona and Kohler (1984) ANTI-IDIOTYPIC ANTIBODIES AND INTERNAL IMAGE, IN MONOCLONAL AND ANTI-IDIOTYPIC ANTIBODIES: PROBES FOR RECEPTOR STRUCTURE AND FUNCTION, Venter J. C. et al. (Eds), Alan R. Liss, New York, N.Y., pp 141-149, 1984). Vaccines incorporating internal image anti-idiotype antibodies have been shown to induce protective responses against viruses, bacteria, and parasites (Kennedy et al., (1986) 232, 220-223; 1047; McNamara et al., (1985) *Science* 226, 1325-1326). Internal image anti-idiotypic antibodies have also been shown to induce immunity to tumor related antigens (Raychauhuri et al., (1986) *J. Immunol.* 137, 1743-1749; Raychauhuri et al., (1987) *J. Immunol.* 139, 3902-3910; Bhattacharya-Chatterjee et al, (1987) *J. Immunol.* 139, 1354-1360; Bhattacharya-Chatterjee et al., (1988) *J. Immunol.* 141, 1398-1403; Herlyn et al. (1989) *Intern. Rev. Immunol.* 4, 347-357; Chen et al. (1990) *Cell Imm. Immunother. Cancer* 351-359; Herlyn et al., (1991) in vivo 5, 615-624; Furuya et al. (1992) *AntiCancer Res.* 12, 27-32; Mittelman, A. et al. (1992) *Proc. Natl. Acad. Sci., USA* 89, 466-470; Durrant et al., (1994) *Cancer Res.* 54, 4837-4840; Mittelman et al. (1994) *Cancer Res.* 54, 415-421; Schmitt et al. (1994) *Hybridoma* 13, 389-396; Chakrobarty et al. (1995) *J. Immunother.* 18, 95-103; Chakrobarty et al. (1995) *Cancer Res.* 55, 1525-1530; Foon, K. A. et al. (1995) *Clin. Cancer Res.* 1, 1205-1294; Herlyn et al. (1995) Hybridoma 14, 159-166; Sclebusch et al. (1995) *Hybridoma* 14, 167-174; Herlyn et al. (1996) *Cancer Immunol Immunother.* 43, 65-76).

Anti-idiotypic antibodies for NgR may be prepared, for example, by immunizing an animal, such as a mouse, with a immunogenic amount of a composition comprising NgR2 (SEQ ID NO:2), NgR3 (SEQ ID NOs:4 or 14), or immunogenic portion thereof, containing at least one antigenic epitope of NgR. The composition may also contain a suitable adjuvant, and any carrier necessary to provide immunogenicity. Monoclonal antibodies recognizing NgR may be prepared from the cells of the immunized animal as described above. A monoclonal antibody recognizing an epitope of NgR is then selected and used to prepare a composition comprising an immunogenic amount of the anti-NgR monoclonal antibody. Typically, a 25 to 200 μg dose of purified anti-NgR monoclonal would be sufficient in a suitable adjuvant.

Animals may be immunized 2-6 times at 14 to 30 day intervals between doses. Typically, animals are immunized by any suitable route of administration, such as intraperitoneal, subcutaneous, intravenous or a combination of these. Anti-idiotypic antibody production may be monitored during the immunization period using standard immunoassay methods. Animals with suitable titers of antibodies reactive with the target monoclonal antibodies may be reimmunized with the monoclonal antibody used as the immunogen three days before harvesting the antibody producing cells. Preferably, spleen cells are used, although other antibody producing cells may be selected. Antibody-producing cells are harvested and fused with myeloma cells to produce *Hybridomas*, as described above, and suitable anti-idiotypic antibody-producing cells are selected.

Anti-anti-idiotypic antibodies are produced by another round of immunization and *Hybridoma* production by using the anti-idiotypic monoclonal antibody as the immunogen.

Antibodies of the invention are useful for, e.g., therapeutic purposes (by modulating activity of NgR), diagnostic purposes to detect or quantitate NgR, and purification of NgR. Therefore, kits comprising an antibody of the invention for any of the purposes described herein are also comprehended.

Kits

The present invention is also directed to kits, including pharmaceutical kits. The kits can comprise any of the nucleic acid molecules described above, any of the polypeptides described above, or any antibody which binds to a polypeptide of the invention as described above, as well appropriate controls, such as positive and/or negative controls. The kit preferably comprises additional components, such as, for example, instructions, solid support, reagents helpful for quantification, and the like. For example, the kit can comprise: a labeled compound or agent capable of detecting NgR protein or mRNA in a biological sample; means for determining the amount of NgR in the sample; and means for comparing the amount of NgR in the sample with a standard. The compound or agent can be packaged in a suitable container.

Screening Assays

The DNA and amino acid sequence information provided by the present invention also makes possible identification of binding partner compounds with which a NgR polypeptide or polynucleotide will interact. Methods to identify binding partner compounds include solution assays, in vitro assays wherein NgR polypeptides are immobilized and cell-based assays. Identification of binding partner compounds of NgR polypeptides provides candidates for therapeutic or prophylactic intervention in pathologies associated with NgR normal and aberrant biological activity.

The invention also provides a method (also referred to herein as a "screening assay") for identifying modulators, i.e., candidate or test compounds or agents (e.g., peptides, peptidomimetics, small molecules (e.g., molecules of less than 1,000 Daltons) or other drugs) that bind to NgR proteins or have a stimulatory or inhibitory effect on, for example, NgR expression or NgR activity.

In one embodiment, the invention provides assays for screening candidate or test compounds which bind to or modulate the activity of a NgR protein or polypeptide or biologically active portion thereof. The test compounds of the present invention can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam (1997) *Anticancer Drug Des.* 12, 145).

Examples of methods for the synthesis of molecular libraries can be found in the art, for example in: DeWitt et al., (1993) *Proc. Natl. Acad. Sci. USA* 90, 6909; Erb et al., (1994) *Proc. Natl. Acad. Sci. USA* 91, 11422; Zuckermann et al. (1994) *J. Med. Chem* 37, 2678; Cho et al., (1993) *Science* 261, 1303; Carrell et al., (1994) *Angew Chem. Int. Ed. Engl.* 33, 2059; Carell et al., (1994) *Angew Chem. Int. Ed. Engl.* 33, 2061; and Gallop et al., (1994) *J. Med. Chem* 37, 1233.

Libraries of compounds may be presented in solution (e.g., Houghten (1992) *BioTechniques* 13, 412-421), or on beads (Lam (1991) *Nature* 354, 82-84), on chips (Fodor (1993) *Nature* 364, 555-556), bacteria (Ladner, U.S. Pat. No. 5,223, 409), spores (Ladner, above), plasmids (Cull et al. (1992) *Proc. Natl. Acad Sci USA* 89, 1865-1869) or on phage (Scott and Smith (1990) *Science* 249, 386-390; Devlin (1990) *Science* 249, 404-406; Cwirla et al. (1990) *Proc. Natl. Acad. Sci. USA* 87, 6378-6382; Felici (1991) *J. Mol. Biol.* 222, 301-310; Ladner, above).

1. Cell-Based Assays

The invention also provides cell-based assays to identify binding partner compounds of a NgR polypeptide. In one embodiment, the invention provides a method comprising the steps of contacting a NgR polypeptide expressed on the surface of a cell with a candidate binding partner compound and detecting binding of the candidate binding partner compound to the NgR polypeptide. In another embodiment, an assay is a cell-based assay comprising contacting a cell expressing a membrane-bound form of NgR protein, or a biologically active portion thereof, on the cell surface with a test compound and determining the ability of the test compound to modulate (e.g., stimulate or inhibit) the activity of the NgR protein or biologically active portion thereof.

In one embodiment, an assay is a cell-based assay in which a cell which expresses a membrane-bound form of NgR protein, or a biologically active portion thereof, on the cell surface is contacted with a test compound and the ability of the test compound to bind to a NgR protein determined. The cell, for example, can be of mammalian origin or a yeast cell. Determining the ability of the test compound to bind to the NgR protein can be accomplished, for example, by coupling the test compound with a radioisotope or enzymatic label such that binding of the test compound to the NgR protein or biologically active portion thereof can be determined by detecting the labeled compound in a complex. For example, test compounds can be labeled with $^{125}I$, $^{35}S$, $^{14}C$, or $^{3}H$, either directly or indirectly, and the radioisotope detected by direct counting of radioemission or by scintillation counting. Alternatively, test compounds can be enzymatically labeled with, for example, horseradish peroxidase, alkaline phosphatase or luciferase, and the enzymatic label detected by determination of conversion of an appropriate substrate to product. In one embodiment, the assay comprises contacting a cell which expresses a membrane-bound form of NgR protein or a biologically active portion thereof on the cell surface with a known compound which binds NgR to form an assay mixture, contacting the assay mixture with a test compound, and determining the ability of the test compound to interact with a NgR protein, wherein determining the ability of the test compound to interact with a NgR protein comprises determining the ability of the test compound to preferentially bind to NgR or a biologically active portion thereof as compared to the known compound.

Determining the ability of the test compound to modulate the activity of NgR or a biologically active portion thereof can be accomplished, for example, by determining the ability of the NgR protein to bind to or interact with a NgR target molecule. As used herein, a "target molecule" is a molecule with which a NgR protein binds or interacts in nature, for example, a molecule on the surface of a cell which expresses a NgR protein, a molecule on the surface of a second cell, a molecule in the extracellular milieu, a molecule associated with the internal surface of a cell membrane or a cytoplasmic molecule. A NgR target molecule can be a non-NgR molecule or a NgR protein or polypeptide of the present invention. In one embodiment, a NgR target molecule is a component of a signal transduction pathway that facilitates transduction of an extracellular signal (e.g., a signal generated by binding of a compound to a membrane-bound NgR molecule) through the cell membrane and into the cell. The target, for example, can be a second intercellular protein that has catalytic activity or a protein that facilitates the association of downstream signaling molecules with NgR In a preferred embodiment, the detection comprises detecting a calcium flux or other physiological event in the cell caused by the binding of the molecule.

Specific binding molecules, including natural ligands and synthetic compounds, can be identified or developed using isolated or recombinant NgR products, NgR variants, or preferably, cells expressing such products. Binding partners are useful for purifying NgR products and detection or quantification of NgR products in fluid and tissue samples using known immunological procedures. Binding molecules are also manifestly useful in modulating (i.e., blocking, inhibiting or stimulating) biological activities of NgR, especially those activities involved in signal transduction.

2. Cell-Free Assays (a) Direct Binding:

The invention includes several assay systems for identifying NgR binding partners. In solution assays, methods of the invention comprise the steps of (a) contacting a NgR polypeptide with one or more candidate binding partner compounds and (b) identifying the compounds that bind to the NgR polypeptide. Identification of the compounds that bind the NgR polypeptide can be achieved by isolating the NgR polypeptide/binding partner complex and separating the binding partner compound from the NgR polypeptide. An additional step of characterizing the physical, biological and/or biochemical properties of the binding partner compound is also comprehended in another embodiment of the invention. In one aspect, the NgR polypeptide/binding partner complex is isolated using an antibody immunospecific for either the NgR polypeptide or the candidate binding partner compound.

In still other embodiments, either the NgR polypeptide or the candidate binding partner compound comprises a label or tag that facilitates its isolation, and methods of the invention to identify binding partner compounds include a step of isolating the NgR polypeptide/binding partner complex through interaction with the label or tag. An exemplary tag of this type is a poly-histidine sequence, generally around six histidine residues, that permits isolation of a compound so labeled using nickel chelation. Other labels and tags, such as the FLAG® tag (Eastman Kodak, Rochester, N.Y.), well known and routinely used in the art, are embraced by the invention.

(b) Immobilized NgR

In one variation of an in vitro assay, the invention provides a method comprising the steps of (a) contacting an immobilized NgR polypeptide, or a biologically active fragment thereof with a candidate binding partner compound and (b) detecting binding of the candidate compound to the NgR polypeptide. In an alternative embodiment, the candidate binding partner compound is immobilized and binding of NgR is detected. Immobilization is accomplished using any of the methods well known in the art, including covalent bonding to a support, a bead or a chromatographic resin, as well as non-covalent, high affinity interactions such as antibody binding, or use of streptavidin/biotin binding wherein the immobilized compound includes a biotin moiety. Binding of a test compound to NgR, or interaction of NgR with a target molecule in the presence and absence of a candidate compound, can be accomplished in any vessel suitable for containing the reactants. Examples of such vessels include microtiter plates, test tubes, and micro-centrifuge tubes. In one embodiment, a fusion protein can be provided that adds a domain that allows one or both of the proteins to be bound to a matrix. For example, and not by way of limitation, GST-NGR fusion proteins or GST-target fusion proteins can be adsorbed onto glutathione sepharose beads (Sigma Chemical, St. Louis, Mo.) or glutathione derivatized microtiter plates, that are then combined with the test compound or the test compound and either the non-adsorbed target protein or NgR protein, and the mixture is incubated under conditions conducive to complex formation (e.g., at physiological conditions for salt and pH). Following incubation, the beads or microtiter plate wells are washed to remove any unbound components, the matrix immobilized in the case of beads, and the complexes determined either directly or indirectly, for example, as described above. Alternatively, the complexes can be dissociated from the matrix, and the level of NgR binding or activity determined using standard techniques.

Other techniques for immobilizing proteins on matrices can also be used in the screening assays of the invention. For example, either NgR or its target molecule can be immobilized utilizing conjugation of biotin and streptavidin. Biotinylated NgR or target molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with NgR or target molecules, but which do not interfere with binding of the NgR protein to its target molecule, can be derivatized to the wells of the plate, and unbound target or NgR trapped in the wells by antibody conjugation. Methods for detecting such complexes, in addition to those described above for the GST-immobilized complexes, include immunodetection of complexes using antibodies reactive with the NgR or target molecule, as well as enzyme-linked assays that rely on detecting an enzymatic activity associated with the NgR or target molecule.

Detection of binding can be accomplished (i) using a radioactive label on the compound that is not immobilized, (ii) using of a fluorescent label on the non-immobilized compound, (iii) using an antibody immunospecific for the non-immobilized compound, (iv) using a label on the non-immobilized compound that excites a fluorescent support to which the immobilized compound is attached, (v) determining the activity of the NgR, as well as other techniques well known and routinely practiced in the art.

Determining the activity of the target molecule, for example, may be accomplished by detecting induction of a cellular second messenger of the target (i.e. intracellular $Ca^{2+}$, diacylglycerol, $IP_3$, etc.), detecting catalytic/enzymatic activity of the target an appropriate substrate, detecting the induction of a reporter gene (comprising a NgR-responsive regulatory element operatively linked to a nucleic acid encoding a detectable marker, e.g., luciferase), or detecting a cellular response, for example, cell survival, cellular differentiation, or cell proliferation.

(c) Competition Experiments

In yet another embodiment, the assay comprises contacting the NgR protein or biologically active portion thereof with a known compound which binds NgR to form an assay mixture, contacting the assay mixture with a test compound, and determining the ability of the test compound to interact with a NgR protein, wherein determining the ability of the test compound to interact with a NgR protein comprises determining the ability of the test compound to preferentially bind to NgR or biologically active portion thereof as compared to the known compound.

In yet another embodiment, the cell-free assay comprises contacting the NgR protein or biologically active portion thereof with a known compound which binds NgR to form an assay mixture, contacting the assay mixture with a test compound, and determining the ability of the test compound to interact with a NGR protein, wherein determining the ability of the test compound to interact with a NgR protein comprises determining the ability of the NgR protein to modulate the activity of a NgR target molecule.

The cell-free assays of the present invention are amenable to use of both the soluble form or the membrane-bound form of NgR. In the case of cell-free assays comprising the membrane-bound form of NgR, it may be desirable to utilize a solubilizing agent such that the membrane-bound form of NgR is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)$_n$, 3-(3-cholamidopropyl)dimethylamminiol-1-propane sulfonate (CHAPS), 3-(3-cholamidopropyl)dimethylamminiol-2-hydroxy-1-propane sulfonate (CHAPSO), or N-dodecyl-N,N-dimethyl-3-ammonio-1-propane sulfonate Modulators Agents that modulate (i.e., increase, decrease, or block) NgR activity or expression may be identified by incubating a putative modulator with a cell containing a NgR polypeptide or polynucleotide and determining the effect of the putative modulator on NgR activity or expression. The selectivity of a compound that modulates the activity of NgR can be evaluated by comparing its effects on NgR to its effect on other NgR compounds. Selective modulators may include, for example, antibodies and other proteins, peptides or organic molecules which specifically bind to a NgR polypeptide or a NgR-encoding nucleic acid. Modulators of NgR activity will be therapeutically useful in treatment of diseases and physiological conditions in which normal or aberrant NgR activity is involved. NgR polynucleotides, polypeptides and modulators may be used in the treatment of such diseases and conditions associated with demyelination. NgR polynucleotides and polypeptides, as well as NgR modulators, may also be used in diagnostic assays for such diseases or conditions.

Methods of the invention to identify modulators include variations on any of the methods described above to identify binding partner compounds, the variations including techniques wherein a binding partner compound has been identified and the binding assay is carried out in the presence and absence of a candidate modulator. A modulator is identified in those instances where binding between the NgR polypeptide and the binding partner compound changes in the presence of the candidate modulator compared to binding in the absence of the candidate modulator compound. A modulator that increases binding between the NgR polypeptide and the binding partner compound is described as an enhancer or activator, and a modulator that decreases binding between the NgR polypeptide and the binding partner compound is described as an inhibitor.

In another embodiment, modulators of NgR expression may be identified in a method wherein a cell is contacted with a candidate compound and the expression of NgR mRNA or protein in the cell is determined. The level of expression of NgR mRNA or protein in the presence of the candidate compound is compared to the level of expression of NgR mRNA or protein in the absence of the candidate compound. The candidate compound can then be identified as a modulator of NgR expression based on this comparison. For example, when expression of NgR mRNA or protein is greater (statistically significantly greater) in the presence of the candidate compound than in its absence, the candidate compound is identified as a stimulator of NgR mRNA or protein expression. Alternatively, when expression of NgR mRNA or protein is less (statistically significantly less) in the presence of the candidate compound than in its absence, the candidate compound is identified as an inhibitor of NgR mRNA or protein expression. The level of NgR mRNA or protein expression in the cells can be determined by methods described herein for detecting NgR mRNA or protein.

High Throughput Screening

The invention also comprehends high-throughput screening (HTS) assays to identify compounds that interact with or inhibit biological activity (i.e., affect enzymatic activity, binding activity, etc.) of a NgR polypeptide. HTS assays permit screening of large numbers of compounds in an efficient manner. Cell-based HTS systems are contemplated to investigate NgR receptor-ligand interaction. HTS assays are designed to identify "hits" or "lead compounds" having the desired property, from which modifications can be designed to improve the desired property. Chemical modification of the "hit" or "lead compound" is often based on an identifiable structure/activity relationship between the "hit" and the NgR polypeptide.

Another aspect of the present invention is directed to methods of identifying compounds that bind to either NgR or nucleic acid molecules encoding NgR, comprising contacting NgR, or a nucleic acid molecule encoding the same, with a compound, and determining whether the compound binds NgR or a nucleic acid molecule encoding the same. Binding can be determined by binding assays which are well known to the skilled artisan, including, but not limited to, gel-shift assays, Western blots, radiolabeled competition assay, phage-based expression cloning, co-fractionation by chromatography, co-precipitation, cross linking, interaction trap/two-hybrid analysis, southwestern analysis, ELISA, and the like, which are described in, for example, Ausubel et al. (Eds.), Current Protocols in Molecular Biology, 1999, John Wiley & Sons, NY, which is incorporated herein by reference in its entirety. The NgR proteins, for example, can be used as "bait proteins" in a two-hybrid assay or three hybrid assay (see, e.g., U.S. Pat. No. 5,283,317; Zervos et al., (1993) *Cell* 72, 223-232; Madura et al., (1993) *J. Biol. Chem.* 268, 12046-12054; Bartel et al., (1993) *BioTechniques* 14, 920-924; Iwabuchi et al., (1993) *Oncogene* 8, 1693-1696; and Brent WO 94/10300), to identify other proteins that bind to or interact with NgR ("NgR-binding proteins" or "NgR-bp") and modulate NgR activity. Such NgR-binding proteins are also likely to be involved in the propagation of signals by the NgR proteins as, for example, upstream or downstream elements of the NgR pathway.

Other assays may be used to identify specific ligands of a NgR receptor, including assays that identify ligands of the target protein through measuring direct binding of test ligands to the target protein, as well as assays that identify ligands of target proteins through affinity ultrafiltration with ion spray mass spectroscopy/HPLC methods or other physical and analytical methods. Alternatively, such binding interactions are evaluated indirectly using the yeast two-hybrid system described in Fields et al., (1989) *Nature* 340, 245-246, and Fields et al., (1994) *Trends Genet* 10, 286-292, both of which are incorporated herein by reference. The two-hybrid system is a genetic assay based on the modular nature of most transcription factors used for detecting interactions between two proteins or polypeptides. It can be used to identify proteins that bind to a known protein of interest, or to delineate domains or residues critical for an interaction. Variations on this methodology have been developed to clone genes that encode DNA binding proteins, to identify peptides that bind to a protein, and to screen for drugs. The two-hybrid system exploits the ability of a pair of interacting proteins to bring a transcription activation domain into close proximity with a DNA binding domain that binds to an upstream activation sequence (UAS) of a reporter gene, and is generally performed in yeast. The assay requires the construction of two hybrid genes encoding (1) a DNA-binding domain that is fused to a first protein and (2) an activation domain fused to a second protein. The DNA-binding domain targets the first hybrid protein to the UAS of the reporter gene; however, because most proteins lack an activation domain, this DNA-binding hybrid protein does not activate transcription of the reporter gene. The second hybrid protein, which contains the activation domain, cannot by itself activate expression of the reporter gene because it does not bind the UAS. However, when both hybrid proteins are present, the noncovalent interaction of the first and second proteins tethers the activation domain to the UAS, activating transcription of the reporter gene. For example, when the first protein is a NgR gene product, or fragment thereof, that is known to interact with another protein or nucleic acid, this assay can be used to detect agents that interfere with the binding interaction. Expression of the reporter gene is monitored as different test agents are added to the system. The presence of an inhibitory agent results in lack of a reporter signal. The compounds to be screened include (which may include compounds that are suspected to bind NgR, or a nucleic acid molecule encoding the same), but are not limited to, extracellular, intracellular, biological or chemical origin.

The function of the NgR gene product is unclear and no ligands have yet been found which bind the gene product. The yeast two-hybrid assay is useful to identify proteins that bind to the gene product. In an assay to identify proteins that bind to a NgR receptor, or fragment thereof, a fusion polynucleotide encoding both a NgR receptor (or fragment) and a UAS binding domain (i.e., a first protein) may be used. In addition, a large number of hybrid genes each encoding a different second protein fused to an activation domain are produced and screened in the assay. Typically, the second protein is encoded by one or more members of a total cDNA or genomic DNA fusion library, with each second protein-coding region being fused to the activation domain. This system is applicable to a wide variety of proteins, and it is not even necessary to know the identity or function of the second binding protein. The system is highly sensitive and can detect interactions not revealed by other methods; even transient interactions may trigger transcription to produce a stable mRNA that can be repeatedly translated to yield the reporter protein.

Other assays may be used to search for agents that bind to the target protein. One such screening method to identify direct binding of test ligands to a target protein is described in U.S. Pat. No. 5,585,277, incorporated herein by reference. This method relies on the principle that proteins generally exist as a mixture of folded and unfolded states, and continually alternate between the two states. When a test ligand binds to the folded form of a target protein (i.e., when the test ligand is a ligand of the target protein), the target protein molecule bound by the ligand remains in its folded state. Thus, the folded target protein is present to a greater extent in the presence of a test ligand which binds the target protein, than in the absence of a ligand. Binding of the ligand to the target protein can be determined by any method which distinguishes between the folded and unfolded states of the target protein. The function of the target protein need not be known in order for this assay to be performed. Virtually any agent can be assessed by this method as a test ligand, including, but not limited to, metals, polypeptides, proteins, lipids, polysaccharides, polynucleotides and small organic molecules.

Another method for identifying ligands of a target protein is described in Wieboldt et al. (1997) *Anal. Chem.* 69:1683-1691, incorporated herein by reference. This technique screens combinatorial libraries of 20-30 agents at a time in solution phase for binding to the target protein. Agents that bind to the target protein are separated from other library components by simple membrane washing. The specifically selected molecules that are retained on the filter are subsequently liberated from the target protein and analyzed by HPLC and pneumatically assisted electrospray (ion spray) ionization mass spectroscopy. This procedure selects library components with the greatest affinity for the target protein, and is particularly useful for small molecule libraries.

The methods of the invention also embrace ligands, especially neuropeptides, that are attached to a label, such as a radiolabel (e.g., $^{125}I$, $^{35}S$, $^{32}P$, $^{33}P$, $^{3}H$), a fluorescence label, a chemiluminescent label, an enzymic label and an immunogenic label. Modulators falling within the scope of the invention include, but are not limited to, non-peptide molecules such as non-peptide mimetics, non-peptide allosteric effectors, and peptides. The NgR polypeptide or polynucleotide employed in such a test may either be free in solution, attached to a solid support, borne on a cell surface or located intracellularly or associated with a portion of a cell. One skilled in the art can, for example, measure the formation of complexes between NgR and the compound being tested. Alternatively, one skilled in the art can examine the diminution in complex formation between NgR and its substrate caused by the compound being tested.

Another aspect of the present invention is directed to methods of identifying compounds which modulate (i.e., increase or decrease) activity of NgR comprising contacting NgR with a compound, and determining whether the compound modifies activity of NgR. The activity in the presence of the test compared is measured to the activity in the absence of the test compound. Where the activity of the sample containing the test compound is higher than the activity in the sample lacking the test compound, the compound will have increased activity. Similarly, where the activity of the sample containing the test compound is lower than the activity in the sample lacking the test compound, the compound will have inhibited activity.

The present invention is particularly useful for screening compounds by using NgR in any of a variety of drug screening techniques. The compounds to be screened include (which may include compounds which are suspected to modulate NgR activity), but are not limited to, extracellular, intracellular, biologic or chemical origin. The NgR polypeptide employed in such a test may be in any form, preferably, free in solution, attached to a solid support, borne on a cell surface or located intracellularly. One skilled in the art can, for example, measure the formation of complexes between NgR and the compound being tested. Alternatively, one skilled in the art can examine the diminution in complex formation between Nogo-R and its substrate caused by the compound being tested.

The activity of NgR polypeptides of the invention can be determined by, for example, examining the ability to bind or be activated by chemically synthesized peptide ligands. Alternatively, the activity of the NgR can be assayed by examining their ability to bind calcium ions, hormones, chemokines, neuropeptides, neurotransmitters, nucleotides, lipids, odorants and photons. Alternatively, the activity of the NgR can be determined by examining the activity of effector molecules including, but not limited to, adenylate cyclase, phospholipases and ion channels. Thus, modulators of NgR activity may alter a NgR receptor function, such as a binding property of a receptor or an activity. In various embodiments of the method, the assay may take the form of an ion flux assay, a yeast growth assay, a non-hydrolyzable GTP assay such as a [$^{35}S$]-GTP S assay, a cAMP assay, an inositol triphosphate assay, a diacylglycerol assay, an Aequorin assay, a Luciferase assay, a FLIPR assay for intracellular $Ca^{2+}$ concentration, a mitogenesis assay, a MAP Kinase activity assay, an arachidonic acid release assay (e.g., using [$^{3}H$]-arachidonic acid) and an assay for extracellular acidification rates, as well as other binding or function-based assays of NgR activity that are generally known in the art. NgR activity can be determined by methodologies that are used to assay for FaRP activity, which is well known to those skilled in the art. Biological activities of NgR receptors according to the invention include, but are not limited to, the binding of a natural or an unnatural ligand, as well as any one of the functional activities of NgRs known in the art. Non-limiting examples of NgR activities include transmembrane signaling of various forms, which may involve phosphatidylinositol (PI) association and/or the exertion of an influence over PI; another exemplary activity of NgRs is the binding of accessory proteins or polypeptides that differ from known GPI proteins.

The modulators of the invention exhibit a variety of chemical structures, which can be generally grouped into non-peptide mimetics of natural NgR receptor ligands, peptide and non-peptide allosteric effectors of NgR receptors, and peptides that may function as activators or inhibitors (competitive, uncompetitive and non-competitive) (e.g., antibody products) of NgR receptors. The invention does not restrict the sources for suitable modulators, which may be obtained from natural sources such as plant, animal or mineral extracts, or non-natural sources such as small molecule libraries, including the products of combinatorial chemical approaches to library construction, and peptide libraries.

Other assays can be used to examine enzymatic activity including, but not limited to, photometric, radiometric, HPLC, electrochemical, and the like, which are described in, for example, ENZYME ASSAYS: A PRACTICAL APPROACH, Eisenthal and Danson (Eds.), 1992, Oxford University Press, which is incorporated herein by reference in its entirety.

The use of cDNAs in drug discovery programs is well-known; assays capable of testing thousands of unknown compounds per day in high-throughput screens (HTSs) are thoroughly documented. The literature is replete with examples of the use of radiolabelled ligands in HTS binding assays for drug discovery (see Williams (1991) *Med. Res. Rev.,* 11, 147-184; Sweetnam et al., (1993) *J. Nat. Prod.* 56, 441-455 for review). Recombinant receptors are preferred for binding assay HTS because they allow for better specificity (higher relative purity), provide the ability to generate large amounts of receptor material, and can be used in a broad variety of formats (see Hodgson (1992) *Bio/Technology* 10, 973-980; each of which is incorporated herein by reference in its entirety).

A variety of heterologous systems is available for functional expression of recombinant receptors that are well known to those skilled in the art. Such systems include bacteria (Strosberg et al. (1992) *Trends Pharmacol. Sci.* 13, 95-98), yeast (Pausch (1997) *Trends Biotechnol.* 15, 487A94), several kinds of insect cells (Vanden Broeck (1996) *Int. Rev. Cytol.* 164, 189-268), amphibian cells (Jayawickreme et al. (1997) *Curr. Opin. Biotechnol.* 8, 629-634) and several mammalian cell lines (CHO, HEK293, COS, etc.; see Gerhardt et al. (1997) *Eur. J. Pharmacol.* 334, 1-23). These examples do not preclude the use of other possible cell expression systems, including cell lines obtained from nematodes (PCT application WO 98/37177).

In preferred embodiments of the invention, methods of screening for compounds which modulate NgR activity comprise contacting test compounds with NgR and assaying for the presence of a complex between the compound and NgR. In such assays, the ligand is typically labeled. After suitable incubation, free ligand is separated from that present in bound form, and the amount of free or uncomplexed label is a measure of the ability of the particular compound to bind to NgR.

In another embodiment of the invention, high throughput screening for compounds having suitable binding affinity to NgR is employed. Briefly, large numbers of different small peptide test compounds are synthesized on a solid substrate. The peptide test compounds are contacted with NgR and washed. Bound NgR is then detected by methods well known in the art. Purified polypeptides of the invention can also be coated directly onto plates for use in the aforementioned drug screening techniques. In addition, non-neutralizing antibodies can be used to capture the protein and immobilize it on the solid support.

Generally, an expressed NgR can be used for HTS binding assays in conjunction with its defined ligand. The identified peptide is labeled with a suitable radioisotope, including, but not limited to, $^{125}I$, $^{3}H$, $^{35}S$ or $^{32}P$, by methods that are well known to those skilled in the art. Alternatively, the peptides may be labeled by well-known methods with a suitable fluorescent derivative (Baindur et al (1994) *Drug Dev. Res.* 33, 373-398; Rogers (1997) *Drug Discov. Today* 2, 156-160). Radioactive ligand specifically bound to the receptor in membrane preparations made from the cell line expressing the recombinant protein can be detected in HTS assays in one of several standard ways, including filtration of the receptor-ligand complex to separate bound ligand from unbound ligand (Williams (1991) *Med. Res. Rev.* 11, 147-184; Sweetnam et al. (1993) *J. Nat. Prod.* 56, 441-455). Alternative methods include a scintillation proximity assay (SPA) or a FlashPlate format in which such separation is unnecessary (Nakayama (1998) *Curr. Opin. Drug Disc. Dev.* 1, 85-91 Bosse et al (1998) *J. Biomol. Screening* 3, 285-292). Binding of fluorescent ligands can be detected in various ways, including fluorescence energy transfer (FRET), direct spectrophotofluorometric analysis of bound ligand, or fluorescence polarization (Rogers (1997) *Drug Discov. Today* 2, 156-160; Hill (1998) *Curr. Opin. Drug Disc. Dev.* 1, 92-97).

Examples of such biological responses include, but are not limited to, the following: the ability to survive in the absence of a limiting nutrient in specifically engineered yeast cells (Pausch (1997) *Trends in Biotechnol.* 15, 487-494); changes in intracellular $Ca^{2+}$ concentration as measured by fluorescent dyes (Murphy et al (1998) *Cur. Opin. Drug Disc. Dev.* 1, 192-199). Fluorescence changes can also be used to monitor ligand-induced changes in membrane potential or intracellular pH; an automated system suitable for HTS has been described for these purposes (Schroeder et al. (1996) *J. Biomol. Screening* 1, 75-80). Melanophores prepared from *Xenopus laevis* show a ligand-dependent change in pigment organization in response to heterologous NgR activation; this response is adaptable to HTS formats (Jayawickreme et al. (1997) *Curr. Opin. Biotechnol.* 8, 629-634). Assays are also available for the measurement of common second messengers, including cAMP, phosphoinositides and arachidonic acid, but these are not generally preferred for HTS.

Preferred methods of HTS employing these receptors include permanently transfected CHO cells, in which agonists and antagonists can be identified by the ability to transduce the signal for the binding of Nogo in membranes prepared from these cells through the putative GPI anchor. In another embodiment of the invention, permanently transfected CHO cells could be used for the preparation of membranes which contain significant amounts of the recombinant receptor proteins; these membrane preparations would then be used in receptor binding assays, employing the radiolabelled ligand specific for the particular receptor. Alternatively, a functional assay, such as fluorescent monitoring of ligand-induced changes in internal $Ca^{2+}$ concentration or membrane potential in permanently transfected CHO cells containing each of these receptors individually or in combination would be preferred for HTS. Equally preferred would be an alternative type of mammalian cell, such as HEK293 or COS cells, in similar formats. More preferred would be permanently transfected insect cell lines, such as *Drosophila* S2 cells. Even more preferred would be recombinant yeast cells expressing the *Drosophila melanogaster* receptors in HTS formats well known to those skilled in the art (e.g., Pausch (1997), above).

The invention contemplates a multitude of assays to screen and identify inhibitors of ligand binding to NGR receptors. In one example, the NgR receptor is immobilized and interaction with a binding partner is assessed in the presence and absence of a candidate modulator such as an inhibitor compound. In another example, interaction between the NgR receptor and its binding partner is assessed in a solution assay, both in the presence and absence of a candidate inhibitor compound. In either assay, an inhibitor is identified as a compound that decreases binding between the NgR receptor and its binding partner. Another contemplated assay involves a variation of the di-hybrid assay wherein an inhibitor of protein/protein interactions is identified by detection of a positive signal in a transformed or transfected host cell, as described in PCT publication number WO 95/20652, published Aug. 3, 1995.

Candidate modulators contemplated by the invention include compounds selected from libraries of either potential activators or potential inhibitors. There are a number of different libraries used for the identification of small molecule modulators, including: (1) chemical libraries, (2) natural product libraries, and (3) combinatorial libraries comprised of random peptides, oligonucleotides or organic molecules. Chemical libraries consist of random chemical structures, some of which are analogs of known compounds or analogs of compounds that have been identified as “hits” or “leads” in other drug discovery screens, some of which are derived from natural products, and some of which arise from non-directed synthetic organic chemistry. Natural product libraries are collections of microorganisms, animals, plants, or marine organisms that are used to create mixtures for screening by: (1) fermentation and extraction of broths from soil, plant or marine microorganisms or (2) extraction of plants or marine organisms. Natural product libraries include polyketides, non-ribosomal peptides, and variants (non-naturally occurring) thereof. For a review, see Cane et al., *Science* (1998) 282, 63-68. Combinatorial libraries are composed of large numbers of peptides, oligonucleotides, or organic compounds as a mixture. These libraries are relatively easy to prepare by traditional automated synthesis methods, PCR, cloning, or proprietary synthetic methods. Of particular interest are non-peptide combinatorial libraries. Still other libraries of interest include peptide, protein, peptidomimetic, multiparallel synthetic collection, recombinatorial, and polypeptide libraries. For a review of combinatorial chemistry and libraries created therefrom, see Myers (1997) *Curr. Opin. Biotechnol.* 8, 701-707. Identification of modulators through use of the various libraries described herein permits modification of the candidate "hit" (or "lead") to optimize the capacity of the "hit" to modulate activity.

Still other candidate inhibitors contemplated by the invention can be designed and include soluble forms of binding partners, as well as such binding partners as chimeric, or fusion, proteins. A "binding partner" as used herein broadly encompasses non-peptide modulators, as well as such peptide modulators as neuropeptides other than natural ligands, antibodies, antibody fragments, and modified compounds comprising antibody domains that are immunospecific for the expression product of the identified NgR gene.

Other embodiments of the invention comprise using competitive screening assays in which neutralizing antibodies capable of binding a polypeptide of the invention specifically compete with a test compound for binding to the polypeptide. In this manner, the antibodies can be used to detect the presence of any peptide that shares one or more antigenic determinants with NgR. Radiolabeled competitive binding studies are described in Lin et al., (1997) *Antimicrob. Agents Chemother.* 41, 2127-2131, the disclosure of which is incorporated herein by reference in its entirety.

In other embodiments of the invention, the polypeptides of the invention are employed as a research tool for identification, characterization and purification of interacting, regulatory proteins. Appropriate labels are incorporated into the polypeptides of the invention by various methods known in the art and the polypeptides are used to capture interacting molecules. For example, molecules are incubated with the labeled polypeptides, washed to remove unbound polypeptides, and the polypeptide complex is quantified. Data obtained using different concentrations of polypeptide are used to calculate values for the number, affinity, and association of polypeptide with the protein complex.

Labeled polypeptides are also useful as reagents for the purification of molecules with which the polypeptide interacts including, but not limited to, inhibitors. In one embodiment of affinity purification, a polypeptide is covalently coupled to a chromatography column. Cells and their membranes are extracted, and various cellular subcomponents are passed over the column. Molecules bind to the column by virtue of their affinity to the polypeptide. The polypeptide-complex is recovered from the column, dissociated and the recovered molecule is subjected to protein sequencing. This amino acid sequence is then used to identify the captured molecule or to design degenerate oligonucleotides for cloning the corresponding gene from an appropriate cDNA library.

Alternatively, compounds may be identified which exhibit similar properties to the ligand for the NgR of the invention, but which are smaller and exhibit a longer half time than the endogenous ligand in a human or animal body. When an organic compound is designed, a molecule according to the invention is used as a "lead" compound. The design of mimetics to known pharmaceutically active compounds is a well-known approach in the development of pharmaceuticals based on such "lead" compounds. Mimetic design, synthesis and testing are generally used to avoid randomly screening a large number of molecules for a target property. Furthermore, structural data deriving from the analysis of the deduced amino acid sequences encoded by the DNAs of the present invention are useful to design new drugs, more specific and therefore with a higher pharmacological potency.

Comparison of the protein sequence of the present invention with the sequences present in all the available databases showed a significant homology with the transmembrane portion of G protein coupled receptors. Accordingly, computer modeling can be used to develop a putative tertiary structure of the proteins of the invention based on the available information of the transmembrane domain of other proteins. Thus, novel ligands based on the predicted structure of NgR can be designed.

This invention further pertains to novel agents identified by the above-described screening assays and uses thereof for treatments as described herein.

Compositions and Pharmaceutical Compositions

In a particular embodiment, the novel molecules identified by the screening methods according to the invention are low molecular weight organic molecules, in which case a composition or pharmaceutical composition can be prepared thereof for oral or parenteral administration. The compositions, or pharmaceutical compositions, comprising the nucleic acid molecules, vectors, polypeptides, antibodies and compounds identified by the screening methods described herein, typically comprise the nucleic acid molecule, protein, or antibody and a pharmaceutically acceptable carrier. As used herein, "pharmaceutically acceptable carrier" is intended to include any and all solvents, dispersion media, coatings, antibacterial and antifungal agents, isotonic and absorption delaying agents, and the like, compatible with pharmaceutical administration. The nature of the carrier or other ingredients will depend on the specific route of administration and particular embodiment of the invention to be administered. Examples of techniques and protocols that are useful in this context are, inter alia, found in Remington's PHARMACEUTICAL SCIENCES, 16th ed., (1980) Osol, A (Ed.), which is incorporated herein by reference in its entirety. Preferred examples of such carriers or diluents include, but are not limited to, water, saline, Ringer's solution, dextrose solution and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include oral and parenteral (e.g., intravenous, intradermal, subcutaneous, inhalation, transdermal (topical), transmucosal and rectal administration). Solutions or suspensions used for parenteral, intradermal or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a NgR protein or anti-NgR antibody) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel or corn starch; a lubricant such as magnesium stearate or Sterotes; a glidant such as colloidal silicon dioxide; a sweetening agent such as sucrose or saccharin; or a flavoring agent such as peppermint, methyl salicylate or orange flavoring.

For administration by inhalation, the compounds are delivered in the form of an aerosol spray from pressured container or dispenser which contains a suitable propellant, e.g., a gas such as carbon dioxide or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811. It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved.

The nucleic acid molecules of the invention can be inserted into vectors and used as gene therapy vectors. Gene therapy vectors can be delivered to a subject by any of a number of routes, e.g., as described in U.S. Pat. No. 5,703,055. Delivery can thus also include, e.g., intravenous injection, local administration (see U.S. Pat. No. 5,328,470) or stereotactic injection (see e.g., Chen et al. (1994) *Proc. Natl. Acad. Sci. USA* 91, 3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells that produce the gene delivery system.

The pharmaceutical compositions can be included in a container, pack or dispenser together with instructions for administration.

The dosage of these low molecular weight compounds will depend on the disease state or condition to be treated and other clinical factors such as weight and condition of the human or animal and the route of administration of the compound. For treating human or animals, between approximately 0.5 mg/kg of body weight to 500 mg/kg of body weight of the compound can be administered. Therapy is typically administered at lower dosages and is continued until the desired therapeutic outcome is observed.

Another aspect of the present invention is the use of the NgR nucleotide sequences disclosed herein for identifying homologs of the Nogo-R, in other animals, including but not limited to humans and other mammals and invertebrates. Any of the nucleotide sequences disclosed herein, or any portion thereof, can be used, for example, as probes to screen databases or nucleic acid libraries, such as, for example, genomic or cDNA libraries, to identify homologs using screening procedures well known to those skilled in the art. Accordingly, homologs having at least 50%, more preferably at least 60%, more preferably at least 70%, more preferably at least 80%, more preferably at least 90%, more preferably at least 95%, and most preferably at least 100% homology with NgR sequences can be identified.

The present compounds and methods, including nucleic acid molecules, polypeptides, antibodies, compounds identified by the screening methods described herein, have a variety of pharmaceutical applications and may be used, for example, to treat or prevent unregulated cellular growth, such as cancer cell and tumor growth. In a particular embodiment, the present molecules are used in gene therapy. For a review of gene therapy procedures, see e.g. Anderson *Science* (1992) 256, 808-813, which is incorporated herein by reference in its entirety.

The present invention also encompasses a method of agonizing (stimulating) or antagonizing a NgR natural binding partner associated activity in a mammal comprising administering to said mammal an agonist or antagonist to one of the above disclosed polypeptides in an amount sufficient to effect said agonism or antagonism: One embodiment of the present invention, then, is a method of treating diseases in a mammal with an agonist or antagonist of the protein of the present invention comprising administering the agonist or antagonist to a mammal in an amount sufficient to agonize or antagonize NgR-associated functions.

Methods of determining the dosages of compounds to be administered to a patient and modes of administering compounds to an organism are disclosed in U.S. application Ser. No. 08/702,282, filed Aug. 23, 1996, and International patent publication number WO 96/22976, published Aug. 1, 1996, both of which are incorporated herein by reference in their entirety, including any drawings, figures or tables. Those skilled in the art will appreciate that such descriptions are applicable to the present invention and can be easily adapted to it.

The proper dosage depends on various factors such as the type of disease being treated, the particular composition being used and the size and physiological condition of the patient. Therapeutically effective doses for the compounds described herein can be estimated initially from cell culture and animal models. For example, a dose can be formulated in animal models to achieve a circulating concentration range that initially takes into account the $IC_{50}$ as determined in cell culture assays. The animal model data can be used to more accurately determine useful doses in humans.

Plasma half-life and biodistribution of the drug and metabolites in the plasma, tumors and major organs can also be determined to facilitate the selection of drugs most appropriate to inhibit a disorder. Such measurements can be carried out. For example, HPLC analysis can be performed on the plasma of animals treated with the drug and the location of radiolabeled compounds can be determined using detection methods such as X-ray, CAT scan and MRI. Compounds that show potent inhibitory activity in the screening assays, but have poor pharmacokinetic characteristics, can be optimized by altering the chemical structure and retesting. In this regard, compounds displaying good pharmacokinetic characteristics can be used as a model.

Toxicity studies can also be carried out by measuring the blood cell composition. For example, toxicity studies can be carried out in a suitable animal model as follows: (1) the compound is administered to mice (an untreated control mouse should also be used); (2) blood samples are periodically obtained via the tail vein from one mouse in each treatment group; and (3) the samples are analyzed for red and white blood cell counts, blood cell composition and the percent of lymphocytes versus polymorphonuclear cells. A comparison of results for each dosing regime with the controls indicates if toxicity is present.

At the termination of each toxicity study, further studies can be carried out by sacrificing the animals (preferably, in accordance with the American Veterinary Medical Association guidelines Report of the American Veterinary Medical Assoc. Panel on Euthanasia, (1993) *J. Am. Vet. Med. Assoc.* 202; 229-249). Representative animals from each treatment group can then be examined by gross necropsy for immediate evidence of metastasis, unusual illness or toxicity. Gross abnormalities in tissue are noted and tissues are examined histologically. Compounds causing a reduction in body weight or blood components are less preferred, as are compounds having an adverse effect on major organs. In general, the greater the adverse effect the less preferred the compound.

For the treatment of cancers the expected daily dose of a hydrophobic pharmaceutical agent is between 1 to 500 mg/day, preferably 1 to 250 mg/day, and most preferably 1 to 50 mg/day. Drugs can be delivered less frequently provided plasma levels of the active moiety are sufficient to maintain therapeutic effectiveness. Plasma levels should reflect the potency of the drug. Generally, the more potent the compound the lower the plasma levels necessary to achieve efficacy.

NgR mRNA transcripts have been found in the brain and heart. SEQ ID NOs: 1 and/or, 3 will, as detailed above, enable screening the endogenous neurotransmitters/hormones/ligands which activate, agonize, or antagonize NgR and for compounds with potential utility in treating disorders including CNS disorders (e.g., stroke) and degenerative disorders such as those associated with demyelination.

For example, NgR receptor activation may mediate the prevention of neurite outgrowth. Inhibition would be beneficial in both chronic and acute brain injury. See, e.g., Donovan et al., (1997) *J. Neurosci.* 17, 5316-5326; Turgeon et al., (1998) *J. Neurosci.* 18, 6882-6891; Smith-Swintosky et al., (1997) *J. Neurochem.* 69, 1890-1896; Gill et al., (1998) *Brain Res.* 797, 321-327; Suidan et al., (1996) *Semin. Thromb. Hemost.* 22, 125-133.

Pharmacogenomics

Agents, or modulators that have a stimulatory or inhibitory effect on NgR activity (e.g., NgR gene expression), as identified by a screening assay described herein can be administered to individuals to treat (prophylactically or therapeutically) disorders (e.g., a disease condition such as a demyelination disorder) associated with aberrant NgR activity. In conjunction with such treatment, the pharmacogenomics (i.e., the study of the relationship between an individual's genotype and that individual's response to a foreign compound or drug) of the individual may be considered. Differences in metabolism of therapeutics can lead to severe toxicity or therapeutic failure by altering the relation between dose and blood concentration of the pharmacologically active drug. Thus, the pharmacogenomics of the individual permits the selection of effective agents (e.g., drugs) for prophylactic or therapeutic treatments based on a consideration of the individual's genotype. Such pharmacogenomics can further be used to determine appropriate dosages and therapeutic regimens. Accordingly, the activity of NgR protein, expression of NgR nucleic acid or mutation content of NgR genes in an individual can be determined to thereby select appropriate agent(s) for therapeutic or prophylactic treatment of the individual.

Pharmacogenomics deals with clinically significant hereditary variations in the response to drugs due to altered drug disposition and abnormal action in affected persons. See e.g., Eichelbaum (1996) *Clin. Exp. Pharmacol. Physiol.* 23, 983-985 and Linder (1997) *Clin. Chem.* 43, 254-266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare defects or as polymorphisms. For example, glucose-6-phosphate dehydrogenase (G6PD) deficiency is a common inherited enzymopathy in which the main clinical complication is haemolysis after ingestion of oxidant drugs (anti-malarials, sulfonamides, analgesics, nitrofurans) and consumption of fava beans.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. At the other extreme are the so called ultra-rapid metabolizers who do not respond to standard doses. Recently, the molecular basis of ultra-rapid metabolism has been identified to be due to CYP2D6 gene amplification.

Thus, the activity of NgR protein, expression of NgR nucleic acid, or mutation content of NgR genes in an individual can be determined to thereby select appropriate agent(s) for therapeutic or prophylactic treatment of the individual. In addition, pharmacogenetic studies can be used to apply genotyping of polymorphic alleles encoding drug-metabolizing enzymes to the identification of an individual's drug responsiveness phenotype. This knowledge, when applied to dosing or drug selection, can avoid adverse reactions or therapeutic failure and thus enhance therapeutic or prophylactic efficiency when treating a subject with a NgR modulator, such as a modulator identified by one of the exemplary screening assays described herein.

Monitoring Clinical Efficacy

Monitoring the influence of agents (e.g., drugs, compounds) on the expression or activity of NgR (e.g., the ability to modulate aberrant cell proliferation and/or differentiation) can be applied not only in basic drug screening, but also in clinical trials. For example, the effectiveness of an agent determined by a screening assay as described herein to increase NgR gene expression, protein levels or upregulate NgR activity, can be monitored in clinical trials of subjects exhibiting decreased NgR gene expression, protein levels, or downregulated NgR activity. Alternatively, the effectiveness of an agent determined by a screening assay to decrease NgR gene expression, protein levels, or downregulate NgR activity, can be monitored in clinical trials of subjects exhibiting increased NgR gene expression, protein levels, or upregulated NgR activity. In such clinical trials, the expression or activity of NgR and, preferably, other genes that have been implicated in, for example, a disease or disorder, can be used as a "read out" or markers of the immune responsiveness of a particular cell.

For example, genes, including NgR, that are modulated in cells by treatment with an agent (e.g., compound, drug or small molecule) that modulates NgR activity (e.g., identified in a screening assay as described herein) can be identified. Thus, to study the effect of agents on demyelination disorders, for example, in a clinical trial, cells can be isolated and RNA prepared and analyzed for the levels of expression of NgR and other genes implicated in the disorder. The levels of gene expression (i.e., a gene expression pattern) can be quantified by Northern blot analysis or RT-PCR, as described herein, or alternatively by measuring the amount of protein produced by one of the methods as described herein or by measuring the levels of activity of NgR or other genes. In this way, the gene expression pattern can serve as a marker, indicative of the physiological response of the cells to the agent. Accordingly, this response state may be determined before, and at various points during, treatment of the individual with the agent.

In one embodiment, the invention provides a method for monitoring the effectiveness of treatment of a subject with an agent (e.g., an agonist, antagonist, protein, peptide, peptidomimetic, nucleic acid, small molecule, or other drug candidate identified by the screening assays described herein) comprising the steps of (i) obtaining a pre-administration sample from a subject prior to administration of the agent; (ii) detecting the level of expression of a NgR protein, mRNA, or genomic DNA in the preadministration sample; (iii) obtaining one or more post-administration samples from the subject; (iv) detecting the level of expression or activity of the NgR protein, mRNA, or genomic DNA in the post-administration samples; (v) comparing the level of expression or activity of the NgR protein, mRNA or genomic DNA in the pre-administration sample with the NgR protein, mRNA or genomic DNA in the post administration sample or samples; and (vi) altering the administration of the agent to the subject accordingly. For example, increased administration of the agent may be desirable to increase the expression or activity of NgR to higher levels than detected, i.e., to increase the effectiveness of the agent. Alternatively, decreased administration of the agent may be desirable to decrease expression or activity of NgR to lower levels than detected, i.e., to decrease the effectiveness of the agent.

Methods of Treatment

The present invention provides for both prophylactic and therapeutic methods of treating a subject at risk of (or susceptible to) a disorder or having a disorder associated with aberrant NgR expression or activity.

Diseases and disorders that are characterized by increased (relative to a subject not suffering from the disease or disorder) levels or biological activity may be treated with Therapeutics that antagonize (i.e., reduce or inhibit) activity. Therapeutics that antagonize activity may be administered in a therapeutic or prophylactic manner. Therapeutics that may be utilized include, but are not limited to, (i) a NgR polypeptide, or analogs, derivatives, fragments or homologs thereof; (ii) antibodies to a NgR peptide; (iii) nucleic acids encoding a NgR peptide; (iv) administration of antisense nucleic acid and nucleic acids that are "dysfunctional" (i.e., due to a heterologous insertion within the coding sequences of coding sequences to a NgR peptide) are utilized to "knockout"

endogenous function of a NgR peptide by homologous recombination (see, e.g., Capecchi (1989) *Science* 244, 1288-1292); or (v) modulators (i.e., inhibitors, agonists and antagonists, including additional peptide mimetic of the invention or antibodies specific to a peptide of the invention) that alter the interaction between a NgR peptide and its binding partner.

Diseases and disorders that are characterized by decreased (relative to a subject not suffering from the disease or disorder) levels or biological activity may be treated with Therapeutics that increase (i.e., are agonists to) activity. Therapeutics that upregulate activity may be administered in a therapeutic or prophylactic manner. Therapeutics that may be utilized include, but are not limited to, a NgR peptide, or analogs, derivatives, fragments or homologs thereof, or an agonist that increases bioavailability.

Increased or decreased levels can be readily detected by quantifying peptide and/or RNA, by obtaining a patient tissue sample (e.g., from biopsy tissue) and assaying it in vitro for RNA or peptide levels, structure and/or activity of the expressed peptides (or mRNAs of a NgR peptide). Methods that are well-known within the art include, but are not limited to, immunoassays (e.g. by Western blot analysis, immunoprecipitation followed by sodium dodecyl sulfate (SDS) polyacrylamide gel electrophoresis, immunocytochemistry, etc.) and/or hybridization assays to detect expression of mRNAs (e.g., Northern assays, dot blots, in situ hybridization, etc.).

In one aspect, the invention provides a method for preventing, in a subject, a disease or condition associated with an aberrant NgR expression or activity, by administering to the subject an agent that modulates NgR expression or at least one NgR activity. Subjects at risk for a disease that is caused or contributed to by aberrant NgR expression or activity can be identified by, for example, any or a combination of diagnostic or prognostic assays as described herein. Administration of a prophylactic agent can occur prior to the manifestation of symptoms characteristic of the NgR aberrancy, such that a disease or disorder is prevented or, alternatively, delayed in its progression. Depending on the type of NgR aberrancy, for example, a NgR agonist or NgR antagonist agent can be used for treating the subject. The appropriate agent can be determined based on screening assays described herein.

Another aspect of the invention pertains to methods of modulating NgR expression or activity for therapeutic purposes. The modulatory method of the invention involves contacting a cell with an agent that modulates one or more of the activities of NgR protein activity associated with the cell. An agent that modulates NgR protein activity can be an agent as described herein, such as a nucleic acid or a protein, a naturally-occurring cognate ligand of a NgR protein, a peptide, a NgR peptidomimetic, or other small molecule. In one embodiment, the agent stimulates one or more NgR protein activity. Examples of such stimulatory agents include active NgR protein and a nucleic acid molecule encoding NgR that has been introduced into the cell. In another embodiment, the agent inhibits one or more NgR protein activity. Examples of such inhibitory agents include antisense NgR nucleic acid molecules and anti-NgR antibodies. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant expression or activity of a NgR protein or nucleic acid molecule. In one embodiment, the method involves administering an agent (e.g., an agent identified by a screening assay described herein), or combination of agents that modulates (e.g., upregulates or down-regulates) NgR expression or activity. In another embodiment, the method involves administering a NgR protein or nucleic acid molecule as therapy to compensate for reduced or aberrant NgR expression or activity.

Gene Therapy

Mutations in the NgR gene that result in loss of normal function of the NgR gene product underlie NgR human disease states. The invention comprehends gene therapy to restore NgR activity to treat those disease states. Delivery of a functional NgR gene to appropriate cells is effected ex vivo, in situ, or in vivo by use of vectors, and more particularly viral vectors (e.g., adenovirus, adeno-associated virus, or a retrovirus), or ex vivo by use of physical DNA transfer methods (e.g., liposomes or chemical treatments). See, for example, Anderson (1998) *Nature*, supplement to 392(6679):25-20. For additional reviews of gene therapy technology see Friedmann (1989) *Science* 244, 1275-1281; Verma (1990) *Sci. Am.* 68-84; and Miller (1992) *Nature* 357, 455-460. Alternatively, it is contemplated that in other human disease states, preventing the expression of or inhibiting the activity of, NgR will be useful in treating disease states. It is contemplated that antisense therapy or gene therapy could be applied to negatively regulate the expression of NgR.

The present invention provides for both prophylactic and therapeutic methods of treating a subject at risk of (or susceptible to) a disorder or having a disorder associated with aberrant NgR expression or activity.

Diseases and disorders that are characterized by increased (relative to a subject not suffering from the disease or disorder) levels or biological activity may be treated with Therapeutics that antagonize (i.e., reduce or inhibit) activity. Therapeutics that antagonize activity may be administered in a therapeutic or prophylactic manner. Therapeutics that may be utilized include, but are not limited to, (i) a NgR polypeptide, or analogs, derivatives, fragments or homologs thereof; (ii) antibodies to a NgR peptide; (iii) nucleic acids encoding a NgR peptide; (iv) administration of antisense nucleic acid and nucleic acids that are "dysfunctional" (i.e., due to a heterologous insertion within the coding sequences of coding sequences to a NgR peptide) are utilized to "knockout" endogenous function of a NgR peptide by homologous recombination (see, e.g., Capecchi (1989), above); or (v) modulators (i.e., inhibitors, agonists and antagonists, including additional peptide mimetic of the invention or antibodies specific to a peptide of the invention) that alter the interaction between a NgR peptide and its binding partner.

Diseases and disorders that are characterized by decreased (relative to a subject not suffering from the disease or disorder) levels or biological activity may be treated with Therapeutics that increase (i.e., are agonists to) activity. Therapeutics that upregulate activity may be administered in a therapeutic or prophylactic manner. Therapeutics that may be utilized include, but are not limited to, a NgR peptide, or analogs, derivatives, fragments or homologs thereof; or an agonist that increases bioavailability.

Increased or decreased levels can be readily detected by quantifying peptide and/or RNA, by obtaining a patient tissue sample (e.g., from biopsy tissue) and assaying it in vitro for RNA or peptide levels, structure and/or activity of the expressed peptides (or mRNAs of a NgR peptide). Methods that are well-known within the art include, but are not limited to, immunoassays (e.g., by Western blot analysis, immunoprecipitation followed by sodium dodecyl sulfate (SDS) polyacrylamide gel electrophoresis, immunocytochemistry, etc.) and/or hybridization assays to detect expression of mRNAs (e.g., Northern assays, dot blots, in situ hybridization, etc.).

In one aspect, the invention provides a method for preventing, in a subject, a disease or condition associated with an aberrant NgR expression or activity, by administering to the subject an agent that modulates NgR expression or at least one NgR activity. Subjects at risk for a disease that is caused or contributed to by aberrant NgR expression or activity can be identified by, for example, any or a combination of diagnostic or prognostic assays as described herein. Administration of a prophylactic agent can occur prior to the manifestation of symptoms characteristic of the NgR aberrancy, such that a disease or disorder is prevented or, alternatively, delayed in its progression. Depending on the type of NgR aberrancy, for example, a NgR agonist or NgR antagonist agent can be used for treating the subject. The appropriate agent can be determined based on screening assays described herein.

Another aspect of the invention pertains to methods of modulating NgR expression or activity for therapeutic purposes. The modulatory method of the invention involves contacting a cell with an agent that modulates one or more of the activities of NgR protein activity associated with the cell. An agent that modulates NgR protein activity can be an agent as described herein, such as a nucleic acid or a protein, a naturally-occurring cognate ligand of a NgR protein, a peptide, a NgR peptidomimetic, or other small molecule. In one embodiment, the agent stimulates one or more NgR protein activity. Examples of such stimulatory agents include active NgR protein and a nucleic acid molecule encoding NgR that has been introduced into the cell. In another embodiment, the agent inhibits one or more NgR protein activity. Examples of such inhibitory agents include antisense NgR nucleic acid molecules and anti-NgR antibodies. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant expression or activity of a NgR protein or nucleic acid molecule. In one embodiment, the method involves administering an agent (e.g., an agent identified by a screening assay described herein), or combination of agents that modulates (e.g., upregulates or downregulates) NgR expression or activity. In another embodiment, the method involves administering a NgR protein or nucleic acid molecule as therapy to compensate for reduced or aberrant NgR expression or activity.

The present invention is not to be limited in scope by the specific embodiments described herein. Indeed, various modifications of the invention in addition to those described herein will become apparent to those skilled in the art from the foregoing description and accompanying figure. Such modifications are intended to fall within the scope of the appended claims.

The following Table 5 contains the sequences of exemplary polynucleotides and polypeptides of the invention.

TABLE 5

The following DNA sequence NgR2 <SEQ ID NO. 1> was identified in humans:

ATGCTGCCCGGGCTCAGGCGCCTGCTGCAAGCTCCCGCCTCGGCCTGCCT
CCTGCTGATGCTCCTGGCCCTGCCCCTGGCGGCCCCCAGCTGCCCCATGC
TCTGCACCTGCTACTCATCCCCGCCCACCGTGAGCTGCCAGGCCAACAAC
TTCTCCTCTGTGCCGCTGTCCCTGCCACCCAGCACTCAGCGACTCTTCCT
GCAGAACAACCTCATCCGCACGCTGCGGCCAGGCACCTTTGGGTCCAACC
TGCTCACCCTGTGGCTCTTCTCCAACAACCTCTCCACCATCTACCCGGGC
ACTTTCCGCCACTTGCAAGCCCTGGAGGAGCTGGACCTCGGTGACAACCG
GCACCTGCGCTCGCTGGAGCCCGACACCTTCCAGGGCCTGGAGCGGCTGC
AGTCGCTGCATTTGTACCGCTGCCAGCTCAGCAGCCTGCCCGGCAACATC

TABLE 5-continued

TTCCGAGGCCTGGTCAGCCTGCAGTACCTCTACCTCCAGGAGAACAGCCT
GCTCCACCTACAGGATGACTTGTTCGCGGACCTGGCCAACCTGAGCCACC
TCTTCCTCCACGGGAACCGCCTGCGGCTGCTCACAGAGCACGTGTTTCGC
GGCCTGGGCAGCCTGGACCGGCTGCTGCTGCACGGGAACCGGCTGCAGGG
CGTGCACCGCGCGGCCTTCCGCGGCCTCAGCCGCCTCACCATCCTCTACC
TGTTCAACAACAGCCTGGCCTCGCTGCCCGGCGAGGCGCTCGCCGACCTG
CCCTCGCTCGAGTTCCTGCGGCTCAACGCTAACCCCTGGGCGTGCGACTG
CCGCGCGCGGCCGCTCTGGGCCTGGTTCCAGCGCGCGCGCGTGTCCAGCT
CCGACGTGACCTGCGCCACCCCCCCGGAGCGCCAGGGCCGAGACCTGCGC
GCGCTCCGCGAGGCCGACTTCCAGGCGTGTCCGCCCGCGGCACCCACGCG
GCCGGGCAGCCGCGCCCGCGGCAACAGCTCCTCCAACCACCTGTACGGGG
TGGCCGAGGCCGGGGCGCCCCCAGCCGATCCCTCCACCCTCTACCGAGAT
CTGCCTGCCGAAGACTCGCGGGGGCGCCAGGGCGGGGACGCGCCTACTGA
GGACGACTACTGGGGGGGCTACGGGGGTGAGGACCAGCGAGGGGAGCAGA
TGTGCCCCGGCGCTGCCTGCCAGGCGCCCCCGGACTCCCGAGGCCCTGCG
CTCTCGGCCGGGCTCCCCAGCCCTCTGCTTTGCCTCCTGCTCCTGGTGCC
CCACCACCTC

The following amino acid sequence <SEQ ID NO. 2> is the predicted amino acid sequence derived from the DNA sequence of SEQ ID NO. 1:

M L P G R L R R L L Q A P A S A C L L L M L L A L
P L A A P S C P M L C T C Y S S P P T V S C Q A N
N F S S V P L S L P P S T Q R L F L Q N N L I R T
L R P G T F G S N L L T L W L F S N N L S T I Y P
G T F R H L Q A L E E L D L G D N R H L R S L E P
D T F Q G L E R L Q S L H L Y R C Q L S S L P G N
I F R G L V S L Q Y L Y L Q E N S L L H L Q D D L
F A D L A N L S H L F L H G N R L R L L T E H V F
R G L G S L D R L L L H G N R L Q G V H R A A F R
G L S R L T I L Y L F N N S L A S L P G E A L A D
L P S L E F L R L N A N P W A C D C R A R P L W A
W F Q R A R V S S S D V T C A T P P E R Q G R D L
R A L R E A D F Q A C P P A A P T R P G S R A R G
N S S S N H L Y G V A E A G A P P A D P S T L Y R
D L P A E D S R G R Q G G D A P T E D D Y W G G Y
G G E D Q R G E Q M C P G A A C Q A P P D S R G P
A L S A G L P S P L L C L L L L V P H H L

The following DNA sequence NgR3 <SEQ ID NO. 3> was identified in mouse:

ATGTCTTGGCAGTCTGGAACCACAGTGACACAATCTCCCGTGCAGGCTGC
TCAGGTCTCAGGGTGCTGTGTGGAATTGCTGCTGTTGCTGCTCGCTGGAG
AGCTACCTCTGGGTGGTGGTTGTCCTCGAGACTGTGTGTGCTACCCTGCG
CCCATGACTGTCAGCTGCCAGGCACACAACTTTGCTGCCATCCCGGAGGG
CATCCCAGAGGACAGTGAGCGCATCTTCCTGCAGAACAATCGCATCACCT
TCCTCCAGCAGGGCCACTTCAGCCCCGCCATGGTCACCCTCTGGATCTAC
TCCAACAACATCACTTTCATTGCTCCCAACACCTTCGAGGGCTTTGTGCA
TCTGGAGGAGCTAGACCTTGGAGACAACCGACAGCTGCGAACGCTGGCAC
CCGAGACCTTCCAAGGCCTGGTGAAGCTTCACGCCCTCTACCTCTATAAG
TGTGGACTGAGCGCCCTGCCCGCAGGCATCTTTGGTGGCCTGCACAGCCT
GCAGTATCTCTACTTGCAGGACAACCATATCGAGTACCTCCAAGATGACA
TCTTTGTGGACCTGGTCAATCTCAGTCACTTGTTTCTCCATGGTAACAAG
CTATGGAGCCTGGGCCAAGGCATCTTCCGGGGCCTGGTGAACCTGGACCG
GTTGCTGCTGCATGAGAACCAGCTACAGTGGGTTCACCACAAGGCTTTCC
ATGACCTCCACAGGCTAACCACCCTCTTTCTCTTCAACAACAGCCTCACT
GAGCTGCAGGGTGACTGTCTGGCCCCCCTGGTGGCCTTGGAGTTCCTTCG
CCTCAATGGGAATGCTTGGGACTGTGGCTGCCGGGCACGTTCCCTGTGGG
AATGGCTGCGAAGGTTCCGTGGCTCTAGCTCTGCTGTCCCCTGCGCGACC
CCCGAGCTGCGGCAAGGCCAGGATCTGAAGCTGCTGAGGGTGGAGGACTT
CCGGAACTGCACAGGACCAGTGTCTCCTCACCAGATCAAGTCTCACACGC
TTACCACCTCTGACAGGGCTGCCCGCAAGGAGCACCATCCGTCCCATGGG
GCCTCCAGGGACAAAGGCCACCCACATGGCCATCCGCCTGGCTCCAGGTC
AGGTTACAAGAAGGCAGGCAAGAACTGCACCAGCCACAGGAACCGGAACC
AGATCTCTAAGGTGAGCTCTGGGAAAGAGCTTACCGAACTGCAGGACTAT
GCCCCCGACTATCAGCACAAGTTCAGCTTTGACATCATGCCCACCGCACG
ACCCAAGAGGAAGGGCAAGTGTGCTCGCAGGACCCCCATCCGTGCCCCCA
GTGGGGTGCAGCAGGCATCCTCAGGCACGGCCCTTGGGGCCCCACTCCTG
GCCTGGATACTGGGGCTGGCAGTCACTCTCCGC

The following protein sequence <SEQ ID NO. 4> is deduced protein of SEQ ID NO:3:

M S W Q S G T T V T Q S P V Q A A Q V S G C C V E
L L L L L L A G E L P L G G G C P R D C V C Y P A
P M T V S C Q A H N F A A I P E G I P E D S E R I
F L Q N N R I T F L Q Q G H F S P A M V T L W I Y
S N N I T F I A P N T F E G F V H L E E L D L G D
N R Q L R T L A P E T F Q G L V K L H A L Y L Y K
C G L S A L P A G I F G G L H S L Q Y L Y L Q D N

TABLE 5-continued

H I E Y L Q D D I F V D L V N L S H L F L H G N K
L W S L G Q G I F R G L V N L D R L L L H E N Q L
Q W V H H K A F H D L H R L T T L F L F N N S L T
E L Q G D C L A P L V A L E F L R L N G N A W D C
G C R A R S L W E W L R R F R G S S S A V P C A T
P E L R Q G Q D L K L L R V E D F R N C T G P V S
P H Q I K S H T L T T S D R A A R K E H H P S H G
A S R K D G H P H G H P P G S R S G Y K K A G K N
C T S H R N R N Q I S K V S S G K E L T E L Q D Y
A P D Y Q K H F S F D I M P T A R P K R K G K C A
R R T P I R A P S G V Q Q A S S G T A L G A P L L
A W I L G L A V T L R

The following protein sequence <SEQ ID NO. 5> is NgR1 from humans:
M K R A S A G G S R L L A W V L W L Q A W Q V A A
P C P G A C C Y N E P K V T T S C P Q Q G L Q A V
P V G I P A A S Q R I F L H G N R I S H V P A A S
F R A C R N L T I L W L H S N V L A R I D A A A F
T G L A L L E Q L D L S D N A Q L R S V D P A T F
H G L G R L H T L H L D R C G L Q E L G P G L F R
G L A A L Q Y L Y L Q D N A L Q A L P D D T F R D
L G N L T H L F L H G N R I S S V P E R A F R G L
H S L D R L L L H Q N R V A H V H P H A F R D L G
R L M T L Y L F A N N L S A L P T E A L A P L R A
L Q Y L R L N D N P W V C D C R A R P L W A W L Q
K F R G S S S E V P C S L P Q R L A G R D L K R L
A A N D L Q G C A V A T G P Y H P I W T G R A T D
E E P L G L P K C C Q P D A A D K A S V L E P G R
P A S A G N A L K G R V P P G D S P P G N G S G P
R H I N D S P F G T L P G S A E P P L T A V R P E
G S E P P G F P T S G P R R R P G C S R K N R T R
S H C R L G Q A G S G G G G T G D S E G S G A L P
S L T C S L T P L G L A L V L W T V L G P C The following amino acid sequence <SEQ ID NO: 6> is a Consensus Sequence of NgR bases on homology with NgR1
C P X X C X C Y X X P X X T X S C X X X X X X X X
P X X X P X X X X R X F L X X N X I X X X X X X X
F X X X X X X X X L W X X S N X X X X I X X X X G
X X X X X L E X L D L X D N X X L R X X X P X T F
X G L X X L X L X L X X C X L X X L X X X X G X G
L X X L Q Y L Y L Q X N X X X X L X D D X F X D L
X N L X H L F L H G N X X X X X X X X X G R G L X
X L D R L L L H X N X X X X V H X X A F X X L X R
L X X L X L F X N X L X X L X X X X L A X L X X L
X X L R L N X N X W X C X C R A R X L W X W X X X
X R X S S S X V X C X X P X X X X G X D L X X L X
X X D X X X C X X X X X P X X P X X X X X X X X X
X X X X X X X X X X X X X X X X X X X X X X X X X
X X X G X X X X X X X X X X X X P P X X X S X X X
X X X X X X X X X X X X X X X X X X X X X X X X X
X X X X X X X X X X X X X X X X X X X X X X X X R
X X X X X X X X X X X X X X X X X X X X X X X X X
X X L X X X X X X X X X X L The following protein sequence <SEQ ID NO: 7> is the 66 amino acid active domain of Nogo:
R I Y K G V I Q A I Q K S D E G H P F R A Y L E S
E V A I S E E L V Q K Y S N S A L G H V N C T I K
E L R R L F L V D D L V D S L K The following protein sequence <SEQ ID NO: 8> is the amino acid sequence of the mature NgR2:
C P M L C Y C Y S S P P T V S C Q A N N F S S V P
L S L P P S T Q R L F L Q N N L I R T L R P G T F
G S N L L T L W L F S N N L S T I Y P G T F R H L
Q A L E E L D L G D N R H L R S L E P D T F Q G L
E R L Q S L H L Y R C Q L S S L P G N I F R G L V
S L Q Y L Y L Q E N S L L H L Q D D L F A D L A N
L S H L F L H G N R L R L L T E H V F R G L G S L
D R L L L H G N R L Q G V H R A A F R G L S R L T
I L Y L F N N S L A S L P G E A L A D L P S L E F
L R L N A N P W A C D C R A R P L W A W F Q R A R
V S S S D V T C A T P P E R Q G R D L R A L R E A
D F Q A C P P A A P T R P G S R A R G N S S S N H
L Y G V A E A G A P P A D P S T Y L R D L P A E D
S R G R Q G G D A P T E D D Y W G G Y G G E D Q R
G E Q M C P G A A C Q A P P D S R G P A L S A G L
P S P L L C L L L L V P H H L The following protein sequence <SEQ ID NO: 9> is the amino acid sequence of the mature NgR3:
C P R D C V C Y P A P M T V S C Q A H N F A A I P
E G I P E D S E R I F L Q N N R I T F L Q Q G H F
S P A M V T L W I Y S N N I T F I A P N T F E G F
V H L E E L D L G D N R Q L R T L A P E T F Q G L
V K L H A L Y L Y K C G L S A L P A G I F G G L H
S L Q Y L Y L Q D N H I E Y L Q D D I F V D L V N
L S H L F L H G N K L W S L G Q G I F R G L V N L
D R L L L H E N Q L Q W V H H K A F H D L H R L T
T L F L F N N S L T E L Q G D C L A P L V A L E F
L R L N G N A W D C G C R A R S L W E W L R R F R
G S S S A V P C A T P E L R Q G Q D L K L L R V E
D F R N C T G P V S P H Q I K S H T L T T S D R A
A R K E H H P S H G A S R D K G H P H G H P P G S
R S G Y K K A G K N C T S H R N R N Q I S K V S S
G K E L T E L Q D Y A P D Y Q H K F S F D I M P T
A R P K R K G K C A R R T P I R A P S G V Q Q A S
S G T A L G A P L L A W I L G L A V T L R The following amino acid sequence <SEQ ID NO:10> is a conserved cysteine motif (Cysteine domain 1) of the NgR and homologs based on the Consensus Sequence:
C P X X C X C Y X X P X X T X S C The following amino acid sequence <SEQ ID NO:11> is a conserved cysteine motif (Cysteine domain 2) of the NgR and homologs based on the Consensus Sequence:
N X W X C X C R A R X L W X W X X X X R X S S S X
V X C X X P X X X X G X D L X X L X X X D X X X C The following amino acid sequence <SEQ ID NO:12> is a conserved Leucine-rich domain of the NgR and homologs based on the Consensus Sequence:
R X F L X X N X I X X X X X X X F X X X X X X X X
L W X X S N X X X X I X X X X F X X X X X L E X L
D L X D N X X L R X X X P X T F X G L X X L X L X
L X X C X L X X L X X X X F X G L X X L Q Y L Y L
Q X N X X X X L X D D X G X D L X N L X H L F L H
G N X X X X X X X X X F R G L X X L D R L L L H X
N X X X X V H X X A F X X L X R L X X L X L F X N
X L X X L X X X X L A X L X X L X X L R L Unless otherwise indicated, X is any amino acid. For example, X where indicated may be no amino acid. Additional features of the invention will be apparent from the following Examples. Examples 1-5 are actual, while the remaining Examples are prophetic.

As shown by the following Examples, a gene encoding novel NgRs have been identified by computational analysis of DNA sequence data. The proteins encoded by NgR2 and NgR3 have a putative signal sequence, eight leucine-rich repeat domains in a conserved leucine-rich region (SEQ ID NO:12), a conserved cysteine-rich region (SEQ ID NO:10) N-terminal to the leucine-rich region, a second cysteine-rich domain (SEQ ID NO:11) C-terminal to the leucine-rich region, and a putative glycophosphatidylinositol-linkage (GPI-linkage) site. NgR2 and NgR3 differ from the previously identified NgR sequence. The NgR homologs, when compared to known NgRs, show a consensus sequence (SEQ ID NOs:6). The putative mature NgR2 and NgR3 are shown in Table 5 as SEQ ID NOs: 8 and 9, respectively.

EXAMPLE 1

Tblastn Query of the HTG Database

The protein sequence for the human NgR (NgR1) (SEQ ID NO:5) was used to query the high throughput genomic (HTG) database the use of which is familiar to those skilled in the art. The HTG database is a part of GenBank, a comprehensive NIH genetic sequence database, which includes an annotated collection of all publicly available DNA sequences (*Nucleic Acids Res*. (2000) 28, 15-8). The HTG database includes sequences obtained from genomic DNA. Within genomic DNA, genes are typically encoded by multiple segments of DNA called exons. Thus when one aligns a cDNA sequence (or a protein sequence encoded by a cDNA sequence) to a genomic sequence, the sequence will be broken up into segments depending on the number of exons in the gene.

The BLAST algorithm, which stands for Basic Local Alignment Search Tool is suitable for determining sequence similarity (Altschul et al., (1990) *J. Mol. Biol*. 215, 403-410, which is incorporated herein by reference in its entirety). Software for performing BLAST analyses is publicly available through the National Center for Biotechnology Information (http://www.ncbi.nlm.nih.gov/). The basic BLAST algorithm involves first identifying high scoring sequence pair (HSPs) by identifying short words of length W in the query sequence that either match or satisfy some positive-valued threshold score T when aligned with a word of the same length in a database sequence. T is referred to as the neighborhood word score threshold (Altschul et al., supra). These initial neighborhood word hits act as seeds for initiating searches to find HSPs containing them. The word hits are extended in both directions along each sequence for as far as the cumulative alignment score can be increased. Extension for the word hits in each direction are halted when: 1) the cumulative alignment score falls off by the quantity X from its maximum achieved value; 2) the cumulative score goes to zero or below, due to the accumulation of one or more negative-scoring residue alignments; or 3) the end of either sequence is reached. The Blast algorithm parameters W, T and X determine the sensitivity and speed of the alignment. The Blast program uses as defaults a word length (W) of 11, the BLOSUM62 scoring matrix (see Henikoff et al., (1992) *Proc. Natl. Acad. Sci. USA* 89, 10915-10919, which is incorporated herein by reference in its entirety) alignments (B) of 50, expectation (E) of 10, M=5, N=4, and a comparison of both strands.

The BLAST algorithm (Karlin et al., (1993) *Proc. Natl. Acad. Sci. USA* 90, 5873-5787, which is incorporated herein by reference) and Gapped BLAST perform a statistical analysis of the similarity between two sequences. One measure of similarity provided by the BLAST algorithm is the smallest sum probability (P(N)), which provides an indication of the probability by which a match between two nucleotide or amino acid sequences would occur by chance. For example, a nucleic acid is considered similar to a NgR gene or cDNA if the smallest sum probability in comparison of the test nucleic acid to a NgR nucleic acid is less than about 1, preferably less than about 0.1, more preferably less than about 0.01, and most preferably less than about 0.001.

To query the HTG database with the NgR protein sequence, we used a variation of the BLAST algorithm known as the tblastn program, which compares a protein query sequence against a nucleotide sequence database dynamically translated in all reading frames (*J. Mol. Biol*. (1990) 215, 403-410: *Nucleic Acids Res*. (1997) 25, 3389-3402). The results of the tblastn search indicated the presence of genes in the database with a significant identity to the NgR. In addition to finding hits to genomic clones which contain the human and mouse NgR genes, we found hits to clones where the identity was not as high, but still very significant. Three human clones were found (Accession numbers: AC068514, AC016869, AC013606) with an e-value of 4e-43 and one mouse clone was found (Accession No. AC021768) with an e-value of 1e-78. The three human clones all appeared to encode the same gene, so further analysis was confined to AC013606.

EXAMPLE 2

Prediction of the Human NgR2 Protein Sequence (AC013606)

The human NgR protein sequence aligned with two regions of translated sequence from nucleotide sequence AC013606, indicating that the new gene was encoded by at least two exons. In order to define the complete gene, we used the computer program GENSCAN™ (*J. Mol. Biol*. (1997) 268, 78-94) which can identify complete exon/intron structures of genes in genomic DNA. The gene prediction by GENESCAN™ contained seven exons. By comparing these predicted exons to the NgR, it was concluded that the new human gene contains two of these exons and a part of another (containing the initiating methionine). The predicted cDNA (mRNA) encoded by these three exons was assembled from AC013606 (HTG11; deposited March 2000; length=143899; GenBank release 118.0; SEQ ID NO:15) by combining nucleotides from the three exons whose coordinates are: 123292-123322 (exon 1); 130035-130516 (exon 2); and 138589-139335 (exon 3). The sequence for this cDNA sequence is SEQ ID NO:1 (nucleotide sequence of human NgR2; AC013606). The translation of this cDNA provides the protein sequence of human NgR2 (SEQ ID NO:2).

We used the protein sequence of human NgR2 as a query sequence against the human EST database. A number of hits of high significance were found indicating that the NgR2 mRNA is expressed in a number of tissues including fetal brain. Furthermore, two of these ESTs provided support for the exon structure that we deduced. One EST (Accession No: GB_EST19:AI346757) contains 565 nucleotides corresponding to amino acids 84-271 of the human NgR2 (SEQ ID No:4). This spans the second intron located between amino acids 171 and 172, and provides positive evidence for the splicing of exons 2 and 3 at the mRNA level. Another EST (GB_EST26:A1929019) contains 545 nucleotides, part of which corresponds to amino acids 1-75 of the human NgR2 (SEQ ID NO:2). This spans the first intron located between amino acids 10 and 11, and provides positive evidence for the splicing of exons 1 and 2 at the mRNA level

EXAMPLE 3

Prediction of the Mouse NgR3 Protein Sequence (AC021768)

The human NgR protein sequence aligned with only one region of translated sequence from nucleotide sequence AC021768, indicating that most of the new mouse gene was encoded by one large exon. However, upon inspection, the protein encoded by this exon was missing an initiating methionine. In order to define the complete gene, we used the computer program GENSCAN as described above. The gene-prediction by GENSCAN contained two exons; the large one found by visual inspection and a short one at the 5' end which provided an initiating methionine. The predicted cDNA (mRNA) encoded by these two exons was assembled from AC021768 (HTG14; deposited March 2000; length=215980; GenBank release 118.0; SEQ ID NO:16) by combining nucleotides from the two exons whose coordinates are: the complement of 164265-164325 (exon 1); and the complement of 155671-156992 (exon 2). The sequence for this cDNA sequence is SEQ ID NO:3 (nucleotide sequence of mouse NgR3; AC021768). The translation of this cDNA provides the protein sequence of mouse NgR3 (SEQ ID NO:4).

We used the protein sequence of mouse NgR3 as a query sequence against the mouse EST database. One hit of high significance was found indicating that the NgR2 mRNA is expressed in the heart. This EST (GB_EST20:AI428334) contains 463 nucleotides, part of which correspond to amino acids 45-193 of mouse NgR3 (SEQ ID NO:4).

EXAMPLE 4

Similarity Between the NgRs

An alignment between NGR1 and the two new receptors is shown in FIG. 1A-1B. The similarities between these proteins include:

(1) The SignalP program, which locates the signal sequence cleavage position, predicts a cleavage before the first conserved cysteine in all the proteins. Thus the mature protein in all cases will have a cysteine at the N-terminus.

(2) All proteins contain eight Leucine Rich Repeats (LRR). LRRs are short sequence motifs present in a number of proteins with diverse functions and cellular locations. These repeats are usually involved in protein-protein interactions. Each LRR is composed of a beta-alpha unit.

(3) All three proteins contain a leucine rich repeat N-terminal domain (LRRNT), in which four cysteines are conserved. LRRs are often flanked by cysteine rich domains at both their N and C termini.

(4). All three proteins contain a LRR C-terminal domain (LRRCT). The LRRCTs of the three NgR proteins can be distinguished from those of other LRR containing proteins, by the pattern of typtophans and cysteines which are completely conserved in this domain.

(5) All three proteins contain a conserved cysteine in the fourth LRR domain.

(6) All three proteins contain a conserved potential glycosylation site in the eighth LRR domain.

(7) NgR2 and NgR3 have a hydrophobic C-terminus, as does NgR1, an indication that they probably also undergo a modification similar to NGR1, where a GPI moiety is covalently linked to a C-terminal amino acid. This allows the protein to remain tethered to the cell.

EXAMPLE 5

Preparation of Nogo Proteins

A Nogo binding assay was developed which utilizes a method widely used in examining semaphorin and ephrin axonal guidance function (Flanagan & Vanderhaeghen (1998) *Annu. Rev. Neurosci.* 21, 309-345; Takahashi et al., (1999) *Cell* 99, 59-69). It involves fusing a secreted placental alkaline phosphatase (AP) moiety to the ligand in question to provide a biologically active receptor binding agent which can be detected with an extremely sensitive colorimetric assay. For Nogo, an expression vector is created encoding a signal peptide, a His6 tag for purification, AP, and the 66 amino acid active domain of Nogo. The fusion protein can be purified from the conditioned medium of transfected cells in milligram amounts. This protein is biologically active as a growth cone collapsing agent with an $EC_{50}$ of 1 nM.

Alternatively, a glutathione-S-transferase Nogo (GST-Nogo) fusion protein may be prepared. For GST-Nogo, an expression vector (e.g., a pGEX vector) is created encoding a signal peptide, GST, and the 66 amino acid active domain of Nogo. GST-Nogo may be purified from the culture medium and used as a GST fusion protein, or GST may be cleaved from the Nogo portion of the fusion protein with an enzyme that recognizes the specific amino acid cleavage sit engineered between the GST portion and the Nogo portion of the fusion protein. Such sites are part of the commercially available GST vectors. The specific cleavage sites and enzymes may be used in accordance with the Manufacturer's specifications.

It has been found that AP-Nogo is actually slightly more potent than GST-Nogo, perhaps because the protein is synthesized in a eukaryotic rather than a prokaryotic cell.

Binding of Nogo to immobilized NgR homologs may be performed in an ELISA-type assay in which AP-Nogo is allowed to react with an immobilized receptor homolog Specificity of binding may be demonstrated in a competitive binding assay using increasing amounts of GST-Nogo in the type of assay to show a decreasing amount of binding of AP-Nogo (as judged in the calorimetric assay).

EXAMPLE 6

Transfected COS Cell Binding Assays

The homologs of the present invention may be used in transfection studies in COS cells to demonstrate binding of Nogo. Specifically, nucleotide sequences encoding NgR2 and NgR3 may be transfected into COS cells using a suitable vector. Non-transfected COS-7 cells do not bind AP-Nogo. However, transfection of COS cells with nucleic acid sequences encoding NgRs will make them capable of binding Nogo. AP alone does not bind with any stable affinity to these transfected cells, indicating that any affinity of Nogo for NgR2 or NgR3 would be due to the 66 amino acids derived from Nogo. Furthermore, specific affinity of Nogo for the NgR2 or NgR3 proteins may be tested in displacement of AP-Nogo assays using GST-Nogo. NgR2 and/or NgR3 may also bind homologs of Nogo, which may also be tested using this assay.

EXAMPLE 7

Expression of NgR in Human Cell Lines Using Northern Blot and a Random-Primed Probe A Northern blot is purchased from a commercial source, or RNA samples from cells of interest are run on an agarose gel and blotted to a membrane using any of the well known techniques for Northern blotting. The blot is probed with a fragment of NgR2 (SEQ ID NO:1) or NgR3 (SEQ ID NO:3). The probe is prepared from 50 ng of cDNA labeled by a random-primed method (Feinberg and Vogelstein (1983) *Anal. Biochem.* 132, 6-13). Hybridization is carried out at 68° C. for 1 hour in ExpressHyb™ solution (Clontech, Cat. No. 8015-1) followed by washing with 2×SSC/0.05% SDS at room temperature and two washes with 0.1×SSC/0.1% SDS at 50° C. Expression of NgR2 and/or NgR3 can be assessed by the presence of an appropriately sized band on the blot.

EXAMPLE 8

Cloning of cDNA Corresponding to NgRs

To obtain the full-length clone corresponding to NgR2 from a cDNA library, the following method may be used. A cDNA library is generated using standard methods from a tissue known to contain NgR2. Such a tissue was identified in Example 2. $1\times10^6$ plaque forming units from the cDNA library may be screened in duplicate on OPTITRAN™ filters. The filters are hybridized with $^{32}P$-labeled oligonucleotides that are generated from the ESTs corresponding to portions of NgR2. The hybridization reaction may consist of 400 mls plaque screen buffer (50 mM Tris pH 7.5, 1M NaCl, 0.1% Sodium pyrophosphate, 0.2% Polyvinylpryolidine and 0.2% Ficoll) containing 10% Dextran sulfate and 100 μg/ml tRNA and 80 pmol each $^{32}P$-labeled oligonucleotide at 65° C. overnight. The filters are washed twice with 2×SSC/1% SDS and twice with 1×SSC/1% SDS and exposed to film. Duplicate positives are purified. DNA from each of these clones is analyzed by restriction enzyme digest followed by agarose gel electrophoresis and Southern blotting. The filters are hybridized to the $^{32}P$-labeled oligonucleotides used for the original hybridization to confirm that inserts hybridize to the probe. The insert is then sequenced to confirm that it represents the cDNA for NgR2. Similar methods may be used to generate a full-length clone corresponding to NgR3.

Alternatively, a full-length clone of NgR2 or NgR3 can be obtained by a person of ordinary skill in the art employing conventional PCR techniques.

EXAMPLE 9

Hybridization Analysis to Demonstrate NgR Expression in the Brain

The expression of NgR in mammals, such as the rat, may be investigated by in situ hybridization histochemistry. To investigate expression in the brain, for example, coronal and sagittal rat brain cryosections (20 μm thick) are prepared using a Reichert-Jung cryostat. Individual sections are thaw-mounted onto silanized, nuclease-free slides (CEL Associates, Inc., Houston, Tex.), and stored at −80° C. Sections are processed starting with post-fixation in cold 4% paraformaldehyde, rinsed in cold phosphate-buffered saline (PBS), acetylated using acetic anhydride in triethanolamine buffer, and dehydrated through a series of alcohol washes in 70%, 95%, and 100% alcohol at room temperature. Subsequently, sections are delipidated in chloroform, followed by rehydration through successive exposure to 100% and 95% alcohol at room temperature. Microscope slides containing processed cryosections are allowed to air dry prior to hybridization. Other tissues may be assayed in a similar fashion.

A NgR-specific probe may be generated using PCR. Following PCR amplification, the fragment is digested with restriction enzymes and cloned into pBluescript II cleaved with the same enzymes. For production of a probe specific for the sense strand of NgR, a cloned NgR fragment cloned in pBluescript II may be linearized with a suitable restriction enzyme, which provides a substrate for labeled run-off transcripts (i.e., cRNA riboprobes) using the vector-borne T7 promoter and commercially available T7 RNA polymerase. A probe specific for the antisense strand of NgR may also be readily prepared using the NgR clone in pBluescript II by cleaving the recombinant plasmid with a suitable restriction enzyme to generate a linearized substrate for the production of labeled run-off cRNA transcripts using the T3 promoter and cognate polymerase. The riboprobes may be labeled with [$^{35}S$]-UTP to yield a specific activity of about $0.40\times10^6$ cpm/pmol for antisense riboprobes and about $0.65\times10^6$ cpm/pmol for sense-strand riboprobes. Each riboprobe may be subsequently denatured and added (2 pmol/ml) to hybridization buffer which contains 50% formamide, 10% dextran, 0.3 M NaCl, 10 mM Tris (pH 8.0), 1 mM EDTA, 1× Denhardt's Solution, and 10 mM dithiothreitol. Microscope slides containing sequential brain cryosections may be independently exposed to 45 μl of hybridization solution per slide and silanized cover slips may be placed over the sections being exposed to hybridization solution. Sections are incubated overnight (15-18 hours) at 52° C. to allow hybridization to occur. Equivalent series of cryosections are then exposed to sense or antisense NgR-specific cRNA riboprobes.

Following the hybridization period, coverslips are washed off the slides in 1X SSC, followed by RNase A treatment involving the exposure of slides to 20 μg/ml RNase A in a buffer containing 10 mM Tris-HCl (pH 7.4), 0.5 M EDTA, and 0.5 M NaCl for 45 minutes at 37° C. The cryosections are then subjected to three high-stringency washes in 0.1X SSC at 52° C. for 20 minutes each. Following the series of washes, cryosections are dehydrated by consecutive exposure to 70%, 95%, and 100% ammonium acetate in alcohol, followed by air drying and exposure to Kodak BioMax™ MR-1 film. After 13 days of exposure, the film is developed, and any significant hybridization signal is detected. Based on these results, slides containing tissue that hybridized, as shown by film autoradiograms, are coated with Kodak NTB-2 nuclear track emulsion and the slides are stored in the dark for 32 days. The slides are then developed and counterstained with hematoxylin. Emulsion-coated sections are analyzed microscopically to determine the specificity of labeling. The signal is determined to be specific if autoradiographic grains (generated by antisense probe hybridization) are clearly associated with cresyl violate-stained cell bodies. Autoradiographic grains found between cell bodies indicate non-specific binding of the probe.

In some cases, such as using a probe to detect a NgR homolog in a heterologous species, in order to achieve optimal hybridization, it may be necessary to decrease the stringency conditions. Such conditions are well known to those of ordinary skill in the art and examples are provided above.

Expression of NgR in the brain provides an indication that modulators of NgR activity have utility for treating neurological disorders. Some other diseases for which modulators of NgR may have utility include depression, anxiety, bipolar disease, epilepsy, neuritis, neurasthenia, neuropathy, neuroses, and the like. Use of NgR modulators, including NgR ligands and anti-NgR antibodies, to treat individuals having such disease states is intended as an aspect of the invention.

EXAMPLE 10

Northern Blot Analysis of NgR-RNA with a PCR-Generated Probe

Northern blot hybridizations may be performed to examine the expression of NgR mRNA. A clone containing at least a portion of the sequence of SEQ ID NO:1 may be used as a probe. Vector-specific primers are used in PCR to generate a hybridization probe fragment for $^{32}P$-labeling. The PCR is performed as follows:

| | | |
|---|---|---|
| Mix: | 1 μl | NgR-containing plasmid |
| | 2 μl | fwd primer (10-50 pM) |
| | 2 μl | rev primer (10-50 pM) |
| | 10 μl | 10xPCR buffer (such as that provided with the enzyme, Amersham Pharmacia Biotech) |
| | 1 μl | 10 mM dNTP (such as #1 969 064 from Boehringer Mannheim) |
| | 0.5 μl | Taq polymerase (such as #27-0799-62, Amersham Pharmacia Biotech) |
| | 83.5 μl | water |

PCR is performed in a Thermocycler using the following program:

| | | |
|---|---|---|
| 94° C. | 5 min | |
| 94° C. | 1 min | 30 cycles |
| 55° C. | 1 min | 30 cycles |
| 72° C. | 1 min | 30 cycles |
| 72° C. | 10 min | |

The PCR product may be purified using QIAquick PCR Purification Kit (#28104) from Qiagen, and radictively labeled with $^{32}$P-dCTP (#AA0005/250, Amersham Pharmacia Biotech)) may be done by random priming using "Ready-to-go DNA Labeling Beads" (#27-9240-01) from Amersham Pharmacia Biotech. Hybridization is carried out on Human Multiple Tissue Northern Blot from Clontech as described in manufacturer's protocol or on a Northern Blot prepared by running RNA samples from cells of interest on an agarose gel and blotting to a membrane using any of the known Northern blotting protocols. After exposure overnight on Molecular Dynamics Phosphor Imager screen (#MD146-814) bands of an appropriate size are visualized.

EXAMPLE 11

Recombinant Expression of NgR in Eukaryotic Host Cells

A. Expression of NgR in Mammalian Cells

To produce NgR protein, a NgR-encoding polynucleotide is expressed in a suitable host cell using a suitable expression vector and standard genetic engineering techniques. For example, a NgR-encoding sequence described in Table 4 is subcloned into the commercial expression vector pzeoSV2 (Invitrogen, San Diego, Calif.) and transfected into Chinese Hamster Ovary (CHO) cells using the transfection reagent FuGENE6™ (Boehringer-Mannheim) and the transfection protocol provided in the product insert. Other eukaryotic cell lines, including human embryonic kidney (HEK 293) and COS cells, are suitable as well. Cells stably expressing NgR are selected by growth in the presence of 100 μg/ml zeocin (Stratagene, LaJolla, Calif.). As an alternative to FuGENE6™, the expression vector may carry the gene for dihydrofolate reductase (dhfr) and selection of clones with methotrexate (MTX) drug pressure allows for stable transformation of CHO cells. Optionally, NgR may be purified from the cells using standard chromatographic techniques. To facilitate purification, antisera is raised against one or more synthetic peptide sequences that correspond to portions of the NgR amino acid sequence, and the antisera is used to affinity purify Nogo-R. The NgR also may be expressed in-frame with a tag sequence (e.g., polyhistidine, hemaglutinin, FLAG) to facilitate purification. Moreover, it will be appreciated that many of the uses for NgR polypeptides, such as assays described below, do not require purification of NgR from the host cell.

B. Expression of NgR in CHO Cells

For expression of NgR in Chinese hamster ovary (CHO) cells, a plasmid bearing the relevant NgR coding sequence is prepared, using a vector which also bears the selectable marker dihydrofolate reductase (DHFR). The plasmid is transfected into CHO cells. Selection under MTX drug pressure allows for preparation of stable transformants of a NgR (NgR2 or NgR3) in an expression plasmid carrying a selectable marker such as DHFR.

C. Expression of NgR in 293 Cells

For expression of NgR in mammalian cells 293 (transformed human, primary embryonic kidney cells), a plasmid bearing the relevant NgR coding sequence is prepared, using vector pSecTag2A (Invitrogen). Vector pSecTag2A contains the murine IgK chain leader sequence for secretion, the c-myc epitope for detection of the recombinant protein with the anti-myc antibody, a C-terminal polyhistidine for purification with nickel chelate chromatography, and a Zeocin resistant gene for selection of stable transfectants. The forward primer for amplification of this NgR cDNA is determined by routine procedures and preferably contains a 5' extension of nucleotides to introduce the HindIII cloning site and nucleotides matching the NgR sequence. The reverse primer is also determined by routine procedures and preferably contains a 5' extension of nucleotides to introduce an XhoI restriction site for cloning and nucleotides corresponding to the reverse complement of the NgR sequence. The PCR conditions are 55° C. as the annealing temperature. The PCR product is gel purified and cloned into the HindIII-XhoI sites of the vector.

The DNA is purified using Qiagen chromatography columns and transfected into 293 cells using DOTAP™ transfection media (Boehringer Mannheim, Indianapolis, Ind.). Transiently transfected cells are tested for expression after 24 hours of transfection, using western blots probed with anti-His and anti-NgR peptide antibodies. Permanently transfected cells are selected with Zeocin and propagated. Production of the recombinant protein is detected from both cells and media by Western blots probed with anti-His, anti-Myc or anti-NgR peptide antibodies.

D. Transient Expression of Nogo-R in COS Cells

For expression of the NgR in COS7 cells, a polynucleotide molecule having a nucleotide sequence of SEQ ID NO:1, for example, can be cloned into vector p3-CI. This vector is a pUC18-derived plasmid that contains the HCMV (human cytomegalovirus) promoter-intron located upstream from the bGH (bovine growth hormone) polyadenylation sequence and a multiple cloning site.

The forward primer is determined by routine procedures and preferably contains a 5' extension which introduces an XbaI restriction site for cloning, followed by nucleotides which correspond to a nucleotide sequence of SEQ ID NO:1. The reverse primer is also determined by routine procedures and preferably contains 5'-extension of nucleotides which introduces a SalI cloning site followed by nucleotides which correspond to the reverse complement of a nucleotide sequence of SEQ ID NO:1.

The PCR consists of an initial denaturation step of 5 min at 95° C., 30 cycles of 30 sec denaturation at 95° C., 30 sec annealing at 58° C. and 30 sec extension at 72° C., followed by 5 min extension at 72° C. The PCR product is gel purified and ligated into the XbaI and SalI sites of vector p3-CI. This construct is transformed into *E. coli* cells for amplification and DNA purification. The DNA is purified with Qiagen chromatography columns and transfected into COS 7 cells using Lipofectamine™ reagent from BRL, following the manufacturer's protocols. Forty-eight and 72 hours after transfection, the media and the cells are tested for recombinant protein expression.

NgR expressed from a COS cell culture can be purified by concentrating the cell-growth media to about 10 mg of protein/ml, and purifying the protein by, for example, chromatography. Purified NgR is concentrated to 0.5 mg/ml in an Amicon concentrator fitted with a YM-10 membrane and stored at −80° C. NgR3 may also be expressed using this method and the nucleotide sequence of SEQ ID NO:3 or SEQ ID NO:13.

E. Expression of NgR in Insect Cells

For expression of NgR in a baculovirus system, a polynucleotide molecule having a nucleotide sequence of SEQ ID NO:1, 3 or 13 can be amplified by PCR. The forward primer is determined by routine procedures and preferably contains a 5' extension which adds the NdeI cloning site, followed by nucleotides which correspond to a nucleotide sequence of SEQ ID NO:1 (or SEQ ID NO:3 or SEQ ID NO:13, respectively). The reverse primer is also determined by routine procedures and preferably contains a 5' extension which introduces the KpnI cloning site, followed by nucleotides which correspond to the reverse complement of a nucleotide sequence of SEQ ID NO:1 (or SEQ ID NO:3 or SEQ ID NO:13, respectively).

The PCR product is gel purified, digested with NdeI and KpnI, and cloned into the corresponding sites of vector pACHTL-A (Pharmingen, San Diego, Calif.). The pAcHTL expression vector contains the strong polyhedrin promoter of the *Autographa californica* nuclear polyhedrosis virus (AcMNPV), and a 6XHis tag upstream from the multiple cloning site. A protein kinase site for phosphorylation and a thrombin site for excision of the recombinant protein precede the multiple cloning site is also present. Of course, many other baculovirus vectors could be used in place of pAcHTL-A, such as pAc373, pVL941 and pAcIM1. Other suitable vectors for the expression of NgR polypeptides can be used, provided that the vector construct includes appropriately located signals for transcription, translation, and trafficking, such as an in-frame AUG and a signal peptide, as required. Such vectors are described in Luckow et al., Virology 170:31-39, among others.

The virus is grown and isolated using standard baculovirus expression methods, such as those described in Summers et al. (1987) A MAnnual OF METHODS FOR BACULOVIRUS VECTORS AND INSECT CELL CULTURE PROCEDURES, Texas Agricultural Experimental Station Bulletin No. 1555.

In a preferred embodiment, pAcHLT-A containing NgR gene is introduced into baculovirus using the "BaculoGold™" transfection kit (Pharmingen, San Diego, Calif.) using methods established by the manufacturer. Individual virus isolates are analyzed for protein production by radiolabeling infected cells with $^{35}$S-methionine at 24 hours post infection. Infected cells are harvested at 48 hours post infection, and the labeled proteins are visualized by SDS-PAGE. Viruses exhibiting high expression levels can be isolated and used for scaled up expression.

For expression of a NgR polypeptide in a Sf9 cells, a polynucleotide molecule having the nucleotide sequence of SEQ ID NO:1 (or SEQ ID NO:3 or SEQ ID NO:13) can be amplified by PCR using the primers and methods described above for baculovirus expression. The NgR cDNA is cloned into vector pAcHLT-A (Pharmingen) for expression in Sf9 insect. The insert is cloned into the NdeI and KpnI sites, after elimination of an internal NdeI site (using the same primers described above for expression in baculovirus). DNA is purified with Qiagen chromatography columns and expressed in Sf9 cells. Preliminary Western blot experiments from non-purified plaques are tested for the presence of the recombinant protein of the expected size which reacted with the NgR-specific antibody. These results are confirmed after further purification and expression optimization in HiG5 cells F. Expression of Soluble Forms of NgR2 and NgR3 as NgR-Ig Fusion Proteins.

To generate a NgR2-Ig fusion protein, standard methods may be used as described in the literature (e.g. Sanicola et al. (1997) *Proc. Natl. Acad. Sci. USA.* 94, 6238-6243). For example, a DNA fragment encoding NgR2 without the sequence encoding the hydrophobic C-terminus (GPI anchor signal) may be ligated to a DNA fragment encoding the Fc domain of IgG1 (which may be human IgG1), and the chimeric fragment may be cloned into an expression vector to generate a plasmid. The plasmid may then be transfected into Chinese hamster ovary cells to generate a stable cell line producing the fusion protein. The fusion protein is then purified from conditioned media using standard methods. For example, clarified conditioned media from the cell line may be loaded by gravity directly onto Protein A Sepharose. The column may then be washed with five column volumes each of PBS, PBS containing 0.5 M NaCl, and 25 mM sodium phosphate, 100 mM NaCl (pH 5.0). The bound protein may then be eluted with 25 mM $NaH_2PO_4$, 100 mM NaCl (pH 2.8) and immediately neutralized with 1/10 fraction volume of 0.5 M $Na_2HPO_4$ (pH 8.6).

Similar methods may be used to generate a NgR3-Ig fusion protein.

EXAMPLE 12

Interaction Trap/Two-Hybrid System

In order to assay for NgR-interacting proteins, the interaction trap/two-hybrid library screening method can be used. This assay was first described in Fields et al. (1989) *Nature* 340, 245, which is incorporated herein by reference in its entirety. A protocol is published in CURRENT PROTOCOLS IN MOLECULAR BIOLOGY 1999, John Wiley & Sons, NY and Ausubel, F. M. et al. 1992, SHORT PROTOCOLS IN MOLECULAR BIOLOGY, fourth edition, Greene and Wiley-interscience, NY, which is incorporated herein by reference in its entirety. Kits are available from Clontech, Palo Alto, Calif. (Matchmaker Two-Hybrid System 3).

A fusion of the nucleotide sequences encoding all or partial NgR and the yeast transcription factor GAL4 DNA-binding domain (DNA-BD) is constructed in an appropriate plasmid (i.e., pGBKT7) using standard subcloning techniques. Similarly, a GAL4 active domain (AD) fusion library is constructed in a second plasmid (i.e., pGADT7) from cDNA of potential NgR-binding proteins (for protocols on forming cDNA libraries, see Sambrook et al. 1989, MOLECULAR CLONING: A LABORATORY MANUAL, second edition, Cold Spring Harbor Laboratory Press, Cold Spring Harbor, N.Y.), which is incorporated herein by reference in its entirety. The DNA-BD/NgR fusion construct is verified by sequencing, and tested for autonomous reporter gene activation and cell toxicity, both of which would prevent a successful two-hybrid analysis. Similar controls are performed with the AD/library fusion construct to ensure expression in host cells and lack of transcriptional activity. Yeast cells are transformed (ca. 105 transformants/mg DNA) with both the NgR and library fusion plasmids according to standard procedure (Ausubel, et al., 1992, SHORT PROTOCOLS IN MOLECULAR BIOLOGY, fourth edition, Greene and Wiley-interscience, NY, which is incorporated herein by reference in its entirety). In vivo binding of DNA-BD/NgR with AD/library proteins results in transcription of specific yeast plasmid reporter genes (i.e., lacZ, HIS3, ADE2, LEU2). Yeast cells are plated on nutrient-deficient media to screen for expression of reporter genes. Colonies are dually assayed for β-galactosidase activity upon growth in Xgal (5-bromo-4-chloro-3-indolyl-b-D-galactoside) supplemented media (filter assay for b-galactosidase activity is described in Breeden et al., (1985) *Cold Spring Harb. Symp. Quant. Biol.,* 50, 643, which is incorporated herein by reference in its entirety). Positive AD-library plasmids are rescued from transformants and reintroduced into the original yeast strain as well as other strains containing unrelated DNA-BD fusion proteins to confirm specific NgR/library protein interactions. Insert DNA is sequenced to verify the presence of an open reading frame fused to GAL4 AD and to determine the identity of the NgR-binding protein.

EXAMPLE 13

Antibodies to Nogo-R

Standard techniques are employed to generate polyclonal or monoclonal antibodies to the NgR receptor, and to generate useful antigen-binding fragments thereof or variants thereof, including "humanized" variants. Such protocols can be found, for example, in Sambrook et al. (1989), above, and Harlow et al. (Eds.), ANTIBODIES A LABORATORY MANUAL; Cold Spring Harbor Laboratory Press, Cold Spring Harbor, N.Y. (1988). In one embodiment, recombinant NgR polypeptides (or cells or cell membranes containing such polypeptides) are used as antigen to generate the antibodies. In another embodiment, one or more peptides having amino acid sequences corresponding to an immunogenic portion of NgR (e.g., 6, 7, 8, 9, 10, 11, 12, 13, 14, 15, 16, 17, 18, 19, 20, or more amino acids) are used as antigen. Peptides corresponding to extracellular portions of Nogo-R, especially hydrophilic extracellular portions, are preferred. The antigen may be mixed with an adjuvant or linked to a hapten to increase antibody production.

A. Polyclonal or Monoclonal Antibodies

As one exemplary protocol, recombinant NgR or a synthetic fragment thereof is used to immunize a mouse for generation of monoclonal antibodies (or larger mammal, such as a rabbit, for polyclonal antibodies). To increase antigenicity, peptides are conjugated to Keyhole Limpet Hemocyanin (Pierce), according to the manufacturer's recommendations. For an initial injection, the antigen is emulsified with Freund's Complete Adjuvant and injected subcutaneously. At intervals of two to three weeks, additional aliquots of NgR antigen are emulsified with Freund's Incomplete Adjuvant and injected subcutaneously. Prior to the final booster injection, a serum sample is taken from the immunized mice and assayed by western blot to confirm the presence of antibodies that immunoreact with NgR. Serum from the immunized animals may be used as polyclonal antisera or used to isolate polyclonal antibodies that recognize NgR. Alternatively, the mice are sacrificed and their spleen removed for generation of monoclonal antibodies.

To generate monoclonal antibodies, the spleens are placed in 10 ml serum-free RPMI 1640, and single cell suspensions are formed by grinding the spleens in serum-free RPMI 1640, supplemented with 2 mM L-glutamine, 1 mM sodium pyruvate, 100 units/ml penicillin, and 100 μg/ml streptomycin (RPMI) (Gibco, Canada). The cell suspensions are filtered and washed by centrifugation and resuspended in serum-free RPMI. Thymocytes taken from three naive Balb/c mice are prepared in a similar manner and used as a Feeder Layer. NS-1 myeloma cells, kept in log phase in RPMI with 10% fetal bovine serum (FBS) (Hyclone Laboratories, Inc., Logan, Utah) for three days prior to fusion, are centrifuged and washed as well.

To produce hybridoma fusions, spleen cells from the immunized mice are combined with NS-1 cells and centrifuged, and the supernatant is aspirated. The cell pellet is dislodged by tapping the tube, and 2 ml of 37° C. PEG 1500 (50% in 75 mM HEPES, pH 8.0) (Boehringer-Mannheim) is stirred into the pellet, followed by the addition of serum-free RPMI. Thereafter, the cells are centrifuged, resuspended in RPMI containing 15% FBS, 100 μM sodium hypoxanthine, 0.4 μM aminopterin, 16 μM thymidine (HAT) (Gibco), 25 units/ml IL-6 (Boehringer-Mannheim) and $1.5\times10^6$ thymocytes/ml, and plated into 10 Corning flat-bottom 96-well tissue culture plates (Corning, Corning, N.Y.).

On days 2, 4, and 6 after the fusion, 100 μl of medium is removed from the wells of the fusion plates and replaced with fresh medium. On day 8, the fusions are screened by ELISA, testing for the presence of mouse IgG that binds to NgR. Selected fusion wells are further cloned by dilution until monoclonal cultures producing anti-NgR antibodies are obtained.

B. Humanization of Anti-NgR Monoclonal Antibodies

The expression pattern of NgR as reported herein and the potential of NgRs as targets for therapeutic intervention suggest therapeutic indications for NgR inhibitors (antagonists). NgR-neutralizing antibodies comprise one class of therapeutics useful as NgR antagonists. Following are protocols to improve the utility of anti-NgR monoclonal antibodies as therapeutics in humans by "humanizing" the monoclonal antibodies to improve their serum half-life and render them less immunogenic in human hosts (i.e., to prevent human antibody response to non-human anti-NgR antibodies).

The principles of humanization have been described in the literature and are facilitated by the modular arrangement of antibody proteins. To minimize the possibility of binding complement, a humanized antibody of the IgG4 isotype is preferred.

For example, a level of humanization is achieved by generating chimeric antibodies comprising the variable domains of non-human antibody proteins of interest with the constant domains of human antibody molecules. (See, e.g., Morrison et al., (1989) *Adv. Immunol.,* 44, 65-92). The variable domains of NgR-neutralizing anti-NgR antibodies are cloned from the genomic DNA of a B-cell hybridoma or from cDNA generated from mRNA isolated from the hybridoma of interest. The V region gene fragments are linked to exons encoding human antibody constant domains, and the resultant construct is expressed in suitable mammalian host cells (e.g., myeloma or CHO cells).

To achieve an even greater level of humanization, only those portions of the variable region gene fragments that encode antigen-binding complementarity determining regions ("CDR") of the non-human monoclonal antibody genes are cloned into human antibody sequences. (See, e.g., Jones et al., (1986) *Nature* 321, 522-525; Riechmann et al., (1988) *Nature* 332, 323-327; Verhoeyen et al., (1988) *Science* 239, 1534-1536; and Tempest et al., (1991) *Bio/Technology* 9, 266-271). If necessary, the β-sheet framework of the human antibody surrounding the CDR3 regions also is modified to more closely mirror the three dimensional structure of the antigen-binding domain of the original monoclonal antibody. (See Kettleborough et al., (1991) *Protein Engin.* 4, 773-783; and Foote et al., (1992) *J. Mol. Biol.* 224, 487-499).

In an alternative approach, the surface of a non-human monoclonal antibody of interest is humanized by altering selected surface residues of the non-human antibody, e.g., by site-directed mutagenesis, while retaining all of the interior and contacting residues of the non-human antibody. See Padlan (1991) *Mol. Immunol.* 28, 489-498.

The foregoing approaches are employed using NgR-neutralizing anti-NgR monoclonal antibodies and the hybridomas that produce them to generate humanized NgR-neutralizing antibodies useful as therapeutics to treat or palliate conditions wherein NgR expression or ligand-mediated NgR signaling is detrimental.

C. Human NgR-Neutralizing Antibodies from Phage Display

Human NgR-neutralizing antibodies are generated by phage display techniques such as those described in Aujame et al. (1997) *Human Antibodies* 8, 155-168; Hoogenboom (1997) *TIBTECH* 15, 62-70; and Rader et al. (1997), *Curr. Opin. Biotechnol.* 8, 503-508, all of which are incorporated by reference. For example, antibody variable regions in the form of Fab fragments or linked single chain Fv fragments are fused to the amino terminus of filamentous phage minor coat protein pIII. Expression of the fusion protein and incorporation thereof into the mature phage coat results in phage particles that present an antibody on their surface and contain the genetic material encoding the antibody. A phage library comprising such constructs is expressed in bacteria, and the library is screened for NgR-specific phage-antibodies using labeled or immobilized NgR as antigen-probe.

D. Human NgR-Neutralizing Antibodies from Transgenic Mice

Human NgR-neutralizing antibodies are generated in transgenic mice essentially as described in Bruggemann et al. (1996) *Immunol. Today* 17, 391-397 and Bruggemann et al. (1997) *Curr. Opin. Biotechnol.* 8, 455-458. Transgenic mice carrying human V-gene segments in germline configuration and that express these transgenes in their lymphoid tissue are immunized with a NgR composition using conventional immunization protocols. hybridomas are generated using B cells from the immunized mice using conventional protocols and screened to identify hybridomas secreting anti-NgR human antibodies (e.g., as described above)

EXAMPLE 14

Assays to Identify Modulators of NgR Activity

Set forth below are several nonlimiting assays for identifying modulators (agonists and antagonists) of NgR activity. Among the modulators that can be identified by these assays are natural ligand compounds of the receptor; synthetic analogs and derivatives of natural ligands; antibodies, antibody fragments, and/or antibody-like compounds derived from natural antibodies or from antibody-like combinatorial libraries; and/or synthetic compounds identified by high-throughput screening of libraries; and the like. All modulators that bind NgR are useful for identifying NgR in tissue samples (e.g., for diagnostic purposes, pathological purposes, and the like). Agonist and antagonist modulators are useful for up-regulating and down-regulating NgR activity, respectively, to treat disease states characterized by abnormal levels of NgR activity. The assays may be performed using single putative modulators, and/or may be performed using a known agonist in combination with candidate antagonists (or visa versa).

A. cAMP Assays

In one type of assay, levels of cyclic adenosine monophosphate (cAMP) are measured in NgR-transfected cells that have been exposed to candidate modulator compounds. Protocols for cAMP assays have been described in the literature. (See, e.g., Sutherland et al., (1968) *Circulation* 37, 279; Frandsen et al., (1976) *Life Sciences* 18, 529-541; Dooley et al., (1997) *J. Pharmacol. Exp. Therap.* 283, 735-41; and George et al., (1997) *J. Biomol. Screening* 2, 235-40). An exemplary protocol for such an assay, using an Adenylyl Cyclase Activation FlashPlate® Assay from NEN™ Life Science Products, is set forth below.

Briefly, the NgR coding sequence (e.g., a cDNA or intronless genomic DNA) is subcloned into a commercial expression vector, such as pzeoSV2 (Invitrogen), and transiently transfected into Chinese Hamster Ovary (CHO) cells using known methods, such as the transfection protocol provided by Boehringer-Mannheim when supplying the FuGENE 6 transfection reagent. Transfected CHO cells are seeded into 96-well microplates from the FlashPlate® assay kit, which are coated with solid scintillant to which antisera to cAMP has been bound. For a control, some wells are seeded with wild type (untransfected) CHO cells. Other wells in the plate receive various amounts of a cAMP standard solution for use in creating a standard curve.

One or more test compounds (i.e., candidate modulators) are added to the cells in each well, with water and/or compound-free medium/diluent serving as a control or controls. After treatment, cAMP is allowed to accumulate in the cells for exactly 15 minutes at room temperature. The assay is terminated by the addition of lysis buffer containing [$^{125}$I]-labeled cAMP, and the plate is counted using a Packard Topcount™ 96-well microplate scintillation counter. Unlabeled cAMP from the lysed cells (or from standards) and fixed amounts of [$^{125}$I]-cAMP compete for antibody bound to the plate. A standard curve is constructed, and cAMP values for the unknowns are obtained by interpolation. Changes in intracellular cAMP levels of cells in response to exposure to a test compound are indicative of NgR modulating activity. Modulators that act as agonists of receptors which couple to the $G_s$ subtype of G proteins will stimulate production of cAMP, leading to a measurable 3-10 fold increase in cAMP levels. Agonists of receptors which couple to the $G_{i/o}$ subtype of G proteins will inhibit forskolin-stimulated cAMP production, leading to a measurable decrease in cAMP levels of 50-100%. Modulators that act as inverse agonists will reverse these effects at receptors that are either constitutively active or activated by known agonists.

B. Aequorin Assays

In another assay, cells (e.g., CHO cells) are transiently co-transfected with both a NgR expression construct and a construct that encodes the photoprotein apoaquorin. In the presence of the cofactor coelenterazine, apoaquorin will emit a measurable luminescence that is proportional to the amount of intracellular (cytoplasmic) free calcium. (See generally, Cobbold, et al. "Aequorin measurements of cytoplasmic free calcium," In: McCormack J. G. and Cobbold P. H., eds., Cellular Calcium: A Practical Approach. Oxford:IRL Press (1991); Stables et al., (1997) *Anal. Biochem.* 252, 115-26; and Haugland, Handbook of Fluorescent Probes and Research Chemicals. Sixth edition. Molecular Probes, Eugene, Oreg. (1996)).

In one exemplary assay, NgR is subcloned into the commercial expression vector pzeoSV2 (Invitrogen) and transiently co-transfected along with a construct that encodes the photoprotein apoaquorin (Molecular Probes, Eugene, Oreg.) into CHO cells using the transfection reagent FuGENE 6 (Boehringer-Mannheim) and the transfection protocol provided in the product insert.

The cells are cultured for 24 hours at 37° C. in MEM (Gibco/BRL, Gaithersburg, Md.) supplemented with 10% fetal bovine serum, 2 mM glutamine, 10 U/ml penicillin and 10 μg/ml streptomycin, at which time the medium is changed to serum-free MEM containing 5 μM coelenterazine (Molecular Probes, Eugene, Oreg.). Culturing is then continued for two additional hours at 37° C. Subsequently, cells are detached from the plate using VERSEN (Gibco/BRL), washed, and resuspended at 200,000 cells/ml in serum-free MEM.

Dilutions of candidate NgR modulator compounds are prepared in serum-free MEM and dispensed into wells of an opaque 96-well assay plate at 50 μl/well. Plates are then loaded onto an MLX microtiter plate luminometer (Dynex Technologies, Inc., Chantilly, Va.). The instrument is programmed to dispense 50 μl cell suspensions into each well, one well at a time, and immediately read luminescence for 15 seconds. Dose-response curves for the candidate modulators are constructed using the area under the curve for each light signal peak. Data are analyzed with SlideWrite, using the equation for a one-site ligand, and $EC_{50}$ values are obtained. Changes in luminescence caused by the compounds are considered indicative of modulatory activity. Modulators that act as agonists at receptors which couple to the $G_q$ subtype of G proteins give an increase in luminescence of up to 100 fold. Modulators that act as inverse agonists will reverse this effect at receptors that are either constitutively active or activated by known agonists.

C. Luciferase Reporter Gene Assay

The photoprotein luciferase provides another useful tool for assaying for modulators of NgR activity. Cells (e.g., CHO cells or COS 7 cells) are transiently co-transfected with both a NgR expression construct (e.g., NgR in pzeoSV2) and a reporter construct which includes a gene for the luciferase protein downstream from a transcription factor binding site, such as the cAMP-response element (CRE), AP-1, or NF-kappa B. Expression levels of luciferase reflect the activation status of the signaling events. (See generally, George et al (1997) *J. Biomol. Screening* 2, 235-240, and Stratowa et al. (1995) *Curr. Opin. Biotechnol.* 6, 574-581). Luciferase activity may be quantitatively measured using, e.g., luciferase assay reagents that are commercially available from Promega (Madison, Wis.).

In one exemplary assay, CHO cells are plated in 24-well culture dishes at a density of 100,000 cells/well one day prior to transfection and cultured at 37° C. in MEM (Gibco/BRL) supplemented with 10% fetal bovine serum, 2 mM glutamine, 10 U/ml penicillin and 10 μg/ml streptomycin. Cells are transiently co-transfected with both a NgR expression construct and a reporter construct containing the luciferase gene. The reporter plasmids CRE-luciferase, AP-1-luciferase and NF-kappaB-luciferase may be purchased from Stratagene (Legally, Calif.). Transfections are performed using the FuGENE 6 transfection reagent (Boehringer-Mannheim) according to the supplier's instructions. Cells transfected with the reporter construct alone are used as a control. Twenty-four hours after transfection, cells are washed once with PBS pre-warmed to 37° C. Serum-free MEM is then added to the cells either alone (control) or with one or more candidate modulators and the cells are incubated at 37° C. for five hours. Thereafter, cells are washed once with ice-cold PBS and lysed by the addition of 100 μl of lysis buffer per well from the luciferase assay kit supplied by Promega. After incubation for 15 minutes at room temperature, 15 μl of the lysate is mixed with 50 μl of substrate solution (Promega) in an opaque-white, 96-well plate, and the luminescence is read immediately on a Wallace model 1450 MicroBeta scintillation and luminescence counter (Wallace Instruments, Gaithersburg, Md.).

Differences in luminescence in the presence versus the absence of a candidate modulator compound are indicative of modulatory activity. Receptors that are either constitutively active or activated by agonists typically give a 3-20-fold stimulation of luminescence compared to cells transfected with the reporter gene alone. Modulators that act as inverse agonists will reverse this effect.

D. Intracellular Calcium Measurement Using FLIPR

Changes in intracellular calcium levels are another recognized indicator of receptor activity, and such assays can be employed to screen for modulators of NgR activity. For example, CHO cells stably transfected with a NgR expression vector are plated at a density of $4\times10^4$ cells/well in Packard black-walled, 96-well plates specialty designed to discriminate fluorescence signals emanating from the various wells on the plate. The cells are incubated for 60 minutes at 37° C. in modified Dulbecco's PBS (D-PBS) containing 36 mg/L pyruvate and 1 g/L glucose with the addition of 1% fetal bovine serum and one of four calcium indicator dyes (Fluo-3™ AM, Fluo-4™ AM, Calcium Green™-1 AM, or Oregon Green™ 488 BAPTA-1 AM), each at a concentration of 4 μM. Plates are washed once with modified D-PBS without 1% fetal bovine serum and incubated for 10 minutes at 37° C. to remove residual dye from the cellular membrane. In addition, a series of washes with modified D-PBS without 1% fetal bovine serum is performed immediately prior to activation of the calcium response.

A calcium response is initiated by the addition of one or more candidate receptor agonist compounds, calcium ionophore A23187 (10 μM, positive control), or ATP (4 μM; positive control). Fluorescence is measured by Molecular Device's FLIPR with an argon laser (excitation at 488 nm). (See, e.g., Kuntzweiler et al. (1998) *Drug Dev. Res.* 44, 14-20). The F-stop for the detector camera is set at 2.5 and the length of exposure is 0.4 milliseconds. Basal fluorescence of cells is measured for 20 seconds prior to addition of candidate agonist, ATP, or A23187, and the basal fluorescence level is subtracted from the response signal. The calcium signal is measured for approximately 200 seconds, taking readings every two seconds. Calcium ionophore A23187 and ATP increase the calcium signal 200% above baseline levels. In general, activated NgRs increase the calcium signal at least about 10-15% above baseline signal.

E. [$^{35}$S]GTPγS Binding Assay

It is also possible to evaluate whether NgR signals through a G protein-mediated pathway. Because G protein-coupled receptors signal through intracellular G proteins whose activity involves GTP binding and hydrolysis to yield bound GDP, measurement of binding of the non-hydrolyzable GTP analog [$^{35}$S]-GTPγS in the presence and absence of candidate modulators provides another assay for modulator activity. (See, e.g., Kowal et al., (1998) Neuropharmacology 37, 179-187.).

In one exemplary assay, cells stably transfected with a NgR expression vector re grown in 10 cm tissue culture dishes to subconfluence, rinsed once with 5 ml of ice-cold $Ca^{2+}$/$Mg^{2+}$-free phosphate-buffered saline, and scraped into 5 ml of the same buffer. Cells are pelleted by centrifugation (500×g, 5 minutes), resuspended in TEE buffer (25 mM Tris, pH 7.5, 5 mM EDTA, 5 mM EGTA), and frozen in liquid nitrogen. After thawing, the cells are homogenized using a Dounce homogenizer (1 ml TEE per plate of cells), and centrifuged at 1,000×g for 5 minutes to remove nuclei and unbroken cells.

The homogenate supernatant is centrifuged at 20,000×g for 20 minutes to isolate the membrane fraction, and the membrane pellet is washed once with TEE and resuspended in binding buffer (20 mM HEPES, pH 7.5, 150 mM NaCl, 10 mM $MgCl_2$, 1 mM EDTA). The resuspended membranes can be frozen in liquid nitrogen and stored at −70° C. until use.

Aliquots of cell membranes prepared as described above and stored at −70° C. are thawed, homogenized, and diluted into buffer containing 20 mM HEPES, 10 mM $MgCl_2$, 1 mM EDTA, 120 mM NaCl, 10 μM GDP, and 0.2 mM ascorbate, at a concentration of 10-50 μg/ml. In a final volume of 90 μl, homogenates are incubated with varying concentrations of candidate modulator compounds or 100 μM GTP for 30 minutes at 30° C. and then placed on ice. To each sample, 10 μl guanosine 5'-O-(3[$^{35}$S]thio) triphosphate (NEN, 1200 Ci/mmol; [$^{35}$S]-GTPγS), was added to a final concentration of 100-200 pM. Samples are incubated at 30° C. for an additional 30 minutes, 1 ml of 10 mM HEPES, pH 7.4, 10 mM $MgCl_2$, at 4° C. is added and the reaction is stopped by filtration.

Samples are filtered over Whatman GF/B filters and the filters are washed with 20 ml ice-cold 10 mM HEPES, pH 7.4, 10 mM $MgCl_2$. Filters are counted by liquid scintillation spectroscopy. Nonspecific binding of [$^{35}$S]-GTPγS is measured in the presence of 100 μM GTP and subtracted from the total. Compounds are selected that modulate the amount of [$^{35}$S]-GTPγS binding in the cells, compared to untransfected control cells. Activation of receptors by agonists gives up to a five-fold increase in [$^{3}$S]-GTPγS binding. This response is blocked by antagonists.

F. [$^{3}$H]Arachidonic Acid Release

The activation of NgRs may also potentiate arachidonic acid release in cells, providing yet another useful assay for modulators of NgR activity. (See, e.g., Kanterman et al., (1991) *Mol. Pharmacol.* 39, 364-369.) For example, CHO cells that are stably transfected with a NgR expression vector are plated in 24-well plates at a density of 15,000 cells/well and grown in MEM medium supplemented with 10% fetal bovine serum, 2 mM glutamine, 10 U/ml penicillin and 10 μg/ml streptomycin for 48 hours at 37° C. before use. Cells of each well are labeled by incubation with [$^{3}$H]-arachidonic acid (Amersham Corp., 210 Ci/mmol) at 0.5 μCi/ml in 1 ml MEM supplemented with 10 mM HEPES, pH 7.5, and 0.5% fatty-acid-free bovine serum albumin for 2 hours at 37° C. The cells are then washed twice with 1 ml of the same buffer.

Candidate modulator compounds are added in 1 ml of the same buffer, either alone or with 10 μM ATP and the cells are incubated at 37° C. for 30 minutes. Buffer alone and mock-transfected cells are used as controls. Samples (0.5 ml) from each well are counted by liquid scintillation spectroscopy. Agonists which activate the receptor will lead to potentiation of the ATP-stimulated release of [$^{3}$H]-arachidonic acid. This potentiation is blocked by antagonists.

G. Extracellular Acidification Rate

In yet another assay, the effects of candidate modulators of NgR activity are assayed by monitoring extracellular changes in pH induced by the test compounds (see, e.g., Dunlop et al. (1998) *J. Pharmacol. Toxicol. Meth.* 40, 47-55). In one embodiment, CHO cells transfected with a NgR expression vector are seeded into 12 mm capsule cups (Molecular Devices Corp.) at $4\times10^5$ cells/cup in MEM supplemented with 10% fetal bovine serum, 2 mM L-glutamine, 10 U/ml penicillin, and 10 μg/ml streptomycin. The cells are incubated in this medium at 37° C. in 5% $CO_2$ for 24 hours.

Extracellular acidification rates are measured using a Cytosensor microphysiometer (Molecular Devices Corp.). The capsule cups are loaded into the sensor chambers of the microphysiometer and the chambers are perfused with running buffer (bicarbonate-free MEM supplemented with 4 mM L-glutamine, 10 units/ml penicillin, 10 μg/ml streptomycin, 26 mM NaCl) at a flow rate of 100 μl/minute. Candidate agonists or other agents are diluted into the running buffer and perfused through a second fluid path. During each 60-second pump cycle, the pump is run for 38 seconds and is off for the remaining 22 seconds. The pH of the running buffer in the sensor chamber is recorded during the cycle from 43-58 seconds, and the pump is re-started at 60 seconds to start the next cycle. The rate of acidification of the running buffer during the recording time is calculated by the Cytosoft program. Changes in the rate of acidification are calculated by subtracting the baseline value (the average of 4 rate measurements immediately before addition of a modulator candidate) from the highest rate measurement obtained after addition of a modulator candidate. The selected instrument detects 61 mV/pH unit. Modulators that act as agonists of the receptor result in an increase in the rate of extracellular acidification compared to the rate in the absence of agonist. This response is blocked by modulators which act as antagonists of the receptor.

EXAMPLE 15 mNgR3 Does Not Bind hNogo-A(1055-1120)

To functionally test the mouse NgR3 (hereinafter, mNgR3) for its ability to bind hNogo-A(1055-1120), a cDNA expression vector for a myc epitope-tagged mNgR3 protein was created. The mouse NgR3 cDNA was amplified by PCR from mouse adult brain cDNA, from the signal sequence to the stop codon, and ligated into the pSecTag2 vector such that the vector encodes a signal sequence followed by a myc tag followed by the mature mNgR3 sequence. This plasmid was transfected into COS07 cells, and expression of a myc-tagged protein of the predicted size was verified by immunoblot analysis. Alkaline phosphatase-hNogo-A(1055-1120) binding studies and myc immunohistology were conducted as described (Fournier et al., supra).

The cells expressing mNgR3 express the myc-tagged protein but binding to AP-hNogo-A(1055-1120) was not observed under the conditions employed (FIG. 8).

EXAMPLE 16

Identification of Partial Human NgR3 cDNA and Protein Sequences

The tblastn program was used to search for the human homolog of mouse NgR3. The mouse NgR3 protein sequence (SEQ ID NO:4) was used to query a proprietary human expressed sequence tag (EST) database from Incyte yielding one highly significant hit: Incyte Template ID 190989.1. This sequence (937 nucleotides) contains an open reading frame of 312 amino acids in the second reverse frame that exhibits 88% identity with residues 66 to 381 of mouse NgR3 (SEQ ID NO:4), strongly indicating that it is part of the human NgR3 homolog.

A query of SEQ ID NO:4 against the public human EST database in Genbank also produced a hit with a 465-bp EST (Accession number: R35699; Version number: R35699.1; GI: 792600). There are a number of single nucleotide deletions and insertions within this sequence which cause frame shift errors. All of the reliable sequence contained in this public EST is present in the Incyte EST (Template ID 190989.1).

To obtain more nucleotide sequence that would extend the amino acid sequence at that carboxy terminal end, the I.M.A.G.E. Consortium clone No. 38319, which corresponds to Genbank accession No. R35699, was purchased from Incyte Genomics Inc. and subjected to further DNA sequence analysis. This clone consists of a NotI/HinD III fragment containing the sequence of interest, cloned into the NotI/HinD III sites of the vector Lafmid BA (http://image.llnl.gov/image/html/libs/lafmidBA.shtml). The clone was received as an agar stab, which was streaked out on LB agar plates containing 50 ug/ml ampicillin to isolate individual colonies. Six colonies were grown in LB medium with antibiotic, and plasmid DNA was prepared using the Promega Wizard Plus Miniprep DNA Purification System (Promega #A7500). These DNAs were subsequently digested with NotI and HinD III restriction enzymes to confirm that the clones contained an insert. The insert of one isolate was sequenced using a combination of vector specific and gene specific primers yielding a partial nucleotide sequence of human NgR3 of 1176 nucleotides (SEQ ID NO:13). A translation of this sequence provides a partial sequence for human NgR3 of 392 amino acids (SEQ ID NO:14).

The nucleotide sequence of SEQ ID NO:13 differs from the Incyte EST sequence at three positions. Nucleotide positions 12-13 in SEQ ID NO:13 are CG, whereas the corresponding nucleotides in the Incyte Template ID 190989.1 are GT (i.e., positions 12-13 of the complement of Incyte Template ID 190989.1). In addition, position 641 in SEQ ID NO:13 is a C, whereas the corresponding nucleotide in the Incyte Template ID 190989.1 sequence is an A (i.e., position 641 of the complement of Incyte Template ID 190989.1). This results in two changes in amino acids when comparing SEQ ID NO:14 to the ORF encoded by Incyte Template 190989.1: SEQ ID NO:14 contains a valine at position 5, whereas the ORF encoded by Incyte Template ID 190989.1 contains a leucine; SEQ ID NO:14 contains an alanine at position 214, whereas the ORF encoded by Incyte Template ID 190989.1 contains a glutamic acid.

The nucleotide sequence of SEQ ID NO:13 differs from the public EST (Accession number: R35699; Version number: R35699.1; GI: 792600) sequence at two positions (within the first 200 nucleotides of reliable sequence). Nucleotide positions 12-13 in SEQ ID NO:13 are CG, whereas the corresponding nucleotides in the public EST are GT (i.e., positions 12-13 of the public EST; Accession no: R35699; Version no: R35699.1; GI: 792600) This leads to a single amino acid change when comparing SEQ ID NO:14 to the ORF encoded by the public EST: SEQ ID NO:14 contains a valine at position 5, while the ORF encoded by the public EST contains a leucine.

A Bestfit analysis of the partial human amino acid sequence with the full-length mouse amino acid sequence indicates that the human NgR3 amino acid sequence is complete at the carboxy terminal end and that they share 89.54% identity. An alignment of all the NgR proteins is shown in FIG. 9. Although the human NgR3 amino acid sequence is missing the first 25 amino acids, it can be determined that the human NgR3 protein contains the following features in common with the other NgR sequences: (1) eight Leucine Rich Repeat (LRR) domains; (2) an LRR carboxy-terminal (LRR-CT) domain; (3) a conserved cysteine in the fourth LRR domain; (4) a conserved potential glycosylation site in the eighth LRR domain; and (5) a hydrophobic carboxyl terminus.

As those skilled in the art will appreciate, numerous changes and modifications may be made to the preferred embodiments of the invention without departing from the spirit of the invention. It is intended that all such variations fall within the scope of the invention.

The entire disclosure of each publication cited herein is hereby incorporated by reference. This application claims benefit from U.S. provisional application 60/238,361, filed Oct. 6, 2000, which is incorporated by reference herein in its entirety.

Key for Sequence Listing:

| | |
|---|---|
| SEQ ID NO:1 | human NgR2 cDNA sequence derived from genomic sequence AC013606 |
| SEQ ID NO:2 | human NgR2 amino acid sequence |
| SEQ ID NO:3 | mouse NgR3 cDNA sequence derived from AC021768 |
| SEQ ID NO:4 | a mouse NgR3 amino acid sequence |
| SEQ ID NO:5 | a human NgR1 amino acid sequence |
| SEQ ID NO:6 | a consensus amino acid sequence for NgRs |
| SEQ ID NO:7 | #1055-1120 amino acid residues of hNogoA (Nogo-66) |
| SEQ ID NO:8 | a mature human NgR2 amino acid sequence |
| SEQ ID NO:9 | a mature mouse NgR3 amino acid sequence |
| SEQ ID NO:10 | a consensus NgR LLRNT amino acid sequence |
| SEQ ID NO:11 | a consensus NgR LRRCT domain amino acid sequence |
| SEQ ID NO:12 | a consensus NgR LRR domain amino acid sequence |
| SEQ ID NO:13 | a partial human NgR3 nucleotide sequence |
| SEQ ID NO:14 | a partial human NgR3 amino acid sequence |
| SEQ ID NO:15 | a genomic sequence encoding a human NgR2 sequence. |
| SEQ ID NO:16 | a genomic sequence (complementary strand) encoding a mouse NgR3 |
| SEQ ID NO:17 | a mouse NgR1 amino acid sequence |
| SEQ ID NO:18 | a consensus sequence for the NTLRRCT domain of NgR |
| SEQ ID NO:19 | an consensus NgR LRRCT domain amino acid sequence |

What is claimed is:

1. An isolated polypeptide comprising an amino acid sequence that is at least 90% identical to amino acids 1 to 310 of SEQ ID NO:2, wherein said polypeptide decreases inhibition of axonal elongation.

2. An isolated polypeptide comprising an amino acid sequence that is at least 90% identical to amino acids 1 to 310 of SEQ ID NO:2, wherein said polypeptide decreases inhibition of axonal elongation.

3. The polypeptide of claim 2, wherein said polypeptide comprises amino acids 31 to 310 of SEQ ID NO:2.

4. The polypeptide of claim 2, further comprising a heterologous polypeptide.

5. The polypeptide of claim 4, wherein said heterologous polypeptide is selected from the group consisting of Fc, Glutathione S-transferase (GST), a Histidine tag (His tag), and alkaline phosphatase (AP).

6. The polypeptide of claim 1, wherein said amino acid sequence is at least 95% identical to amino acids 1 to 310 of SEQ ID NO:2 and wherein said polypeptide decreases inhibition of axonal elongation.

7. The polypeptide of claim 6, wherein said polypeptide comprises amino acids 1 to 310 of SEQ ID NO:2.

8. A composition comprising the polypeptide of claim 1 and a pharmaceutically acceptable carrier.

9. The polypeptide of claim 1, further comprising a heterologous polypeptide.

10. The polypeptide of claim 9, wherein said heterologous polypeptide is selected from the group consisting of Fc, Glutathione S-transferase (GST), a Histidine tag (His tag), and alkaline phosphatase (AP).

11. The polypeptide of claim 2, wherein said amino acid sequence is at least 95% identical to amino acids 31 to 310 of SEQ ID NO:2 and wherein said polypeptide decreases inhibition of axonal elongation.

12. A composition comprising the polypeptide of claim 2 and a pharmaceutically acceptable carrier.

13. An isolated polypeptide comprising, except for 1 to 10 conservative amino acid substitutions, amino acids 1 to 310 of SEQ ID NO:2, wherein said polypeptide decreases inhibition of axonal elongation.

14. A composition comprising the polypeptide of claim 13 and a pharmaceutically acceptable carrier.

15. The polypeptide fragment of claim 13, further comprising a heterologous polypeptide.

16. The polypeptide fragment of claim 15, wherein said heterologous polypeptide is selected from the group consisting of Fc, Glutathione S-transferase (GST), a Histidine tag (His tag), and alkaline phosphatase (AP).

* * * * *

UNITED STATES PATENT AND TRADEMARK OFFICE

CERTIFICATE OF CORRECTION

PATENT NO. : 7,456,255 B2
APPLICATION NO. : 11/544013
DATED : November 25, 2008
INVENTOR(S) : Strittmatter et al.

It is certified that error appears in the above-identified patent and that said Letters Patent is hereby corrected as shown below:

Column 451
Line 31, please replace "1 to 310" with --31 to 310--.

Signed and Sealed this

Seventeenth Day of August, 2010

David J. Kappos
*Director of the United States Patent and Trademark Office*

UNITED STATES PATENT AND TRADEMARK OFFICE

CERTIFICATE OF CORRECTION

PATENT NO. : 7,456,255 B2
APPLICATION NO. : 11/544013
DATED : November 25, 2008
INVENTOR(S) : Strittmatter et al.

It is certified that error appears in the above-identified patent and that said Letters Patent is hereby corrected as shown below:

In column 1, above "REFERENCE TO A SEQUENCE LISTING SUBMITTED ON A COMPACT DISC" at line 12, insert the following:

--GOVERNMENT LICENSE RIGHTS

This invention was made with Government support under NS033020 awarded by National Institute of Health. The Government has certain rights in the invention.--

Signed and Sealed this
Thirtieth Day of October, 2012

David J. Kappos
*Director of the United States Patent and Trademark Office*

SEQUENCE LISTING

```
<160> NUMBER OF SEQ ID NOS: 19

<210> SEQ ID NO 1
<211> LENGTH: 1260
<212> TYPE: DNA
<213> ORGANISM: Homo sapiens

<400> SEQUENCE: 1

atgctgcccg ggctcaggcg cctgctgcaa gctcccgcct cggcctgcct cctgctgatg      60

ctcctggccc tgcccctggc ggcccccagc tgccccatgc tctgcacctg ctactcatcc     120

ccgcccaccg tgagctgcca ggccaacaac ttctcctctg tgccgctgtc cctgccaccc     180

agcactcagc gactcttcct gcagaacaac ctcatccgca cgctgcggcc aggcaccttt     240
```

-continued

```
gggtccaacc tgctcaccct gtggctcttc tccaacaacc tctccaccat ctacccgggc    300
actttccgcc acttgcaagc cctggaggag ctggacctcg gtgacaaccg gcacctgcgc    360
tcgctggagc ccgacacctt ccagggcctg gagcggctgc agtcgctgca tttgtaccgc    420
tgccagctca gcagcctgcc cggcaacatc ttccgaggcc tggtcagcct gcagtacctc    480
tacctccagg agaacagcct gctccaccta caggatgact tgttcgcgga cctggccaac    540
ctgagccacc tcttcctcca cgggaaccgc ctgcggctgc tcacagagca cgtgtttcgc    600
ggcctgggca gcctggaccg gctgctgctg cacgggaacc ggctgcaggg cgtgcaccgc    660
gcggccttcc gcggcctcag ccgcctcacc atcctctacc tgttcaacaa cagcctggcc    720
tcgctgcccg gcgaggcgct cgccgacctg ccctcgctcg agttcctgcg gctcaacgct    780
aacccctggg cgtgcgactg ccgcgcgcgg ccgctctggg cctggttcca gcgcgcgcgc    840
gtgtccagct ccgacgtgac ctgcgccacc cccccggagc gccagggccg agacctgcgc    900
gcgctccgcg aggccgactt ccaggcgtgt ccgcccgcgg cacccacgcg gccgggcagc    960
cgcgcccgcg gcaacagctc ctccaaccac ctgtacgggg tggccgaggc cggggcgccc   1020
ccagccgatc cctccaccct ctaccgagat ctgcctgccg aagactcgcg ggggcgccag   1080
ggcggggacg cgcctactga ggacgactac tggggggggct acgggggtga ggaccagcga   1140
ggggagcaga tgtgccccgg cgctgcctgc caggcgcccc cggactcccg aggccctgcg   1200
ctctcggccg ggctccccag ccctctgctt tgcctcctgc tcctggtgcc ccaccacctc   1260
```

<210> SEQ ID NO 2
<211> LENGTH: 420
<212> TYPE: PRT
<213> ORGANISM: Homo sapiens

<400> SEQUENCE: 2

```
Met Leu Pro Gly Leu Arg Arg Leu Leu Gln Ala Pro Ala Ser Ala Cys
1               5                   10                  15

Leu Leu Leu Met Leu Leu Ala Leu Pro Leu Ala Ala Pro Ser Cys Pro
            20                  25                  30

Met Leu Cys Thr Cys Tyr Ser Ser Pro Pro Thr Val Ser Cys Gln Ala
        35                  40                  45

Asn Asn Phe Ser Ser Val Pro Leu Ser Leu Pro Pro Ser Thr Gln Arg
    50                  55                  60

Leu Phe Leu Gln Asn Asn Leu Ile Arg Thr Leu Arg Pro Gly Thr Phe
65                  70                  75                  80

Gly Ser Asn Leu Leu Thr Leu Trp Leu Phe Ser Asn Asn Leu Ser Thr
                85                  90                  95

Ile Tyr Pro Gly Thr Phe Arg His Leu Gln Ala Leu Glu Glu Leu Asp
            100                 105                 110

Leu Gly Asp Asn Arg His Leu Arg Ser Leu Glu Pro Asp Thr Phe Gln
        115                 120                 125

Gly Leu Glu Arg Leu Gln Ser Leu His Leu Tyr Arg Cys Gln Leu Ser
    130                 135                 140

Ser Leu Pro Gly Asn Ile Phe Arg Gly Leu Val Ser Leu Gln Tyr Leu
145                 150                 155                 160

Tyr Leu Gln Glu Asn Ser Leu Leu His Leu Gln Asp Asp Leu Phe Ala
                165                 170                 175

Asp Leu Ala Asn Leu Ser His Leu Phe Leu His Gly Asn Arg Leu Arg
            180                 185                 190
```

-continued

```
Leu Leu Thr Glu His Val Phe Arg Gly Leu Gly Ser Leu Asp Arg Leu
        195                 200                 205

Leu Leu His Gly Asn Arg Leu Gln Gly Val His Arg Ala Ala Phe Arg
    210                 215                 220

Gly Leu Ser Arg Leu Thr Ile Leu Tyr Leu Phe Asn Asn Ser Leu Ala
225                 230                 235                 240

Ser Leu Pro Gly Glu Ala Leu Ala Asp Leu Pro Ser Leu Glu Phe Leu
                245                 250                 255

Arg Leu Asn Ala Asn Pro Trp Ala Cys Asp Cys Arg Ala Arg Pro Leu
            260                 265                 270

Trp Ala Trp Phe Gln Arg Ala Arg Val Ser Ser Ser Asp Val Thr Cys
        275                 280                 285

Ala Thr Pro Pro Glu Arg Gln Gly Arg Asp Leu Arg Ala Leu Arg Glu
    290                 295                 300

Ala Asp Phe Gln Ala Cys Pro Pro Ala Ala Pro Thr Arg Pro Gly Ser
305                 310                 315                 320

Arg Ala Arg Gly Asn Ser Ser Ser Asn His Leu Tyr Gly Val Ala Glu
                325                 330                 335

Ala Gly Ala Pro Pro Ala Asp Pro Ser Thr Leu Tyr Arg Asp Leu Pro
            340                 345                 350

Ala Glu Asp Ser Arg Gly Arg Gln Gly Gly Asp Ala Pro Thr Glu Asp
        355                 360                 365

Asp Tyr Trp Gly Gly Tyr Gly Gly Glu Asp Gln Arg Gly Glu Gln Met
    370                 375                 380

Cys Pro Gly Ala Ala Cys Gln Ala Pro Pro Asp Ser Arg Gly Pro Ala
385                 390                 395                 400

Leu Ser Ala Gly Leu Pro Ser Pro Leu Leu Cys Leu Leu Leu Leu Val
                405                 410                 415

Pro His His Leu
            420


<210> SEQ ID NO 3
<211> LENGTH: 1383
<212> TYPE: DNA
<213> ORGANISM: Mus sp.

<400> SEQUENCE: 3

atgtcttggc agtctggaac cacagtgaca caatctcccg tgcaggctgc tcaggtctca      60

gggtgctgtg tggaattgct gctgttgctg ctcgctggag agctacctct gggtggtggt     120

tgtcctcgag actgtgtgtg ctaccctgcg cccatgactg tcagctgcca ggcacacaac     180

tttgctgcca tcccggaggg catcccagag gacagtgagc gcatcttcct gcagaacaat     240

cgcatcacct tcctccagca gggccacttc agccccgcca tggtcaccct ctggatctac     300

tccaacaaca tcactttcat tgctcccaac accttcgagg gctttgtgca tctggaggag     360

ctagaccttg gagacaaccg acagctgcga acgctggcac ccgagacctt ccaaggcctg     420

gtgaagcttc acgccctcta cctctataag tgtggactga gcgccctgcc cgcaggcatc     480

tttggtggcc tgcacagcct gcagtatctc tacttgcagg acaaccatat cgagtacctc     540

caagatgaca tctttgtgga cctggtcaat ctcagtcact tgtttctcca tggtaacaag     600

ctatggagcc tgggccaagg catcttccgg ggcctggtga acctggaccg gttgctgctg     660

catgagaacc agctacagtg ggttcaccac aaggctttcc atgacctcca caggctaacc     720

accctctttc tcttcaacaa cagcctcact gagctgcagg gtgactgtct ggcccccctg     780
```

-continued

```
gtggccttgg agttccttcg cctcaatggg aatgcttggg actgtggctg ccgggcacgt    840

tccctgtggg aatggctgcg aaggttccgt ggctctagct ctgctgtccc ctgcgcgacc    900

cccgagctgc ggcaaggcca ggatctgaag ctgctgaggg tggaggactt ccggaactgc    960

acaggaccag tgtctcctca ccagatcaag tctcacacgc ttaccacctc tgacagggct   1020

gcccgcaagg agcaccatcc gtcccatggg gcctccaggg acaaaggcca cccacatggc   1080

catccgcctg gctccaggtc aggttacaag aaggcaggca agaactgcac cagccacagg   1140

aaccggaacc agatctctaa ggtgagctct gggaaagagc ttaccgaact gcaggactat   1200

gcccccgact atcagcacaa gttcagcttt gacatcatgc ccaccgcacg acccaagagg   1260

aagggcaagt gtgctcgcag gacccccatc cgtgccccca gtggggtgca gcaggcatcc   1320

tcaggcacgg cccttggggc cccactcctg gcctggatac tggggctggc agtcactctc   1380

cgc                                                                  1383


<210> SEQ ID NO 4
<211> LENGTH: 461
<212> TYPE: PRT
<213> ORGANISM: Mus sp.

<400> SEQUENCE: 4

Met Ser Trp Gln Ser Gly Thr Thr Val Thr Gln Ser Pro Val Gln Ala
  1               5                  10                  15

Ala Gln Val Ser Gly Cys Cys Val Glu Leu Leu Leu Leu Leu Leu Ala
             20                  25                  30

Gly Glu Leu Pro Leu Gly Gly Gly Cys Pro Arg Asp Cys Val Cys Tyr
         35                  40                  45

Pro Ala Pro Met Thr Val Ser Cys Gln Ala His Asn Phe Ala Ala Ile
     50                  55                  60

Pro Glu Gly Ile Pro Glu Asp Ser Glu Arg Ile Phe Leu Gln Asn Asn
 65                  70                  75                  80

Arg Ile Thr Phe Leu Gln Gln Gly His Phe Ser Pro Ala Met Val Thr
                 85                  90                  95

Leu Trp Ile Tyr Ser Asn Asn Ile Thr Phe Ile Ala Pro Asn Thr Phe
            100                 105                 110

Glu Gly Phe Val His Leu Glu Glu Leu Asp Leu Gly Asp Asn Arg Gln
        115                 120                 125

Leu Arg Thr Leu Ala Pro Glu Thr Phe Gln Gly Leu Val Lys Leu His
    130                 135                 140

Ala Leu Tyr Leu Tyr Lys Cys Gly Leu Ser Ala Leu Pro Ala Gly Ile
145                 150                 155                 160

Phe Gly Gly Leu His Ser Leu Gln Tyr Leu Tyr Leu Gln Asp Asn His
                165                 170                 175

Ile Glu Tyr Leu Gln Asp Asp Ile Phe Val Asp Leu Val Asn Leu Ser
            180                 185                 190

His Leu Phe Leu His Gly Asn Lys Leu Trp Ser Leu Gly Gln Gly Ile
        195                 200                 205

Phe Arg Gly Leu Val Asn Leu Asp Arg Leu Leu Leu His Glu Asn Gln
    210                 215                 220

Leu Gln Trp Val His His Lys Ala Phe His Asp Leu His Arg Leu Thr
225                 230                 235                 240

Thr Leu Phe Leu Phe Asn Asn Ser Leu Thr Glu Leu Gln Gly Asp Cys
                245                 250                 255

Leu Ala Pro Leu Val Ala Leu Glu Phe Leu Arg Leu Asn Gly Asn Ala
```

-continued

```
            260                 265                 270

Trp Asp Cys Gly Cys Arg Ala Arg Ser Leu Trp Glu Trp Leu Arg Arg
        275                 280                 285

Phe Arg Gly Ser Ser Ser Ala Val Pro Cys Ala Thr Pro Glu Leu Arg
    290                 295                 300

Gln Gly Gln Asp Leu Lys Leu Leu Arg Val Glu Asp Phe Arg Asn Cys
305                 310                 315                 320

Thr Gly Pro Val Ser Pro His Gln Ile Lys Ser His Thr Leu Thr Thr
                325                 330                 335

Ser Asp Arg Ala Ala Arg Lys Glu His His Pro Ser His Gly Ala Ser
            340                 345                 350

Arg Asp Lys Gly His Pro His Gly His Pro Pro Gly Ser Arg Ser Gly
        355                 360                 365

Tyr Lys Lys Ala Gly Lys Asn Cys Thr Ser His Arg Asn Arg Asn Gln
    370                 375                 380

Ile Ser Lys Val Ser Ser Gly Lys Glu Leu Thr Glu Leu Gln Asp Tyr
385                 390                 395                 400

Ala Pro Asp Tyr Gln His Lys Phe Ser Phe Asp Ile Met Pro Thr Ala
                405                 410                 415

Arg Pro Lys Arg Lys Gly Lys Cys Ala Arg Arg Thr Pro Ile Arg Ala
            420                 425                 430

Pro Ser Gly Val Gln Gln Ala Ser Ser Gly Thr Ala Leu Gly Ala Pro
        435                 440                 445

Leu Leu Ala Trp Ile Leu Gly Leu Ala Val Thr Leu Arg
    450                 455                 460


<210> SEQ ID NO 5
<211> LENGTH: 473
<212> TYPE: PRT
<213> ORGANISM: Homo sapiens

<400> SEQUENCE: 5

Met Lys Arg Ala Ser Ala Gly Gly Ser Arg Leu Leu Ala Trp Val Leu
  1               5                  10                  15

Trp Leu Gln Ala Trp Gln Val Ala Ala Pro Cys Pro Gly Ala Cys Val
            20                  25                  30

Cys Tyr Asn Glu Pro Lys Val Thr Thr Ser Cys Pro Gln Gln Gly Leu
        35                  40                  45

Gln Ala Val Pro Val Gly Ile Pro Ala Ala Ser Gln Arg Ile Phe Leu
     50                  55                  60

His Gly Asn Arg Ile Ser His Val Pro Ala Ala Ser Phe Arg Ala Cys
 65                  70                  75                  80

Arg Asn Leu Thr Ile Leu Trp Leu His Ser Asn Val Leu Ala Arg Ile
                 85                  90                  95

Asp Ala Ala Ala Phe Thr Gly Leu Ala Leu Leu Glu Gln Leu Asp Leu
            100                 105                 110

Ser Asp Asn Ala Gln Leu Arg Ser Val Asp Pro Ala Thr Phe His Gly
        115                 120                 125

Leu Gly Arg Leu His Thr Leu His Leu Asp Arg Cys Gly Leu Gln Glu
    130                 135                 140

Leu Gly Pro Gly Leu Phe Arg Gly Leu Ala Ala Leu Gln Tyr Leu Tyr
145                 150                 155                 160

Leu Gln Asp Asn Ala Leu Gln Ala Leu Pro Asp Asp Thr Phe Arg Asp
                165                 170                 175
```

-continued

```
Leu Gly Asn Leu Thr His Leu Phe Leu His Gly Asn Arg Ile Ser Ser
            180                 185                 190

Val Pro Glu Arg Ala Phe Arg Gly Leu His Ser Leu Asp Arg Leu Leu
        195                 200                 205

Leu His Gln Asn Arg Val Ala His Val His Pro His Ala Phe Arg Asp
    210                 215                 220

Leu Gly Arg Leu Met Thr Leu Tyr Leu Phe Ala Asn Asn Leu Ser Ala
225                 230                 235                 240

Leu Pro Thr Glu Ala Leu Ala Pro Leu Arg Ala Leu Gln Tyr Leu Arg
                245                 250                 255

Leu Asn Asp Asn Pro Trp Val Cys Asp Cys Arg Ala Arg Pro Leu Trp
            260                 265                 270

Ala Trp Leu Gln Lys Phe Arg Gly Ser Ser Ser Glu Val Pro Cys Ser
        275                 280                 285

Leu Pro Gln Arg Leu Ala Gly Arg Asp Leu Lys Arg Leu Ala Ala Asn
    290                 295                 300

Asp Leu Gln Gly Cys Ala Val Ala Thr Gly Pro Tyr His Pro Ile Trp
305                 310                 315                 320

Thr Gly Arg Ala Thr Asp Glu Glu Pro Leu Gly Leu Pro Lys Cys Cys
                325                 330                 335

Gln Pro Asp Ala Ala Asp Lys Ala Ser Val Leu Glu Pro Gly Arg Pro
            340                 345                 350

Ala Ser Ala Gly Asn Ala Leu Lys Gly Arg Val Pro Pro Gly Asp Ser
        355                 360                 365

Pro Pro Gly Asn Gly Ser Gly Pro Arg His Ile Asn Asp Ser Pro Phe
    370                 375                 380

Gly Thr Leu Pro Gly Ser Ala Glu Pro Pro Leu Thr Ala Val Arg Pro
385                 390                 395                 400

Glu Gly Ser Glu Pro Pro Gly Phe Pro Thr Ser Gly Pro Arg Arg Arg
                405                 410                 415

Pro Gly Cys Ser Arg Lys Asn Arg Thr Arg Ser His Cys Arg Leu Gly
            420                 425                 430

Gln Ala Gly Ser Gly Gly Gly Gly Thr Gly Asp Ser Glu Gly Ser Gly
        435                 440                 445

Ala Leu Pro Ser Leu Thr Cys Ser Leu Thr Pro Leu Gly Leu Ala Leu
    450                 455                 460

Val Leu Trp Thr Val Leu Gly Pro Cys
465                 470
```

<210> SEQ ID NO 6
<211> LENGTH: 440
<212> TYPE: PRT
<213> ORGANISM: Artificial Sequence
<220> FEATURE:
<223> OTHER INFORMATION: Description of Artificial Sequence: Consensus sequence
<220> FEATURE:
<221> NAME/KEY: MOD_RES
<222> LOCATION: (3)..(4)
<223> OTHER INFORMATION: Variable amino acid
<220> FEATURE:
<221> NAME/KEY: MOD_RES
<222> LOCATION: (6)
<223> OTHER INFORMATION: Variable amino acid
<220> FEATURE:
<221> NAME/KEY: MOD_RES
<222> LOCATION: (9)..(10)
<223> OTHER INFORMATION: Variable amino acid
<220> FEATURE:
<221> NAME/KEY: MOD_RES -continued
<222> LOCATION: (12)..(13)
<223> OTHER INFORMATION: Variable amino acid
<220> FEATURE:
<221> NAME/KEY: MOD_RES
<222> LOCATION: (15)
<223> OTHER INFORMATION: Variable amino acid
<220> FEATURE:
<221> NAME/KEY: MOD_RES
<222> LOCATION: (18)..(25)
<223> OTHER INFORMATION: Variable amino acid
<220> FEATURE:
<221> NAME/KEY: MOD_RES
<222> LOCATION: (27)..(29)
<223> OTHER INFORMATION: Variable amino acid
<220> FEATURE:
<221> NAME/KEY: MOD_RES
<222> LOCATION: (31)..(34)
<223> OTHER INFORMATION: Variable amino acid
<220> FEATURE:
<221> NAME/KEY: MOD_RES
<222> LOCATION: (36)
<223> OTHER INFORMATION: Variable amino acid
<220> FEATURE:
<221> NAME/KEY: MOD_RES
<222> LOCATION: (39)..(40)
<223> OTHER INFORMATION: Variable amino acid
<220> FEATURE:
<221> NAME/KEY: MOD_RES
<222> LOCATION: (42)
<223> OTHER INFORMATION: Variable amino acid
<220> FEATURE:
<221> NAME/KEY: MOD_RES
<222> LOCATION: (44)..(50)
<223> OTHER INFORMATION: Variable amino acid
<220> FEATURE:
<221> NAME/KEY: MOD_RES
<222> LOCATION: (52)..(59)
<223> OTHER INFORMATION: Variable amino acid
<220> FEATURE:
<221> NAME/KEY: MOD_RES
<222> LOCATION: (62)..(63)
<223> OTHER INFORMATION: Variable amino acid
<220> FEATURE:
<221> NAME/KEY: MOD_RES
<222> LOCATION: (66)..(69)
<223> OTHER INFORMATION: Variable amino acid
<220> FEATURE:
<221> NAME/KEY: MOD_RES
<222> LOCATION: (71)..(74)
<223> OTHER INFORMATION: Variable amino acid
<220> FEATURE:
<221> NAME/KEY: MOD_RES
<222> LOCATION: (76)..(80)
<223> OTHER INFORMATION: Variable amino acid
<220> FEATURE:
<221> NAME/KEY: MOD_RES
<222> LOCATION: (83)
<223> OTHER INFORMATION: Variable amino acid
<220> FEATURE:
<221> NAME/KEY: MOD_RES
<222> LOCATION: (87)
<223> OTHER INFORMATION: Variable amino acid
<220> FEATURE:
<221> NAME/KEY: MOD_RES
<222> LOCATION: (90)..(91)
<223> OTHER INFORMATION: Variable amino acid
<220> FEATURE:
<221> NAME/KEY: MOD_RES
<222> LOCATION: (94)..(96)
<223> OTHER INFORMATION: Variable amino acid
<220> FEATURE:
<221> NAME/KEY: MOD_RES
<222> LOCATION: (98)
<223> OTHER INFORMATION: Variable amino acid
<220> FEATURE:
<221> NAME/KEY: MOD_RES
<222> LOCATION: (101)
<223> OTHER INFORMATION: Variable amino acid
<220> FEATURE:

-continued

<221> NAME/KEY: MOD_RES
<222> LOCATION: (104)..(105)
<223> OTHER INFORMATION: Variable amino acid
<220> FEATURE:
<221> NAME/KEY: MOD_RES
<222> LOCATION: (107)
<223> OTHER INFORMATION: Variable amino acid
<220> FEATURE:
<221> NAME/KEY: MOD_RES
<222> LOCATION: (109)
<223> OTHER INFORMATION: Variable amino acid
<220> FEATURE:
<221> NAME/KEY: MOD_RES
<222> LOCATION: (111)..(112)
<223> OTHER INFORMATION: Variable amino acid
<220> FEATURE:
<221> NAME/KEY: MOD_RES
<222> LOCATION: (114)
<223> OTHER INFORMATION: Variable amino acid
<220> FEATURE:
<221> NAME/KEY: MOD_RES
<222> LOCATION: (116)..(117)
<223> OTHER INFORMATION: Variable amino acid
<220> FEATURE:
<221> NAME/KEY: MOD_RES
<222> LOCATION: (119)..(122)
<223> OTHER INFORMATION: Variable amino acid
<220> FEATURE:
<221> NAME/KEY: MOD_RES
<222> LOCATION: (124)
<223> OTHER INFORMATION: Variable amino acid
<220> FEATURE:
<221> NAME/KEY: MOD_RES
<222> LOCATION: (127)..(128)
<223> OTHER INFORMATION: Variable amino acid
<220> FEATURE:
<221> NAME/KEY: MOD_RES
<222> LOCATION: (136)
<223> OTHER INFORMATION: Variable amino acid
<220> FEATURE:
<221> NAME/KEY: MOD_RES
<222> LOCATION: (138)..(141)
<223> OTHER INFORMATION: Variable amino acid
<220> FEATURE:
<221> NAME/KEY: MOD_RES
<222> LOCATION: (143)
<223> OTHER INFORMATION: Variable amino acid
<220> FEATURE:
<221> NAME/KEY: MOD_RES
<222> LOCATION: (146)
<223> OTHER INFORMATION: Variable amino acid
<220> FEATURE:
<221> NAME/KEY: MOD_RES
<222> LOCATION: (148)
<223> OTHER INFORMATION: Variable amino acid
<220> FEATURE:
<221> NAME/KEY: MOD_RES
<222> LOCATION: (151)
<223> OTHER INFORMATION: Variable amino acid
<220> FEATURE:
<221> NAME/KEY: MOD_RES
<222> LOCATION: (154)
<223> OTHER INFORMATION: Variable amino acid
<220> FEATURE:
<221> NAME/KEY: MOD_RES
<222> LOCATION: (162)..(170)
<223> OTHER INFORMATION: Variable amino acid
<220> FEATURE:
<221> NAME/KEY: MOD_RES
<222> LOCATION: (175)..(176)
<223> OTHER INFORMATION: Variable amino acid
<220> FEATURE:
<221> NAME/KEY: MOD_RES
<222> LOCATION: (184)
<223> OTHER INFORMATION: Variable amino acid
<220> FEATURE:
<221> NAME/KEY: MOD_RES
<222> LOCATION: (186)..(189)
<223> OTHER INFORMATION: Variable amino acid -continued
<220> FEATURE:
<221> NAME/KEY: MOD_RES
<222> LOCATION: (192)..(193)
<223> OTHER INFORMATION: Variable amino acid
<220> FEATURE:
<221> NAME/KEY: MOD_RES
<222> LOCATION: (196)..(197)
<223> OTHER INFORMATION: Variable amino acid
<220> FEATURE:
<221> NAME/KEY: MOD_RES
<222> LOCATION: (199)
<223> OTHER INFORMATION: Variable amino acid
<220> FEATURE:
<221> NAME/KEY: MOD_RES
<222> LOCATION: (202)..(203)
<223> OTHER INFORMATION: Variable amino acid
<220> FEATURE:
<221> NAME/KEY: MOD_RES
<222> LOCATION: (205)
<223> OTHER INFORMATION: Variable amino acid
<220> FEATURE:
<221> NAME/KEY: MOD_RES
<222> LOCATION: (208)
<223> OTHER INFORMATION: Variable amino acid
<220> FEATURE:
<221> NAME/KEY: MOD_RES
<222> LOCATION: (210)
<223> OTHER INFORMATION: Variable amino acid
<220> FEATURE:
<221> NAME/KEY: MOD_RES
<222> LOCATION: (212)..(213)
<223> OTHER INFORMATION: Variable amino acid
<220> FEATURE:
<221> NAME/KEY: MOD_RES
<222> LOCATION: (215)..(218)
<223> OTHER INFORMATION: Variable amino acid
<220> FEATURE:
<221> NAME/KEY: MOD_RES
<222> LOCATION: (221)
<223> OTHER INFORMATION: Variable amino acid
<220> FEATURE:
<221> NAME/KEY: MOD_RES
<222> LOCATION: (223)..(224)
<223> OTHER INFORMATION: Variable amino acid
<220> FEATURE:
<221> NAME/KEY: MOD_RES
<222> LOCATION: (226)..(227)
<223> OTHER INFORMATION: Variable amino acid
<220> FEATURE:
<221> NAME/KEY: MOD_RES
<222> LOCATION: (232)
<223> OTHER INFORMATION: Variable amino acid
<220> FEATURE:
<221> NAME/KEY: MOD_RES
<222> LOCATION: (234)
<223> OTHER INFORMATION: Variable amino acid
<220> FEATURE:
<221> NAME/KEY: MOD_RES
<222> LOCATION: (236)
<223> OTHER INFORMATION: Variable amino acid
<220> FEATURE:
<221> NAME/KEY: MOD_RES
<222> LOCATION: (238)
<223> OTHER INFORMATION: Variable amino acid
<220> FEATURE:
<221> NAME/KEY: MOD_RES
<222> LOCATION: (243)
<223> OTHER INFORMATION: Variable amino acid
<220> FEATURE:
<221> NAME/KEY: MOD_RES
<222> LOCATION: (246)
<223> OTHER INFORMATION: Variable amino acid
<220> FEATURE:
<221> NAME/KEY: MOD_RES
<222> LOCATION: (248)..(251)
<223> OTHER INFORMATION: Variable amino acid
<220> FEATURE:
<221> NAME/KEY: MOD_RES
<222> LOCATION: (253)

-continued

<223> OTHER INFORMATION: Variable amino acid
<220> FEATURE:
<221> NAME/KEY: MOD_RES
<222> LOCATION: (257)
<223> OTHER INFORMATION: Variable amino acid
<220> FEATURE:
<221> NAME/KEY: MOD_RES
<222> LOCATION: (259)
<223> OTHER INFORMATION: Variable amino acid
<220> FEATURE:
<221> NAME/KEY: MOD_RES
<222> LOCATION: (261)..(262)
<223> OTHER INFORMATION: Variable amino acid
<220> FEATURE:
<221> NAME/KEY: MOD_RES
<222> LOCATION: (264)..(267)
<223> OTHER INFORMATION: Variable amino acid
<220> FEATURE:
<221> NAME/KEY: MOD_RES
<222> LOCATION: (269)
<223> OTHER INFORMATION: Variable amino acid
<220> FEATURE:
<221> NAME/KEY: MOD_RES
<222> LOCATION: (272)..(273)
<223> OTHER INFORMATION: Variable amino acid
<220> FEATURE:
<221> NAME/KEY: MOD_RES
<222> LOCATION: (275)..(277)
<223> OTHER INFORMATION: Variable amino acid
<220> FEATURE:
<221> NAME/KEY: MOD_RES
<222> LOCATION: (279)..(281)
<223> OTHER INFORMATION: Variable amino acid
<220> FEATURE:
<221> NAME/KEY: MOD_RES
<222> LOCATION: (283)..(287)
<223> OTHER INFORMATION: Variable amino acid
<220> FEATURE:
<221> NAME/KEY: MOD_RES
<222> LOCATION: (289)..(290)
<223> OTHER INFORMATION: Variable amino acid
<220> FEATURE:
<221> NAME/KEY: MOD_RES
<222> LOCATION: (292)..(328)
<223> OTHER INFORMATION: Variable amino acid
<220> FEATURE:
<221> NAME/KEY: MOD_RES
<222> LOCATION: (330)..(341)
<223> OTHER INFORMATION: Variable amino acid
<220> FEATURE:
<221> NAME/KEY: MOD_RES
<222> LOCATION: (344)..(346)
<223> OTHER INFORMATION: Variable amino acid
<220> FEATURE:
<221> NAME/KEY: MOD_RES
<222> LOCATION: (348)..(399)
<223> OTHER INFORMATION: Variable amino acid
<220> FEATURE:
<221> NAME/KEY: MOD_RES
<222> LOCATION: (401)..(428)
<223> OTHER INFORMATION: Variable amino acid
<220> FEATURE:
<221> NAME/KEY: MOD_RES
<222> LOCATION: (431)..(439)
<223> OTHER INFORMATION: Variable amino acid

<400> SEQUENCE: 6

```
Cys Pro Xaa Xaa Cys Xaa Cys Tyr Xaa Xaa Pro Xaa Xaa Thr Xaa Ser
  1               5                  10                  15

Cys Xaa Xaa Xaa Xaa Xaa Xaa Xaa Xaa Pro Xaa Xaa Xaa Pro Xaa Xaa
             20                  25                  30

Xaa Xaa Arg Xaa Phe Leu Xaa Xaa Asn Xaa Ile Xaa Xaa Xaa Xaa Xaa
         35                  40                  45

Xaa Xaa Phe Xaa Xaa Xaa Xaa Xaa Xaa Xaa Xaa Leu Trp Xaa Xaa Ser
     50                  55                  60
```

-continued

```
Asn Xaa Xaa Xaa Xaa Ile Xaa Xaa Xaa Xaa Phe Xaa Xaa Xaa Xaa Xaa
 65                  70                  75                  80

Leu Glu Xaa Leu Asp Leu Xaa Asp Asn Xaa Xaa Leu Arg Xaa Xaa Xaa
                85                  90                  95

Pro Xaa Thr Phe Xaa Gly Leu Xaa Xaa Leu Xaa Leu Xaa Leu Xaa Xaa
            100                 105                 110

Cys Xaa Leu Xaa Xaa Leu Xaa Xaa Xaa Xaa Phe Xaa Gly Leu Xaa Xaa
        115                 120                 125

Leu Gln Tyr Leu Tyr Leu Gln Xaa Asn Xaa Xaa Xaa Xaa Leu Xaa Asp
    130                 135                 140

Asp Xaa Phe Xaa Asp Leu Xaa Asn Leu Xaa His Leu Phe Leu His Gly
145                 150                 155                 160

Asn Xaa Xaa Xaa Xaa Xaa Xaa Xaa Xaa Xaa Phe Arg Gly Leu Xaa Xaa
                165                 170                 175

Leu Asp Arg Leu Leu Leu His Xaa Asn Xaa Xaa Xaa Xaa Val His Xaa
            180                 185                 190

Xaa Ala Phe Xaa Xaa Leu Xaa Arg Leu Xaa Xaa Leu Xaa Leu Phe Xaa
        195                 200                 205

Asn Xaa Leu Xaa Xaa Leu Xaa Xaa Xaa Xaa Leu Ala Xaa Leu Xaa Xaa
    210                 215                 220

Leu Xaa Xaa Leu Arg Leu Asn Xaa Asn Xaa Trp Xaa Cys Xaa Cys Arg
225                 230                 235                 240

Ala Arg Xaa Leu Trp Xaa Trp Xaa Xaa Xaa Xaa Arg Xaa Ser Ser Ser
                245                 250                 255

Xaa Val Xaa Cys Xaa Xaa Pro Xaa Xaa Xaa Xaa Gly Xaa Asp Leu Xaa
            260                 265                 270

Xaa Leu Xaa Xaa Xaa Asp Xaa Xaa Xaa Cys Xaa Xaa Xaa Xaa Xaa Pro
        275                 280                 285

Xaa Xaa Pro Xaa Xaa Xaa Xaa Xaa Xaa Xaa Xaa Xaa Xaa Xaa Xaa Xaa
    290                 295                 300

Xaa Xaa Xaa Xaa Xaa Xaa Xaa Xaa Xaa Xaa Xaa Xaa Xaa Xaa Xaa Xaa
305                 310                 315                 320

Xaa Xaa Xaa Xaa Xaa Xaa Xaa Xaa Gly Xaa Xaa Xaa Xaa Xaa Xaa Xaa
                325                 330                 335

Xaa Xaa Xaa Xaa Xaa Pro Pro Xaa Xaa Xaa Ser Xaa Xaa Xaa Xaa Xaa
            340                 345                 350

Xaa Xaa Xaa Xaa Xaa Xaa Xaa Xaa Xaa Xaa Xaa Xaa Xaa Xaa Xaa Xaa
        355                 360                 365

Xaa Xaa Xaa Xaa Xaa Xaa Xaa Xaa Xaa Xaa Xaa Xaa Xaa Xaa Xaa Xaa
    370                 375                 380

Xaa Xaa Xaa Xaa Xaa Xaa Xaa Xaa Xaa Xaa Xaa Xaa Xaa Xaa Xaa Arg
385                 390                 395                 400

Xaa Xaa Xaa Xaa Xaa Xaa Xaa Xaa Xaa Xaa Xaa Xaa Xaa Xaa Xaa Xaa
                405                 410                 415

Xaa Xaa Xaa Xaa Xaa Xaa Xaa Xaa Xaa Xaa Xaa Xaa Leu Xaa Xaa Xaa
            420                 425                 430

Xaa Xaa Xaa Xaa Xaa Xaa Xaa Leu
        435                 440
```

<210> SEQ ID NO 7
<211> LENGTH: 66
<212> TYPE: PRT
<213> ORGANISM: Homo sapiens

-continued

<400> SEQUENCE: 7

```
Arg Ile Tyr Lys Gly Val Ile Gln Ala Ile Gln Lys Ser Asp Glu Gly
  1               5                  10                  15

His Pro Phe Arg Ala Tyr Leu Glu Ser Glu Val Ala Ile Ser Glu Glu
             20                  25                  30

Leu Val Gln Lys Tyr Ser Asn Ser Ala Leu Gly His Val Asn Cys Thr
         35                  40                  45

Ile Lys Glu Leu Arg Arg Leu Phe Leu Val Asp Asp Leu Val Asp Ser
     50                  55                  60

Leu Lys
 65
```

<210> SEQ ID NO 8
<211> LENGTH: 390
<212> TYPE: PRT
<213> ORGANISM: Homo sapeins

<400> SEQUENCE: 8

```
Cys Pro Met Leu Cys Thr Cys Tyr Ser Ser Pro Pro Thr Val Ser Cys
  1               5                  10                  15

Gln Ala Asn Asn Phe Ser Ser Val Pro Leu Ser Leu Pro Pro Ser Thr
             20                  25                  30

Gln Arg Leu Phe Leu Gln Asn Asn Leu Ile Arg Thr Leu Arg Pro Gly
         35                  40                  45

Thr Phe Gly Ser Asn Leu Leu Thr Leu Trp Leu Phe Ser Asn Asn Leu
     50                  55                  60

Ser Thr Ile Tyr Pro Gly Thr Phe Arg His Leu Gln Ala Leu Glu Glu
 65                  70                  75                  80

Leu Asp Leu Gly Asp Asn Arg His Leu Arg Ser Leu Glu Pro Asp Thr
                 85                  90                  95

Phe Gln Gly Leu Glu Arg Leu Gln Ser Leu His Leu Tyr Arg Cys Gln
            100                 105                 110

Leu Ser Ser Leu Pro Gly Asn Ile Phe Arg Gly Leu Val Ser Leu Gln
        115                 120                 125

Tyr Leu Tyr Leu Gln Glu Asn Ser Leu Leu His Leu Gln Asp Asp Leu
    130                 135                 140

Phe Ala Asp Leu Ala Asn Leu Ser His Leu Phe Leu His Gly Asn Arg
145                 150                 155                 160

Leu Arg Leu Leu Thr Glu His Val Phe Arg Gly Leu Gly Ser Leu Asp
                165                 170                 175

Arg Leu Leu Leu His Gly Asn Arg Leu Gln Gly Val His Arg Ala Ala
            180                 185                 190

Phe Arg Gly Leu Ser Arg Leu Thr Ile Leu Tyr Leu Phe Asn Asn Ser
        195                 200                 205

Leu Ala Ser Leu Pro Gly Glu Ala Leu Ala Asp Leu Pro Ser Leu Glu
    210                 215                 220

Phe Leu Arg Leu Asn Ala Asn Pro Trp Ala Cys Asp Cys Arg Ala Arg
225                 230                 235                 240

Pro Leu Trp Ala Trp Phe Gln Arg Ala Arg Val Ser Ser Ser Asp Val
                245                 250                 255

Thr Cys Ala Thr Pro Pro Glu Arg Gln Gly Arg Asp Leu Arg Ala Leu
            260                 265                 270

Arg Glu Ala Asp Phe Gln Ala Cys Pro Pro Ala Ala Pro Thr Arg Pro
        275                 280                 285
```

-continued

```
Gly Ser Arg Ala Arg Gly Asn Ser Ser Ser Asn His Leu Tyr Gly Val
    290                 295                 300

Ala Glu Ala Gly Ala Pro Pro Ala Asp Pro Ser Thr Leu Tyr Arg Asp
305                 310                 315                 320

Leu Pro Ala Glu Asp Ser Arg Gly Arg Gln Gly Gly Asp Ala Pro Thr
                325                 330                 335

Glu Asp Asp Tyr Trp Gly Gly Tyr Gly Gly Glu Asp Gln Arg Gly Glu
            340                 345                 350

Gln Met Cys Pro Gly Ala Ala Cys Gln Ala Pro Pro Asp Ser Arg Gly
        355                 360                 365

Pro Ala Leu Ser Ala Gly Leu Pro Ser Pro Leu Leu Cys Leu Leu Leu
    370                 375                 380

Leu Val Pro His His Leu
385                 390


<210> SEQ ID NO 9
<211> LENGTH: 421
<212> TYPE: PRT
<213> ORGANISM: Mus sp.

<400> SEQUENCE: 9

Cys Pro Arg Asp Cys Val Cys Tyr Pro Ala Pro Met Thr Val Ser Cys
  1               5                  10                  15

Gln Ala His Asn Phe Ala Ala Ile Pro Glu Gly Ile Pro Glu Asp Ser
            20                  25                  30

Glu Arg Ile Phe Leu Gln Asn Asn Arg Ile Thr Phe Leu Gln Gln Gly
        35                  40                  45

His Phe Ser Pro Ala Met Val Thr Leu Trp Ile Tyr Ser Asn Asn Ile
    50                  55                  60

Thr Phe Ile Ala Pro Asn Thr Phe Glu Gly Phe Val His Leu Glu Glu
 65                  70                  75                  80

Leu Asp Leu Gly Asp Asn Arg Gln Leu Arg Thr Leu Ala Pro Glu Thr
                85                  90                  95

Phe Gln Gly Leu Val Lys Leu His Ala Leu Tyr Leu Tyr Lys Cys Gly
            100                 105                 110

Leu Ser Ala Leu Pro Ala Gly Ile Phe Gly Gly Leu His Ser Leu Gln
        115                 120                 125

Tyr Leu Tyr Leu Gln Asp Asn His Ile Glu Tyr Leu Gln Asp Asp Ile
    130                 135                 140

Phe Val Asp Leu Val Asn Leu Ser His Leu Phe Leu His Gly Asn Lys
145                 150                 155                 160

Leu Trp Ser Leu Gly Gln Gly Ile Phe Arg Gly Leu Val Asn Leu Asp
                165                 170                 175

Arg Leu Leu Leu His Glu Asn Gln Leu Gln Trp Val His His Lys Ala
            180                 185                 190

Phe His Asp Leu His Arg Leu Thr Thr Leu Phe Leu Phe Asn Asn Ser
        195                 200                 205

Leu Thr Glu Leu Gln Gly Asp Cys Leu Ala Pro Leu Val Ala Leu Glu
    210                 215                 220

Phe Leu Arg Leu Asn Gly Asn Ala Trp Asp Cys Gly Cys Arg Ala Arg
225                 230                 235                 240

Ser Leu Trp Glu Trp Leu Arg Arg Phe Arg Gly Ser Ser Ser Ala Val
                245                 250                 255

Pro Cys Ala Thr Pro Glu Leu Arg Gln Gly Gln Asp Leu Lys Leu Leu
            260                 265                 270
```

-continued

```
Arg Val Glu Asp Phe Arg Asn Cys Thr Gly Pro Val Ser Pro His Gln
        275                 280                 285

Ile Lys Ser His Thr Leu Thr Thr Ser Asp Arg Ala Ala Arg Lys Glu
    290                 295                 300

His His Pro Ser His Gly Ala Ser Arg Asp Lys Gly His Pro His Gly
305                 310                 315                 320

His Pro Pro Gly Ser Arg Ser Gly Tyr Lys Lys Ala Gly Lys Asn Cys
                325                 330                 335

Thr Ser His Arg Asn Arg Asn Gln Ile Ser Lys Val Ser Ser Gly Lys
            340                 345                 350

Glu Leu Thr Glu Leu Gln Asp Tyr Ala Pro Asp Tyr Gln His Lys Phe
        355                 360                 365

Ser Phe Asp Ile Met Pro Thr Ala Arg Pro Lys Arg Lys Gly Lys Cys
    370                 375                 380

Ala Arg Arg Thr Pro Ile Arg Ala Pro Ser Gly Val Gln Gln Ala Ser
385                 390                 395                 400

Ser Gly Thr Ala Leu Gly Ala Pro Leu Leu Ala Trp Ile Leu Gly Leu
                405                 410                 415

Ala Val Thr Leu Arg
            420


<210> SEQ ID NO 10
<211> LENGTH: 17
<212> TYPE: PRT
<213> ORGANISM: Artificial Sequence
<220> FEATURE:
<223> OTHER INFORMATION: Description of Artificial Sequence: Consensus
      sequence
<220> FEATURE:
<221> NAME/KEY: MOD_RES
<222> LOCATION: (3)..(4)
<223> OTHER INFORMATION: Variable amino acid
<220> FEATURE:
<221> NAME/KEY: MOD_RES
<222> LOCATION: (6)
<223> OTHER INFORMATION: Variable amino acid
<220> FEATURE:
<221> NAME/KEY: MOD_RES
<222> LOCATION: (9)..(10)
<223> OTHER INFORMATION: Variable amino acid
<220> FEATURE:
<221> NAME/KEY: MOD_RES
<222> LOCATION: (12)..(13)
<223> OTHER INFORMATION: Variable amino acid
<220> FEATURE:
<221> NAME/KEY: MOD_RES
<222> LOCATION: (15)
<223> OTHER INFORMATION: Variable amino acid

<400> SEQUENCE: 10

Cys Pro Xaa Xaa Cys Xaa Cys Tyr Xaa Xaa Pro Xaa Xaa Thr Xaa Ser
  1               5                  10                  15

Cys


<210> SEQ ID NO 11
<211> LENGTH: 50
<212> TYPE: PRT
<213> ORGANISM: Artificial Sequence
<220> FEATURE:
<223> OTHER INFORMATION: Description of Artificial Sequence: Consensus
      sequence
<220> FEATURE:
<221> NAME/KEY: MOD_RES
<222> LOCATION: (2)
<223> OTHER INFORMATION: Variable amino acid
```

-continued

<220> FEATURE:
<221> NAME/KEY: MOD_RES
<222> LOCATION: (4)
<223> OTHER INFORMATION: Variable amino acid
<220> FEATURE:
<221> NAME/KEY: MOD_RES
<222> LOCATION: (6)
<223> OTHER INFORMATION: Variable amino acid
<220> FEATURE:
<221> NAME/KEY: MOD_RES
<222> LOCATION: (11)
<223> OTHER INFORMATION: Variable amino acid
<220> FEATURE:
<221> NAME/KEY: MOD_RES
<222> LOCATION: (14)
<223> OTHER INFORMATION: Variable amino acid
<220> FEATURE:
<221> NAME/KEY: MOD_RES
<222> LOCATION: (16)..(19)
<223> OTHER INFORMATION: Variable amino acid
<220> FEATURE:
<221> NAME/KEY: MOD_RES
<222> LOCATION: (21)
<223> OTHER INFORMATION: Variable amino acid
<220> FEATURE:
<221> NAME/KEY: MOD_RES
<222> LOCATION: (25)
<223> OTHER INFORMATION: Variable amino acid
<220> FEATURE:
<221> NAME/KEY: MOD_RES
<222> LOCATION: (27)
<223> OTHER INFORMATION: Variable amino acid
<220> FEATURE:
<221> NAME/KEY: MOD_RES
<222> LOCATION: (29)..(30)
<223> OTHER INFORMATION: Variable amino acid
<220> FEATURE:
<221> NAME/KEY: MOD_RES
<222> LOCATION: (32)..(35)
<223> OTHER INFORMATION: Variable amino acid
<220> FEATURE:
<221> NAME/KEY: MOD_RES
<222> LOCATION: (37)
<223> OTHER INFORMATION: Variable amino acid
<220> FEATURE:
<221> NAME/KEY: MOD_RES
<222> LOCATION: (40)..(41)
<223> OTHER INFORMATION: Variable amino acid
<220> FEATURE:
<221> NAME/KEY: MOD_RES
<222> LOCATION: (43)..(45)
<223> OTHER INFORMATION: Variable amino acid
<220> FEATURE:
<221> NAME/KEY: MOD_RES
<222> LOCATION: (47)..(49)
<223> OTHER INFORMATION: Variable amino acid

<400> SEQUENCE: 11

```
Asn Xaa Trp Xaa Cys Xaa Cys Arg Ala Arg Xaa Leu Trp Xaa Trp Xaa
  1               5                  10                  15

Xaa Xaa Xaa Arg Xaa Ser Ser Ser Xaa Val Xaa Cys Xaa Xaa Pro Xaa
             20                  25                  30

Xaa Xaa Xaa Gly Xaa Asp Leu Xaa Xaa Leu Xaa Xaa Xaa Asp Xaa Xaa
         35                  40                  45

Xaa Cys
     50
```

<210> SEQ ID NO 12
<211> LENGTH: 196
<212> TYPE: PRT
<213> ORGANISM: Artificial Sequence
<220> FEATURE:
<223> OTHER INFORMATION: Description of Artificial Sequence: Consensus
sequence -continued

```
<220> FEATURE:
<221> NAME/KEY: MOD_RES
<222> LOCATION: (2)
<223> OTHER INFORMATION: Variable amino acid
<220> FEATURE:
<221> NAME/KEY: MOD_RES
<222> LOCATION: (5)..(6)
<223> OTHER INFORMATION: Variable amino acid
<220> FEATURE:
<221> NAME/KEY: MOD_RES
<222> LOCATION: (8)
<223> OTHER INFORMATION: Variable amino acid
<220> FEATURE:
<221> NAME/KEY: MOD_RES
<222> LOCATION: (10)..(16)
<223> OTHER INFORMATION: Variable amino acid
<220> FEATURE:
<221> NAME/KEY: MOD_RES
<222> LOCATION: (18)..(25)
<223> OTHER INFORMATION: Variable amino acid
<220> FEATURE:
<221> NAME/KEY: MOD_RES
<222> LOCATION: (28)..(29)
<223> OTHER INFORMATION: Variable amino acid
<220> FEATURE:
<221> NAME/KEY: MOD_RES
<222> LOCATION: (32)..(35)
<223> OTHER INFORMATION: Variable amino acid
<220> FEATURE:
<221> NAME/KEY: MOD_RES
<222> LOCATION: (37)..(40)
<223> OTHER INFORMATION: Variable amino acid
<220> FEATURE:
<221> NAME/KEY: MOD_RES
<222> LOCATION: (42)..(46)
<223> OTHER INFORMATION: Variable amino acid
<220> FEATURE:
<221> NAME/KEY: MOD_RES
<222> LOCATION: (49)
<223> OTHER INFORMATION: Variable amino acid
<220> FEATURE:
<221> NAME/KEY: MOD_RES
<222> LOCATION: (53)
<223> OTHER INFORMATION: Variable amino acid
<220> FEATURE:
<221> NAME/KEY: MOD_RES
<222> LOCATION: (56)..(57)
<223> OTHER INFORMATION: Variable amino acid
<220> FEATURE:
<221> NAME/KEY: MOD_RES
<222> LOCATION: (60)..(62)
<223> OTHER INFORMATION: Variable amino acid
<220> FEATURE:
<221> NAME/KEY: MOD_RES
<222> LOCATION: (64)
<223> OTHER INFORMATION: Variable amino acid
<220> FEATURE:
<221> NAME/KEY: MOD_RES
<222> LOCATION: (67)
<223> OTHER INFORMATION: Variable amino acid
<220> FEATURE:
<221> NAME/KEY: MOD_RES
<222> LOCATION: (70)..(71)
<223> OTHER INFORMATION: Variable amino acid
<220> FEATURE:
<221> NAME/KEY: MOD_RES
<222> LOCATION: (73)
<223> OTHER INFORMATION: Variable amino acid
<220> FEATURE:
<221> NAME/KEY: MOD_RES
<222> LOCATION: (75)
<223> OTHER INFORMATION: Variable amino acid
<220> FEATURE:
<221> NAME/KEY: MOD_RES
<222> LOCATION: (77)..(78)
<223> OTHER INFORMATION: Variable amino acid
<220> FEATURE:
<221> NAME/KEY: MOD_RES
<222> LOCATION: (80)
```

-continued

<223> OTHER INFORMATION: Variable amino acid
<220> FEATURE:
<221> NAME/KEY: MOD_RES
<222> LOCATION: (82)..(83)
<223> OTHER INFORMATION: Variable amino acid
<220> FEATURE:
<221> NAME/KEY: MOD_RES
<222> LOCATION: (85)..(88)
<223> OTHER INFORMATION: Variable amino acid
<220> FEATURE:
<221> NAME/KEY: MOD_RES
<222> LOCATION: (90)
<223> OTHER INFORMATION: Variable amino acid
<220> FEATURE:
<221> NAME/KEY: MOD_RES
<222> LOCATION: (93)..(94)
<223> OTHER INFORMATION: Variable amino acid
<220> FEATURE:
<221> NAME/KEY: MOD_RES
<222> LOCATION: (102)
<223> OTHER INFORMATION: Variable amino acid
<220> FEATURE:
<221> NAME/KEY: MOD_RES
<222> LOCATION: (104)..(107)
<223> OTHER INFORMATION: Variable amino acid
<220> FEATURE:
<221> NAME/KEY: MOD_RES
<222> LOCATION: (109)
<223> OTHER INFORMATION: Variable amino acid
<220> FEATURE:
<221> NAME/KEY: MOD_RES
<222> LOCATION: (112)
<223> OTHER INFORMATION: Variable amino acid
<220> FEATURE:
<221> NAME/KEY: MOD_RES
<222> LOCATION: (114)
<223> OTHER INFORMATION: Variable amino acid
<220> FEATURE:
<221> NAME/KEY: MOD_RES
<222> LOCATION: (117)
<223> OTHER INFORMATION: Variable amino acid
<220> FEATURE:
<221> NAME/KEY: MOD_RES
<222> LOCATION: (120)
<223> OTHER INFORMATION: Variable amino acid
<220> FEATURE:
<221> NAME/KEY: MOD_RES
<222> LOCATION: (128)..(136)
<223> OTHER INFORMATION: Variable amino acid
<220> FEATURE:
<221> NAME/KEY: MOD_RES
<222> LOCATION: (141)..(142)
<223> OTHER INFORMATION: Variable amino acid
<220> FEATURE:
<221> NAME/KEY: MOD_RES
<222> LOCATION: (150)
<223> OTHER INFORMATION: Variable amino acid
<220> FEATURE:
<221> NAME/KEY: MOD_RES
<222> LOCATION: (152)..(155)
<223> OTHER INFORMATION: Variable amino acid
<220> FEATURE:
<221> NAME/KEY: MOD_RES
<222> LOCATION: (158)..(159)
<223> OTHER INFORMATION: Variable amino acid
<220> FEATURE:
<221> NAME/KEY: MOD_RES
<222> LOCATION: (162)..(163)
<223> OTHER INFORMATION: Variable amino acid
<220> FEATURE:
<221> NAME/KEY: MOD_RES
<222> LOCATION: (165)
<223> OTHER INFORMATION: Variable amino acid
<220> FEATURE:
<221> NAME/KEY: MOD_RES
<222> LOCATION: (168)..(169)
<223> OTHER INFORMATION: Variable amino acid
<220> FEATURE:
<221> NAME/KEY: MOD_RES -continued
<222> LOCATION: (171)
<223> OTHER INFORMATION: Variable amino acid
<220> FEATURE:
<221> NAME/KEY: MOD_RES
<222> LOCATION: (174)
<223> OTHER INFORMATION: Variable amino acid
<220> FEATURE:
<221> NAME/KEY: MOD_RES
<222> LOCATION: (176)
<223> OTHER INFORMATION: Variable amino acid
<220> FEATURE:
<221> NAME/KEY: MOD_RES
<222> LOCATION: (178)..(179)
<223> OTHER INFORMATION: Variable amino acid
<220> FEATURE:
<221> NAME/KEY: MOD_RES
<222> LOCATION: (181)..(184)
<223> OTHER INFORMATION: Variable amino acid
<220> FEATURE:
<221> NAME/KEY: MOD_RES
<222> LOCATION: (187)
<223> OTHER INFORMATION: Variable amino acid
<220> FEATURE:
<221> NAME/KEY: MOD_RES
<222> LOCATION: (189)..(190)
<223> OTHER INFORMATION: Variable amino acid
<220> FEATURE:
<221> NAME/KEY: MOD_RES
<222> LOCATION: (192)..(193)
<223> OTHER INFORMATION: Variable amino acid

<400> SEQUENCE: 12

```
Arg Xaa Phe Leu Xaa Xaa Asn Xaa Ile Xaa Xaa Xaa Xaa Xaa Xaa Xaa
  1               5                  10                  15

Phe Xaa Xaa Xaa Xaa Xaa Xaa Xaa Xaa Leu Trp Xaa Xaa Ser Asn Xaa
             20                  25                  30

Xaa Xaa Xaa Ile Xaa Xaa Xaa Xaa Phe Xaa Xaa Xaa Xaa Xaa Leu Glu
         35                  40                  45

Xaa Leu Asp Leu Xaa Asp Asn Xaa Xaa Leu Arg Xaa Xaa Xaa Pro Xaa
     50                  55                  60

Thr Phe Xaa Gly Leu Xaa Xaa Leu Xaa Leu Xaa Leu Xaa Xaa Cys Xaa
 65                  70                  75                  80

Leu Xaa Xaa Leu Xaa Xaa Xaa Xaa Phe Xaa Gly Leu Xaa Xaa Leu Gln
                 85                  90                  95

Tyr Leu Tyr Leu Gln Xaa Asn Xaa Xaa Xaa Xaa Leu Xaa Asp Asp Xaa
            100                 105                 110

Phe Xaa Asp Leu Xaa Asn Leu Xaa His Leu Phe Leu His Gly Asn Xaa
        115                 120                 125

Xaa Xaa Xaa Xaa Xaa Xaa Xaa Xaa Phe Arg Gly Leu Xaa Xaa Leu Asp
    130                 135                 140

Arg Leu Leu Leu His Xaa Asn Xaa Xaa Xaa Xaa Val His Xaa Xaa Ala
145                 150                 155                 160

Phe Xaa Xaa Leu Xaa Arg Leu Xaa Xaa Leu Xaa Leu Phe Xaa Asn Xaa
                165                 170                 175

Leu Xaa Xaa Leu Xaa Xaa Xaa Xaa Leu Ala Xaa Leu Xaa Xaa Leu Xaa
            180                 185                 190

Xaa Leu Arg Leu
        195
```

<210> SEQ ID NO 13
<211> LENGTH: 1176
<212> TYPE: DNA
<213> ORGANISM: Homo sapiens

<400> SEQUENCE: 13

-continued

```
gagggcatcc ccgtggacag cgagcgcgtc ttcctgcaga acaaccgcat cggcctcctc     60
cagcccggcc acttcagccc cgccatggtc accctgtgga tctactcgaa caacatcacc    120
tacatccacc ccagcacctt cgagggcttc gtgcacctgg aggagctgga cctcggcgac    180
aaccggcagc tgcggacgct ggcacccgag accttccagg gcctggtgaa gcttcacgcc    240
ctctacctct acaagtgtgg gctcagcgcc ttgccggccg gcgtctttgg cggcctgcac    300
agcctgcagt acctctacct gcaggacaac cacatcgagt acctccagga cgacatcttc    360
gtggacctgg tcaacctcag ccacctgttt ctccacggca acaagctgtg gagtctgggc    420
ccgggcacct tccggggcct ggtgaacctg gaccgtcttt tgctgcacga gaaccagctg    480
cagtgggtcc accacaaggc attccacgac ctccgcaggc tgaccaccct cttcctcttc    540
aacaacagcc tctcggagct gcagggtgag tgcctggccc cgctgggggc cctggagttc    600
ctccgcctca acggcaaccc ctgggactgt ggttgtcgcg cgcgctccct gtgggaatgg    660
ctgcagaggt tccggggctc cagctccgct gtcccctgtg tgtcccctgg gctgcggcac    720
ggccaggacc tgaagctgct gagggccgag gacttccgga actgcacggg accagcgtcc    780
ccgcaccaga tcaagtcaca cacgctcacc accaccgaca gggccgcccg caaggaacac    840
cactcacccc acggccccac caggagcaag ggccacccgc acggcccccg gcccggccac    900
aggaagccgg ggaagaactg caccaacccc aggaaccgca atcagatctc taaggcgggc    960
gccgggaaac aggcccccga gctgccagac tatgccccag actaccagca caagttcagt   1020
tttgacatca tgcctacggc ccggcccaag aggaagggca agtgtgcccg caggaccccc   1080
atccgtgccc ccagcggggt gcagcaggcc tcctcggcca gttccctggg ggcctccctc   1140
ctggcctgga cactggggct ggcggtcact ctccgc                             1176
```

<210> SEQ ID NO 14
<211> LENGTH: 392
<212> TYPE: PRT
<213> ORGANISM: Homo sapiens

<400> SEQUENCE: 14

```
Glu Gly Ile Pro Val Asp Ser Glu Arg Val Phe Leu Gln Asn Asn Arg
  1               5                  10                  15

Ile Gly Leu Leu Gln Pro Gly His Phe Ser Pro Ala Met Val Thr Leu
             20                  25                  30

Trp Ile Tyr Ser Asn Asn Ile Thr Tyr Ile His Pro Ser Thr Phe Glu
         35                  40                  45

Gly Phe Val His Leu Glu Glu Leu Asp Leu Gly Asp Asn Arg Gln Leu
     50                  55                  60

Arg Thr Leu Ala Pro Glu Thr Phe Gln Gly Leu Val Lys Leu His Ala
 65                  70                  75                  80

Leu Tyr Leu Tyr Lys Cys Gly Leu Ser Ala Leu Pro Ala Gly Val Phe
                 85                  90                  95

Gly Gly Leu His Ser Leu Gln Tyr Leu Tyr Leu Gln Asp Asn His Ile
            100                 105                 110

Glu Tyr Leu Gln Asp Asp Ile Phe Val Asp Leu Val Asn Leu Ser His
        115                 120                 125

Leu Phe Leu His Gly Asn Lys Leu Trp Ser Leu Gly Pro Gly Thr Phe
    130                 135                 140

Arg Gly Leu Val Asn Leu Asp Arg Leu Leu Leu His Glu Asn Gln Leu
145                 150                 155                 160
```

-continued

```
Gln Trp Val His His Lys Ala Phe His Asp Leu Arg Arg Leu Thr Thr
                165                 170                 175

Leu Phe Leu Phe Asn Asn Ser Leu Ser Glu Leu Gln Gly Glu Cys Leu
            180                 185                 190

Ala Pro Leu Gly Ala Leu Glu Phe Leu Arg Leu Asn Gly Asn Pro Trp
        195                 200                 205

Asp Cys Gly Cys Arg Ala Arg Ser Leu Trp Glu Trp Leu Gln Arg Phe
    210                 215                 220

Arg Gly Ser Ser Ser Ala Val Pro Cys Val Ser Pro Gly Leu Arg His
225                 230                 235                 240

Gly Gln Asp Leu Lys Leu Leu Arg Ala Glu Asp Phe Arg Asn Cys Thr
                245                 250                 255

Gly Pro Ala Ser Pro His Gln Ile Lys Ser His Thr Leu Thr Thr Thr
            260                 265                 270

Asp Arg Ala Ala Arg Lys Glu His His Ser Pro His Gly Pro Thr Arg
        275                 280                 285

Ser Lys Gly His Pro His Gly Pro Arg Pro Gly His Arg Lys Pro Gly
    290                 295                 300

Lys Asn Cys Thr Asn Pro Arg Asn Arg Asn Gln Ile Ser Lys Ala Gly
305                 310                 315                 320

Ala Gly Lys Gln Ala Pro Glu Leu Pro Asp Tyr Ala Pro Asp Tyr Gln
                325                 330                 335

His Lys Phe Ser Phe Asp Ile Met Pro Thr Ala Arg Pro Lys Arg Lys
            340                 345                 350

Gly Lys Cys Ala Arg Arg Thr Pro Ile Arg Ala Pro Ser Gly Val Gln
        355                 360                 365

Gln Ala Ser Ser Ala Ser Ser Leu Gly Ala Ser Leu Leu Ala Trp Thr
    370                 375                 380

Leu Gly Leu Ala Val Thr Leu Arg
385                 390


<210> SEQ ID NO 15
<211> LENGTH: 143899
<212> TYPE: DNA
<213> ORGANISM: Homo sapiens
<220> FEATURE:
<221> NAME/KEY: modified_base
<222> LOCATION: (2044)..(2144)
<223> OTHER INFORMATION: a, t, c, g, other or unknown
<220> FEATURE:
<221> NAME/KEY: modified_base
<222> LOCATION: (6609)
<223> OTHER INFORMATION: a, t, c, g, other or unknown
<220> FEATURE:
<221> NAME/KEY: modified_base
<222> LOCATION: (6625)..(6724)
<223> OTHER INFORMATION: a, t, c, g, other or unknown
<220> FEATURE:
<221> NAME/KEY: modified_base
<222> LOCATION: (14153)..(14252)
<223> OTHER INFORMATION: a, t, c, g, other or unknown
<220> FEATURE:
<221> NAME/KEY: modified_base
<222> LOCATION: (19512)..(19611)
<223> OTHER INFORMATION: a, t, c, g, other or unknown
<220> FEATURE:
<221> NAME/KEY: modified_base
<222> LOCATION: (22595)..(22694)
<223> OTHER INFORMATION: a, t, c, g, other or unknown
<220> FEATURE:
<221> NAME/KEY: modified_base
<222> LOCATION: (27825)..(27924)
<223> OTHER INFORMATION: a, t, c, g, other or unknown
<220> FEATURE:
```

-continued

<221> NAME/KEY: modified_base
<222> LOCATION: (34953)..(35052)
<223> OTHER INFORMATION: a, t, c, g, other or unknown
<220> FEATURE:
<221> NAME/KEY: modified_base
<222> LOCATION: (40783)..(40882)
<223> OTHER INFORMATION: a, t, c, g, other or unknown
<220> FEATURE:
<221> NAME/KEY: modified_base
<222> LOCATION: (49000)..(49099)
<223> OTHER INFORMATION: a, t, c, g, other or unknown
<220> FEATURE:
<221> NAME/KEY: modified_base
<222> LOCATION: (62884)..(62983)
<223> OTHER INFORMATION: a, t, c, g, other or unknown
<220> FEATURE:
<221> NAME/KEY: modified_base
<222> LOCATION: (75528)..(75627)
<223> OTHER INFORMATION: a, t, c, g, other or unknown
<220> FEATURE:
<221> NAME/KEY: modified_base
<222> LOCATION: (87944)..(88043)
<223> OTHER INFORMATION: a, t, c, g, other or unknown
<220> FEATURE:
<221> NAME/KEY: modified_base
<222> LOCATION: (111030)..(111129)
<223> OTHER INFORMATION: a, t, c, g, other or unknown

<400> SEQUENCE: 15
aagcacatac aggtgacatt acagaactga cagttatgcc aggcactgta cttagcccct 60
ataccatcct caaacagctg tatgatgtag attgggtatt aaccccatta ataacaaaag 120
tacagggaac aaagtgactt tccaaaggtc atgccattca aaggagggtg aatcttaggt 180
tggacgcagg ctgtctgact ctggagtctg aggtgttaat gctgcctcct ccatgggaac 240
agcccaagtg aaaaacagct gatccactct tcatttactt ggcatctgtg ctaagctggt 300
ccctgagcca agctctgagc aacagaaaca gaagctctgc attaggagct tgtgagcatg 360
tcaatgccgg gtaaaggagt gctggaaacc gctgggatgg ccgccgagca ctaggccgtt 420
gaaggtgggc tctgtgtgac tggttcctct acactctggc ctggctgcct gcaggaagaa 480
gatcaagctg agtgggctgg ccctggacca caaggtgaca ggtgacctct tctacaccca 540
tgtgaccacc atgggccaga ggctcagcca gaaggccccc agcctggagg acggttcgga 600
tgccttcatg tcaccccagg atgttcgggg cacctcagaa aaccttcctg agagtgagtg 660
tctggtcaag gtgccggcct tgggggatag tgatggtggg tcctcatatt cagtgagcac 720
tcatggttga gtatttattc gcacccctct tcagtcctta caacacccca tgatgtaggt 780
ggggcatgct cctcatttac agatgggcac atcaaagctc agctaacgct gggaagttca 840
gattcagggt taccctgctg gattcctggg attggggagg gaggagcttc caaaatgggg 900
acaaggtctc tgggcctgtc gggtagctgg tttcctcagg gccccttgca acctctgagc 960
ttattgcatc aggtgcagcc aggcccgtga gcctcctggc aggggtcctc cacacctggc 1020
tgtcttttgc cccctgctgg tcacaggagg agctgcagca cctgcctggg ctgcttctca 1080
ggagggtaca tgaagatccc aggaccgcca gctccatgat aagtggaagg agctccttgg 1140
agtcaggagc gggagttgag gagtttgagt cctgctctcc agttataggc tatgtgactt 1200
gtgtagatca cctaaccttg ctcttgattt ccttacctct taaactagca ctaaaagcac 1260
cccacaaact gtaaagttag ttgtgatgat tgaatgacac catgggtgtg gaagctcttt 1320
gtaaagtgca aaacggtgtg cagtttgagg gtggttaccc ccagtgccga ttctcagagg 1380
gcaacatggc taagggcacg agctggagtt aggctgacct gctgcttcca gccctgtgag 1440
cttgagcaag tcatttaact tcctgagctg cagtttcctc atcagtaaaa tgtgataagg 1500

-continued

```
atagggttgt tgtaagattt tattaaatgg ggtaataaat gtcaagtatg tagcccatag   1560
tgagtgcttc agagtttttt tcttttgttt ctttcccccc cgccccgaga tggagcctta   1620
ctctgttgcc caggctggag tgcagtggca tgatcttggc tcactgcaac ctccgcctcc   1680
cgggttcaag caattctcct gcctcagcct cccaaatagc tgggactaca ggcgtgcacc   1740
accatgctcg gctaattttt gtatctttag tagagacggg gtttcaccat gttggccagg   1800
ctggtctcga actcctgacc tcatgatgct cctgcctcag cccccgaaag ttttgggatt   1860
acaagtgtga gcccccgtgc cctgccaggt tttttttttt tttttttttt tgtaaaacac   1920
ccacagggta ttgctgttgc ctgggctgga gtgcggtagt gcaatcatag ttcactgcag   1980
ccttgacctc ctgggctcaa gtgatcctcc tgcctcagcc tcctgagtag ctgggaatac   2040
aggnnnnnnn nnnnnnnnnn nnnnnnnnnn nnnnnnnnnn nnnnnnnnnn nnnnnnnnnn   2100
nnnnnnnnnn nnnnnnnnnn nnnnnnnnnn nnnnnnnnnn nnntttttgta ttttaagtag   2160
agacagggtt ttcccaatgt tggccaaggc tggtctaaaa ctcccaacct caggtgatcc   2220
acccacctca gcctcccaaa gtactgggat tacaggcgtg agacaccgtg cccagccagg   2280
aggcttattt tcttgataaa ttacccagtc tcaggtattt ctctacagcg atgcaagaac   2340
agcctaatac atccaggctc agcatcagtg gacccaggtg ggagagctta agatgtcaag   2400
gtctgaatgc cgcttccaca cacctttggg acctagggac tccctctctt tttctttttt   2460
cagtagaaga tgttatcttc tcctttctct gaccagtagt tggtgatggt ttcagagata   2520
gtttttcagt caagatatat ttcagtggct tcactgagcc caagttccct cgcctctcta   2580
ggactttatt tccttgtttc tagaagaggg ataacacata ttttctaagg tggttgtgag   2640
attaagggag ctggtaccgg gtggtgcata aggacaggat agagcaatgg tgagaccact   2700
caaaaagcga aaagttgacc tgcgagggtg acacttatca aatcagcaca cagtgggagt   2760
ggaaggaatg tccctcatca gttacaatat ttggagagtg caagttatag aaaacccagc   2820
cctggccggg cgcggtgggt catgcctata atcccagcac tttgggaggc tgaggcaggt   2880
ggatcacgag gtcaggagtt caagaccagc ctgaccaacg tggtgaaacc ccacctctac   2940
taaaaataca aaattagctg ggcgtggtgg tgtgtgcctg taatctgagc tactcaggag   3000
gctgaggcac gagaatcact tgaaaccggg aggtggagtt tgcagtgagc cgagatcgca   3060
ccactgcact ccagcctggg caacagagcg agactccatc tcaaacgaaa aaaaaaaaag   3120
aaagaaaacc cagctctaac tggcttaaac agtaagaaga tctattatat tatccatctc   3180
aggcagcagc aagcccagag gtaggggact ccaaggttgg ttgatccagg gcttaacgat   3240
gtcatcaaag acccaggttc tttctgtctc ggcacctctg tctgcagggc cagcttcatc   3300
ctaagccaga ttgttcttgt cttgattaca agttggctgc tgggccagca gacgctgcct   3360
gcctccctgt tcatcttcag aagtagaaag tggcccttcc ccagtcatgg aatgaaagag   3420
tttcctttct gtctgggatt gcttaggtcc acccacctga agccaatgac tgtcaccagg   3480
aaggtaatat acactgattg tcttaagtca gggttcctga gccagtcttg ggcaaggagt   3540
gtgatactgt catgattgtc ttgggctcat cagggcagct ctgcagatga gatcaaactc   3600
caagctacat tattctgaac agtgggaagt aggaaagaga cattttggga gatacaaaac   3660
acaatgtcta tcccatatcc ctaggtccag gtcacagtgt cttggttgga catcaaatgt   3720
agaaaaagaa agactgtcca tccatttatc tacctattca tctggttttt gatttttttt   3780
aaattttatt ttaagacatt ctcactctgt cacccagact ggagtgcagt ggtttgatca   3840
```

-continued

```
tggctcatgg cagcctcaac ctcccaggct caagtgaccc tcccatgctc aagtgatcct   3900
cctacctcag cctcccaagt agctagaact aaaggtgcat gccaccacgc tcagttaatt   3960
tttgcatttt ttgtagagat ggggtttcgt catgatgccc atgctagtct ggaattcctg   4020
aactcaagca atatgcctgc ctttgcctcc caaaatgctg ggattgtagg catgagccac   4080
tgctcctggc tcatctgttt aataatttat gaaacaacta ctgggtgctg agcacggggc   4140
caggggctgg agatctagca gggaccaggc agatctctgc caagtcgttg gtttcttaaa   4200
ggttttgctc ataattcccc ttttcttttc tctttcgttt tttttctttt ctttctttct   4260
ttctttcttt ttttttttt gagacagagt ctcactctgt tacccaggct ggagtgcagt   4320
ggtgcgatct cagctcactg caacctctgc ctcctgggtt caagcgattc tcctgcctca   4380
gcctcccgag tagctgggac tacaggcgcc tgccaccatg cccggctaat ttttgtgttt   4440
ttagtagaga ctgggtttca ccatattggc caggctggtc ttgaactcct gaccttgtga   4500
tccgcccgct tcggcctccc acagtgctgg gattacaggc gtgagccacg gcgcccagcc   4560
agtttccctt ttcaatgagg cctccctgac ctccatactc tactcctcca cctggcccac   4620
tcagctctac tttttcttcc ccatagcact caagacctcc taacatacta cgtaagttat   4680
ttatttacta ggcttactgt gtattgtctg tcttcctcta ctagaatgta aactccatga   4740
gaatagaaat ttttgccttt ttatttagtg tggtgtctgc agcccctggc ttagtccctg   4800
gcatacaaca gtcactccac ccacagttgc tgaataagtg actaaaggtc cctgccctca   4860
tattgttatg agggagtgtg catgttgtta gagaaaaatc tgaggcacaa taaaatttta   4920
tagagtttaa gttttctttt ttaagcaatc cacgaattgg ggtagtttca gaggtagttt   4980
ttcagtcatg acgtatttca atggcttcac tgagcccaag ttctttcacc tctctaggac   5040
tttatttcct tatttctaga acggggataa cacatagttc ataaggcagt tatgagagta   5100
agggagctgg tatggggtga tgcataagga caggatagag cagtggtgag accgctcaga   5160
tgacaaagcg tcagagacca gtatttacga cggaaatgtg gaagcatgat aaagaaatta   5220
tttgggctgg gcacaatgac tcacaactaa taaaactttg ggaggccaag gtgggaggat   5280
cacttgactt gcagaaggtc aaggctgcag tgagctgtga ttttgccact gcactccagc   5340
ctggtcaaca gagtgagacc ctggctcgaa acgttatttg attggttaca gttatacagt   5400
tgccttattt ggtctattcc atttgaaagt tcctagttct ataattttaa gtttgttggc   5460
tgtttctgat tggttaagct taagttttgt tttcctttaa tacagttaag tgccccataa   5520
tgacattttg gtcaaggaca gaccacatat acagtggtgg tcccataaga ttataatgga   5580
gctgaaacat tcctattgtc tatggcgtag tggtcctgat gttgtagcgc aatgcattag   5640
ttatatgttt gtggcaatgc tggtgtaaac acacctactg cactgccagt gatataaaag   5700
aatagcacat acagttatat atagtacata atatctgata atgataatac ataactatat   5760
tactggttta tatatttact atattattta tctttatttt atttttgaga cagagtctca   5820
ttctgtcacc caggctggag tgcagtggcg cgatcttggc tcaccgcaac ctccgcttcc   5880
tgggttcaag tgattctcct gcctcagtct cctgagtagc tgggattaca ggtgtgcacc   5940
atgacaccct gctaatatgt tttgtatttt tagtagagat ggggtttcac catgttggcc   6000
aggctggtct tgaactactg acctcaagtg atcaccccgc ctcggcttcc caaagtgctg   6060
ggattacagg cgtgagccac cacgcatggc ctatttataa ttattttaga gtgtacgcct   6120
tatacttata aaaaaaagct aactgtcaaa cagcctcggg caggtccttc aacagatatt   6180
ccagaagaca ttgttatcat aggagatgac agctccgtgc atattattgt ccctgaaaac   6240
```

-continued

```
cttctagtgt ggaagtggaa gacagtgata ttgatgatag gacccagtgt aggcctaggc   6300
taatgtgtgt gtttgtgtct ttgcttttaa caagaaagtt taaaaagtta aaataaaata   6360
caaaaatttt taaatagaaa aaagctgccc aggaacaatg gctcacacct gtaatcccac   6420
cattcgggga ggccaaggtg ggtggattgc ttgagctcag gagttcaaga ccagcctggg   6480
caacatggtg aaaccccatc tctacaaaaa atacaaaaat tagccgggtg tggtggcatg   6540
cggctatagt tccagctaat cgaggggctg aggtgggagg atcactgggg gggaggtggt   6600
tgaggctgna gtgagctgtg attgnnnnnn nnnnnnnnnn nnnnnnnnnn nnnnnnnnnn   6660
nnnnnnnnnn nnnnnnnnnn nnnnnnnnnn nnnnnnnnnn nnnnnnnnnn nnnnnnnnnn   6720
nnnnatattc ttaaaaaaat ttttttttat ttttgagaca gaatttctct cttgttgccc   6780
aggctggagt gcaatggcgc tatctcagct cagggcaacc tccacctcct gggttcaagc   6840
gattctcctg ccttagcctc ccaggtacag gcgcccgcca ccatgctcgg ctaatttttg   6900
tatttttagt agagatgggg tttcaccatg ttgtccaggc tggtcttgaa atcctgcctc   6960
aggtgatcca ccccccctcgg cctcccaaag tgctggaatt tacaggcgtg agccactgtg   7020
cctggcctcc tttacatttt tttaaattta attttaattt tttaattttt aatttctcat   7080
atatatatat ttttaagact agccaagtga agcagtggga gtggaaaagg aactggtttt   7140
gatcaatagg tgtaaacacc actgcactgg gaccagccta ttttacattc ctgttagcag   7200
tgatgagggt tcactttctt tgtagcctca acaatatgtg tcgttgccca tctttttttt   7260
tttttttttt tttttttttg agatggagtc tcactctgtt gcctaggctg gaatgcaatg   7320
gcatgatctc agctcactgc aacctccgcc tcccaggttc aagtgattct tgtgtctcag   7380
cctcctgagt agatgggatt acaggcgtcc accaccacgc ccggctaatt ttttgtattt   7440
tcagtagaga tggggtttca ccatgttggc caggttggtt tcgaactcct gacctcaagt   7500
gatccgccca cctcggcctc ccaaagtgct gggattacag gcatgagcca ccgcgcccgg   7560
cctgcccatc ttttttttgt tatagccatc ctagtggatg taaagttttt ttgtgatttt   7620
gatttgtgtt tccctactga tcaatgatgt tgagcatctt ttcctgtgct tattggcttt   7680
tggtatatct ttggagaaag gtctattcag gtcctttgcc cactttaaaa ttaggttatc   7740
tttctattac tgagatgtaa gagttcttta tgttctagat ataagtctcc tacatatgat   7800
ttgtaaaaat tttccttcca ttattgggtt gtctttcact ttcttttggt gtcctttagt   7860
gcacaacagt ttttaatatt gaagtccaat ttctatttt tctcttttgc cacttgtatc   7920
ttggtgtcat gtttaaggaa ctattgccta atctcaggtc acaaagattt acacctgtgt   7980
ttccttcttt ccttccttcc ttccttcctt ccttctttcc ctccctccct ctctccctcc   8040
ctccctctct ccctccctcc ctccttccct tcctccctcc ctccctcctt ccttccttcc   8100
ttccttcctt ccttccttcc ttccttcctt ccttcctttg tccttctgac ggaatcttgc   8160
tctgtcaccc aggctggagt gtagtggcac gatcttggct cactgcaacc tctgcctcct   8220
gggttcaagc aattctcctg cctcagcctc ctgagtagct gggactacag gcacacacca   8280
ccatgcccag ctaatttttg tatttttagt agagacgggg tttcaccaca ttggccagga   8340
tggtttcgat ctcctgacct cgtgatccac ccgccttggc ctcccaaagt gctgggattg   8400
caggtgtgag ccaccatgcc cggcctgtgt tttcttagag ttttgtagtt ttagctctta   8460
tagttagatc cttgatccat tttgagttga ttttgtatat agtgtgagat atccacctgg   8520
tgttgtaaat tgcccagaag tgggtatgct tctaaatctg gctgttaggg attactagag   8580
```

-continued

```
gtgaccaaag tgaatttttt ctttgtttct tttttttttt ggagacagag tctccgtcac   8640
ccaggctgga gtgcaatggc ttcatcttgg ctcagtgcaa cctctgcctt ctggtttcaa   8700
gcagttctcc tgcctcagac tcctgagtag ctggtattac aggcgtgtac caccatgctt   8760
ggctaatttt tgtattttta gtaaagatgc agtttcacct gttggccagg cttttctgga   8820
actcccggcc tcaagtgatc catctgcctc tacctcccaa agtgctggga ttacaggtgg   8880
gagccaccgt gcccagtcct tttctcagaa tttatttgtt tttttttgtt ttgtttcatt   8940
tttgagatag ggtctcactc tgtcagctag gcaggagttc agtggtgtga tcattgctgc   9000
agccttgaac ttctggactc acgtgatctt cccacctcag cctcctgagt agctaggatt   9060
acaggcatgt gcttccacac ctggctaatt ttttaatttt ctaggactta tttgtccatt   9120
cttgcaaagc agggtacaac atgcctatct ctacctacct ctcttccctt caagggactc   9180
cagccaaaat ccttgaggct ctcgggctga ctgtgggtgc tgttgcctga tctgcctcag   9240
tcatgctgca tgatcaaaag tgtccgtttt ctgcttcttg gaactttatt cactttgggt   9300
gtcagtcttc ctctgcagtg tcccaagaac acagaattag accaggaatc tgtgttgcca   9360
tagtgtgtgg aaagaggcag acttccaact ccgctatgtg ctgttgggtg attgaagctt   9420
aattttcttt ctatctttct ttcttttctt ttcttttttt tttttggag atggaatctc   9480
gctctgttgc ccaggctgga gtgcagtggt gcgatctcac ctcactgcaa cctccgcctc   9540
ccaggttcaa gcgattctcc tgcctcagcc tcctgagtag ctgggattac aggtgcatgc   9600
caccatgccc ggctaatttg tgtaatttta gtagaaacag tgtttcacca tattggtcag   9660
gctggtctcg acctcctcac ctcaggtgat ccacccgcct tggcctccca aagtgtcggg   9720
attacaggcg tgagccaccg tgcctggcac ttaattttct taatacctca attaccccat   9780
atggtaaaat gggactagta atccatacct tatagcgctg ttgtgaaaat gaaatgaggg   9840
taagcagata aaatttcaga ctacggatgg gattgttact acattctgaa cctggctttg   9900
ctgttatttg ctatgtgacc ttatcttctc tggatctcca ttctttccaa gtctataaaa   9960
caaagtggac aattgtcaac ctttcttcca aagagcaatg atttaaggat caaatgatgt  10020
catttaacaa aaatatgaag agctcaacaa atgaggaact cattattatt attacaatta  10080
ttattatttt agaaataggg tcttgttctc ttgcctaggc tggagtccag tggtataaac  10140
acagctcaat gcatcttcag cctcctggat acaagtgatc ctcatgtctc atccccctaa  10200
gtagctggga ccacaggcat gtaccaccac gcacggctaa tttttattt tttattttta  10260
ttttttgaga cagtcttgct ttgtcgccca gactggagtg cagcagcgca atcaccgctc  10320
actgcaacct ccgcctcctg ggttcaagtg attctgctgc ctcaacctcc caagtagctg  10380
ggattacagg cctgtgccac catgcccggc taattttttt gtatttttgg taaagacggg  10440
gtttcaccat gttgcccagg ctgatctaga acccctggcc tcaagtgatc cccctttctt  10500
ggcctcctaa agtgctagga ttacaggcgt gagcctctgc acctggcctc ggctaatttt  10560
ttattttttg tagagacagg ttctcactat gttgccaggg ctggtcttga actcctgggc  10620
tcaagtgatc ttcccacctc agcctcccaa agtgctgaga ttacagatgt gagccactgt  10680
gcctggcctg gaactcatta ttgaagcatt cactagtatc aactttgggg ttacctggcc  10740
acatcctctg acctacctat aagggtatca cagctaacgg agcctctgtt tctcagaatt  10800
taggcagaag cagttcaatt tatcacaaac tactctatat ccagcataag tgcccaaata  10860
aaacaattgc taaagttctt taggcattta ctgtttgtta gttagatatt tagtcctcac  10920
tacaaatctg tgatacaggt attattttta ttaaccccat tttatagaag agaaacctga  10980
```

-continued agctcagaga tgctaagtaa cttgtgcaag gtcacacagc tagtaaataa agggcagagt 11040
aaagatttag tttcacattg gactccagaa cctttctact gggactcatg ggaatagtgt 11100
ggatgtccct gaccttcagt ggcccagggc tctcctgggg gaatccagcc atagacaaga 11160
caccagcgag agcccaatcc taagattttg tttgtttgtt tttgagacaa ggtctcactc 11220
tgtcaccaga ctggagtgca gtggcatgat caatgctcac tgcaaccttg atctcccagg 11280
ctcaagcaat cctcccacct cagcctcctg agtagcttgg actacaggtg cacaccacca 11340
cacctgacta attttaaaat tttatttaat taattactta ctattatttt ttgagacagg 11400
gtatcacttt gtcacccaag ctggactgca atggtgtggt ctcagctcat tgcgtcctcc 11460
acctcccagg ttcaagtgat cctcccacct cagcctctgg agttgcaggg actgcaggtg 11520
tgcgccacta tgctcagcta atgtttttat tttttgtata gatggggtct cactatgttg 11580
ccagggctag tctcaaactc ttggactcaa gcgatcctcc tgtcttggcc tcccaaagtg 11640
ccgggattac aggcataaac caccacaccc aacccctaag gtgtttttgc tgaatgtgac 11700
catgtcagag gcaggaaagg gaagcatcat ggggttagga aaggaacact gagcagggag 11760
acaaagaaaa tgggatcatt ttgtgagtgt tcgctgtgtg tgtatgtgtg acaattctca 11820
gagccagcct ctcaggtggt tgagaccaca gtccccattt cccagatgag ataatggagc 11880
ctcagagagt ttctgcagca cagctagtgg aattagaatt tgaacccggc tcttccagac 11940
tccaggtgct tcacaaccat cccaaaccta gtcatttgca gtttaccttc atgattttac 12000
catttccctt tgccatagct agtgttattt acttaataat tccttttgaa tcagtctgct 12060
taaaaaaaaa tagcttcatt ctaaagtgta atattcttgg aatatcgggt ttgctgttac 12120
ccacccccac acgttataca tatacatgta tgtttctaat acatatatat gtacgtatat 12180
acgtgtatcg ttttttgtta tttttttttgt tgttgttagt ttttttttaga tggagtctct 12240 ctctgtagcc caggctggag tgcagtggtg tgatttcggc tcactggaac ctctgcctcc 12300
tgggttcaag cgattctcct gcctcagcct ctggagtagc tgggattaca ggcacccacc 12360
actacacccg gctaatgttt gtatttttag tagagacagg gtttcaccat gttggccagg 12420
tgggtcttga actcctgatc tcaagtgatc cacctgcttt ggcttcccaa agtgctggga 12480
ttataggtgc gagctactgc ggctggccaa tgtatgtttt taatacacat tcaaataacg 12540
aataactatg aaacctgaaa aactgctcca tgttacttcc tgaacccatc ttgagtgctc 12600
acatgctgtg cataccacat attgggaaac actgctttcc ctggcttcca agcccagctt 12660
aatcactgtc ccatcctatg cttcgcttta tttgtctata aatgttgggg ttgggggttg 12720
atgccaaaga ccttttctgt tgtcattaac atggacacag ctctaagagg tcttggcatc 12780
ttgggctggc tctcctttta gttcagaatt tggattttta tccaactact cagagtgatc 12840
aagccttcct tatgaatgaa ctcgttggtc aaactcataa aaggctgatc gataaaacag 12900
gaatgaatgt atgaattgac actaagtcat tagcatttca cgggaatgga ttctccgtta 12960
gtggaagagc acatgtcctt tctggcactg atgtgtgctt gggaaactta ctgagctaac 13020
tggcccatgt aacacagagg cccctttggtg cagtggaaaa ctgttgactt tggagattat 13080
cttgagtttg aatctgagcc tgcctgtaag aagctggcta actgaattgc tttgcttctt 13140
ggacccttac catttataaa atggggacca ttgtactcac cctttagggt tattgcatgg 13200
attaaatggg attctctata gaaaatattg gcacaaagta ggtgtaaatt tgcacgctag 13260
tgggattgtt tgtgagggaa attgtcattt gattatcaaa gacttaggag caggaacagt 13320

-continued

```
gtctaattca gggactgcaa atggaaatgc cagctgaggc caggcatttg ctaataattg  13380
ggtaaagcag ggcaggtgta gaatagcaat gtctgggaat taaaagagag gtgaggacgt  13440
gtatgacctt gagaaggcaa gccctggcaa aaggggatgg cctccactca gctacagtca  13500
tgcctagatc ttctaacttt ttatttttat ttttattttt tgagacggag tcttgctctg  13560
tcacccaggc tggagtgcag tggcgcgatc tcggctcact gcaagctccg cctcccgggt  13620
tcacgccatt ctcctgcctc agcctcccaa gtagctggga ctacgggcgc ccaccaccat  13680
gcccggctaa tttttttttt gtatttttag tagagatggg gtttcaccgt gttagccagg  13740
atggtctcga tctcctgact ttgtgattta ccctccttgg cctcccaaag tgctgggatt  13800
acaggcttga gccaccgcac ctggccgatc ttctaacttt ttaaagagaa gcaagacatc  13860
tggattttta tgtgataact cctgatttta aactggcacc caattataat ttacaacact  13920
ataagggtca acattgccag cagagcaaaa catgggtggg ggcaactgct ggtcaccggt  13980
gtgcagcctc tggtctaaaa tcatctttgt atttcttctt gctttacgca ttgtcccagc  14040
acagtgctgt tgtatagtaa atatccagta agtgggtgta gaatgaataa accaatgcag  14100
ataaacctgt agagaggccg ggcacagttg ctcatgtctg taatctcagc acnnnnnnnn  14160
nnnnnnnnnn nnnnnnnnnn nnnnnnnnnn nnnnnnnnnn nnnnnnnnnn nnnnnnnnnn  14220
nnnnnnnnnn nnnnnnnnnn nnnnnnnnnn nntagtccca gcactttggg aggccaaggt  14280
gggtagatca cctgaggtca ggagttcaag accagcctgg ccaatatagt gaaaccccgt  14340
ctctacaaaa ataaaaaaat tatctgggca tgattgcagg tgcctctaat cccagctact  14400
cgggaggctg aggccggaga attgcttgaa cctgggaggc ggaggttgta gtgagccgag  14460
atcatgccat tgcactccag cctaggtgac ggagcaagat tctgtctcaa aaaaaaaaaa  14520
aaaaaaaaag aaaaaagaaa agaaaaagaa acaatgaatg agtgtgaggc tcatggtagt  14580
attggttcct gagagtagcc aaccttattg gtcatcccag ccacgaagtg aaatggtacc  14640
cctggcttgg gccaatgaat gaggaagaat aatggcaaat gggggtctat gcctccaccc  14700
tccaccacta gggaggtctc aagcttgaaa tccagtgacc aggtttttag gtcctggacc  14760
tggccagtcc tcctacagtc aagtagataa gtggagggtt tggtccgttg ggctacggag  14820
atagtgatca aggccgttac tctgcaatca gactcagaaa tggcctctca gttacttctc  14880
catttgtggg tcttttggaa gagcagagaa gaggaaggaa tttaggtctt ctcaccctct  14940
gggctgcctg tccctgctcc ctgagccatg gagggctggg gtggaatatg gggaataaat  15000
ctgtactttt tttttttttt ttttttgaga cagagtctcg ctccgtcgcc caggctggag  15060
tgccgtggcg tgatctctgc tcacagcagc atctgcctcc cgggttcaag ttattcttcc  15120
acctcagtct cctgagtagc tgggattaca ggtgcccacc accacgcccg gctaattttt  15180
gtatttttag tagagacagg gtttcactgt gttgggcagg ctggtctcaa atacctgacc  15240
tcaggtgatc cacccgcaca tgcctcccaa agtgctggaa ttacaggcat gagccaccgt  15300
gcccggtcct accaatctgc acattttaat tgacaagggt caccctccac tcatgtgcca  15360
ggcatagttc tgagaagcat cccacaagga tgcctctgag ttcaccctga caagtccact  15420
agctcttggc agagacatct ggcaaattca aggcttgaga catgctggcc tctctttaaa  15480
gtgcagcaaa ttttgtctag agcttggtca gttaaaattt tgatgttttg ttttgcatta  15540
atttcaattt ttaagaaatg ttgcattaaa atgttattta tcttgaatag taaatttctt  15600
agtgtcccct taatttctta gtgtgtctga gttgagagcc tcccctgcct gattctagtc  15660
cagaccctgg ggtgacagaa gactggtggg agatgggagg tgaggagggg agtgttggtt  15720
```

-continued ggagaggatg atctacagag tgctggagag actctgtatg gagcttttca tgctgcctgt 15780
ttgccagccc tgaagctatg ccttgaggtt gggcaaggtg gcatatccta gatcagagat 15840
cctcaactgg ggccattttt ctccccagag gacatttgga aacatgtgga gacatttttg 15900
atcatctgcg ggggtgggga gaggggctac tgacatctgg tgagtagaga ccagagggac 15960
cattaaactt tctacaacgc ccaggacagc ccctccacaa taaagagtta tttgacctca 16020
catattaata gcacaaagtt gaggaacctt gatctagatc cacagcacag aagaaaggat 16080
gtagattttt cacacattaa agatgagaaa gcttgtgcct gtaatccctg tgactcagga 16140
ggctgtggca ggaggattac ttgagcccag gaattcaggg ttacagtgaa ctatcatcgc 16200
agcactgcac tccagcctgg gtgacagagc aagattttgt ctcttaaaaa aaaaaaagat 16260
gaggacaggc acagtggctc atgcctgtaa tcccagcatt ttgggaggcc gaagtgggtg 16320
gatcacgagg tcaggagttc aagaccagcc tggccagcat agtgaaaccc catctctact 16380
aaaaatacaa aaaattagcc agctacttgg gaggctgagg caggagaagc gcttgaaccc 16440
gggaggtgga gcttgcagtg agccaaaatc ttgccattgc actccagcct gggcgacaga 16500
gcaagactcc gtctcaaaaa gaaaaaaaaa aaagatgaga aagaggaagg gagagaaaaa 16560
agagagagag gaaagaaaga gagaaggttt tggagtcaaa aagacttaga aattccagtt 16620
cttccacttc ccatggaacc ttggcaagtt gccttctctc tttctctgaa tctcacattt 16680
tgcctctgtg aagtaggggt ggtacctggt ggagatgatg cggagatgag ggtgaggggt 16740
gtgttgcaca ctatgcccct aggatgggtg agagcttggg agcactgaac ctccctttcc 16800
cctcttgttt cttcccccca ttgtctccca ccagctccct gggatctcca cttcactctc 16860
tgggattcca ccagcaggag gctactcctg gagttaaggc gtgttgttca gactggggca 16920
ttttaggggg cataaataat aattatgcct ggacaatgga cataacatct agggccttct 16980
gaagcaaacc agggtgtggg gtacccaaac aaggcagtag gccccaggag gcaggtccct 17040
gcagtcccag cagagagcag ggcacagggt tgagaagact gagcaaactt cattatcagc 17100
tcctttgtcc cccactctgt cctggagcaa tcattctggc ctcttcccac ttccccaaaa 17160
acccagtata aaggctgctt ctggcccctg aagccagagg cactgagagt ggaggtctca 17220
gactcttgga aggtgagttc ttttctggct gcccaggcag gaccagtgta ggccctggga 17280
agaagcagca cctcataggg caaacacgta ggaggcctgt ccttaggaac atcatagcta 17340
agcagacctg tccccgcagg ggcaggagtc tgggctaagg gtgatactgg agagcagcaa 17400
cggagactgg aagacaaatg aaatttggta cctgagttat ccctcccacc attccttttc 17460
tagactctcc agctcagggt ctgttcatgg caagaggaga aagcaatctt gtttgctctt 17520
taatcaaaca attaaacaaa tattccctct atactatgtg ccaggggcta tactagacac 17580
acaaagacag ccccaagaag gacggtggag tagtgtcctc gctaaaagac agtagatatg 17640
caatgcctct tgctcctgcc ctttctcctg ctgggaacag tttctgctct tcatctgggt 17700
aagtctctcc cttccctcct catgcgtctt tccctttttt ccttttttcct acactcccct 17760
ccccccgctt ttatttgcac tcatgaggcc aggaccacag ccttccctct ttagctgata 17820
cagctcatct ccggtaagat atcacttgga ctcagaactg taacctggaa ctttctcttt 17880
tttgtttgat tttttttttgt tgttgttgtt tttgtttttt tttttgtttg ttttttgttt 17940
tgttttgaga cggagtctcg ctctgttgcc caggctggag tgcagtggcg cgatctcggc 18000
tcaccacaaa ctccgcctcc cgggttcaag caattcttct gcctcagcct cctgagtagc 18060

-continued

```
tgggactaca ggcacatgcc accacgcctg gctaatcttt gtatttttag tagagatggg  18120
gtttcaccat atttgccagg ctggtctcaa actcctaacc ttgtgattcg cccgccccgg  18180
cctcccaaag tgctgggatt acaggcgtga gccaccgcac ccggcaaact gtaacctgaa  18240
ctttcagaag gaaaaaccac ccacctgtta agatgaaggg ctggtgactg ccccaggctt  18300
ctcacacgtg ctttctccca ccttcaaaac acacactcgt ggtgtcggcc agaagtcagg  18360
ttcttgtcca tttgtgggtg tgacccgaga gatctctcct tacctaacac caaggaaatc  18420
ctccagtctt gtcttcaggt ggaattccta ggaaagctcg agcgacgttg ctggagctgt  18480
ccacggtgct ggaactagga agctcttgac ctgatggcag gttacctctt cttcccagag  18540
aatgatgccc cccatctgga gagcctagag acacaggcag acctaggcca ggatctggat  18600
agttcaaagg agcaggagag agacttggct ctgacggagg aggtgattca ggcagaggga  18660
gaggaggtca aggcttctgc ctgtcaagac aactttgagg atgaggaagc catggagtcg  18720
gacccagctg ccttagacaa ggacttccag tgccccaggg aagaagacat tgttgaagtg  18780
cagggaagtc caaggtgcaa gatctgccgc tacctattgg tgcggactcc taaaactttt  18840
gcagaagctc aggtaagtag tagggaggct actgcggagg acctggggga aaagagagta  18900
cattcagtct tctgttccct attcatttag gctagtggtt ctcaaagcct cgcatgcatc  18960
agaatcacct ggagttgttg ttaaaacaca gctttctggg cctcacctgc acgacttctg  19020
atttaggagg gctgaggtga agcctgagaa tttgcattta caacaaatcc ccaggtgatg  19080
atgatattgt tggtctgggg agaaccaccg atttaaacaa aaggctttgg tgttagaaac  19140
gcctgtgtta aattctggtt ctgcctttta ttagctgtgt tacctgggca agttgctttg  19200
cctttcaaag ctttagcacc ttcatttgta aaacgaagat atatagcacc aacttcttag  19260
agttgtggtg agcattaaat gagataatac atgaaaagtg tttggaatag tcactgggct  19320
gtaataaact ctcaataagc ggtggttata attattatga gtattatcat ttcctgtagg  19380
attgtcctga cagctaatta agaagcaaaa gataggatta agggaggcaa gtaggtttat  19440
ttttaacctg aaaagggatg ccgggctctt gcctggagac tcagaaactt gaaataaatg  19500
agagggaatt cnnnnnnnnn nnnnnnnnnn nnnnnnnnnn nnnnnnnnnn nnnnnnnnnn  19560
nnnnnnnnnn nnnnnnnnnn nnnnnnnnnn nnnnnnnnnn nnnnnnnnnn ngaattctct  19620
gttagcacat agccagaaca tctagaaggg gtggtaggag tggggattag aggttccagc  19680
tggaggcaat ggcacttgca aaggctttgt tgaagtggcg taagtgtgga ggtggagcat  19740
tcaggaaagg agagcttcag cttcagtgtg gctggagtgc tgggtgtgaa gagaggtgaa  19800
gatgaggctt ggaggctggg cagattttgc tccaaaagag cttggtgaac tgtgataagg  19860
agtttggatt ttctcctact aaggacaaca gcaaactatt gaagagttta aatcgttcag  19920
tgacaatgac acgtttgcgt tttggtggct cactcgagct gccagccagg tagacagtgg  19980
cagaagatgg aagataaagc actaaagggt gatgaggcag gaagccagtg aggagagaaa  20040
ggggacgatg tgagtgacag taaatcattt gttgggttgc tattgtgtgc taagctctgt  20100
gctaaattct tcacgtgtat tatttcagct aatccatcta acaactctgt aaggcaggta  20160
caatcgttcc cagctgaaga agctgaggct ctcaaaagct agtaacttgc ctaagttcat  20220
gcagcatgca agttgtccag ccaggattct aacttagaca ccagaggcca cttttaacca  20280
ctgctctagg actgggggaa atggtcccta gtgagatatg tgtcgagttt catatttcat  20340
tcaacaatat tgttggcctg ctacatgtga agagctgtgg aaagcgccca aagtgagtta  20400
gatccctatg agcaagtggg atgggggtgg agtggacagt aggagggctg gaacacacat  20460
```

-continued

```
aaaagggtat aagaaataac aattaggccg gccaggggtg gtggctcacg cttttaatcc  20520
cagcactttg ggaggccgag gagggtggat cacttgaggc caggagtttg agaccagccc  20580
ggccaacatg gtaaaacccc atctctacta aaaatgcaaa aattagctgg gctggtggtg  20640
cacgcctgta atcccagcta cttgggaggc tgaggcacga gaatcacttg aacccaggag  20700
gcagaggtta cagtgaactg agattgcacc actctactcc agcctgggag acagagtgtg  20760
accctgtctc aaaaaaagaa aacaaaacaa gtaggtactt tctgccatag ggaggattca  20820
taaactgcta gtcctcaggt gcatttttgc ttatcagttt taaaaatcag agaatgtctc  20880
aaagaattag gatgtcagct tcttttgaaa atttgggcca gaagcggtgg ctcacgcctg  20940
taatcccagc actttgggag gctgaggtgg gtagatcacc cgaggtcagg agttggagac  21000
cagcctgacc aacatggcga aaccccgtat ctactaaaaa tacaaaaatt agctgggctg  21060
gtggtgcatg cctttagttc cagctactca ggatgctgag gcatgagaat cacttgaacc  21120
cgggaggcag ggttacagt gaaatgagat tgcaccactg cactctagcc tgggagacag  21180
agcaagaccc tgcctcgaaa aaaagaaaaa gaaaatttgg aagatctgac aacagttgac  21240
ctgcattcct gctcggcaac agcctgatgg tggatgggca gaggctcagt tgtctgccaa  21300
acctcccatc actgatgtct tccctcgctg tcatcatctg cttgacatgt aggcatttgg  21360
tgtgtgcctt ctgctctggg tgcccagatg aattggatgc tatatgagaa aacattctgt  21420
aaatgtcttg tggtaggcaa cctcaaagat cactggggcc tccaatgatc cctccttcct  21480
ggtattcatg cctgtgtata atcctctccc ttgagtgtgt actacacctg gatacttgct  21540
tctaataaac agaacacagc aagggtaatg ggatgctact tctaaggtta aattacaaga  21600
gtgtaaagtc tgtcttgttt gtttccctct cttgatcttc ctctcattct ctctctctcc  21660
ctctctctca ctttcttact gtcttgtcct tccctttgtt tactctgatg aagcaagcta  21720
gcaagcatcc atgttgtgag ctgacctatg aagaggccca tgtggtggta aggaactgag  21780
ggcagcctct acccagcaag gaactgagtc actcatcata tgggtgagct tggagacaaa  21840
tccttcccca cttgagcttt cagatgacgg cagccctggc tgatgctttg caggcttgtg  21900
agagaccctg agacagaaca ctcagctaag ctatacccta tctcctgaga tagagtataa  21960
tacatgtagt tttaagctac tatgttttgg gataatttgt tactcagcaa tagataacca  22020
atacatatac catgtacata actgtttcag ttgtctgaga ctatatttag tcattttaca  22080
cctacatcaa gaatgtgtca ggcaccattc caggtacttg gaatacatca attaacagaa  22140
taggtaaaga ggccaggcat agggctcaca tctataatcc cagcactttg ggaggcccag  22200
gtgggaggac tgcttgagcc caggagttga gaccagcctg ggtaaaatag tgagacactg  22260
tctcaactaa aaaaaaaaaa aattagttgg gcacagtggc acatgcctgt ggtgccagct  22320
gctcaggagg ctgaggtggg aagatcgctt gagcccagga gtttgaagct ccagtgagcc  22380
acggtcacaa aactgcactc tagcctgagc aacagaaaaa gaccctgtct caattaaaaa  22440
aaaaaaaaaa aaaaggaaag aaagaaaaaa ataggtaaag atccttgatt cttgccctct  22500
tggaacttct attctagagg gggatggttt ttcacagtag aagtctgtgt tgacagcgct  22560
gtttaaagct ccttcagcat ctggggaaaa ggttnnnnnn nnnnnnnnnn nnnnnnnnnn  22620
nnnnnnnnnn nnnnnnnnnn nnnnnnnnnn nnnnnnnnnn nnnnnnnnnn nnnnnnnnnn  22680
nnnnnnnnnn nnnnattttt tagagatagg gtcttgctat gttgcccacc aggctggtct  22740
tgaactcctg ggctcaagca atcctcctgc ctcagcctcc tgagtagctg ggaatacagg  22800
```

-continued

```
tgtgcaccac catgcctggc ttatttcata tatatatatt tttatatata tgtatattta  22860
tatatataaa tatatatata atttctgtat ataaataaat aaatatatat atatatatat  22920
ttttagagat agggtcttgc tatgttgacc accaggtctt gaactcctgg gctcaagtga  22980
tcctcctacc tctgcctttc aaagtgttgg gattacaggc gtgagccatg gcacctaact  23040
gagttatttt taccacacga agcataggac atacatccaa aaatgttctg agctgagcaa  23100
gagcctggag gcaagtgaat ctgaactttc ccgtctttga agaaaccagt ctctctccaa  23160
agtcacatag ttagtgtcac tccccccaag aactgcatga gctgggacaa tcagagggca  23220
gtggaaggtc tggggctcag gggcgccccc tgctgtctcc ccagggtctg tccccttacg  23280
caagagcctc tgctccccca ctttcctgtg gagcctcctc accatgggca tgacccagct  23340
gcggatcatc ttctacatgg ctgctgtgaa caagatgctg gagtaccttg tgactggtgg  23400
ccaggagcat ggtgaggcac cgctgaggcc cctgggggtt gggggcacag gcgggtcacc  23460
ctggctgagc tcccctcacc atacgtttcc ctacccacag agacaaatga acagcaacaa  23520
aaggtggcag agacaggtag ggctatgaaa gcagggccct ggctcacgcc caccccactg  23580
caacccgctt ctcagggggc gggactcctc taggcctggg cccacccagg taacccttt  23640
gtgggatgta agagtctggg ttcagaggaa ggctattttg gtgctctctg gcctccgctg  23700
gaaggggtga tagtgtccac tgagtgccag ttcctgaccc cactgccctt cccatcctgc  23760
ccagttgggt tctactcctc cgtcttcggg gccatgcagc tgttgtgcct tctcacctgc  23820
cccctcattg gctacatcat ggactggcgg atcaaggact gcgtggacgc cccaactcag  23880
ggcactgtcc tcggagatgc caggtgacct gcctgtacag ggatggtgac agcaagtggt  23940
caggcagtgc ttttcatttt ctctgtgcgt ttacatccag cagcttgttg ctttctccca  24000
agaaccctag gagatcaggg gtacctcccc attttacaga tgaggaaact gaggctagga  24060
agggacctgg cttgcttaat aataagaata gctaatgcag agtgctgact gtgcacttgg  24120
caccttgcct tgtttagtcc tacaacacct ctttgaggta gatgcgttaa tatcttcatt  24180
ttgcagttga ggaaaccgag gtacagggtt gcacagttag gtcattcacc caagatcaca  24240
cagctttcag tggcagcctc cagaacctgt gttataaggg tacacgctaa agtcttgtta  24300
gggctagaat aggtagagtt ggtatattag atatttattg ctgtataaca aatcacccca  24360
aggcttggca ttttaaaaca acaaacactt ctcatctcat acagtttctg acagtcagaa  24420
atcagggaga gactcagccg gctgattctg agtcacagtc tctcatgaag acatagtcag  24480
gctgtcagcc agggctgcag tcatctgaag ggctgactgg ggttggagaa tctatgtcag  24540
ttcaattacc cccatggcct ctccataggg ctgctcagga cacagcacct gctttccctt  24600
gagcaagagg gctaagcgac agagaccccg tatcttctct cacataatct cagacgtagc  24660
ataccatcac ttctgttacg ttctattata ggcacagagc aaccctgata tactgtggaa  24720
ggagactgga caaagcaggg gaataccagg aggcaggatc cttgagggct gtcttgttgg  24780
ctggagacca ccattgaggg tttttttttt tttttttatt gagacagtct tgctctgtcg  24840
cccaggctgg agtgcagtgg cacgatctca gctcactgca acctctgcct cccaggttca  24900
agcgattctc ctgcctcagc ctcccgagta gctgggattc accatggagt cttgaaccca  24960
gattctgtga ctgcttttgc tctttttgtg ttcatccaaa cagtccctgt ttatcctaag  25020
aggatgggag aaagagactg ggagagaagg aaatccagtg gcctccctcc ctgctagcag  25080
agcctggccc tggcactgag ccttcctcct ctaccctctg ctcctaatgg tgagggtccc  25140
ctagcagggc ccttctgtcc aggacacatg ggccgcctgt cctcacccca gcctactgac  25200
```

-continued

```
ctctctcctg ggctggcctc agtgcccttg attgtgccgg agagaggaag cgctggacag  25260
tcaggccaag ctgctgtccc caggagggca tctgcttatg tctagggcag ggacaccttc  25320
ctgaggactt ctgatgagag acggtgtgag agcttcccac ttcccacctt ccttcccatc  25380
cttggttctc aaaccttcaa gtgtgcatga gaatcactta gtgggggata tttgtccaaa  25440
tgcagatttg cagatatccc cgctgagatt ctgagggccg agatgaggcc tgtgaatctg  25500
catgttaaga aagcacccgc tttgatgcgt gtgtcattgg gtaggggagc aacactttga  25560
gaaacatgga gctagagaac gtgggtttct atgggtttcc catagaaaca tggatttctg  25620
tgttttctgc tgccctgaca tcgaaggcac atctgaaggg ggaggggcca ggccaagaac  25680
cagggagtcc tgggaacgta gaggcagcag ccagtgactt cccgtactcc tcagggacgg  25740
ggttgctacc aaatccatca gaccacgcta ctgcaagatc caaaagctca ccaatgccat  25800
cagtgccttc accctgacca acctgctgct tgtgggtttt ggcatcacct gtctcatcaa  25860
caacttacac ctccaggtac ccaccttcat ccttcccctc tccctgcctc ccgaggctcc  25920
tccaaaggga tggtccatcc agcacctgcc ttccaggaag cgcagttctg gtcttctgat  25980
ctggatctat tttccgggtt ctccaggaag tgtttctagt agattgggtt ggcgaggggg  26040
tgggaattga ggcccagttg gcctcttcgc cctacccctc cttcctccag cctccacaca  26100
ctctcctaac ctcttcactc tctcttttg gttttagttt gtgacctttg tcctgcacac  26160
cattgttcga ggtttcttcc actcagcctg tgggagtctc tatgctgcag tgtgagtctg  26220
ttgggctgaa atgccttcct gagctttgca accgtgatca gagaacccca gggaagggtt  26280
gggagggccc caggcatccc ctaatgcacc tctctctgag accctctgat ggcagggagc  26340
tcacttcctt aaaggcagcc tatcctgctg taattgactc cccctgttgg agtcttccct  26400
tagaggaagc tgaaatacct ggcttgatga cactttggtt ctatgtctgc tgtttgaaac  26460
ggcccccaga atggcctccc ctccatgccc accctgaaga aatttcccaa gggcagccat  26520
ttgccttata attttcctct tcatgttgga cagtccccac ttgcatctct ctcctggttt  26580
cccctgctgg gcgctgctga gggactctcc cctgtgtatg tgatggagta acaggacatt  26640
acaataatga tgacaaaatg acaaccatta tcaagtgctc cgttggtgca ggcagcaggc  26700
aggatccttg accatcactc cctgagttca gcctcactgc agcggtctcg gcagagggca  26760
gctctctttc cttcatctgc tcaagccaga accctggagt ttccttgatg tttctctccc  26820
tcacactcca tgttcactcc atcctcagta cagccagcag cagcttctac acaccccaaa  26880
tctgaccctt cttgtcacct ccactgctgc ctctccagtc ctagccacca acatctctag  26940
cctggattat tgtggcagcc tttagtctcc cacatctgcc ctggccccgc tgtctcagtc  27000
tatttttaac acaggggctg cagtcacctg tcaggacata agtctcttca catcactctg  27060
tggtgtcctg tctcatctgt ctcagagtaa aagccaaagg ctttactatg gcctaaaaag  27120
ccctgcaagc tctggcccca gcacttcact cccctctagc tccccctcct ccattgttca  27180
ctctgccaca gccacagtgc ttcctagtgc tccggaagtc tcaagtgtgt tccctgcttg  27240
gcatctttgc atgtactagt ccctgtttct agaacattct tctccagata tctgcaaggt  27300
gcccaatctt accttctctc cttcttcagg tctttccctg actgtcctct tctcagtgag  27360
gcctcccttg gctgtcccat gtacaattgc aacctcccta ctgcccgctt ctctgcttgg  27420
tttttctcag cgtttatcac taacactctg cctatctctt gcttattgtc tgaccgccac  27480
ctgctccatg ggaatgccac ctcctcgatg gcaggaatct gttgacttgc ttgatcgtgg  27540
```

-continued

```
tatctccagc acctagagca gtgcctggca catagtaggt tctcagctaa atgtttgttg  27600
acagaataca gtggacagtc ctgcgaggtc aatgccatcc ctgttattag tggaggaagt  27660
ggggctcagg gagtttgagc cacttgccaa tatcacacat acaggaggtg tgagaaccca  27720
gctcagtggc cctgaagttg gagcatttgc cctcaaggct ggggaccaaa gagcccatgc  27780
aaagagcccg aacgcttaag caccaccctg cctggccagc ggggnnnnnn nnnnnnnnnn  27840
nnnnnnnnnn nnnnnnnnnn nnnnnnnnnn nnnnnnnnnn nnnnnnnnnn nnnnnnnnnn  27900
nnnnnnnnnn nnnnnnnnnn nnnncccact gcgcctggcc cattactttt aatggcaaaa  27960
accacaatta cttttgcacc cacataaata gttaccatgg gctgagcatg gtggctcagg  28020
cctgcaatcc cagcactttg ggaggctgag ccaggcggat cacttgaggc caggagttca  28080
agaccagcct ggccaacatg gtgaaacccc gtctccacta aaaaatacaa aaattagctg  28140
ggtgtggtgg cgcgtgcctg taatcccagc tattcaggag gcagaggttg cagttcactg  28200
aaatcatgcc actgcactcc agcctgggcg acagaatgag actctgtctc aaaaataaat  28260
aaataaataa ataaatattt accatgtttt gaccacctgt tatgtgccaa ctgtattact  28320
taaaaacacc catgggaggc tgggcacagt ggctcacgcc tgtaatcgga cactttggaa  28380
gggcaagcgg ggaggatccc ttaaggccag gagttcaaaa ccagcctagg taacacagta  28440
agccctgtct ctacaaaaaa taaaaaaatt aactgggcat ggtggtgtgt gcctgtaacc  28500
ccagctcctc gggaggcaga gggagaggtt cgcttgagcc cagcagtttt aggttgcagt  28560
gagccaggac caagacacta cactccagcc tgagtgacag agcaagacac tgcctctaaa  28620
caaacaaaca aacaaaagcg acctgtgggt aggtaggaac aggctcatag tacagatgag  28680
aaagcagagc ttggagggct caagcgattt gccaagcaga ggtccaagcc gaggtctctc  28740
tgaatccaaa gttaattccg tctatcatat caccacagcc ctctctgccc cagggagagt  28800
ctctgcccac tccagccact cacgtgtaat tgacttcctc aggggcagga aaggcttcga  28860
tgggccagtt gagggtgcag ttcagaaaga taaggcaggc caggccagac caggtgaaca  28920
tgatgaccac gaaggccaca ccggcatcgt agatcagctg tgagaggagg gggcaggccc  28980
gtgggggaga ctgcctggcc ccagacccca ccaaggtaga tcccaggcct cagaggcctt  29040
aaagaagttc tcttctcccc ttgtccttgt gcccaatttg cagatgagga aaccaagacc  29100
agaagtttag agtcagactc agaagaccca tcattccttt ttctttttca cttgaggccc  29160
cctagagagc tatgaaatag tctccacaaa gcctgaagtt gctggccact ggctcaaaat  29220
atctctgaaa tttccattat cttaaaaaaa tacatacatt tttgcctatg actccacaaa  29280
cattcatgtt catgttcgca caaaaatgtc catttcatag tacgtacaaa ggaaacttag  29340
tgctctaggt ttaccgggcc taatcgtgtt tatcctgccc cttcctggca cattccccag  29400
gggaaaaggc aaacccagac tgctcatgct cagccttttc tcacctttcc caggtcctcc  29460
cacgtgcaac aactgggggg gttggggaga gggaggtgca agtgctctgc ccaagggctc  29520
tcaaccccag ggcaggtaag ttctcaattg aatgagattc tgtgcaaatg tgtcagccct  29580
tcttatggaa gaagctgatg caccatctgt cctcttgtcc tccccatacc atctgaccag  29640
gataattaat gtctgctctc ccctcaggct cctgctcaaa cctttttctc tgcagtcttg  29700
gaccttggtg ccttttcctc cctaggggca ggacagagct tcaaagggcc acaccccaa  29760
atgtgtggag gtaagatctg gctcttcaaa cactacttca gttgaaaaga agggagaact  29820
gcccaccctc catgcctgcc caccagaaca actgatggcc cccccaccca tgcgctctct  29880
caaactcctt tggagacact gagcaaaagt accttcttta gtactctttg taaagtgcaa  29940
```

-continued aacggtatgc agtttggtac tgcccaccgt ggaggttgag gagcatggca tggctcaaag 30000
ggtcctttga tatttgacag aggaaattga ggcccccatc ttgcactgag ctaaaacttt 30060
ggtcccctgg cttcgaggta caccaggttg acctgtccag gatccagcct ggcataaact 30120
cactttgtga ccttggacca aaccacccat cctctctgga aggtgtggaa aaatgtggcc 30180
ccaaaggctg aataaagcca gagagtcagg gaccttgaac gcatgtgaag gggctggact 30240
tgattctgta ggtgaagcta aaccactgaa ggtttttcag cagtgtgtga gccagttccc 30300
catctgagat ctttctggaa gtcacgtgag tgacagagta cagagaaaaa gaatcagagg 30360
cagggagacc agctgagaaa gcttgctgtg gcccaggaga gagggggaag gcctgcattg 30420
ggatgatgac agagaaagga gagcggagaa gtcagacccg tgggtcagca ctagctgctg 30480
ctcactcggc cccacccggt tcttgtgtca agacaaaaag aaaacccagg tggcctcata 30540
ccttgattcc tgggaacgta atggcagaag aggcgtaaga gccaatcatg agggccatta 30600
acgtggagcg caggttccca aacatgttgg gcagctgagg agggaaagca gcacccatga 30660
ggtggggaca ccgtgaccct tgcccagcat tcccagccct gctccataca atagctccag 30720
gagacgcagc agaaaagccc caaggtaaaa caaacagaaa aatcaatgtg ggaaactgta 30780
ctctgccccc tgcctacaca gtcacagtgc cctttagctt caaaaaggct cccagacacc 30840
cctcagagag acattttgtt aattttgttt aattccaggt ttcccaagtt tgttacgtaa 30900
cacctctgaa aaacacatgg aataggtgct taagaaacac tgatcttggc tgggcgcagt 30960
ggctcatgcc tgtaatccca gcactttggg aagccgaagc tggtgggaag cttgaggtca 31020
ggagttcaag accagcctgg acaacatggt gaaaccccat ctccaccaaa aatacaaaaa 31080
ttagctaggc atggtggcat gcgcctgtaa tcccacctac tccagaggct gaggcaggag 31140
aatcgcttga acctgggagg tggaggttgc agtgagccga gatcgcacca ctgcacttta 31200
gcctgggtga cagagcgaga ctatgtcccc accccccaaa aaaaaagaaa agaaaagaaa 31260
gaaacagtga tcttgtccaa cccatttgag atgagacaat tgagacccag ggaggaaaag 31320
tgtactcaag ttcacagagc acattaatgg ctttctcccc attgtcgttg tcccagccct 31380
aacccaaggc tgtgaccatg gctgtgtccc ggtaataggc agtgcctctt aaccctctcg 31440
gttgacgtcc cagcccagtt tctgcctaat caggacaaat cacatcctgg gaggtgaggg 31500
tggaaataag ggagggaact gagccagggc agacagtctc cagaggaggt ggctctgacg 31560
cagagcaggg tcagaaccca caccaggaga gaatttaatt gatcatgtgt tccactcacc 31620
tgcctcagcc aagccctcag ggcaggggaa ggcaaagtca ggatgccctt cgcacacacc 31680
ctcctctggc cccaccatcc tccccaagtc actagatccc acagctgaga aggaccttag 31740
gatccgtaca aagcctaaac acactccaca gagggggaaa ctgagactct gaagggaggc 31800
ctcaacagct ctggtaaaaa aggcgtttag gccgggcgca gtggctcaca cctgtaatcc 31860
cagcactttg ggaggccgag gcgggtggat tgcctgagct caggagttcg cgaccagcct 31920
gagcaacacg gtgaaacccc gtctccacta aaatacgaaa aaattagccg ggcgtggagg 31980
cgtgcacctg tagtcccagc tactcgggag gctgaggcag gagaattgct tgaacctagg 32040
aggcagaggt tgcagtgagc cgagatcgcg ccactgcact ccagcctggg cgacactgcg 32100
agactccgtc tcaacaacaa aaaaaaaaaa atggtgttta aacacatata actaaattat 32160
ccttccccct tcccctgaag tggctggctc aggaaaaacc tctacccact caggcagagg 32220
ttttcctgca ccctgcatcc gtgaggcacc actgccaagg acgccaggga aggctgccag 32280

-continued

```
gcctggagag gggcagggcc ccctcccctc caaggggcca caaacgctgt ctgcgcccag  32340
taccgtgggt aaggcgaggc cggccggcta accccgggct ggcggccttg cagcgtgcgt  32400
ggcaacagca gctgggcccg caagactcag cacgggacgt cctcgtccaa gtctgggcca  32460
agagcagcgg cccagggggc ggggccggcc agagggagcg gggagaggct gaggggcggt  32520
gccagcgccg gaccctgcca ttggctggag attacaggag gcggggacat agcagggagg  32580
agccgctgga caagccccac ccggccgcca gggagggtct gaggtcaaga gccggagaga  32640
agggatttag ggccctgggc caagttgcac agcagggaga aggggctgcg cagaggggcg  32700
gggagaaagg gatccgcttc cttcctttag agctgtgaaa tgtccccggt tggaattaaa  32760
ggcggctgct ggggagaggt gaaattcagc caaaaccacc cagtcaggca gcccttctca  32820
gagataaaca gtccgagcca gcccggccag gaaccttccc ctccaacctc cctaagcctt  32880
taacactcct aagcctttaa cgcgtttaca cactcacata aataaacaca ctttgagcaa  32940
cacacataca ccactcacca catgtaatag gtcaagccat gtgcacgacg aggtgtcgac  33000
aatttcatat ggttcaacct agtacactca caaacacacc taccaactca tggctttcac  33060
agggacgggg tcacacaccc actctcccac gacatggcaa gcgtgcacac gctatctcaa  33120
gctgctccct cccccctcaag atcatgttac ccagttttat tttcttccca gcacctatga  33180
cgactgacat aatttattag tttacttgtt tattgggtta tctgtgcccc tcacccccaa  33240
aatgtaacct ccagcaggga ggatgactcg gtcagtcctg attgtgctgt agtccaggac  33300
ctagaacaga gctccatgga cattcatggg ctctgtacac acaaacacac acattaacat  33360
acaccccgac acacagcctc atccacacac acacagcctc acacctgctc tttgcagcca  33420
cctgcacagt ttctcacaca ctcacttgat ctagtgatct gcgtccacag gcccctcccc  33480
cagcccactc atactgccct caccccactc actctgccct caccccactc gggggaactc  33540
tgctgccagg ccaggcctgt gacactcacc gtgagtgaag tgaacgttag gcagatgcca  33600
ccaaagccat tcagggacag cgccaggaat atcaacggag acagagctgg aaaggggaaa  33660
gcagcagatg agggcatttg gggagctgtg ggaagccaag ggcgggagct ggggtaaaca  33720
tccgccttca tcccacctat tcttttcttg tggggccaca agaggacaga caactcacct  33780
tccacgtccc gggaggccag ggccatgagg gtgcaggacg cagtgaagca ggcactgtgg  33840
agacacaggg aagggcgagg ggttggcctg tgagcacccc ccctcccctc cccctgcagc  33900
acggtccctg tcctcccgtt ccccatagcc cagccacctc acctgccaac cagccgcacg  33960
ggtcgggggc caaagcggtc catgaggatc cccagtggca gggtggtggc gctgagcacg  34020
aaggaaccaa tggtgaagcc caggttgagc atctcgtcct gctggtcaca gcctggccac  34080
ctgcgctgct catcctgggt ggtgttggtg ctgctctcag ctgaggaggg ggaagggagg  34140
gctcagcaca tgacaccagg aacagctggg cacaggagac agcagcccac agtcaggcgg  34200
cctgctttca aatcccatgc caagtgcctt tgggggtacc ctagagtcac atctcctctg  34260
atggggctgc tccagaaatg gcagccatta gtacctgacc ctgggagagt cttgtgcaca  34320
cacagcctga ggcttcaact agctcaaatg aaatactgga cataaaagta tttactaagt  34380
tgtaatatgc actcagtgtc caagcttagg gggttgtgga cccccaacaa gaagtgcccc  34440
catatctaga ggcaaaggca aaggcagtga gtggtactct aatggctata acaagaattc  34500
attaaaatgg cccggcgtgg tagttcatgc ctgtaatccc accactgtgg gaggctgaga  34560
caggcagatc gcttaagcct acaagtttga gaccagcctg ggcaacatgg taaaacccca  34620
tctctaaata aaaaaaagaa atttagaaag aacactaaaa cttagaggaa gctttcccga  34680
```

-continued

```
taaatgatag tctgataaaa taatagctaa tacttattga gcacttaact atgctccagg  34740
cactgttata agtcagttaa taaagtatcc cgttccctag gtgatgaagc tgaggcacag  34800
aatgagaacc aggcactgcc ctccagtccc ctctagaagt ccacttggag gacttgtcct  34860
taacggtaaa ctgccaactt ggagttgtga caagttaagg agaaaagcta gtgataggag  34920
acaaagggct gcttcgcttt actcaatgct cannnnnnnn nnnnnnnnnn nnnnnnnnnn  34980
nnnnnnnnnn nnnnnnnnnn nnnnnnnnnn nnnnnnnnnn nnnnnnnnnn nnnnnnnnnn  35040
nnnnnnnnnn nntccctccc tccctccctc cctcccttcc ttccttcctt ccttccttcc  35100
ttccttcctt ccctccatct tctccacacc tggtatcatc atacagaagc agagaggact  35160
gcacttggtg aaagtttcaa ttctcctgtg tggagaggtg agcactgagg aaggggtggg  35220
ggctgtcaaa ggagacttac ccaatctttc cagcccacca atcccttgcc cagtgtttct  35280
ataaaataag ggccttttgc atctgattta agtaggaagc tgattcctga gcccctcaga  35340
tctgctgaat cagatagcta aggggggcct ggaatctgca ttttagcaag cggaggtggg  35400
ttatgaagca ctccaaagtt tgagacacgc ctcaaaggtg gagtggttct gtgggggggca  35460
gaaaggaaaa tgcaaagggg gaaggggtca cacttgggga aggtttcaga caataccgag  35520
tggaaagggt gatgccaggt gtggggagta acagatagag gaggcaaagt gagtggagac  35580
caagccagac cggggaggag ggggccacag ccaaggtgag acaggtcagc agccagaaac  35640
cgaagcagac acttgcaggg tgcaccccgc cctctcttcg tggcaatctg agaccgagga  35700
cgtggagacc ctggagagcc cccaaccttg tttctggggg gtgggtcaga gaggaagcct  35760
ctcatccccg ggcaccagcg gccttcccgg gaggctcaac acgcagatac ctggataggc  35820
gtccatcact cccccggcca gagcccacca acgctcctcg aggtccgacc ttgtccctcc  35880
ttctacccca cagtccccag tcctagctca tctgcataaa gctccaatta acatgttttt  35940
cctttgctat ttgcgatccc agaactcgtt ccccaccccg agcccgtttc ccgccgcttc  36000
ctcgcccctg ggagggcggc cccattaacc ctcgcgaccc gggccgctcc tggcggtcct  36060
gaccccgcca ccccgtcccg cggcgggggt ctgggggtga ggggcgcgcc ctggggcaga  36120
ggattgcgcg gcagggtctg ccacagggca gaggccaggg ctctccggga aaaaggcagg  36180
cgcatatatg cccccctttc tgggaaaaga cggggagggg ggcttctcct gggagactcc  36240
aggcttcgaa attcctcgtt ccctatcctc cggcccccgc acccctcctc ctccccgcca  36300
cgcaccctct cccctcccca gccatctgtt ccactccgca gcgccgcgac aaacacggct  36360
ccagctcgct tccgcccctg cccagccccc tccccaagcc ccggggagtg ggggagtgag  36420
cagacgccct tctcctagga ggccggaatt tctgcctcca tctcccaccg gggtccggct  36480
ggccagaggc aagcttcgag accccccacc aaccaccacc accgttgcga gggccggtga  36540
ggctgcagat aacgcttgca aggacgggag tcggggaggg tgtagggcga gtttaaagga  36600
cgggcagagc aagccccggg aagaggcagg ggttttccct cccgggtcgc cgcccccccgc  36660
accctcggag ccagccgcag ccacgcagcg ccgcctgccg ggcacaccaa ggacctggcg  36720
cgcacgtggc gcttaccccc acccccgggt ccgctcctgg ctcgcgctca gcctccccag  36780
actattcgca aattgaggat cccggacaca gagtgcagag accccggcaa gcctactgaa  36840
agccagccga acccgctggt gggtgctagc caattctgat tttgtacttt acaaaaacaa  36900
aaaaagtcag tgttggaagt cgggagtctg ggctcagagc agcagggatc tgcgatgtga  36960
ctttgccaag tctccagacc cctgaggaca ggttttccta tctgaaaacg gaggggacag  37020
```

-continued

```
tctctcttat taacttctca agagaaacaa agacaaaggg agggaaaatg gcttagctgg  37080
aatgctgtct tacagagcca acctttggag gtgggggaga tggccaaggc ctctgaggtc  37140
actcttggcc ccaggagcag ctgagaaccg gaaagaagct tgggacctcc tttctgcaga  37200
gctatccttt ccacagactg ccgaggttcc aaattgagct ccaccaccta acactgtgtg  37260
cccttgggtg tgtgccttaa cctctctggg cttgtttcct acagcgacaa gaaagaatga  37320
caacaccaac ctcttaggct atagtttgga taaaatgaga tagctgtgta gaacagacag  37380
atcctaaacc aatgttagtt ttcccttcat ttggggactt gctctaacct ccagggctta  37440
tgtcccagag gcacaagcag gtgcagggct ggataaataa ggtatgtctt tctgcaggat  37500
ctcttgtcct cactgatggt gtcttctctt gatatagata attttaaagc ttcacgttat  37560
ttatttattt actttaaagc ctcactttaa tgttaaaggt aaatgtaaat atagtataac  37620
aaggaagctc aaaatttgca taaagtttta agataaaata ggagactcca aaaaagtgtt  37680
actttcggca ggccctaggg atgctatggt gggaagtttg agtcatacct tagcattctt  37740
tctaaagcat tctgtcctaa tcctctgtat ggagaaaagc cagcttcctg gatgtacccc  37800
aaatcctggg aagtaggggg caggagctgg actccctcca agcactaagg gcagggcatg  37860
gttgggaaca gggaggtgag ccagacagcc agaggcgaac gggctggcat gccaagcgtc  37920
ctagttaatg cccagctgag cctgggtgaa gaaggatggg ggtgtgggga agacaccccc  37980
caccaaccgc caaagacagg cgcacaccag ccagtctctc acttcccttt ttatttcctc  38040
taagacttgc aagcagcagc accagagagg gaacctgccc tcctggccct ggaaggggcc  38100
gacccccaac ccctaaccca ggacacagct ggcacctcag gcccctttcc ttctgaaagg  38160
agggctgtgt ctctctcaca ttcacacata cacagacaca tgcatgtgtg cacactcatg  38220
gcacatggga cctcaggggt agcctgtttg ccgatccccc caagaggtac caggaggcag  38280
accgctagaa ggagataaga ggcaccctgg tctcctccaa cccaaggagg aagaaagctc  38340
aacccctcta ggatagggac tgtcttcagt caatggagcg ttgacttagg gggcgttttt  38400
gaaggttttt tttcctcctt tttgcagtct ttacaaaaat agaacttctc ttggtattta  38460
taaatctacg gccatggctc tatgtgcatg ttacaggtag aaaagccata tggggcactc  38520
cttttggttg ctcaggcctt gattgcctgt catccaggtc ccttggtctg agaagtctat  38580
gcggtcacct cagagccgct aagcaccttc agtgggccca tcccattggc ggcgtactcc  38640
tgctggagcc gggcacggta atagaagagg taggaaggca acaggaatcc caggagtgag  38700
aatagcagga ggcccagatt cacctttagg gcaaggagag agaaacagag tcaagtaggt  38760
agtcatctgc ccttagcctc ccacagggag gagaaggcgg ccatttttct ccaggtcctg  38820
agccagaata aatacagcta gtacttatta tgtgtagtca ttgttccacc agtatctcac  38880
ttaatgttca gcaattctgc aaagtggctg agatgagact tctcaggtat aacaagtggc  38940
agggcctggt gggtgcccac accatatggc actcactagg taggtatgag gaaggcacag  39000
cactgtagga gtctgggctg gtcaggctgc tcccgaaatg gggccttctg ggctcacccc  39060
tctgaccttt ggagatgtta accaatggga tcccgttcag ggtggcgaga ggaggctctc  39120
agacacagtt caaggaactg ggatgcacag cctggtggac agaaggcttg gaaggcccag  39180
gacacgcggg ctctgactcg gttcacatcc cactctgcat tactcactgt gtgactttgg  39240
gcaaataatg gcaattctta ctgagtgcct ccttctcagg gctgttgtgg cgaagatgta  39300
agttaaaaaa aagtatgcat catgcttagc acatagtgag tgcttggtaa atagaagcag  39360
ttatttcatc acaattcttt gggaggaggg tttacgtgtg ggtggcccca cagggcagat  39420
```

-continued

```
gaaagatcag cgtcagggag gcagatgagt tcaatgtaag gaaaagactt actaacagca  39480
gcagggctgc ctcgtgcagg agtgggtgcc ctaccactga gggtatctaa gctaagaggg  39540
aagggtcccc tttcaggggt gctggagaca ggatcccaca ctaggtagaa ctggattgga  39600
ccaatggtgc ctgaacacag gcccaagagt caggactggc cacttcacaa agcacctgga  39660
gtttactaaa aacagactcc taggaggtca ggcactgtgg ctcacgcctg taaccccagc  39720
actctgggag gccaaggtga gaagatcatt tgaggccagg agtttaagac tagcctgtgc  39780
aacatggcaa gaccctgttt atctgtacaa aatttttttt taaaaaatta gccaggtatg  39840
gtagccatca cctgtggttg cagctactca gaaggctggg gccggaggat cgcttgagcc  39900
caggaatcag aggctgcagt gagctgtgat tttaccaccg cactccagac tgggcaacag  39960
aacaagacac cttctctaca aaaaaaaaaa aacaataggg ccgggcgcgg tggctaaggc  40020
atgtaatccc agcactttgg gaggctgagg agggcagatc acgaggtcgg gagatcgagg  40080
ccatcctggc tagcacggtg aaaccccgtc tctactaaaa atccaaaaaa aaaaaaaaaa  40140
ttagctgggc gtggtggtgg gcgcctgtgg tcccagctac ttgagaggct gaggcaggag  40200
aatggcatga acccgggagg cggagcttgc agtgagccga gatcgcacca ctgcactcca  40260
gcctgggcaa cagaatgaga ctccgtctca aaaaataaaa ataaaaataa ataaataaat  40320
aaaataacaa taaattaaaa acaaaaacag actcctacgg tcaggctgag atatcctgat  40380
tcaggggact ggggaatctg tatttttaac actccgtgag ggttctaaa aggcagacaa  40440
cttggaaacc tgcagattag agacctctga ggtgcctctg gctgagatga gtgagggatg  40500
gcaccacata caaggcccta cccctgcccc caggagagtg gctcctgctc cccccacacc  40560
aaccctcgct ctcacccaga agggctctcc tttcaggggt cccaccatcc ccatgaaaag  40620
tggctgctga agcaaggcga acacagcact ggtgagggac tgcaggcctg tcagcgtccc  40680
aaaaggggtt ggatgggaac ctgtccccaa aacgggagat caaagggtgg tgggggcctt  40740
tcagcccagg caagaacttt ttcttttcct tcccaacatg ggnnnnnnnn nnnnnnnnnn  40800
nnnnnnnnnn nnnnnnnnnn nnnnnnnnnn nnnnnnnnnn nnnnnnnnnn nnnnnnnnnn  40860
nnnnnnnnnn nnnnnnnnnn nncactccag cttgggtgac agagtgaaac cctgtctcaa  40920
aagaaaaaaa aatcttaaag aataaggata taaagaaaga aaatattttt gtgtagctgt  40980
tcaatgtttg tatttcaagc caagtgttat tacaaaacag tcaaaagttt ttaaaaattt  41040
aaaagtttat aaagtaaaaa agctaagtaa gctagggtta atttttttat cgaacaaaga  41100
aaaatatctt tgtataaact tagtgtagtc taagtgtaca ttgtttttat tttatttatt  41160
ttttattttt ttgaaatgga gtttcactct tgttgcccag gctggagtgc aatggcatga  41220
tcttggctca cggcaagctc tgtctcctgg gttcaagcga ttctcctgcc tcagcctccc  41280
aagtagctgg gattataggc acccgccacc atgcatggct agtttctttg cattttttt  41340
ttgaaatgga attttgctct ttgacccagg ctggagtgca atggtgcaat ctgggctaaa  41400
tgcaacctcc acctcccagg ttcaagagat tctcctgcct cagcctcctg agtagctggg  41460
attacaggca tgcaccacca cactcggcta atttttgtat ttttagtaga gacagggttc  41520
tcaactaaag agaaccatgt tggccaggct ggtctagaat tcctgacctc aggtgatcca  41580
cccacctcgg cctcccaaag tgctgggatt gcaggcatga gccaccatgc ccagccagta  41640
tacagtgttt ataaagcctc cagtagtgta cagcaatgtc ctagaccttc acattcactt  41700
actactcact cactcactca cccagagcaa ctgccagtcc tgcaagctgc atgcatgata  41760
```

-continued

```
agtgccctat ataggtgaac catttttttaa tattttatac tatattttta ctgcaccttt  41820
tctatgatta gctacacaaa tgcttaccat tgtgttacaa ctgcctacag taatcagtac  41880
agtactatgt atgggtttgt agcctaggct ataccatgtt gcctacgtgt gtagtcgtct  41940
atactgtcta gtttgtacac tctatcatgt ttgcataaag ataaaatcac ctaatgacac  42000
atttctctga gtgtattcct gttgttaagc aacacatgta taaacattta caagaaatag  42060
ctcaaatttt tttttctttt gatacagggt cttgctttgt cacccaggct ggagtgcagt  42120
ggcgcaatct cggcgcactg cgacatctac ctccccggtt caatcgattc tccggcctta  42180
gcctcctgag tagttaggac tacaggcacg caccaccacg cctggctaat ttttttgtat  42240
ttttattaag agatggggtt ttgccatgtt ggctaggctg gtctcgaact cctgacctca  42300
ggtgatctgc ccgccttggc ctcccaacat gctgggatta caggcatgag ccaccatgcc  42360
cagccattac gtttttttgg ttgtttaatt tttttttttt taagagacag attctcactc  42420
tgtcatcaag gctggagtgc aatggcacaa ccatagctca ctgcagcctc caactcctgg  42480
gctcaaggga ccctcctgcc tcagccttcc cagtaactga gactacaggt gtgagccacc  42540
atgctcagct aattattttt tatcttttat tttttgtaga gggggggtct ttctatgttg  42600
ctcaggtttg tctcaaactc ctgggctcaa tcaattctcc tgctttggcc tcccaaaggg  42660
ctgggattac aggtgtgagc ctgaaaacct tctagtgtgg aagtggaaga taggcccagg  42720
ccacttatgt tttcaagtta agcaaggttt aggtcactta tgaagcctga ctagttttgt  42780
ttgcttaagg gatctgcagg cctgacctcg gttttcattt gttttaacag tgtctatgtg  42840
tatgtgtgtg tttatgtacg tgcatgatgg ggggaaagct cagaaatcaa gtaagccaaa  42900
cacaaacatg taattataag cagggataaa ttctatgatg aagaagtatg ggccacggga  42960
gagtacttgt gccagtctgg tgatcaggaa caatgtcctt tgggaagtga catttgagcc  43020
atgccctgaa gtacggtagg agttggttag gggtgaggca gtaagaccca gagctggggc  43080
ttcctgcaca agctcagctg ggcactgagg acccagtgga ctctgctaca gggcagtgag  43140
gagcagaaag gctgaggaag gctgggtgtg gtggctcaca cttgtaatcc cagggctttg  43200
agaggctgat gggggaaaat cggtagagct caggagtttg agaccagcct gagcaacata  43260
gcaagactcc atccctgtaa aaagctttta aaaattagct gggtgtggtg gtatgcatct  43320
gcagtctcag ctactcaaga ggctggggta aggattgctt gagcctagga ggtggacgct  43380
gcagtgcgcc acgattgtgc cactgtactc caacctagga gacaaagcga gatcctgtct  43440
caaaactgaa tgaataggct gtgtgcggtg gctcactcct gtaatcccag cacttttgga  43500
ggctgaggtg ggtggatcac ctgtgattgg gagtttgaga ccagcctggc caatatggtg  43560
aaacccgata caaaaattaa ctgggcatgg tggctcacat ctgtaattcc agctactcgg  43620
gaggctgagg catgagaatg tcttgaaccc ggggggcaga gggtgcagtg agctgagatc  43680
gcaccactgc actccagcct gggagacagc gagactccat ctcaaaaaaa aaataataat  43740
aataacaatt aaaaaaaaat taaaaggcca gggagcactg gcagcctgtc caaggtttca  43800
ggtcacttta gtaaagggag aacaatggct cctcccagga cctctgggat ctcagcattg  43860
atacgacagt catggaaatg ctagggccca ggcagaccat ctcagggaaa acaagtggct  43920
ctgccctgcc ttggccactt cctggccctc tgcatgcccc agggtctcag caccaagctg  43980
ttctcagtga gtagctctca tttagtgcca gggctctcgg gcttacatcc tacgatgacg  44040
atggaatgca taaaagatgg ggctgtgata gcccagagct aggggtttga atctcatgag  44100
atgttcatgg agccctggga gggagctcag tgcaagttca tttctctttt ttggttgaga  44160
```

-continued

```
tggggctcag aggaggaagg acttgttcaa agacacacag ggagtgtttc agtgtgggac  44220
ggaggtttat ggagaaaggg tgaccatcca aggcttggac aaagatcatg acttcgacca  44280
gcaagcctca actctgtaga cttggtgggg gccaggccct cccaaacaca cctgacaggt  44340
gtctgtggtc ttggggacat tgtcgctccc cttcctgctg atgctctgct gtccctctcc  44400
catgaagcgt atctcttcgc cgtcccccat ccttgctgag agaggatggg ttctcttctg  44460
accaatactg aagatcttta gtaaagttct cttttttttc attttctgaa agtccctctc  44520
ttgagaaatc aggacaagtg agtcagggcc aggacaaaaa acagtgtggg acgagtgtgg  44580
tggctcacgc ctgtaatccc agcactttgg gaggccaagg tggcggatca cttgaggtca  44640
tgagtttgag actagcctgg ccaacatggt gaaacctcgt ctctacaaaa tacaaaaatt  44700
agccaggcgt ggtggtgcat gcctgtaatc ccagctattc gggaggctga ggcaggagaa  44760
tcacatgaac ccaggaggcg gaggttgcag cgagctgaaa ttgggccact gcactctggc  44820
ctcttggcaa cagagccaga ctacctctca aaacaaaaac aaaaacaaac gacaaacagt  44880
gtagactttg tgtttttctc aaaagcactg tcaagccagt gcccgcagca gtgggcctag  44940
acacctccag tcttgcctca gggtcagttt ccagcctccc tggacacttc ccccaggtat  45000
gtgtactttt tgattgtcct aaatccagag tctgtggcct gacctggttt gtcacagctc  45060
tcagtccctc cccatcccga atcccaggga gccgcaggtg tgtgcagaag aggcacacca  45120
cactcaatac atcttgcatc ctcgctggac ccaatccatt ggcttggtga tgtacagact  45180
gagcctcatt atagccgttc gttcctgttg acctttccag atcaatctgc cagcttggct  45240
tctccgagtt tcgcttgtca gcatttctcc aatcccatca tgtactttgg acctctttgt  45300
tgggtggctt gctttatctg aaattttcag atttgacttc aggtctctcc tttgtccctt  45360
aatatggctt aatggtggac cctgtcaggg gtagagaaaa tattgaggag ccctgacttt  45420
gaggtgcaca agttagaggg ttagacaagt ccagccacaa ccagcccaag ctgcagtgta  45480
gggaggcctg tccagctgct ccacggttga gggtggagca tacaggaagg cttccttctt  45540
gctgcagccc aggtgttctg gctgccctag ctgcctggct ttggtagaag aaagaaaggc  45600
tctgtctctg acttgtcaac taatggcact atgagattgc acataattaa cctgggtctg  45660
ctcttccaaa agccttgggc ctctgactgc aacatggagt ctgggtatca ctccccatcc  45720
ctgcgccact cacctgctct ggcgctaggc gtgtgcctaa tcacttaatt tctctgtgct  45780
gcctcttagg tatcacttcc cctgatccca aatacttacc aggtgtggga tgacacctga  45840
ctagttactc cttggaggta tctgcttctc accggggact ccgaaaccaa acgaaaagca  45900
aggccaagcc cagcctaaag gacgcttcct acatgacttc aggcttgcgg gggctggagc  45960
gtgggggtgg caatggagtt ggggggggct cagggagggg atgtggaagt gctttgcttt  46020
gcaaactcta gagaaccgtg taaataggag tgattattct gtcccttccc tttctttcca  46080
acaggaatca gcatcccaca gcccatgttc agctatgaag aatggaaact gaggctccgg  46140
gaggggtata gggaggagcc agcagggtct tgagttcata ttagtgccct ttcctccata  46200
ggcacatctg tgtttctttt tattttattt tgaatttaat tttttttttt tttggcagag  46260
tcttgctctg tcgcccaggc tggagtgcag tggcgcggtc tcagttcact gcaatctccg  46320
cctcctgggt tcaagtgatt ctcctgcctc agcctcccga gtagctggga ttacaggtgt  46380
acaccaccac acccagctga tttttgcaat tttagtagag acagggtttc acagtgttgg  46440
ccaggcttgt cttgaaatcc tgacctcaag tgatctgcta gcctcggcct cccaaagtgc  46500
```

-continued

```
tggtattata ggtgtgagcc actgcgctcg gccacatctg tgttttaaat gagaggaaag  46560
gggataatgt gcattttgtg gaagcttggg ccgtttgtgt ctaggactct tatgatcttc  46620
ataagttttc ccccagggag gacactgttc cacttaggga gtcaggaccc ccagtcctta  46680
caagattcag cctctcaaaa tggagacagc agttccaggc ctgggctggg ttctgttcac  46740
actaggagag ggcaagtgag tggtgtttgg gatgtgggga agtattatga aaacagagat  46800
gctccaattc ctagtgatag gaaaccatta agctacttgg catcttaaaa ccaagagcgg  46860
ttcaagttct gagattgtta acacacctta caacaccgcc gccgttatta ggaagaagct  46920
ctgtttgatg acgtcccaca ctgtgggtac ctttatgaac aggaatttgc tttttcaaat  46980
cccagagaag taagattaaa gttggctgtt ctccatcctt gaaaaatttg gttttagggt  47040
gaattcaaga atgactgacc atacagaatg gggagcaaac ttgggaagaa agaaggcaca  47100
gttcagagct ctcccaatag tcacccctga actgcacccg gaccatcagt tatctctgtg  47160
ggtagagctc aggaatctaa aatccatttt aaaattaaag tatatcgggg ctgggcgcgg  47220
tggctcatgc ctgtaatccc agcactttgg gaggccgagg tgggaggatc acgaggtcag  47280
gagtttgaga ccagcctggc cacatggtga aaccccgtct ctactaacaa tacaaaaatt  47340
agccaggcat ggtggcagac acctgtagtc ccagctattc ggaaggctga gtcagaagaa  47400
ttgcttgaac ctgggaggca gaggttgcag taagccaaga ttgtgccact gcactccagc  47460
ctgggcaaca gagggagact ctgtctcaaa aaaaaaaaaa aaaaaattaa agtatgtcat  47520
acatactgtt acaggcacag accttaagtg tacagcccaa tgaaatttta cacatctata  47580
cagctatata actaccacct atatcaagac acattccagg aactcagact ccatcatacc  47640
cctcctcagc agaggtaaca gacccacacc tctcctgctc cggtggtaat taaccactat  47700
tctaactttt ctatcaatta gttttgccca ttcttgagct tcacacagat atacattgtc  47760
aggcatgatg actcatgcct gtaatctcag cactttggga ggccgagacg ggagtatcac  47820
ttgagcccag gagttggaga ctactctgga caacatagtg agacccccga ctctacaaaa  47880
aaaataaatt agctggtcat ggtggtgcgt gcctgtagtc ttagctattt gagacgctga  47940
gagaggagaa tctcttgagc ctgggaggtt gaggctgaag tgagccgtga ttgcaccact  48000
gcactgcagc ctaggtgaca gagtgagatt ctgcctcaaa aaagaaaaaa tatggccggg  48060
cgcggtggct caagcctgta atcccagcac tttgggaggc caaggcgggc ggatcacgag  48120
gtcaggagat ggagaccatc ctggctaaca cggtgaaacc ctgtctctac taaaaataca  48180
aaaaaagaaa gaaaaaaaaa ttagccaggc atggtggcgg gctcttgtag tcccagttac  48240
ttgggaggct gaggcaagag aatggtgtga acccgggagg cagagcttgc agtgagccga  48300
gatcgcacca ttgcactcca gcctgggcga cagagtaaga ctctgtctca aaaaaaaaaa  48360
ggaaaaagaa aaaatatata tacattgtgt actttttggc atctggttta ttttgctcaa  48420
tatcacatct gcgaaattaa tctacactgt gtgtatgaaa ggttggttct ttttgttgtg  48480
atgcagtatt ccgtcgtgtg actacgggac aatttgctta tccgtattcc tatcggtggg  48540
catttgggct gttaccaggt tctggctgtt atgaataaag ttgctatgga tattcttgta  48600
cactacttct ggtgagcgta tgcactcatt tcgcttatgt aaatatcttg ggtggaatta  48660
cctgatcata aggtaggtgt gttggctttg taatgtgctg acttggttat gctgaattcc  48720
ctttttgtg tatttctggt tagagcggaa catgagggtg tctcttcagg gaatctggag  48780
ggtggaaggg aagcaggagt cggtttctgg ctcacacatg ttgtgactga actgctggta  48840
cacctggttg gcatggagct ggcttctcct ttggcgttgc ctactgttgg ggcaggtgtg  48900
```

-continued

```
tatgtggtta gctccatgca atgaacccgg gcttctgcaa aatacattaa caacgacaga  48960
gacaacaaaa gctgatgtgg atttaaaggc ttcagttcan nnnnnnnnnn nnnnnnnnnn  49020
nnnnnnnnnn nnnnnnnnnn nnnnnnnnnn nnnnnnnnnn nnnnnnnnnn nnnnnnnnnn  49080
nnnnnnnnnn nnnnnnnnnc cagcagtggt tctcaactga gcatagtttt gcctcagagg  49140
ggacatttgg taatgtctgc agacattttt tgattgtcac agcccagccg agaaggtact  49200
actagtatct ttttggtaga ggctagagag gctgctaaac atctaacaat gcacaggaca  49260
ggcctctgta acaaaaaagt atccagtcaa aaatgtccac agtgttgaga ggtttaggta  49320
agtaggcgct aaaacataag gagactgtgc ctgagagcaa gaaggagtaa ttggaaagtg  49380
ctggtgtgat tagctctggg ttttagaaag ctcattttgg ctgcttgtag acagtgcatc  49440
agaggtggag gagggtggta agactggagg cagggaaagt aatttgggag ccactgaaat  49500
gatccaggtg aaaaacggtc agcaggtgac taggaaagtg gcagaggcaa tggggatggg  49560
tggctggatg agatggtgaa gaaagcacta taactaacta atgtgtggat gatgggcagg  49620
aggggtgaag gatgaccaga gtcctgcctt gcaggtctag ttggaaggtg atggtttctc  49680
ctgagaaagt gaccacaaaa agtgaagcag gtttgtgcgt gtgtgtgtgt gtgtgtgtgt  49740
gtgtgtgttg agttcagtct gagatgtgtt ggactcacaa tgtccatggg acatccaagt  49800
ggagaagcat cttgggtgac catatgtgtg agtctgcagc tcagaaacag gcctggggct  49860
ggagatgaag acttgggaat gatctgcgta tatatttggt agcttgagcc acaagagtag  49920
atgacataac ccgtggtggg tgtgcagaat taggagagac gtgcaccaag aagccaggtg  49980
atccccaata tttaaccatc tggaagaata agaggagcct gccaacagaa attgggaggg  50040
aatggccaca aaggctactg agaagggaag cagttcttaa gaagggggaa gtgaagaggt  50100
atcactactg cagaggtcaa gtaggataag aactgaagaa tgtctgttgg gtttggcaat  50160
ggggtagtca gtgggcacct gggcaaaagc agttttggtg gagcaatagg gataacagaa  50220
acaagactgc tatggtaaga ggaggaagag ggtgttgagg aagtggccag cgagtctaca  50280
ccacttgctg gaggagcttg gctttggtgc aaagcagaga agccagctca ctcattgact  50340
taacctccaa gaaacacaaa atcatccata tcctggctca aattccagca ctaccaggag  50400
atggttggcc cctagaaatg ccatcccact tctcctctgc ttatcctatc ctatctgtca  50460
gtctgttgag cccaggctaa gcgctacctc ctcaagcaag ccttctctgc ctgccgtcac  50520
actttaagtg atcctgacaa cactgaaaat gtgtgtctct tccattcatg ttagttctac  50580
acttctgagt atctcctcaa tatattgcct tgttttacta atatgctcgt tctgtttgcc  50640
ttatttatca gctaccttaa acctccctgc aactagagat tctctttaag tatttgttga  50700
ataaatgaat gaatcaatcg atgatccaga gcctggtaga ggcttgtgtc catggtggat  50760
gaggctcaga aaatacctgt agaatcgaaa taaatgcatg tgtgctctga tctaaactca  50820
gctaaacttt ctccaggggg taaagttcaa gttgattagt caattgatta attaattcat  50880
tatgtaatgg aaaaactcct tctatgacct gggcagagtt ataggcagtg aacaagacag  50940
acaaggtcct tgttgtcatg aagtttgctt tctgaaggag agagataata aacaagaaac  51000
cagtaagaaa gcaagattat atcattttgg taaatgttct tgtggaaata aatgtgatga  51060
tgtgtaacaa aagtaccaaa taggagagtg gggtgggtgg gcttctttta gaaagagttc  51120
tcggagaagg cttatctgag gaggtggcct tttaaccagt acaaatgctt tagcttggcc  51180
agtggagctg ggaccaggat gacaagggtc acttgtcatg ccagtgagtt tgagcttgta  51240
```

-continued

```
gacaagagcc tgatcatgaa agactttgca gatggtggta atgggtttgg gttaattgct  51300
actatgtggg aagactttga atgggaagca tggggacaat ggcctgtgat acatgttatc  51360
aaatatggtc gcaggggcta gtgaggtggc agcagagata gggagaagta gacggactgg  51420
ggaaggtaga agatggggca ggggaggcaa ttactgcaaa gacatattcc ttctaagctc  51480
actgagtgtt catggtctct gggagcagag gttcctggag gggaaagagg ataatgtcac  51540
ttcctgagga agcgggaaga acccatctga gacgtgggga ctgtgctggt tcgtttctaa  51600
ggggccttcc agatctcaca tgccaatcgt cttggtctat gtcaattgtt ggggcatcca  51660
aatggggaac tgttgtccag gccgatttca cagaacaacc gcccagtcca tatctcccga  51720
gccattcacc cttgcagtgg cgttagctct ttcaccagct tttatctgcc ccgtggggat  51780
gttggccaag cccagttaac aagcagttga tcagccccag agatcaggtc cctggagtct  51840
gtcacttttc tgagggtggg gagagaatcc tggagcagaa catgtaacta gaagggccac  51900
ctggcttcct atggtctgag ggagagaatg gtgggatctc tggcctgaat caaacctccc  51960
tttctcagtg tccatcttac ctctctgctg taccttcgtt attttccagc agctcctcag  52020
cccgttcctg tgggaccctt ctctgccaat ccctacaccc actgtaaatt tcaccgtggg  52080
agggagatgg gccttgaggg ctgtattagt cttctattct gcataacaaa ttgcctcaaa  52140
tttagcagct tcaaacaact catgtttatt agctcatcgt gagttcatca gcagtgtggg  52200
cccagcatgg ctaggttttc tgctcagggt ctcacaaggc taaaatcaag atgttgtctg  52260
ggctgtgtgc tcatctggag tttagggttc tcttccaggc tcacgtggtt gtggcagaat  52320
tctgttccct ggagttgcag ggctgaggtc ctgttttctt gctgactgtc agatgagggc  52380
tgctctcagg tcctcgaggc tgcccacatt gcttgccacg tgcgtggtct tttccatcct  52440
tgaagccagt gatggagaat ttcccttgga ttgaatcacc cacatggttg gactctctga  52500
cttcaggaag agagccctgt ctcttttatg ggatcacctg attagatcat acccatagag  52560
ggcagttcct tttccttaaa gtcaactgtg gcatgtaaca tcacacaacc acaggagtaa  52620
aatccatcat atttacagtc ccagggatta tgcacagtgc accaggggac aactgaattc  52680
tgcctgtcaa aagggccaag caggacttta ttggtgaaga acagtggaat gtcattcttg  52740
gttcttccag aaaaaaatca ctcagtaaag ttagaggttc tcttgccttt tgggaagtca  52800
tcaaagaatc tcatggaggg tttggacctt caccctagaa acatcacacc atgttttcta  52860
taattgcagg gttcatggtc ccttgaagcc tattcatagt ttccaggttg aaaagctctg  52920
ctgcagggtg tggggaggga tgcaggtgga ggtgagggct gaatagtgtg agctgcatat  52980
ctggagctgt ggtggttttt ttagtcttta agctgtcatg tgttgggggt tgggcatggg  53040
aggggcatcc caagagctcc ttggtattga caccatctcc aaggtgatct ctgctctgcc  53100
tggtgcacac atgtttttct cctgttgcaa cagcccactc ttgtagaaga gcagacccct  53160
cagtaccagg tctgaccctg gacagcttgt accaggagct acagcacact cccccacaag  53220
cctaaagttg ggatgagccc cccgagaatt agatcagaaa agattaaatg cagaggtgat  53280
ctgtcaggtc ccctttggaa gtgctggtat ggagaggatt gactgagtct gtttaggaac  53340
ctccaagctc tgtagtaact ttagggctag aaaggaggat gcctaagatt caggatcctg  53400
cagtgatgag tcaacatttc ttggggaagg aggcagggct gaggattaaa cggagatgat  53460
gggtatcgtt ctcttgctca aaggcactgg accccaaggc ctccagctct tcgctcccat  53520
ttgaaattca agtcctgagc acaccacagt tgtgatgcag ggaaagaatg tgcttatcag  53580
agagcctggg caagtgggcc ccttgtgagt accgttcaac ctcatttatg tcattggcac  53640
```

-continued

```
caaaagtaga catcagtctc ttgaaagttt gattaatgct ggtcacactc aaagaccctg  53700
ggtagcattc atttactaag caattactaa ataccagttt ctgtgctaaa tgctgcatca  53760
gtcagggctc ttaatggcag gcagcagaaa ctctccttgg ctgatctaag tagaaaaatc  53820
caggactgaa aggaaacgga gtagctcatg aaattgcagg aagggccgga aaaccagaca  53880
tggagccaaa gtcaggctgc agaacaggtc tagggaggat cccactgctg ctgagaccta  53940
gaccttgtgt ctggcaccca ggatgttgta gggctcagac cctggatcaa tgtatcctgc  54000
agtgcctctg tgggtactgc aactccagga actcaatctt gtcaacgcca ccgccagaga  54060
gaggccttct tggcctccat ctttttggtc actagctcca gattcaaaat cttgaataga  54120
tgcttcttct ctttgataga gcccagtcat atgcgttagc tgcaaaggaa gctgaaaatc  54180
tattaggaac ttttgtcttc aaaaatgaga ggcctgtcct ccaccaagat ccataggaaa  54240
tggaatccaa gaaaccacag gaaggggtga ggtgactggg cagctcacag catgcatgct  54300
acatgtgaat tatctcattc atttctcaca ctacccagtg aggtaggtat tgtcatccct  54360
acttcataaa tgatgatatg aggtacagaa agtttaagga acttgcccag gacacgacac  54420
gcagctatta agtgctagac ccagtcaatt tgagtctgac ttggactgtc tgactccaga  54480
agccaccctc tcagacactg ctgtatactt ccagtgaatg ttgatgaaat tttcagggtt  54540
gctaagctgt ggatttcaga tcctggattg tatgacctaa aagagagact tccctaggag  54600
tgagggtccc tgaacagtca actggtttcc aagaatgggc tccctctcat caccttatga  54660
cagtaatcct ctgtccaaca gccaaagagg tcctgtgggg agggcttgca gatgggagtg  54720
cgcagagccc agctcaaagc tcctgactag gctcttgttg agtattcctt tgattcctgc  54780
ttctgtcttt ttaaatcaat ggagacaggg gagggttatc tccatcctcg gctcaagatg  54840
aaatgcatcg ttcctcgttt ttctcattcc ttcccaatgt gtgtactgtt aactttagtt  54900
atgaaggaaa ttacagtgtc ctgtgcatat accaaggctg tccaacctcc acacctttgc  54960
tcaagctgtt ccttctactt gaaatgcctg tttccttccc ttctaattgc atctttccat  55020
ccaggtagga atcagctcct tggttcatgg agccttttct gctctgtttt actatgcatg  55080
gacttccttc tgaattagca gaggatgttt cctagcttgg tcttaaccct tctccttttg  55140
tttgacctca atttactcat cttacaaatt aggttgtaag ctaattgaat acaggatcta  55200
tgcttcactc tgattttatc tccacctgga tagcatcatt tttgacacac aagcaggcat  55260
atgggagggg agagaagttt ggtgccagaa agaactggat ttgaattcta accctgttgt  55320
ttacgtgagt acgttactta accattaatt acttcaatgt atatttatta agtacctact  55380
atgtgccggg cactgtacta agcaccaagg atacaatggt gagtaaagag atgcagcctt  55440
caccatcacg aaggaagaca gatgttaatc cattaaccaa gtaatctcac aagaaaagta  55500
aaatgactaa ctgataagga caagcccctg gagctacaag agggtgtata cagggcatcg  55560
atccaataag ggcagtgttg cggggagatc aggagccaca cagagcctgg gttgtctcac  55620
ttggaaaatg gggtatcaac cacctacctc actaggtttt taaaatcagg ttaaatgagg  55680
taatacttgc catgaacagt attttgttga ttgatgattg attgaaacgg agtctcactc  55740
tctcgcccaa gctggagtgc agtggtgcaa tctcagctca ctgcaacctc tacttcctgg  55800
gttcaagtga ttctcctgcc tcagactccc aagtagctgg gattacaggc agccacccct  55860
atgcctgact aatttttgta tttttagtag agacaaggct ttgcaatgtt gaccaggctg  55920
gtctcaacct cctgacctca aaagatccac ccacctcagc ctcccaaagt gctgggatca  55980
```

-continued

```
caggcatgag ccactgcatc cagccacttg ccatgcatgg catttaaaaa tgttcagtaa  56040
atgttaccat aatgaaggct ggtaggttgg ccaactgagt ggtctgattc agaaggaaag  56100
aagttagaca tacgtgaaca tttcctgtac ttgaagatcc tcaggacagt gactcctaga  56160
cccatcttcc atcacagtca gctgggaagc ttttaaaaaa atgcagacat ctgaccttca  56220
cgctagacct attagccaag cagaagtttc tgggcagggc atctgcatat ttttaaaaat  56280
ctttaataag gcagcctcaa aattacagat tcagcacgca tttaccataa ccactgaaga  56340
aatgcaaagt tataaaaaga agataaacaa caatctgtct cctgctttct tccctctcct  56400
cccctgcttc tggaggcaac aaggtcaact atttggtgtg attcctttta gcattccctc  56460
catcaatggt cacataagga tgctcacaga taagcaccta tgcgggggtt tttttttcc  56520
ttgtaaaact attcacatac taaatacttt cctcagtatc ttgccttttt tcacttcatg  56580
tcacagaaac atctcttcag gtttatagat acaggtccag ctcttctttt catagccata  56640
taacattctg tagaatagag aggacacatt ttactcagtg tccgattgat ggatatcaat  56700
attgttttca tttctacaaa tagtcaagga ataacataac tctgtaaaag ttttattact  56760
tataggcgca tttatgccta aaggatagtc tcaaaagagt gaaactgatc aaatgtgcat  56820
ttttttattt taataggtat ggacagattt gttctcaaaa tgtttgtggc agttcaaaac  56880
accagtaaaa caggggagat atgtattttg gaaaagcacc caaggcgatt ctgaagtgta  56940
gcccaggata agaaccattg cccagagctg ttccagatgg cccctgggtt cctgaagtgg  57000
gtatcgggag agaaatcttc actgaatgaa tgagtgggct ccccagggaa gtgatgaaat  57060
ggtccttatc agccttgcta tctccctctg acagaggcaa actctctctc cctgggggaa  57120
gttcctccaa ggcctctata taagaagtct ttgtgagagg aagcaaagaa ggacctgggc  57180
tttgggaaga tctaaagacc caggaaggtc tctgggtggg tgagtgcttt ctctgctgtg  57240
gtggagctgg tgacagttta ttctcccagg aggtccctgg ctgtggctga cagtttctgg  57300
agggctggca ggcgtctacc tgtggctttc aggttatgag gatgtcagca ggggcagcct  57360
tcatcctctg ccttgcacat tccttctgcg ggatgtgaaa gtgctccttg gctggggaaa  57420
ggagatggtg gagacatgga ggagggtgtg ggtggcttct tgaactctga ggaggggaca  57480
taccttctaa gtcctatgtg ttcctaggaa agccaataat cattgcttct cccgcctttt  57540
ttatgtcata gactctgagg gacccattaa gtacaaacaa ataagcgtaa tagtcccttc  57600
tttacttccg ggcctgaagg aaagccagcc tcagccaccc ctcagggttt gctgcgttct  57660
gtttagaaag aggtccttgc gtcctggatc ctggagcatc aggagctggg cttggcatga  57720
gcttttctgg cccatcctga tttctattca ggccttcttt ttctccacct cactcccacg  57780
gtcccctaat ggtgtgattg tgatgtgtgt gcatgtgtgt ctgtgtgtgt caatgacaaa  57840
ctgtgttctc cgttgcagga taaagccaag atgaaactcc ccttacttct ggctcttcta  57900
tttggggcag tttctgctct tcatctaagt aagtgttttt tgccttcagt ctttctttct  57960
ctgtttttc cctttctatg gtagatgggg tcagagttac acacccaccc ccttctttga  58020
tcgtcttcta tttctgaatt tctgtgtgct taaagggatg gggactctat ggccaggagt  58080
tgaaaggatt tctcaaggcg tctgttatgt ctgtggtctt ggttctactg tgacattccc  58140
aattttgtcc tttctccatt atgcttactt tgagcttact gagtgccttc tctcctttaa  58200
ctctcttagc atcgccatga agtaggtggt attgtatacc catttcacag aaatacagct  58260
ggtggatgat ggaaccagta cccaagccca tgactgcccg actctaagtc catgctctta  58320
accaccttga ccttgtcagg cagcttgggt tcccctcata gagactgggt tccaggttcc  58380
```

-continued

```
ccttcccagg cagagttgag cactctgatg cccagggcaa ggtgtgagct gtctgtggtt  58440
ctggggagga acaaggggag atgtgaagga aggacactta gctatcctcc ctgccagggt  58500
ctgagacttc cacctttgag accccctttgg gtgctaagac gctgcctgag gatgaggaga  58560
caccagagca ggagatggag gagacccctt gcagggagct ggaggaagag gaggagtggg  58620
gctctggaag tgaagatgcc tccaagaaag atggggctgt tgagtctatc tcagtgccag  58680
atatggtgga caaaaacctt acgtgtcctg aggaagagga cacagtaaaa gtggtgggca  58740
tccctgggtg ccagacctgc cgctacctcc tggtgagaag tcttcagacg tttagtcaag  58800
cttgggtgag tggcctatgg ctgaggctga ggtgggagca tggaacgggt gtgggatatg  58860
cccccagcat tgctatcact ggctcttttt cccattgagg gccctggggg tgtcagtaga  58920
acctgagcct cagagaggtg ttggggtaag aggggagggc cacctacaaa cagaagttgc  58980
attttggtct ccaaccttca aatggttgtg gcaggggagg gagggaatga attgtgggga  59040
ctcaagaccc atgtgaattc atgtaggaag gatgctccat tctttgtctt ttatcctgcc  59100
ctgtagttta cttgccggag gtgctacagg ggcaacctgg tttccatcca caacttcaat  59160
attaattatc gaatccagtg ttctgtcagc gcgctcaacc agggtcaagt ctggattgga  59220
ggcaggatca caggctcggt aagagaagtg tgaacactaa atggggtgca cctgctgatc  59280
tcagccagca ctcagcttgc atcagatttg tctgtttttc tcctgtataa tctccagaag  59340
aaccagggat agatggacac ccacagacaa cactgagggg gctgcctggg cattcaggga  59400
agagctaagg atttagaatc aggaggtttg ggtccaagtt cctttccatc tctcactatc  59460
tatgtaactt aagttagctg ggcatggtgg tgcatgtctg taatcctagc tacttgggag  59520
gctgaggcag gagagtcact ggaacctggg agacagaggt tgcggtgagc cgagatggag  59580
ccattgcact ccagcctggg caacaagagc gaaactccgc ctcaaaaata aataaataaa  59640
taaataaaat aaaaaaaaaa ttaaaacaag accatgagtt tgtttcctca tctctaggat  59700
gagttggcaa cccttgttct accttttgtt agggctggaa ggacaagcct gtcactggga  59760
tgcatagaat ctgatggtga taattgccgt ggatcagcat ttcagatgac taggacagtt  59820
cccatcatgg tccagcaggg aagggcccat tgcccggtgg gcagcagaaa gagctggcag  59880
atacggggcc aggtctgctt ctctgccttc cctctgcccc atcccttctt cccctcttgc  59940
tttctccagg gtcgctgcag acgctttcag tgggttgacg gcagccgctg gaactttgca  60000
tactgggctg ctcaccagcc ctggtcccgc ggtggtcact gcgtggccct gtgtacccga  60060
ggtgaggtgg ggctggggat gaacgatgga aaggtctggg agatgggaag tgccccaagg  60120
aggagatgct acaaagagcc tgaccctttg tgggagaggc ttcctgggtc ttttatatac  60180
tctgactcca cagcagtgtg tgggtgggaa aagaggccct cctgtgggtt gagttgggat  60240
ggacaagagg ctgaaagtcc ctttctgttc tgccttcaca ggaggccact ggcgtcgagc  60300
ccactgcctc agaagacttc ctttcatctg ttcctactga gctggtccca gccagcagtt  60360
cagagctgcc ctctcctggg cagctgcctc ccctcctctg cttgccatcc ctccctccac  60420
ctccctgcaa taaaatgggt tttactgaaa tggatttatt ttctcctctg atcgcggatc  60480
cactctgctt agccctcatt gaaacttctt ccttatcatc tctccccaca ccacaacttt  60540
catagaagtg tcagaagcta ctactccttg aggaggagga tggagggtgg agttgggtct  60600
atggagcctt ttggagatgg aggaatgggc tcagctagtt ctcttcatag aacacctgat  60660
tactgggcac ctgcatagtg ctgccaggac ctttcaaggt tgtaggtaga ctcccaatgg  60720
```

-continued

```
cccagtttgc atctctgtaa ccaaaggcct tttctctctc tctctccaac cccagaactg  60780
tggttggttt tatatgtaag gaagttaaca tgtccctggg aacagtccac aacattcagg  60840
aatgaatgta taagtaccgc aatccccggc ccctcaagtg gaataaatct aacatgtatt  60900
gggcaccatt tcccagtggc ctgctgtggt agttggcctt attccatgca tttttatggg  60960
ctgccttccc ttcctcaact gcattctctg ctccttccta ctctctgcaa ctcccaaata  61020
aacacttgta cgcaactccc tctctcagga tctccttctg gggaaacctg atataagaca  61080
gcttgccatg cgtcagactc tgaatgaggc ctgggaatac aagacatagt cctctggcac  61140
ttgggatata tggttatttg taacataggc acaaaaacat ctactagttg ttatcgctta  61200
ttgagcaccc acaacatacc ccctgctgtg gcaggcacct tgcctagatg acctcatgtg  61260
atcaataatt atgagcccta ttttacagaa ccaggctcag agaagttagg atctgtcaaa  61320
agacttgccc aagactgaac ctctaaatgc aactcatatt gaaattcaac tctgctccaa  61380
agcatgttac tttaaccctt gtgcttttac agctggctac tctcccctta tggtcacacg  61440
gggatgaagc acggggggag gaaagccaga ctgtctcact cttgggttca tcttgggaca  61500
caggacacca gcccagctgg aggtgaggga gctttaatca gaggggaggg aggaaggcat  61560
tctcaacccc ttctgtacta gggaggtcag cagaagaaaa taattcaatg ttctaaagcc  61620
atttttttct ccagcattcc tccaattcat agatcttcat atgggattag gggctcagag  61680
aggggtgaaa caagaactct atttttttgg agtgtggtat agagaaggga tgctacttct  61740
ctaaggtcac atagtaagtt gagaaagaga gagaaatcaa actcaggttc atttcaacta  61800
ttgttccaca agaatctgtt gatttcaaag atggtggact atgggttcat ccctgtggtg  61860
agtgctgtga ggatgcagct gaggtggaac tttcactcct tgccctcttg gactttatat  61920
tctggtgtgg aaaggcattg cttcccttat ttcaatatta acaacaaagg gtaataaatat  61980
ttcccattta ttaagcattt actaggtgtc aggtactgtg ctaaatgtta ggtgaacttt  62040
gtcttgttcc tcataaatct ctgccgctgt gggtgtgtac tttgacagaa gtttgacttc  62100
cagtccacag agatcttctt tgggggagta atatcaagaa ggggcacgaa ggaagctgca  62160
gggctcctag tcccatcctg tatctcgacc taggcatgtt tacattggtg cattcactgt  62220
gaagtttccc tgagcagtcc actctatagt gtgctttata ggagcacatt gtacatccat  62280
tgaaaaattt ttcttggccg ggcacggtgg ctcatgtctg taatcccagc actttgggag  62340
gccgagacag gcggatcacc tgaggtcggg agtttgagac ctgcctgacc aacatggaga  62400
aaccccgtct ctactaaaaa tacaaaaaaa ttagccgggt gtggtggcac atgcctgtaa  62460
tcccagctac tcaggaggtt gaggctggag aatcgcttga acctgggagg cgaaggttgc  62520
agtgagccga gatcgtgcca ttgcactcca gcctgggcaa caagagcgaa actccgtctc  62580
aaaagaaaga aagagatttt ttctttttct taaaaagtaa aaatcatgaa ataaggggac  62640
tgggctaata ttccaaaata tgggtttgtg tgtgaatttt cctctccagt aagatactaa  62700
ctaagctctg tgaaactgtt tatctatggt tctttatcat tgaatccttg gagttcctta  62760
cactgtgcag agcacagagt aggggctcaa tcaacagtgc actcattgct ttttcataga  62820
caagggccac cctcactcaa ctcatgtgcc aggcatagtt ctgagagctt tgcttaagct  62880
gatnnnnnnn nnnnnnnnnn nnnnnnnnnn nnnnnnnnnn nnnnnnnnnn nnnnnnnnnn  62940
nnnnnnnnnn nnnnnnnnnn nnnnnnnnnn nnnnnnnnnn nnnggtcact aatttggtat  63000
agagttatgt tcattgattt cattttattt tgtttctgat ttttaaagat tgttttactt  63060
gttttcttcc tattattatt ttattttatt tgtaaaacat ttacatatca gacatttaca  63120
```

-continued

```
ttttcccaaa ggtaaaactg tgaaacaaga tatattcaaa gaagtttact ttccctctct  63180
gtttcttgta cccctttttcc tcttctttag gtaaccattt ttattttttt aaatataaac  63240
attgtgtagg tgtatataca tgtattagtc tgttttcatg ctgctgataa agacctatct  63300
gagactggga agaaaaagag gtttaattgg acttacagtt ccacatggct ggcaaggcct  63360
cagaatcatg gcaggaggtg aaaggcactt cttacacggt ggtggcaaga gaaaaatgag  63420
gaagaatcaa aagtggaaac ccctgataaa cccatcagat ctcgtgagat ttattcacta  63480
tcacaagaat agcgtgggaa agactggccc ccatgattca gttaccctcc cccactgggt  63540
cccacccaca atacgtggga attctgggag atataattca acgtgagatt tgggtgggga  63600
cacagccaaa ccatatcaat acatttccct ctcttttaga taaaaggtag tatactgtat  63660
acactattct gcagagtttt ttttttttt gatgtaactc tatcctgagg gtgctctgta  63720
gcagggacct ctcatgcctt ttaaccactg cctgggtctc cattacatgg ctgcagcata  63780
gttgccacag cattcctgta ctgatgacta tttggattgt ttccagtctt ttgctattac  63840
cagtagtgtt acaaagagga tctggctaca tgttcagggt ggggaggggc agatgtgtag  63900
cctgtcagga gggtattgca gtaatccatg actgagttaa tggtagttta aagctaggat  63960
gagtcagtgg ggttggagag aagtgggcac atttgaatga tatgtaggag gtgaatgatc  64020
agcattattg atgagtttga ggtggggcat gtggggaaag gattcgagga tgactcccag  64080
gtttctgttg ggacagtgga tggatagtgg ctcctcccct ttttccaatc ttccttggcc  64140
cttcgctgac ttctgttggg ttggcctaca gagagcttct ttttcctctc tgttcgccca  64200
ggttcctcca ctttggcggt ggccctctgc tcgacggtgc cttcgctggc cctgacatcc  64260
ctgctgtgcc tgggcttcgc cctctgtgcc tcagtcccca tcctccctct ccagtacctc  64320
accttcatcc tgcaagtgat cagccgctcc ttcctctatg ggagcaacgc ggccttcctc  64380
acccttgcgt aagtggcctt ggggcgggct ctgtggagac ggacacactg gggcaaagag  64440
aagctggagg taaagaaatt gggaggcaag gcggggcctg gaggcagtca ggtgcgggag  64500
actgggtttg gggcaggtg tggagggggt gagaccagag gtggtgggaa ggatagaaca  64560
ttcatgcact tgagccttta catctgcggt gccctctccc tctgttttct acctggtgaa  64620
ctcgtattca tcctctgagg cccacttctg tttcagttct ccagggaaga aatggaaaag  64680
tgtcttccct tctttgtgcc cttagtactc tagtcttact tcctttgcta gtgcgtgcat  64740
tgtctggcat gccatccatt tacatgcctg tcttttcttt cctggtgcag cctgcatgag  64800
ggtcctgtct gtttttccag ggccccgcat gtgccttctt ctgggttctg tgggtcaaat  64860
gtctgagcag agctgaagag ggaaaggcca gacaggtgtg gttggagggc aggcctagga  64920
caggggagct ggggacaagc ggccgacagc ccccagaggc caggcttctg cttggaggga  64980
gggtccctga agctcactgg aacccctctg gtttctctcc ccagtttccc ttcagagcac  65040
tttggcaagc tctttgggct ggtgatggcc ttgtcggctg tggtgtctct gctccagttc  65100
cccatcttca ccctcatcaa aggctccctt cagaatgacc cattttacgt gagtactggg  65160
aggatgggga tccctggcag gaggcctggg ccttaggcct tggctgcccc aaatctggct  65220
gtgatggcct gggtatgtag catggtgcag cttcccaaag ggtctgtgtt attcaagtat  65280
ttggggcaaa agtatttgtg tgtgtgggga aacagacatt ctggagtagg gtggggaatt  65340
ctcacgaaac ttcaagcaaa atcctgagac ctcaaaggtg tttcctgctt gtggtgagtg  65400
caggcccacc ctggcctctc ccctaggccc acacagggtt tccacagttg gccccaggga  65460
```

-continued

```
caggacctct gtgctttcac ctctgtgtcc ttacacctgg agggatgctc tgaggtcctg  65520
ctctaggagg tggtcgtgag tctcctgctc tttgcagaaa ctgaggctca aagaggttac  65580
ttacgtgttc agaggcacca gctaaggagc aaaagtcaac tttgaattct gtgttttgac  65640
tactgcacag ctctatttgc ctcatttttt atttttaaag cagcaaatct tagaatagga  65700
gtttaaatcc atcacttgga gaaaagaaag actaaatgtt ttttgttttt gttttggaga  65760
cacgatcttg ctttgtcacc caggctggag tgcagtggca caatctcggc tcactgcagc  65820
ctcgatctcc tggactcaag cgatcctctc atctcagcct cctgagtagc tgacactaca  65880
ggcatgtgcc accatgccaa gcttatttta ttttattttt ttgatagaca ctggggtttc  65940
gctatgttgc ctgggctggt tttgaattcc tggcctcaag cgatccaccc gtctctgcct  66000
tccaaaatgc tgtgattaca ggcgtgaacc actgtgcatg gccaaaagag taaacttgaa  66060
atctgaggcg aatgacttga ttgtgacatc aggtgaccta gtaatcagct gtgtattcta  66120
gctggtgcct ctaccagctt cccatgtgac cttgaacatg tcattgaatg ctcgctaggc  66180
ctctgtttct ttatctgtga aatgggcttg atattcctcc tctaccccaa ccgatagtgc  66240
agaatgaaaa gtaactgaaa gtccttcctc cagggcacca tagtgtctgg gtgaaaagta  66300
gaatataaac tcggtagact tctggtccct tcattggtca tggaatggac cagtgcttgc  66360
ttcattgagc aacagttctg ttgttcagaa ttcctggatt tcacctcact tctgctctcc  66420
ctgcaggtga atgtgatgtt catgcttgcc attcttctga cattcttcca cccctttctg  66480
gtatatcggg aatgccgtac ttggaaagaa agtccctctg caattgcata gttcagaagc  66540
cctcactttt cagccccgag gatggttttg ttcatcttcc accacctttg aggacctcgt  66600
gtcccaaaag actttgccta tcccagcaaa acacacacac acacacacac acacacaaaa  66660
taaagacaca caaggacgtc tgcgcagcaa gaaaagaatc tcagttgcca agcagattga  66720
tatcacacag actcaaagca aaggcatgtg gaacttcttt atttcaaaac agaagtgtct  66780
ccttgcactt agccttggca gacccttgac tccaggggag atgacctggg ggaggaagtg  66840
tgtcaactat ttctttaggc ctgtttggct ccgaagccta tatgtgcctg gatcctctgc  66900
cacgggttaa attttcaggt gaagagtgag gttgtcatgg cctcagctat gcttcctggc  66960
tctccctcaa gagtgcagcc ttggctagag aactcacagc tctgggaaaa agaggagcag  67020
acagggttcc ctgggcccag tctcagccca gccactgatg ctggatgacc ttggcctgac  67080
cctggtctgg tctcagaatc acttttccca tctgtaaaat tgagatgaat tttggtgttg  67140
aaagttcttc ctggagcaga tgtcctagaa ggttttagga atagtgacag agtcaggcca  67200
ccccaagggc catgggagcc agctgacctg cttgaccgaa ggatttctga cagactatct  67260
ttggggatgt tttcaagaag ggatataagt tatttacttt gggcatttaa aagaaaattt  67320
ctctcgggaa taattttata gaaaaataaa gcttctgtgt ctaaggcaac tactgtttcc  67380
atctctctag gctttgggcc ggggctgtgt gtgtgtgtgt gtgtgtgttt gtgtgtatgt  67440
gtatgtttct gaggaggccc taccctggca tgagagggta gggaatctgg ctacacatct  67500
agtgtggcag ctggacccag aggtggggca ggaaccctga ctatgattca ccccgctggt  67560
cctgggatgt gggcccagag acttcctccc ccaggaaccc ctctgcttcc tcttcctctc  67620
cacatcctta actaacttta gcagaaccct actcctcact acacaccccc agctagaagc  67680
gctggatgga atcagaaatt cctagtttga gtttcaattc tgcccctcag cagctgggca  67740
agccccttaa ccactctgag tcactagttc cccacctgca aagtgcagtt aatcatttct  67800
atctctgatg gcgattgtga gaatgtaaag tcattgcaac tgcctagcac atggtaggag  67860
```

-continued

```
cacatgaggg tttgctcctg tgtttactca tgacccttgg ggaggacggg ggcaaagagg  67920
gagaagttga gggtgcagga ggagagatgg caggtgggtg ggatgggaga atctggggca  67980
cacctgctgt ctcattccca ccttgctagg agagggacta ggaaagaaca gtgggaggca  68040
gggggatggg ggtggaaggc agggggtggc aggcaggttc atccatccat tcattcaaca  68100
aatgtttatt gagcacctgc cacgtgtcag gccctgtcct gggtgctggg gctataaaga  68160
tgcagaaggg tctgaaaccc agctcttcct tcttcctgtg gatgtcgggg tgtaatttcc  68220
aggggccagg agcctgggtc tgagggcgga caccaaagtt ctagtggtgt ctattagcag  68280
cgtttaaatc taatggatgg atttggtctt gttaccctgc tcaaaagctt tcagcagctc  68340
cccactgtcc acaggacaaa aatccagatg ctagcctggc attcaaggct gtcactagtg  68400
tgatctcaac ctctcccctt ccctctttac ctcctaccaa cagcggggca gagcccaccc  68460
ctgtggacca agattcccag tctctgggtc tgtgtgtgca ccagttcctc tgcgtgggtg  68520
gctcaccctg cctcagcttg tgaaatccat ctggtctgct gggatcctgc tcaaaatgtc  68580
atcttctcca aaaatcatta ctcaggcttt ccagcatgtc tgagtccctg gcacttggtc  68640
acacccttcc tggtgactgg catttgcctc cacatcatga ccctcccacc ccttgcctgg  68700
gcagcatact ccaggaggca aggtctgttc tcgcctggct ctaattaatc tgtgcttacc  68760
atccacatgg taccagctaa ttcttgttga atgaatgatc gttgaatgag tggattcttg  68820
ttttggcctc agaaccaatt agaaggagcc agaaaaacac atgggggtgg gggaggtgca  68880
gtgtggtgca gtggaaaaaa acccttctgg aaatctcagc tctgtcactt actttgtcag  68940
ctctgtgact ttggatggac cacttctttg tcagtatggt gggagaaata gacatgcctc  69000
tctgggctgt tgtaaggatt acaaattagg tcgagtgctt ggcatgtggt gggttgaaca  69060
gatcacagct agcattacag atgatatatt aaagccaaaa aaagatgcct aatgtccacc  69120
agttggtgaa cggacaaagg aaatgtacca tatttgggat attatttggc aatcaaaaaa  69180
agtactgaca cctgctacaa cacggatgaa tcttgaaaac attagactaa gtgaaagaag  69240
ccagacacaa gaaactgcta atgattccat ttaaatatga aatatcgggc cagggtgcag  69300
tggctcatgc ctgtaatccc agcactttgg gatgccaagg tgggcagatc acttgaggcc  69360
aggagttcgt gaccagcctg gccaacatgg cgaaaccccg tctctactaa aaattagccg  69420
agtgtagtgg catgcacctg taatcccagc tacttggttg gctgaggcac aagaattggt  69480
tgagcctggc aggtggaggt tgcagtgagc caagatcgtg ccactgcact ccagcctgga  69540
tgacacagtg aggttccgtc tcaaaaaaaa aaaaaaaaaa ggaaaaagaa aaaaagaaat  69600
ttccagaata ggccaatctg tagaggcaga aagtagattc atgattgggt aggcctgggt  69660
gtggaggcca tgggtagtga tggctaatgg ggaaggggtt tcttttgggg tgatgaaaat  69720
gggtggactt atggtatgtt aattatacct caataaaact gttatttaaa ggaagaaaag  69780
atgcctggat tccccaggaa gtgtacagta gacttctgtg agaatcagaa atgatttctg  69840
gggaagatgg gcgagaggag agtaagtggg agaagtgacc acgtgcgcaa ctctcatcgt  69900
tctgccctga gagccttcct cctgcaactt tatttattta tttattttga aacaggttct  69960
cactctgtta ccctggctgg agtgcagtgg tgtgatctca gctcactgca gcctcgacct  70020
gccaggctca agcaatcctc ctgtttgagc tcctgagtag ctgggactac aggcgcatgc  70080
caccacatct ggctaatctt ttatttattt atttatttat ttatagagat tggggagtct  70140
cactctgttg ctcaggctgg tgtcaaacgc ctggactcaa gtgatcctcc caccttggcc  70200
```

-continued

```
tcccaaagtg ttgggattat gggtgtgagc cactgtacct ggcacctcct gcaacttctt  70260
cctcaagtgg aaccaatgag gaagcaagca actcagagct ttcacaagtt ttgatttcaa  70320
tcagcaacgg gcttccaatg caacccttct ctcctgtaac cagcctcagt agagaggaac  70380
tggaggtgaa ttggccccca tcacaccccc acagtgccaa gctgggccct tccatcaggg  70440
ggagaacaca tgccgtgtaa gggacagcca acagcataaa ataggaattg tgtgatgatc  70500
ccttttaagc ctattcagcc cagggaagtg catatgatca gccccatttc atagatgaag  70560
aaagtcaggt tcacccatta gcacattgtg ggctggtat ttaaaccagg tctgtctggc  70620
tcccaaggtc acattcattt agacattacc tttactttac atttcttctt cttttcttct  70680
tcttcttctt cttcttcttc ttcttcttct tcttcttctt cttcttcttc ttcttcttct  70740
tcttcttctt cttcttcttc ttcttcttct tcctcttctt cctcttcttc ctcttcttcc  70800
tcttcttcct cttcttttct tcttcctctt cttcctcttc ttcctcttct tcttcttctt  70860
cttcttcttc ttcttcctct tcttctttct tcttcttctt cttttttttt tgaggtgggg  70920
tcttgctcta ttgcccaggt tgaatgcagc atcatcatac ctaaatgcag ccttgaactc  70980
ctggccttaa gcaatccccc tgcctcggcc tccaaaagtg ccaagatttc aggcatgagc  71040
caccatgccc agcctgcatt tattctcttg taagaaagat atcatttaaa acagacgaga  71100
aaataaagag ggacatgaaa aagacgcatc accattaatt ggaccactca gagataatca  71160
tggttaacat gttggtatgt tccctcccgt catttgactg gatgtatgtg ataatttaaa  71220
tgatctcata agcttttcct tatgtaatca aatagtagcc aaaaacatga ttttaaatgg  71280
ctgctcacaa ccccatctcg tggttctgcc acgccttgtt tatccccatc cacccccctac  71340
tccctttccc cttccctgcc tgtgtggggg tcctagatga cggtgagcca gagggcagcc  71400
ttggtcagca gattggagag tgcaaataat aaaaacactc agaaggcgag ctgttgtcaa  71460
gtgggcttat cacaaaagag caccttggga tattccagag aatgacctca tacccgctaa  71520
tcactatcca taatctggtg ctaactgtac tttagctgaa ggtgctggca ggtcctgccc  71580
aggtgctgct aagaacactt ctattctgtg agaatcagag atgatttcta gggaaaatgg  71640
gcgagaggga gtaagcagga gaaacaaccc acaggcacag ctctcatctt tctgccctga  71700
gagccttcct cctgccacgt ggttttgttt gtttgtttgt ttgtttgttt cagatagggt  71760
ctcactctgt cacccaggct ggagtgtagt ggcaagatca tggctcactg aagcctcgac  71820
ctcccaggct caagcagtcc tccccaaatt caaagcttgg agtgatggtc ccagtggtta  71880
tgtctaggag cccttttttcc tgccagcccc tcaggggatt gatgactctc aaatgcttca  71940
ggtgtgacat gggcacagca gtgagtcatt cctctgacat tctttgggaa gaacattttc  72000
catccaggct tccaggcata agatccagtc ctctggtgat aaggagttca cagacaggac  72060
aatgtctgag tgtatcttaa acccaggacc atggcttgtg ttcacaccag accctccagg  72120
gattttgagg tgttttgttt gtttgtttgt ttgtttgttt gttttttgag acagagtctc  72180
tctctgtcgc caggctggag tgcagtggca cgatctcagc tcactgcaac cttcgcctcc  72240
cggttcaagc gattctcctg tctcagcctc ctgagtagct gggactacag gtgtgcacca  72300
ccacacccgg ctaatttttg tatttttaat agagactgtg tttcaccatg ttggacagga  72360
tggtcttgat ctcttgacct cgtgatcctc ccgcctcggc ctcccaaaat actgggatta  72420
caggcatgag ccaccgtggc ccgcccaatt ttgagttttt atgttctaat cccaaacatc  72480
tgctcacagg cccctcagca tattctttcc tgggtccagt gtcacctccc aggcctgcag  72540
gctggctaga gcagtagggt gtgtgggaaa gctctgggct ttgcaggcac tgatcagctg  72600
```

-continued

```
tgtgacctta accaccctga acctcagttt cctcacctgt aatggaaata ggtaccacgg  72660
cagtttgttg caaggactag agagtaacct tgggaataaa aggtagcagc agcttgggct  72720
ctggagatgg actgtccaag accaacttcc agttcctccc cacacaagct ctggcactta  72780
gattcctggt acctccgctg cttcatctgt aaaatggagt aacaatagga atactttata  72840
gagttgtaag gattgagtgg ctggatgaac gtcaagcact tcaaagggga cctggcatgt  72900
agtgagtgat caatataaac cacctggctt gtagcaggtg tgctgtgtgt ggctgcaggt  72960
gttattagta acatctgtgt gcccttcaga gcgtgcacca cacttcacac cttgtggagt  73020
ctggaatgcc actattatag ttcaggatag aaaacctccc tgcaagcact cgctttagct  73080
tgtctccacc gaacaaaaca acacaagttc tttattactt ggaatgggaa aacttcaaag  73140
gcaaaaaaaa aaaaagactt tcgagttacc ccaaatctta agccaaagtc aatgaaaaat  73200
atcaatcttc atattcaatt tttgcgatac ttttgtctcc ccagcagtca atggagagaa  73260
tccaagcaca cagaaatgtc aattaccagg ggcagggcta tgaattcctt tcagagccct  73320
gggctgggga agagtgcagg cagacagatc tgggtcctgt tatcacgttc ttagattggg  73380
tgtccttgta ggagtcatga agcatcttag tgcctttgtt tgctacctat aatgcctacc  73440
tcagagagta ataaggataa gtaaggctct acgtgaaaag tgctcggccc tggcacatag  73500
taggtccttc attaatggca gctactaatt tttattacat acgcaaaatc acattacagg  73560
tcaagtacgc tacatgacag tgaaacagtt tttttgtttg tttgttttga gacagagtct  73620
cgctctgtca cccaggctgg agtgcagtgg cacgatcttg gctcaccgca acttctgcct  73680
tcaagcaatt ctcctgtctc agcctcccga gtagctggga ttacaggcat gtgccaccac  73740
gccagctaat ttttttggt atttttagta gagacggggt ttcaccatat tggccagact  73800
ggtctcaaac tcctgacctt gtgatctgcc caactcagac tcccaaagtg ctgggattac  73860
tggcatgagc caccgcacct ggctgtgaaa cagttttatt gtgtttctgt ggaatgtgtc  73920
ctacccaacc tatagctaac tcctatagtt ccctcagttc tcagctcaga tatcccttcc  73980
tttctgtact gttacctagt actggttttc atagcaccag gtacctctct ggcatagagc  74040
ttgtcacagt tgcagtttaa tgtaccatca taggatttta aaaatattca gttgtgtctt  74100
ccattaggct ttcatttggg aactccacgc aggcagcagc tgtatatttt gtattgccta  74160
ctgtatcctg agaactttgt accctactta gcacagaatg gaggctcagt aaatactgga  74220
catgagagag agagagagag agagaggaga gggagagaga gagagagaga ttcaacctac  74280
aatcccagct ctgagcttct agttccctga tggtgaggac tgtgatgtgt ctcacacggt  74340
aatgagcact tatgcagaag aggctcagaa aatttctcct catggccaac ggaagactta  74400
gagttctttt ccaagctcca ccgtttgctg gcatgcaaaa tttggactat cacttaagtt  74460
ttccaagcct tgctttttct atccctaaca taggacaata ttcagcattg ttgtttgttt  74520
gttgggggca ccatgtttca ggcacttagt agattattgt accaccacat ttcaattggt  74580
cctcctcaag ccctgcaaca tctgtgaggt ggtcatcctt aacaactcac agatgagcaa  74640
caggagactg gggggatgag ggaactgcca aggaggtcca gcttatgggc agcagagcca  74700
agaatggaac cagggtcttt tatttttta tttttttatt tttatttttt aaccagggtc  74760
ttttaacatc cgaggaccac attctttgtg ctttccaaat catcacctgc cccatgcaac  74820
ttacagggta agttacatta aacaacgtat gtaaatggct ttgtgctagt tattcaccac  74880
cacaggggaa gtgagtcacg gacaagagtg cagccgctcc attcggatcc tggctctgac  74940
```

-continued

```
acttacctgg aaaatgactt aaccattccc aggatcagct gtttgtctgt aatttaggta  75000
gtttaatggc acttgtgtcc tagagttgtt tagaaggttg aataatatgg agcacttaac  75060
atacttagca cctagaaaca cttcctaaat attagttgct gctgttgtta tcgttattaa  75120
aatttctgcc taagatctca tttcagggag cccaactcaa tctttgacaa gcttaaacaa  75180
aaattgcttt tcttcattta ttcacttaca cagcaaacat gaattgagcc tgtactgtgt  75240
ttccagaact gtgcaggacc agagaggcac aggtgaagga agcaaggctc tggctctact  75300
ggggaaacag caagaagatt gctacaatga ggtgggaaga gggctggact agagagaagc  75360
cctgattagt gtccttgcta cctttctctg ggagagccaa ggcaggcttc ctggaagagg  75420
tgatccttgg ctgaaacttc gatgaagaaa aggaaagagc gcagtggtta gggaggaaag  75480
ggcattctgg gcagatgaaa tgacatgtga caaaatatgg gtgatcannn nnnnnnnnnn  75540
nnnnnnnnnn nnnnnnnnnn nnnnnnnnnn nnnnnnnnnn nnnnnnnnnn nnnnnnnnnn  75600
nnnnnnnnnn nnnnnnnnnn nnnnnnngca ctccagcctg ggtcactgag tgagagaccc  75660
tgtctcaaaa aaattaaaaa aaaaaagtcc agaagaacat ttgggtctca ctctgtggcc  75720
caggctggag tatagtggca caatcatagc tcactgcaca ttcaaactcc tggcctcaag  75780
tgatcctcct gccttagcct tgaaataagc ttggattaca gatgagccac cacacccagc  75840
cagaccatta ttcataatag ccaaaatgtg aaaacaaccc aaatctccat caactgacaa  75900
atggataaat agaatggtgg ttgatccata caatggagta tttactcagc aataaaaaga  75960
agtcctgata catgctacaa ggatgaacct cgaaaacatt atgctaagtg aaagcagcca  76020
atcacaaaag gctacatatt acaagattcc atttaaatga aatgttcaga ataggtaaat  76080
ctaactttta tcacaggcaa agctatgaca ggaaatagat gagtggttgc ctagtgcttg  76140
ggggcagagg tgggggtgag gcgagtgagt actgctaatg gtacagagtt acttttgggg  76200
ataaagaaac tgttctgaaa tggactctgg tgatggttgc actactctga acatactaaa  76260
actgttaaat tatatacttg aaatgggtga cttgtgaggc atggaaatta tatcttaata  76320
aagctgtttt acatatttta catatttaaa aatgcaggtg gagggatgag ccctctaaag  76380
agaagcagga gtttgaggag gttctaaata ttgtgtggtg ggtactgagg catataaatt  76440
tgtcagacct catcaaaatg tatgatgtaa tcttcaagaa agttgatttt aaagaaacac  76500
caccagcacc aggtggagaa ggcaggaaga agttacacaa ggggtaggcc aagagtggtg  76560
gctcatgtct ataatcccag cactgcggga ggccgagctg ggtgggtgac ttgaggtcag  76620
gtgttcgaga ccagcctggc caacatggtg aaagcccgtc tctactaaaa atacaaaaat  76680
tagccagacg tgctcgcgtg aacccagggg gagaaggttg cagtgagcga agatcatgcc  76740
aatgcactcc agcctgggtg acagagtgag actctgtctc aaaaaaaaaa aaaaaagtta  76800
catagggac agtggcaggt gtcaagggca ggcagggtct ctcctatctc caggataaac  76860
tcatagggga cttagatgcc atgtgggtcc ctaatagccc tccacttggt tcttgcagcc  76920
actcttatgt gtatcatttc atgtcaggcc tcttcttccc aacccaccca gccatcccag  76980
cctggctgcc aaccccacct cctccagccc ctgtcacccc ataattgggg ccaggaggca  77040
tgggagagtc gccatctctc ggtgccatct gttgcatctt tacagataac catggctgga  77100
tgcggcagat cctggggtgg agcagccgct gttcagagca gtgatcaaga cctccccatc  77160
tccacccctc aaggaatcgg ttttcttcca tagccacatc aggtgctgtg caggaaggag  77220
ttgaaacgag aagccaggag caacgagaag gacactaaca tttattaagc actgcagact  77280
ctcacagcac tcccacggaa tcgatattat tatccccatt ctgaagacca ggcaactgaa  77340
```

-continued

```
gctcaatgtt taaggaactc accgaagtca ccaactgata aaagtgatgg aagctgggat  77400
tcaaatccaa gctaaacttc cttccaagct tactccacaa cacagaggtt ggggaaaggg  77460
gataaaaaga gaggggagcc caattccatt tccacccagc tcctgaggcg gagcttgtca  77520
gcacagctct ctccttccca gaataggaag atacccatca gaggcaagtc ctagacacca  77580
gcagtggtaa ctccctgccc caaggcagct gcagacagcc tatggctgta gttactgctc  77640
ccaaagagtg ttagaattcc cactcccagc ttcggggcca ctcacacaag gtgattgaag  77700
tggaaaccag agactctcca caatgccctc ctagagtaaa tgaggctatg taactttgtc  77760
caaatgagta atttgaaaac ctgggggctc ccagctcctg aaaagggaag gatgtggggc  77820
cctttatatt catactccac tttgtgcagc tctcccttgt cttatgatag ccctattaag  77880
aaattcctct cccagcacgt ctccttcaaa gagctctaga cctgaggctg tcagaggctt  77940
aggactctgc ctattagtcc cagggtctgg atgaccagca ggacacctgg cattcagtga  78000
ccactggatt agataaatga aacagtgggc agagtgccac ccaatctccc cctgaagttt  78060
gaagaggtcg agaagtgagg ctgtccaact gctgaccctg ctttctgtcc acctggccac  78120
ctaacctttt ctggcttcca cctgcccctt tgccatccct ccccccagcc cacccagccc  78180
attttcaggc atacctgggc acgtgctgga atagaagccc tcgttcttca gaatgatcaa  78240
cagggagccc cagcccagga gtacagcaga gaagaagagg ttctccagca cagccgtgca  78300
ggccatccac cagcgcctcc ggtacgcctg ttgcagcgtg gggcccatgc tggccccgag  78360
cctgcacaga aacagagcgc tgggtgaagg gccccccagt ggccccaggg aagggtcctg  78420
catcatggtg gcacccgaga cctctcgggc cagcccgcga ggagcccctc atggaggccc  78480
catagagccc tgggcttccc agccggtgcc aaggagctgg ctccgcgcgc actagcagtg  78540
ccagaggtgc acgcggcacg gggctcccgc tgagccacta tcggaaacaa ggaaggtcct  78600
gtctgcgcgc tgcagcttcc tagcaggctg ccgggttctc tcacccaggc cagggcgctc  78660
agggccgggc tgctggggag aaagtccgca tctgcccagg tccccagagg acagcaaggg  78720
gcagagcgcg ctctgaagca ccgcgggccc atgtccggac tctcgcgcca ggaaagaccc  78780
ctagaagctg gcaggaagaa gggcaagttc aaggctaccc tacgacccca tcttccagtt  78840
gcccctccaa gacctctcct tccctctggg gccgggcgac agcaagccct ccccctttcc  78900
gtatcaggtg acccacgacc ctacagtctc tcgggccaag ccaacagctg ccacgtggag  78960
ggagacccag gacgggctct cctcggttcc ctcctccccc gcgcgcccct cactcactcc  79020
gcagggctcg gggcaccagg ctttgcacct cggaacccgc ttgcccccct ccagccccgg  79080
gagggggctc ggacttcggc aggaagtctg gcggctgctg actttataag ggcagcggtg  79140
gcggatgggc tggcgggcgg gtgtgtttac caaagggagg gaaagagccc cagctccccc  79200
cgccgcggcc gctgcagcct cggcgggagg agagggaacg cgggcagcgc gggggcgggg  79260
agcgacaact gggatgagac cgaggaaagc ggagaggaga agggcaagaa agacccagag  79320
agaggggagg aagtaccagt cacttcttcc agggggactc ggtattctca tctgtgaaac  79380
ggggctttgg gttcaagcgc tccaggaggt ccgctggaac tctggcaaac gcgcagctct  79440
aagcagagga agtgcagcga gcggggaccc gggaggaaga gaagagtcgg aggggtcaga  79500
gaaaagaaaa gggaaggacg cgcttggcga gatgggacac tgtgccgcgg gaccgcgggc  79560
gcaagtaacg gtctttcctt gggaagcctg gcagtgtcgg cgggagccgg cctcggtgtc  79620
tctcagccga cgcatagccg gagaccctac gcgcgccccc tccccgccca cgctgctcac  79680
```

-continued

```
ctccggtcac cggcaaatga gcagccagca gctgcggacg cctccgggag cgcaacgctt  79740
tcgcggcgcg tccggagtcc cgtgggccca gccctgagcc gcgccggcgc tggggtcttc  79800
tctgcgtgca ggacccggcc gccacggagc ttcagcctga cagcccggtg gcctcgcctc  79860
cgctgtctcc tcggaagaag cgggggaact gggaacccgc cgggcgccag aggtctgcga  79920
agctgggctt ggatgaagtg gatctgcgga gttgatagtt gtatttacac gcgtccggag  79980
ctgcgccccg aggtgggggc gggggctccc ttcttttccc ctccccttag gtcgagtttc  80040
acgcgcacgt gactcgcccg ctggtcccgg acactctccc tctggcacag ccccagcacc  80100
tacatttcca ccctggaccc ccatcttctc ccccaagccc ccagactaac atcaggcagc  80160
gccctctgta tccttgttca aaacaaagtg cgattcggct gaagccgact gaccgcgatt  80220
cagggccgcc ttgggtgggg ttttgaactg tgcagctgga agcagtgttt tccgagaggc  80280
agagtggcac gggtttcttt ggagttagtc agatcgaggt ctgagtcttg actttttaac  80340
tgactaccct gggttaccta gggcaagtta cctctctgag cctcagcttc ctcctcttta  80400
aattcggtta aaatggaacc tacctaactg cccaaaggaa tcgcgattgt gatgcaggta  80460
aaatgctaag catagcattt ggcatagtaa gcataatgtt aattgttgct gctgtcatta  80520
tttcagaaga cctggtgatc ggatgcttcc agatcaacaa ttgattgact ccaggtaaat  80580
ctctcagcct ccctgagcct cagtatcctc atctgtaaaa tagactacta tggtgtggag  80640
taatgagaag taatctcatt acatgtgagt ttaattgtgt gttaagagtg ctgctaatgc  80700
atgctgagct taatacctag gtgatgggtt gataggtgca ataaaccacc atggcataca  80760
tttacctacg taacaaacct gcacattctg cacatgtacc ccagaactta aaataaaaat  80820
aaaatttttt taaaaaaaga gtgatactgg tggccaggtg tggtggttca tgcctgtaat  80880
cccagaactt tgggaggcca aggcaggagg atcgcttgag ctcaggagtt cgagaccaac  80940
ctggacaaca tggtgaaacc ccgtctctac aaaaaaagaa aaaaaatagc caggcatggt  81000
ggtgtgcacc tgcagtctca gctacccagc aggctgaagt gggaggatca ctgagctgga  81060
gagatggagg ctgcagtgag ccaagatcat gccactacac tccagcctgg gtgacagagt  81120
aagactctgt ctcaaaaaca aaacaagaat gactacagaa agctccaaga aggcctcaga  81180
taaaagggaa cccctgaaca gatgagccac caagccaaga gaggaactaa tggctaccat  81240
agacagggca ctttccaaaa taaaaatact gttattaatt cctcaagaca tcatggtccc  81300
atttaaacct catagctttt cacagaggga gaaactgcag gcttgaagct ggagcaaggt  81360
tagaggtagg atgcagagtc aggtcggcct ggcatttaag tacggctcct tccattcctc  81420
ccagaaggag aatggcaaga gcaaaggctt agctgtggga atggcacaag gagttctcgg  81480
tggccaaagc acatgtcagg ctctgatggt ttaacttctt aaaatgcaat actgcctccc  81540
agaacttcca gatcaaggtc aaactcctca gctctacaca gggggaccta gagtcaactt  81600
tctaagctag gagagtcatg gatccctttg agaatacaaa agacagtggg cgcggtggca  81660
gtggctcatg cctgtaatcc caacattttg ggaggctgag gcaggaggat cacttgagcc  81720
caggagttca agacctgctt ggtcaacata gtgagacccc tatttctaca aaaaattcag  81780
ctgagcatgg tggcatgtgc ctgtagtctc agttactggg gaggctgaag taggatgatc  81840
cctgagcctg ggaggtccag gaagctggag tgagccgaca tctcgccact gcactccagc  81900
ctgggtgaca gagaccctgt ctcaaaaaaa aaaaaaaaaa gaagaaatat gttattgatc  81960
tactcttgac aaaaatgctt gtgtgaacat ggacacacac actcatcaac attcacattt  82020
caaggttttc atggaccctt tccatgaggc tctagtggtc catggacccc catggctgga  82080
```

-continued

```
acacttgctc ttcctcatct caacccacat ttccatggag ttggactgtc tgctgcatga  82140
ggacacaggc ctcatttggt gtgttcattc actgctgtgt atcccagcac ccagaacagc  82200
acctcaccta aggggcactc agcacatgtg cagtgaagag tcagtcagct ggtttcacac  82260
ctcccagtct ttgcacctgc tattccttct tgtgggaatg acagatttcc ttcatttctt  82320
ttttttttt ttttgacaga ttccagctct gttgcccgag ttggagtaca gtggcacgat  82380
ctcagctcac tgcaacctct gcctcccagg ttcaagcaat tctcatgcct cagcctccca  82440
agtagctggg attacaggtg cacaccacca cctgtgagct gatatttttt tcttttcttt  82500
tcttttttcc tgagacagag tctcactctg ttgcccaggc tggagtgcag tggcgtgatc  82560
tcggctcact gcaagctcca cctcccgggt tcaagtgatt ctcctgcctc agcctcccaa  82620
gtagctgaga ctacaggcgc gcaccaccat gcctggctaa tttttgtatt ttttagtaga  82680
ggcggggttt caccatattg gacaggctgg tctcgaactc ctgacctcgt gatccgccca  82740
cgttggcctc ccaaggtgct gagattacag gtgtgagcca ctgcactcgg ccattttttg  82800
tatttttta gtagagatgg ggtttcacca tgttggccag gctggtcttg aactcttggc  82860
ctcacgtgat ccacccacct tggccaccca aagtgttggg attacaggca tgaaccactg  82920
cgctcagcct ccttcttcat ttctaatgta ctcatccttc acaactcagc tcaagtttca  82980
cttctctctg gaagctctac tctaggctgg attcagggcc ttgtccacat acccaccaaa  83040
tactctgctt acctctatgg aagtccccac actgatctag aataatcagc ttagttttct  83100
gcccccatcc cgccccatga gatgtacatc ttgtgggggc aggaaccacc acgtggtagg  83160
tgatttgtgt gcctgctgcc tatcacaggg cctggcgcct aataagcttg cggccaacat  83220
ttgttgaata aatgaaaagg gaatggtggg aaaggaagct gaaaaggtag gctaaaatca  83280
gtttggaatt acctctggga ggccaaggac tttcagtctt gcagggtagg taacaggaaa  83340
ctcctggatt ttgttttctt ttggttttgt ttgtttttaa tgaagggtag cgttatcgtc  83400
aggtttttgt gtttaattaa tggagcatat attggaaagg acagagacct taaagcagtt  83460
aggagaccac cataatagtt cacattttgc agccataaaa aggaatgagg ccaggcatgg  83520
tggctcactc ctgtaatctt atcacttcgg gaggttgagg caggcggatc acctgaggtc  83580
aggagtttga gaccagcctc accaacatgg agaaacccca tctctactaa aaatacaaaa  83640
ttatccaggc gtggtggtac atgcctgtaa tcccagctac tcaggaggct gaggcaggag  83700
aatagcttga atctgggagg cagaggttgc ggtgagccga gatcgtgcca ttgcattgca  83760
ggtacatgga tgaagctgga agccatcatc ctcagcaaac taacacagga acagaaaacc  83820
aaacaccgca tgttctcact cataagtagg agctgaacat tgaaaacaca tggacacaga  83880
ggggaacatc acacactagg gcccgttggg gagtgggggt tgggggtaa ggggagggaa  83940
cttagaggac gggacaatag gtgcagcaaa ccaccatgac acacgtatac atatgtgaca  84000
aacctgcaca ttctgcacat ggatcctgtt ttgttttaag aagaaataaa gaaaaaacca  84060
agaagaaaca aacaaacaaa aataattccc atttaaaaca ataaaaaata ggccaggcat  84120
ggtgactcag gtctataatc ccaacacttt gggaggccaa cgcgggcaga tctcttgagc  84180
ccaggagttc aaggccagcc tgggcaacat ggcaaaaccc tgtctctaca aaaaatataa  84240
aacaaacaaa caaaatagcc aggagtggtg gtgcatgcct gtcatcccag ctactcaggt  84300
ggctgaggtg ggagaatcac ttaagcctgg gaggcggagg tagcagtgag ctgagatcgt  84360
gccactgcac tccacctgga gcaacagagc aagattttgt ctctaaataa ataaataaaa  84420
```

-continued taataaaaaa cagagaagag gaaagacacc tgagatatat ttccatatct gaatcaatag 84480
gatttatcaa cgttctcctc tacccccaaa actaattcct tcctaaactc tgttctcctg 84540
acactactca taggttaagt ataacagcat tatcacattg gctgtcatgt gggctcctgg 84600
ctagaggctg cttcacagct taatggacaa gagcactgag acagggtggg tctaaatcct 84660
ggctctgcag ctgattattt gtgtgatttt gtccaaatca ctccatctca tgagcctcac 84720
tcttctagtc tgttaagtgc tgaaaataaa agtatccaat tcaattcatt atttaatgaa 84780
ttatttagcc taacaaatag ctattataaa tatttaggct gggcacagtg gctcacgcct 84840
gtaatcccag cactttggga ggccaaggtg ggcagatcac ctgagtcagg agtttgagac 84900
cagcctgacc aacatggtga aaccccgtct ctactaaaaa tacaaaaatt agctgggtgt 84960
ggtggcatgt gcctgtaatc ccagctactc aggaggctga ggcaggagaa cgcttgaacc 85020
caggagacag aggctgcagt gagccaagat cgtgccactg cactctagcc tgagcaacag 85080
agcaagactc tgtctcaaaa aaaaaaaaaa aatctctgca tgaagaatgt acataaaatg 85140
gtgcagccat ttcggaaaac agtttggcag gtcctcaaat agttaaacat agagttacca 85200
ctatagccca gcaattccac tcctaaatat actacaccca agagaattga gaatatttgt 85260
taacacaaaa atgtgtatac aagtatttat agctgtatta ttcattacag ctaaaaagtg 85320
caaacatccc agcagtccat cagctgatga acggagaaac aaaatgtggt atacccatac 85380
aatgtcatat tatttggcca taaaaaggaa gtactgatac atgctacaac atggatgaac 85440
cttgataatg ttattctaag tgaaagaaac cagacacaaa agaccacata ttgtatgact 85500
gcatttatat gaagtgccca gaataggcaa atccacagag acagaaagta gattagtggt 85560
tgccagagac tggagggagg agataatggg aaatgtggaa tgactgctaa tggtatgggg 85620
tttcttcttg ggtaatgaa aatgttgtac aattagataa tggtgatcat tgtaaaactt 85680
tgtgaatata caacatgctg aattttatac tttattatat tttatttttt ttgagacaag 85740
gtctcgctct gtcacccagg ctggagtgca gtggcacgat ctcagctcac tgcaatctct 85800
ctgcctccca ggctcaagca atcctcctgc ctcagcctcc tgagtacctg acactacagc 85860
atgtgctacc atgcctggac aatttttgca tttttagtag agacagggtt tcgctatgtt 85920
gcccaggctg attttgaact cctggactca agtgctccgc ccacctcagc ctcccaaagt 85980
gctaggatta caggtgtaag ccaccactcc cggcctaaat tgtattcttt aaaagactga 86040
attgtatggt gtgcgaatta tatctcaatt taaaaaaaac aaaacaaaac aaaaaaaaaa 86100
cctttgcgtg tgtcaggcac tagggattcg atgctgaata agacacagac cctaccctca 86160
gagaacacag agcccagcag gagagagtca cagatgaatc aagtgttaca tcatctatag 86220
gaagcgccat ggaagaaaga catggtgcca tgagaacata cgcttagaga agggaatttc 86280
atctagactg gggctcaggg aggaatcttt cagggtgatg cttgtgctca gagttttcca 86340
tgtcagaatc agtagaattt atcaatcctc cagaggagga aacagcaaat gaaaaatctt 86400
acaacaggag gatgcggaga cattccgaga gctgatcaag ggctggtgtg aacaaagcac 86460
ataggatgca gagcctgtgg tgtgaggttg cagctggaaa ggtaaaacac taattacatt 86520
ggatcttctg agacaataaa gagtatgcaa taatctcaaa cgaccgaaac tgaccttcct 86580
cctccctaac ttgcttgctt ccactgttgc ccgtatcata aaagcaccac cctcttctac 86640
ccagtggctt aagacacgaa actcaagtca tcccaggctt tctccccacc tcactctcca 86700
catccagcct atcagcgagc ttgtgggtct taccacgtaa agacttctca tctccagcta 86760
ctaccatccc ccaagcccag atcaccatca gctcaggcct ggactcctgc aacctttcta 86820

-continued

```
accgggtctt cccaatccta cccccgcaac atgaccccaa tagcccatca gaatggacta  86880
atcgagatgt agatttgatc aggccacatc ccttgaaagg cttcctgtga ccctcgggga  86940
aatgcacaaa ctcccaatga tggcccctga gtcctgtgcc atctgggtct gccctctgcc  87000
ctctgtgtct ttgccatggt aacctccttc acacccatta atactccatg ctctctccta  87060
cctcaagttc ttcctgggct ggaacattct ctgcactagc ctagccaact aaccctttag  87120
atcttttgtt tgtttgtttg tttgtttgtt tgtttttgag acagtcttgc tctgttgcca  87180
ggctggagtg caatggtgca atctatctcg gctcactgca acctctgcct gccgggttca  87240
agcaattctt ctgccttagc gtcctgagta gctgagacta taggcaccta ccatcacgcc  87300
cggctaattt ttgtattttc agtggaggtg ggttttcacc atgttggcca ggctggtctc  87360
gaactcctgg cctcaaatga ccaccctcct cggcctccta aagtgctggg attacaagca  87420
tgagccactg tgcccaggca acacttcaga tcttaatgat catttccttt aagtgcctga  87480
cctcttgtag taactagcct gactccagca atgaatcctt ttgcaatgta acctatataa  87540
catctgagtt tccctttgat aaaactcatc atatatttgt tcctctgaca gttcagaggg  87600
caagggcctt tgcccacctt cctcaccact atcctctcac cacttaacac agaactcacc  87660
acccaccatg cctcctgcct gacaaattcc taaccatcct tcaaatctca ctcacctatt  87720
accttctggg aggcagtctt ccctgagcac caagacaatg ggacacattc ctttatacac  87780
cctgctgaac atctcttttt tgaggggcgg gtagagatga gtgtctcact atgctgccca  87840
ggctgacctc aaactcctgg cctcaagcga tcctcctgcc ttggcctccc aaaatgctgg  87900
gattacaggc atgagccact gtacctgacc gcaactgggt tagnnnnnnn nnnnnnnnnn  87960
nnnnnnnnnn nnnnnnnnnn nnnnnnnnnn nnnnnnnnnn nnnnnnnnnn nnnnnnnnnn  88020
nnnnnnnnnn nnnnnnnnnn nnncctgggc aacaaagacc cttcctctac aaaaaaaaaa  88080
aaaaaaaaaa aaaaaaaaaa aaattatttt aaattagcca gacatggtag tgcatgcctg  88140
tagtccaagc tacttgggag gctgaaggga gaggatcact tgagcccagg aggttgaggc  88200
tgcagtgagc cgtgatcgta ccactgtact ccagcttggg caacagagtg agacctcatc  88260
cctaaaaata aagaagaaaa tatggcaatt tgactgtaca tctctaatgg gatatatcct  88320
aaggatgaga aaggaataag gaaggacaga aaaaaggaaa caaagaagta gcaacagtat  88380
ttagcaattg tattgttatc aagtaacatc aatattggta aaaccagtaa ttatatttaa  88440
aatactatat atgtgtatgt acatttacat atgcatatgt taggaaccaa gtttatcaga  88500
ggaagagaaa gggctacaaa tgtaaaatca aggaaataaa aatttgaata aaaatatcag  88560
tattaagtat tttatgatatt tttcttataa aaaaattata tatatgttaa ctctatccaa  88620
aacccaaaag cagtgacaac ccaggagcaa taaaaaacct cagcatccag actgtagtct  88680
ctaccatttc caattaaaga aacccagggc tagttgggaa aaatgacaat ttcatgtcta  88740
gggcaagaaa cacacctagt gaaatggacc tgaacattta attgtgttag aaagtaagga  88800
aactctctag aaataatgtg atttcatcta aaagacacag attctgggct ggtaaagttt  88860
tcaatggcca aaggtgagac aatttgagca tcaagaagaa tcatgacaga acagattaaa  88920
acatgtcaaa tatattttaa aatgaaatat tataaaagaa acaattagta gccatccctg  88980
aaggtcacta gggcaccaac tcatatttca aactggtaaa taaatgtgta agccaagcat  89040
ttatttctgg gtaacaaaat agtaaggaat gtttttcttt ctagaagaat tctagtgatt  89100
aaaagtagaa gatagaaata gaaaatcatc cttttggcca ggggcagtgg ctgtaatccc  89160
```

-continued agaactttgg gaggccaagg caggtggatc actggagatc aggagtttga gaccagcctg 89220
gccaacatgg tgaaacccca tctctactaa aaatacaaaa attagccagg tagtgggtgc 89280
ctgtaatgcc agctactcgg gatgctgagg caggagaatc gcttgaacct gggaggcgga 89340
ggtcgcagta ggctgagatt acgccactgc actccagcct aggcaacaca gtgagactct 89400
gtctcaaaaa aaaaaaaaga aagaaaagaa aatcatcctt ttgcgatcct aatgaaataa 89460
tgggcctagg cattgatcat taatggctcc taaaatcact aagtatatgg ttgatgggaa 89520
actttatagt ggatggatca gactcgcaat gtctaaacca gttgatcaat cttaacatcg 89580
taacaagaca acagacacca ggggctgctg acaggagaac agaggaaacc catagctcta 89640
ccactgagtt attcacggca aaaaaaaaaa aaaaaaaatt aaactgcgtt tcctccaagc 89700
ttctaatcct gttgtttaca ggaaataccc aaggaaagga atacttttaa atgacacatt 89760
aaaacaacgc caaatccaaa atatggggaa atgacccagt ttcttcaaca aataaacaag 89820
aaaaggtagg ggggaggact gttctagatt ttaaaagcta tagaagacac agcaaccaaa 89880
tacactgcat ggaccaggca tggatcctaa ttggaacaaa ccaactgtaa aaggatgtat 89940
ttgaaatgat tggaggaatt tgaacagtga ctgcacagta gatgatatga agaaattatt 90000
gttatttttt aggtgtgatc atgattttat ggtgatgttt aagtaaaaga ggccttattt 90060
gttagagata catgtacggg tatagagaaa tatttacgga tgaaatgata cgatgtctga 90120
gatttgcttt gaaaactcta gcaggtgtgg gagaagcagg tgcatgggtg ggggaaggga 90180
tagatgaaat aagtatgcaa aatgttagtc tacttttgtc cctcctgacc cagcaggtta 90240
aaatacctca gcatacctct actcctccaa ccaggtccaa ggatcaggcc aaaactccct 90300
gatgtggtaa acagcctgac cccttcttac ctctctctct ccagccactt ccctaagatt 90360
ccccagtgct ctgtgcccta gccagcccga ctcatctgcc cagattcctc aatgtttcac 90420
tctctcattc accattttga ccccactgtg ctcctgggcc actctccaag gccccgcctc 90480
ttcatctcct ccctccttac tcatccttca ggtcttggct taggtgccat tccctccagg 90540
aagccttccc tgacaccaat cccatcctca cctagaacag attatgtgcg cttctttgtg 90600
ccccccatgg ccccctgtgg gtttgcttca cggattataa ctgcctgact acctgccttt 90660
ctccaccctc tagactgaga acaccttgag aaaaagaaca catctatctt gtctgtcatt 90720
gaatccctgg tgtctggcac catggctgac acataactat cactcagtga ctagtgtttt 90780
aatgaatgaa tgagtgcaac tagacagggt taagaacaaa agagaagacc aggcatggtg 90840
cttcacgcct gttatcccag cattttggga ggctgaggcg ggcagatcac ccgaggtcag 90900
gagttcaaga ccagcctgac atggtgaaac cccgtctcta ctaaaaagac aaaaattagt 90960
gggggatggt ggcacacgcc tgtaatccca gctacttggg aggctgaggc aggagaatct 91020
cttgaaccca ggaggtgcag gctgcaatga tctgagatca caccactgca ctccagcctg 91080
ggcaacagag taagactcta tcacaaaaaa aaaaaaaaaa aaaaaaaaaa gagcgagaga 91140
agatgtcatg gggtaaatga agacctccct tcctggttcc ctgaccagcc cctgccctcc 91200
cccgcatctc acctgtcttt cttgcttcct tctggtactt ctgtttaagc cggtccatga 91260
gcaggccatt ccagggggca cacagcactc cgaactgagt gaaggcaaag gcatttgtgt 91320
aggtgctgac tgcagaagga agagagaggt tggttgatga gaagtttcca aaactccctt 91380
ccaggcaggg actctcccac cttacccttg tctgcatgtc cctcctcccc acaccatcag 91440
accctcctct ggtgtgtaca gccctgctgg gaggctctgt gttcccagct gggacatgca 91500
gatgggctac ctcccagccc taccacatac ctcgtgccat gtccccaccg gccatgttgg 91560

-continued

```
tcagcaagga gttgagagtg ccaatgaaga ggtagtgcca caactgtatc acagacagcc  91620
acaccaggtg ccaggcaaag cgccgagaga aagcgtagct ccagaaggag cggagttcct  91680
gcttctgccc tgcccctggg gtctctaatg gggagaggag gatctgggcg tgaattacga  91740
ggaaagtgga caggtaggat ggggagtgtg gaggcttcaa tggaacattt cagatccggg  91800
cccaccttct acccttggct cccagaactc acccggcgtg ctctgcacct gcctcggact  91860
cacacatccc cacctccctg ctttgtcatg ctggccctac caccttggat gaccctctgt  91920
gttcttctct attgaaatcc gatctgtctc tcacagcctg gtcaatgaca cttcttgcag  91980
taataccttc ctgatctttc tcagcgagaa aggtgaaagg aacgacaagg agaggagaaa  92040
gtcagaaggg agaggagaat gagtgtggat actctgttct aacctgctcc tcagcacctc  92100
cctttctttt gataccagta tcctgagttt ctttgggaaa tcttcctcta ccctaatctt  92160
catggtccag atgggaccat gaattcagtg ttctgttcct ctctcaaggt taaccaatga  92220
gatggttcct cctaacaagg cagaccggcc atgagtttag attaggatgg acttaatcta  92280
aaataggtcc tacaccctgg caagttcaat gtcctccctt gattttggaa gcttcccaga  92340
accctattct tctttcttta aaataaataa ataaatacat gttttggatc caattgtcag  92400
atggtaaaaa taaaaacaaa aaaatcaatt ttattctgta tatttaagat atacaatatg  92460
aggtcatagg atacatatag ctactaagat ggttactaca gttaagcaaa ttaacatatc  92520
catcatctca catttctacc tgttttgtga caagagcagt taaaatctac ttgtttagga  92580
aagtcccaaa cacaatgcag tttgatgacc tacagtcttc gtgctgtgca ttagatctct  92640
aggcctgttc atcctgctca tctgctcctt tttgtccttc gacctgcatc tcccatctcc  92700
tctcccaccc cgttcttatt tctactgtag ctagctgcgg tttgtgatgt gtgtaaccaa  92760
agacgcagaa cagagaggaa ggaaaggaag cagtgataga gttgggacaa taagagaggg  92820
cggacccagg agacctggag aaatgggggc actgtaccag acttagtgca atggcatcac  92880
agaagagggc agaaccgagg agtgggggga agggaaggca acccatggca ggcgggcttc  92940
aaggggtggg gaagtgatag gatgcgaaat agagaaaaga gggacagaaa agagacgaaa  93000
gccctggacc ctccattaag tgagagggtt gggaagatgc ctaaggccct ttttctgtcc  93060
tgcctttcct gattctgggt ccctggggga gctctggagg tgaggggcca ggaaaggcac  93120
aaggagaggc ttgggtctgg aggagagatg ggttagccag cagggctcac cttccttcgc  93180
tgaaaggaac tcctttgact gtagctccct gttttcatgc tcagctgttt ccttctcttc  93240
ctttgtggtg ccattcccag ggcacaggct atggaaacaa aagccccacc agcaaggcca  93300
aggactgtga gccgaacctg agactcagac tggagggaat agcatggtga atcccacatt  93360
ccaccgcact ttggaatcac cttttagcca ctctgatgcc caggttgcag accagaccag  93420
ttaaatcaga atgtctggag gtgagagcca ggcttccttt tctaagatct ctatgtgaat  93480
ctagtgattc taataagcag caaagtttag gaagcatgaa aagagtaggg caggcccagg  93540
ttcaaatccc agctctgcct cttcctagca acagaaagat ggctcagact taacccttct  93600
gagcctcatt ttttgcattt agaaaatgga gataaggata tctcagagga ttattgtgag  93660
gatgaaatca gagagcacat ggggtctgac aattagtaag tgagcagcaa aggaatgccc  93720
ttcctctact ccttgtggca aatgactgca aaaatgatca catttcttca cctcctctgt  93780
atttccccca atttgaatga gactgcagct ctatttcccc atgccctgaa tctgggccag  93840
ccttgtgaac tgcttcagcc aaaagaatgc agcagaagtg gctgtgccaa ttccaagctt  93900
```

-continued

```
aaatctcaag aacgcttgtg catttctgca ctctttcaga accctgaaat cacggtgtga  93960
atgagcccac gctggcttgc tggaggatga cagccacgtg acccaggcat ccctgtcact  94020
ccaaacctat gtgagtgagg ccatcctagc atagccagcc cccatgtaat cctccaaatg  94080
atcagatgta tgaatgagcc ctgtcaaaat catctacatc tggccctgat cagcggaact  94140
agccagctac ccacagactt gtgaaaaata ataaatgctt aacattttag gctgctgagt  94200
tttgagatag tttgttatgc agcaatagct aacagatgca ctgctccagt cctcctcctc  94260
tcctgtgata ggtttgcttt accctgtcca tcccacccta gggccaatga ggggctctgg  94320
cccacaatca ccagatagtc cttacccata gctgtagttg gggggcagtg ggtatgggat  94380
gtgcccccgg ggcatcagga ggaaagtgcg tgctacatgc caggtactgc agacagagat  94440
gaagatgaag gaggccctga ggctgatgcc tttttcataa agaagctgca gaaggagaag  94500
gaaaaagtca gtgtcacacc cacgttcata gcagcactat tcacaatagc caaaggatgg  94560
aagcaaacta agggtccatc agcagatgaa cagctaaaca taatgtgatc tatacacaca  94620
atggaatatt attcagcctt aaaaaaggaa agaggcaacc atgctggctc acacctacaa  94680
tcccagcact ttgggacgca cgaggatcac ctgagcccag ttcaagacca gccttgacaa  94740
catagtgaga ccctcacccc ttctctagaa aatttttatt taattagctg ggtgtggtgg  94800
catacacctg tagtgccagc tactcaggag gctgagtggg aggatttctt gagcccagaa  94860
gtttgaggct gcagtgagtc atgactgggc cactgcaccc cagcctggac aatgaaacat  94920
gaccttgcct ccaaataaaa aaaaaaaagg aaaggaaaga aattctgaca catgctgcaa  94980
catggatgaa ctttaagagc actatgcagg gccaagctca gtggttcctg cctgtaattc  95040
tagtgcttta gaagaccaag acaggaggat tgcttgagtc caggagcttg agaccagcct  95100
gggaaacagc aagacctcat ctctactaaa aataaataaa taaatcagct gggcgtgatg  95160
gtgcacgcct gtaattccag ctacttggga ggctgaggtg agaggatatg attacatgat  95220
tacatgcctg taatcccagt actttgggag gctgaggcaa gcagatcacc tgaggccagg  95280
agttccagac cagcctggcc aacatggtga aaccccgtct ctactgaaaa tacaaaaatt  95340
agtggggcat ggtggcacgc acctgtaatc ccagctactc gggtggttaa ggcaggagaa  95400
tcgcttgaac ccgggaggcg gaggttgcag tgagccaaga tcctgccacc gcactccagc  95460
ctgggcaaca gagcgagact ctgtctcaaa aaaaaaaaaa ggttaagata gtaaatttta  95520
tgttatgtat attttattgc atacaaaaac atcagcagaa gaggcagggg ctggaaccct  95580
gttttctaag gagtcctagt acaagccatc acctactatc ctgtaagctg attagggaca  95640
cctggtacac acatgccccc acccacccca agacacaccc ggcagtagag gagtcctcat  95700
acgacccatc cccacagccg gtggagcctc ctcgtgtggc tccccagaga tcttctagcc  95760
cagtgccttt tttcccccaa cgacagcaaa ggccttttgt tcaaagaaaa ttttacacaa  95820
aaattcatct tacaaaacac accaatgggg agcttgccag tcatctccct ctttattctc  95880
cttggtgact ggtatgacat caaagagaat ccctaagttc ctcaacagct cagtttgaaa  95940
accaccgacc tagcccaacc tcctcccatt ttacagagag tgacgttgag gtccagagag  96000
gtgcagtgaa ttgctcaata aattgacaga gtaagcagca gcaaagtcag attaaactaa  96060
gaattcctgt tcctgctccc tttccccttc caactctaga gagacaggag agaggctggg  96120
catggtggct catgcctgta atttcagcac tttgggaggt caaggaaggc ggattacttg  96180
aggtcaagag ttcaagacca gcctggccaa catggcgaaa ccccatctct actaaaaata  96240
caaaaataag ctgactgtgg tggcacgcct atagtcccag ctactcagga ggctgaggca  96300
```

-continued

```
ggagaattgc ttaaacccac taggcagaga ttgcagtgag ccaagatccc accaatgcac  96360
tccagcctgg gagacaaagt gagactccaa ctcaataata aaaaaaaaaa aaaaagagag  96420
aggaaagaaa gatgaggcag ccatctgggt tctccagggg aaggagggag aacccagaaa  96480
gtgactctta tgccaggagt agaaaggctt gagtgcctca ggggctcagt ctctgcataa  96540
ccctccaaac ctccaaagct tatgggacta agctagactc atgtctgggt ggtgactgcc  96600
agagatcctc ttctctgccc ccataacctg caggcagtgc caactgcctg tgacctaaca  96660
ctaagcccag agagaagtcc caggttggat ggcttgagat ccacactctt cccttccttt  96720
cactcagcca tctgtggtgt gctggcttta gtcctccagc ttgctgcctc ataattgaag  96780
catggttgcc acaactccag ctatcacatc ctcacaccac aacattcaat gaggaagact  96840
ttgtttttac tctgctttca ccttgcgtca gggaagaaaa gtccccttga atcttccact  96900
atatacactc cctttatctc attaaaaagg actggatcat atgctgacct ccacctatca  96960
ctagcaacgg gtaaatggat tgccatggtt ggctttaatc aatcaggatt catcccctgg  97020
gctaagcggg tcactgccca gataaaactg ttcgcaatga ataagacaga atggttgttg  97080
attgacctct aatagccttg gcaacagttc atcccctgat accccaacat cagccactgg  97140
gacagctgga caagcctctg tgtctgcccc tgctgtaccc actagccact tgccaccttc  97200
ttgtccaaac tagaagctca cagcagcaaa cgccccactc taaaggtccc ccagcctcta  97260
cccaacactg gcccaagcac attatgacca ctgccacaaa agcttgggca agtctgaaga  97320
aggggcttag cggttacaag ctcaggctct agaaccgaca agcctgggtt caagttccag  97380
tatcatggct actagctgca gaaccttcaa caagcttttt aacctcagag actcaaatgc  97440
ttcatctgta aaatgggggt aacacagtac ctacctcacc gagttgatgg agacaaataa  97500
tgcaggttca caagacaagt gtctggcata tacaagtgcc cagtgaatgt aggctgttgc  97560
tatatttacc ttaataataa ggaagactgc cgaggaagag tcaaatgctc cattgtacag  97620
agtgatgatg gtcgaacggt gttggccaaa taggttccca atctggggat gataggacta  97680
gcctggatca cttatttatt catgaaacag atacttcctg agcacccagc atgtggcaga  97740
ccctccttat acccaaactc accctccacc gctagagctc ccacctcagc ttgggccaac  97800
cccatctgag gcagccaatt atagaaaagg gtctctcctt ccctccacct tcccgccacc  97860
ctgccgagtg cctgggatta gggaaggctc ccacctgcag gttggtgatg agaaacagga  97920
ttcccccaat ggtgagcatt ggcatggcca ggaagagcag cacggctgag cctggaccat  97980
caaagtcaga ggtagggtgg tgtcatagtg caacccaaac atggagcccc aaactctgct  98040
cccacctgct ccaaattccc aacaatcctg gtatccaggc cccaattcta gccagcgttc  98100
cagcgtcctt caagggtttt taggataccg gccaaggctt ccccagatat ctctgtggaa  98160
gtcttctgag ccaccttctt cccaaccaaa gttggtcctc agtctgtggc aggccaggaa  98220
gtctacagac agaggcagag ctctaagtga agccacctct ctcttccctc agtaaaccac  98280
aagctgcctc tccctttcat ccttgacact cctggaaaag aagaccctgg actcaggtcc  98340
ctggctcaac cctctagccc attccctaat tcatggtatt ggccttgagc ttcaatcatc  98400
tgtttaatgg gaacaacagt tcctgctctt cctgtctcag gtgctatgag aactgagtga  98460
gaaaaggacc atggtctttt ctttgttcac taaactctga gcacttcttt ggtgccaggc  98520
attgtgcttg gcactggaaa tgcaagatga atcagatagt ccttgccctt aaatagactg  98580
acatgcaaac aaatggttat aacaggtctg gtaagtgtga gaccacagca aaaaagctca  98640
```

-continued

```
agagctgggc taggggaacc cttgacaaat tcttcctccc caaaccagac ttctgcccac  98700
cattattctg gccacaacct atgcctgtcc tattatttgc taaaatgttt taagttgact  98760
cactttttatc caaaaagtat ctatttttaa aggacacttt atatcactac tgtagatgaa  98820
aacactggca ttacttgtca tgaatagaaa gtaactgtca aaataaatac aatgaaagga  98880
aaacaatgtt attcaattgt agctggatgc atttgacctt agaatgttca aagcctaaga  98940
cctgctcttc ccatcagtgt taaaatcaca ctggccccac atgaagacat tctttcatga  99000
aatcagaagg actgaaagag aaataaaaag ggaatagctg ttctaccagg tgatttgatg  99060
tttgttagtg tagttcacgt agtatgcgtg tgcccctaac atcctcttaa ctaccgtgct  99120
ataccttaag aagcactgcc aagagctaat tttagagtat tcacacagtt taccattcaa  99180
tttctgtctt tataaaatgt acatctctcc tactactaaa ggttggagac tcctttcaca  99240
atagagtcct tatgggctca atgctttttt caaaactgaa aagccctata ttatggagga  99300
agaggaggat tgttgctcag acgatttgca ggcacgagtc aaacattacc cagccaccac  99360
ctccacattc agttgcttaa aaatcattta caggctttta gagtagatga tgctggtttg  99420
ataaggagag tggtttgaaa taattggttt gaggtgctgg gccatctcat gagatctgtg  99480
tgaacaaaga cactcagcct ctgtgtttgc ccagcatgag tgcagacaat ctcatgatgc  99540
tgtcagcttt agcatagctt acacacacaa gagtaatgta ctttctttcc taaaccaaaa  99600
attgagccac gggtctaaca ctaggaagga atattgggag gcatctcgtg gccaccataa  99660
ccaaggcaat gacagaaaga agagtgaggg atcaggaggc ctgcacatca ggcccacctc  99720
ccacttgctt tctctgtggc catggacatg tctttgcaag gggtcctgct gtggcttcag  99780
tttctcctct gtgtaatggg tggaagggtg gtggaaaata aaccagattg gagttccaga  99840
cttaacagac tggtgaaatt ttaaaacaaa gattttgagt acaatagggt tgtcaacttt  99900
taccctgcta agtaaggata tttgcaaaat ggtcattcat ataatcattt cattaaaaag  99960
agaaagagaa cattttaaca cataggagaa ggatgtaaag gttttttgtt gttgttttgt 100020
tttttagggt tttttgtttg ttttttggta gagtctcact ttgtcaccca ggctggagtg 100080
caatggtgtg atcttggctc actgcaacct ctgcctcctg ggttcaggca attctcctgc 100140
ctcagcctcc tgagtggctg ggattacagg cgcgcaccac catccagcta atttttgtat 100200
ttttttttagt agagaaggga tttcaccatg ttggccaggc tggtcttgaa ctcctgacct 100260
cagatgatcc acccgcctca gcctcccaaa gtgctgggat tacaggagtg agccactgca 100320
cctggccaga tgtaaagttt tgaataaatt ctactctctg aagtaatccc tctccatcat 100380
ccttgctttt cacattttct caataaactg ttttcacaga ccagcaatag ctcaagatcc 100440
ttccaggatt ctttcaagct gcagatctct gaataaccat gtggtctgta tatcttgcct 100500
atagccctct gctcacacct gccccagcca ccaggtgcct ctgagcttgc atccctccca 100560
cccacctgac agcactcacc tgcagaggtg aaggctatga tgagtgtggc ggtggtgtag 100620
aaaaatctga aacacataac aggaaaagca gaatattgtc aaggagggag aaacctggga 100680
gaaaaaaacat gattctgctc agccagccca caagtgtagg acttgaccgc accctcagcc 100740
tgggatgcaa cgggcactga tgcctctgag ccccaggctc aaaaccaggc gcaagaagcc 100800
gcgatgagat tgagatgtgg tcctgacctc atggacagtg cattttgctc attctgaggc 100860
ccaaggctag catggaaagt cttggacaat gagctcagct gacgatgtga ttggcttggg 100920
acttagccag gacagaatgg gcaaagcgaa ggtcctccca cctggaagcc ccaacagccc 100980
aacccccttgg agaaaggggt tagtgcctgg tctgcaaatc aaggccttga gttctaactc 101040
```

-continued ctcctcactc tgtgaccttg ggcaaggcgc tgtccttctc tgggcctcag gagccttttc 101100
tataaaaaga aatgatcgga ctgatctagc tcagagtgct atgatttcag gactacagtc 101160
ccaaggttat caggctccct tagcatttgg gggtcttgta aggcatggag taaaaaaaaa 101220
aaagcaatat cctaaggctg gagaagaggg aggggacaaa ggaaggggag gaaaggggag 101280
gtagcaggga gccaaggacc aagaaggact gaggtacagt cattctgcat ccaaaggctt 101340
aaattgtaag ggactggctt tactctggct gtttccggaa aggcaggccc agccagccct 101400
cccgtctctc tctctgacag ccaatctcac atgtgcctcc ctgggagcac ctgctctgag 101460
ctgtatcagc ccccagcagg ccgctgatta ccactgagcc tggccacaga gcacgagatt 101520
aggatgcagc aacacactgt gtgtgagatc acgtcccgaa ccttctgact catctgcaca 101580
ggaaaccccc ccagtctccc ctccagtcag aagggacctg aaattccacc agtggcaata 101640
ccaaagaaac ttcctattag ctaagcccct agggagtgat tggctgttgg ggcggggagg 101700
gggggcggtg aggaggatga ggatgaagcc tgggcaacct ggatgtgagg ctgtgcaggg 101760
gatgaggaca aggatccttg gggtgaagga agagaagagc aattttaggt tttgctaatt 101820
ttgtaaccct ggctccaagc cagcccttac aggaagtcac cctggcctcc ggctcaattc 101880
agcacgtgat agggaagcca catttatgca gagcagggaa cgaggtaagg aaatggaagt 101940
ggggctgtgg tgaagtgggc aagtctagag agagtcccgc tgcctggggc tgttcctaac 102000
agctgctggg agcgagctgc aggtgtggtg cctggcaggg tggccgggct gtctgactct 102060
ggatttcact ccaagctagg ctgctgcctg aaggattcct cttacccacc tttgcctggg 102120
ctggcctttg ggacttacat ggctatgagg cgtgccacgg tggtcttgaa ccggtcaaag 102180
atgtagccag tggggaatgt catgaagttg ttcatgaagg accccagggt gaagatgagt 102240
gagaacctct catcctgggc tttgcagtct ggagtagaaa aaaggtctcc catgcatccc 102300
agccttcctg ccaaatgagc acacaggctg ggctcccctc cacctcagac agcttgtcgg 102360
tcgcaaactt gtcccttaag ctgagttgaa atgtggctgc ccctaattac ccctcaggag 102420
ctggtgcctc cctcccaggc acttcccaga tcaagtgggg tgagagctgc tgacccttcc 102480
tctcatcata gaaagagggg tgggcagggg gcagagtcct tcctgctcct tgccaccacg 102540
tgggagccag acttaacttc cttagaaaag tcatccctgc ccttaccagc ctgccctgtg 102600
gcattgccaa tcggcccagc atctggtcca cacagatcct taaagtaatc ttcattcttg 102660
aagacaaaca ctagtgaagg ccagccaaag aggacgccag caaagcccag gcattccagc 102720
agcccagtca gcagtgtggc cacgtgcagg ggcaggccct ggcccgccat gagcagaagt 102780
ggagtggatc ttcaaatccc actttgtcct cctggacgga tcacaggcgc cgtaagcctg 102840
gcgtttgagc acttggaaaa ttcctctggc aagccaagcc cttcctttcc cgtagctctc 102900
tggttgtttc aggcctgggc aaaaaccatc agcgggtgat tctctggatc ctgtagaata 102960
aagatagagg ctgctggaag aggaggcctg cgggaaaggg aaaggtagac tagagttatt 103020
tgtgaggtgc attaagaggc aggatgatca tggccgctgg cagcaaatgt ggggaataaa 103080
tactccaata catcatctta ggcactgcat ttgagtaacc acgtggcaag tagagaggca 103140
ggtcttgatg gccacctgga gtcacaggtg agataaacga cttacccaat agctccccgg 103200
gagcaggtgg agaagcggag ctcctgcgct cgaattctga ataccgtccc ctaaaataat 103260
gacagcaact caaccaggtg cagaggcagg gagatttcat acagaagaca caaactcccg 103320
ctgccaagtt ggtgttatct tcagtttact gacaatgaaa caaaagctcc catggatttc 103380

-continued

```
aggaacttgc ccaaggtcac agggctagtt tagtcacgac gcaggccatt ctactgccag 103440
aaataccccc aactcccatg accctcgcct aggactcgca aacctggtcc ccgccgccct 103500
tcctcgcatc aacttctacc aggaaagcct ccgggggccg ctccccgcca gcctccgcac 103560
cccgctccag cctgcggcct gccctccccg cagaggagcc cgaggggcca ggccgcgctc 103620
ggcgccccat ggcgcccgaa aggggaccct tcgccctacc cgcctgctcc gcgccggggc 103680
tctccgcgcc ctttccgcac gggccaggtt cgcattcgcg cctctcgcag cccctcccag 103740
tcccctgctc gcctccgccc cctcctgccc gcccggaagg ggctggggca gacctcccac 103800
tctccatcac ttccttcttc ttttcccttg ctcacagcct cccgcgccct ttttacctct 103860
ccctcttgaa acttctccct ctagaacccc ctagaacccc agcggtgtct ttccctccct 103920
cctcgctgcc tttcagcctc ccagccccct tgcctctgcc tcccctaacc aagttagttg 103980
aatgctgtta ctcgctcagg cccacctagg gaaaatgtca cacccagcac ccagaggaca 104040
cacagacagc acatgagggc atagggacac acacactcta tttgtgcatt ttgccttgac 104100
cgctgggttg gcagggaaca tatttttcct atttgctcac cagcttaacc gtctctccca 104160
gtttcacact cccagagctg ccaaaaaaat cccaaccaca gaatcaggaa gccaagaacc 104220
aggactgagg gcttttcaga aaccatcccc tggaggactg ccccatattt tcactcccaa 104280
aaacccctta gatgactccc tgcctcaccc ccgcccccca ggttctgaaa gagccttccc 104340
gccagactgc attgattaac cattcattgc cccatttttt attaatcaaa gacatatata 104400
attgctcatc ggagcttgtg atcagcgtga ggccttacta agcagctgcc ttactatcct 104460
tccagcccag agcacgtgag ctgacgtctt ctttggcctg tgtggccgtt tccttgccaa 104520
aagctcagtt tggggagagc ttcttgcgta ttagatgcag tctgcagact cccaacccca 104580
gctacctgga tcccctgagg gcccaggaac tccagctatt ccaagcccac tcctcttttt 104640
tttaagagga agaaatagag gttacgatag gggacagcca gaactgagga ttttccagct 104700
caccaccaaa gcacaaaaga taaaagtctg caaccaccct agtgacttga ctgaatggag 104760
gaagggtggc tggggtcctg taccccaagc tactcactag ttatacaacc tgaggcaagc 104820
tctttggctg ccccacctgt aagacgagga caatagtacc ttaattatag gaattgtcat 104880
aaaagaagta taagatgggt gtatgaggtc cctgcatggc gcaggtgcta taggcagatt 104940
gtagggtagt agattttcta gtctgcagtt atgtagacag agccagagaa gcagctctgg 105000
ggaggaattt caaaggaact tgcccacggt cattctacaa agctgcagta ccttcccaac 105060
tctgaaacgt atgctctcat caccccgtct taacaaacat ttggacatta gagaaaacaa 105120
gtcttttctt aaaataacat tatttatggg agaaaatcca caaaaatata gcatcccagg 105180
acaaacaggg cttaagatgc aagattttct attttactgc aagacacaaa gactctgaaa 105240
ttaatgcatg ccctatcttc tgctctggca tacattttag tctcctgggg ggatcagtaa 105300
gtgtggaagt agcaagggag aaacagaaaa aagtcaaagt aaagagacag attttagaat 105360
gttaatctgc aggagcctgc cagaaagatc tagctcatgg gctatctgta catccaggac 105420
tgaagcacgg gacacggggc aggtcgtcca gggttctgtc caccttatct tgttacctct 105480
cttgactctt agagcctcca ctccacatct cccatcaatg tctgcagaag acgtggcctc 105540
cactaacaca agtcttactg aactgatggg acaggaaatt agaatatcct ctgaaccatt 105600
cccatgttct ttggttcgaa ttccagcagc tagaaaaggc agatgctatt ctgatcactc 105660
tcctgcgtgg ctccaatgag gattaatgag taacatcaga gagagaagtg attataataa 105720
ggtctgacgg tgcacccgat gtcttcatcc ttttctcttc gcctccttcc tcatcatctc 105780
```

-continued acaccttttt ttttttaatt gactgattgg ttcaacaaat acatgtggta cctcaggctc 105840
tgtgccaagt gccgggattc gtagagaaga gattcagtgc ctgctctcaa ggggctcatt 105900
ctcttgtggg agagacagac aaagaaaccc aagatttctg gagtgtggga atggtcttcc 105960
aggcagatgc tagcacagca cattgaaagg cacggaacct caacaaaaca ataacattta 106020
ggaaccagct agagcacagg gtggtgaaga aagtggaaag atttgaggcc agcgtcgcca 106080
tctaagtgag ggcattaaga attcagccca catcaatcaa tcatgtccta ttgatttcac 106140
cccttaatat ctctcctatc tatccgtggc cactgctcta tgcagacact catcatctct 106200
cacagaggca tcatctgctt ccaagccatc gccattctcc tgcaagagtt tatttccatg 106260
gttcccactg gatggcttca cttaactgct caaaaccctt ctgaggtcca gtcaactggc 106320
tggtaaggac cagtccaggg tctggggatg ccagccatga gacattgctt tgaggggaag 106380
agggagcata gaactggatc tcctgcatcc tactgcccaa gtaccaatgc tggaggtggt 106440
tttccttccc atcatcagca agtctggata tccaggatcc accctatgga tgtttttatg 106500
gacagagtgg gaagatggat atgtttaggt tagggaaaga gggtttgcca aagagggcag 106560
tataagtgag ctgcactcca tcattcccct ggcacaaaca atggctagta tcctctagtc 106620
ctcaagagca ccaccttcca atgcagtccc tgcctgtcca cagacctctc tcctcaaact 106680
tcctctgaac aacctcagcg agggcaattg ccactctctg ggcagagtcc agatattctc 106740
tcctaccctc tgacatcact ttctaaattt gtatatgtag ataaactctg agccattcac 106800
ataaagggct ttgatttcgg atacgccaaa cacataaaca aacaaacata agctttcctt 106860
tcacaatggg ctcatgtaaa ttaaaatgtt tggttttcca cctacggtct tgaaaggggt 106920
ttctacagcc tgttttggaa gtcagaaagc aaaaggtaaa tgcaaacatc atttcacctg 106980
cagagaaaat tctaatcctc ttgaggcagt gccaaaaata atacaagcac actgctatcg 107040
agccaattac tggtatctct gagcttccgt ctcctcatct ataaaattgg aatcgagctg 107100
tatggattaa agataatgta tgaaaactgc ccaattagta cactattaat aaatagcagc 107160
tactgttgtt aacaaatatt attgacttac tggaaaacaa agaggaaata aagtcacatt 107220
tagggagaat ttcaaagtgt tcctaaccta aaaaagaaat aaattagggg gaaaaccact 107280
aagtaatggg tgagctcagt ttaccttgct taagaagtcc caccctagag aactgatctc 107340
tagatgacac ccaaatgcac tcagtacaac cccccaagac tgtctgggct taaggcaggg 107400
gcttggattg tcctgtaagc tgtgggaagt ctgttcatga gccacagtag acaggaaggg 107460
gatggagtct tagagctggc tcttcagggt atctcctagt gtgttcaaag cagttctcag 107520
gagggtgggg aactactaca tagccaagta aatatgaggc ctccttgctc tggggagacc 107580
tttctcttta acagaggtga atctgaaagg atacccaaag aggcactgga gggtgggggc 107640
cactctggcc cctcagagca gccagctcag cttcagtgga tgctagaggc agcagaggat 107700
cagcctggat cagcctccct ttcaccatgc agaaaacaga gctcccccac cagaccagat 107760
actggaagca ctgggccagg cctaagagaa agcagagccc caagccccac cacaccaggg 107820
cttatgaggc tactgctacc caccctccca agccccagct ccacttctat gttcatcaag 107880
caactgttta ctggtaactg cacttcccga tagactttgc tagaaaggaa tgcctcagtg 107940
cactgacaat atctaaacct gcaactctaa ggactaggct ggggaacact gtgtcaacat 108000
ggaggcacgt cctacccctg agaagaaaaa taaggaatat caataatacc tgctgggcac 108060
tgagcactga ctatgtatct gattcgaagc gctttttgct taatctgtca ctgaatctca 108120

-continued cgataggtgt tgttattagc atctattatc tgggccaact gaggcctaga gggacgaagc 108180
aactccccca acatcaccag gtagcagtgt caggactggg atagaaacct gatgctctga 108240
ctgaaactaa tgcttttttt tttttttttt tttttttttt tgagacagca tctcactctg 108300
tcaccaaggc tggagtgaaa tggtgtgatc tcagttcact gcagcctcca cttcccaggt 108360
tcaagtgatt ctcctgcctc agcctcccga gtagctggga ttacaggcgt gcaccaccat 108420
gcccagctaa tttttttgca tttttgtag agatggggtt tcgccatgtt ggccagactg 108480
gtctcaaact cctgggctca agtgttctgc ctgccttggc cccacaaagt gctaggatta 108540
caggcgtgag ccaccatgcc cagccagctg atgctcttaa tctgtgccct acccagcctt 108600
cctgggaggc ttcccaagag ctacacagag catgagttct ggaatcgggt tgatgggggt 108660
accagttatt actaatagga atgaagatgg gtaattcttt cagacagcac ccttgattaa 108720
aacaagagag tagtgctgcc tctctgtgat tctgtgtctc cctgccctgc tcacacagac 108780
accacaccca cccacacgca tgatcatgaa aagaggaaat ggatccagga gaaggagacg 108840
actcctgagt gaaaacaacg gggtttttca cattgagagc tttgcccaac accccaaaga 108900
tgaaaagagc aggaaactgc tggggccgat tgaacactgg acttttgttg tggaaaaagg 108960
caaagggaag ccggaagaga ctggaacagt ttccatggtg ctggaggatg gggaagtggg 109020
tagggattag ctggagggag aaggagaagc tggggtggga ggggaacctc cacttgccag 109080
gagagcacat gtaggatggg aaccccagat gatactcaag gcatggcatt agaccagaag 109140
caagtctgtg gtgaaattag ggaaggctcc actgcggact gtagacagag cactggacaa 109200
ggaagtggga gacccagggt ccagtcctgg ctctggagcc ccctgggtgg gctgccccgg 109260
gcacctttct ctcttggggc ctccattcct acctctgtga agcgagtgct gaacctctct 109320
tagccctgac ttgctgaaat gctgggactc tgtacagagg ctgacattaa gcagggatct 109380
gtcgtggggt gctgcaatgt tcctccagat gctgcacggg agagggcaga aaaggcctat 109440
atggtgagtc cgccctggga gcctctgctt ggaagctgaa gtggcctgag agtgactcag 109500
aaaccacgga agttcccggg gctgatgggt tcttatagat tgtacatgca gctctcctcg 109560
tgggctgcaa aaccgcaaga tgggctgtga ccactctcaa ggaaagagcc ctatctgcaa 109620
aaagcattct gccctccagg tcttaaagca aacacagact caatccttat tccttttaag 109680
acaaaattgc ctcaggggca tcagggaggc agcaggcctc aaatgtgtgc ctttctagaa 109740
ttctcaatga aagcaccctt ttgggtatta ataatgacaa cagtaatgac agtcatttac 109800
tgagtgctgc ttttgggaca ggcattgggc taagagctat atgtaatata tattattatt 109860
tgatgcccac agccacccca taaggaggcg gaggtactat cattatgcca actttaaaga 109920
tgaagaaact gaggcctcaa gagatgaagt aacttggcca agtcactcag ccagtaaatg 109980
ggaagagata gacttcccag tatccagagc ccatgttttc accattatgc tgaagtacct 110040
cttttcctgt gccaatgtga tctgcctcca ggaatcctgt cttgatgttc ccttccccat 110100
acagaagtcc tctctgtgtc ctcttcagcc tgatagtata tcttttcata ccattctttg 110160
gacatctctg ttatactact ccaatggtgt tccctcccct acccctccct gggagcttag 110220
ttgttgtgat taagtatagg ggaaatgacc cacactaaac aaactcataa gagactgatt 110280
gataaacctg aaatgcaatt tattaattaa cactgagaaa tgaaaccacc cagcagatgg 110340
gaatcctaag gctgactggt cagcacaatc tctttcagga aggacaggct tttgggaaag 110400
gaaatcaata ccagaaggtt ctttgttgag tacaaagtca gagggaaggg agttgatgga 110460
ttgacacata ggtgaagctt gacatacctc tataaagcct ccatcctgcc aaggatcaga 110520

-continued atatccaagg cagggagcca tctgggtgtc ctctcctttg gacagtgctg gatttttctg 110580
gatcctatga agatcttacc tttctggctg catttatcat gattgtggaa ggctttttgt 110640
ttccttgttt gcttagatta atttctgcgt atttaataga actgaaaggc aatttcccat 110700
tgagacccac tgaagaggaa taatcaatac atactagttg tgttgccctt tgcagagaat 110760
tcacttctgt gttgtcactg tatcctcatg cttccttata atggagggac agagatggta 110820
aaaacatgga cttggaagcc agaccgtctg ggtttgaatc ctggctctgt tacttataag 110880
ctctgcaacc tcgggcagat tacctaagtc agtttcccct tctctgaatt ggggatataa 110940
tagcacccac ctcaacatct gtcaagagga ttcaatgagg gaatacacat aaagtgctca 111000
gaacagtgtc tgccatctgg taagcagtcn nnnnnnnnnn nnnnnnnnnn nnnnnnnnnn 111060
nnnnnnnnnn nnnnnnnnnn nnnnnnnnnn nnnnnnnnnn nnnnnnnnnn nnnnnnnnnn 111120
nnnnnnnnnc taatttttgt atttttggta gagacagggt tttgccatgt tggccaagct 111180
ggtctcaaac tcccgacctc aggtgatcca cccgcctcgg cctcccaaag tgctgggatt 111240
acaggcatga gccaccacgc caggccccac acacctttta aacaaccaga tttcattcat 111300
cgggaagtgc ctgtggggct ggtgtggaca tgtgggtgaa ggtggcactg ggagaagtta 111360
ggattctcca tgacctctgt tactcatatt cccacactcc tcaaattagc ctgagtctcg 111420
aggacagtct gatggctggg caaaccctgc ggcaaaccat tccccagccc tgccctctca 111480
accagagtcc ttccgataca tgattctggg cagctgttgt tacccgtgtc ctccatgttc 111540
ttccagagat atccatgcat gcatcggcat atgtgtataa ttattatatc tatatttcat 111600
cccacaagct tttgacatca atagtagcat attattaaat tgttctgtac attattttat 111660
taacttggta tctctggtac tgctcaatat aagaacatat agacctggcc aggcacagtg 111720
gctcacatct gtaatcccag cattttggga ggctgagatg ggtggatcac ttgaggtcag 111780
gagttcgaaa ccagcctggc catcatggtg aaacccccat ttctactaaa aatacaaaaa 111840
ttagccaggt gtggtggcag gcgcctgtaa tcccagctac ttgggaggct gaggcaggag 111900
aattgcttga acctgggagg cagatgttgc agtaagccga gatcacgcca ctgcactcca 111960
gggtaggcaa caaagcgaga ctctgtctca ataaaaaaaa aaaaggaatg tatagacctt 112020
ctttattctt tttgatggct gtaggtggat gttctaaaat ttgtgtaacc aatctcctat 112080
tgataatatt taagttatgt cttcagcatc atatgaaact tacaaacaag gttgcattga 112140
ctatccatct gtaaatgtct ttttgaacat ttctagaata attgcaggat aaactcctaa 112200
aatgagaatt tctgggtcaa agaggatatg cattttacat ttaatagata tttgtcaaat 112260
tgtcttccaa agtggtcgta ccaattaaca ccccgacctg taatgaatga gagtgccttt 112320
tttccccaca ccctggagag atgaaaaatt tatgggccca ctttggagtg catggtggag 112380
gaagctgttg gccgttatat aaccctcgtc attaataagc ctgggggtgg gggggggagaa 112440
agagaggtta gttagtgggt gcaaacatac aattagatag aagtaataag ttctaatgtt 112500
cgatagcaga ggagggtgac tatagttaac aacaatgtat tgtatatttc aaaatagcta 112560
gaatggagga cttaaaatat tccaacacat agaaataata aatgcttgtc tgcggccatg 112620
ccaccctgaa tgtgccagat cttgtttgtt cttggaagct aagcagggtt gaacctggtt 112680
agtatttgga tgggagaaat gataaatgct tgaggtgata gatatcctaa ataccctgtc 112740
gaacattata cattctatat atgtaacaaa atatcacacg tatcccataa atatgtacaa 112800
atataatgta tcagtaaaga gagggctggg cacggtggct cacatctgta atcccagcaa 112860

-continued

```
tttggcaggc cagggtggga ggatagcttg aggccaggag ttcaagatca gcctgggcaa 112920
catagcgaga ctctgtctcc acaaaaaata aaaataaaaa cgaattagcc aggcgtggtg 112980
atgcatgctt atagtcccag ctacttggga ggctgatgca ggaggattgc ttgagcccag 113040
gagtttgagg ctgcagtgag cctacgactg caccactgca ctctccagcc taggcaacag 113100
aggaagacca tgtttctaaa agaaataaat taaataaaat aaataaaaat aaaaagactg 113160
aaaagcagag tggtaagaga aaggactttg gggctcaaca gtactagcct tgaaccctgg 113220
ctgttactta cccatcgtgt gataagcaaa tgccttaacc cctgtgtgcc tcactttctt 113280
aacatataaa atagaagtaa aaatcatacc cacttcaagg gtcattataa aaagccaata 113340
gagataatgt atataaagct tctggaataa tgcctggcac acagtaggag tttaataact 113400
ggaaattcat tgttgtagtg ggcagccttc tgaatctgtg tcctctttgt ccactaatgg 113460
ctttgatctg gatttggctc aggcaagacc tggggaaggg cagagactga gggcaactgg 113520
aggtataggg tggtctgagc ttccccagca gagtgaggct gggaaaggtc tgggagacag 113580
accaggcagg tgctgataag accggaatgg gaggctggag cataaggcag ttcagttttt 113640
cccaaagggg ggtgtacaaa acgatctcgt atgactcctt tatactgtta atgttttcat 113700
tttatcgcgc actgaaaaac aaaaccaaca tatttaatga atgattccaa ggggattctt 113760
gcttttacaa aaaatgctaa agtaggcatt cacatgttta aaaattgagt tgatttaaat 113820
tttaaaatta ctaagtcata gtacataatg tgtgagccac agctatcccc aaaatcatga 113880
tagcgataca ttaatgactg aagttcttta aacatcaaca tacaatgcca attccagaat 113940
tcagctcaaa ttctgcaatt acacaggctg ggttgaaac ccagcttttt tgctaactgt 114000
gtaaaattag gcaggagggc taacctcgct gaatctcaga tgtctagtct gtaaattgaa 114060
gataatgttt gtttttatct cacagagttg ttgtgaagat tcaataaaat cacaacatgt 114120
gaggatgatc tggctgtgac acctgtcacc ccactgatct ccagagttga ttcggctgat 114180
caggctggct gggcaggtgt cccctttctc cctcaccact ccgcatgcat tcctcccgaa 114240
actgcacact tggtcaaaga ggaagacctt tcctgataga ggaggaccat tcttcagtca 114300
agggtatatg agcacctgtt ctgtcctgcc agaatctccg aaggagctct cagtaaaatc 114360
acaagatttt attgtgcatg gtagcatgag cctgtaatcc cagctactca ggaggccgag 114420
ctaggaggac tgcttgagcc caggagtttg agaccagcct gcgcaacata gtgagaccct 114480
gtctcaaaaa aaagaaagaa agaaagaaaa gaataataat agtaataaat cacctgtgca 114540
acgtgctcac ttctctcttt ggaatgtagt aagtgtacct aataaatgtg atcattgtaa 114600
tcatcacagt gagcacaggc taaagcatct tgactttatt ctataagcaa taaaagagga 114660
tttgttttta cagaactcat tatgttgtga aaataatttt ccaacattaa caaagaacat 114720
tcttcaagta aaaggaaaac cacccatcat tctcccaacc ttcaataatt ttcaattttg 114780
catattctcc agactttgtc aacatgaata cttactttac atggtcgcaa tcagtgttca 114840
tgcaaattct tttatcctga cttttataaa caaatatgat gttataaacc ggtctccatg 114900
tttctgcata ttctttataa ttatcatttt gtggctgcat aatattgcat tgactatgtt 114960
aactgcagtt ttcttaacca tttcactgtc tggggaaatg gaggataatg ccagggtcat 115020
gcctggagct ttttttgtc tattgcatta tattcttaag atcaaatccc agcagtgaga 115080
ttagtcagtc aaaaagtaat aatattttca aggctcttgt tatattttac tagattgttt 115140
tccagagttt tgcacactgc tcccagagat gtaggaacac agacgtcatc caaccttgcc 115200
agtgctgggt gatggtgttt ataaacttct gctaatttaa taagtatgaa atgctatcct 115260
```

-continued cacacggctt tcatttctat ctctttgatc attaacaggt tgaactattt tccaagtatt 115320
tgtttactct ctgcataccc tcttgggtga agtagtcatc cacttccttc acctgtttat 115380
ctgttgaagt cttgaggctt gttttataaa tgtgagcgag cacttcagag tcaatagaca 115440
ttaattgctt ccagccagat ttggccactg aggctcctga gcaggggaat gcatgatcaa 115500
aactacaccc tggacagatt aaattaattg gagaaaatgg gctgagaggc agagatatgt 115560
gtcactggcc tactgtgttt gatcctatag tgggggcctg aactggggca acggcctgag 115620
tcccccacta ccagtagcag gaggctccat gtgtccccca tattagagct tgcggcactt 115680
ccatttgccc cacctcctac aataccccac atacatgtac tcactctccc ttgcaaatct 115740
agtggcttca acccacagaa tttaagggga aaggaattgt tctgtcctgt tcacttactg 115800
cagaaatgag aaaagcgttg ttcacatggg atcacctaat gaagggatgc catccccaac 115860
ggtgcctata aggaaatggg ggagggttgg agagttgtgc aaaatgcaac agggaatcat 115920
cagagtctct tgccccatga tagagggttc tcaaattaag agagtctaca gcaactaatc 115980
tcacggccac tctaggcagg gcttcccaat gcttccccaa ccccacctcc atcctagact 116040
ttacccactc tgctgaacac agatgttacc catagcacct tgcaccatga ttgtttgatt 116100
agcacctccc acagtagact gtgtttctga taggtcagca acatttgctg agcacctact 116160
ctgcagggct gtgccaggtg cacaaaataa acaaagccaa agacaacatg gaccctgaac 116220
tcagcaagtt cagagtcaag tgggataggg aggctctctt cactggaagg taactccaag 116280
aaacaatggg actcaacttt ctaaccaaga gaactccagg gagctaaaat tctgacttct 116340
ggttaagact ggtgtggagc ttcattaaag aagaaaagat tcacccagac ttgagttcat 116400
agcctggctt tgcagctttt aagtcatgta acctttgatg aagttatgtg acctctccac 116460
ccagctgccc ctaacacctt gcaggggcag ggctggagtg caaagggagg cactggtacc 116520
acagcctggg aggcaccacc ccactagtgc aagccgggca acctctgccc ccaaggcatc 116580
cctagcctcc caactgcaag catcaatctt gcacttggaa aggaacctca cctttgaaat 116640
ctaggttcaa atttagaatg atccagctcc ttgaagttct atacagaaat acagccagca 116700
gccaggcccg gtggctcacg cctgtaatcc cagcactttg ggaggctgag gtgggtggat 116760
cacttgagga cagaagttcg agaccagcct gaccaacatg gtgaaacccc gtttctacta 116820
aaaatacaaa attagccagg catggtggta cacgcctgta atcccagcta cttgggaggc 116880
tgaggcagga gaattgcttg aacccaggag gcagaggttg aagtgagcca agatcgtgcc 116940
attgcactcc agcctgggca acaagagcga aactccatct caaaaaaaaa caaaacacac 117000
gcagcttccc tccacttccc aaccacagct ccatctcaga caacaagggg cctcatgtcc 117060
atgcacatga atatccaacc aacatgtcta aggcccaacc acaccctctc caaacatctg 117120
ccccttggcc accctttggc catgggttca tgcactggca gaaaggtagt tcagagaaga 117180
agcccacaaa gggccgggaa gtccacttgg gctttttgag attccagggt ccaggataac 117240
ctaagtgtgg tctagaagag agatgcagct tctgggaggc acattccttg gtcttaggga 117300
cttcttgccc ccatggaggg aaactggcta gatgagggcc aaagcagagc cctctaaagc 117360
acagggctca gggaaggact ctttttgacc agatctaaga gcagcactac ctctctgagc 117420
ctgtttctcc atctgtaaga aggggacatt aatagactct ccccgctaga gttactctac 117480
atcagccagc acacgtaagt tcatgacatg aagcaagggc ttaatatata cccgttgtac 117540
tataaataat aggccaggcg tggtggctca cacttgtaac cccagcactt tgggaggccg 117600

-continued aggaggatgg atcacaaggt caggagtttg agatcagcct ggtgaaacct catctctacc 117660
aaaaatacaa aaattggccg ggtgtggtgg cgtgcacctg tagtcccagc tacttgggag 117720
gctgaggcag gagaattgct tgaacccggg aggcagagtt tgcagtgagc caagatctca 117780
ccattgcatt ccagcctggg tgacagagca agactgcatc tcaaaataaa taaatacaca 117840
catacataca tacatacata catacataca tacatacata catacaatac atggacaggg 117900
accctaaaaa tgagacaggg aaagagaaaa acatgttctg acaaccttgc cctttatact 117960
aatttaggtt ttcttgcctg ttttagaaag ggcctggaca ggagccctgt tcccctcagg 118020
ccaggcagaa caaggtgtgg aactcactgt ggaagggttc tgggtgacaa gtgcagcccc 118080
gtccctccac ctcccagcac agtaggcagc acgtgtctcc attgactggc tcaggagcag 118140
gcctggtgac cagtgggaga gctgaggagc ccagggtggg gtctgaagga atccctagaa 118200
aatctgattt tcccccaggg cccacatcac gtgcccagag ctgggaaagt ggaggcagca 118260
tgggatctag ctgagaggct ccatttttgg tagcttctag tttgggagtc acagagacac 118320
ctggatgata cgaagatgta gctttgcagg actctctaga acatggagtc caagatattc 118380
ccttcaatga tgggacactg aagcccacag aggagaggtc tgtcccagtt actcagccat 118440
tcggaggcag agaccaggct agaactcagg acttttaatt tggaccagga ttccttttac 118500
cacagtgggc agccctagca agtgccaggt agggtggaac tgtgaaggtc atccgagggg 118560
tagtacacgt gggtaggaag tcatatctaa gaactgaccc ccagacctgg ctctgccact 118620
cactccttat gagaccacag gtgctgggtg cagtggttca cacctgcaat cccagcactt 118680
tgggaggcca aggcaggcag attgcttgat tccaggagtt cgagaccagc ctgggaaaca 118740
tagtgagacc cccacctcta ccaaaattag ccaggcgtgg tggtgtctgc ctgtagtccc 118800
agctacttgg gaggctgagg tgggaggact gcttgagcct gggaggcgga ggttgcggtg 118860
agccaggatc atgccactgc acaccagcct ggatgacaga gtgagacaga atgacacact 118920
gtctcaaaat aaataaataa atgacagcag atcatcattt ttctttctgc ctctagactg 118980
caatgcctat ttctccaggt agtcactagg ataaaagtaa aaataatatt atcagcattt 119040
accaaataca gggtcagcta ctctgttatg ttctttcatg ctttgtttct tttaagcctc 119100
aaacaactct atgagctggg aacaagtatc gtccttcttc ctcccatctt atttatttat 119160
ttatctatgt atttatctat ctattcattt atttatttat tttgagacaa ggtccttcta 119220
agtcaccagg gatggcctca aacttgagct aggaactagt gtcaccaccc cccaatttct 119280
tttattgatt gattgattga ttgattgact ggttaatttt gaggcagggg tctcgctaag 119340
tcgacagggc tggtcttgaa ctcctagtct taagcaatcc gcccgcctca gcctcccaaa 119400
ttgctgggat taccaacacg agccaccatg cccagcccct cccatcttct gaataggaaa 119460
actggggttt gaaaaggtaa gcgacttgcc caaggtcccc tccctagcta gagagcttca 119520
gagccagggc acaaacccat caaagcctgt gctctcgccc attgagccac cggacctcgt 119580
acactaaccg ccaagtgttc tacacagtga aggtgacaaa gaggtgaagg gaagagccag 119640
ggaggttctg tggactcact cggtgggtat gcccagaggg aagggggatc ttgggtggca 119700
cattgagagt agctgcgctg ttagtaagtg agaactcgga agtccagact catccagtct 119760
gtgccaataa acccctcctt ctacctggtc tcctttccaa agccagctgt tctccagaca 119820
atggggtggg cgggggcggg tgtcctcctc cttctcaggg aaaatccgac gctgagccca 119880
tctccagaga tcttggcttc ccgtggggct gcagatccac ctagagccac cagagggcgg 119940
gccagcactg cggccaaggc ttgaagaccc agcacaccaa agcccggcca agcctccagc 120000

-continued ccagtgtcca agagtccagc cagaggccga gtcctcgatc tcaaaatgtc taactgcaga 120060
agcccaactc atgttcaggc atgatgtgtc tgattctact gggacaatca ttgccaccaa 120120
agaattactg ccaaaatagt aacgacatta gctacctacc acccctccac acaccaacac 120180
acctcatttt accaagcact ttctcatgcc tggggtgcct ggagacttaa tgcagcctcg 120240
cgatgaccgg gtagcctcac cgtacagatg aggaaactga ggcacaagga aggggagtac 120300
attgtctagg gtcacctgga gaactctgat ctccagactc aaatttccaa ttcgtccccc 120360
ctccccccaa ccctaaccgg agctaggtgg ggtggggaca gcaaatgtgg atggggggag 120420
gtaagagggg tcagagtgct ctacagagaa gaccaaatgc attgtggcac ctactgtaaa 120480
atgagaccag ccagccaccc acccaccagc cagccaccta aaagtcttca gtgggcacct 120540
gctggaaaca cgacaatgga tgacacgagt tccctgccct caaaaagctg gtagtctagt 120600
tgggggtgga gggggtgagt cagcagataa ttatgggaaa ccgtgacacc tgtataaggg 120660
gcggggatga gcagaggggc tgcgactgcc tggagccagg gattcccgga cggggcttcc 120720
ctttcctcgc agctcgtccc aggaggagga gctccccccc agcttcgggg ttccgcctgc 120780
cttgggggcc cggggtcccc tcccacccct ccccgaagag cgcgggcccc gggaaccgat 120840
gacagcacac ctgagtcagc ccgccgccca cccgcccctc agcgtctgtc tccgcatctt 120900
gtgatatttc gctccccggg agccagcccc actgcgctcc ggaggcagct cggcaaacaa 120960
acccagcgac agattgtgcc gcggctcatt ccggggaagg acgccaaacc ccaccctgct 121020
acccccaaca ctccctcccc gccgccgcct ccaggccctc cccccaggcg caggccctag 121080
tcggggtggg tcctggggaa acgcagggtc ctgtcctgcc tcctggaaat agggggagcc 121140
ctgggtgagg gaagacggga gccccagaga cttttctttc tgtttctacc tgatccgaaa 121200
acgagagggg cgggaaagga aatttagggg cacagagagg agctgggggg ccgagaaggt 121260
ccgaaaatgg aaccagcagg gggcacccga gagccgaggt gcccacgggc cgggagcctg 121320
ggaatgaaac tggggaagag ggggagagaa agggaggcag agacaccgag acacacagag 121380
acgagagaca gagacgcagg gagccccgcg gggaggagga gagagacgaa gacacagaga 121440
gacagtgaga aagacagaag accgggcagg gaaacagacg agtagagaca gaaaaggtcc 121500
gagagagagt gagggaggga gggaacagag agacagagac cacgaaatat gagtaagagt 121560
cgggggagaa aaccagagaa atcgaatgag aacgcgagaa gaacgagaga ccgtggaggg 121620
agcagagaat gaatgggaag aataagacca acatttatca agagccgact gtatgccagg 121680
cactgcattg gaccctggca cggataggaa aggaggagcc gcggcgcggg cagcggggcg 121740
aggggcttct gtgctcgcgg gagcggcagc ccagggggct cagcagcccc ggcaccgccg 121800
cacctgcggc tccagcagcc ccaaccccgc cagcgctgcc tggccaccgt acccgaagcg 121860
gctcccccga gggccccgag cctatcctac gccggggcgg ctccgcggac gcgccgggcc 121920
gagtcaagac ctgggtcaac cgccctgcag cctttgtagg gaagtgccta ggtgatgggt 121980
ctgctgatac cgcctgtgac caggccatga agggccagag gggctccagt gagaccataa 122040
tccgcccctc tttaaaaggg ggtagaggaa gttcacgcga agccaacagt cttctcccca 122100
gctttgggtc ctctcctgca cccccgcggg agataaggtc tcccctcccg gacacatcat 122160
acatacacaa aaaaacgcac acactcgcac gcgcgcccat ctcgcacccg cttgtaaatg 122220
cactaagggg catacacaca ccgggcacat atttctttcc acccatcccc aagatcgcaa 122280
gcgcaaaacc tcgcacagcc tcacgtttcc caccagctca gacatgcacg ctggcggact 122340

-continued ttcagcggct cacccgtgtg cacactcacg tgcccccccc cccgcttccc caagcccgta 122400
caaagggtaa cgggcaagca tcctgagtca cacctgcaca agcatccttg cgcgcacgtg 122460
cacgctcata tgcactcgat cttgcacgca caaactcttg catatactat tcttatagtc 122520
gcacactggg cttgaggtct gggagtggaa ggaaaagtgg aatcttggag ctgtcccagg 122580
ggacagaaat gctggaggct gggacactgg cgcgagggac gcggctgggg gcgggggagg 122640
gggtgaccca gaagctcatc ttctcctgga aagttgggag gggggaacag gacaagtcca 122700
cggcgttcct ctaaactacc gcattccccc aagaagggat ttctctagaa gagtggcgcc 122760
gcgaggacga tcgaacacag tcctccgggt cgcttaagcg ggggggaggg gggcggggtg 122820
gagggggtta gaaagccgct cccgcctcct agtggtcgag aaagggttaa gtcggcaagc 122880
cagcaaacga gggaggagcc agcgagtgcg ggaaggagtg ggggtggttg ggaagagctt 122940
cctcgctgtc cccactctcc ctcggctagc agcctgggca cacggacaga cggactgacg 123000
gactctcgag cggacagcgc agctagcggg gcgcgggcgc tgggcgtcga cggccagccc 123060
cagccttccc cgccccgtcg cgccccgccc cgtcccgtcg gggccgatgg ctcctcccga 123120
ggcccgcagc ccgggcggcg cagggtagag cgccgcggcc cggccacgca gcccggggac 123180
tcccgggccc tcccggagcc ccgcggggtc cccgccgtgc atccggcggg ctcagggagc 123240
gagtgggagc gccctccccc cgctgccccc tcccccgagc atcgagacaa gatgctgccc 123300
gggctcaggc gcctgctgca aggtaagaac gccagcggcg ggagagcgga gggcatcctg 123360
gggagagaag cagggcgtcc cctctttcag ggattgaggg tggggcagtt ggggaggtgg 123420
ggtaacctgg ggaaggggaa aagctcagcg ctggggccgc gccccccgccg ccagggctgt 123480 tctcagcagg agggcacttg gctgggagcc cgcgggcgcg tgcgaggagc tcgtgaccga 123540
ggtgggacgc agggggcagg tggacccggc ccggagcggg gagggaggct caggttccgc 123600
tgtccccgct ccacctgctc cgggggacgc tgaggactcg ggccggctgg ggaagcgccg 123660
actcagcaac tcctcctgcc cggtgcctca gcactttctg gccacctggg aagacaggag 123720
atgtgggtag ggggctgtct ggggaggtag gaggcgcaga gggaaatcca agtggccctc 123780
tctggtagga gagatggagg gcgctagaaa gaggatagtt ctactgattg agtgacagat 123840
aagggtgtgg gccagagact gggggtgggg tggggagggg tcagggggag agggatagga 123900
aggagaactc aaagatggag aaagtggtga gggaagctca aaggaggagg gagatggagc 123960
gggggagggg gagaaggaat aaaggttaga tgggaaaagc gtggagggaa gtgggaccca 124020
ggtgaagacc aaggaagagg gaaggagagg aaaagaccaga tcaggggagg gatgggaaga 124080
agactatgga cagggaccca gaatcctggg atggaggtag cgggaaagag aatcaggact 124140
gggaccctgg ggactggaat ggaaaaggag aatggaaaga tcagaaacca gagaaggatg 124200
gggatggtga ctagagaagg ggtatcagga accggcgaag agggttggag acagggaacc 124260
atggatggga gaggggctgg agaggaggga agaggaggag gaagagaaag gctgagagag 124320
agggactggg gattgggggt gctgcccagg gatgagacaa agaggcttct ggtaaccact 124380
tccacgtggg aagccctcca ttcccaaagc gcctgcctgc cacatttctt ctctcaggga 124440
gtggctggtg ggccagatgg ggggtgcttt gagctcaggg ccctgggggt ggctgtgagg 124500
gacagagggt gaggactttg gaaggggagt gacagcctcc gagggtgggc aaacaggctg 124560
gctcctgtgc tgccatttat ttatccggcc cggacgttgg attctgcagc cgctgccgcc 124620
accacggtgg ctgcttattt tggggtgtta cattctggca gagtgagaag ctgtttgcag 124680
cagctctaaa cctccgtcac ccgcgtcagt gcctccccag gcccctgcgt cactggcatc 124740

-continued accaccacct ccatcccact cctcagctcc cacctcctca gcccctgccc cctcagcatc 124800
tgcccgcagg ccccagccct tccctgaagc agcccgttgg gtgtggagcc cttgcttctc 124860
gtctgggacc ctgtgcccct ccttccagag cgagaggcct ctgctgcctt tccagggagc 124920
atcctttcct gggaccactc tgcaccagcg actctgccct gtgggtgggt agcctggatc 124980
ctgcccccta ctttgggtcc agttttcttc tcctcaagtt ccttcttcta caggggcctc 125040
cggcccaaag agtggcctgt gggctgagaa ctttgtttct gagccttggt actccaaggt 125100
ttgatagcca gagtcctgga cagtggtccc tcagtgaaca gatacttttg gctctggaca 125160
cttcagcctt ccgggatcaa taccatgttc tggcctctct tggctccctc ccctggtcag 125220
ttctggccat atattctgga caggggtcat ctcttcttga ctcccacatg taatcactac 125280
tctagaacaa ccgcaactgg aagcctagga ggtgaaagtt gcagagagag ctggagtccc 125340
ttccttgcct tgaccctgaa tagccaaaca gactcagcat tgtggctggc ccagccctag 125400
gcacctgggt gcaatttctc tcctgtcttt acctcaaggg cagtgtctca cacattcagg 125460
cgtggtttct gcggaggatg tggccacctc ttaaagaaag atcagagtgt ctctctgaca 125520
tgggcttgat gtccctcttt tccaatctgg gttccacctt gtactagctg catgacctga 125580
ggccactgtg tcatgtttct ggggctccct tccttcatct gcaaattggg ggccacaata 125640
ttgacctcca ggggattatg tgtgttgtgt tcaatgtata aagaagttaa cctgtacaaa 125700
tgcagtgcct aggacaaaat aggtgcttct tggtttcctc ctaccctgct gtactctccc 125760
ctgcagctct agccatcccc tgctgacttt agaggagggg gtgagcagag agggtggggg 125820
aggctgctac aaagggcttt cctctgtcca tgaagtagtg gagggatgaa atgaaggctt 125880
ctgagaaaga caatgaaggc gagctgtaga gacctggtca ggaggcctgg ggtgctcaga 125940
aactcacact tcccctcccc agccctcaat ggtgttacct atgatgtgag gggtcggctc 126000
taggtggcca ccgaggtatc cccctttcca gctctgatac tctgtgcatc ttgccccagt 126060
ctccaccggg aattcacaaa atgaaggcca ggagtggagc cgtggtcctc gggagagaca 126120
ggaggcctgg gcctggaggg aaggagtggt ggtgctgagg aggagtgaga acagggggtg 126180
gggaagggac gtggcaagaa agaaaagggc acacactggg cagggcaggg actgagggcg 126240
ggggagagag ggaaaggcac agctctctag tcccccaacc ccccagtccc accacctctg 126300
ccctggagtg ctcgctccag ccccagcagg cctggggcag tgaagcccag agccccctcc 126360
cctcccctcc tccttgcctc cagtgagagc cgctgcgtga attatggatg agctccttgg 126420
gttacagctg ctttgcacgg cagtggcaag ggccagaaat ggcaacagag tcactgttat 126480
gcagcagctg ttatggagga gcccccagca ccgggtcgct cttcagagag cctgcaggga 126540
ccactatcat gggctggggg aggtgagccc tggttggggg agacatggga acaagatgga 126600
aggagagtgg ggaaagagaa gagaagtagt ctaatgtggg caggtgggga gcaggagagt 126660
ctagggagag aaagaggagt aggcaccctt gccagctcct gcagagttta ccctcaaggc 126720
cggaaggaac cctgatgcca ggggaatggg ccttgcctct gagattgcac atccttccct 126780
ctgtctctcc tggggcagcg gtcagtccgg aggctggggg aaagctctgt aatcctccag 126840
gggctagcgg ccatcagggc tcacactctg gtgagcttgt ggataagggg taggattaag 126900
ggatcagaga aggatttggc ttcttttggt gtcaagtcct tagggaagtg gagatcagag 126960
ggtgactctg acaggaaggg aagtgccctg gctgggcatc aagagacttt tctggccctt 127020
tccctgccaa cactttgctg tgtgaccttg ggtaagtcgc ttgctctctc tgagctccag 127080

-continued tcatcacctc agtagaactg atgcttgaac cagaggaatc gaggggacct ttgcggcttt 127140
gaaatctcca gttctaagcc ccaaacctca accctcatga aacccactca gggtccccac 127200
tgtgcttcca cactccacct ctgcctggtt cagatgaggg gtaagagaca ttgctcctcc 127260
accccacgtg ggtctaagaa actcgggagg agaaagtaat cgtgaaacgc cgcacggggg 127320
aggggtgaga agggccgaga aacgcggagg tggtgtgaac gaatggaaca gcagccgctg 127380
tgtcactgag tattacatca cacccagcct acacacgcac ggggcccggc gctcacacac 127440
acgcggagga cagccagcac gcaccgacgc agcaccgacg cagcgccagg aggggccggg 127500
gacactcacg gtggggccca aaagcgagga gcagcacact gggagtgtgg atcttccacc 127560
ccgcacctgt gtgctccccc ctctggagga ggaacaccag ggcagctggg atgccagcgc 127620
cacactcggg gcctgtcagt cccatgcgtg cacacctggc tgagcagcac tgcatttggt 127680
gagcacctgg ctcacgccac tacccaaaat cacagataca tacacacatt cacgcacacg 127740
gcaacctcag gagcgtgaca caacacacac aaaaccacca ctaagcaagt gcaatttgca 127800
gccttggaga ccccacactc aaaatcacca accoctcagt ctctcccagg gtctctgaac 127860
cccaaggagc cccaggatgt cagagtgcag aaacaagtct tcctcccctc tgccttcaaa 127920
agcctaggac gttgcttgaa gcagaaggtg ttcagtcact gtgtgcccag ggaatgactg 127980
cctggctttg ggggtgcagg ctcccttttt ccccaggcaa aactgccaga agaaaatccc 128040
aggagtcacc tggaaatcat aagaaagtgt agaggtcaag ctagttccgg cctagaactt 128100
tatcagctat agtgacggca aaggccaggg atgatgggag gccctgcacc cctattaaaa 128160
tatgagtaca gacacctgca ctccactctc tagcccccag gctctctggg cctgcttttc 128220
catcagtatc ataataagga tggatcatat ccaaccttca aaagttactt tgggggaaaa 128280
aaaaaaaaaa gctttggctg gatgcggtag cttatgcctg aaatcccaac actttgggag 128340
gccaaggtgg gaggattgtt tgaggccagg agtttgagac cagactgagc aacatagcaa 128400
gaccccatgc ctacaatttt tttttttttt tttttttttt tttgatacag agtctcgctg 128460
tgtcacccag gctggagtgc agtggtgcga tctcggctca ctgcaagctc cgcctcccgg 128520
gttcacacca ttatcgtgtc tcagcctccc aagtagctgg gactacaggc gcccgccacc 128580
atgcccggct aaattttttt tttgtatttt tagtagagac ggggtttcac cgtgttagcc 128640
aggatggtct cgatctcctg acctcgtgat ccacccgcct cagactccca aagtgctggg 128700
attacaggcg tgagccaccg cgcccggcca aaaattttta aaaaattagc tgggtgcagt 128760
ggcacgggcc tgtggtccca gctcctcagg aagctgaggc aggaggattg cttgagccca 128820
agtgatccaa gctgcaataa gctgtgatcg taccactgca ctccagcctg ggcgatggag 128880
caagaccctg tctccaaaag aaaaaaagaa agaagttttt aagtaactgc gaatgaggag 128940
agcctggggt gtaaaatgca gattcccagg ctgtccccccc aggaattctg catagttcct 129000
aggactggct ggtggcctca cttagagacc cgacccttaa ggcccctccc ggcacaaaga 129060
ggctctgact ctgcaagggc gaaaagtaca ggaaagtaag ggcactgggc accagtgggc 129120
tggcaagacc agaccccaga gtgagtccat ttcacacggg cctcagatct ccaaagggtc 129180
ccaagttact tccagtcatt ctccaatggg gtgactttgc cccccagggg acatttggca 129240
atgtctggag acattttggt tgtcacaact ggaggcaggg tgctgctggc atctagtggg 129300
tagaagacag agatgctgct aaatgcctta tatagggctg cccccacaac gaggaactat 129360
ccggcccaac tgtcaatact gaggcagaga aaccctgacg ttagtctttt gacattaatc 129420
tctagacaag gtcaaacatg caatagtgaa aacaggaatg aagagatgat cattcttcaa 129480

-continued ccaatttgca gtgctttcta caatggcctt ttggcattat tttttaatat atgagaagcc 129540
tcagaaagtg gaagtggcca ggccacttga ggctataacg ttgtcccctg agcccccaga 129600
catgggagca ccagggctct aggcctttat ttttattttc tattttttcc cctgaaacag 129660
ggtcttgttg tgttgcccag gctggagtgc aagggtgtga tcgttgctca ctacagcctc 129720
aaactcctgg gttcaagcga tcctcctgcc tcagcctccc aagtagttgg gactacaggc 129780
acatgccacc atgcctggct aatttttttt tttttcttgt aaagacaggg atctccctta 129840
tgttgcccag gatagtctca aactcctggc ctcaagcaat cctcctgcct tggcctccca 129900
aagtgctggg attacaggtg tgagccacca tattcagccg ggtctaggcc ttttaccaag 129960
ttggggggct ggcccccagc tggcactcct gccctggaag cccacctagt aagttctgct 130020
tcccctcccc acagctcccg cctcggcctg cctcctgctg atgctcctgg ccctgcccct 130080
ggcggccccc agctgcccca tgctctgcac ctgctactca tccccgccca ccgtgagctg 130140
ccaggccaac aacttctcct ctgtgccgct gtccctgcca cccagcactc agcgactctt 130200
cctgcagaac aacctcatcc gcacgctgcg gccaggcacc tttgggtcca acctgctcac 130260
cctgtggctc ttctccaaca acctctccac catctacccg ggcactttcc gccacttgca 130320
agccctggag gagctggacc tcggtgacaa ccggcacctg cgctcgctgg agcccgacac 130380
cttccagggc ctggagcggc tgcagtcgct gcatttgtac cgctgccagc tcagcagcct 130440
gcccggcaac atcttccgag gcctggtcag cctgcagtac ctctacctcc aggagaacag 130500
cctgctccac ctacaggtga gcctgccctg cccccaccct cagcccctttt ctggtttcct 130560
ctctctgtgg gcccctctgc tccccgaccc tggcgtgcgt ccctcctctc tccccaggcc 130620
acccttcctg cctcagcatc tccatttctc tctgtctatg tctcttttct ctcttacatt 130680
ctccaggggc tttacttttt cccttctgcc tctctacctg tttaggtccc ttgctgttcc 130740
tctctctctc tctccctcta actccacaac cttcacctct ctgcctctgc ctgtctgtct 130800
gtctatccct ttccatccat cactgcctct ctcactaact tgcctccccc atctgtcttc 130860
tgcctcttct gtctgtctcc cttcacacac ccactccgca tacaccccca tgtctgtctg 130920
cgtgtgtgta tctgtctctt tctgtgatct cacgtgtttg ccttcagggc actctgcctt 130980
cccccagggt cccctgccca aaggcctttg cagctgtttt tctcacccac cctcaagtct 131040
gcccacatca cggtgaagta gagagagaag gcagagccac agccactggc atcccacaga 131100
aagttgcgct tctctccaat tcactgggca atgggacggg agaagcccac accccttcta 131160
gattcccatt ttccaaacct gtcatctcaa tgcaggggaa gaaagaaaag ggtaaatctc 131220
tgttatgcag ctggagaatg gatgctctga aaatggaagg aataccagta attgttattc 131280
attgttatta ttattgatct aattattgtt tattgttgtt atgctgactg tttgacacgc 131340
aaatcatccc actccatttc cccaggaagc aataacacac cctccaaacc accctgagag 131400
aaaatcttcc cttggctaca gagcctccgg ctggaagggg gtgaaaatat ccaaattctg 131460
ccctctccct acttgaacct ggaacgtgct tcctctgcct catccagggc tagtgcctaa 131520
ctagttatca atctgctagt tggaaaatca ggtcagtgct gatgatgcta atgataataa 131580
caatagccat aacaacctaa caaacatact gagcacccac tacgagctag atgctaagaa 131640
tacagtagtg aacagaacag accaaacccc ctgccttcac agagatacca ttcccatgag 131700
gagggaaaga agtaaaatgc acggtatatt ggaaaaatat gtcttatatt attcttattg 131760
ttgcctaaat agtgacagta atagcagtag ccgccaccac ttagtgggta cacagggtca 131820

-continued

```
gccacagtgc caagcacttt ataggtatcc actctgccat ttacaagcgt gtgacatttt 131880
tttttttac ctcctcagac ctcagttttc tcatctgtac aatggggtag caagagcacc 131940
catctcctag ggattttgaa agcattaaat gcatgaataa tttgtaaagc acttagaata 132000
gtgcttggca tacggtaagt gctatataaa tgcttgttaa aatactattt taaaaaaaga 132060
aacgagcctt atttaacatt ggtttcagtg aagtggccca acttggactc catcctgaag 132120
atgtgggtca acttcaagga ttatactaag gtcatgagtg agtcccagaa attgcacctc 132180
acagtttatg aagtgcactc agccacctca tctcatttct acagcccagt tgggagatta 132240
ttttcacctc cttgttaaca atggagaagc tgaggctggg ggccctgaag accctataga 132300
gatatagtca cctccaatca taaatctttt caaccattgt cggtgtgacc ggaggcttat 132360
gtcttctcac catcatgttg agcctcacaa caacctggtg atagggacag ttaggggcac 132420
tagggacatg gaatgaatgt tcctgaggcc acacacccag gaagagctgg cgcttgaacc 132480
tcatggtctg gctacaaggg gacagtactc tggagtacaa ttgagcaggc tcatttttga 132540
aagcacacag tttggactca gcaagaccta ggttcaaatc ctggctccta tatatatgac 132600
tttggacaaa ttacttaacc tctctcagtc tccatttcct catctctaaa atggcaatca 132660
ggatagtact taataataat cttttttttt tgagacgacg tcccactcta tcgcccaggc 132720
tggagtgcag tagtgcgatc tcggctcact gcaacctctg cctcccaggc tcaagtgatt 132780
ttcctgcctc agcctcctga gtaactaaga ttacaggcat gtgtcactac acccagctat 132840
tttttgtatt tttagtagag aagggtttca ccatgttggc caggctggtc ttgaactcct 132900
gacctcaggt gatccactca cctcggcctc ccaaagtgct gggattacag gtgtgagcca 132960
ccatgcccag ccaataataa tccttattta agaagttttg taaggattaa aatgtaaggc 133020
atttagcaca aggattaaaa tgtaaggcat ttagcacata tgggcactat aataataatt 133080
actactacta ctactactaa tactgagatc aaatactact acaaattgat catgcattta 133140
atgctttcaa aatctcctta tcaatatata ttagttattt aggaggaatt tggagtcaga 133200
gggcctgagc ttgaatcccc gatctactat tttctgactt atttaacttt aagcaggttg 133260
ctaaccctct ctgaacctca cttactttat ctgcaaactg ggaataatga aaataatacc 133320
ttccaccaag aatggctgta aataggaaac gagttagtgt atagaaagcc catagttcag 133380
gctggtgtgg tggcccatgt ctgcaatccc agcacttcgg gaggccaagg tgggtggatc 133440
acttgaagtc aggagttcga gaccagcctg gccaatatgg tgaaaccctg tctctactaa 133500
aaatacaaaa attaggcagg cggggtggca ggtgtctgta atcccagcca ctagggaggc 133560
taaggcagga gaatcacttg aacctgggag gtggaggttg cagtgagctg agatcgtgct 133620
actatactcc agcctgggtg acagagcaag actctgtctc aaaaaaggaa aaaaaaaaaa 133680
aaaagcccat agttcagtgc tgaagaaatc atgttattat gaccccatcc tccattgact 133740
ctcaggccaa caacagcaat caggacctga ggtcagcaaa ggcttgggca gaggggacct 133800
caggtggaca ttggggtctt ctgaaatggg aagtgtttgt tctctacgcc cctggcatga 133860
atggtaccag gcatcatggg aaggaagcaa cttcacacct ggccttttat agaggagatg 133920
gaaaacacag cctctgcctg tgaactgcct ggtagggctg ggctgggaga tgccacaggc 133980
aggtgaggaa acatgggctg gggtgagatc cgcagggtgc aggtgtgacc caagatggag 134040
ccaggcctgc cccaaagggg agctttggag gaaactccac cagaggacca cagcttttca 134100
gaatggggaa gggccaggca ctgtgccagg tgagttcatt catcaacaga tatttactga 134160
gtatctacca catgccaggc aatgttccag gtgccaggga ttcaggagag aacagaaaca 134220
```

-continued gtggccctgt tctcccagag catattccct actcaagtgt agccagatga taaagacact 134280
tgttttcttt cttttttttt tttgagacga agtctcgctc tcttgctcag gctggagtgc 134340
agtggcacga tctcggctca ctgcaacctc tgcctcccag gttcaagcga ttctcctgcc 134400
tcagcctccc aagtagctgg gattacaggc atgtgctacc atgcctggct aatttttgta 134460
tttttagtag agacggggtt tcaccatgtc ggccaggctg gtcttgaact cctgaccaca 134520
ggtgatctgc ccaccttggc ctcccaaagt gttggattac aggtgtgagc caccgcaccc 134580
gccgacactt gttttctctt tcagtcatta cagtggcctg catggttttt gtttgttttg 134640
ttttgttttg tttttgtttt tgagacagtc tcactatgtc acccagctgg agtgcagtgg 134700
cgcaatcttg gctcactgca gcctcacctc ctggggtcaa acaattcccc catcttagcc 134760
tccccagtag ctggaactac agacatgtgc caccatgtcc agctaatttt tctattttat 134820
agagacgggg tttcaccatg ttgcccaggc tggtctcaaa ctcctgaact taagcaatcc 134880
acccgcctcg gcctcccaaa gtgctgggat tacaggcatg agccaccgta cacagctggc 134940
ctgaatggtt taaaaatagt ctttatgctc aagcagatca gatctcagtt tgaattccag 135000
ccacacctct aatttgctct atggctttgt gcaagttatt taaccactct gagcctcgat 135060
ggacccatct gtgaaatggg gataacctgt accttggcga gcaggggttg tgaggattaa 135120
aggagatact actgagctca cagcccaatg tctggtacaa agtgagtatc caatgaatgg 135180
tagctatcca ttaacaccag ggaggacacc aactgaagct cagcaaaata aaagcacagt 135240
ccaaggtcac ccagctagta aggaacatga cctagaattg gcccaggtct gtctgactcc 135300
agagtgcagt tgttcagagg tctctggagt tggaagccac gttccactgc atattagctg 135360
ttggacccta ggcgagtcac ttcacttctc tgaggctcca tctcgtaatc tctgaaatgg 135420
agataataat agtatccacc tcatagggtt gtgacaatta agttactata taggatctgt 135480
gtagcacaga gcttggcaca tggtaagagc tcaatcagtt acctgcttga caatgctgac 135540
gccgatgatg acgatgatac ccatcctaga ctgatgagct ctgtaagcgg gggtgcctgg 135600
cacagagtag acactcggta cagctctgtg gaatgaatga ggcacatccc agaactcacc 135660
aattcataaa aatcagatgc agatgggatc ttaaagatca cctatcctaa gtcccttgtt 135720
tcacagatga aaagacccag gcccagagag gtgcttggag ctgcgcaagg tcacacagcc 135780
aagcagctca tttgattagt gtcagagcca agagctggga gtttggaggg aggcaaggtt 135840
aagaacagga tgctgtcagg gaagcaggca gggatgctgt gttaagattc caaatggatg 135900
cagagagctg tgaaccggcc agtggggagg caagggaaat gtggtttttg aaatggaaga 135960
ggatgacttt agcagaggct ctcagcccag agggagggga gatagggagg ggagataggg 136020
aggggcgggg ggagggctag ggctgtgaaa gtcaagagct tattaatgca tagagaacgg 136080
ttttaacagt ggagagagga aggaccggat ttgaaagcta cattcaagga agtggcaacg 136140
ggatttggca acagcttgga tggggggagg aggcaatgga ccccaaggca gaggctcaga 136200
gaagggaggg gcaggacttt ttgcagagaa acaaaaggag aggagaggag gttagaatca 136260
agaaattctg tgggccaaaa cctggggctg tgggtcaaag gcacctgaat tccctaggat 136320
ctctggaact ttggtctact cttctgacct cccgaggtcc cccaaaatgt ggattacccc 136380
tgctcactct cccccaaccc ccggcccctt atcgatcctc tgaccataca tctctgggtg 136440
tgtcctactc ttgctgacac ttcataaaaa gaggaacccc atttaggtgt tttgagtggc 136500
agggattcca agcctacccc ctggatgggc ctggaagaga acaagagcac caggccatgg 136560

-continued tgagtcaggc tgaggccagg gaggtgcaag gagccagctg gaggcctgag ccaggatttg 136620
gggtggtggc agcagggggc ggagaatggt ggtgtcagag gcagccgaga aggttgaggg 136680
ggacggatct caatgtggcc aagaggaggg ctcttggcac gctcagttcc tgtagcgaag 136740
agggcggaag ccagatggga gggggcgaga acaggcagga gcacaggaag gtggaggctg 136800
tgggtgtagg ctgggagtca atgccctccc ccaacctgag gcctccgacc aggctcctgg 136860
gtggcaggca tggggaggaa agcgtctccc caggcagtga gggagggaga gccacagtca 136920
gggaacaggc cccctgggtg aactggcctg agcagagtgg atgctcctgt tctgagaccc 136980
agacctcctg gaacctgctg accacagtga tgccctgcac aagaggggag gacctcaagg 137040
cagtgaggtc agggagctga agtcctgctt ccctctctgg caagccctta tctctttgag 137100
ccccagtgct ctcctctaaa aaagtgagct gggctgatgg gtgccaaggc attagctccc 137160
aagtcagctg atcatcagaa tcccctggtg agctggttat aatgcagagt ccaggaatcc 137220
ccactggccg tgggccacac acacccgccg ccccccgctg ttaattctga accatagttc 137280
caaggtcctt tctgcactaa tgtggcctga ttaggtgact ccctagcacc aggcaggtgg 137340
gacagcgcct ctaaggggag tagtaatgca atgtggcttc cttcctctcc tcccctgccg 137400
cctctggggg tggagctgat gcccctcacc ccaataccca gcctagtagc agtactttgg 137460
ttcccccagg gagctcctct tttaaagaaa agggacagga cccaattgtt actgagcccc 137520
tattgtcata gtagccacca tttattgatg gttgactatg cacctgccag atactgtacc 137580
cttaacagca tttatcatcc aaccctcctt tagcctgctg aggggggttat acataataag 137640 gaatattgta catactgagg aacctgagac tccatgaggt taaaacttgc ctaaaataac 137700
acagctaggg aaaaggcaag ctggattttg aactagggct ctaagtgctg agcctgtggg 137760
cttcataatt ggaccaaatc cctgtgtgct gggcacgtgt ccagcacttc cctcatatga 137820
tctttatgtg aaccatcctc tggaatcctc agaacaaacc caggaagtag gtatactcat 137880
ccccatttta cagatgagga aacaggcaca gagagatgac tggcttggcc aagttaagaa 137940
taatggctaa caaacaaaaa caaaaacaaa aattaaaaaa aaaaaaagaa taatggctaa 138000
ctcatggaac tcatagaact ccacaaggaa aggtgttcta agcaccttca tacatgctgc 138060
ttcatttaat ctctacatta tacagatgag gaaactgagt cacagatatc ctgagtgact 138120
tgcccacggt ggcatcagtt aatgacagat ccaagatttg aaatcagaaa ggctggctcc 138180
ccagtctcca tacttcacca aaccagaagt tctgaaactc aaactgtggt cctgccaatg 138240
gccacactgg cttccctggg gaacctgtag acatggggat tcccaggctc caccccaaac 138300
ctcctgaatt agaaactctg ccccccgccc caccccgctc agagatccgc aggggatcct 138360
aatacacccg aaagtttagg aaccactgac ctcaccaata ccactttttc cacagcaaat 138420
aggttagagg aggcagaatc caaatccagg atgctatgaa tcaaaaggtc aaccctttct 138480
cttctgccac ggtgcacccc cttccctccc ccggccaagg ccccagcggg gtctgcaccc 138540
tgcctcaggc ccattctctt cttctgtgcc ccactccacc ccacccagga tgacttgttc 138600
gcggacctgg ccaacctgag ccacctcttc ctccacggga accgcctgcg gctgctcaca 138660
gagcacgtgt ttcgcggcct gggcagcctg gaccggctgc tgctgcacgg gaaccggctg 138720
cagggcgtgc accgcgcggc cttccgcggc ctcagccgcc tcaccatcct ctacctgttc 138780
aacaacagcc tggcctcgct gcccggcgag gcgctcgccg acctgccctc gctcgagttc 138840
ctgcggctca acgctaaccc ctgggcgtgc gactgccgcg cgcggccgct ctgggcctgg 138900
ttccagcgcg cgcgcgtgtc cagctccgac gtgacctgcg ccaccccccc ggagcgccag 138960

-continued ggccgagacc tgcgcgcgct ccgcgaggcc gacttccagg cgtgtccgcc cgcggcaccc 139020
acgcggccgg gcagccgcgc ccgcggcaac agctcctcca accacctgta cggggtggcc 139080
gaggccgggg cgcccccagc cgatccctcc accctctacc gagatctgcc tgccgaagac 139140
tcgcgggggc gccagggcgg ggacgcgcct actgaggacg actactgggg gggctacggg 139200
ggtgaggacc agcgagggga gcagatgtgc cccggcgctg cctgccaggc gcccccggac 139260
tcccgaggcc ctgcgctctc ggccgggctc cccagccctc tgctttgcct cctgctcctg 139320
gtgccccacc acctctgact gcggtgctga gatcgaagag gccagtgtcc gatccccgct 139380
tcccgtccac ccggggctgc ggctccggcc ccagtcgccc caccttccct ggccttgctg 139440
cctccctttc ccctcccagc tcctctcctc cccggggagc aggccgcctc tccttgcctg 139500
ccccctgggc tgtcctgact tgtggcagcc ccaagagggc gtgtgtggtg gctcagccct 139560
gccctcccca gttctggcca ttaactcttc cccatcccaa ggctggggtg gggcccccca 139620
ggcagccgct gacccgcact cctaagggcc cacagcggac accagagggg cttttgtctg 139680
cagagcgtct tccaccagca gagcctttgg aagctccccc agggagcccc acccaggacc 139740
ctttggggga tgcctcagtc agggccaggc tgaccctgac ccctgcttac cctagtcccc 139800
tcaacctcct gacactggag gaatactttt ctcctaagtc taccctggac actttttagg 139860
gcacctggag agaactttcc tctccactgt ggcccctgcg tggtgaagat caaaagaagt 139920
tgtttgggaa aaaaaattta ttaaaaaatt ctattatttt atctactgta agatttgttg 139980
acttgggacc ccgaaagcgg gatgaggtct cagaatgtaa ggattgcagg gccaggaggg 140040
ttggagaagg ggagccgtcc cccgccatca aagagcttcc tggtggctgg aggtggtgtg 140100
cgctcccccg ccatgaggag gagctgaagc cctgcattct aggtgaggcg cagtgtggca 140160
gccaagagtg ggtgctggtg gcacctcttc tcttcatttg tccaggggaa gagctgcagc 140220
caaccctgag tggtctggcg cctgaggaac taagcctggg gaagacctgc tgtctggtta 140280
acagccctct tccagaccct gttccttcag gaaacaagag cagttctcct gcaaggagga 140340
gtcacataca cactcctggt cacagacagc cccaacatgg ctttgggtaa atgtgaacaa 140400
ggcactgctc cctcagggaa acacagcccc atgccagagc aaacacctta gcaaacagag 140460
accaaggctg ggtttccgcg tacacttgcc tccttggcta agtgcccttg tgcagtgcac 140520
agcgtacaca cctgcacaca gcaaccctgt gggtatgtgg tctctctctc agctcctgtg 140580
aggtagaagc catcagggat gaaccaggtc agagaagcag gtttccaaac aggctagaag 140640
agggaccgag gaactcgggt gatcagaggg acaggaatcc caaattggga tgcattactg 140700
gcttgaggta caatcagaac cttcatcttt ctggtgtgtg gaagagaggc tggggactgg 140760
gaagagctca ggctaagaag gacttgggtt gggatttagg ggtgagtctc atcagactga 140820
gcacttggag agaagtttgg tagtttgaat ttggagctaa gaatctagct tgggcagggt 140880
gtggtcgctt gcacctgtaa tcccagctaa ttgggaggct gacgtgggag gatcacttga 140940
ggccaagaat ttgagactag cctggacaac atatcgagac tgagtctctt aaaaatgttt 141000
ttttaagaat ctagtttgga gtggggtgtg atgtctcaac gtctgtaatc ccagcactct 141060
gggaggctga ggtggacaga tcacttgagg tcaggagttc aagaccagcc tggccaacat 141120
ggcagaaacc ccgtctctac taaaaattca aaaaaattag ccaggcgtga cggcgggtgc 141180
ctatagtccc aggtactcag gaggctgagg cacaagaatc actccagcct gggtgacaga 141240
gactctgtct aaaaaaaaaa aaaatctagc ttgggaggtg ggaatagaaa gatagagggg 141300

-continued gcctagatgc tagggcttga ggaagcaggc tgaggttctg tgattctggc tagggaggtc 141360
aaatgatctt gagaagaaga gaagaaagga gaagaaatca gcatctaagc ctgaggcagg 141420
tagactccgg ttaagggtgt ggggtgggct gggggagagt gagagcagct ggtcagaaac 141480
ccagggagct cggagtctgg ggtcttgcag gggcttgtgt caggctggct gtgaggaggt 141540
taatgggttg gattggaggg acagccagac aagagctctg gtggaggagg ggctgctggg 141600
gcctgggcag ggggagggga gctgctggta aattagaggc aggctgtcca ggtcatagaa 141660
ttatcattgt gaaatattca tgggccatcg gtccagatgc tatttcagaa cagtgaaagc 141720
aagaggagtg tgtgagcctc aggaagaagc ctgaagcaaa gccactctcc accaaccccc 141780
acccctccca ccaccagccc agacagaccc acggacgccc atcacgtgca cacccacact 141840
cccgagctct cacacacact cgcaccaagc agagccatgt agcacgtgca agcacaccaa 141900
ccacccacgg gtcccacaaa caggcaggtg tcccctaaat tctgacatgc acactgacat 141960
gcacacccac tcaatcagga cccagcagag atcacctcca gcgatctcac atgcgcagac 142020
ccccaaactc tccaaacaac ccagattcac caccttgacc cacacaccct gagataggag 142080
ggatgttcaa ggccatccag cccaaccccc accaatgctc tgatggggaa actgaggcca 142140
tagaaaggaa gggatttgtc tgagattcct ctatcccctg aaaaaagcaa aattcattca 142200
cctcccacat tctgagtgta cccccattct gcattttcgt ctgccagaca cccagcctag 142260
ttgtaattaa ctcctccctt tctctaattt cctgcatcta ttcagttacc cagtccccca 142320
cccagccaca gtctatccct tccttcccat tctccccacc acctccctgc tccagctact 142380
cattacctca tgcctggaat ataaaagaaa actgcgataa cctcctcgct ggtttcctac 142440
atggaatctc tccctccctc ccacccagcc ataccgtggt gaccagattc atctgatcaa 142500
aatttgcata tgttatgatg tcactcagga gcctgtaatg gcttcctaat gcctataggg 142560
taaaggtaaa acaccttagc agagcatcaa agatccctca gagtctggta ccaactgctt 142620
ttctagcctt ttctctcaca atctcatccc aaaccttcac tccagctaga acgtttgtat 142680
catactggcc accagttatc atgtatgtga aacccaccaa ccgactttga gtgccccccct 142740 aaaatttctc agtctctcct gaagtaggaa acctcttccc cctcctcaga tctcagactc 142800
cagagccctt tcccaaggcc aagactgcac ctctctgacc atatacaggg gttcttcaaa 142860
gcagcagaca gaggctcagg ctctggctcc ctccaagcag acggctgccc ccgactggcc 142920
accttgggaa gcacagccag gtttcagtcg tctagaacag agaatgagca tctaaccgcc 142980
tggggagagg actaggacac cagatgataa ggtttataag cccttaagcc tctaaggttc 143040
ttacacccag agtagggggg ggacggttct cagccctgtt tccctagctg cgggctccca 143100
attttcgatc cctaatccga gaggaactcc tctccaatga aatacagact tgggactctc 143160
aggacactgt ggaagggaaa tttcccaaca gactctgaga gtccaggagg ccagggatag 143220
accaggtggc aggcccaagg tccagctggg gtcaggtttc tatatgaatt tttaatgctt 143280
ccagatagac ttgtcagatg ttctgaaaac tgagcatctc ctttcacctc tgtacatgat 143340
gcccttctcc aaccccattg cccctgcagg agggcaggcc tgggacagat attcagtggc 143400
ctctggagaa acggttttgg gacagtagaa gggtaaatga cctagttatg ttcccactag 143460
taagctgtgt gaccttgggc aagttactta acctctctga acattagagt tctgtgggtt 143520
tgtttttgtt ttgtaagctg gggacaatag tgccagccta aatcaatttg ttgtggggac 143580
tcagtgcaat agcccatggc aaagtgacct acatgcttgc tgttattatt ctctttcctc 143640
aagttctgcc tccctcttcc agcttttctt ccaaccccaa agatgtctct ggctattgct 143700

-continued

```
tcgaaggtag gaactttggt tggttctccc ctttctcttc aggcccaaac tccccacctc 143760

aagatccttt ggcctttgta gaaacttcag gtgaggaggt ggcagagaaa taagaaagtg 143820

tgcaaggctg gtggagtgag agaggaggat agatggcgaa gccctagcag aggggaggga 143880

agtgggcagt ggagagagg                                              143899
```

```
<210> SEQ ID NO 16
<211> LENGTH: 215980
<212> TYPE: DNA
<213> ORGANISM: Mus sp.
<220> FEATURE:
<221> NAME/KEY: modified_base
<222> LOCATION: (1001)..(1100)
<223> OTHER INFORMATION: a, t, c, g, other or unknown
<220> FEATURE:
<221> NAME/KEY: modified_base
<222> LOCATION: (2123)..(2222)
<223> OTHER INFORMATION: a, t, c, g, other or unknown
<220> FEATURE:
<221> NAME/KEY: modified_base
<222> LOCATION: (3728)..(3827)
<223> OTHER INFORMATION: a, t, c, g, other or unknown
<220> FEATURE:
<221> NAME/KEY: modified_base
<222> LOCATION: (5168)..(5267)
<223> OTHER INFORMATION: a, t, c, g, other or unknown
<220> FEATURE:
<221> NAME/KEY: modified_base
<222> LOCATION: (7481)..(7580)
<223> OTHER INFORMATION: a, t, c, g, other or unknown
<220> FEATURE:
<221> NAME/KEY: modified_base
<222> LOCATION: (8849)..(8948)
<223> OTHER INFORMATION: a, t, c, g, other or unknown
<220> FEATURE:
<221> NAME/KEY: modified_base
<222> LOCATION: (10375)..(10474)
<223> OTHER INFORMATION: a, t, c, g, other or unknown
<220> FEATURE:
<221> NAME/KEY: modified_base
<222> LOCATION: (12270)..(12369)
<223> OTHER INFORMATION: a, t, c, g, other or unknown
<220> FEATURE:
<221> NAME/KEY: modified_base
<222> LOCATION: (13438)..(13537)
<223> OTHER INFORMATION: a, t, c, g, other or unknown
<220> FEATURE:
<221> NAME/KEY: modified_base
<222> LOCATION: (15902)
<223> OTHER INFORMATION: a, t, c, g, other or unknown
<220> FEATURE:
<221> NAME/KEY: modified_base
<222> LOCATION: (15939)..(16038)
<223> OTHER INFORMATION: a, t, c, g, other or unknown
<220> FEATURE:
<221> NAME/KEY: modified_base
<222> LOCATION: (18223)..(18322)
<223> OTHER INFORMATION: a, t, c, g, other or unknown
<220> FEATURE:
<221> NAME/KEY: modified_base
<222> LOCATION: (20974)..(21073)
<223> OTHER INFORMATION: a, t, c, g, other or unknown
<220> FEATURE:
<221> NAME/KEY: modified_base
<222> LOCATION: (24403)..(24502)
<223> OTHER INFORMATION: a, t, c, g, other or unknown
<220> FEATURE:
<221> NAME/KEY: modified_base
<222> LOCATION: (27574)..(27673)
<223> OTHER INFORMATION: a, t, c, g, other or unknown
<220> FEATURE:
<221> NAME/KEY: modified_base
<222> LOCATION: (30892)
<223> OTHER INFORMATION: a, t, c, g, other or unknown
<220> FEATURE:
```

-continued

<221> NAME/KEY: modified_base
<222> LOCATION: (30901)..(31000)
<223> OTHER INFORMATION: a, t, c, g, other or unknown
<220> FEATURE:
<221> NAME/KEY: modified_base
<222> LOCATION: (34443)..(34542)
<223> OTHER INFORMATION: a, t, c, g, other or unknown
<220> FEATURE:
<221> NAME/KEY: modified_base
<222> LOCATION: (38205)..(38304)
<223> OTHER INFORMATION: a, t, c, g, other or unknown
<220> FEATURE:
<221> NAME/KEY: modified_base
<222> LOCATION: (42373)
<223> OTHER INFORMATION: a, t, c, g, other or unknown
<220> FEATURE:
<221> NAME/KEY: modified_base
<222> LOCATION: (42386)
<223> OTHER INFORMATION: a, t, c, g, other or unknown
<220> FEATURE:
<221> NAME/KEY: modified_base
<222> LOCATION: (42393)
<223> OTHER INFORMATION: a, t, c, g, other or unknown
<220> FEATURE:
<221> NAME/KEY: modified_base
<222> LOCATION: (42461)
<223> OTHER INFORMATION: a, t, c, g, other or unknown
<220> FEATURE:
<221> NAME/KEY: modified_base
<222> LOCATION: (44809)..(44908)
<223> OTHER INFORMATION: a, t, c, g, other or unknown
<220> FEATURE:
<221> NAME/KEY: modified_base
<222> LOCATION: (51380)..(51479)
<223> OTHER INFORMATION: a, t, c, g, other or unknown
<220> FEATURE:
<221> NAME/KEY: modified_base
<222> LOCATION: (56740)
<223> OTHER INFORMATION: a, t, c, g, other or unknown
<220> FEATURE:
<221> NAME/KEY: modified_base
<222> LOCATION: (56765)..(56864)
<223> OTHER INFORMATION: a, t, c, g, other or unknown
<220> FEATURE:
<221> NAME/KEY: modified_base
<222> LOCATION: (62818)..(62917)
<223> OTHER INFORMATION: a, t, c, g, other or unknown
<220> FEATURE:
<221> NAME/KEY: modified_base
<222> LOCATION: (68518)
<223> OTHER INFORMATION: a, t, c, g, other or unknown
<220> FEATURE:
<221> NAME/KEY: modified_base
<222> LOCATION: (68534)..(68633)
<223> OTHER INFORMATION: a, t, c, g, other or unknown
<220> FEATURE:
<221> NAME/KEY: modified_base
<222> LOCATION: (74552)..(74651)
<223> OTHER INFORMATION: a, t, c, g, other or unknown
<220> FEATURE:
<221> NAME/KEY: modified_base
<222> LOCATION: (81446)..(81545)
<223> OTHER INFORMATION: a, t, c, g, other or unknown
<220> FEATURE:
<221> NAME/KEY: modified_base
<222> LOCATION: (88519)..(88618)
<223> OTHER INFORMATION: a, t, c, g, other or unknown
<220> FEATURE:
<221> NAME/KEY: modified_base
<222> LOCATION: (93791)
<223> OTHER INFORMATION: a, t, c, g, other or unknown
<220> FEATURE:
<221> NAME/KEY: modified_base
<222> LOCATION: (93794)
<223> OTHER INFORMATION: a, t, c, g, other or unknown
<220> FEATURE:
<221> NAME/KEY: modified_base
<222> LOCATION: (96565)
<223> OTHER INFORMATION: a, t, c, g, other or unknown -continued
<220> FEATURE:
<221> NAME/KEY: modified_base
<222> LOCATION: (96570)..(96573)
<223> OTHER INFORMATION: a, t, c, g, other or unknown
<220> FEATURE:
<221> NAME/KEY: modified_base
<222> LOCATION: (96579)
<223> OTHER INFORMATION: a, t, c, g, other or unknown
<220> FEATURE:
<221> NAME/KEY: modified_base
<222> LOCATION: (96590)
<223> OTHER INFORMATION: a, t, c, g, other or unknown
<220> FEATURE:
<221> NAME/KEY: modified_base
<222> LOCATION: (96596)
<223> OTHER INFORMATION: a, t, c, g, other or unknown
<220> FEATURE:
<221> NAME/KEY: modified_base
<222> LOCATION: (96602)
<223> OTHER INFORMATION: a, t, c, g, other or unknown
<220> FEATURE:
<221> NAME/KEY: modified_base
<222> LOCATION: (96616)
<223> OTHER INFORMATION: a, t, c, g, other or unknown
<220> FEATURE:
<221> NAME/KEY: modified_base
<222> LOCATION: (96629)
<223> OTHER INFORMATION: a, t, c, g, other or unknown
<220> FEATURE:
<221> NAME/KEY: modified_base
<222> LOCATION: (96633)
<223> OTHER INFORMATION: a, t, c, g, other or unknown
<220> FEATURE:
<221> NAME/KEY: modified_base
<222> LOCATION: (96668)
<223> OTHER INFORMATION: a, t, c, g, other or unknown
<220> FEATURE:
<221> NAME/KEY: modified_base
<222> LOCATION: (96715)..(96814)
<223> OTHER INFORMATION: a, t, c, g, other or unknown
<220> FEATURE:
<221> NAME/KEY: modified_base
<222> LOCATION: (104447)..(104546)
<223> OTHER INFORMATION: a, t, c, g, other or unknown
<220> FEATURE:
<221> NAME/KEY: modified_base
<222> LOCATION: (114521)
<223> OTHER INFORMATION: a, t, c, g, other or unknown
<220> FEATURE:
<221> NAME/KEY: modified_base
<222> LOCATION: (114527)..(114626)
<223> OTHER INFORMATION: a, t, c, g, other or unknown
<220> FEATURE:
<221> NAME/KEY: modified_base
<222> LOCATION: (127063)..(127162)
<223> OTHER INFORMATION: a, t, c, g, other or unknown
<220> FEATURE:
<221> NAME/KEY: modified_base
<222> LOCATION: (139133)..(139232)
<223> OTHER INFORMATION: a, t, c, g, other or unknown
<220> FEATURE:
<221> NAME/KEY: modified_base
<222> LOCATION: (151051)
<223> OTHER INFORMATION: a, t, c, g, other or unknown
<220> FEATURE:
<221> NAME/KEY: modified_base
<222> LOCATION: (153242)..(153341)
<223> OTHER INFORMATION: a, t, c, g, other or unknown
<220> FEATURE:
<221> NAME/KEY: modified_base
<222> LOCATION: (164706)
<223> OTHER INFORMATION: a, t, c, g, other or unknown
<220> FEATURE:
<221> NAME/KEY: modified_base
<222> LOCATION: (164708)
<223> OTHER INFORMATION: a, t, c, g, other or unknown
<220> FEATURE:
<221> NAME/KEY: modified_base
<222> LOCATION: (164710)..(164809)

-continued

<223> OTHER INFORMATION: a, t, c, g, other or unknown
<220> FEATURE:
<221> NAME/KEY: modified_base
<222> LOCATION: (182242)..(182341)
<223> OTHER INFORMATION: a, t, c, g, other or unknown
<220> FEATURE:
<221> NAME/KEY: modified_base
<222> LOCATION: (192158)
<223> OTHER INFORMATION: a, t, c, g, other or unknown
<220> FEATURE:
<221> NAME/KEY: modified_base
<222> LOCATION: (192192)
<223> OTHER INFORMATION: a, t, c, g, other or unknown
<220> FEATURE:
<221> NAME/KEY: modified_base
<222> LOCATION: (198842)..(198941)
<223> OTHER INFORMATION: a, t, c, g, other or unknown
<220> FEATURE:
<221> NAME/KEY: modified_base
<222> LOCATION: (199437)..(199438)
<223> OTHER INFORMATION: a, t, c, g, other or unknown
<220> FEATURE:
<221> NAME/KEY: modified_base
<222> LOCATION: (208276)
<223> OTHER INFORMATION: a, t, c, g, other or unknown
<220> FEATURE:
<221> NAME/KEY: modified_base
<222> LOCATION: (215974)
<223> OTHER INFORMATION: a, t, c, g, other or unknown
<220> FEATURE:
<221> NAME/KEY: modified_base
<222> LOCATION: (215976)..(215977)
<223> OTHER INFORMATION: a, t, c, g, other or unknown
<220> FEATURE:
<221> NAME/KEY: modified_base
<222> LOCATION: (215979)
<223> OTHER INFORMATION: a, t, c, g, other or unknown

<400> SEQUENCE: 16
ttgggggtat aaacccagaa gtgggattac tgcaccatac aataatcctc taacttcaag 60
caatttttcc acaatggttg tatcatttta cattcccact ggctacgaga agggttccca 120
cttctacaca tcttcaccac catttctgtt tttgtttttg agtaacagct gcctaatgac 180
tgtgaagtgg tatcttatct cagtgttgat ttgcatttct ctgatcatta atgtgggaag 240
gcatcgtttc atatgtttat tggctgtttg tgtatcatct tctttggcga tgttgattca 300
agttatttgc ttgttttttt aattggagtt ttaaaaaatt gttgttgagt tgtgggagtt 360
cttcattagc tctgcatatt aataccctga tgaaaatgat taacaagtat ttgcttccat 420
tttgggggct tccattctgg gctgttttta ttcttttgat actcttttga ttctcaacag 480
tttaatctga ctaaaattca gtttatttct tcttttaatg gccatgctat tgacacatcc 540
cgtaatcact gccaaatcca gtcatgaaga gtttctttca agagatttat agttttagct 600
ctttaagttt gtcatgtctg tttcacttaa ttttgtatag tgtacaaaag tctaacttca 660
ttcttttcta tatggcttgc tactagtata cgaagagcta aatttctctt tccttgagtc 720
tcaacctctg atgtgtagca atttcttcag aggaaaacat ggtgggaagt tccttaaaca 780
taggatgctc catggaggtg aaatagttca tcctacaggg aagcttgtta aacacaggaa 840
gtacatactc agcagctcta gtaagtgagt gaaactgact ggaggcacta ggtccctcct 900
tccctacgca tatagaagct gtaaggattg ggaagagata ctgtcaggtc agctcagctg 960
ctgcccggaa gaagctcaga cccactggcc tggctccaag nnnnnnnnnn nnnnnnnnnn 1020
nnnnnnnnnn nnnnnnnnnn nnnnnnnnnn nnnnnnnnnn nnnnnnnnnn nnnnnnnnnn 1080
nnnnnnnnnn nnnnnnnnnn atcactcttt actcaggcca cctacacgct gtttatagcc 1140
tgcctttgtc tctttggcta tacttcctgt ttatgtctat gcctcccctc tttctttttc 1200

-continued

```
tttctcttct cttctcatct catctcatct ttcttcaggg gggagcctgg tctagaactc   1260
acaaagattt gactgtctct gtctccttgc actaattaaa aaatctttta caagcatctt   1320
ttagcaattc ttacagggaa attttggaat gttaaactct gattgttagc gggctgaaga   1380
taacaatagc tctgatgata aattgcttgc caggcaagtg tgaaaatctg agtttgatcc   1440
aaaaagccgg gtacagaggc caaagagtcc ataatcctag taggggcagg aatcagggat   1500
gggtgggtcc ctggggtttc ctggtttgtc agcgtagccc aattgggaat agccaggttt   1560
cagtgaacga tgctttctgc aagctgagag aggtccttgt tcaatctctg tgacccaact   1620
ggagggagaa gagagccagc tctccagaag tggtcctctc aactttgtgc atgcatgtcc   1680
atgttcacac agggaatgga taatgcttaa aaggaagacc ggcagggggt tggtaatgca   1740
cctcctttgg tgacatgctt tcctcttgtt catgctgctc caggtgtggt cggcagcacc   1800
aaaaaccagg tgtatgtttg taatcccagt attctctggt cgtcagtagg aaatgaaaag   1860
cgaggtcatc ttcgtataga gttagcaaac tctaagccag cctcggctac atgagacttt   1920
gtctcaaaac aaaggaaaaa tcaaggagga cggctcccga gcactgtcac ctgaagctga   1980
cctctggcct ccacatgcat gtgcgcaaac acatgtcctg cacaaacaca cagacacccg   2040
catctgctcc ccgacaaaag aacctgaaac cagtatactt tgagaatttc ccattcatag   2100
ttaccattgt gtgttccttg tgnnnnnnnn nnnnnnnnnn nnnnnnnnnn nnnnnnnnnn   2160
nnnnnnnnnn nnnnnnnnnn nnnnnnnnnn nnnnnnnnnn nnnnnnnnnn nnnnnnnnnn   2220
nnggtggtgc ctttctctta cccagtctag aagggctgga ggcagggtgg atggggcact   2280
ttgaactccc acctaggcaa aaaacccagt gatctctggg ccagtgtgtt gtttgcaagg   2340
gaataaggta gagagccgcg gaggaagaca ttgggggttc tatgagtatg tgaaggggtg   2400
cacacaccac acacacacat ttttttgtt ttaaatttac aaacattaaa ataggctgta   2460
atgtggctca gtgggtagaa aaacctgctg tctaagcctg gtacgagttc aatccctgac   2520
aagctggaag gagacaacca accacaactg ctagcagcca gaagcactgc ttgctaacac   2580
tcaagagagc ctggagtgga agacactgga tccccagcag gcaagcctgc aagaagatgt   2640
gccttgccta gacaacggca gaacaaacat caaggctggc agagctgtcc aggactgttc   2700
atattaatca tgtatagata agagggaatg gcacagacag aacaattcaa cacacggggt   2760
atgaaaggaa aggaacaagg cacacaaagg acaaagaacc tagcatacaa gaaagcctaa   2820
gcagagagtg gcacttccca gaagggagtc ataaaataga ctgaattcat taaaacaaga   2880
gccaaagata aacggctcaa aaaactcacg gaaaacaggt caaaataacg tcacccatct   2940
gacagttgat actgtcaact taaccgtatc tagaactcca gcaggcacat ctccaggcat   3000
gcccctgaag gggtctttgg actaggttaa ctgacgtggg agtgacacca tctatggacc   3060
gaagcctcag acagaataaa aaggagccag tgagctgagc gtcagtgctc attgcttctg   3120
gcttcctgtc tgtggctgca gcgagacacg gtgcttcctg ctttagctgc catgacagac   3180
cacaccctca aaccgtgaac caaaataacc tcctctctac attgctttta ccaggcattt   3240
ggtcacacca atgagaaagg ttaactaata cagcactcaa tacttaaaaa cataaacacc   3300
aaccttgttt gcatgtgtga gactttgaag ctcacgggcc agttatgccc aatgccaggt   3360
ctgctggcta agggtgagag tgcacaccta taatcccagc tgctgtggaa tcagcaaaag   3420
cgctacagat ggaaggcagc cagggcagct gagactgact caaactgata gaggtgggag   3480
gcatagagaa aaccagatta atagagtgtt ccccactatg caagaagccc tgggtttcag   3540
```

-continued

```
gacgagagaa ctaagaatac agaagtctac tgtgtagaag cactgctagg tcacacagaa   3600
acatcactca agtgtctctg gatgctacac ggagggcgtg tgaagtattg cttcctgatg   3660
atctgtatct actacagcac tgctgtttta gtatgcgctc ctccactaca gctcctcacc   3720
acaccaannn nnnnnnnnnn nnnnnnnnnn nnnnnnnnnn nnnnnnnnnn nnnnnnnnnn   3780
nnnnnnnnnn nnnnnnnnnn nnnnnnnnnn nnnnnnnnnn nnnnnnnaat taatcaaaga   3840
aaacacacac caccagttag agaaagttaa tcaggccgaa tggcggcttt cccctgtatc   3900
caggctaccg tcaggacggc tcactgccac tggcaactct gcctgaacaa agcccgcagc   3960
caacgtgggc ttcaggggct ctaaacactg caatcaaagg ttgtgtgtgg gggtgggggt   4020
gctgctgcta ttcaaggatt cccaaagctt agatgtattc atcatactca caggaaagcg   4080
tgttcaaccc atcactcatg agcagtcggt accggggtga cctattccct gtagaaatgg   4140
gacggatgtt ctggaaaagt tgacagaaaa gttgattcat taggcaggct ctttgcccaa   4200
gccctgaggg taagcaaagc taactggcag gagactaggt ttgccattaa tctgagacaa   4260
gatgaaccac ttgcccatcc tcctgacacc taaatactaa tgaaagaaca atggattgag   4320
ctggcattat taaaaacgat agaaacagaa gtatcaatag tcatgtgttc tttctcccat   4380
atgtcaaaac aatgtgtaag atggcatcga acacatgcag aaactgttta gggaacatgc   4440
tgaaaatatg aagtaaaatt aaaattggaa agaaagacaa tttgcctaaa gcagctcaga   4500
gctggagaag ggaccgaggc agagataaca gcaacgtgtg gacatacgga tctggggcag   4560
agcagtcacg gactcagccg gaaagggtgg ggcagcctct gaaggaagtt aaggtaaata   4620
gagccacaag gtgattggcc caggagtggt gccaccttca cctcctgcct caaagtctga   4680
aggaatgatc ctggagtctc ccatctattg atatatgaaa ttcacagtat gttttagaac   4740
ccactgaatg atgggtagat taactaaaag aaatttaagc ggggtggtgc aggtctttta   4800
atcccagcac ttgggaggca gaggcaggtg gatctctgtg agttcgaggc cagcctggtt   4860
ccaggacagc cagagataca tagagaaacc ctgactcgaa aaaacaaaat taaaagctca   4920
tcaaaacaac aacaacaaca aaaaaaacaa aaaaacaaaa caaaacaaca aaacacccta   4980
tagtacctgt tggtgagttt gagtgagtga gtgagtgtgt gttagagaga ggggcgggga   5040
aagtgtgttc tggaaatggg agaaagagaa tgtgcatgtg tgtttctggg atgtagacaa   5100
aactacatgt cttccatcaa atgcaatgtt taattatcta tgagttgaac catcttcatt   5160
ctgctaannn nnnnnnnnnn nnnnnnnnnn nnnnnnnnnn nnnnnnnnnn nnnnnnnnnn   5220
nnnnnnnnnn nnnnnnnnnn nnnnnnnnnn nnnnnnnnnn nnnnnnnaac aaaaataaac   5280
caaaccagta aacaaaatcc tgtaagataa agcctaagac aagacacttc ctggggctgg   5340
ggagttgctt agaccataag gagttcataa tccaggcgtg agagcccgag ttcaggtccc   5400
tgggcttcca agtcaggagg agaccaagga atcaacaagt ctcgactttg gtctctagtc   5460
ccatgcacac acacgcgtgt aaatacgtag atgttcactc acacacagaa gactgcacct   5520
ggctctctca catctcagcc aacatataaa gcctgcatta tcagaacatt ctaggttcta   5580
gtttcagtca actcttacac agaatggcca tcatactccg tctacaactt ctcctgatct   5640
acccacgtgt cattgcttca gtattaacaa aacccagaat aaccagctgc gtagatcctc   5700
cctgatgccc cagtcattgt cttactgaga ctactaagtc acaaggtagc actctggatc   5760
caaaaagcaa tatccaattg agagttacaa cctataagga ggagtttacc ttcattatag   5820
ggcactggat tcccaatctt taatccaacg tcttcagcag atttcataac ttccaagtcc   5880
atcaaaacaa ctactttcct acaaagacag acacaagtta gaattaagaa ctctgcagcc   5940
```

-continued

```
tttcagatga gttactaaga agcttacttt agtagttgtc tggctaaaac tgtatccttt   6000
accaaccttt tctcattctg gactaacttg agaagtatta attcctaagt aaatacttca   6060
cttattcttt ccccacatct ccaatgtttt tgtctttaat ttattatagg gcaattcatt   6120
tcctatctag ttccctgatt aaaacagtag accttgctgc atgccattat cctcatggag   6180
gcactgatac aatttagatt attaaataca aaaccctaaa acacaaaaag atgatttttt   6240
tttaaaacaa gattttaaaa aaagcatgtg ctacgcttcc ttctgccact aagcctacac   6300
atggtcctct gactgaattt ttcccctcat tctgcttcat ctaatatgtg cttttcaaac   6360
ctggaattga accagggact tattcatgct aggcaaatgc tctaccatag agctataccc   6420
ctccaactcc catctcaaat atcatttcca aagacatttt cttggtctct tatttagatc   6480
aggtttcttt gtcctcctgc agctatgact tcattccttc agaacactcg tcttagcttt   6540
aagttctgta ttaattagtg attgttttca ttctctctgc tagaatgcac tttcaataaa   6600
ggcaggtagc cagccacagt gcttaattaa gcaacagccc aacgatgtca ttcactacat   6660
actgggacaa gatgcctaac atcatctgca gataaagacg aactactggt gtcaggagac   6720
agctaagggg tccagggctt gggcacgctg agtgtgagca ctggagtccg ggtgcccaga   6780
aacgcacata aatgcaatat ggatgtggca atctacctct aattccttct ttaagacagt   6840
ggctctccag agcaagctgg ctagcaagac aagccatatc agtgagctct gggcttgacc   6900
aagaccctgc ctccaggtgt aactcccaag caaaaggatg atggctcaca aatctcaggc   6960
tatcatgttc atgtacaaaa tgtcaaccgg catacacaca tgcacacaca tgaaaactgg   7020
gagaaaataa gaagaattgc aaccaaaaaa tgtaatttga ggacacataa ttgcaggcgg   7080
ggagtggggg gatgacagaa ggtgaactga gtggaccgag ggaaagctgt gctagcggca   7140
atgagaagaa gggtggggca gtctgagcaa gggttcagca atcaccacgc tttactgtct   7200
gcacagcctg gctgtagaat gctgggcttt atcacacaga attattcagt atgtgctatc   7260
tttacagtaa agttattcta tcaggctatg ctacttcaat agaacaagcc tgaaaaagtg   7320
gtctgctgct gagaacctga caaagatgac ctgttagaac tgtctgccaa gtgtggaatt   7380
ccagcactgg ggaccaggag ctcgagggtc accccagatg cagggagtta gaggccagtc   7440
ttggcaacat aacatcatgc ttcagaaatt aaaaacaaaa nnnnnnnnnn nnnnnnnnnn   7500
nnnnnnnnnn nnnnnnnnnn nnnnnnnnnn nnnnnnnnnn nnnnnnnnnn nnnnnnnnnn   7560
nnnnnnnnnn nnnnnnnnnn catgagatag ttaataaact gaagaaagcc atacaaggag   7620
taaagtagat agttgcaagc atgaagaaag acaaaccact tgagcttttc ttttgtcgta   7680
aggaggaaac cagacaggtc cagagagatg gctcagagat taagagcact gactgctctt   7740
ccgaaggtcc tgagttcaaa tcccagtaac cacatggtgg ctcacaacca tctgtacagc   7800
tacggtgtac tcatatacat taaataaata aataaataaa taaataaata aatcttaaaa   7860
gaaaaaaaaa aaaaacctaa ccaatcagcc aggcgatggt gacacatgtc tttaatccca   7920
gcacttggga ggcagagaca ggtggatttc tgagttcgag gccagcctgt tcttcagagt   7980
gagttccagg acagccaggg tgatacagag aaaccctgtc tcaaaaaaca aacaaacaaa   8040
caaacaaaca aacaaaaaag gaggaagcca gacaggatgc actttatacg tgaatggaat   8100
tgacaaaaga caagttctat aagtgttagg gaaaggggga ggacaacggg ggttcatgtc   8160
tgtggtggaa cacgtattag aaggctctgg gtatcctgtt tccgacaaac aggcactccc   8220
aatcacacag gccactggat gtctcaggca gagaaagatg tgatagattg actttttaac   8280
```

-continued

```
aatcacagac tgtgtggaaa atatttgtaa ggttgtcatt gtcacccagg atagagctga   8340
tggttattca aacgaggatg ggacaacaga aatgggagag agggatgtga gaaccatttt   8400
gaaccagggt gatttactgc gcacgtgtat agggtctaca gggagtggga tatgtagagg   8460
aggcctatgt tcctaacttt ggtaatgagc ttattacagt tactatgcac agcctggaag   8520
atactggaaa aggtgcaggc taggctagaa aggtactaac tgagggtttg acagcccctt   8580
ggatgtcagg atgcagcaag cctacctctg tatgtagtca atcccttctc aggctatggg   8640
tcctgcagat catccgtctc tgtatccatt attcccagtc catcctctga gtggctccct   8700
cttatccagt ttaacaaaat gctgactgca agctcccaag cccagggctc tggctccttt   8760
actccttgtt attgtacttt accctgtttg cttgggatag agtgtgccct ttataaacat   8820
ttgtgaaagg gggaatgaag aagaataann nnnnnnnnnn nnnnnnnnnn nnnnnnnnnn   8880
nnnnnnnnnn nnnnnnnnnn nnnnnnnnnn nnnnnnnnnn nnnnnnnnnn nnnnnnnnnn   8940
nnnnnnnnag agagctcaat ggttaggagc actggatgct cttccaaagg tctccagttc   9000
aattcccagc atcaccatgg cagctcacaa ctgtctgcaa ttccagttcc aggggattca   9060
acactcagaa acataagtgt aggcaatcta cgtaacataa aaataaataa atgagctgga   9120
aaagaaaaca tgtttcaaaa tatacaagta atggggctgg aggagatgtc tcaatgggta   9180
agatcattgg ctgctctttt ggaggttctg ggttcaattc ccaccaccca catgacagct   9240
cacaactgtc tgtaactttg gtcctgtggg agctgatgcc ctcttctggt gtgcagacat   9300
acatgtagac aaaacacctg catacataaa ataagttttt aaaaaagtta cacatacacc   9360
cgtgtgtaat ataacacaca ctggcttaac ttcctcagca ctgactgttc accatacgga   9420
ttcccatgag gttttggttg cattctatca ccgaaaaaaa aaaaaaaaaa ttagaagaaa   9480
gtatatacat ataaacctct ccctaaaata aagttttctt ttctaaaagt acatccttat   9540
tttttatttt tttttttttt ttaagaaatg ggaacaacag ttctgctcac actgtatttc   9600
tagcatgtaa catcttgcaa gtacttaacc gtattctata tcagctcaac acacttacta   9660
ccgaagactc aagatcacaa aaaaaaaaaa aggacccaga ctggataatt aaacgtttct   9720
tttgttgtag taagcgacct cttccttaga agatactaca gtaatgctga agaaatgaca   9780
catctactgt aatctgttct ctgggattcc aacttgtttc ctctgctact cctcccttgg   9840
cggcaatgtt cgtctgcatc cggctgagct cctcgctgcc ttgttaaacc tccttcctga   9900
acttccgacc tgtagttccc gctctacagt gcaagcgagt ggataaggaa gcgcatacct   9960
gccgtctttc agggtgttga cgatgaactt gtggacctgg cagacacagt tgctggccag  10020
ctgccctccc tcgaccaggg tgttcagctg cgtggccagc atgaacgctg caaaagcaga  10080
gagagagggg ctcagtctcc aagcctttcc ttaacccgaa agctcatcac aaggagaacc  10140
attaaataca gctgtttaaa actcctccgc cctgcagaga ggaaagcagc atcaatccgc  10200
cccatgtaaa agtctgaggc tcttcctaaa tggtatctgt ttctcacagt ctccaaatca  10260
tttttactgt aattctagtt tctggggaaa gacctttctc ggtctttagc cccgtgacta  10320
gagacaacag gcaaatattc cagaaaggcc cccattttct ttttaaagct tctannnnnn  10380
nnnnnnnnnn nnnnnnnnnn nnnnnnnnnn nnnnnnnnnn nnnnnnnnnn nnnnnnnnnn  10440
nnnnnnnnnn nnnnnnnnnn nnnnnnnnnn nnnngcacat cttgtgaagt gtccacatct  10500
ttcggtccct cgaatttggg tttcttctgg gacgtggtag catgtgactg tcactccagt  10560
gcttggagca gcagaggggt caggaactcc aggctggcat tagctgcaga gctggagcag  10620
gtcctggaga acagaaactt tggttgcagc attaatgaac tagaagaatt tttttgtctt  10680
```

-continued

```
ctgttaaata taaatacctc cattatcttc tcataaacag tgttgccttt ttatttaagt  10740
ttttaaggat caggcacaga gactccatgc cagactacca ctcaaccact gagctacacc  10800
cccaacttgc ctttctgcta ttttttaaat tgtatcagtg gccaccaaac atggggagag  10860
gtcagggggc tacgtggagg aattgtttct ctcctaccaa gtgggcccca ggtttcaaat  10920
tcaggtgacc tggcttggca gcaagcacct ttacccctaa gccatctcat tggcttcatc  10980
ttttaatggc cccttcccct gctctgaggc aggctctccc tatatagccc tggctggcct  11040
caggctcgca ggtccaccag tgagcaccag gtttctgctt gtccttacct ccccagcact  11100
gtggttataa gcatgtgcca ctgtgtcaaa ctcagtcact aagctttgcc aagccatagc  11160
ccagcccttg agtttactgt ttgtctgtgt ggtgatttgt caaaccactt ttgttccact  11220
gaggtatttt gtcaagtttg acaaaattag ttgagtatgt aggtcttttt ttctggaatc  11280
ttctgttata gcttagtctg gtcttgaact catgatcttg cctcaacctc acgattattg  11340
aggattattg agatggacag gctgtgtgac catgctcggc tgtgtgtttt agcatgcatt  11400
agtcatttga aaaacgttgg ctcatgacac tttacaggtc ttccatgttt gatatgtttt  11460
atttaatcca aagtaattcc agcaccagag gctgagacag gaggatctca aggtcaacct  11520
agagatgcat agcaggcggg gccccactcg gttaggttaa tatcatcact gacttcagga  11580
gaaaagtctt aagtattggg gactaaaagc aggaggatct gaagttcaag gtcatcttta  11640
ggaacttagc agacttgagg ccagcttggg cgctgtggga ccctgttttt aaaccagaaa  11700
acaaattgaa aggaaaaaaa aaaaaagctg gaggaagtga atgtgagtgt tcacatagtc  11760
ctgtttccac aagaaaacag ggttactttt ggcaacaaat aggtgctttc tttgaaggct  11820
ggcatttttg tgacttgtca ttggagaaat gatttaatta agacttttct actgagtgcc  11880
tctgaagagg ctcttttaaa tttagtttaa ttttatctca ttgttagtgt ggtgtgcttg  11940
tgcacacaga aggcagcttt ctagagtctt ttcactctct cctccacagc tcctggagtc  12000
aaactcaggc cctggctagg caagctctta ggacagtgtt agctgtagct tattaagttt  12060
ttaagaattt ttataagact ctgtttttct ttctcaggtc atgatacagc aggaaaatac  12120
atccataaag cccatcctgc aggtcattgt aagtaccggc atgtgtgttt agcataatga  12180
agatggttca cttatagtta attaaacatt ggattggatg gaagacatgt agttttggtt  12240
acttcccaga aacacaaatg cacattcttn nnnnnnnnnn nnnnnnnnnn nnnnnnnnnn  12300
nnnnnnnnnn nnnnnnnnnn nnnnnnnnnn nnnnnnnnnn nnnnnnnnnn nnnnnnnnnn  12360
nnnnnnnnng aattcagagc tgatatgtag tactaactcc tactcaatga atcctttgtt  12420
cttctattcc ttcattacat tactgttaat agtggtaact atgtaccaaa gagtcaaata  12480
actcttggac catccaaggc agaaggaagg ctggcaaaaa tgtatgatga tctgggatgg  12540
gaatgtactt cagtttgtac aggaggccct tggttcattc catttctggc aatgcataga  12600
cctgtaggat ctcagcactg gtggggggtg gggggtgagg gtgaaggggc gggaggttaa  12660
aggcagaata gtcataaatt caaagtctgg gtcctggaaa gaggactaaa cgattaagag  12720
ctttagctgt tcttctagag aacctggtgt gatccccagc acatggtgcc tcacgactgt  12780
ccgaaactct gattctaggg ggatctgaaa accctcttct gccctctgta gatacagaac  12840
acacatggtg cacatacata catgcaaccc aaacaaccca tatacataaa atattttttt  12900
ttcaaaaaga cattcaaatt cttcctcggc tatatagtgt ttaccaaacc tcaaaaacaa  12960
aacaaaacaa aacaaaacaa agaatcatta atgttttgcc ttcatgtatg tctgcccacc  13020
```

-continued

```
acggacatgc ctggtaccca gggagattaa aagaagacat tagctcccct ggaatggaga  13080
taggtatgat ctaccacttg ggtgctggga acctgggtcc cctgcaaaag cagtaaatct  13140
ttttaacccc taagctgtct ctcccaacgc ctaaagattc ttgtaacaca gcatgatgag  13200
cactggcaag catagcatgg taatctgact tcagggcgcc agattttgag cttaatgctt  13260
gattattaga agtaacgtac tagatttaat gcctggagct tcaagcaaca aaattaactg  13320
aagaataaaa ataaaaaccc tgccagccat gatggtaatc ccagaacttg agaggcagag  13380
gcaggtgatc tctgtgtttt gcaaggccag ccacaatcta catagcacgt tgcagtannn  13440
nnnnnnnnnn nnnnnnnnnn nnnnnnnnnn nnnnnnnnnn nnnnnnnnnn nnnnnnnnnn  13500
nnnnnnnnnn nnnnnnnnnn nnnnnnnnnn nnnnnnncga ataaatctac acatgtaaaa  13560
agaaattcaa agaaacaaat gccaaataaa tacacatatt gtaataaaga gataattgtc  13620
taaaaaactc aaggctttaa atggtaagat atcatattct tggatgaaaa gatctaatgt  13680
caaaatatat caatttaatg caattatgta tattcaggag atctctggtt ggcttttgaa  13740
cttgatagca ctcttataat tcacatagaa gaaaaaaaac catgaaaact gccaaacatt  13800
attagaatac tccacagatg gtattttggc agcacataca tcgaagggct gtgaaagatg  13860
tgtagatcat ccacgccttg ctagggagag ggcgggtgtg tgtgggggt atagctgttt  13920
gggaaaataa cctggtaatt cctcattagt taaatcatag tcagaacctg gactagcaac  13980
ttctctctaa aatacattca ccctcagcat ctgcattgcc aggaaaccac tcctagcagg  14040
atctgtacgt ggatcaaggt agtagcatct gcatttaatt gacattctcc taaatgcttt  14100
aaattatctc tagattactt atagtagcca agatgatgca aattatgtta cactgtatta  14160
tctggggcgt aacaagaaaa tgtctctact caggttcatt caggtgcagt acttcccctg  14220
aatacttctg aatacacgga tcaagaagcc acagaaagag ggctaaccat atacaagcat  14280
atagtacact aataaccatg tacaaccata tagtacacta atattcagtg cattactcaa  14340
aatgcaaaca gatggaaaca atccaacagc ctgtaagctg aaaaacaaga taagcaaaat  14400
gtgctgggcc tagaggccca ggtctataat tccaactaag gtcgaggcag gaggatctca  14460
agttcaaggc cagcctagac aacttagcaa gaccttgtct caaaacaaaa agtaaagagg  14520
ctgaggatat agctcagtat agagcatctg cttagcatgt gcactgacag ccgtatcaca  14580
gaggaaaaaa aaaaataagc aaaatgtgat ctgtctgcac aacaggatat cacagccccc  14640
taccacaggg gaacgacaca gtaacacaac aaaaacttag ccctgaaaat actatggtaa  14700
ataaagaagt gtcactgagg atcaggaaat gcatgactcc atttacatta tatagaaatg  14760
agaagatcag tgagcctcta ggactcaaga gatttgggat tggcagctaa agggtactgg  14820
gtttctttat gggggtaaga aaacattcta aacttaactg tgagaatgac tactcaacaa  14880
tgtcaagtgt tcaaaaatca tacttttttt ttttttggt ttttcaagac agggtttctc  14940
tgtgcagtcc tggaactcac tctgtagacc aggctggcct cgaattcaga gattcacctg  15000
cctctgcctc ccaagtgctg ggattacagg catgcgccac cattgtccgg ctcaaaatca  15060
tacttttaaa aattgcccag tgactcatga atacaatcag aggcgggaga ggacagtggc  15120
aaactcagga taccagtgtc ttttatgtct gctgcccaac tatcaatttc ccatagttac  15180
cagagaactt tttggtttgt ttcatcttat ttgttgcttt tggtagaatc tcaatatagt  15240
aagatacaag gctggcctca tactatatag ctgaggacga ctttgaactt ctaatcctcc  15300
tgcttccatc tcccaagtgg tgggattaca ggggtgtacc gctatgccca gcaagcacaa  15360
agccatttga accacacccc agccttttca gagaaacctg tacaagcctt agtgccttag  15420
```

-continued catattaagg caacaaaaga cataatgcgt ggctaccata gagtgtttgc ctaccatgtg 15480
tgaggctcta ggctaaatgt ccagcactta taaaaaagag ttaaaaacac tcatgactca 15540
aggatgacta tgcagtcttg tgtacaaagc cccgcattca atccccagca ccgtgcacat 15600
caggcaggct ctgtagagga cccagcttaa ggtcatcctt aggtaagtta gaggccttag 15660
atggctacat tagatgagac cctttctcat aaacagaata aataatttaa agctcctgat 15720
caaacactat gccttcccat cacactcaga ataaagcact ctactggccc tttaaggact 15780
gcccatctgg aagagaaacc taagttacat tccttgcttg tgtcatatgt gataacaaac 15840
tcactggaaa tacgaaaata cagtcttaag cttggtcaga aagcttcccc agcaacatga 15900
tntcagagga cataatgcag aaagtggaca aatgcaaann nnnnnnnnnn nnnnnnnnnn 15960
nnnnnnnnnn nnnnnnnnnn nnnnnnnnnn nnnnnnnnnn nnnnnnnnnn nnnnnnnnnn 16020
nnnnnnnnnn nnnnnnnnaa tcagaggaca tctttcagga gttagttctt tcctccctct 16080
atagctttca gggatcaaac tcaagtgtgt actgagcgct tatgcccagt gcgccatcgc 16140
accaggcctg cttctttgtt ttttatgggt ctgaatcaat tagcaccatt acaacaatgt 16200
tgacaatcag caagtacctt tctctacctg gctagtaaga gaagtaagtg cctttggtgt 16260
gtgaacgcag tttctcttgt gaagtgcatg gacttgatct ttgctcacaa cgtttttttag 16320
gtccttaagt tgcttgggtt ttatgggaaa ggctcttggg ttttttgaaa agattttact 16380
acaacttgat ataatcatta tttttaatcc tttaaatagt atgacttatt ttaacagatt 16440
aatattgaac tgttctttca ttcttacata ataaatcctg ccttaaaaaa taatcctctt 16500
agcttccttt ctctatttc aaatttgttt tatattttg catgattttg aacatttata 16560
aaagtaggca gacaacacag tagaaccaag tccccatata gctgtgcaca tagcttcaga 16620
ttattgcctg ataataggtc ctgttttgtc tctgttttct cacagggatg tgttattgtg 16680
tgtgtgtaca catacataca tatatgtatg tatgtatgta tgtatgtatg taatgaactc 16740
cctttaacaa aacaagtact gggctgggaa gacagcacag ttagttatgt gtttaaccgc 16800
acaagcatga caaccagagt tgagatcccc accaaccgca taaaaagctg ggcatagtgg 16860
cattgacctg tagccctggt gctggatgaa agctggggag gcaggtagat cggcagagct 16920
tactggcaac aaatctgccc agtaggtaag ctctgggctc agacatccta tataggaaaa 16980
agatgaaggg cgaggcgcag cggcacacac ctttcgtggt agtgcttgag aggcaggggc 17040
aggccagtct ctgtgaccag cagcctggcc tacatgtcaa gttgcaggac agccagagcc 17100
accacctact gagactgtct cagaaataag ttttttaaaa aattgagatg aaggagctgg 17160
taagatggct tagaaggtaa aggcacttat cactaagcct gaagccccga gtttgaccct 17220
ggaccccaca ctgtagaacc aactcctcca agttcttctc agacctccag cagagcacaa 17280
gtgtatgcag acacacacac taagtaagtg aatgtaaaaa acatgacgta gtggcactgg 17340
cctttaaacc cagcattggg aggaagaagc gggtggatct cttgagtttg agaccagctt 17400
agcctacata aggaatttca aggcagccag ggctacctag aaagtagctg tttatgaatg 17460
aatgaataga aggaaggaag aaagagagac agacttaaaa aatatatgct ggagagtaac 17520
agaagaggac accggcttgc tggtgtcttg acctctggct tgtacacata cacatgtgta 17580
gtgcatacac ccacatacaa ttgtactcag acacacacaa acatgtactc attcatatac 17640
tgcacacctc aacactcaga aaatgaaaaa acaggtacca tttacacctc cgtgttcggt 17700
ttccaaccac tcatatgtat gggttgtaaa tgcttatatc tgtatgtgtc tgtatatttg 17760

-continued

```
tgtatacatt caaagttgag tcaggatcca acgtaaactt ggatagtagt gggttgatgg  17820
tctggaagcc tgctcgcagc tgtctttttc tcctcgtacc ttttcccctg tttgtttcta  17880
cgacagcagg tcatttgtct ctaagtgtta gtttcccatc ctctctcttt tgctgatggt  17940
agccttgtag tagtcacctg tgttctctgt aaaatggctt tgccgtgtta tttcaatatg  18000
ctatcatcct catcttgcta tatttcattc aatatatgta tatattacaa gatagattaa  18060
aattatttta attttatgct tatgaatgtt ttgcctaagt atattgcacc ttgtgtgtct  18120
agtgtccaca gaactcagaa gaaagtgtca catattctgg aactggaatt gcaggtggtt  18180
gtaagccacc atgtgggacc tggaaaccaa atccaggcgc cannnnnnnn nnnnnnnnnn  18240
nnnnnnnnnn nnnnnnnnnn nnnnnnnnnn nnnnnnnnnn nnnnnnnnnn nnnnnnnnnn  18300
nnnnnnnnnn nnnnnnnnnn nncctttggt caaagatcct cagtttcgac tttgattacc  18360
cagacttcct gtttctctca tggaacagtt tccccctgag atttactagt ggaagaaagg  18420
cactcaaaaa gcagggagcc ctcgtacaaa tgagacttcc tagctatata attaggccga  18480
gatgcacaca tccacagtca ttacccttct tcagagcctt tgtcatgtca agtgtatttc  18540
gcccatgtga actttagaac tggcttgttg tgtttcataa aaagtgtagt tgggctcttg  18600
attgggattg tgttaaattt atagattcat ttagggagag ctgacaactt tacagtatta  18660
aatgttttca tccgcggaaa aggttgtctt gccacttact tgggctttct tttatgccct  18720
taagtaaagg tttatagttt tctttatatc agtcttgcac atttcctgtt agatttattt  18780
ttgcttgtaa ggtttccttg gttggtattg tgtataaaca ttttctccca attacatacc  18840
ataattgatg gttaggagta taaataaaag gtagaatttt aaaattgctg tatgaatgac  18900
tgctttgcta taattcaaca tcttttcatt tttatgccaa tctacttgac atgtttaggt  18960
taaatgatga tatctgtaca gagtaatcct ctgatccagt atttgcacat cttactttct  19020
aacgtccata gcatagatac acatcttata ctgttgagta catatatatt taaggtattt  19080
accatagtct tataatatgc agcgtgcttt ggttcaagac agttgccctg tgttcctcaa  19140
cattaacatt tttttcatca caaatacaca ttgaccttta tcaaattttt aaaactatct  19200
tgagagaaat gaccattttt cttaatctgt taatgtaaaa tttttataaa aatagttata  19260
aataatatta gcctacatat ttcttctgtt ctctttttca actcttagaa tcagagtatg  19320
gtagtctcag actaaaccag gagcttccta tctgtttctc tgttcttaag tcacttatat  19380
aatgtaagga tgctgtgtat atctgccagc taggccttat atacaaaagg cacccatcac  19440
aaccttctaa aacagtctta ccacttagag accatgttca aacatatggg cctttgaggt  19500
aattgccaca ttcaagctat aatattgtta tctaagggaa tatcttcact tctagcagat  19560
gcctaaaaat atctaaaggt aaacactggt aattgctgtg tttgttgatg ctgctcttcc  19620
tcctcctcct cctcctcttc ctcctcttct tcctcctcct cttcttcctc ctcctgcttc  19680
tccttttctt catcctcctt tcttttctta tttttgaggc atgatttcac catgtagccc  19740
taggtaaccc gtaacttact atgtatgtag accaggctag cctctgtctc ctgagtgctc  19800
atattaaagg tgtgtatcac catatccagc aacacttgct ttgagatggt tagaggaaaa  19860
aaaaatatac gtaaataaag atggatgcca attactaaat tgttacttcc agtcaaactt  19920
tgtacctagt ctaaggccaa aatagggatt ttttttctac tttgcaagtt ggctccatta  19980
agaggctttt cttctcttgg tctcactaga taggaaggag agagaggagg gaaggagaga  20040
aagcggttga ggagtgggag gtagtgtgac cgagaatacc cagtaggctc atatatttaa  20100
atatttggtc cctagttgat agaactgttt agaaagatta ggaagcatgt cttaggggct  20160
```

-continued

```
ttgaggtttc aaaatttaat gctagaccca gtctttcaag ggagggggcg gtctgtctct  20220
ctctgcctgc tgcatgcaga gctctcagct actactctag tgtcaagcct gtgtgcttcc  20280
tgcctcaatg atcataaatt aactgtaagc aagcctccaa ttaaatgctt tcttttatag  20340
ttaccgtgat catggtgtct cttcacagaa atagtaacct gtggtgattt taatatgcct  20400
ggaccaggga gtggcacttt taggaggaat ggccttgtta agaggaagtg tgtctctgtg  20460
ggggtgggca atgagaccct cgtcctaacc atgtgagaac cactcttctc ctattggcct  20520
tcagatgaag atgtagaact ctcagatcca cctgcaccat gtctgcctgg aagctgcctt  20580
tgttcccacc ttgctgcccc aattaaatgt tgtacttata agaattgttt ttggggggct  20640
ggagagatgg ctcagcagtt aagagtactg actgctcttc cagaggtcct gagttcaatt  20700
cccagcaacc acatggtggc tcacaaccat ctgtaatggg atctgatgcc accttctggt  20760
gtgtcagaag acaggacagt atacccacat acattaaata aataaataaa taaataaata  20820
aattcttttt aaaaaagaat tgctttggtc atggtgtctg ttcacagcag taaaacccta  20880
acataaccct gactaagaca acaagtgagg aaaggtgttg tgtgacactc tggatctctg  20940
gaagctcacc tcagcatgaa gcttgtcgaa gcgnnnnnnn nnnnnnnnnn nnnnnnnnnn  21000
nnnnnnnnnn nnnnnnnnnn nnnnnnnnnn nnnnnnnnnn nnnnnnnnnn nnnnnnnnnn  21060
nnnnnnnnnn nnnatctaag tacactgtac tgtcttcaga cacaccagaa gagggtgtca  21120
gatctcatga cagaggttgt gaactcagac ctttggaaga gcaatcagtg ctcttaactg  21180
ctgagcatct ctccagccca aaataattct tactagtaac atggaacaat caagttttat  21240
tatatgatac atattaatca acttataagt acatgattat gcacatttat catatcgtgc  21300
aaccatcact gctgtcgttt tgttttgttt tgttcttttg aggcccggtt tctgtgttgt  21360
tctggaactc actctgtaga ccaggctggt cttgaactca atgatctgcc tgcctctgcc  21420
tcccaagtgc tgaaaacaaa tgtgtgcacc accacctctg gctatcactg ctgtcttttt  21480
ttttttttta acagttattt atttcgtgca tgcatgtgtg tataagcatg taacgtatgc  21540
catggtatgc atgtggaggt cagaggacaa ctttcaggag ttagttcttt cctcccactg  21600
tgggttctag gaaccaagct caggttgtta gacttgcatg gcaagtgcct ttaccacaga  21660
gccatcctgc tggccctact ataggtcctt atataaaaag atcatatgcc gggcaaaaac  21720
caaacaaaaa ataaacctca aaaaacaaaa ggaccatata atattgtggg ggagtggatg  21780
aagtcctgaa cgaatgtgtt ctgttgacat gtctgtactt cagacccatg ggaattggca  21840
aagccttcct ctggtcctgt gaggatgctg atagtctgtc taaaaactag agatcacagc  21900
tttctcctct ggatgactgt aaccccagat tgttcctctt cagagactgt ccaccaagct  21960
accctgccta cttaagctgt acacaatgaa tgagctgagt ttccaggtta cagcacagta  22020
gacactgtcc atcagtgaga gcacagccta gcctaacagt acacatgtct gctttcttca  22080
cgtttccaga accaagcctt gctggataga gcatatttgt ctgtttggct tatttcactt  22140
gataaaaagt tttcaaggag ggccaggtgt ggtggcacac gcctttagtc ccagcactcg  22200
ggaggcagag gcaggcaaat ttctgagttc gatgccagcc tggtctacaa agtgagttcc  22260
aggacagcca gggctataca gagaaaccct gtctcaaaaa accaaaaaaa accaaaacaa  22320
aacaaacaaa caaacaaaca aaaagccaaa aatccaaccc cccccaaaaa aaaaaccaaa  22380
ccaaaaacca aaaaacaaca acaacaaaaa gtttttgagg tttaatttat tgcatgtcac  22440
agaatttcac tgtttaaaaa aatggctgaa taatatttca ctatccattc acgtatttgt  22500
```

-continued

```
aggcattcat gtgtgtagtg gtttaaataa aaatagcccc cataggcttc tacagttgaa  22560
tgcttagtca ttgagtagca gtactagaga gggaattgaa ggtgtggcct tattggagta  22620
ggagtggcct tgttgcagga attgtgtcac tttgaggtcc cagcaacaag gttgctctga  22680
tcacatccaa agacattcta ggtctatgtg atctggctgg aattcagaca tgcccttaat  22740
acacaccttt aatcccaaac aatgaaggta aagttagttt ataaaaagaa gcacccatgt  22800
ttgaaagtga cgtttaatta agagtgatga attagagaaa gatctgctgt cacagagcag  22860
agaggaaaga gaggcagcat aagagggagc atggcagagg gagagggagg aggggttttc  22920
accagggcat ttgtacagag acaggttgca gagctagaac aggtgaagac agaacaagcc  22980
agagaatgag aaggagccag gagattagga cagattgcca atgttaatag gctaagcaga  23040
gcattttagt cagaaactga gagaagtcaa attgaatcag ttagcttgga aaggagtttg  23100
agcagcaaca gctgagttaa actagccaac agaatccaga aagaactaga aaagatgagc  23160
ttactcagca gcaaatctca gaggctaaaa acatcttaga cctagattag actgcatgga  23220
ggctagacgc ttccagggct aggcctaggt tagcagacgg agagagtaat aagccttgga  23280
gacaacagtt aatacagaag actatgtaca gacatggata tgaacctctc agccacttct  23340
ccagcgtcat gcctgtctgc attgttagga gtcatctagg aaaggctaag ggcaggcaag  23400
caacttttcc agagatggtc cactgttttt tgcatggctt ttgagaggcg agctctgaga  23460
gggaaggttc caagagactt catcccagga ttgctgctta attacgacat gccttttctt  23520
gtcactgtta tttagtataa tgactcctga gctttagccc atcctattgg gcatatttcc  23580
tgcagatcaa cataaagatg aactttcaca aattaatgct gtttagatga ataaatgatt  23640
ttataaaatt cctgatttga tttaaataat tttaggaaga aagctttagg agatagttta  23700
gttggtttgc cagaaagatg taataacgtc agaatcaaga atagaatgtg gctgggcagt  23760
ggtggcagat gcctttaatc ctagcacttc ggaggcagag ataggcggat ttctgagttc  23820
gaggacagcc tggtctacag agtgagttcc aggacagcca gggctacaca gagaaaccct  23880
gtcttgaaaa acaaaacaaa aagaaaagta agtaaaggct gcataataaa gaatacaatg  23940
agctttcaca actacaccaa aaagagacat gcttgggaca aatttgtgat caaggaaaaa  24000
tattcattct agatcaggtc caaggatgaa gccacaagtg tgtgatatga tgaacaagac  24060
catggataaa ctgttgtttt gagcttaaag aataaaacac tgctttgaaa ttaactatca  24120
acattctact gtaactttcc tttttataaa ttttatctat gagataattt tctaaagaac  24180
ttgtgtctat aaaggtatag aaggacagag agaaagaaat aaggtgtggc atctgggctc  24240
tgctccatcc acccaaataa atatgtgtgt gtgtgtatgt atgtatgtat gtttatctat  24300
atgtatgtat atacatacat gtgtaggtag gtatatgtgt atgtatataa gtatgcatga  24360
acacttggga agttgatgag acaagtgaga ggttgggccc ccnnnnnnnn nnnnnnnnnn  24420
nnnnnnnnnn nnnnnnnnnn nnnnnnnnnn nnnnnnnnnn nnnnnnnnnn nnnnnnnnnn  24480
nnnnnnnnnn nnnnnnnnnn nngaattcac tctgtaaacc atgctggcct tgaactcaga  24540
gaaccgtgtg cctctgcctc taaagtgctg ggattaaagc atgtaccacc acaacccagc  24600
tagtttaaat gtttcttatt tttttgttta tgggtctttt acctgtatgt atgtgtgtgc  24660
accatgtgga tgcatggtgc ccttagagtc cagaagaggg tatcagatcc cctggaactg  24720
gagtgacaga gggttgtgag ctgggacttg aacctaggac ttctaaaaga gcagcaggtg  24780
ctcttaatag ctgagcctta tctccaggcc gtcccatgga tttggggggc tttgtttcat  24840
tttattttgt tttgagacag ggtgtgtagc tcatgcttga atttactatg aagccctgac  24900
```

-continued

```
tcccctcaaa gtaaagatcc tcctgcctct gtctacagct gctaggattc gaggtcttgt  24960
accacatgct cagcacagcc atgattcata acaataaaaa aagaaagaga gacctaaatg  25020
gccttagaga taaataaatt attttttttt taaagattta tttatttatt tattacatgt  25080
aatgcacact gtagctgtct tcagaccccc cagaagaggg agtcagatct cattacagat  25140
ggttgtgagc caccatgtgg ttgctgggat ttgaacttcg gaccttcgga agagcagtcg  25200
ggtgctctta cccactgagc catctcacca gccccgagat aaataaatta taatgtatgc  25260
gtaaggtggg atcatctcag tctccgggaa tcttgcctgt tactccttcg ctctcccttc  25320
tattcatgct tgggtaactg gccctggctg attgatgaga gctgatttcc ccactgccct  25380
gtggcaggga ccactgcgcc cacagggctc cctcaggatc ctcagtacag agctgcacag  25440
ctgggtggaa gtagagggct gcatatataa cacgatctca actttatttc tttaaataaa  25500
aattttattt aaattttata cagctctata taaacgaagg aactattgaa ggttcagcaa  25560
ggacctgcca acggttgtca agggtaatgg cgatgtagtg atttttttc cccttccat  25620
tttacttcca tactttctac attaccccac aactggcaag tattatttta aaatgaaagt  25680
aaatagtgac agatgacttt gaaggaaaat tgaatcggta aaaagaaagc tgagagacca  25740
cccgggaagc ccaggctaaa tgtaatctgg gtcaggcctc ccaggcctgg ggtctcaaga  25800
tggtcagctg agggaccctg gtgaccctct tgggccagca gggacgggga ggagccggaa  25860
gctgagtacc caaagtgctc ctctgggctc caagggcctg cacagagact gtgtgggaat  25920
caaaggatac aggcatgagg actgaggcct gacgaaccca gctatcattc gtcctagaac  25980
aggaggcaga gctccaagag tccaaccaag aggcaggaag ctttgggacc cgagatgggc  26040
gatgggatta gaaaggcatg tttgcaaata ctttcaaatt tacgatgcac actcactgga  26100
aaccccaccc ctgggtgtcc cttccctgcc tcttgccaca cccaatagct gacatcactg  26160
gagaaagtcc caagaccagg ctggctggag ctcctgatag gttccaccct cctgcagagg  26220
gccctcgaag actagcttgc tcgcccacac cgccagatgt ctgtgtcttt ctctcttttg  26280
cctcccaccc tcgtctcttc ctccaacctc agtggagggt cccctgcttc ctggggaaag  26340
tagaacttgc cagtgctcac tgtaatgtcg tccctgtagg tgtcatggtc ccccattact  26400
gggagcaggt atgcctcaga tctccctcta ttcgctgccc tttcaggctg tctcagtttc  26460
tctctgacag ttcctctcct cctgaatcct gcttgttggc atgcgaacag gctcaatatc  26520
ttccatctca aaaaacaaac actgggaagg tgttgagaga cagagagcat gggtaatggg  26580
tgccccagct tggctgggaa ggggtaactt acaatgctct actgcccagt agggtagctg  26640
cagttgtcaa ttaattgtaa atttcaaaat agctagtaga gaggatttta gatgttccca  26700
atcccaacac aaagaaatga taaacattca aggcgatggg tatgctaatt gctctgatct  26760
gatcaccgca cattgtatac atgtttttga aatgtcaggc tgtaccccat aaatatgtac  26820
aattaccgtg cagtgattca agataaaaac tataatttta aaaagctaaa aacagaagga  26880
aatagctgcc cttgaccccc ccaccccac aaggtccttc ctgtttgtcc agccacttaa  26940
tgtcagagct tcctgtggga gggtggtttt ggtgtacaca gacactcctt cctccctcct  27000
tccccataag aggagtcacc cctgtcccac gatgccatgc agggccacat gcgtgatatt  27060
aaccagtaag atgtgagcag ggatgatacc tgtctcttat aacaaacgga aaaaaaacca  27120
caccaaacca aaaacaaaca aacaaacaaa caaacaaaaa cagggttggt ctgtccctgt  27180
gtcttttccc acataaagtt aagcacacaa agtagccacc atttatttat ttgtcccctc  27240
```

-continued

```
ccccacccct ccccgagaca atgtttctct gtataacagc cctagctgtc ttggaactca  27300
ttttgtagac caggctggcc tggaactcac agagacacag agattcacct gcctctgcct  27360
cccaaatgca gggattaaaa gcatgagcca cgaactaacc agtaccccag agctcttgac  27420
tctagctgca tacgtatcaa aagatgacct agttggccat cactggaaag agaggcccat  27480
tggacacgca aactgtatat gcctcagtac aggggaacgc cagggccaaa aaaatgggaa  27540
tgggtgggta gggaagtggg ggggagggta tggnnnnnnn nnnnnnnnnn nnnnnnnnnn  27600
nnnnnnnnnn nnnnnnnnnn nnnnnnnnnn nnnnnnnnnn nnnnnnnnnn nnnnnnnnnn  27660
nnnnnnnnnn nnnggcagga tcctgtgttc atgtgcaaca ctcgatgcaa gctgtgtagt  27720
gtttggttct gagcacctga aggggaccaa gcaggctgat gcccaggcca cgggttcttt  27780
ctggccccac tgcccactcc caccctctgg catccccatg atgaacatgg ccacagatca  27840
cactactctg ctcctctccc agatccacgg agccataggg tccccagatt catctctgca  27900
gctaacaagc tgggcagtgt cacctccctc aaggttcctt tcctgctctg agcagcagtg  27960
tctcccacag tgagacactc atgtccactg gaagatattg tagccattaa attcctgtgc  28020
taaaataact agggggactt gtcaatcact acactcttag ccccggactt ctgactcata  28080
gagggtggtg acagctcagg gacctgcatt ctaccaaata gccatgtgtc cctgatggag  28140
gaactgcccc tggacaacct ctgcagcaac tgaaccctct gtggtctcct agttcttctg  28200
gacaggtgtg accccagtac ctagtgccag gtgagagagt gctagggcca cactaagggg  28260
tgacaggaca aggttggagc tggtagatgt ttgggccacc aaagagaaca ggtcagtagt  28320
aaaagccatc atggcctgag ccagcctgcg agtctcctct gcagttggga cactcttgca  28380
gtgtcctggg gacctcttga gggtagcatg gtcaccaaaa tcctacaagg acagatcaga  28440
agtcagtgag gtcaagggaa cagctctagg ttctctgtgt ccctcacgga ccttttttt   28500
ttttttttt tttttaagat ttatttattt attatatgta agtacactgt agctgtcttc  28560
agacagctcc agaagagggc atcagatttc gttacggatg gttgtgagcc accatgtggt  28620
tgctgggatt tgaactcagg accttcggaa gagcagtcgg tgctcttaac cactgagcca  28680
tctctccagc cccctctcag tcctgatgcg acagggcagc aaaggccttg tcccagatct  28740
gaggagagtc atgctgaagt ccttcctacc ccaccccttc cgaacccctg aacatcagcc  28800
ccataactac tgactccccc acccccattc ccttgcttcc actgatccgg tcctcctctt  28860
ccctctggcc ccacccattc ttccccagcc ccacctgatt gtacctggtt gtccaacttg  28920
aagagggcag gcaggggcag cttctgctgg gcctgctcac tcactggctg tagaaatgag  28980
aaaggagatg aagaaaaggc ccttcccatg ggtccccatc ttgccaagac ataggtgagt  29040
ccctttggct cttcccccta aacctctcac ttttgagtac ctgctggccc gggagatcca  29100
cggcgctcac cggagagaac tgttgagaaa agggagaaca gagaactcag cgttcctccc  29160
tctccaccct tctggcctct cccagatttg cccccgcccc ccagcatctc cttcagcctg  29220
actgaccact tcccactcag acctcagctc tgcctcaccg tgaaacaggg accttgcagg  29280
caggacaagc tgagtacgag gagcccccgg agcagtgcca tgttcctgta tccagaacag  29340
ggagtgttag ttcctacctc acgctcgaag gccaagcagt agactgctat ccatgggttc  29400
cttgaccgca ccaggctgcg gaacctggac tcaaaacata gcagctgtgg acctcactca  29460
ctctgagagg tgggatttcc ataagctttt tttttcacct gtacatttag tcttcattct  29520
tttcgtctta cactgtggat cagtcctggg ttcaaattta aagccctcat cttgcaagag  29580
gaccttgcgc atctcccttc atgcctttgg ctttaccctg tcttggtaat tcatggcaga  29640
```

-continued

```
agttcttcct gctcccatgt agatgttgag gacccaaata agaatctctg taaatactga  29700
gcatgatgcc tggcccccac cctagcaaag ccacctgacc tgttgttcat ttcatccagc  29760
ctttctcagg ctgccctggt cctacccaaa ggctctgaga gctaatctgg gctggcaggg  29820
cagccagaaa cttctttgtt gaccaatgaa tgactggccc agacaccttt ggacttacgg  29880
gaactacaag cctcatccca cttctgctcc aagttctgat ccagggtgct tcggggaagc  29940
ccagctggcg gaagggggga ggctctcagc ctagagagcc ttcctttcca tcctcagccc  30000
cctacccagg ccttatttca ggcaccagct cttctaaaag gtccttctgt tatccctaga  30060
cctccacaac tgtgttcaag aaccttcagc cagggcctca tctccaatct ggatatatga  30120
tttttctcgc caagagtagg cctccaggtt ttggagttct agaggtttct cctggagctg  30180
cctggacctc tgctcctcac caccccagga cgctgtgaag ctgcaggctc cctgaataaa  30240
ttcatccaga ccccttgcca aggtgccagc tgtctacttc ctctgctgcc caagcagcag  30300
gctgcaccac ccctccatcc tacctcttca ggcttcttag cgcagcacac gcagcacacg  30360
gtgttctcct ggaccagctt gctccccacg ctcccccagt gcagccagca gggcctagct  30420
ctctcctccc acaggacctt tgctctcagc caaccccgt tcagcttgtg ttcagtgctg  30480
gtaaatattg acctgtacat ccggttaaac attgatatgg gggccagaag accctttccc  30540
atcaaggcta cccagaaccc tgcctgagcc tggagaaggg gtttacagga gcagataagt  30600
gaggaggttg ggcctggcaa gccttctaat gatccctcaa catagggat tatccacagt  30660
cagtgaggct cagagaggct gtgtggcctg tgtaagggcg cagagtgggc tccagagtca  30720
cagccaaagt cccaccacca ccaccaccac caccaccacc accaccacca ctaccaccac  30780
caccaccacc accaccacca ccaccaccac caccaccact accaccacca ccaccaccac  30840
caccaccacc accaccacca ccaccaccac cacctcatct acccatacta anttgaggct  30900
nnnnnnnnnn nnnnnnnnnn nnnnnnnnnn nnnnnnnnnn nnnnnnnnnn nnnnnnnnnn  30960
nnnnnnnnnn nnnnnnnnnn nnnnnnnnnn nnnnnnnnnn tctatgaggg ttacatttta  31020
gaacatctct cctttttcc tttttgagac aatcttacta tatttaggct cccttgaac  31080
gtgtgatcct tctgcctctg cctcccaagt gctgaggtta caggcatgca cagtcacatc  31140
tgcctacaca atgtcttagc agcccttagc agcaccaggg gtcaggaagc cctcaactgt  31200
ccctttagct ggcttctctt gtgaagggct atgtcttctt ccccttccta gcatggagac  31260
ggctcttagc cccagagcct tccttccttc aggttaaaca gcaccagttt ttggtgggac  31320
ctcccatttc cctctatctc cctaagcaac gaccttttct gctctgactc tcatctggca  31380
cttggaccac aagacaaaac tgcagcctgg gctgtgtgtc ctcgcacatc attcctgtgc  31440
cccctggag tcaggtctag gggaggaaga cagggttcac gactcagaaa agaccactgg  31500
ctgtcctagt gtgccctcac ccatcctata gcacgcacat gctgatgtgc cccctccgct  31560
ccatcaccat cctctcatgt acacgtgccc tccctcgcca gacacatgca tcactaactt  31620
ttctgacttc ccagaaaaat atctgatctg agaagttagg agtctgccat catcagctat  31680
ggtccttaaa attaagtcag acaatccatg ggacatgaag ggcaacaacg agaagactcc  31740
tcgttccttg ttcactctgc ttttggcagc accaccagca ggaaccaacc tggctctccc  31800
taatccctca tctatagcag gtctcccggt gggaatttta gggacctctg tgttctcatc  31860
caggggcact gccactcagc tgctcaggga gagacccctt agaacaacaa agaaatcaat  31920
gcagatttag gcttcttgtt tcccttccca gcccctccca tcacaggcaa cagcctccct  31980
```

-continued

```
tggctgagcc tcaggaggct gatttatcag agaggtgctc agagaggcac ctctggtccc  32040
tctgggtagg tagcaactga gacaggagga gatggtcacc ctgggcatcc tctaccagga  32100
agtaaatgag ataccccttgc agatgggacc cctgaagttc ctcccggggg cgggggtggt  32160
ggtggtggga gtctaagtca cagatctttg ttaccacgtg gttagactga ggactgaatc  32220
tgaggtggga aatctgatgt gcatggggaa acacagaggt ccaatgctgg ccaagagcta  32280
caagcaggga caggtgctag gggatgtct gaatgttcca ccccaagcca caggaataac  32340
ggaaatggag actctaaagg gcagaaagtg agggtgtgca gcaggggctg cacaggacac  32400
atgcaaggcc ctggctgcaa taactgggtt ggggaggcag tcattggcta gccaggggca  32460
ccaggacagt gatgccatcc tgtccaaagg gcagtgtcca agccagattt ctaggctcca  32520
gggggaggag ggtccgggga gaggggtcaa gattctcccc ctctgagtca aggttggcct  32580
tcccatgtgc cccaaatcag gaggcacaga aactgggatg ttgtggtctc acatccaagc  32640
tgagaagaca agtgggagcc agtacatgtg tttcagatta aacccagtcg gagacaaaca  32700
tgttgctcct cctcctccca gagccaagct gccttcaagc cacatggcag tgaatatgcg  32760
gacagtgcag gggaggacac ctctctctcc actggctcaa ggacagtttc aaggggttca  32820
ggctggctgg ctcatggcta cgccgctcac cccctggaca gtttggggtt tttccctcct  32880
gaaatcttgg aatctgaatc agcctgagat accccataat tgtacctccc aacaccccca  32940
gaaaggtcag ccctgcagaa cagaactctt tggtccccac ccatccccct cagccctgga  33000
ggctgaactg atgggcagct aaggtccaga cagtggctgg ctcttggaaa gcctgtctct  33060
ttcctttgac tcagaccact ccctgccgtg gcttacatca ggaggtgcaa gggctgcagg  33120
agggcagcca gaccccacaa accagctagg ctaaatggtg cttattgttc gcaagaggcc  33180
atgacctcat ttgtctccca gctcttttgg taagagagaa tgagaggaag ctggacagag  33240
aacctagcag gcctcaggca gcccactgct ccttgctgta agggaaccag caccgatggt  33300
tctgaaaagc agcgatccga atggagtcag gctgagctgc aggaagctca ccttccttgc  33360
tcactgctgg tggaagcaac ttcaggaaga gcccagccta tgggactata gctcctccgg  33420
ggtactgctg agtccagccc cagagcttag ctccctgctt cccaccaccc accaccacat  33480
cctttcccaa caccattcaa aaccccagtc cagcctctcc tactggtcta cagtgagcgg  33540
ctaatagagt cctgggcctc tgtcccccca attctctctc ccctctcatc tgttcacctt  33600
ggttcctaaa ctgcaggggc tactataacc ctacctccac ttccttgcac ccctcttttc  33660
tgctctctgg ggtgcccctg ccactcccag tccctctagc cagggagcct cttccatatc  33720
tgtcttcccc aggctagacc aggcgctgcc ttacctgtgg ttgcggcagc ttctctcaca  33780
gcctgcactc tgaggggctc caggaagcag tgaggggagt agctgcctct caaccagcgt  33840
ccagcaggct tcagattaca gctactcttt tcttaaagtg acctgactcc atttggaatc  33900
tgtgattgca tcattgtctg gtgttaactt taacccactg ctgcccttcc gccatgtggc  33960
tccaagacca cacgttggcc accctcctct cccaccacat ctcccttgga tctttatctc  34020
tcttcattgg gaccttcatt gggacatgat ggctaacttc aggggcactt gggccagcct  34080
ggggtaggtc atgagtctga acttgaacat ctgaaaggat tggctgagag gcaggctgca  34140
tggagagact gtgagccagc cggtatggag atgctgggtt cttccaggcg cttggctctg  34200
gctcactgca ggtgggagca aggtgattct tctcccctcc tcacctggaa aatgaaggaa  34260
tgggactgta cctgacagct ctgaaggttc caaaggacag tggggtgggg actagagagt  34320
tggcccagtg cttatgagca ctggctgctc tcgcagagga cctgagttct gttcccagct  34380
```

-continued

```
cacatagcaa ggactcgaaa ctgcttggaa ctccagctcc agagaatctg acgctatctg  34440
ctnnnnnnnn nnnnnnnnnn nnnnnnnnnn nnnnnnnnnn nnnnnnnnnn nnnnnnnnnn  34500
nnnnnnnnnn nnnnnnnnnn nnnnnnnnnn nnnnnnnnnn nnatgtcagg catggtggtg  34560
catgccttta atcctagaac tcaggaggca aagcagatgg acatctgaat ttgaggcccg  34620
cattgtctac atagcaagtt ctaggctagc caggtacatc ataagaacct ttctcaaaaa  34680
ataaataggg ccagttggca aaatttagct tgccctccta acacaagaac ccaaagtcaa  34740
ccccagcaac catgtaaaaa gaagcaaggt gtggtggcac ttgcttgtga tccagcattg  34800
tcaaggtgga gacagacgga tccatggggc tcactggcca gccagctagc tggtctactt  34860
agtatgctcc cagccagtga gagactgaaa aataaataaa taaataaggg gttaggaaga  34920
ggtaacatgg tggctcagtg agaaaagata cttgtcatac aagcctagca accctcaatt  34980
ttcagtggcc actaaaggtg gaaggagaga accaactcca aagaattgtc tcctgacagt  35040
tttatgctgt ggtacacaca cacgcacaca cacacttgtt acatgcatat gcatacaatt  35100
aataatttaa aatgttatgt gtatgggtgt tttgcctaca tgcatatctt tctgtgcacc  35160
acatgtgtgc aatgcctgtg aaggctagaa gaggacatca gatcccctcg gagttacaca  35220
gggttgttag ctaccatgtg gattctggga acaaaaccat gggttttcca aaagaggctc  35280
ttaatcactg agccatctct ccatcccctc aatagtatat atttctgggg ctggagagat  35340
ggctcagagg ttaagagtat tgactgctct tccagaggtt ctgagttcaa ttcccagcaa  35400
ccacatggtg gctcacaacc atctgtaatg gaatctgatg ccctcttctg ctgtgtctga  35460
agacagctgc agtgtactca tatacataaa gtaaataaat aaaccttttt ttttttgtt  35520
ttgttttttt tgtttttcga gacagggaga cagggtttct ctgtatagcc ctggctgtcc  35580
tgaaactcgc tctgtagacc aggctggcct tgaactcaga aatccgcctg cctctgcctc  35640
ccaagtgctg ggattcaggg tttgcgccac cgccaccacc tccaaggctg ctgctgcggc  35700
caccaccacc ccaccaccac actacctgac tatttaactt ttaaaggcag ccatctcatg  35760
gaaaatgaca cctagcattg tcctctggtc cctacatgac cccatgtgca aacacatacc  35820
tgcataaaca cacataaata cataagtaaa cttagtctgg ttgttttgga aatgtgctat  35880
ggtttggatt gtgtcccccc aagggaaaaa ttgggtccca gagtagtact attggaagag  35940
agtagaactg ttagggttta ggcctggtgg gaagtggcca tggctagaga gacatgccaa  36000
ccaaggggaa tctctggctt catcttttcc ctttgctttc aggtcctaag acagtcacaa  36060
ggctgcttca ccacatgccc agaagcaagg ggagcagtca tggctgggac cgctaatgca  36120
gctgttgatt tccccagata tttgtagtag taagagacag gtgaggaacc ccacagcaag  36180
tgttagtaat tgtgtgtgga ggtgccctcc ggggacgggg gccctcctgg ggcaggacgt  36240
tcctcttcct catccacctg cactccgaga acaggaaatg gtgactttgg cagagcttaa  36300
gcagagcccg ttcatgttac aagtatgtaa attcataagg accagtttct ctccatatga  36360
aacagcttca aacaggagaa ggaagaagca aacattaagg aaaagctctt ttattgcaga  36420
ggctacactg aagctaccgg ccgccttcct ggaatgtata atcagcttcc ctctgggggt  36480
tctgtagagc actgagacat taagtactac tggggtccag gattctgcct atgaagagga  36540
gggcccccgt gtccgtgtcc ctcagaacaa agaggaaagg ttggttaagg tgatagtcta  36600
gcgggaaggt gaggcggacg ggctggaggc ctgggctggg gctgcttcct gccccctctt  36660
cattccactc gaaagcagcc ctgtgttcca cttgggtgag cttcacgggt ttgccagtaa  36720
```

-continued

```
tcttgctgaa gtcgggtgat tcaaacaacg actgtagctc tgtggagatt cagagattcc  36780
attaacacca cacacacaca cacacacaca cacacacaca cactccctgt ttgtgtaggc  36840
tgattttcaa gaaagcaagc tagaagtgga gtacctcaca gtgacttgtg agctatgagg  36900
cactctgtga caggctcagt gacctacctg agaacttata gccaagatgg ctgaagccag  36960
acctggcctg agagaatgtt ttgggctgtt ataggacaca tagagataca cacacacaca  37020
acacacacac acaccaagga ctgagtctaa tgggaggtgg ttcttcattc ccctcccctg  37080
taatggtgtc acatgttccc tgagccaccc tacaaagaaa gccacaggac tcagttctgt  37140
cagcaaggtg gcaggctcca agactcagcc ccgagcgcaa agtggccttg caaacatact  37200
catgtcctgc agagacttgg taagttcgcc ttcgaagctc agcttcagct tggggacagt  37260
cagcacagct tggatagtct tcagttctcg gtcgatgtca tgaatgaact cagaggtgag  37320
gctctcttct atcatggtca agttctgggt cacggtcagg ggcaggaaga agatgatgct  37380
catacttcct gtcaagggca gctgggcaat ctaacccaac agagatgcgc acaggttagt  37440
tgtgagccag aaaaaacaaa acaaacaaac aaaaaaacac caacagctgc cttcccctct  37500
gctgtaacgg ggccccagcc ttgtgctccc cagcctcagc ctgggctgta ggctactggt  37560
tactggcagt ccttccatga gtagggagtt ttcttctcag cctaaaaccc acagaagttt  37620
aatgaacaca cgtttgtttg tggttccgct acggtttcta ttgtgataaa acatgactga  37680
aagcaacttg gagaggaaag ggtttatttc atctgacaat tcgcagggtg tcttctcatc  37740
actaagggga ctcagggcag gaactgaagc ggaagccgtg gaggaacgct gctttctggc  37800
ttgctccccg tggcttctta gcctgctttt ttatgctatc cagaaccact tgcccaggag  37860
tgacactgcc cattgtgggc tgggcccccc cacatcaatc actaatctag aaaatgaccc  37920
acgggtttgc ccagaggcca gtctggtggg ggcattttat caattgagtt tcacccttcc  37980
aaatgactct aacttgtgtc aagttgacca cacgaatcag ggcctggttc ttaggagctg  38040
aagtggaatg tcccccagag actgcctgcc agcactgctg accatttgct ttgtatagag  38100
cattgaacca gaaatgaaca ataaaatgga tcctttgaac agatgtgttg atcctagggc  38160
ctgtggacac agcgactggg cttcccagag cccccatgga atcannnnnn nnnnnnnnnn  38220
nnnnnnnnnn nnnnnnnnnn nnnnnnnnnn nnnnnnnnnn nnnnnnnnnn nnnnnnnnnn  38280
nnnnnnnnnn nnnnnnnnnn nnnntggcct catcaggtat cagagagaga gagagagaga  38340
gagagagaga gagagagaga ggataaaagg ttagcccagt ggtggtggca catacccttta  38400
attccaacac ttgagaggca gaggcagggg gagctctgtg ggccagtttg gtttacagag  38460
taagtttcag aatagccagg gctacacaga gaaaccctgt cttgaagaga aacacacaca  38520
cacacacaca cacacacaca cacacacaaa taagatcttt aagaagaaaa gaaaggatag  38580
tggggaaaca tctgagcaga ggaagaaatg gggtgcgcag gacacccacc ctcagaggag  38640
gccctcactg gaggtgtctg cacaggagaa cacttgcact cagcttgccc tagggcgtca  38700
gaactcagaa ttcagtttca aagcactgac aggagcagtg actggggacc ccaggttgaa  38760
tccccccttt atctaaaatg agtaagaacc aaaaaaacaa aagtgtttgg gatttggaat  38820
ctgggttatt tgcatctaca aaagaggtct tggggaggaa acccagttct acccctggaa  38880
ttcatcagtt tcctataccg ctgactacac aggggctgaa ggtaatctca atgttttcat  38940
aactggtgtg gtgctacttg ctcatgatcc caacacttgg aaggtaggtc agaagttcaa  39000
gagcagtctt gactactcag tgaatttgag gctagcctgg gctacatgaa aactcataaa  39060
acaataaaag aaaagaaaag gtggcgagtg aggtggccca tcaggtaaaa gtgccaacca  39120
```

-continued

```
cctcgcctga aagcctccac acggaagggg aaagccagct tctacatgtg gtcctctgcc  39180
ctccgcatgc accatggctc gtgcaccccc acacccaccc acccacccac ccacatgaca  39240
taaatacttg taatgattag tttctgaaga acaatatttt cgttgatctt gtttagggaa  39300
caaagttcgt gcacattgac ctgtcgaccg tgtagtacgg gatccgctcc aggaagctaa  39360
agattttggg atgcttcatg ttgcagctac tctgatgaac agtgttgctt tctgggccag  39420
gtaatggtgg catatacctt tgatcccagc acttgggagg cagaagcatg tagatctctg  39480
tgagttcgag atcagcctgg tctacagagt gagttccagg atatccaagg ctatacagaa  39540
aaacccctgt ctctaaaaat cactaattta aaaaaaaatt cctttctaaa cctatataac  39600
aaatgttttg taggctgcct taacaaagcc caatggccat tcagagaagg ctcaaaagag  39660
aaagtttagg ggactctaca agcatcctca ggaaggccac agaaagcaga gcctgggcca  39720
gtgagacttt gcagtgggca aggttcagct ctttatgtag gaagaagaga gtcaacagtc  39780
agagtccagc tttccataaa acctgtgcag ggcctctagg caaagccctg tgttaggggc  39840
aaaggcattt gcagtctaag cccggtgaca tgagctcaat ccttggaacc caggtggaag  39900
gagtgtgctg actccacaaa tttgtcctct gatctataca tgtatgcacg tgcacgcaca  39960
ctcacataca tgtccacatg cacacatgca tatacatgcg catgcgtgca cccacacaca  40020
gggtcaaaag cagcaagaga tgccctgtga aaaacgtctc attcagtctc ccatcatcca  40080
gtgccacact ctgagcacag gtggtactga tatcgttcct gattgatcga tcagttgatt  40140
tgagaccccg cctcactatg tagcccaggc tggcctggaa ctcacagtga tcctcttgct  40200
tctgcaagat gagcccatca tgcccaccat gttattgaag caataccatg ctctataaag  40260
caaacctagg caggcaggat ggtggactcc tgtaatctca ggacttgaaa agtagaaggg  40320
agatgaggag ttcacatcaa tctcccgtat gcgttggagg ctggagtggc tgttccctgg  40380
gcgcttctgc cagcacctga ccaatgcaga tgcagatgct cacagccaac catcagactg  40440
agctcgggac cccagtgagg gtgctggggg gaggactgga ggagctgaga cgggattgca  40500
agcccatagg aagaacaatg tcagctggcc aaaccaccca gagctcccag ggactagacc  40560
acgaaccgag gactgcacat gaagggatcc atggctccag atgcatatgc agcagaggac  40620
agccttgtct gacagcatgg gaggggaggc cattggtcct gtggaggttt gatgccccag  40680
tgttggagga tgctggagcg gtggggcagg agtgggtggg taggtgggga gcaccttcat  40740
agaggcaaaa gggatggggg agaaggcaga tgggatgggg gggttgtgga ggggtaagaa  40800
agaaaaaaga tgtctctgaa agtaaaaagt acttgtcact aagcatgagg atatgagtca  40860
acccccaagc cccacagggt ggaaggagag aaatgagtcc cacaagttat tttctgatct  40920
atacgtgcaa tccatggcat acgcagaaac gcaaagacag acaatgagtt gggtgtggtg  40980
gtgcacatgt aattccatca ttcaggagac agaagcagca gagttgttgg aaatctaagg  41040
ccaacctaaa gacctacacc caaagaagga caaactataa ggaaaaaggt ggtcgaccaa  41100
tgtaacatta aagttagaaa tctctcttca cactgtgtag atactgtaca aggaagagaa  41160
aaggcagcca catcaaaaca gtgtaaatca acgagaaaac cagaaacaac tcaagagaag  41220
gctgcagggg cctgaattct gttctcagaa cctgcatcaa gccaagagaa tcaaaactgt  41280
ctgtaactcc agctccctgg gatccaacac ccatttctgg cctccatcag catcactcac  41340
aggtgtgcac acatacacat caataaaaat caaaaccagg gatgaagggg tagggaggtg  41400
catgtggatc tgggaggagc tgagaggcac tgggtgaata caataaaaaa tttggtgcat  41460
```

-continued

```
ggtggtgcac gcctttaatc ccagcacttg ggaggcagag gcaggcgaat ttctgagttc  41520
aagaccagcc tggtctacag agttagttcc aggacagcca ggtctacaca gagaaaccct  41580
gtctcaaaaa aacaaaacag ccgggcggtg gtggcacacg cctttaatcc cagcacttgg  41640
gaggcagagg caggtggatt tctgagttcg aggccagcct ggtctacaaa gtgagttcca  41700
ggacagccag ggctacacag agaaaccctg tcttgaaata aataagcatt tgttgctgtt  41760
acagaaaact ccagcccagt ttccagcaca cacagggtga ctcacaacat cataactcca  41820
cttccagggg atccaatgcc ttcttctgac ctctgtgggc accaggattg catacagtgc  41880
acagacatgc acataggcaa aacactcaca aaataaaata aatctagcaa aaaaaatttt  41940
aactaataat ttaaagaaaa aaataaggaa gccgggggtg gtgtcgcacg cctttaatcc  42000
tagcacttgg gagacagagg caggcggatt tctgagttcg aggccagcct ggtctacaaa  42060
agtgagttcc aggacagcca gggctacaca gagaaaccct gtcttgaaat aaataaataa  42120
ataaaaaata aggccaagta attcttggaa gaatcccaag gggacactaa gtgtatataa  42180
aggcgttcca tagggctagg aatgaggctt agcgagagca acttcgctgg tgtatgaaag  42240
tccctcagct gcatgtggta cctttaatct aggctctccc gaagcagagg cagaaggatt  42300
tctgtgagtt caaggccagc ctggtgtaca tagctagttc caggacagaa agggcgatat  42360
aatagaaaca tcntacctag agcccngcca aanaaagggg agacctgaga ccagagagat  42420
gactcagtgg ctaagagcat tgactgctct tccagaagtc ntgagttcaa ttcccagcta  42480
aaaatttatt taaatgttta ttacttgtat tattatttaa atttaaataa ataagtaaat  42540
gggagcctag gtttgagtcc ccaaatcacc aagaaaaaat gttatcattg ctaataatca  42600
aattaagagc ataagaactt ctttttaaag aattcttatt tattttatgt atgtaagaac  42660
actgtagctg tcttcagaca caccagaaga gggcattgga tcccattaca gatggttgtg  42720
agccaccatg tagttgctgg gaattgacct caggacctct agaagagcag tctgtgctct  42780
taagtactga gccatctcta cagctcttat caggttgata aaatttaatc tcgtggagcg  42840
ctgagaccaa gaactaaagc tgggagattg aaaaatgcag accaccaagg ccctgctcat  42900
ttctccagtt ctgatcagct cccgtaccag gggtctaacc aggcctgtgt ctgcttccct  42960
gagtagacca gaggccccat ctaaacagcc tgcctgcagc agctcctctc tctaggtgga  43020
cagatgggaa tttcagacca atgtcatttc ccaggacatc aacacagcag ccaaatttat  43080
tggtgctgtg gctgccacag ttggtgtggc aggatcaggg gctggcattg gcacagtgct  43140
tgattattgg ctatgccagg aaccagtctc tcaagcagca gctcttctcc tatgccatgc  43200
tggggtttgc cctgtctgag gccatgggac tcttctgttt gatggtcgcc ttcctcatcc  43260
tcttcgccat gtgaggctcc ctggggtcac ccagccgtcc ctgctgcctt gactccatgc  43320
cagtcctggt gctggagtct actgagattt accattaaac agcaacgttt ctctaaaata  43380
ctattaatta attaattaat cacgtgacaa ccccagcgtc catatgggtg tggaaaatga  43440
ggaactctac ccatcataca tggcgactat gaagaacaat gtgacagaaa atgctaacat  43500
catgtgtgac cgcatgcatc agccctgact gctaaaagtg gacaagcccg aagcgaaagc  43560
ccaatgttct acttctaaat gcatgcacca aacgcctccc acaggaccag aggtgcagct  43620
ctgatagggt ccttgcctgg catgcatgaa gctgtggaca cgaggcatta ttcgcaagaa  43680
cattctagct gtctggaggg ccctcaatcc actgtgttcg cgctgttcca gcaccagtgc  43740
ctcctggggc tgcacctgaa aaaggggact gcttaagagg gctcctacca agcctactgc  43800
cacagatgca tgatgggaaa gccttctgga agcaactggc tgccaaaggc tctggacaag  43860
```

-continued

```
agatcaccct ctactggaaa ggtggtttca gtctaggttc tgtgggattc caggaaatta  43920
gacaacactg gcagtccaac agacagacga tctaaacttc caaggcacag ctggtagaac  43980
ttgctgcgga accagacaac aaggtacgag ctactcccat acaacataca aaaaagcaga  44040
gagagagtca gagacagaga cacacagaga gagacagaga gagagtctaa agagagtcag  44100
ggtctcagga ctgagggtat agtctactgt agagcatttc cccagcatat acaagaccct  44160
ggattcaatc tgaacacagg aaaaaagggg gggggggact tcgattatct caaattctcc  44220
tttttgtgac acacccctaa agtcactgcc tacttccctc accgccatga agtaaagagc  44280
tgtttgcgct tatgtctaca cagtctcggc tcccacttcc tcctcccctc tgcttctgtg  44340
ctcatctcct ctgaaaccac tgcagcaagt gacttgtgtt gactgccaca cggaaactct  44400
cctcagtagc aggcagcaga gcagagctct gtcttctcgg agcttcttct ctcttgtcgc  44460
cattttctcc cacccttaag taccctatct tctctgtctc tgcttgttga tccttggacc  44520
cttttccttt ctatgaacaa aatatctcct taaaggatct cttctagttc agggtccccc  44580
cgcccccact gtggagaaaa cccagggcct tgcacatgct cagcaggagc tccatccagt  44640
ctctagctcc atgacttaaa gcatctctgt gctgtcaaat atacacttcc agcccttacc  44700
aaaatattca gtcaactcct tgccattcaa aatggatgac ctcaaagcca gagtcagcgg  44760
tgctatgact cccagatcca tccacttggt agcccaggaa tgaactcann nnnnnnnnnn  44820
nnnnnnnnnn nnnnnnnnnn nnnnnnnnnn nnnnnnnnnn nnnnnnnnnn nnnnnnnnnn  44880
nnnnnnnnnn nnnnnnnnnn nnnnnnnngg ttactgggat ttgaactcag gacctttgga  44940
agagcagcca gtgttcttaa ctgctgagcc atctctccag ccaccaccac caccaccacc  45000
accaccacca ccaccaccac caccccacca ccaccccgcc ccacctgctc attcctgatt  45060
ggttggttag tttagtctgt gagacaggag ctgtcccttt tctatagtgg aaggtgaata  45120
agaaactcct gaaagtgaag gcctacaaaa cagccacact tatttgttgg aaaatactgt  45180
aaatgtgaca tgtaaataca tgctaaaata attcgttaag tcagtgaaca accttaaaac  45240
acagtctgta gcctgaatta cagacacgac acgagccatg acagaggctg aaataagacg  45300
cctttgcaag gagaagggca gaagcttcca tccttgctag caaatctttg ttccaagctt  45360
tatcagattt tattgctttc tctttctgtt tttctttatc atatttgttt atttgttggg  45420
ggaaagccta atcttcatag cccatgtatg tgagcacttc agcatatgtg tgtgaacacc  45480
aacagcacac gtgtatgagc accacagcat aggtgtgtga gtaccacagc acatgtgtgt  45540
gagtacgata gcacgtgtat agagttcaga ggagaactga gagagtccgt cttttcctcc  45600
tactgtgtag gtctcagggg tggaacttgg gctcagcctt ggtggcaagc tcctttatcc  45660
acagagtcat cctgccagcc cagctttctc tttttctctc tgttatgtct atccactctg  45720
ttcaaggcta actcactgac tctgagttat cagaactgct tgtgagagca ggagtaactt  45780
tggacatctg tgctggtagg aacaccatcc ccactcggct tggatgacga aggggaaaaa  45840
aagcatcacc aaggagttcc accacctcaa ccagcaaata tttacctcct atacatggat  45900
aggtggggtg ggtgagcctt gtgatttatc gttaggatct catgggagtg attacagctg  45960
gtctactcca tgaccaaaat ggtgacggtg gctgaccaaa aagaaacagc tacacctggc  46020
tctagttttc tttctttctt ttttcttttt cttttacccc acggtactaa ggattgaacc  46080
caggaatgca agagctctgc caagtgagct acattcccag atctgttttt ccatttcttt  46140
ctttcctttt agattttatt tcgatttatt tgtctatgtt tgtgtgtatg tgtgtatgct  46200
```

-continued tatgtgtacg tatcagtatg ccatgggtat acagaaacct gagaaggcca gaagagagtg 46260
tctgggttac aggagtttcg agctgtcctg tgggttctca aatgcagcag caccaccacc 46320
aatcaccccc acccccaccc agccttcgag ttcaattctc atcatcacaa aaacacacac 46380
acagacaagg gcctgcaaga tggctcagca ggtaacgaag ctcgtgtcat aagcctgaga 46440
acctgagttc actgtctgga acccgcgtaa agggggaagg gaagaatcaa ctctatgatg 46500
ttgtcctctg ctctccccat gtgtgccatg gaatgaacag ccctcccaaa cacacatcaa 46560
gaataaataa aactaaaatt agcttagtaa cttttatgtt gaaagtggtt tttacatgcg 46620
tgggcaacaa taacaccgag agtagaaagg caagcatgta tgtcactgaa cagcattgaa 46680
gaaaaaacaa acacatttcc tgtacatcgt tctgggagtc tgagttaggg tttctatgct 46740
gggataaaaa caccctgaca aaaattaacc tggggaggaa gctgtttatt tcagctttta 46800
tgtctacaac atgacctgtc acccagggaa gtcagggcag aaattcaaac aggtcagaag 46860
cctggaggta gaagctgata cagaagccat ggagctgctt ctggcttgct ctagcacaca 46920
ggagtactag cctaggggct gtactgccca cagtgggcta ggctctccca cagcaatcat 46980
aaatttagaa aatgcactac aggtttgcac acaggccaat ctggtagggc cattttctca 47040
attgaggttc cttcttccaa aaggacttta gcttgcatta tgttgacata aaaactagcc 47100
agcatattgg gattatagat attctcataa aaaaaagaca tttagattcc cacataacac 47160
catattcaga aattaactca atgtgaacca gaagctctga aagtaagagt taaaactatg 47220
aaaaattctt acaaccatcc ataacaaaaa tctgatgccc tcttctggag tgtctgaaga 47280
cagctacagt gtacacacat ataaataaat aaataaatat ttaaaaaaat atatgaaaaa 47340
tcaggctggt gagatggctc agtgggtaag agcacccgac tgctctttcg aaagtccaga 47400
gttcaaatcc cagcaaccac atggtggctc agaaccatcc gtaataagat ctgactccct 47460
cttctggagt gtctgaagac agctacagtg tacttacata taataaataa ataaatctta 47520
aaaaaaaaaa aaactatgaa gaactatgaa ctacaagaag tcaggaatag ggctgggggt 47580
gtaacccaac agaaaaacac ttgcctggcc tgcgtttggt ctctagcacc accaacgtag 47640
aaagagaaca gcagaggatg agggcatcct gacttgagtc aagtgacaag tgataatcct 47700
cgagacacca aaatcacaat gataaaagag atcaacaagt tgggctttat ctgaataaag 47760
agctgtgtcg ttaaatacca cgcaggaagt gaagaggagc tgagtctggt aacacaggcc 47820
tgaaatccaa gctactgggt ggactgaggg aggacaacag ctagctcaag gcccacctgg 47880
acgccagagt taactcagag agcagcttgg gtagctttaa tgagactctg cccaggccag 47940
tgcacaggag agatggctca gtggttaaga gcattactcc tcttgcaaag gacctgagtt 48000
caattcccag cacccacgtg ggcacttaca atcatccata actttagttt caggggatcc 48060
aatgcccttt tcacagtacc aggcatgtac acagtgcaat tacatacata catgcatgca 48120
tgcatacata cacaggcaaa acttacataa aatactaagc agataaatct taaaagaagc 48180
cgggcgtggt ggcgcatgct tttaatccca gcacttggga ggcagaggca ggtgtatttc 48240
tgagttcgag gtcagcatgg tctacagagt gagttccagg acagccagga ctacacagag 48300
aaaccctgtc ttgaagaaaa taaaaaaaaa aaagaaaaaa atcttaaaag aaaaggagag 48360
gactggagag atggctccac agttaagaac acttgttctg aggtctacag agtgagttcc 48420
aggacagcca ggactataca gagaaaccct gtttcgaaaa accaaaacca aaacaacaac 48480
aacaacaaca acaaaaccac ttgttcttac agaggacttt ggtttgattc tcagaatcca 48540
catgatggtt cacaaccatc agttgcaggg atccaaggtc ctgtcttctg tgggcaccag 48600

-continued

```
gcatatatgt ggtgtacata catgtataca ctcatataca taaaataaaa agttttaaaa  48660
aggaggctgg gtttgtagcg cagaggtaga ggtaaaaaga ctctagcttg tttaatgttg  48720
acatgaaaaa aaaaagacat ttagattcct gcatcacacc atatccaaaa attaactcaa  48780
tgtgaatcat aagctctgaa agtaagaata agcctagtat gcactgtaag gctctgggtt  48840
cactccccag cactgcaaaa gatcatgaaa ccagaaatgc agatcctctg aaccacagca  48900
tgggaatgta actcagccga tgcagtgctc acctgtcgta tacagagcac aggataaatt  48960
gattgtggtg gtgcatacct ataagctcac tacgtggaaa gtagaggcag gacgaccaaa  49020
ggttcagtga catccttggt cacatagaga atttgaggcc agtctggtct gctggtctat  49080
ttggaatgct gtctcaataa ataaaagaaa gaaagaaaaa gaaaagaaga agtcctatga  49140
ttgtcttaac ctctgacctc tgtgttcatc aagtctcctc ctcaggaact cactggtcat  49200
cttgtgaaaa cctaccccag agtctctgtt cagaggaccc aggctccagc tgtggttacc  49260
acataggatt tttatactag aaaaataaaa tgaataagta tgtatttttt aaaaaggtgc  49320
agagctggat atggtggtgt ctagttatag catccagaac tgagacagga tagccatgag  49380
gttgagaaca gctagactat acggtctcaa caaacaaaag taagggatct gagtagatga  49440
ggttttaatt tttttctttg tgtttgttac ctaacgtgta tggttgtttt gaatacatgc  49500
atgtctgtgt atcacttgtg tgcctgaaac ccaaggaagc cagaggaggg catcgggtcc  49560
cccggaagta ttattacaga aggttgtgag cagccatgtg ggtgctggga atcaaatctg  49620
aaagagccac ctcgggctgg agagatggct cagtggttaa gagcactcaa tggctgctct  49680
tccagaggtt tggagatcaa atcccagcaa ctacatggtg gctcacaacc atatgtaatg  49740
ggatccgatg ccctcttctg gtgtgtctga agacagctaa agtgtactca aataaataga  49800
tcaaaaaaga aaaaagaaac agccacctct ccactctccc tttttaaaat cctcttgcct  49860
ctgtccctta atgttaataa cacaggtata tgatactatg ccttgtttat gaatagaaaa  49920
tacacgtgct aaagcaagtg tgaaccttaa atacattatg ctgagtaaaa ggagtgagtt  49980
gcacacaaga cttttctgct caagagtatc tgtatgaagt attgaacatg tgaactctga  50040
aatcgggagc tgaggaagat atggggagtt ctaatggcta caacatttct ttttggaatg  50100
atgaggatgt tctagaactc aaaaatggtg ataactcagc atatatacta aaactcattg  50160
aattgtacac tttaaatgaa tgcaataaaa cttgtctcag taatgtggtt tagaagatgt  50220
acagacatgt gtgtgtgtgt gttaaaacat ttcttggcat ggcaataaaa atacagtttt  50280
agccaggtgg ttgtggctca aaaaataatg ataataacaa taataaaaat aatgaaaaca  50340
gaggctggag agatggctca gcggttaaga acactgactg ctcttccaga ggtcctgagt  50400
tcagttccca gtaaccacat ggtggttcac agacatctgt aatgggatct gatgccctct  50460
tctgatgtgt gtctggaaac agctacagtg aaagtcattg caaggacttt acaatagtga  50520
ccatgataac attgaagcta gacttgctac tactgctgag tgtgtctgct ggctctttct  50580
aaggagtaat gttagctttt tgtcctaaat ttgtttcctt cctttcctct ctccctctgc  50640
tgtttttct taccccctcttt ttactttgct ttcccctctc atctcctctc ttaacagagt  50700
tgtcctatgc agcccaaatg ccatcttcct gcctcagcct ccccagtgtt gaaaaatact  50760
ctttccacag gttatgttag gagactggag tctgctcagt cggggaggga gcctgggtca  50820
agttctgagc tcaattcctt ttctttcttt ctttctctct ttctttcttt ctttctctct  50880
ttctttcttt ctttctttct ttctttcttt ctttctttct ttctttcttt taagacaggg  50940
```

-continued

```
tttctttgta taccctggct gtcctggaac tcactttgta gctggcctgg aattcagaaa  51000
tctgcctgcc tctgcctccc aagtgctggg attaaaggtg tgcaccacca ctgcccagcc  51060
ctgggctcaa ttcttaacat tgtggagaga aaagtattgt agctgttctg gccacctgga  51120
attactttgt ttctgatctt ttgctgcagt caaatccttc tcatccatct ttcctcgtca  51180
ggctataata tagactctcc ttgcaatact tggaaatgct ctacagtcag ctacatcctc  51240
agtcctgctc ctatattttt tcctaagctt ccttctaagg tctttattgg tttatgattt  51300
acacagaaca tttttttttc ttgtctatag catgcgttag agtgatcgtt gccagataga  51360
ggaaagagaa atgagagaan nnnnnnnnnn nnnnnnnnnn nnnnnnnnnn nnnnnnnnnn  51420
nnnnnnnnnn nnnnnnnnnn nnnnnnnnnn nnnnnnnnnn nnnnnnnnnn nnnnnnnnnt  51480
cagctactga ttcctcctcc tccctcctcc ttcctccctc ctccccagcc tcatgctctg  51540
ctcatcttgg acttctgcgc atgtcctcag cccagacctt ctgctcttgc ttctcctctc  51600
cccagcagcc ccccagttct cttcctgaaa cttctgaggt actctccatc acctcctttg  51660
gctcctgctc tgattggtgt cacctgctgg ataggcttgc tcctgactcc actgttcgtg  51720
tctcaattag ggaccctcac cctctgatat accacacatt tccctagtgt ctccacctcc  51780
cacccccacc ctatacgcac atacacactt agctgcatca ggatcctaca ccagggactt  51840
cttacccttc taatcctccc caccggacac tgcccaggga cactggggct ccagagggct  51900
attgccacac ggacacacag gagatctcat caaggagatg tgcctacccc agagggtagc  51960
tctcaccatt cacaagcaca ccacttctgc ctccagcttc tactctctcg caggaagtag  52020
ccagcccggt gccaagtatc cccaactaca tccccaaaat tctcagacac tgccagcctc  52080
cagctgtcag cctggccccg gctggcgggc gcctgctcct ggcatagcga ctagggtgta  52140
attagaaacc cgctagctcc ctaattgcca gttctgagct gtccttgtta ccggctgccc  52200
gaggcacaca tagaggaaaa ggctgagagc tgagccaggc tggcatggag gtagccctag  52260
tagacctaga gaggactggc atgtggccag ggaccaaacg tggcacagag agggctcagt  52320
gcaatctgcc ccgtgggtgc ctcccagcca catccatttg cccagaactg tgacgtcaaa  52380
ccagcccggc ccattcattc tttattcagg tggcataaaa atcactacaa aaactttaca  52440
aaagagtctt gggagctaaa gggtcccttc cttgcctcag tccccaagat tcctggcagg  52500
ggaggacaag agagagaaga aggaggaaga ctcctggcag tgttggcatc tccaaatacc  52560
agaggggtga cttgggtgac aggacacagg ttggggacct gaatgtcttc agcaagggac  52620
actcttgtag ggtaggtcag cctccaacca tgaagtataa caccaaggcc agtctaagct  52680
tgggagacca acacttgtct ctccttttcc cacccagggt gtctggaata tgtctaaaga  52740
tggcctctcc agcctctgct tacaaatgtg gagggaccct aagttaggga cttgcctaac  52800
ctacctctag ccaaaactgt gtccacaagt gccagcccac aaaagatcac cccctgagcc  52860
ccttgggaag aaatgaagat tccccatgcc tgccttcctc caggccccac cccacctgct  52920
gcaagagaac agcttctaca ctggtgatgg tccttccggt cccaccctat cccacaaagc  52980
tggttagaaa gagtcacagg agctgagagg ctgatccagg tggggactca ggatgctgct  53040
gcccagggcc cctcctcact tgggggagct gaactggggg tagtcttcct ccatgcgggg  53100
tgcaagtttc aagtcaggac caaaggtctt gcctccatgg aagtcagctt tgtcattctg  53160
gcctatgagc ctgttgtcag gggaatctcg ctgttcctgg agctggggca gcgcgctggg  53220
gttagggttc ctcacactgc ccacaaagag gggcacgcct atggtgtcct ccatgatgaa  53280
gaagaggaag ggtcggttca cagtgaagga ggagagggac attcgattca tggctacgct  53340
```

-continued

```
ggtagctgcg gctgcctcca caccagcctc gctgagctcc atggtagact gatgttgcac  53400
gctagacacc accagattct gctcagagat cccacgaagg tctgggccct ggaacaattc  53460
ctgcaggcct gcccagaaca gcagatgact ggtcagtgct gccccaaggc tatgtggatc  53520
tgtctagcat cctggctaaa gggaacactt gaacccagcg gttgattgga atctgttaga  53580
cctcagtcta gacaacactt ctagaaacct ttttttttt ttttttttt ttttaaatca  53640
ggatctgcgc taggtacagg acagaaagtc tagaggagca tatcaaatgc tcccatccag  53700
gaagcagggc cacctctggc tcaggcacac tggcagctcc cgtactctgc ccagaccacc  53760
taggggcacc ctatccccaa gctccttacc cagttggctg agggtggcca ccaggtccag  53820
ctgctgttgc agatggagtt taggcagcca caccttggtg ggcctctcct gcagcgaggg  53880
atggtacaga gtatcccagg tcaggttggc tagtacctcg gacacgttcc actcaaaata  53940
agtgggcatc acgaccacaa agctcatgtt gttcttaaag gggaaatgag ccacctacag  54000
ataagaaaag gagagaacat gaggaccaga cagcacctgg acctgtctgg agtctgggcc  54060
aaaattactt ctgtactttt gagacaagag ccagaaattc agggttagca tgctttcact  54120
taactggtga agtggaataa taccacttac ccctttgcaa ggtgacatgg gaccaaatga  54180
gataatgctt ttacacctct ctgtgtgcac acataagcat atatgtttgt atcggtgtga  54240
gtgtgtttgc tcatgggtat atggagtcag aagtaggtaa acatcagtcg tcttcctaca  54300
ttgctctcca cttttttttt tttttttttg gtgttgccat ctttttgttg ttgttatttc  54360
aagacaggct ttctctgtgt agccctggct gtcctggaac tcactctgta aatcaggctg  54420
gcctcgaact tgcagagacc cacctgcctc tgcctcctga gtgctgggat ctaagatgtg  54480
tgtaactaca catagctccc tctttttttgg acacagggtc tcatggatcc caagctggct  54540
ttgaaatgac tgtttggggc tggagagatg gctcagcggc taagaacact gactgctctt  54600
ccaaaggtcc tgagttcaaa tcccagcaac cacatggtgg ctcacaacca tccgtaacaa  54660
gatctgactc cctcttctgg agtgtctgaa gacagctaga gtgtacttac atgtaataaa  54720
taaattaatc tttttaaaa agagaaagaa atgatggcta catacttctc tctcgtctct  54780
ctgccccaag tgctgggatt acagagctgt acaacaagcc caagtttgtt gtgttttaga  54840
catgctaatg tatcccaggc tgtcctcaga ctctctatgt aattcagaac gaccttgaac  54900
ttcttttaag gtttattttt atcttatgtg tatgggtatt ttgcctgagc atttgtctgt  54960
gtaccgtgtc cttgcagtac cctcacagtc cagaggaggg caccatttcc ccctgaactg  55020
gttgtgagct gcatggtggg tgctgggaat caaaccctgg tcctctgcaa gagaagccag  55080
taagtactct taactgctga gccacttctc caccttgagc ttttcttcct cctatctcga  55140
tctaaaagta ctagggatgg cggatgtgcg ttcatgtgcc tggtttatgt gttgctaagg  55200
gttgaacaaa gggctttgtg catgccaggc aagcactcaa caactgagct acacatcccg  55260
acagactttg actcttctag tagtagtgtc tccactacag cctgagttct ctatctgctg  55320
tcagcaagct gtacaaacaa gctatgggcc ttcctgtcct tgcctctcag ttctctccgc  55380
aggtggggct actggctttc aaaatgaccc atagaggagc cacagcaaac agtaggaagc  55440
ttgcccctcg tctttcaccc tctcccagag agtcagctat aattcgagtt tttttttcct  55500
ctctctctct ttaaacagga tctggttatg tggccctaac tatcttcaac ttcagtcttc  55560
ctgcttcaac cttctgagtg ctgggattat ggtgtaagcc accacactca gctcacacaa  55620
cctttttttt ttttttttt tttaaagaat ccatgcagtt aggacagcat ggaaatgacc  55680
```

-continued

```
aggctcaggc ctccctgggt accagcataa tgcctgcagg cgggtcctct gccagtgggg  55740
ggatggaaag atggagccag aggatctttc ctctctgaac ctcaatgtcc cacagtgaga  55800
cactcatgtc cactgggaga tactgtagta ttcaaggaag aagcaacagg aaggtgagag  55860
ctaagtggag ctgagcaggc tcgtatcctc tcaccacggg ctacagagaa gtctggctgc  55920
cccctccaca tggctcctcc ctgcagaact ggcaatgctg ggcccggctt gcccagtcaa  55980
actaaccaac agaatggatg agcatgtgtg gtgccacaca cctgggaccc cagcactcag  56040
acagctgggg cagaagggtc atgagtccaa agcgaacttg tgtaacattg tcagaccctc  56100
gaacaaacaa aactagcccg tcctgttatc tcagccacag atgatgggcc caaggatcag  56160
tactctagcc aaggagtcac ggttaggcta gaagcaaggg aagccttagc tgagacagct  56220
tggcacggag cttcatccaa tcagaatgtt cagagcaata agctttgaaa cccgacttcc  56280
atctatgaag cactgtgtgg gaactcctct cttcccttac gagcagggcc ctggtcctct  56340
tgggctccgc taaaacccca gcacagagaa cagttacctg gcacgtgaca aaaactcaat  56400
atattttctt tgaggagatg aacctcaaag aagctgtgtc ctggatagac acagcataat  56460
aaacccttca ggagctacct acccagggac cagactttac ctcccagtac caggcctcgt  56520
ttgccagcca aaggcaaagt ccagactgac ctgtatctca ggttgctcca gcaggaacca  56580
tcgaagagga tatgacaccg cgtgcatcat gtccaccgac actgtgaacc gctcatccag  56640
gtggaagaaa tctttctggg tgaggctcgg gtcaaacttg gtcctccaga aacctgcagc  56700
caggcagagg gcaggagcca tgtaacataa aatcagcctn ctgcctgtct tgcctagaac  56760
ctatnnnnnn nnnnnnnnnn nnnnnnnnnn nnnnnnnnnn nnnnnnnnnn nnnnnnnnnn  56820
nnnnnnnnnn nnnnnnnnnn nnnnnnnnnn nnnnnnnnnn nnnnaaccaa ggcaggtctt  56880
ggaaaaagga atcttaaatt agaagatgcc ttgataagat tggcatgtag gtatgtctca  56940
ctaatgattg atgtggaaag tcacgaggga tggtgtcacc ctgggcagat ggcctggggt  57000
atataaaaac acaggctgaa caaaccacaa agcagtagtc ctcaatggct tctgctttag  57060
tttctgtctc aggttcctac cttgacttcc ctcagtgaag gcatgtcaca tgagagttgt  57120
aagaggaaat aaaccctttc ctccccacat agtttttggt tatgatgtta tatgtcaaca  57180
acagaaacta taactaatat agttggtttt cttttttttgt ttgttttgtt ttgttttgag  57240
acagggtttc tctgtatggc cctggctgtc ctggaactca ctttgtagac caggctggcc  57300
tcgaactcag aaatccacct gcctctgcct ctgcctccca agtggtggga ttaaaggcat  57360
gcgccaccat tgcctggctg gttttctttt ttttttaata catttataat gcattttaga  57420
tttaaaaaaa aaaatggcca tggcatataa tataaaaaga agtgcttaca aatcaccatg  57480
tgcccttgcc ataaattatg taaaaatttc catatggaca tcagtctcaa gcttacaatc  57540
tcagcactca tgagcctgag gcagaggcag gaggatggtg agctcaaggc cagcttagtc  57600
tacataacaa gatcctgtcc aaataataac aacagtaata atttcataca tagaactaga  57660
aggggccact gcaaagacag tatgacaaaa ccactggccc tgcctaattg tattttaaat  57720
aactgtcctc ctctctgtaa ttttcagttt ctaattttta cataactacc atgtattctt  57780
tttgtaattt taattagttt tttaataata gaaacaagct aagtgctaag aatattttca  57840
tatgaacatt ttcaaggcac ttgatacata cctcagattt gccctccagg tgagcagtac  57900
caattacgtg ccaccagcaa tgttagcttc cttttttccc taccatctga ttctgtttca  57960
gtctattcgt agttctgatc ttgttatatc ccttttttatt gtttccctgg gttccaacac  58020
ctcccagttg agtgttctca ttgaatttca ttagcagctg tttcattaat ggcacagaag  58080
```

-continued aaggattaca gtgttaacta ggatagactt tgacaaagaa ctatgagaac atatcttatt 58140
atctttgcat aaattctttt taatcaaagt tcctcaaaag cctctctctg ttcccatctc 58200
agggagtagg tctggccact gatgagtgtc caggccacag tacaggtgtg cgtggttctg 58260
tccctgtggg aagggcacat ctgtgttgta acaggattcc tgtcttaaca agccttgctc 58320
aggctctaag tggtcctgag ctagctaact gcccttggct ttcccttgat taccagataa 58380
ctattcactc ttctcatttt gcagagcact taccaggtag ctatgtcctg gaagtacgaa 58440
tgagtccttc tattgttttt cttttactta aatcccattt gaaatgcgcc agggacactt 58500
caatccaagg tacacttttg ctaaagaatc actcattttt atatgcaaaa tgtcacctat 58560
taactgcagc tgatatggta catacatatt ctctcttcct attatccact aataggtgac 58620
taatgcgaaa tattgagtaa tttttaaaaa tcaatactca attttttaga aataattaga 58680
gagacattca actctgacac cagcacccta ctcagttcct gagccttcct ctgccggagg 58740
agaatctata aataactcac gaagctgaca ttactcactg tgttgcagtc attttttttct 58800
gagaaaattt tagcaactgt tctaatagag cctgccagtt atcagtagtt gagaatgcaa 58860
gtcaactttt aattatgcag acgctgatta ttcagacgac aaattgttgg tgcctgcacg 58920
gctccttcct gctgcctacc tttaaccgtt ctcagtgctc attagcacat gttccagaag 58980
gtaggctttg gaggggcgga caggcactca aaccagctaa gcacttagag aagctctgat 59040
gaaagatgtt aatgcagttt gtagaattat tgactaaaat tgagtcattt ggattccctg 59100
tgaattgtat ttacatgccc tgtccctgtc ccccatagca acagataata ggattgtctg 59160
cagagagaca acatagttct tatatttaat tttttccttt gtcgaacatt ttcacatgat 59220
ggttcgtggt gtttcctttg ttcattacat ttgtatccag actagttact tctgataagc 59280
ggttagttag gattcctggc acgcggacag tgacaccaca gttgtctgat cgtttcccac 59340
tttttttacaa aaccgtttgc ctttaagagt cagtgttttg cacatttcac ccagattatt 59400
ggaaatatta tttccctcct gcttaaaccg aagctgtgat cataatttaa gcctttctag 59460
gtagccgatc ttacatgtat catacctatt tctggcatat gtttgtctat tacaaagacc 59520
tcgtaggtat gcagttagaa gcctctagtt aaatgaaatg ttgcgtgtgt gatgaacctg 59580
gagtggggat ggccttttgt gtgccccaag gctgttgtgt ttcacacagt tgttttctgc 59640
ctcctctggt ctatcactat cctgccactg ccagaaaacc ctgctgtgtg ttccccgcgt 59700
ggaggatctc tgcttctgaa cttctttggc ctgagaaact ccataaccaa atcagttagc 59760
attttgttta aagagcaggt aggctgttag agcttgggtc ttacatgtct cccaggtcca 59820
cttgccagcg ccttgaccac tgttaacttt tgttaaccaa ctcatctttt gctgcctgtt 59880
ttttgggggg tttttttggt tttgtttaag ccaagatcag ttatatggcc caggctgagc 59940
ctctcttccc agcctctcaa atgttagaat tacaagcatg catccctcag catacctttc 60000
ctttgctttt tttaaaatag agttttgcca tagcaacaga aatctaacct aactaagcat 60060
agccgtgcac atggtatgag gaactcacat atgtgtgaat ggaagttcat agagaccggc 60120
atcactgcct agaggcccct ttcttccttc cttgcagttg tcgtgctagc tgactgtact 60180
acaaaagagg ttgtctgagg cataagacta ccttcaataa aacatgcaca gacagtttgc 60240
ttctctgaga tttcagagca gtgactacct tcaataaaac atggacagac ggtttgctta 60300
cctgagactg cagagcagtt tccaaaaatt ttagacaaag ggtaggatga agaaggctgc 60360
ggggttttgc acacacttaa ggtgcgtaag taaataaact gagctacact gacaggatgc 60420

-continued

```
tcgttctagt agccaaccaa agagcagttg aaccaaagca cctagacttc aaacatcgtg  60480
gggagataat cttaggagtg ctatgcttct gcgtcctaca agtattatga aactgtctag  60540
aaagcacccc actggtaatc ccttttttgat tatttttttt ataaattcta gtcttggggt  60600
tttgagtggc acacagacat aatggttagg cttcggtgtg tgctcattca ctttgcttcc  60660
tggggaccag agtttgcgat gagtcatgtt ccatctgatt tctgtcggat ccggctgcag  60720
agccatgact cagatgggct tcaggcccag ctgctcagtt catcttctgg ggaatagatg  60780
acaaggacgg gacaaatgtc ctgacgcaca tttccttctg ttcttgcact tccagggtct  60840
aacgagagca tcattaccaa cagcaggcag atacgccttg ccacaggcat cttccctgtt  60900
gtcagcctcc tgaaccactc ctgcaggccc aacaccagtg tgtccttcac tggcactgtc  60960
gccaccgtcc gggcagcaca gaggatcgca aaaggacagg agattctgca ctgctatggt  61020
gagccagcct ttctttccac taccctgctg tgcctcacac ctcacatgaa aaggataagg  61080
ggacaggaat cagcagatat gggcccagtg cctctactca tcctctgagt ctttcctgga  61140
aagggcaatg catccttggg ccaataaaaa aggtcttctg gctgtaataa aaaagcccgt  61200
tgagggcagt gagccatatc cctccatgcc ttgtagacag cctatcctga aaatgagcga  61260
ggagcacttt cttggcttct ttcttcctgc cccagcagct tggaaacgta tccactttca  61320
cccgtgtttt gttgtttttt ctgagatgat agggcagagt acccaacctc atataggcta  61380
ggctagtgtc tatcactgag ccaggacccc aacccagcac caccatgcca gtcacgtgat  61440
gactaggcca gcccctcggt agagtaggca ttgactctct tggtgtgact aggaactgtg  61500
ggtaatctct ctccagggcc tcacgagagc cggatgggcg ttgctgagag gcagcagagg  61560
ctgagttctc agtacttctt tgactgccgc tgtggggcct gtcacgctga gacactgaga  61620
gcagctgcag ctcccagatg ggaagccttc tgttgtaaga cttgcagagc gctcatgcag  61680
gtaaatctct gctgttccca ggggcagggc tccagctaaa ggttgtcagt cgccaggaga  61740
accattcctg cttcccttct tgtaactcct ccctacatgt cgcccggtcc tgcagaaaac  61800
acaggttgta tttcctaata ttttccctat aagtgacaca aaatcttaaa ttacacaaag  61860
ggaccaaaaa aaaaaaaaaa aaaaaagccc tagaaattta cttgctcaaa taagtcatca  61920
aaagttgtgc atcaggccta gcacttgggt actggtaacc ctagcactca ggaggctgag  61980
gaagaaggat ctcaagtcgg aggccagtct caagtgacac cccatctaag agatcaccat  62040
tccaaggagc tatttcagag atggtttaat ctggggaccc agattgtgga ttttctgtct  62100
gttcaattcc atctctctgt gctggcctca tcagacacac tctgtagtaa ctgtgggaaa  62160
atccgaccca catagttttc cctcagcctt tgacccagag ggaagagcca cagtggagag  62220
catgagagca gacccttggg tgctactgcc aggtaatggt gtagacactg gagtcttcaa  62280
cattcatgcc ccaatgcaaa atggtctcca caccagagca tggcattctc attagaaata  62340
agtaaatgga attggctgtg ttgaaaattg taaagccaag ggtcaagaat gaagccttcc  62400
ccagcatgtt ttgttttgtt ttgtgtttta ggcagcgtct ctctgtgtag ccttggctcc  62460
tgccctctgc tacctctccc aggtgtgcca ccatgctggg cctaagcgcc ctgtgcatta  62520
gtgctccctc gatcctgctc actcttgaga cagtcttcct tctactctgt atccccagat  62580
aacctagagt tcacttcaga gcccaggctg gcctcaaact tgagatcctc gtgtcccagc  62640
ttctcaaatg cagtgatatt tacaggccta cacctggctt tccctgatag attcctagta  62700
agatgattat cctttgagcc atatctctct tctgcttctt cctctcttcc tgcagggttg  62760
atctagaatt tattctaaag ctgactggcc tcagaattgc catccttctg cctttagnnn  62820
```

-continued

```
nnnnnnnnnn nnnnnnnnnn nnnnnnnnnn nnnnnnnnnn nnnnnnnnnn nnnnnnnnnn  62880
nnnnnnnnnn nnnnnnnnnn nnnnnnnnnn nnnnnnnaca tagtgtcaac tttcaaattc  62940
tgccttaaga gttctttgtt tatgggaatt tatgggaatg ttccacagaa cccatccagc  63000
ggagttctgg ctgttgtttt ttaatcttta ttcatcttgc gtgtgtgtgt gtgtgtgtgt  63060
gtgtgtatgc gcgcgtgctc aacttgcaaa attgcaaaat tcagtctcct ctttccaccc  63120
tgtaggtcct ggggatcaga ctctgttagg cttggtggta ggtgctttac tgagccatct  63180
tacaggcccc ccatggacaa ctttttcttt gaaaacctgt ttctggcttg ggtgtgatag  63240
ctcacacctg tgaccctacc accactcatg aggaagaggt aggaggacta acagaattgg  63300
aagccagcct ggactacaca gtgagtaaag gctatctata tactcaccac atggcaagac  63360
cccgttttaa aacactgggc aaggtgaaac aaaagtcaat taatttcaca taaagtcaat  63420
agcttcatta acggcctagt tatctttaaa actgtatgca ggttagtact tggtttcaat  63480
tttattactt tttctctgga acatttaaaa gtactttagg ggctggagag tcagttaaga  63540
acagtggctg ctgccaaagg actggagttc actcccaagc acccaggtgg caatcacaac  63600
tgtctgtcat ctaattctag gggatctgac accctcacag actcacaggc agtggaacac  63660
caatgtacat aaaataataa ttaaaaaaat gaaataaaat accaggcaag gtggcacacg  63720
cctttaaccc cagcactcag gaggcagagg caggcagatt tctgaattcg aaggcagcct  63780
ggtctacaga gtgagttcca ggacagccag ggctatacag agaaaccctg tctcaaaaaa  63840
aaaaaaaaaa aaggacttta aattgggctg gagagatgga ttaaaagcat tggctgctct  63900
tcccagaggt cctgggttca attcccagca ctcaaatggt ggctcacaac tgtctatatc  63960
aacgcaatct aacaccctct tcaggcatgc aggttacatg tagacaaaac atccatatgc  64020
ataaaataca taagtaaatg agtcttttaa tgtatactag aagctgggtg gtggtgcatg  64080
cctttaatcc cagcacttgg gaggcagagg caggtggatc tctgagttgg aggccagcct  64140
ggtctgagta aatagagcct tgtacttcta cttatcacta cagttacatt ttataacttt  64200
gggccctagt gcttccattt tccactgttt gcttaaccac tggggcctga agcttttgtg  64260
ctgacacttt tgttcgctaa tcatcaggca accaatggtc tctacactcc atcaccatca  64320
acacaaacaa aacaaaacac aacactacgg atcctggcat ggtggaacat ctttagcccc  64380
agtacgtggg cttgagttca aggccggcct ggtctacata gcaagttcta ggatagtagg  64440
gatagtcttt aaaacaaaac actattttat ttatgaacaa aacatgtaaa gaaagaaaaa  64500
aaactgcaaa tttatctatg aatgaagtct aagtaatact tcaatattgg aaatagcttt  64560
ctaaaatatt tttatttaaa gaaaactcag caaattattc aaacaacctt ataaacgttc  64620
gttataaaag taaagaatta tttgcaattg ccttaagggt ccaaggtggc agcctcttaa  64680
aattcagaac aatccaagct tcacattcca gttcaacatt tctacagccc taacgtattc  64740
aaatacctcc attctgacaa ctgtttcccc tcttcttttc ttctaagctg cttagatgtc  64800
tgtcccaggc ttttcatgat tttagtcatt cacacaacta gcaaacatta tctagggact  64860
aaaacttgcc agatactggg atatcaccct aaagggggac tgaaagtagc tgcaggctac  64920
agtctctaca atctcctgaa tgaaatacaa agtagctaat atttaccaaa taaacatgta  64980
cacctgtgat gattgctagc tgtactagca gaagctaaac actaaatcta gaaactcagt  65040
cctccaacta gccccttgct cggcttcagc ctcattttta caaacaaggg aaagagtttg  65100
gaatgttgcc caaagccata cataagtgaa caaaaaggag ttggagtctc caaatgcatg  65160
```

-continued gatttgggct agttactttg ccaaccaact cagtaacaac tgagctgaac aggaacactg 65220
tggtagcaaa agaaactgga actatcaatg gcctctagag caaaaatata tttaaaaaga 65280
aaaaaacaaa caaggcctgg caaggagact gtgagaagag tgtgctgact gaaattgact 65340
agttcagcca acaaaagact attccagggc tggtgagatg gctcagtggg taagagcacc 65400
cgactgctct tccgaaggtc aggagttcaa atcccagcaa ccacatggtg gctcacaacc 65460
atccgtaaca agatctgact ccctcttctg gagtgtatga agacagctac agtgtactta 65520
catataatca ataaataaat ctttaaaaaa aaaaaagact attccagtgg ggatggaaaa 65580
gttaagtgtg gagttaaaat atacttcaac tggtgatgga ctaggtgtcc agagtcgggc 65640
aaaaggatgc tctgtggtag aggtgcctgc tgtgtaagcc cagctacctg agctcaatcc 65700
acagaatcca cagcggagtg ggaagagaaa caacgtccca gagttgtcct ctggcatccg 65760
acgcacattc gccatcccca agatgtcata catatgtgta catactacac actggcgcac 65820
gcgcacacac actctttttt aaaattcaga cttagaggga cataaaggat ttgctctgat 65880
atatgttcaa ttgaaaatga ctttgaagat agagggcaga tcgaaggaag ctcagcagga 65940
aagaattaat aacatgcagg tgaagggcta taaactagtc tgcagagggc cttggctcga 66000
caaaaaaatc tatggggttt gccggtaaaa taaggaaaaa gttgtcaaca tgaaacacag 66060
aacactagca agagaggagt gttagcagaa agaagccaac aagctcaaac aattaggtcg 66120
gctgaaaaat tttaaaatgt cttctgattt ggctactggg aagccactgg tgacttcggt 66180
cagcgttttc tctctcgtga ccagagagat gtctagtagc aataatgagt taggaggatg 66240
taaaagaagt aaaacagccg aaaacaagtc caaaaagttt ggggtgatgg agaaagggag 66300
gaaacagagg ccgccgaaga tagacagcgg catgtttatt tgtcttgttt tcttagatgt 66360
aaacaaacta aaaaaactcg tgagttcttc tgccagtacc gggttgcctc cagcatcctc 66420
tgatggtctt agagaccccg ggatgctccc ccgcggccgt ataatttcct ccctgacgct 66480
ctcccgatcg acagcggctc cctccccggg tcctctttgc accgctccaa ggccgcgctg 66540
ctagggccat cgagcccgct cagggtcgtc tccttacctc gatggccccc tcgctcaggt 66600
gtcccaccat ggctgcaccg ctaactcccg cgctcgcgct cttgcaccgc ctgagcttct 66660
ctgccggggt cccgcgggct gctcaacgat tggctagagc aactgtgcgt gccgatccgc 66720
ccccagcgtg agcgcggtgc gaggggcggg cctagacgcc gatagccacc gcattggcta 66780
ccgcgcggca ggcagagcac gtgactcttc cgaggccggg ttcgaggcct agtggcggga 66840
tggcgggacg tgagggcggg gcgctgggtc gcagtgcgcc tgtgtcagcg cggtgctact 66900
gagttgttcc cccgccagct gtcggaactt tgcccgccca gtcctttggc ggacagacag 66960
aatggcaacc cagggaacag tcggagctct cccctggtaa ctgctgctaa atatagtcaa 67020
agcagtgacc tgggtacttc ttcacgcagt gcgtgcccgg cgccggtgcc aggcccagag 67080
cttggcactg tgggataaac aaggtaaatc agactcagtc tccgccctct tgagttccac 67140
ctgagagttg tggccgcaag gaacccagcc tcaaggatgg tagacgcgat atgggccaca 67200
catgtggagc tccagagtgg gggtcaaaaa tcaatcaggc tttcgagagg cgatgcggtt 67260
tgaactgagt taaagtgtgt gtagaaattt gtcaggtgga ttccagtgag gatagtgatg 67320
ttcctaaaag cccaaatggc ctatgcaaaa gtattggaga gcctggcgtg ctggctggct 67380
ctgatctgtt tgtaatccca gcctttggga tgtagaagca gcaaaagttc aaggtcaccc 67440
ttaacaccgt tgagttcgag gtcaacctga actaaatgag accctgaaaa atcaaaattt 67500
gggacccagg cgtggtggca ttcgaggtaa aagcaggcag atctctgagt tcgaagccag 67560

-continued

```
ccaggctaac ataagatccg gtctcaaaaa aaaaaagtaa taaaaataaa aagggagaga  67620
ggctatatga actgaaagaa agacctggag atcaaaacag aaaactgagc cgtctaagaa  67680
atgaaaatat ttaacttcat agttgctgga gtaagaagtc tggaaaactt tgggcaacta  67740
aggtaaacag gtctagaaag actggaatag tagccatcta ctggtatttt gatctctgtt  67800
tgtacaacca caacctacta tagtttctca aacagttcca aagaatatgt ctgggtgaat  67860
tggtaccaca ccacagatta actctccttc agcatatcaa cagctataga aaaccccaga  67920
agaaatgatt ttggttgcgt gtcacttggt aggatgaaat ctcgattttc tagaactatg  67980
cattaataga aagctgaatc ttcatgttct gactttacag agctgcggca gcatggatct  68040
accggtggat gaatggaagt cctacctact taagaagtgg gcttcactcc cgaagtctgt  68100
gcaggacaca atttctacag cagagacttt gagcgacatc ttccttcctt cttcttccct  68160
tcttcagtaa gtgaatggaa acttcaggga aattttggtc tggaaaatgt tctgccttgt  68220
catttggtct gaatatctct tttttatagg agagagtagc tttatattct ttatagtatg  68280
gggcatttag cagttactgt tggttttcac gtttctccct agtctgtgat tactagaatg  68340
ggtaggcact aactgctttc ctcttttggc atgtgttata cttaaggaat gtagtatctt  68400
gctgtcgtcc cagtgctgtc actcatagga tctggtgcag gttgtgtagc tgcccctaga  68460
agctcattca gtcctaatgg ggagaaagaa ccctggcact tggttagttg agacccanaa  68520
cttctcaagt tctnnnnnnn nnnnnnnnnn nnnnnnnnnn nnnnnnnnnn nnnnnnnnnn  68580
nnnnnnnnnn nnnnnnnnnn nnnnnnnnnn nnnnnnnnnn nnnnnnnnnn nnntttagtt  68640
tccaagtgcc actttactgc aatgtgtcac cacatccaga gttctgtgtt tgtttatttg  68700
tctgtttttg agacagggtt tctctgtgta gccctggctg tcctggaact cactctgtag  68760
accaggctac cctcaaattc actgagatct gcctgcctct gcctccagag tgctgctgta  68820
cactaccacc acccatccag ctttctatat tggttttcct atggcgtttt aaaatagcca  68880
ttatacgtgt gtttatcatc taaagtcctg gtcccaaaag gagatgagag gggctgctaa  68940
ggtgaaaagg attacaaacg cttatcaatt ctgttcaaaa attaaacctc agagtgggat  69000
tagctgcttc tttcattaga attgctatca gaattcactc aggccttgtt tgcgtgtgtt  69060
attgaagaag tctcttcctc atcaggtcag tgactcctta gctcaagtac atgcaatatg  69120
cagtattgat aactgttctc gcttaggaat aaaaatagaa ctgacttcca cagggaaatg  69180
atgtgctgag ctgtagcaac gaatcttgca caaactctgt cagcagggac cagctagtct  69240
ctcgcctgca ggaccttcag caacaggtct gcatggccca gaagcttctc cgaaccggta  69300
aaccaggtga gattggctcc ctcgccctag gcctcagccc ttcccttgtt tattttggta  69360
tcaccttgcc ttactgagca gtcctcaata aatgactgag gacttgaatt taattatccc  69420
agcaccagcc acaagatggc tatgtaggcc agtgagacca gactgtgacc agctgttact  69480
ctggtgccct tgaaagtctt cctgatggtt taagctgtgt ctgctgcgcc agatagttct  69540
agcagctcga gcaccagaaa ggctgtctga cttccatggg ctttgtgtgg ctccagaggt  69600
ccaatgccat catctgattc ccagcttaag gacctaagct ccgagaaggt tgctctgccc  69660
tcagcagcag cagcaagtcc tgagtgctgc ctgggctcgt ggtgtgactc aggagtagag  69720
ctcggtagct agcctgagct gagagctgag agaaagaaag gactcctctc ttttcagaaa  69780
gggatttgca gaactcgatg ttagaccctg acatggtagg aatctgtttt gactattcta  69840
gcctagattc tgaagttgac ctttagccta gagtcaagaa aactaatgat tacaggagga  69900
```

-continued

```
atgtagagtt ggttgttaaa tgttggttgg aaaatggatg ttagaagccc agggtaaatg  69960
tgaggaagcc tcatctaaca cctcttttac tgaaagagaa aacataagca accaacagct  70020
tccctggaat gcccggctgt tgactccgtg agataaagag gcattttcac tttgacctaa  70080
ccgatagaga ccttgcaacg tggtctctcg tgtccaggac tagatctgta tctgttgtga  70140
ggcatttttc ctttgaatcc atagagcaag ccattcagca gttgttgcgg tgccgggagg  70200
ctgctgagag cttcttgtca gcagagcaca ccgtactggg ggaaattgaa gatggcctgg  70260
cccaggccca tgctacctta ggtatgctac cttaggtata gccggagttc tccttccctg  70320
ccgtgtgttc agtgcggccc ttgccttgtc tgtttggttc tctcttgcca tctgaattga  70380
cgctcttctc cctcccattc tgcattcctt gcccccagag ccttaggcta atggtgtttc  70440
ttttccggaa tgagacattt ctcttctcac agggaactgg ctaaagtctg ctgcccatgt  70500
acagaagagt ctccaggtgg ttgaaactcg ccatgggcca tccagtgttg aaattggcca  70560
tgagctcttc aaactggccc aagtcctatt caatgggtag gcctttcttt ttcctagtgt  70620
ttggccaggg cacacagtgc tctgtgtttt cctaggtgct tctgtgtatg gctttttgct  70680
acagtgcttt aaagcatgtt gaaactcttt tatttcctct ttaggacaga tatttgccct  70740
ctgcttcact gatagacttt aagctttgaa ttccttcctg aggatgtgga gaaagccatt  70800
aggtctgcat ggagcttccc agggaggatt tggaggcagc ctcacccgcc tctagcattc  70860
ctgtctgctt aatcacacct cccttggctg cctcagtccc tgctctctca actccagggc  70920
tcggcccttt ccctggtttg cctcttattc cttttaaagc agtggttttc aactagaagg  70980
gattgcaaat ggcatttggc agtgtttaga gacagttttg attgttatgg ctgccagcat  71040
ctagtaaagg ctaaacctac agtgcacagg accgcctcca cagtggagag acccaagtta  71100
gctatgtgaa ggctgagaat ccctgctttg gagattaaaa aaggaagctg agggaaccac  71160
tcagttggaa gcacccttgg tggcatgcac aaggccctgg ttctgtccct agctctgcac  71220
aaaaaataga atacaaggaa gagtaaccct aatgagctgg tccctcaccc agtgtgccac  71280
tgaggtcact tgaagggaag tctagcccca atttagtatt ttttgtggct gccatacctc  71340
cagccttgat caaatctcat ggtatacatt ggtaagaaaa agggtttgaa acatagacct  71400
gatactcgga catggaaaca gtatgtttgg tcagagagag cgaaggacct gatagacgag  71460
ggcaatatca gagagagggc atcagtcggg ttagacacga gcattccaca gtgagcagct  71520
ctggataagc ttttataaat gctggttaag gttttgaatt tgcccaattt tgtcaggatc  71580
ccagagtcta tcacaaacat acacagtttt ctcaaatctg ctttgcagta tgcccgtgaa  71640
tgtctcttat ctatactttc agatggtaag accctgaggg cagaggaact cagacccttt  71700
gtgccccctg taagaccctg ggggatgcag tggacccgac tttgtgttct ctgcacagaa  71760
aggagtccac tttcgttgag actaaggaag ggaactgaca agcttccctt tctggcttca  71820
ggttggcagt gcctgaagct ctgagtgcca tctggaaggc agaaaggatc ctgttggtgc  71880
actgtggccc tgagagtgag gaggtccggg agctccggga aatgaggtcc tgcttactgg  71940
actcgtcatt cgtccctgtg gggcccttgg tgtagagcaa tcatcctcac cctcaagaag  72000
gagctctggt gatgactgag atgttctgtt ggcttggagc tctcatcaga gaggacggga  72060
ccttcccacc tgacctgagc ctagtgtctg gcacagagag cacttgaaaa cagattgaga  72120
cactcacctg ccatgctggc tgctgcttgc aagagctaac tgccctctga tggaaacccc  72180
atgcccagaa aagactaaat ccagtatcta aaggctgctt taaagggttg tcactgcagc  72240
cgggcttggt ggcacacgcc tttaatccca gcactcggga ggcaggcgga tttctgagtt  72300
```

-continued

```
caaggccagc ctggtctaca aagtgagttc taggacagcc agggctacag agaaaccctg  72360
tcttgaaaaa ccaaaaaaat aaaaaataaa aataagtaaa aaataaataa ataaataaat  72420
aaagggttgt cactgatctg caggcagctc atgctagcct aggcttttgg ctcgatttca  72480
tctcactaaa cgatgaatct gtttccctgg aacattccta tggtttctag tagtaatgaa  72540
gtgctgtgtt ccactccagt gagaacttca attcttagtc ttgtattata attgaaaaat  72600
aatatatagc aagaaatcag tatgactgct tacctcaaga gacatacaat tccacttaca  72660
atatcctgct tccttaaatt tttcattaag actggtgata tataatttgt gaatggagaa  72720
ataaatacgt cttactgttg gcagtttctt cctgggatgg caactctgta ttggtttcct  72780
accagtgtcc taattcttac tcagtggctt tcattgagtg ttcttggcac tcactgtcca  72840
agcactgatg caaggcaacc ctgtagcatg acttcatagc acaggcctcc ttgttagcac  72900
acctgaaagc agaccactct ggctgtttca cttgcagaca gaatcttact ctgtaagcca  72960
gtctagcctc aaacaacatc ctcctgcctc agccttccaa gttctaggtt tataggaaaa  73020
ggccaccttg cccagcttga gactgcttct tactgccatg tctcttcagg ctcacacatg  73080
aagtccaggg cactccagga ggagccgtga gtctgtctgc agggcactcc agggggagcc  73140
atgagtctgt ctgcagggca ctccaggagg agccgtgagt ctgtctgcag ggcactccag  73200
gggaagccgt gagtctgtct gcagggcact ccagggggag ccatgagtct gtctgcaggg  73260
cactccaggg ggagccatga gtctgtctgc aaggcattcc aagagcagcc atgggcgtca  73320
ctcattggta gactgtgagg ctacatctcc agatgccccg agtgctgtgg ttgtgagcac  73380
tgctgctcat ggtttccaac tgagacagag ggaaggactt tgcccctttc cctaaggatg  73440
ggtagtaata gtccagacca caagggacag atagctatgg ggttttctga ctcatcctta  73500
gtacattatt gctgatgacc agtttgtttg gatgagttag tgggaaagaa gacccaagtc  73560
catacactct gctttttaga acttgctcat cctagccatg cccaaggagc agccgttgac  73620
tgtcatggca ttacagtgag gaaataaaca gtcctgaagg tgcctggcag cagcttttca  73680
agaagctggt gttaaaagac agtattcaaa catctgcgga ctgggaactg ggcagcattt  73740
gagtctcctg ctgtctgtta atttaccctg acaaggaggt gacttgaaag gtttgttttg  73800
tttggggtag agctttttca ggaaaaaagt ttagtcctac agacaactct atagttattc  73860
tagtccaaac tcatgccttg tgttttattc ctaaaagccc tgtcacactt tgtaaaatag  73920
gtgctcttcc tcaaaggata tatttaacgt tttatatatc aggccttatt ctgtgcatgg  73980
aagctttttt tagatgcttt gtaagatggc tcagtggtta agagcatgta ctgctcttct  74040
ggaagtcctg ggtttgattc tcagcagcta acaccagctg ttattccagt tcctgggatc  74100
tgatgccctc ttctggccta tgtgagcact gcatgtgcgt agtgcacaga caaatgcagg  74160
caaagcactc atacataaaa ctaaattcaa aaaactcttt cattgtctca tgtgacctag  74220
cttgagaata cctgtgctta tattataatc tagtatgagc cagccacggt agcaacacac  74280
ctattatctc agcactcaga agattgagac tagatggtca agagctagag tctgggttac  74340
aaaacacctg tctcaaaagt aaaagggctg aaaaagtgtc tcagcagcta agagcacaca  74400
ctgcttctcc agagggcctc atttcagttc ctaataccca caccgagtga ctcaaccacc  74460
tgtaactcca ggtccatgag atccaacacc tctggtcgtc tgcataagct cctacactca  74520
attatacaga gagagagaga gagagagaga gnnnnnnnnn nnnnnnnnnn nnnnnnnnnn  74580
nnnnnnnnnn nnnnnnnnnn nnnnnnnnnn nnnnnnnnnn nnnnnnnnnn nnnnnnnnnn  74640
```

-continued

```
nnnnnnnnnn ntctagagtg tttcaggttt tttttgtttt tttttttttt gagacaaggt  74700
ctctctatta tgctgcctgg aactttctat gtagaccagg ctggactcaa acttatagtg  74760
atccactact tctgcctctc agtactggta ttgaaggcat gtgtcaccac accccactac  74820
ttcaagatct tagatttcca aagaagccgt agcctagaaa aggttaataa gtactgattt  74880
aaaacagaaa gaaatcaggt acacttagag ctgtagaatg tcagcatgtg acatttgtga  74940
caagttgtca aaactttgct cttaattcta aagagagaag ctgtcaaaag acttgaactg  75000
gggctgtagc caacttggtc gagcccttgc atgaagctgt gtgtttactc cccagcactg  75060
tggggtttga attgatttga acccagtaga ttcgtatatt tgaatgttta cctcatgggg  75120
aatgacatat tacaaggtgt ggccttgttg gaggaattgt caatttgggg gtgagctttg  75180
aggtctctct gctcaagctc tgcccagggt agaaagggag cctcctcctg gctgtctaca  75240
gaggacatag tctcctggct gccttcagat caagatgtag aactcttggc tcctccagca  75300
ccaagtctgc ctgcacaatg ccatgcttcc taccatgatg ataatgaact gaacctctga  75360
aactgtaagc cagccccaat taaatgtttg tctttataag agttgccttg gtcatggtgt  75420
ctcttcataa caataaaagc ctaactaaaa cacattcctg ctgggcagtg gtggtgcacg  75480
cctttaatcc cagcacttgg gaggcagagg caggaggatt tctgagttcg aggccagcct  75540
ggtctacaga gtgagttcca gaacagccag ggctacacag agaaaccctg tctcaaaaaa  75600
aaaacaaaaa caaacaagca aacaaatgcc agcatttggg aggtagagtt aagaagattg  75660
ggagtacaaa gtcgtctcag ctagtatgtt tgaggccagc atggaccaca tgagacgttc  75720
tcaaaacgaa agaaacgaat gaatagataa acatttgagt gtccagtttt ttcctttctt  75780
tcttgctttg tttttggcgg tgctgaggat taaacccagg accttgttca tactaggcaa  75840
gcattctcca ctgaggaaca ccctggcgag tgcctagtct gtctgtctgc ctgcctgcct  75900
gcctgcctgc ctgcttgtta tgtgtatgag tggtaacctg catgtctgtc tgtataccac  75960
agacatgcct ggtatctgca gaggccagaa gaggatgttg gatcgcctgg aactgggatt  76020
acaaatggtt gtaagctgcc atgtaggtat tcagaattga acctggtgct ctgaaagagc  76080
agccagtgct cttgttgttg gttttattgg gggcaggagg tagttatttg gttggttggt  76140
tggttggttg gttggttggt tttcttgaga cagggtttct ctatgtagcc ttggctgtcc  76200
tggaacttgc tctgtaggct caaactcaga gatctgcctg cccctgcctc ccgagtgctg  76260
ggataaagtc atgtgccacc aactccagac aagcagccag tactcttaac cactgagcca  76320
tcattccagc ccttctttgt gttttgagat ggtcacaaag tacaactcag actgagctct  76380
tgatcaccct ccctcagcct cctgactgct gggggttaca ggtgtgtcac tgtcctcaat  76440
tctgagtgtc agatcttgaa aacccattct cgtgaccttg atccttaaaa caaaccctgg  76500
gagaatgagt tctgataact atttctcact cctcttcaag aaaaggaaag ccagagaaag  76560
gggggggggc aagccccaga aacattgata acttgcccaa agttacacag caaaattcag  76620
acagcctgca catctcagtg gccatctgtg ccatatccac cctgcccttc tctgacctcc  76680
ccacctccat ccctacagac cttgcagttg agatcagagt ccaagccgta tcgtaagatg  76740
gccttaggat ctgacatcat ggggactctc acggtcctgt cctcgtccaa atgaaaatcc  76800
tggagggtcg tctttctcga gtcaaacttg gttacccact gccctggaag gaaacagatg  76860
gagcatcctg agccactgtc cccagaaagg ccacaggtcc acgctgtgcg tccactggcc  76920
aaagcaacct gagctgtcag cagcaagaac acaggagccg ctgggtccca gcatgtgtgg  76980
cacagaccat aggctccatg caccacgggt tctggctatc ctcctgtagt aaactcagaa  77040
```

-continued ataagtgggt gttctctctc tgacttggat caccacgctc cttctgttta aagtggcctt 77100
taatatgctg gtgtgtggta cgtgcctgct ctcctgtccc ctggggactt ggagtaggaa 77160
gccccagggc tttcctctaa gttaggatcc actcttgcta ctactccata agatggtcac 77220
aaagcaacgt aaaatggaaa ttaatcaaac cattcctgcc acaagaataa aacagatctc 77280
aggggaggcc tgtggaaggg tctcctgagg ccttaccact gtctagaagg aagttgacag 77340
cagttcttga gcaggggtgc gactccagga gttgggggct gctctgagag caggacagca 77400
tgtattgtag agtgtctggg agggagctgt gttatcctta ccgtgaagat gaggacacgg 77460
gctcatgggg gcagagccag gattaaacct ggtctgattc aaaaagccag agatctgtgc 77520
ccagccccac gcagccattt cactggtcaa ctaattcaga aacacttggt ctgatatgct 77580
catatgctac aagcactgtg gccttcagat ctccctctgg cctggtacct gcattcaggt 77640
tcaccaccat caccacacac acacacacac acacacacac acactcggcc agagacaagt 77700
ggggaagccc tcacccttga agtaagccac gccaaggaga aggatgctga gggcactggg 77760
catttccctc gtggaccggg caatcttccc tttcatctgg gcctgcaccc agttgttaat 77820
ctcctgaagg tctactcgag ggttgcccgt gaggatccgg ggcctggtcc cataggactt 77880
ctccagaggg gcaacaaagc tggatttgac tcgaagttct tgagaggaaa cagatcaaag 77940
atgagagctg aatcagcacc ctcactttga aagcatgcca gaccccagct tcctgctcag 78000
catcttcctt tgacttgctg gggcatctgc cggcttgccc agaccctggc tagggaacag 78060
tggattccac cgtttgcatt ccccgtccca ggccctcctg ctgtctccca gagcccactt 78120
cctctttctg ttcctctgtg gtctcactgg ctctttcctg cccaccagtg ccaggcctcg 78180
cctgagcaca cacagcctat tgtttagaca tcatggaagc atacagacaa cccaggccaa 78240
tgaagcaact tcacgccagg cataatgggg cgtgcctgcc cttcagaagc agaggcagct 78300
ttatgagttg ggggaccagc tgagactcta tagactttga gaggtggggt gggggtgggg 78360
ctactgactc ctctcaaaca caattctgga agcactcttg aggttcttct caggggcagt 78420
aacagaggca aggagctcct tgtaggtgct gtggatgtca gggttggtga tcaggtcgta 78480
gtagagagcc cggtgaatga cagactctgt tcgatgttca gctcctgcca gagagaaaag 78540
gatgccaagc ttcataactg cccgtgaggc ccgcatcagg atagggacgt tagacatcaa 78600
tccttttgtc ctctgagagc ccgaggaggc cgatattgca gatgttttag ctggacaaga 78660
tcttcagggc gtggaaagaa ataatgaccg ccttgctagg aagagctcta agacagggca 78720
aggttatcag agctacagag agaagagtgg gatgtggtcc tgaagttctc ccatcgtaac 78780
ctaccctgtt ctgaggagga gccagctctg ctcacggcag ctgtacccct agaacctggt 78840
taaatgacta aaacacgata ggaggccact taaggaacca aggtcgagtg ccacttacaa 78900
agtggtaggg attgtgtgtg tggcccccac cgcccctttc ctgttcctct gacggcggca 78960
gcatggaaac tctgagtggg ggaaattcag gtccacctgc agccttcttc agttgacact 79020
cacccagaga aagggcagag agggccgtgg ccacgctgag tggagacagc aggacgttgc 79080
ccgttgggct ggcactggat ctcaggcggt acagatcgta gccgaagttg gagacagctg 79140
ctgccagctt gttcacaggg accttgaaga aggggtcctc ctcctccacg ggctcgcccg 79200
tgctgtccgg gactggggag ccctgggtta gaatacaagg accagtaggg aggcacagtg 79260
agtacatcac ctcctggttg ggttggtcct ctagtccctg gggccatgag tctgaggtca 79320
gaatgagtgt gtgctctctg actccacaac ctgtgtgctg ggaggtgggg agtgggaagg 79380

-continued

```
gcaacacaaa agggcttgcc agacctgaac tgtggtctga gaacctgaag cctggcccac  79440
tttaaaataa aacttgtagg gctggggaga tagcacagta gataaagtac cagcatgcaa  79500
gttcaaggac ctgggttcag tccccagagc tgggcacggg ggtgcatgct tataatccca  79560
acactgggga ggcagagatg ggcaggtcct ggggctcatt ggccaatcag cctgaactaa  79620
tcagcgtatt ccatctcagt gaggggtcct gtttcagagg gcctgaggaa tgactctggg  79680
ttgactacta gcctactctg tgtctgtttc tgtctgtctg tctgtctgtc tgtctgtctc  79740
cacccctctc tgtccccttc cctctgcagg gaacttcctc accaccacca acccccaaag  79800
aaacccaccc tcagaccagt cttccctatt cagcttgctg gctggtccta gtctgcctag  79860
gttctgctgt gacgccctcc ctgtctttcc tgacaagcca tcccctctga ctagacccga  79920
gaggaatttg tcgttttctg acctgtttc agtgtcagcc tcttccttat gagactttct  79980
gctttttgt tttgttccca gggctttgga tcaaagctgg gctcttacat acgttaggca  80040
aatgcttggc cacccagctg tacctcccgt ccctgttgct tttcggtttg gaggactttt  80100
tttttagttt tctgtttggt ttttggtttt gattttttgt tgtttgtttg tttgttttga  80160
gacaggattt cgctatgtga ctctagctgt cctgggactc actatgtaga ccaggctggc  80220
cttagattca gagatccacc tgcctctgcc tcctaagtgc tgggattttt agattttaat  80280
ctgtacctac caacctcaaa ggaagtgtcc atggatagag ttcagtacta catcatgtgt  80340
gtaacatgtg tgagggcctg ggcttcaccc ccaacagaga agggggagtt agtaggtgag  80400
gaataagtga ctggctagtg gcaagacagt attgtctaag gtcactaagc cttaagccac  80460
acttaaagcc cacaatccag gtctaatatg cccatctgcc ttgtccttgt gtgacatgac  80520
cccaccccta cttcctccgt atagtggcag ctcctctgga tcctgaaagg agagggaaga  80580
tattcttgtc tcgatgttaa agtaaccaag gcctagaaga gtgaaggcca aagcccaccc  80640
tggatccagg gctgcctccc tgcactgtct cttctgctgt cccacctacc caccctactg  80700
acctcagagc tgctggggac gttctggctg ctgccgtgcc cgagcagggc tccagtccag  80760
aggagtagca ccagggcctg catcccggaa ctacaagaga aacaagagag caaacgactc  80820
ccctcaccca caccctcccc tgccactgca cattgcacac tgcacaggga caagagtcag  80880
gcagagtgag cccttcccct ccctccagct ctcagcccca agtggaccct tgacttgagg  80940
tcttccgtcc ctgacctgcc cctgcacttc tccttgagct gtgcccccat gttggttcct  81000
atcaggagac ccaccttccc atctaagctc cagcacaggg aagacccagc agcaggctct  81060
tcaggcccca agacaatgct ctagcacaaa cacacaccaa ggcttttccg tggaggcaca  81120
cggccagctc ctttggtagg atttggaacc ctgtctcagg atgggagcag agcccaggtc  81180
atagacttac agaacatctg gtctggtcct gctatccacc aatagttctc tgaccaaagc  81240
ctatgttaaa gacacacaca cactttcttc taggtaggtt cttgtgtatg tagcccaggc  81300
tagccttgaa gttgcagcta ccctacttca tttgcctcct gagtactaca atgccaggtg  81360
tgagccatca tgcctgactt gactcccttc ttctatttca agagcaattc ttagttaaga  81420
gggtatgaac cagggccaca ctgccnnnnn nnnnnnnnnn nnnnnnnnnn nnnnnnnnnn  81480
nnnnnnnnnn nnnnnnnnnn nnnnnnnnnn nnnnnnnnnn nnnnnnnnnn nnnnnnnnnn  81540
nnnnntctta tttttagctt gtttgttttt cttacttgag acctggggag gggaggtgta  81600
tgtgtcttcc atttgcttct tctacctaat aaagtttctt ggtgatgttt gggggggggg  81660
gagggggtag gactcaagaa gggattctcc cataagctgt tccgtttggg tagtactatg  81720
taaggaagtt acaggtgggc agagctcggc tctgcctgac tggcgtgctc tgaggtaaag  81780
```

-continued

```
gtgagatggt gcaagatttg ggccctcagg agttggctct gttggccctg taccttctgg  81840
tctgtgggta aggatgacca gtaggtgaga gatgagggaa ccagaacaga aggtgaaagt  81900
tagtggggcg gagccccaga ctagtcaggt gggggtaaac tagatgactt tctggaaccc  81960
caaggggctc ggagactagt ggtgttggag aagacctcta atgtgttgta aggcctctga  82020
actcagtagc cgaacttgat gccagaaagc cccaaactgc taaacccaag caggagcggg  82080
acgccatccg ttccatggct tcacccgagg tggccccatg gctgcgccaa tcaatgagca  82140
gccgagagat aggggcgtgg acaagccagg aaaagttaca gcacgctgga aagataatac  82200
aggccaggaa gccccaggca cagcagggtg gaaaagctag atcccgattc tgccggaggg  82260
gggccccttc gaggtcccgg gcaccgggtg ccaggatcag agaaactgac tgaaacctag  82320
ctgacctgcc cagaccatgg catcctgggg actccttgtg gctggcgctt ccttcacggc  82380
gtttcgggga ctgcactggg ggctgcagct gctgcccacc ccgaaatctg ttcgggaccg  82440
ctggatgtgg cggaacattt tcgtttcgct gatacacagc ctactctctg gagtaggggc  82500
gctggtcggg tgcggaactt ggggactgac aaagcactga ggggcggggg tggaaaagag  82560
ggcctggaag actgaagttg gaaccttttg gaatggaact ggtttgggtt gtggatgggt  82620
gggagtaccc agtgggagaa tggatctagg tctgggagaa attgacctta gctctttgtc  82680
ttctccaggc tgtggcagtt tcctcaaatg gtcaccgacc caattaatga tcacccaccg  82740
tgggcacggg tcctagtagc agtgtcagtg ggtgagtgta cagaaaaggc tgaatcggga  82800
aaggccttgt tggaccggga attctaggtt cctcccccat ctttggaatg gagcagatgt  82860
tgctggaggt ttgctgtgag gaattaagga cctgagaaaa gtgggacttg agatatctag  82920
gctgtgcatc agctctgagc gaggagcctc atagtcttct ccggtgcctt caggttattt  82980
cgctgcagat ggagttgata tgctgtggaa ccagacattg gcccaggcct gggaccttct  83040
ctgtcaccat ttggcggtaa gactctgaag ggagaggcca ggtagtaagg gagcatgtcc  83100
aactcaaggg cccaacctct ctcttcagtg ttctgtcctc tgacttttcc acaaagcccc  83160
ctgaaaacct atcctctcag acttggattg agttggaggg aggttttgac tggctagcca  83220
ctcctgggca ctgcccaagg agtttggttc tccccacaaa cctccagctg atcataaaaa  83280
aaaaaaaaaa aaagccagga atgaaagcta gggtatgcta tgcaaatagt gtggcttggg  83340
gtaagagaac ctctggtcca gggctgctca tgccccctag ataagggtca gcagaaaggt  83400
caggattgga ggcagtccta aaaaatgctt gggtaatata aagtgaataa ataaaaaata  83460
aataaatact aatttttaaa aagctgatac ctggaaggat gaggcagaga gtagaaaaaa  83520
catgcgtggg tgtccctagg ataaggagct gggacttgtt gggcacaggt catgcaaagc  83580
ctgaaccttg aaccttgcct gcaggtagtg agctgcctca gcaccgctgt tgtgtctggc  83640
cactatgtgg gcttctctat ggtatccctg cttctggagc tgaactccat ctgtttgcat  83700
ctacggaagc tactgctgct ctcccataag gccccatcct tggccttcag agtaagcagt  83760
tgggccagcc tggccaccct ggtcctcttc cgccttctgc ctctgggatg gatgagtctg  83820
tggttgtccc ggcagcacta ccagctgtct cttgctctgg ttctgctttg tgtggctggg  83880
ctggtcaccg tgggcagcat aagcatctcc acagggatcc gaattctgac caaggatatc  83940
ttgcagtctc agccctaccc gtttatcctc atgcacaagg aaaccaagac acgtgagcct  84000
gttgccagga acacttccac tctcagtctg aaaggtgtgg aagttttctc ttctgtcagc  84060
ccccagggag gtggggctgg gaagaggaga tggtagccca ctgcatagtc tactatgtag  84120
```

-continued

```
caaggactag actgtatcat cagagagaga gagagagaga gagagagaga gagagagaga  84180
gagagagaga gaacattgta tgagatctcc attacagtca ggaaatcagg agatctaaat  84240
aactttaaaa gtcccacagt ctttacatat tcttaaaatt tcaatctctt taaaatatcc  84300
atctctttta aaattcaaag tctttttaca attaaaagtc tcaactgtgg gctccactaa  84360
aacagtttct tccttcaaga gggaaaatat cagggcacag tcacaatcaa aagcaaaagt  84420
caatctccaa ccgtccaatg tctgggatac aactcacgat cttctgggct cctccaaggg  84480
cttgggtcac ttctccagcc aggccctttg tagcacacgc gtcatcctct aggctccaga  84540
tacctgtact ccactgctgc tgctgctctt ggtggtcatc tcatggtact ggcatctcca  84600
aaacgctgca tgaccccttc agtcctgggc cttcaagaga gaagactaga gcctggcaaa  84660
gtggcacatg ctgataatgc tagcacttgg gaatgacaag cagaaggatc agaagttcaa  84720
ggccagcctg ggctacaaga gactctgttt caacaaacaa acaaacaaac aaaccaaaga  84780
agagaaagaa aaaactggac atgacagccg gaacattatc tgacattcat aaggtcctga  84840
gttcaatgcc aagttggcag tgcctagttt gataagggtc tagccactct ggtaatacca  84900
tggctgactg aacaccttac ccagcaactt gctgatagac tctgccttcc agcaaaaggg  84960
aggagcttcg ctgaggagag aacattgaac cctattgtat atgaataaat tgctgtgcaa  85020
atgatttcat cagtctcttg tgaatgtgat tgctttgagt catttttctt ggctccagtg  85080
ttatcctggt ctgcagtgtg gtgtggagtt gtggaagctt tgagttggga gggtttcctg  85140
ttaaggtttc tctggctctt ttctttcctc ccggtttttg ttttgtttgc ctggtggggt  85200
tctctggtgt gtgtgtgtgt gtgtgtgtgt gtgtgtgtgt gtgtgtgtgt tagaagttgg  85260
cggggggtgg agggggctgg agagatggct cagcggttaa gagcgccaac tgctcttcca  85320
aaggtcctga gttcaaatcc caacaaccac atggtggctc acaaccatcc gtaacaaaaa  85380
aatctgatgc cctcttctgg agtgtctgaa aacagctaca gtgtgcttac atataataaa  85440
taaataaata ttaaaaaaaa aagaagttgg catggatgat gtagtgaaga ctggcattag  85500
atatctctgg atccccctgc ctctacctct tagacactgt gagtatggaa gtgtaccacc  85560
gcaccaggcc aggctagaac attctctgat ctacaaatac ctagagtatt attcctctat  85620
gatcagaaaa cagacccagg gggccacaga aatgtcttag taggtaaaaa cacttgcttt  85680
caggcctgat aacctgcggt tttttgtttg ttctgggggg cgggagaggc tggctggctg  85740
gctggcctgg aattcacaga gatccacctg cctctgcctc ctgagtgtca ggtaccagga  85800
tcacaggtgt gtgccaccac acttggccta actgcctgag tttgagcatc agtactcaca  85860
tggtactgag gatagaatag actctcacca gctcttctga cttccacatg tgccctgcag  85920
catgggctct ccttccccaa aggaaaaata aatgtaagaa ttaaaaaaaa aaaaaaaaag  85980
caaacccagg tcttgtgtga tggctcagca tcaaagctac ctcccgccac agctgaccac  86040
ctggtgataa cttatagcct tgttatgctc tcctttgacc tccacgggca tgctgtacac  86100
gtatgtgtgc ccacacaaac acacaatcaa gaaataaatg cagccaggcg aggtggcaca  86160
cccctttaat cccagcactt gggaggcaga ggcaggtgga attctgagtt cgaggccaac  86220
ctggtctaca aagtgagttc caggacagcc agagctacac agagaaaccc tgtttcgaaa  86280
taaccaaaaa aaaaccactt taaatattat ttttattttg ttttgtttat cctggaactt  86340
ggtctgcaga ccaggctggc cttgaactca cagagatcca actgcttctg cttcccaagc  86400
acattaaagg atgtcccacc actgcctggc taaagattta ttttttcttt ctttttgttt  86460
tgttttgttt tgttttttct aaaaaatttt tttaaaaaga accatccctc ctagcactca  86520
```

-continued

```
ggagactctg aagtcagggc cagccaggtc tactgagtga gctctagggc agccagggct  86580
ccacaaagaa accctctctc aacaaacaaa caaaagagaa cagacccaac cagacctgag  86640
gacacacact tgtaatctaa gcccttgaga ggctgagaag ttcaaggcta gccacaagtg  86700
tgtggtgcat tcaagagcag cctgggtggg ctacagaaaa agaaagaggg agagagagaa  86760
tggttaatga agatgactct ggaaaagtga aactcaagag aaagcccctc agatttgctt  86820
aagacgagtt gagggtggag aaccgccaaa gcggacgagc cagacagaga ctgccaacaa  86880
agttcaatcg gttcaggtac attacttcca aaacgccatt gccacatcag gatgcttcaa  86940
tcagccaaac caacgcagcg actattgact tctgcatttc agagacttcc gtctctgtcc  87000
agggcaatgt cactttagct ttcctttgca gaaaggaaaa gtccctgcct ctgatgtggt  87060
agatcctcac acaccttctg ccagatccag acactggtat gactcagcct cggggagctc  87120
tatctacaga gataagggta caaggcgtgt gtgtttaaag tatgtgttta aaagtacaaa  87180
gtgagagtcc ctggaaaggg ctccctgccc tcaccatcac cgaaagcaca aaccttaggg  87240
taatatctga cattcctgga aatgtatgta tgtattcatt atgtagccct gactgtcctg  87300
gaatggggta taaaccagga tggcttcaca tctcagagac ccatttgcct ctgcctccca  87360
agaactaaga ttagaggcat gcactaccat acttggctca tgatttactt aactttattt  87420
tatgttcacg aatgttagcc tgcatgtatg tgtgtgcacc atgtgcatgc ctggtgcccc  87480
agaggccaga agaaggtgtt ggttggattt cctggagatg aagtcccaaa caactgtaag  87540
cagtccaatg tgtgtgctgg agatgaaact tggttcatcc acaagagcag tatgtgctct  87600
taactgtgga ggcatatctc cagcctcaga tttcccagtt aatgtttgct ttcgcaccca  87660
ggcccatctg cgcatgcgct ggagacctcc tttaccgcct tgagcctcat tggccaattg  87720
tggctgggag acttgcagat cccaagtggt acaagagaag aataaactgg tgtgctatga  87780
actcacctct tctctgtagc cattggctga gcatactttg cctcaaccta ccgcccttcc  87840
ttcccctaat cctaaatctt tgccctctcc aaatgtgctc ctcccccgca gtaatccagt  87900
ggtcgctggg gctctagaga gatggggggg gggggagcaa cgggtacagc ttaaggcagc  87960
tgcagcagaa ctttttgct gtatattgag tcttaaaaat tcatataaac tttgtgttct  88020
gtttctaaat ataaccccat ctgtttcaac acaaaatgca acaacaaaat gtttcaaatt  88080
gctatttgga ataattaaaa aatttcaata cttgatttaa aaatgcttta actttttaaa  88140
taaattttaa atgttattat ttttaaaaag ttacaagttt aaaaaaaaga aagatagaaa  88200
tcacataatg aaattaacca tacgcaagtg aggctcggtg cactggtaca cagttacagt  88260
agccatttgg agtggaggcc atggcgcttc acattgaatt ttatactttc tttatagaat  88320
attttttatg cacctatcta ctactgataa caaaacaccc atgagagagt tagaattaga  88380
catcaattag ctttgatcct ctgtcataac tcgtgtccac tccctgcctt agtcctacct  88440
catccctgtc ctcttttcta catcttatac tgaatccaca cactcagttg tttacacaaa  88500
cacatacatc actgtccann nnnnnnnnnn nnnnnnnnnn nnnnnnnnnn nnnnnnnnnn  88560
nnnnnnnnnn nnnnnnnnnn nnnnnnnnnn nnnnnnnnnn nnnnnnnnnn nnnnnnnnag  88620
tgcctggctc tgttttgctg ttgttgtttt tgtttgtgtg tgtgtttaga tttggtttgg  88680
tttggtttga ttttgttttt ttttagagaa tcttactatg tagctcaggc tgtccttgaa  88740
ctcacagaga tctcttgtct ctgccttcca agtgctgaga ttaaaggtat acaccacctt  88800
acctggcccc tttcatctat ctatctatct atctatctat ctatctatct atctatcatc  88860
```

-continued

```
tatctatcta tctaaaattt atctgtgtgt gtctgtgtgt acattcccca gagcctgtgt  88920
ggtagtcaat aagtaaccct cagaagttgg ctttctctaa tccttggatc aaacttgaat  88980
tgttaggctt ggtagcaagc atgtttaccc actgagccat ttatgacccc atggcccagc  89040
atcttccatg ggttctgggg acacaaatgt gtactttgat gtttacagga caagcgctta  89100
accaaccaag tcattttccc agccccatcc tgactcccat taagtgttct ttcccccaac  89160
ccaggaccaa atctagagga gtgtccatgc ccaacaaaca ctctgccaag cctctcccct  89220
tactgctctt ctcccttccc ttccttcatt tcttcgttcc ttcttttctt tctttttgaa  89280
acaggtcttt tctctgcatc ccaagctagc cttgaacttg tgatgtagct caggctggct  89340
ttgaactcac agctgtcctc ctacttcagc ttcccaaaca ctgggattat agacctatgc  89400
taccacacct ggctcatttt tcaaataaat aaaaagaaaa tcaaaaagtt cctagaacag  89460
tcacaggatt cacaaaaact ttggaaggag actaaaaatg gatttttaaa aaatgcttga  89520
agcacaaaga gttgttgaaa gaagagagaa gaggaaaagt tagcttagta ggtagaagtc  89580
aatcaagcct cacaccctga gttcaattcc tgaccctatg gtagaaggag aagagcaatg  89640
ccggaaacat tatcctctga cctccagacc cgctgtggca cgtgcatgca cacacacaag  89700
caggagccct tggagggaag tcctagaaat gaatcttact gaagcaggtc tgccaggccc  89760
tgtgctcagc cattttattt ttcctttgtg tacccgacac gcttccattc tcaaagttgt  89820
gagtctgaga ggaagtactc actgtgtccc cagtgagctt ctgtcttacc ctgggtcact  89880
tagatggggt cacttagtgg tagccttggt gtggagaaag agaacacagg tccgagtagc  89940
cagtagacct gagtctttat atctgcaaag ggtgttgggg cataatcaaa tctccccccc  90000
tccccggggt cctgatacca ggttgtatta agtgtatgtg catggtcctt ccaagtcttg  90060
acacatcatc caactccaag tggctttctc atttttcctt gccagtagcc tcttggtgag  90120
gaaatggctg aggaaaacag agttgcagaa agacagggcc atggcctggc tgcaggcttt  90180
ctctgagtct gaagagggtc agcgactctg agaaatgaag ctatttctga gtgagagggg  90240
ccaaagaagg aacacggcag agggagagcc cccgaggaga tggagacaga agccggagag  90300
ggaccctgtg cgaggctgga ggggaggaag agggggaggg agtgagaccc actgtcatct  90360
gttgggcaga gaggggctac attcatctgc agtatggtgt agaggggaca gagagtgatg  90420
gtaacaggaa aaatttgggg ttgagggggg cagcctgtag ggctgggccc cagcagtgta  90480
cagctaggta gagtacacag taactcccag aattctctgg ctccactaaa tccctgttcc  90540
gctccgtgca gagtaaaacc cacacagggt ggatttcagt ctcctttgca ccccccctcca  90600
cccccctcc acccccagct ctggtcacag ccagtcagag ttgggggtgg ggcagatctt  90660
gtaaaagagg ctggtgagga catcggaaag tctgtaccct ccactagcaa agtgccagac  90720
gctccgtgac actttaaatg cctcagataa aacagtgaga gactctcctg gtggcaggca  90780
agatgatggg tcagggacct cagcgcctct gaggctcaga caccaggata aagaataaaa  90840
acaccacgga gacccctgtg accccctcgt gcagagggag aatgccaatg tggcccagct  90900
agctgctgga gcgcaagcct caaggcctgt gctagttatg agtctactgc tgctgccttg  90960
tcccaataaa cccctttccg cccaggatta gtggacacgc cttgctcaag ccgagtccct  91020
gatctgccac cttatcacac acatacaaaa atcccttgag gatggttacc atcctgggac  91080
aaagcctcat tctctgctta acccaagtga cacctatatg gcagatccct gtgtccttct  91140
cctgatgata acaacccttg caatccaata gaggggaact cgggtttctg tcagcttcct  91200
ttatgctgat agaaatgtac tctgcatgtg ggagcctgc cttgctcacc ctgagacccc  91260
```

-continued

```
atggggctgg ctggggcttt gcacatcatt gggactcaga gatgttgact acatgaacgt  91320
cccacacttg gttgcacaag gcagaatgac aggatgttat gcctggtgtg tgagtgtgtg  91380
tgtgtctctg tgtgtgtaaa acgcctctct ctggagccct cctgtctgtc tgcctcttgt  91440
tcaatggctg cacaattgtc ctttctcttt ccaaggacct ctgtatgggt gtgtccttca  91500
ttcagtgcct ttcctctgtg ggtttgtcct gctagccccc tgtcactgag aaagtcttct  91560
gtctgtcctt gggttgtctg gctagaacac agacatcatt gtcttttttt tttttttttt  91620
tttttttaa agatttattt atatgtaagt acactgtagc tgtcttcaga cactccagaa  91680
gagggagtca gatctcgtta ggatggttgt gagccaccat gtggttgctg ggatttgaac  91740
tccagacctt cggaagagca gtcgggtgct cttactcact gagccatctc accagccccg  91800
acatcattgt cttgcccacg actgctctcc agaatggtgg gcaggaggat gtgaccccccc  91860
acccccaggc accgggacac aacatcttct acacgtgtag gtcttgtgca ctggctttgc  91920
tttcttcttc caagcaggtc tcccaggaaa tggcacttac agagattgaa gagtttaata  91980
catgtctcgc tgcctctctt ttcgggaacc ccccagaggg agcagcagaa accagggctg  92040
gcaggggctc taagctgcct gggcaaagga gcagggggta gcatggagcc ttagccaatt  92100
tggaaagcac tgtgacccaa gcacattttg cagcagtaat gtcaaattct gccgttcagg  92160
catgccattg atgtgcacgc tgccacacag aaaccagtga cacaaaggca cagccttctc  92220
caccctcctg gtgcttagga actaacggct ctaatgagaa atgagagctg aaaggagaga  92280
gacgggggcg ggccacagca gcgcaggctg gcactgcgtg ttggaggagg ctgacccact  92340
tctcgtagag gtaaggggcc cactgaaatg tcacttaaat tagccaccac tcccaacact  92400
agatctcctt tgtccccata cctcagcccc acgcttcttt cttttttctt tctttttctt  92460
ctcctctggg gcagcctcaa gcccagcacc cactttttag agctgtaaac caccctggtc  92520
ctagaagccc tcttacgtta ggggatgaca ggaggtagag atcaggaagg agggagggag  92580
gggaggagga aaggaaaagg gaggggagag agggaaagag atcgagagag catgcattca  92640
tcacaaagag ccctcttttc tggctttttg actgcactgt gagttattta gccaacaata  92700
gatgtttatg tattttttta gaacccgtat ttattaacag cctgaaagga gagagacgga  92760
gatttatata ggaagtgcag tgagttaagg ggggcaatta agagagcaga aagagatacg  92820
gaacacagac ttgtaaaggg ttttgtaaca tccaatcaaa ggtgcttcag gtattttcca  92880
aggaagcaga aggtaaaaaa aaaaaaaaat tgtcccatta gaagctgaca ctggatggag  92940
caatggccca ggcggaactc ctgcttgaaa gaaggtgaga agggagggac acagaccagg  93000
atccgatgag ccagagtgtg gccatagctg ggtcatgagg cccagggttg gaaggacccc  93060
actaaagtgt gcactggcct ttccttgaca aaggatgcac ctatagctag gcgtggtggc  93120
aagtggttgt tattctagta cttaggaggc tgaggcagga ggatcaccat gagtgtatgc  93180
ccagcctgga ctgcatagca acacccagtt tcaaaataac aacaaaagga agtgggggtg  93240
gggagggcaa catttggaat gtaaataaat aaaacatttt ttttaaaaaa agaaaggggc  93300
tagtgagtta gttcagcggt taagagcgct gactgctctt ccgaaggttc tgagttcaaa  93360
tcccaacaac cacatggtgg ctcacaacca tccataagga gatctacgcc ctcttctggt  93420
gtgtttaaag tcagctacaa tgtacttaca tataataata aataaattct ggagtgaggg  93480
ggccagagca agtagaggtc ctgagtttaa ttcccagcaa ccacatgatg gctcacaacc  93540
atctgtacaa ttacagtgca ctcatataca taaaataaat aaataaatct ttaaaaaaag  93600
```

-continued aagaaagagg gtggggcagg ggagggaaga agaagaaagg taagaagcta aataaaaggc 93660
acagagatga gcttcatgtg gaaacacagg cctgtagtcc tggcactcag gtggggttgg 93720
ggggggctac agtgagagta tcatgagttc aaggtcaact tgggtgagac cttgtctcaa 93780
aaaatacata ngcnaaaaaa aaaaaaaaaa acatagccag gcatgatggt atacatttat 93840
agtcccagca cttagaggac tgaggcaggg cagaaagaaa aggaattcaa gatcaggctg 93900
agctgtatgc agtcctgatc ctatcccctc cccccccccc ccagagacag acagacagac 93960
agacagacag agagaaacac aaagaaaggg gccttcagat ggctcagcaa ttaaaggcgc 94020
ttgctattca gaccccatga cctgagctca aagcctggga cccaaggtag aaggcaagag 94080
ccaactccac agagctgttc tatgatctct atatgaatgc tggggcatgt gcctacacta 94140
tgttgtgcac acatgcacag attagaaaaa gaggaggaag aaaaacataa gattgtttca 94200
agaaaagaaa ggctggcttc ttccacgtca gtgtgagagg agggtctggc ccctttgtag 94260
ccaggtcctt cccagtccag tgggggctga actgaggcag cggaggaggc aataacggag 94320
ctttcccaac gcagtgtcca gcaaactcaa ctctacagcc tgtcctgatc cacagagaag 94380
ccttcctggc tccctcacca atgcgggggc attggctccc aggctcctgg gccccccccc 94440
acacctgtgg agtgctaggt gatttgctaa tgttgggcaa catttgccca cgtggggttc 94500
ttggctcttt ggtaatagac atgcctagca ggagggcgga gcttggaggg gggagtcctg 94560
gggttgcccg tggctccctg cagctggggt gtctggccag ctgaagaagg agccatggca 94620
cgcaaatggg agagcatgga acagaggctg tggatgctaa gcaatatggg aggcagtcta 94680
agcttggaag cagcaggtgt ctgggaacgg gcctgtggcc caggcagatt tccagtgagc 94740
actccagttt tttggcacaa ggaacaagct ggctgagccc aagaggcaag tggtgataat 94800
gaaacccgca gttgaggaac agcgggtaag ggtgccatgg gagcccatgt gctcatgaag 94860
aggctggggt gtgaagaaga gcccatgcag ggaagccaca catcccctcg agttccaggc 94920
agaggcagag tccctgagtg gggctccctg ggtctcccct tacctaacca gtctcccggc 94980
accccagcaa acaaaatccc atccataatt tgaggtttat agagacctca aaggctgagc 95040
tactgtgtgc cactaaccat cagcctaacc ctcccccact gtcttctcta gctgcccctc 95100
tttcttctga gactgtgata gtggcgggga cgggttggga gtgtgtgtga agccctctcc 95160
gactctccaa ccccagctga gccccttgtt ctgcagctca gtaacacagt aacacaggct 95220
cagttctaca ctggttgaga acactcacgg ctctctcagc tccttagaga gcctgttttc 95280
tcattttcct gtccccaaag cctagacaat ggctggtcca tttgtaagct tatctgagga 95340
tgccaggggc caccccatgt ctccactagg ctggcaatgt tctctgtcac tgtagtacag 95400
aagactgcct ggtgggaggt gagataagga aagggatggt ctcccctggg gttcccacac 95460
agtgctgagc ggaaaatggc agaatgggct gggaggtaac tctgttgcta gagtacttgc 95520
ctagcatgtg caaggaaggg cctgggttcc atccccagca ctacagaacc caggcgtggt 95580
ggttcatgct ggtattctca acattcagga ggtacagtca ggaagagcag aagttcaagg 95640
ccatcctcag ctacatagct agcttgagac cagcctgggc tatgtgagac tttgtctcca 95700
acaaacaaca acaaagcagc agaaggccaa ctggcaagag gagtattacg taaagtaaat 95760
ccatctcaaa aagcaagtag catgtatctt ctttcatttt tttttacatt ctataaaggc 95820
ctatcaagtc atgtatatat gcatgtatgt ttgtatgata tgaaagtagg gggctggata 95880
gatggctcag cagttgagag cacttggatg ctctttcaaa gaacctgggt tcaattccta 95940
gcacccacat ggcagctcac aactgtctgt aattccagtc tcaggggatc tggcaccctc 96000

-continued

```
acacagatat ccacgcacat aaacaccaat gcacataaaa taaataattt ttaaaaaaag  96060
aaattggaag taaaactctc taaggagaca aaagggactg aggggaagtg ggaggggcat  96120
gaagggggag ggcataggtg tgtggtgtgt ttaacatgca gaatacactt ctataaaagc  96180
tttggggttc attatgcaat gtatacatgt gtgggtgcaa gatgtaagct gtgcatatgt  96240
gtgggggcca aaggtctcct cctcaatccc tctctgcctt attttcattt aaattataat  96300
tattactatt agtgtgtggt gtgatgtgtg tgggtgtgtt aagccctcac ggcaatcaga  96360
ggatgtctgt ggtctgagga tgctctctta ccatgttcgt gtgggttctg tggatggaac  96420
tctggtagtc aggtttgcaa agctagtgtc tttatctgcc gagccacctt gctggccttc  96480
aaccttattt tttgcattga acatggaact tcctgagttg cctggacagc aagtccccaa  96540
gaccctcctg ttcctgcctc ccccntgtcn nnntcacang aggacacacn gcttantggg  96600
tntccggatt gctgcncacc tccccgccnc ccnagcctcc tgcctccccg cccctcgccc  96660
ccgctggncc ctcccccccc cccccccccc cccccccccc cttccccccc ccccnnnnnn  96720
nnnnnnnnnn nnnnnnnnnn nnnnnnnnnn nnnnnnnnnn nnnnnnnnnn nnnnnnnnnn  96780
nnnnnnnnnn nnnnnnnnnn nnnnnnnnnn nnnncagaca cacacactca aattaaatat  96840
agctctaact gctgttaaat tcacactcct tcacatcccc acgctaggac tctaaggagg  96900
caccagcaag gcccaggtcc agcttgactt agagcaaagc atcctccccc ctccacacaa  96960
tggaaacgga cggaaagggg catggaagca gaaccagaca acagcagcct agccaagccc  97020
aggactctgc tccttccccc catgcctgcc gtgcaactgg ggaggcaaag ccccagccgg  97080
tgctttctga ccgcttagcg gaagacaagg ggagcctgtg attatgattt ctgctgattt  97140
gcaatgaaac actaatgcag tgggcttttc attaagccag atttattcaa tctaaagatt  97200
ttatttcctt tatgtagaaa gtgcatcttt atatgttgtt ggaggagcag agatgtgata  97260
aaaagaaatt tctcttatga actaatagca ctgatacata gtggtagcta tgcctaggcc  97320
tctctctctc tctctctctc tgtctcctgt gcatgtgtgt gtgtgtgtgt gtgtgtgtgt  97380
atgaatgcac acaaagtagc cccccccccat attatttctt ctgtgggatc tccagactca  97440
gcaaatggtg gtgactggga agtctggcca tgcaattctt gccttttctc ttgccagccc  97500
aatccctttg cattcaaacc cgggctgctt gctgtggcca gccctttcac ctggagtcct  97560
tcctcctcct tacctgtctt cccatccttt gcagacaatt atcctcaata actagccaat  97620
taccccttaag gacaattata ctcttccatc agcaaacacg ggtgttcttt ccttgagtct  97680
tttgatgaag tcgatattaa agagatgctt tatttacata aagtcaaata gctccctttt  97740
agaagggttt gggttcgatg tcaaagtttt aaaatcttaa ctagaggatg ggtgtagagg  97800
gcttttggct agggtagaaa agagatggag atacttattc tgatgttgct ttaaaaggta  97860
ggatgcccag agaaggtgga aggatggggg agggagggtc cctcctcaag ctaatgaatc  97920
taaaagcagg gatgagctgg gcgctaggag tggaaccagt cagaagtgtc tgcctttgac  97980
tgaccacagc tcctgccctc ccctccccca gtctctctgt gaaccgccag cattaggagc  98040
taatcgcttc agaaagccag attggaatgt gttgctcacc ctccactgct cagaaaacct  98100
ttattccagg caaggactga cccaaaccga tcatggcatc tgccaatcag gaggccaaag  98160
gtgccggcag ggcgggacct agctgtgcag aaacagctcc gttatggcgc gcagaaaaag  98220
ctggggggaa aggctaccgt tttatctctt ggcagatggc ttctctcttt gatgctttgg  98280
gccttacctg ttactgcctg cacttgactt gacctaggca aaaatagcag cgagatacag  98340
```

-continued

```
gttctcgaag ttagaaggaa aaaaaaaaag ccccaaacca caacacaacc cggaagtgtg  98400
cccccgctgt gtttctaaag agctgttttc ttcccaagct ctacagcgtg gtggctctaa  98460
tcggaaattt ctttttaatc atagcaggag tcccaattag cgtgttgggt aatctttcaa  98520
gtagagtggg agttccgtgg ccacagagag cagaggcaat attcagcata aagccctaga  98580
gaaagaggtg ttgtgggcct gtgcacacat gtgtgtcaac gcacatgtgg cttgtggagg  98640
ctggcttccc actctcaaga tgaggtgtgt gcaccccagg ccttttgatt ctcaaagctt  98700
tattaggacc agagggactg tgtgtgtgga ggggtgttgc tcacagtgca gaaacccaaa  98760
cctggcttct ccaggagccc acatgccaac aaacaggctg cacactcttg ctagtacatc  98820
ccctaaaggt atggggatga gggaccaagt gctttgcaag acagcaggca cagagttctg  98880
ggacgctcct gtaccccaga ctcagccgcc acccagggcc agctctgatc tggcttgacc  98940
tactttcttc tgttgttgtt tttggaagtg ctgatgtcaa tgcagaattc agcagagtgg  99000
ctgagtgaga aaaaagagga gagggaggaa aagggggggg ggacgggacg ggccgaggcc  99060
aacaggaaag ggcaggcaac aagacaatga ccacaaggtc cctgtaacta cactaactgc  99120
ttacctttcc tgacccccag ggcttagcca atatagctga gacccagtct tggtgctgtg  99180
gcttcaggct aagtaaacag ggaagagttg gacatgggtc tccattctct ctcctcatcc  99240
aacaagggga ggaggcagtg gccaggcagc catgcccacc gatgccatcc ttctgggagg  99300
agccagacat ttcaggcacc tctccttccc tgggtgccta gaggtgctgt gtctgcatcc  99360
atctgccatg cctgccatct gagagaggcc actgggactt ggtagagagg ttctccacac  99420
atgctggcct ggaggaaatt ggtctttagg gacactgaag gcagtttcct ctgttcagtg  99480
gctccttgga aacccacgtg acagagctcg catgacaact tgccggctct caactcccat  99540
tcttagctgc ctcaagcact gtaaggttta ggagagcccc agatgtaagt atggatggga  99600
agaccctcca gggagtcatt gcctaccctt ctgaactcta acatggtcca gcttttccat  99660
tccacaattg aggagacgcc agacctggca ggggagcaag cctttgtttc tgacccattt  99720
gcaaacccca gccactgagg aacttgcata caagaaactg cctctgggcc tctcctggac  99780
tgagccctgc ctcccagggg acaactgggc aacagatcct tccaggtggc tgcagtgaca  99840
gatccatgct tttatgacat agaaaggcct cagtctcagg atttcacaca ctgtatttcc  99900
ctcatcctgg ggaccaggga aggcgagcat cttctgctcc ccccaaacaa gtgtgggaat  99960
gattaaaatc attttttttt tctgctccat gaactcatac agttttcaga taccgaggag 100020
acaaagccct cctgtgctga aattagaccc cgaaaaatag gttagctgac aattacttgt 100080
ttctaagtgg agtgtgatgt agtggcagga gcgcaggatg ggctgccagg gctgcagtct 100140
cccccccccc aaacttactg tctcttaacc tctcgagtcc ctgggtttct tgccgggatg 100200
ataattctcc ccatctccct cctctggtgg gctggtggaa agcgtaatga atcaacgctt 100260
gaagcacgct gaagaggcca gactcgggat gccatgtaag tacacagcat cgccagccac 100320
ctctcaagtc tacacggagc tgatttattt acctcccgtg aaagagacaa caatcatcat 100380
atttacactt catgccgcag cttcctgcgt ggcacggcag cacccccctcc ctctccgctg 100440
ctgaggactc catcaagcac gctgccttgc caggatgaca gcagcccact ctcagcctct 100500
ccctggcctc cttacagatc atgacctcct gccccgtgag gtctgtcacc cgaaaaccac 100560
ggtacaccgg gggctgcagc ctctctatgg gggaggctga ggaaatgaat tccgtaggta 100620
aaaggcttcc taggaaatca gacgctgcta gtaattaagg agcgaagcat aggtgcgtga 100680
aaggtaaatg gatgttattt aaatgttgcg tcatttaaag agtgtcctgg tgcttcagtt 100740
```

-continued ccttgttacc atgcagggct gtggacgggt ggcaattagg ctggcacggg tagagctcac 100800
ctgctgagct gagggagggt ggggacacac cttccggtaa ttgctgctgg gcagctctgg 100860
gtctccccac ccccgccccc gccctcactc cccacccccc acttctttcc tgacagctct 100920
ttcatttgca gcagcttaca gggcttgttg cccttaccca gaaaatcacg ttggaagaaa 100980
tataagaaaa agaggaatga aagagaaagc cagaaaagtt catattaggt tcggatctgc 101040
ggccaaacct ggccgagaga atccatgacg gtccgcgcgc atataaccct gtggcaacag 101100
ggcccggcac aacagggccc gccacaagag cttcttgagt tgccacctgc caggagacag 101160
gatgaatgaa tggatcatct gtccttagag cacaagccag gcctgattct ccaatattga 101220
tgtgtgaggg agatgtcaac agaggttccc taaagaatga tgcttctatt tccatgctaa 101280
tcctggggcg tcagcttcag tcggaacagc cggaccgtta ccttagctct gctgttctcc 101340
tgtctgtaac ccgcagaggg aagggcgggg tcacccagca ttgccactcc ccccaccctc 101400
acgtggtcca gacccctctt gggttgatct gctcctgaaa aacagtgttg gctcaagttt 101460
gcctctgaag gtatgtcacc gctggctcag ccagcttatc tccccggtgc tttcaagatc 101520
aaaacaccca aacgaaagaa aaactttgtt tcaagagcag agtgtggtgc caactctgat 101580
caaagtgttt ttcagcatga caactcactg cccgtgacaa ccagtacttg gctgttgtgg 101640
ctcagagtga gatgcggagg gaagtggatg acaacagctg tatccaggtc caaacagagt 101700
agattcacgg ctggcagaaa atggctgaga gccttgggct gcatccctcc tcccctcctg 101760
cctctctctc ttttcaaggt ggtttttgga aatgtccttc ctgtgggttg tgtgcctttt 101820
ccatgtagga cctggggcct gtgcagatgg ccctgtgttc ctggtgctgc tgttgagatg 101880
tgaacgagtg ataggaaccc aggcactaaa cacacaatgt ggttgtatct gactagaagc 101940
aaggcaagag caggaggcat ttgagggtaa aggagtgtaa ggactgtgta aagagatgag 102000
ggttctatct gggaggcagg agtcccaatg ccagcaaata caatggactc tcctggtcga 102060
cccaaccaga gagaattcaa gatggcagag ggacaggctg tctgagtttc ctatggctgc 102120
accgataaat ggtcataagc agagtagagg aaaaccacag acagaaattc atgccattga 102180
gactagaaat ctagctcaag gttgtgtgtg gcagggttgg ttcctgggtg ttcaaccttt 102240
tcacactgtg acatgatgct gtggtctgca gatgtgttgg gctgcatcca tagctaccct 102300
gggacacatt catggaccgc aggttacaca tgctatttaa aaactccaag ggaagggcta 102360
gagaaatggc ctggtagtta agtatgcttg ctgatcttcc agaagacctg agctctgttc 102420
ctagcagcca tgttgggcag cttacaacta actatgactt ctgagctcca aagctctctt 102480
ctaatacata catacataca tacatacata catacataca tacatacata cgtacacaca 102540
cacacacaca cacacacaca cacacacact ttaaagaaaa aaattctggg ttggagaggt 102600
ggctcagcaa ttaagagcac tgactgctct tacagaggtg ctgagttcaa ctctcaacca 102660
catggtggct cacaaccatc tgtaatggga tctgatgccc tcttctggtg tgcgctgaag 102720
acagatacaa tgtactcata tacattaaat aaataaataa gaaagaaaga aagaaagaaa 102780
gaaagaaaga aagaaagtgt aaacgaggaa aattcctaat taaaaaagaa agaaagaaag 102840
aaagaaagaa agaaagaaag aaggaaagga attctgaggg agaatctgcc ccttttccta 102900
acttccaggg ctataggcaa cctgtggcct ggggaagctg tagacaacct gtggcctggg 102960
gaagctgtag acaacctgtg gcctggggaa gctgtagaca acctgtggcc tggggaagct 103020
gtagacaacc tgtggcctgg ggaagctgta gacaacctgt ggcctgtggc agcatcatgt 103080

-continued

```
caacgcctca ccctctgtgc ccaatttcct gttctctaag gacacatgcc atcaaatgca 103140
taggacactc tacatcaaga tgatcttgtc tcaagatgtt taacaaaatt acatctgcaa 103200
agacctatct ttacatgtga ggtcactcca caggttctag acatattttt gaggagccac 103260
catccaactc actatgtgac agagtcatct agagatttgt gtccaggaca gactggctgt 103320
atctgctctg agagtcccct gcctgcccgt gggaactccc cagtggtcct taagggccct 103380
gaggactttg gatctgcaaa gccacatctt ccaaaaccat tttcctcttt tggagagcta 103440
ctctaccctg aaaccctttt ctctgaggtg gcttttagag aggcaggtct cagcagggca 103500
ctgtgcccac aagaagtccc ggggagaagg gacccaaggg ccagtgctga actatcgctg 103560
agactgagaa cattgtgtct cacctaaaat cggtggtcgc aaggaccaag caggctctat 103620
aaatgtctta ctgcctttat tccttttcct ccgctccatc ttactcctca tttttgtttg 103680
tttgtgtgtt tgtttgtttt cttctgagat gtagcccagg ctggccttca gctcactatg 103740
taactaagga tgactttaaa cttctgatcc tttcttccct ccacttccag agtcctgggg 103800
caggtgtgtg ccaccgtacc ccagctttat ttgagactat gattcaggct ccatacttca 103860
tgcatattag gtaagcatgc taccaacttg gctatattcc cagcctttct ttctttcttc 103920
tttgagacaa tgtctttttt tttttaatta tatgagtaca ctgtatctgt tttcagacac 103980
accagaagaa ggcattggat cctattagag atggttgtga gccaccatgt ggttgttggg 104040
atttgaactc aggacctctg gaagagcagt cagtgctttt aaccgctgag ccatctcgcc 104100
agtccttgag acaatgtctt gctatatggc acatattggc ctcaaactca gaatccttcc 104160
gcttcagcct cctaaatact gggattacat gtgagccatg gtgtttggct tctagccttt 104220
cttccttccc tttcccttcc cttttccctt ccctttccct tttcccttc ctttccttcc 104280
cttcccttcc cttcccttcc cttcccctcc cctcccttcc cttcccttcc cttcccttcc 104340
cttcctttcc ctctctctct ctctccccct ctttcttttc tttcagagag tttctctgtg 104400
taatcctggc tgtcttggaa cttgctctgt agaccaggct ggcttgnnnn nnnnnnnnnn 104460
nnnnnnnnnn nnnnnnnnnn nnnnnnnnnn nnnnnnnnnn nnnnnnnnnn nnnnnnnnnn 104520
nnnnnnnnnn nnnnnnnnnn nnnnnnaaga agaagaagaa gaagaagaag acaacaacga 104580
cgacaacacc ggcgccgctg cctccactgc catccacctg agacaggact caaatccaga 104640
ccaattttta aaaccagtgt ttcaagccgg tacactgaag tagtagtccc acttgggatt 104700
atagctcctt actttgtttt gctttgacgt tttgtgacat ggtgtgatgt agtcttggct 104760
gtcctagaac tcaatgtgta aattaggctg gccttgaact tgcttctgcc tcctgctggg 104820
atgatagact gatggtgtaa aactccactt aggaggcaga ggtgggagga tcagaaattc 104880
aaagtcatcc ttggctatgt tgtgagtttg aggaccaacc ttggctacat gatatcctat 104940
ctcaaaaaga aataaatgta ttgccgggca tggtggcaca cgcctttaat cccagcactt 105000
gggaggcaga ggcaggcaga ttttctgagt tcgaagccag cctggtctac agagtgagtt 105060
ccaggacagc cagggctaca cagagaaacc ctgtctccaa aaacaaaaaa caaacaaaaa 105120
agtgaacccc aacagtactg ccggacagtc tggtgtcttt cctaagtctc ctttcaactc 105180
tgtttaccca ggtgtaccca caaggtgtgt gagcagctct atacccagag gtgatacggt 105240
tgtttgaatg agagaaaagt ttcccatcag ctcgggtgtg tgaatactcg gtccccagtt 105300
ggcagtattg gctggagagg tgatggggag gtgtagcctt ccggtggaga tgggctttgg 105360
gagtttaaag cttcctccac gaagaccact gggctgatct tgttaccaac agaattggat 105420
tggcctgctc ttggctccgg cctcagttta tctaaaattt acatgttacc tgatcaaaaa 105480
```

-continued

```
ctgtttcctc ccccacccct ctccctgtct gtattccctg ccctctagtg gtgctggctg 105540
tatactacac tggtgatctt gactgtattt cagtttacct cttgttctct ctctgctgac 105600
tctagagatg tcctttcatg gctgggacct ggctcagaaa tttctaaggc actgagcctt 105660
cctccatctg aactttagga aacttcttgg cttaaaggtg tatttctgac ttagtatgca 105720
atgagacctt ggagcctgca ctttgttaag caccctgggt ggtggtggtg gtggtggtgg 105780
tggtggtggc agtagtagaa ctctgatgaa cagttagtta ttcaaggccc atctagaaaa 105840
agaaaggctt tgggtgcaca tggctataac tcagtggcga gagacgtgct tcccatgaat 105900
aataatgatg acgatgaaaa taattctctg tgactgttct ccccacttcc ctctctctca 105960
ccctagctct tatctaccga atccctgcac aagcacccat ggggtttaca gaatctgggg 106020
cggaacgtta gtcacttccc ttcgcctact tcagtattgt gtttccagaa gtacccattt 106080
tggctagtca ctgaggaaaa cggcagctgc ctgtgggcca ccagcccatg ccaagtgagg 106140
tcagcaagaa agaagctgac agcaaatgtg ccaactgtgg gtctgctgga tttctactgt 106200
gctaagtggt ttcaagaagt ttcttcttaa ccccctacaa gaaaccacaa attttattat 106260
ctacactgtt ttgtagatga agaaaacacc attccgaagc tcactgccag tcagcactgg 106320
aactggaatt tgtttggcta attcagtggt tctcaaccag ggtggatttg gactccccag 106380
gggatatttg gggacacttc tggtcgtcat aattgggatc atgtgctact ggcacctagg 106440
gtagaggcca gggtggtact gaccttccta ctatgaacag ggcagccatg tacataaatt 106500
ctctcgatca aaacatcaac agtgctaagg ttgagaaatc tcaggctgaa accctgtcat 106560
ttggccttga ggtgggtggg aggaggttag agagtggaat aaaatcagaa gggccaccac 106620
agaggcctcg agtgaggagg gaacagggct cctatgctag ggataatgga gaatagggca 106680
gcttgttgaa actttttcttt cttccaagct tggctagagc cctgctcaat ttcccccaac 106740
tctgccaagt cagtcccggg acttcgcact aagtttgtcc tggagtgacc ctgactccag 106800
cttggagctg gggcaacaca tttacctggg tcttcccagg agtgggttaa aagtcaaaga 106860
taagtggcat ctgagaagtt aaaagtgggg tgagtgggta aaggcaggag gaccccatca 106920
atcagctgac ctaggaagga agagagcaac tgaagcagca aagagctggt ccaggagact 106980
ggattctgac ccactaggct tatcttccac agcctttctt gtttaggctt gggctcagtt 107040
tccctgcatc atccgcagga gcccctggag cacccacatt cagccggccg ccaggacagg 107100
ctccccagca gtggcctccc cactaactga cagtggtgac aggaaatatc tcccattcca 107160
atctcctcag aagtctgaat aagtaaggga cagatgttgg ggagaggcgt cactcttggg 107220
ttgatgaaga aaagatcatg agaagcatac attttacccg ctatggttgg ggttccatta 107280
ccacccatgg cggggttgag ggggaagggc agaaaaaagg agatggagaa ggacagacac 107340
gtaagaagga ggatgtggtt agggctgatt cgtcccctgg ggtcgaacaa tcagctgtta 107400
ctggggcgga aggcaggaag tctccttaaa gacacaatat tctgaacgtt gaactcagga 107460
tttgaagcaa gcccagcagt caccttagtg gagcccatac ttaatttaac acagaagcgg 107520
ctatctcagg cttccctctc atttctttgt ctcagatgct ctcacttaga aagcttagat 107580
gctcttagaa atgactcaaa agtcaagaac cccaggccac aagtttctct ttgggggtgg 107640
ggagggagtg aagaggtggt cccagtcttg tccctttaaa taagcaattc agcagctttt 107700
gccaagtcat tgggttcatt tcggtttttg cccatccccc gcctttcaga ctctgattgg 107760
cccctaggga aggagccgcc tcttcattgg tctccacctt tgaaatcact tccctaagta 107820
```

-continued ggcctgagtc agagaagcgt ttcggagggc gggactgaat gggtgttaat cttagaaccg 107880
ggtttctggt tgatactact ttggtaaaga tcttccccta atttttaaaa agacgcttcc 107940
tctctaaaag tgagggcgaa tcctttgtta agaacgtgcc ccttgagaag ccgtgggctc 108000
ttcagcgact aagacgagac attcactaga aaagatttca ctaaacccac gagggataga 108060
ctagacctcc agtgaagatt gggcctgtgc gggtgacatt tgtccctata ccccgaagac 108120
ctcgagctag ctctccagtg aagactgggg ccgtgcgagt gacagtggtc cctatacccc 108180
gaaaaaaaaa aagtcctatt tgtggaaaaa aaaaaagact tcgggtgttc tgctgcatcg 108240
gtggctggct tccatcttta gttctactca ctcctgttgc ttcgcgtgct ccaccttcgc 108300
ttagctcagg cctcctgtga atcagttttg aggctaaaag aagttccaag aaggaggggc 108360
tgtagccctt taaggacttc cccgcgaccg agtcagagat cagtttaaaa atgccaactc 108420
acagagcgcg ctgcattctg ggaagctgag tgtcaccgta agaacttcat tgaccggaat 108480
gcactgcaaa aatacacgcc tatacttcct tctgctcttt aaactgtagt ttgacgtaaa 108540
gctggtctaa gcaagtcgcc taggccgagg gttagccaca ccttttcagc cattggccag 108600
ttggttagtt ggtaggcgtg gcttagagaa gctcctccag gcaagggggt ggcctccttg 108660
ccaatcagag cccagacgcc tgaatgggcg ggagtaagca gaggtgctgg cgcccccgag 108720
tgggtgtggt cacgttgccc agcaatgggc ggtgattggc cctgggtggt tcattcgcag 108780
ctcgtgcgtc acgacgccgc cagctgatcg gagactggag ccggtgtgtg ctgggcgctg 108840
ggaagagaca gagcggtcgg ccgtgcggac aggtcgcagt gattttgctc ctctgtccac 108900
agcaaccccc gcacccagca tcaggtgggt gtgatctggg gacccggtca tcccgggggg 108960
aaccgcggta accgggtgat ggggaaagta gggtcctgac ggccacaccc tgcccttctg 109020
ggggagggga gagggggcgg cggggacagg ggcgctcttg ggagaggagc ctggactctc 109080
ccgagtagtg tgtctggacg tttaaagaga gagtcccgga caggagtcgt ggcagaaggt 109140
ttggagaagt aactggggag gaatatgaga ggccagaggg ccgggggcgt ctaaccccga 109200
cgccctttgg tttgaggatg cccgagctga ccatttagcc tagggaggat ctggacgagc 109260
gaggggtgcg gaggtgcatt gcctctaccg gcgctgactg ggtcagggcc agttcaagtc 109320
cctggcaggg aaggggtcgc tgggcggtcc ggcccctcct ctcgttccct cccggggatg 109380
ttatgtaagg ggggagggga aaggagtagg gggcggcggt gcggaggcct tatgcaaccc 109440
aaaggttagg gtttcaccgc gggttgggcg gaggttgggg ggggcggaca ggaggagtgc 109500
ctggaaactc tacccgcacc ccccctccca gcctaactgg ctgtcttgga cagagagaag 109560
gtcacctttg cacctccccc ctagtatgtc cggtagagag gcccctagcc cgggcttggc 109620
ctgactgcct gggaagccgg ctggctgggt ggggcgcctg ggttagtcat cgctgggctc 109680
cctctctccc cacctcctgg ccaactcttg gcccctcccc acggcctccg gttaggctaa 109740
cgttcccacc tccctctggc cctagtttca gtctccaact catttggcct gtcaccctgg 109800
ctgttagagt aggctagaag ctgtcatggt gccagagagt tgatggagca gctggtcaga 109860
gggtcagtgc cctgggccca ccccgccccg cagccaaggg cacctgcttg gcacaaactc 109920
tcagcagcca gtgaaccctg tggcctgaac agagctatcc tgggcagaga gaagtggaca 109980
gagactgatc acctaggaga aggaagatcc gacaaagttt atacttccca agaggctttt 110040
ggaatttgaa agttgcccac cctagtgtaa tctttccact ctctgaaaat agaaatccca 110100
aggcaaagtc tccttggccc ttctatctgg cagtggccat gtccttggac tgactgtgca 110160
gaaccaccct ctcgggctcc cagccctcta gcctgccacg cccccagccc cctccctgag 110220

-continued ccatgctgta gggccccggc ttttactgct gattcatgcg ttggaactgt gggggcgggg 110280
cttggaactt ggaacaaagt tcagacgtgg aggggccggc agacagcctg gaattcatac 110340
cagatgtacc cggaatgtgc aagcggaatg cctggcatct ctagtcctga ggaagctgcc 110400
cagccaccct acccatacct ccctcccctc ctgcctttgg tcagctgtcc tccctcagac 110460
tcctgagagc cctgctgac cttccaactc tagtgcccct cccatttcta accctacaca 110520
aaccctcctt gctgctgaat tccctaagaa caagtcattt gagttgatca cagagctcat 110580
atttctgaag tacatttttt tttttaactt gggacttggg ttctacaccc tgccctttga 110640
atgccgaaga tgctgggctc cttagcaggt tgccaagagt tgccagctcc tagtctgtaa 110700
aggggcacaa agcaagtgca tttagaagcc tcttgcttct tattcaagaa cccctcatta 110760
gaaggtactg aaagtcagct agagccaggt ttggatggcc tctgggtcgc tggccctgtc 110820
acccagcttt cctgtttttt tttttcctcc ccttcctttt aggaacctgt gcctccccaca 110880
ccctcacctg gctgagccgc agtagttctt cagtggcaag ctttatgtcc tgacccagct 110940
aaagctgcca gttgaagaac tgttgccctc tgcccctggc ttcgtggagg aagaggagaa 111000
gcagcagctt tgcctatcat ccggaaggtg acagaactgg ggtgggaagg tctggacagc 111060
tggggtgatg gctttatggg agggaaaccc tggtcctctg gggagccctt acccccactg 111120
gcccagtgaa agatttaggt taaaggcact gtctataaat tggggaatag gtgactccac 111180
ctccccaaga ttagttgatg tctgtgtggc agtgggaaga aatagaagga aaagtctgtc 111240
tgtttactga gacttccttg taggcctgcc tttcttatct tcatcatcac catgccaaca 111300
cacacacaca cacacacaca cacacacaca catacacaca catacacaca cacacacaca 111360
cacacacttt cctttccatg aggtccaaaa gtaaatgtac tcaggaaggg ggacattgaa 111420
actccgttct aagtagtcat ttgtgtattt acttttttttg tttatttgtt tgattgactt 111480
tcgagacagg gtttctctgt atagccctgg ctgtcctgga actcactttg tagactaggc 111540
tggcctcgaa ctcagaaatc tgcctgcctc tgcctcccaa gtgctgggat taaaggcgtg 111600
tgccaccacc gcccggctgt atttacattt ctttatttat ttttagtctg gcccagattt 111660
tgggtttagg ggtacttacc cttacacctg tggatttttc cacctgtata atggggaatc 111720
ccatagataa gtaggcagga gggcattaaa agtccaccag tggtgactca gagcctgggc 111780
tcttcttctt ctcgtggatg gaaacgaaac agctcttcac atgaactgtt gtccttcccc 111840
caccccctga ctactcaccc agctcagggg gattaggatg gaaggaaagg ctatggttaa 111900
gtcccaggca agctcgtggg aggctagtcc tctactggct tctcaccatg catgggtggt 111960
ccaaggcttt ccctccacct aaagcaaaac tgtagctctt ggttgggttc tagcaaccac 112020
tgccatttat tttctgcctt tgctttccag gatagtgaga ctctgctcaa tactgtgcag 112080
gcaagaaatt gtcaggggag atgggttgta tgatatgagt cccttctgct gcctctagct 112140
cctgattcat tctcacgtat gggcttggtc tctgattgtg gttcaccttt ggcccagtct 112200
tcctaacaga agatgggttc agggggtaca ggaggctgtt tgttgtattt gacaggagga 112260
ggagttctag cctgttcccc atttgtgaga aactgaaagt catagggggag actagatcat 112320
ctaatccagc cccactgcag tctaagctga gggataggat gtgtaaggga ctgtagcaga 112380
cgggctgggg aggctgagtc ggctcacaca ttgcgacaaa gattgccctt ccctcgacct 112440
cgcttgcttt ctttcctcct cccttccctg gccacagtgt gtccctccag cactgggtac 112500
atggctctgc tgtcctcatc caacatggag cctcagaggt gagaaagggc agcctggaag 112560

-continued

```
caacagaggc aggcacaaga cagtggagga cctggcctgg aaccacaagg gcctatccgg 112620
acattggtca gagaggcacg tagaagcctg gagaacacca ggaaagagag cagccagcca 112680
gcctcagtga aagacacgtg cttccagcca tctcctctca ggacctgcct tcctgggaga 112740
tgaagggcct ccaggaagta tggtcccatc tctaccctgc agtttctata aacagcctca 112800
aggagcatga gccacctctg aaaggaaata cacagcaaat tcaaaaagag attcaaatgt 112860
gtaacactgt gggaaaacat atctatgact ggggttgtag ctcagttggt aggtttgctt 112920
aacatgcacc aagccctggt tctgtcttct gcattgcata aaactgaaca ggttggccca 112980
ggtctgcaat cccggcactc tggaggtggt ggcaaaggag cctacattca aggtaatcct 113040
ctgctataca atgagttctg agccagcctg ggctatatga gactgtctca aaaaataaaa 113100
caaaataaaa taaagcattg gttagtaatt caaagaaagc agatgtggct gaaaccgttt 113160
tccctgatca taatacaaca agcaaatgaa agccagaaga aggctcctgt gccttgtgtg 113220
tggcagtacc aaccattgtg agagatgcct ttggacctgg tagtttgctg tcttagaaat 113280
gtatcctaaa ataaggattt ggttataaaa tgttcatctc agggttgtaa tagagaaaaa 113340
tggaacgcag ctgtttgttt ggaagtccat tccttttctg ctgtcatgaa aatgtatagc 113400
tagggcttgc ctaagtaaat tatattcatc tgatggtggt gttctgtgca gccatccaaa 113460
gtcttacaga agaaaaattg agtggaaata taaatattga atactaaaaa gattataaaa 113520
gtatgagttt gtgactgttt ttaaaatatg aacacatact tgtaatatat ttttttaaaa 113580
accatccaat tgagtggaaa tataaatact gaatactaaa aagattatga aaagtatgag 113640
tttgtgactg tttttaaaat atgaatgcat acttgtaata tattttttaa aaaaacactg 113700
aaagtggatt caaaatgtta agaatggttg tttttgtatg gtgggatagt acaattgtga 113760
attttcccct tgtttttttct gtctttctaa tttttaaata ttgtgcattg ctttcatatg 113820
ttaaataaaa tacaaaagac aaataaatgt tttaaaattt ttactctttt atgagtgttt 113880
tgcctgtgag tggcaggaat ccaacattgt cttctgaaag cagctagcgc taacttctga 113940
gccgtctctt cactccctct gtaattttta aaaaatatat ttgtatgtta tattatgtgt 114000
ctttgtgcac cagagtgtgg gtgcacattc tgcagaggcc agaagagggc atcagattcc 114060
ctggagctgc acgctgtttg gatcttctga tgtggatgct cagaatcgca ctcaggtcct 114120
ctagaagagc agcaaatgct cctagccact aaagccatct ctccctctag tcctcattgt 114180
catgtttaga ttttggagaa tttgcttgta ggaggatggg ctacaccaag tgccaggtga 114240
aagaaaatgt ttgcttggga tacctattgc ttcttgagtg tgtgtgtgca tgcttgtgtg 114300
tgtgtgtgta tgtgtgtgtg tacactggag ctaggaatca tatccagggg ccttttcaag 114360
ctccaccaca ctaaagtcaa ttctatgaac ttcattaatt gtctgaatcc acctactctc 114420
tacacacagg aagcattcct ctgactttct gactgtcagc cagctaagga ggtgtggctt 114480
agaataagaa agaagggaaa tgctcaaaac ctgtcactct ntggggnnnn nnnnnnnnnn 114540
nnnnnnnnnn nnnnnnnnnn nnnnnnnnnn nnnnnnnnnn nnnnnnnnnn nnnnnnnnnn 114600
nnnnnnnnnn nnnnnnnnnn nnnnnncccc tattttacca agcattgcag gataaataag 114660
aacatagctt aaagaattct agagaaaaaa aaaaaagtcc actaatgttc aatgttttaa 114720
ttaattttta atgggaaaaa gtaatatcaa agaaatccat gtctacggca tattaatgtg 114780
gttaatgcaa acaggacaga ttatcttggc caaattaaac cacagtaaca cgttttgaac 114840
taaaagtcat ctatttatac gagatgaaat gtgaattagc gtgcgcgcgc aggtgcacac 114900
atgcacacat acaaacagag tctttttatt cttaagccta ccaaataact ctttaagcag 114960
```

-continued taaataattt taagctctaa aatttaaaaa atagtgaaac cccttcaggc tatgacagaa 115020
tgctgctttt gccattcttt ctgataaaag tcccaaaggg tgtcataatc tgtatccttc 115080
ttagaaaagt aaggagcaca tcctatgagc tggtgacctg agttttacac ccaagtcaca 115140
cgtcagcaca cagcaatgtc ctggaccatt tgtgaggagc cccacgctgg tcctgagcaa 115200
caactcactt ggactggtac ggggtgaggc tggcgatggg caccactttg gactgtgtcc 115260
cacctgaagg ctgcagcagg ccagttccgg caggttttcc aaatggcttt gaggcaccat 115320
aagccttagc tgcagtggaa cctatgcaaa cacacaggaa aagggcagtc attcccgttt 115380
tatttctcga agtgaatgta caggcaccat ggcacgcatc tggaggtcag atgataatct 115440
caaaaaaatc caacttttgt gagacaggct cccttcattg tcttcccacc acacttgcca 115500
ggttaggggc acaagctccc aaggagtatc tgctctccta agggcactgc catcagagac 115560
actctgacta ctacacctgg cttttaggtg ggttctgagg atttgaacgc agatcatcat 115620
ggttgtatag caaattttta ttcaccaagc cagacaaccg ttttttaact ttttttaaaa 115680
aaagatttat ttttatgagt acagtgtggc tgtcttcaga cacaccagaa gaagacatca 115740
gatcccatta cagatggttg tgagccacca tgtggttgct gggaattgaa ctcaggacct 115800
ttggaagagc agtcagtgct cttaaccgct gagccatctc tccagccctt atttaacttt 115860
taaaagttta aaattaattc tcattatgca cgtgccacag ggaagtgtaa cataagcaca 115920
tgtgtttgaa gtatatatgg ggatgtagtt atgtgacggc cagaggacaa ctctgtgaag 115980
ttgattcttt cctttcactg tgggtcctcg gagcgtcaat agggtcagca ggcattttac 116040
cagctgagct atcttgtggg ccaccaaact tatttttaaa aagctagaag ttggttaaag 116100
agaaggaatt catgtaattg aaatagaaaa gcagagttga agagggagga gaggaggtga 116160
gtatgatatg gtaagaaaaa ccaagaaaaa acctctacaa gtaaatctag tcgtgttcca 116220
cagatcacta tgttcaagga tggtgtccca gaaaagggtc ctaaaacaaa gcccaggaag 116280
taatcaaaat gatcccatcc agacctgcta cagagaagct ggggggaagg agggagaggc 116340
cctgtaacct caagtccccg ggcagcacag cagagctgtg cccaatgatc tccgtgatac 116400
aggacaacag gatatctgag aaggagtccc agtgagcgtg tagcagaagc cagaggcctc 116460
gaacaaaacc aacaacttca ccatgatgaa catcatgaag atgtgtggac aaaagggtgc 116520
actctgggac acagtgtcac acactacagc ttccacctgg gacaaaaagt cacacactac 116580
agcttccacc tgggacacaa tgtcacacac tacagcttcc acagtcagat tatttttctt 116640
ctagcggaga ggctgcaagg gtggagggca ggtacaaggg aacaggggtg agtgggatcg 116700
gggtgcatga tgtgaaactt acaaagaacc aataagttag gaaagagaga tgaagacata 116760
gaagccatgg ccaacaaccc cagcactctg gaggcaggca ggagggtctc catgccaaag 116820
gtaatgaatg ctatgtctaa agagatgata aagtcccatg agagttacaa agtcagagga 116880
gaaacttgga cagaaaagcc aaatgtaaca aatgcatggt aggtggggaa aggtggggat 116940
ttaaaagaaa tttcacaaaa aggcacagaa tgtaaggtga aagcgagcga ctaccagata 117000
aagcatcaac taagaggagt caggaacagt gtattttaac tacctttata aaaaaaatac 117060
tcgggctggt gagatggctc agcggttaag agcaccgact gctcttccaa tggtcctgag 117120
ttcaaatccc aacaaccaca tggtggctca caaccatcca taacaaaatc tgatacggtc 117180
ttctggagtg tctgaaggca gctacaagtg tacttacata taataagtaa ataaataaat 117240
aagtattaaa aaatatgcaa taattggaat tattctttgc aattctacta tgaatggagt 117300

-continued ttttgttcct gttgtttgtt ttccgagcct gtttcatgta atccaaactg gcctggaacc 117360
tgctaaatag tggaagatga ccttgaactt ctgattcccc tgtctccacc tcccaagtgc 117420
tggcctaggc tactctgcct gactcaggct cagtgaattt tcaaacactg cttcaacctt 117480
gacccctaac ttccatctct tgggtcccat cttacccatt cccagactcc cattctgtgg 117540
ctggggcttg ctggctggtg gtgtcgctgc agaggctggg gaagggactg cttgctgctg 117600
ctgctgctgc tgctgctgct gctgctgccc atatcctgga gatcaaaaca ggccaattca 117660
gtgcaaaccc agtcaagaga tttcaacacc agcagtaaat accttaggaa aacccacctt 117720
tggctcttag aggagcagac tgcaccacgc tgcacaccct gtgtctgcaa agggctcact 117780
tttttgtctg cgcatagtaa agactggttc catttccctt tcaactgttt agaattgaca 117840
gctttcagtt ttaatgaggt tctccctgaa gccttgccca tttctccttc aagaacctgc 117900
agtaaagtca ctgggctcaa tctgtgatac taccactatt tccatagcaa caaatcgatg 117960
tcatcaacag gacggtgtgt tcgtggcagg atccattaga agagaaagca gggtggtaag 118020
gaaaacctaa aagcagttca attgtctctc aagtgctttg gcttcaaagg aaaaggagac 118080
gtttacaaag ggttctaccc tttcccccaa acaaagcaac cttattttgc aactgacagc 118140
tggtggaaaa tatgagttga aagagtctca ggtaccgtga agtgctagtg aactgtcaca 118200
gcagggagag atgagaacag agttcagaag cagccgtgtc aaggcaacag ggagataaaa 118260
aggaggggga ccgagcacgc ttctaaagca gcaaataaga cgcgccaccc tgtcggagtg 118320
tgtatttgcc cttcaccctt tatacaaatg tttaccaagt tgaagaatgt taacattgta 118380
aattgcctac cactatttct aaaataacga gtttatgggg tttgatttta cttctgtgat 118440
tggctctgaa ggctgaagcc agcctcgttt aggctgctca cctggagtgc ttgtagatga 118500
caaaggcagc taaaaaaaaa aaaatgtccc agagctcctg aaacactaaa actggtgcgc 118560
acaggcagga agtctccctt gccactgagg ctctcccttc tccaactgta agttctaact 118620
cctgctgggc ctcctgaggt cccaactcac cgggcatgct acatgcccat ggaattcatt 118680
tttggcaaaa ttactcttaa gtagctcaag gaatgagacg taattgtgtt gctggagaca 118740
aatacattca gcacaaagtt gagaagatta aatagaattg attatgcttt agttcatcct 118800
acagagagaa aaagtgagac acctatttac ataggagagg ggcccaggct actgacaatg 118860
agccccttcct ttacagctca gccttcccat tatcactcaa ctcagacacc cagcccagtt 118920
cagtctatgt gaagcatttt taaaatcagc aagagaaagg tgagttgctc agtagtacac 118980
tgaaggaaag tagaaatgag cacacagtga cctgctgcat aagacacagt ttaaaaggtg 119040
acctatcttc cagcgaagtt cttgccttct ttaaaaagaa tgtggtattt gctggtatgt 119100
gcacctcacg aaggtgcttg cagctatgtg gagggcagag accatcctga gggaatcggg 119160
tctccttcca ccagagtcct agggatggca caaaggcacc gggcttgaca gatgccttta 119220
cctgctgagc cctttcccca gcctctcctt ttctacagtc tccaaattac ctgaggtagg 119280
agcctcattc tcagaaccat ttctgctgcg catgtctgac tgaactggat atggtcactc 119340
gactcaattt ctataaaaag ataactgagg agccggcttg gttggtagag aaaacataaa 119400
gacccgagtt ttgttcccac atggggcgtg cgtgctagag aggtgaggac ggactaggca 119460
gggagcagag gtaggcagat cccaggcctc aatagccagg cagcccaacc tgagctctaa 119520
gttcagtaag ggagcctgta accacagaag acactgtgcc gtgtaaccac ggcaagcggc 119580
ccgctgcagt ggcatctgct catagccaca gctacccagg aggctgagcc acaagactca 119640
ttgaagctgg aggtcaaggc cagcataggt accataggta gacccccatc tcaaagttga 119700

-continued acagtaaaca tatattttac tacaattaaa aaaacaaggc cgggtgtggt ggcgcatacc 119760
tttaatccca gcactcggga ggcagaggca ggcggatttc tgagttcgag gccagcctgg 119820
tctacaaagt gagttccagg acagccaggg ctacacagag aaaccctgtc tcgaaaaacc 119880
aaaaaaaaaa aaaaaaaaaa aaaaaaccaa aaacccaaca catgtaccta ttctaacata 119940
aaattttcat tttttataaa aattacagtt ataattttta gttgaacata atacaatgat 120000
aagtctccaa cttgataatc tgaggctggg ggtgtagctc atttagtaga gtacctgcct 120060
agcagtcgct aagtccgggt agtcccttgc ctgtatccca gtgcttgggg aacaggcaga 120120
aagaggacca gaagttcaag gtgctcctcc tcttcaggta atgaggagtc tgagccagcc 120180
tgggatgcgt gagacacacc agtaacagca actactgcct ggagtgctca ctctggacca 120240
ggaacaagag ttaagtgcgt tactcccgta actgtctgca caatgatgga gacagtacgt 120300
catctttaac atctttggct gagaagagaa aacctggtat tcctcagctc gttctggcta 120360
agttcatgta cttcatcatc atgcagttaa tttgtaaaca accaatcctg gcagcaataa 120420
ctctaattat atagaacata agatgtggta attaggaaaa gctactaatc cacttaatag 120480
agtaaccttt atctcttgca aatctggtac aagagacagt cccaaatcaa atgatggcaa 120540
gaattccaga gcattgtaaa tagcagcaat tgcccttcaa ttaacgcatt gtaacgcagc 120600
agctgcccac aagacctcaa atcaatcagt ctatagctaa ggaaaaatct ttctaaagcc 120660
aaaaccattc tacaaagcag taacgtaggc tccgtttata ataacctgtt ttgggccacc 120720
tgcaaatcaa gctatcccag gaagccagat cgtaattctt aggctctgct ggctacacac 120780
tggtcccaag ccatgaggga actagattac agcaggctcc gccctcggtg acctgctcat 120840
agctatcatt cttacagtct attatggcaa gtgagctctg ggcagagaaa aattcacaaa 120900
caaacccacc aacttcccaa gcaagcattt tcttaacaaa cacaaagaat aaataaatag 120960
agcctgccat ggtagtgcac acctgtaatc tcagcatgtg ggaggcagag gcaggcagat 121020
ctctgccagg agttccatgc cagcctggtc tagacagttg caagatcaac aacgctatat 121080
ggtgaggccc tgtctcaact cccaaaccac tgaaaacaag taagacgata tggatcaatg 121140
caatatttct cagttcctac tgacagaaaa tggacacaat taggctgggt ataattccaa 121200
tatgaataat aagtatatta tacagtacct agtttaagtc tgagcaagat attatcgcca 121260
acagcacaga tacaggacac acacacagct gcaagcgtga aggatttaaa ggcacccatc 121320
cctacagtat atgcagcatt gactgtctag ttttatttcg cacactttga atcatccatc 121380
catttttgct caatatggca gcagtaataa aatgtatatt tgcattttga tgcatggtgg 121440
aattcttact agcctgggct gtgtttgctc actaactcca gtggacttct gacgtaagag 121500
gcgctggact agcttccaga ggatgtaaat ctaactttgg ttctcggcct cccctgaagc 121560
ctttgctgtg gtgaaaggtg ctgtttctga agccacgaca gtcccatggt ggtttgagta 121620
acaatactcc tggcttggta acaatgccaa aaaataccaa aaaaaccaaa accaaaacca 121680
aaaaaagcac agagctcaca tctgagccaa aaaaaccgac actccctatt ttttgaagaa 121740
ctcacagaaa tcaagaagaa aaacaagcaa acaaacagca cataacaggc taacaacaac 121800
aacaagtcca cttcagaggc caaaaaccaa aaggcaaagg ggctcttaaa catttacaag 121860
gacagacctc actcagaaca caagctatag ccatgatact gctcttcatc catcaattct 121920
taaagacaca gaagatgggc tgctggcatg actgggaaga gaccagtgtg ctcactcatt 121980
gctggggtac gctgtaacaa gcagaggaga atgtctaact gtgtctgcca atcacaggca 122040

-continued cattcccagt taacccagca atcacttctg gcaaaaaaag cccactctgc ccgcacactg 122100
gtgtacccag gaggtaattc actgcggctt ctggtggatc ttttttcctt cttgcagtgc 122160
ttgggttcaa attaggatca agcacacttt tatagtcaga gcacggagac aaaaggatct 122220
aaccacagag ttggttaaat aaacaacaga acagccacac cagaactgct ggggggcggg 122280
gggagggggg ggagggaagg gggagaagct agaatcccag cattcaggat gcagaggttg 122340
gtaaacaagt ttcaggctca gtcggggtat aaggtaagac tttatttcac aaaaataaat 122400
aatttttta aagaggacag aaaaaagaca gcgtagagaa ctagctatct tttatgtaaa 122460
ccatgtgggg tacaggagca gcatttgcat ttggttactt ggcgaatagc cctggtagga 122520
taaagaaacc ttaaactgtg ttatctataa agggcagcag tgggtgcaca atgcagtggg 122580
taggagccca cccattgcac gccatagttt tgattacaaa gtcacgcagc tctactcaaa 122640
aattaaaaca aacattaatg cttgttaaag aaacagggct gcagagatga tggctcagtg 122700
gttaagagca cagcgcccat atggaggctc tcagccatct gcttctccaa ttccagggga 122760
agctaacgcc ctcttttggc cttcaagagc actgcatgca catggtacgc ttacctacat 122820
gcccgcaaac attcaaagaa aaatacaaac tgctataaaa cccatatatg accatcttaa 122880
gattctttca tttttttgag acagggtttc tctgtgtagc cctggctgtt ccagaacttg 122940
ctctgcagac caggctggcc tccaacccag agatctgcct gcctctgcct ccacagtgct 123000
ggaattaaag gtatttaaca cacacattat acatatcttc cttcttcttc ttctttttt 123060
aaagcgtttt gttgtttttt gttaagtttc aattaaaaaa ctacatagtt ttataggcaa 123120
acataattaa aaatgccaat gtgaaataaa taatatatac atatataaca ttctgtaata 123180
gattcactca cacaacttat atacttaaat acaattttca caataatgaa aagctttgaa 123240
atgaagactt ctggatacat tagaaacgta ccctgaaaat cgcaaatgac ggttttcatt 123300
tctttgtgtc agacattagt gtgagtgtct aaacttgcat aaaggctctc ttctctatca 123360
cttcctacct attgcagtgg ttctcgctaa acctggaacc tggggctcct gttccttggc 123420
tggactacaa ggcagcaagt cccagcaatc ctcctgtctc acctttcttg gaaccaatgt 123480
tataagtgtg tgtgggcact agccttgtta catggctgct gggactagaa ctctggtctt 123540
caatattagg catcaagagc tcttaactgc taagccatct ttctaccctg attagaattt 123600
cttgaagcaa aagaaactca cagatggtca gagtttacac acacacacac acacacacac 123660
acatacacac acacacacac tcacacacca aggcttagtg accactgtga aaagggaagt 123720
gcggtgagga actgtaaaaa taaggtgtca ggaaagctct gcacaaaatg gtgtcctctg 123780
gacaagccag ggcctctgcc ctcatcagct cttagtaact atggttgcct acagcaaacc 123840
atgccaggga ccactctaac atggagctgg gatgggctcg agaggccctg ttattaaagg 123900
agaagctgta gagagttgat ttgatggatt ctaaagtagg gggaatcgat ttcctttatc 123960
gatatgggtc agccatgctc tagtgagtgg ccccacaccc acccatgagt atgtgtggac 124020
agcacacacc ggacctggca agtcaataaa acaaaaacaa aaacaaacaa ataaacgttc 124080
tggtccacca tagtggctgc tcgtggttgg gagctgtccc gcacttatgg caggaagaca 124140
gtggctgcaa agaggacaaa agtctctgga actgatcaac tctagagtct gcttgttatg 124200
agaactggga agtacccgct gggacagaag cagactctga aggtgatcag gacagagatc 124260
acagaaggag agactggtta tcggaggaaa tctgaaacat aactcgacgc atactggtcc 124320
aaactggtgc ccatcactac aacagcagta attgaattgg gcacaacatt cagaaaacag 124380
aaaaagacta cagagtacgc accctggcta tcatcaaccc aggcgattct ggcactattg 124440

-continued gaagcaagcc agactggaga aaaggaaaca aaaagttatt taacaaaact tcccagagca 124500
tgttaaaaaa aaaaaaaaga aagccagaca tgggggtgca cgtttttaac cctagcactc 124560
aggaggcaga ggcaggtgag gcaggaggat ccatgagttc gaggccagcc tggtctgtac 124620
agtgggttcc aggaaagcca ggcaacaaag aaaccctgtc tcaaaaatca ctgactgggg 124680
agagaggaag tggatccaag agcaagagag agagagcaga gagagtgggg gtttggatgt 124740
cagcgttatt aaatgacagc agaaaagatg ggcccgacca atgacatccc agaaatggca 124800
aagatgaaaa aataaacaca agttctaaat atcattttaa taatggctgt gtgtctgctg 124860
gctcattctt gttatccaaa caaactaaag caggggtggc cgggatttac ggccagccag 124920
gactagagtg agacactgct ttaaaaaagc aatagatgca cgctaaccat taatcagcgt 124980
aactggagtt tgagggaggg agtgggcccg ggaagcctgt gcctataaac ccaacctgcg 125040
aggcctgaag cccgaaggtt gaactgagaa catctcaaga caaagcacag gcacaatctc 125100
ttacaaacag tttaaacaca ataccagcaa taaattgtca gctttatgac agataggctg 125160
acaggcatac cacaaagatc gggaagaaga aacgggattc ttgcacaaca ttttacaaat 125220
cgacacagct gagcctagtg acaggccgtg ataagctcaa aacatgcaca ctgcaaacac 125280
cacagcatgg ccagagtgac agggtcacag caatacagca acagagacag taagaaacat 125340
tggaaaaggg aagaaggcaa agagcaccac gagagaaaag ttaacccgcg attccatatg 125400
agggcccagc atccctctcc cacctgacag agaaaaccag gaggacgcag ctgaaacact 125460
gtacaactat aaatactcct tcctagtgta gacagagttt accaaagggt atcgtaatct 125520
gaagcacaaa cataacactg taagttacca gaagtttaga cacgttgaga atttaataga 125580
agttgagaca tcaaacacac gtttgatcct aggggaatta aattattggt aacagaaaag 125640
ctctttacaa agtctccaca tttataaacc aaatacactt gtatcagaat tgttgtctga 125700
gccagaggcg gcggcacaat ggtggctgag gcagcaggat caagtctgga gaagcccctg 125760
ggtccaggga gcactagtga attcaagtaa acattaaaca ttaaataaga aagacggatt 125820
ctacaggagc ctagacaccc tgtaaggtca gtactactaa gataccaaaa ccaaactgac 125880
tcagggggct gatgagatgg ctcagtggct aagggcatgc actgctcttg cagaggacct 125940
gagttcagtt cccagaaccc gtatcaggca gttcgcccac ctgtaatgta ccagagaccc 126000
taaacatttc tatcctccaa gcacagacac acataaacat aattaaaaat aaatcttaaa 126060
aaaaaatctc tcgtggacag acagcaaaaa atactgaacg aaatctaatc aggtagactc 126120
agcaaagcaa atccaaatat gcgaaaagga taatacaatg caaatccaga cttatcccag 126180
aaaccccagg tcgctttagc atccaaaaaa ttcaatcatc ataattcacc gtattagcta 126240
accgaaacag aaaaggcatt tgattattaa taaatacagg gaaagcattt gacaacattg 126300
accattcact cttaataaaa atgttaccaa acaggagaaa gaagtaaaat ctcctcaacc 126360
cgatgaacag gaacacaaac tggctgggca cagtggcaca tcctgaaacc ccagcaccca 126420
gatagctgcc agactgggct ggcatgagaa ccaagggtaa gaggcaccca aacacttaat 126480
gatccaaggt gctgcctccc cccccccct gtgtcactta aatccgtaat taaatttctg 126540
ggaggagggg tttgacacag ggtctcactc tgtggcacag gctagcctga atggagtcaa 126600
tgctggcctc aaaactcttc tgcctcagtt ccagagtgag gggaaacaat catgagccac 126660
ctcacccagt tttaatgcca tttaacagta caaggttaaa cgctgcctga aaagaacaag 126720
acaaagaaag atcacacaga caaacatcac acaggtgctg tttgagacta ggtctctagt 126780

-continued gatgtaggct ggtctcaaac ttgcacaaga aaagaatact tttgccatca agatcaaggt 126840
tgctatcacc catggtggca tttcggaagc agaggcagga agatcagtag tacaaggtca 126900
tcctcagcta ccatgggtgt gaggccagcc aaggcagcac gtgagccagc tgtggaagca 126960
cacatctgta accccaccac tcaggaggct gaagcaggaa gttcaagcca cacaagagcc 127020
acttaaaaat aaataaaaac ataaataagg ttggagagag ggnnnnnnnn nnnnnnnnnn 127080
nnnnnnnnnn nnnnnnnnnn nnnnnnnnnn nnnnnnnnnn nnnnnnnnnn nnnnnnnnnn 127140
nnnnnnnnnn nnnnnnnnnn nnggaaaaca cccattagac tgctgaagag actgagaaat 127200
tgtcatcttg aagggttgaa atcactgagg aatggctaat gacaaaactg cttaaggaga 127260
attttattaa aaaacaaaac tccttctgga ggagtactgt gctcccttca gcattaacta 127320
ctgtgccagg gaacccactg ccagcagaca cccaacttca aggataatca agcttgctac 127380
gtaacatggc tgcttacgca gacaccacac acacttcctg tatgctgggc atcacctcta 127440
gcttacttat aatatcaaac ataagtacca tgtgagcgct acagggcctg gccaatgaac 127500
agcgatggga aaaataacct gcacatggtc agtaatgggc aatccactcc ccagacactt 127560
ctaacctcag ctgcagactt gtgggtactg agaacggacg tgactaagtc aattcacaga 127620
agcagagccc tgtgcctgtg ccagggaacg gaggacgctg ctcaatgggc agagcttcag 127680
ggcgggaaga gatggaaagt ggagctaggg cccgatgacg tgaatatggc taatgccata 127740
ttgtgtgtgt gtgtgtgtgt gtgtgtgtat gtatgtgtat gtggtgtgta tgtatgtgtg 127800
tgcatgtgtg tgtgtgtgta tgtatgtatg tgtgtgtatc caaaatggtt ataaaaatcc 127860
catacaatgg ctatgcttat gtgtctttta ccacaagtaa aaaattttaa gtaatcttag 127920
gaacacattt ctaaaatttg gaatacttgt tggggaagct atctgagccc cagcatgaat 127980
caggaaatgg gtaggagagg caggagagat ggcttagtgg ttaacacaca catggtggcc 128040
ctttcctggc accaactagg tcactcacaa ccaggatctg acagcctctc ctggcctcct 128100
caggcaccag gcaggaaagc ggccccacat ccctgcaggt aaaacatttg tactgaaact 128160
aaataaaaac ggagcagaag ctgggcctgg aagtccttta cctccagcac cgggaagcag 128220
gtggatattt tgtgagttcc gggtctacat agtaaaaact tgtcgccaag taaaacaaaa 128280
caaaaactgg gggctggtga gatggctcag tgggtaagag cacccgactg ctcttccaaa 128340
ggtccaaagt tcaaatccca gcaaccacat ggtggctcac aaccatccgc aacaagatcc 128400
tcttctggag tgtctgaaga cagcaacagt gtacttacat atattaataa ataaatcttt 128460
aaaaaaaata cctttaaaaa aacaaaacaa aaactcccac taaaataatt ggaaaagtcc 128520
agggaaagcc acactcgatg gcgcaagcgt gtgatcacag tattctgtag gtaaggcaag 128580
aggatcacag cgggacggag gccagcctca gctacacagg ccggtctggg ctacagtgtg 128640
agaccccggt ctcaaaacaa aacaaaacaa aaaaagcgtt cacattatca tatactcaag 128700
gccacaaaac accttcttct tcccaatcct tgaatgctat cgaatttggt tacttttttt 128760
tggtaatttt ttgtttgctt ttcaaggcag ggtttctctg tgtagccctg gctatcctgg 128820
aactcactct gtagaccagg ctggcctcta actcacagag atgtaattct ttttcaaagc 128880
tggattttga tttgggggtg tgtgggtgat accacaggga cacttgggcc ccaaaccaaa 128940
ccaaagaaaa aacacccccc ccccaaagta tgaacatcaa ctgtatataa aactaacagt 129000
tcatataagc taagtagcct gcaggtacat ggttatggaa acagctttat catacagact 129060
tctttcagta gatgccattt gagaaaaaaa aaaaaacaaa acattctttg gattttcaac 129120
atgtaaacga aaatatgtta aatcttaaaa aaccttaaag cagacgccac tgctctttgg 129180

-continued

```
ggtcagggaa gcacggctgc aggcccccag agcagcacat tccctgaggg aagccttgtg 129240
cgtcctcacc agcaccaaga acagccaact ataataagct cataaaaaat cctgaaaggc 129300
tgcccaagcc tgaaaatctg atatgaaaac agagggcaag acagataaaa ggcaaactat 129360
actttaaaag tcaattccag ctatctgtgt ggaaggactt ctcgggacgg actatctgct 129420
aagaccttgt gggtgattta aacagcgtgg agggcagaaa aagaaaggaa agtgcaggaa 129480
acaatggcaa aagctcctcc tccgtggcct ctacacgcat ccaagcgata tggagggagg 129540
agggaaggac actatacaca ggtaccaatc cccacgaact agaaaacaca gcttttacta 129600
actagtctat ttttttttt accttagcta gtgtctttct tatgtttggc ataatttctg 129660
ctctgcatta aataaaccta gtgtataaga aggcaaatga gtaaaggtaa agtcagttaa 129720
tgttcatttg ttttgactgt gtggtgtgca tgccaggcgc attcgtggag gtcagaggac 129780
aaccgcatgg agcaggtctt ctccttccac caccccaggg gtcgcagggg tcccagggat 129840
ggaactcggg tggtcagatt tgcttggcaa gggcttcact cactgaggcc ccccaagggt 129900
cccaattcac ctgtttactc taatgtatat atttttgaga cagggtcttg ctatgtagtc 129960
caggctagct ttgaactcac tgtggacact agctggcctg gaggtctgag tgaacctcct 130020
gtttccaccc aagtgctggg acaacagaca gcaaccatca aggcaaaatg aagtcttccc 130080
ttcacaccaa agtggcttcc tatgaccttc tcctgacaac cccaaacagc aagtgcccgg 130140
atatgcactt gcgtttctct ttttttactt caagctttga ctccactttc ctaaaaggtg 130200
tttactaggc tgaagcacac ttcaggagac accctgtagc tctggagtga ccggaaacac 130260
accagctctg atgcaaaaac aaaaaacagc gatggggatg gggcaaaggt ggcttgtgct 130320
tctgtgcaat ggcattccct gacgcattac ctcacaccag atacatacag aaaagacaaa 130380
ggtaagtcct cactcagtgc gcgcatccac cacacccaaa gcaagcattc aacagctcag 130440
tggcataagg ccagcattat cacagcgcgg acaaacacaa agccaacctt ctctttgagt 130500
tccccaaggt acatagtgtt ctgtccaagg atggcctctg cagactcctg gaaacacgtc 130560
acccactggt tctcttgaaa atctgcaata tttgcctaaa aaacacaact ctattatttc 130620
agcgaataaa taacaaaagg aagacacccc aaggacgagg gaagattatc ttttcctact 130680
taaagtaact tccaagggag aaatgacatt gccgccacac acagcccccg actctttggt 130740
taacggttcc cccttatgag gaagtattca cttctggtca ccccgtgttt cacttttagt 130800
acagtatcta atgaattaca ggagccactc aatacctttta tcataaagtg ggctttgtgt 130860
taggtgattc tgaccaagcg taggctatgc aaatgctctg agcacactta ggggaggctg 130920
ggccgtgcta gccctgctac atgcaggtaa tgctacgcca gtcttacgcc acaggaagaa 130980
gcttaaaatg tggtcgaact caatctgcta gaggtgtgag tttagacctc gggagacggg 131040
ccaagtaaac ttccgcagat gtcggagcat cagacagagc tgtcccctcc tgatgcaaaa 131100
ggcttcgcac ggcaagtttt taatgagcct ccatggtaat agtgggttcc tctctctcct 131160
cctcccttat caatatgctt gacatctttt agttttttga gacagcaaat aacgtagccc 131220
aatctgcccg catacttact gggcagccac agctggccct gaactcctcc tgcgtctcct 131280
ttaccccgta acaagtgctg gggttacaga catatgccgc catgttcagt gtaagtgacc 131340
gctgcccagc agggcaaagt cttccttatt tacaaagcag cagccaagcc ctgcagccca 131400
ggcctatctg atttcctcag cacaccccca agggtctcac cgatggcagt cagtccatga 131460
acaccgtagg cttctcacaa tccacactac tcaccgataa gatcatgcgg tatttgaaat 131520
```

-continued

```
tgggaaattc ccggtcacac ttctcacagc ggtacaaccc attctgctgg tcaatcactt 131580
tcttattgca gtcctgggtt gggcaggcct ggtacataca gttctctttg cggagaaaca 131640
ccaccgctgc cacagtgctg aaatagtccg cctgcaggcg aaaggaagac cgccatcagc 131700
aagcaacaca ggtctggaac aggcaactca aagctgctct tccttgcaag tggtgagcgc 131760
gtgtacatcc tagctcccac gctcacgagc gatatgcaga atcactaact ctggtttcag 131820
aaatcacacg tgctacacgc agaacccaaa gaagtaacaa accggcactc acgcacctca 131880
ctttttccat tttggagacg gcggctcact agctagcctt gaactcagag tttggtctgc 131940
ctctgtctct atagagtgcc tggctaccac acctgggcac tttgttttcg agacagggtt 132000
tctccggaac tcactctgta gaccaggctg gcctcaaact cagaaatcca cctgcctctg 132060
cctcccaagc gctaggatta aaggcatgtg ccatcagcgc ctgacccaat tctttttatt 132120
tatagttatt atttgttaca tatgtgtatc agtgtgtatg acgtccatat gtatatgact 132180
gtgtgcagtg tgcacatgtg tgcaggtcag aggacaactc tcaggagtca gttctctcct 132240
cctactgtgg cgtttgggga actcaggttc caagatagca ggaaaagtgc ctttaacagc 132300
tgagttatct cgacactgac atgtaatgat tcagtgtgca cacagtggtt ttgcatgtag 132360
tcatataaac cacagcgtgc atgtgcaggc taggaaacaa cctgtgggag ttggtgatct 132420
cccctcacca tgtgagtgag ggagaggaac tcaggctgtc aggctcggtg gcagtgcctt 132480
tactcactga gttcccttgc tggccaagca ttatttataa gatggtgatg tctaccctta 132540
tctttaggga tcagtaagtt tttccccaag acaagccaga aaaacctttt aggcccaatg 132600
agccattcag tcagtctcta ctgccactcc tcaacctgtc tgtggggcag gacaagccac 132660
agacaacctg aagacggaag gtgagccaat aaaatcttac tgacagtaac agccagccag 132720
ctcacaggct tgacaggcaa ttcttggact gaatgcgttt aagagaatgc agaattaccc 132780
atgactaaga tcttctaaat ggaaaaatgt ctggttaagt aacccagcaa ggagctaagt 132840
cacgcaagcg gtggatacct gctttgcctc tgaaccctgc acaggttttg gtttatgttc 132900
aatcatgtca agtacctaca aaatccagat ctagcctgaa ttcaaagata ggctacctac 132960
cctgcccccg gacccccacc cggggtctca ctgtgtagtc ctggctgtcg tagcgctctc 133020
tatacagacc agctgttatc aaattcagag acccacttgc ctcccaagtg ttgggattaa 133080
aggcatttgc cactatgcct ggctctcact ggttgtacca gaggagcaaa acaatgtggc 133140
catttaaaga gacgaagcta gaaaccagtt tagacagctt tggggctgtg ggtgtagctc 133200
agtggaagag cttgcttagc atgcacaagc tgttggtttt aaccctcagc gtgacagaac 133260
cgaatacata agaaggctta gaggaggggg tggtggtgga gagatgggtt agaggttaag 133320
agctggttgc ttaatttccc agtccccaca tggtggctca caacatccat aactgcagtt 133380
ccaggggatc tgatgtcctc ttctgacctc cttggggaca tgcgactcat ttggctcaca 133440
tgcaggatgc ctcgggccac tatgctggct caggggtgaa ggtgcttgct gccaagctgg 133500
gtggatttga gtttggtccc tgggacccac aaggaagagt ttgacttcta tacactgagg 133560
tggaacatgc atgctctacc cgcaaattaa aaacttaaaa tttaaagagg aagctgtaga 133620
gaaatagctt ttaggaggat gcctaaggaa cttctctgcg ttttcaggtg agattcagac 133680
tcaaagccca atttaaaagt ttgagtgctg tcacgtgttc tgtatgccca gttctggctg 133740
tccgttgtct gtctttagtt taagagagca actgggtgag aagtaactga gagtctagcc 133800
gatgtttaat tctcaagatg tcctgtgata gcattataag ttgctgtgga tgacagtgat 133860
ggatcgagca cacagtgaaa tgagacagtg aggaagaaaa cctatattgt atacgaggac 133920
```

-continued aataatggag cagtggcgag cgatattttg ggaatacaat agaaataaat gattcaaata 133980
tccaagagaa cgcaggttag accaaggtag gaagaggatc actgggctgg agagatggct 134040
cagtggttaa gagcactgac tgctcttctg aaggtcatga gttcaaatcc cagcaaccac 134100
gtggtggctc acaaccatcc gtaataatat ctgatgccct cttctggagt gtctgaagac 134160
ggctacagtg tacttacata taataaataa ataaatcttt aattaaaaaa aaaaaaaaaa 134220
aggaagagga ccactgagca cacattgaaa tggaagatgc aactgaaatg caataccaga 134280
gccagtctgt ggcatggcag caggaattac agtctgttca aaacccagca cggacctgag 134340
gctacattat gtccctctac actggccgtg actgaaaagc agcaacgtgg taccctggag 134400
caggcctgag gtcccaggta aggacacagc cctgacctgg cactaggaaa caggtgtaaa 134460
aactcaagcc cctgccgttc tctgggtgtc tggagcgagg ggtgcgaggt accttgtctc 134520
cctggcccag gttctcagat ttagcctcat gcaaagtttt ccagttggtg ttgccccctc 134580
cggcccctcc actcctgtgg tcagagatgg aaacaccatc taaggcttgt ccttctgagt 134640
caaacctagg ggagaaagaa acaaacgtac tgctgacagg aacttcacat ccttctcaaa 134700
tgtgctgtga atgcaccagc cccgagctgc gccccctcgg ctctcaccta ggtctcagca 134760
cacctagtcc actcaagaaa tgcaatgccg ttgctccttc catctcgtgt ccttcaatgc 134820
ccctcctcct ccacccgcaa ggtcagacaa actgccaaag taccacagac cctttcccta 134880
aactgggctc acattgacag cagccatgaa caaaggcagc aacagcaagc cacactggca 134940
cccctccccc caccctcggc ctcaagcctt caccccaatc accaaaatga accagatgaa 135000
aagggacatt tttgtttcat gagtctgcca aaaatgtttt catgggagaa aatcttttaa 135060
gcccaatcag ttatagaact caatcagaag gcattatctg ctgtgttaga gatttgcatt 135120
ctcagtgaga atttgtttat ggaaatatca aggttaaatt catttatatg aaattattat 135180
taaaattgac tatacttctt gaccatctat tggctaatct gaaggaaaag aggccaggga 135240
gaaggtagca aggacaggct agtggcagag gacagtgagc ctgagatgaa aacacctcaa 135300
ctacacgatt ggtggtaact aaagctgccc ccacacagga ctgactccct aaggagactc 135360
ccaacagagt agcggtggcc caaggcaagc agtcacatcc gtcagaggac aaggtccata 135420
aatccgtctc accactacta gccgctcaag tttaacttca cacaggcatc ggcaaccaaa 135480
gacggctcat caggagtgaa cagagccagg agacaggcag cctctcttat agtaaaaggt 135540
ccactcttag agccaagatc taaagatcgc taatccttgc ctgggtaggg ggggtatact 135600
gaacttgtag atcaatgaca gtattttgtt cgggggacag acatgcctgt ttgtgatttc 135660
tgtgatcaca gttactgaca gtgaaatatg aacaccttaa tgtagacaca caattaacct 135720
ggggttgtgc tcagagtctg ggagaaaaac caaccaacaa accagaccaa tgccatggct 135780
gtctctggtc agacttctgt cctacaatgc aacgctagct atcagcacag ttacacagcc 135840
agacccacac cactgaggat gccttaagtg acagacaccc cagatggatg ctctaagtag 135900
taaatattgt tattggttta catcagactc aaaacaaaaa tgaggagcgt gaaatatgag 135960
ctgtttttct tgagtctctt aaattctacg acacagctgg aaaccacaca tgcccaccct 136020
ggtactacag ctattcaatt tccttaagct tgggctaggt aaagtatttt ctttgaccac 136080
ctcaatcctt ctacacaaca ccctcaggat gaagtgctct tccaaggcag agtttaatgc 136140
cttaaaaagc tagatatggt gtggaggttc taacaagctc tcctcatctc ctgagtgctt 136200
tgggaatgac aatgtacagg caacaaagag tccattgttc tcactgtact ttaccgagtc 136260

-continued

```
cagtgacaac acaacagaag atgtgaccag ctccagagac tcagcagagt aagaaagtac 136320
attctacccc cacatcagct gcccacagtg caaactgaag atgctctcag cactgttctt 136380
cagcgcgcag ctgttaaagc cttgccgtac ctggcgggat caaggtcagc acttagattc 136440
taattgcttt ctctggctct ctatgttcat caggggatcg tgggtttgtt ggtttaagag 136500
ggctttcagg ccaccatctc agaagacata atgcctcgaa gaagtatagg aaccactcca 136560
ctcaatagca aaggcttggc aaaacagctt ggcagcagtc cacatgctga cagtgtccag 136620
ctctggttta ccagagcccg agcacagata acccctgagc tgagttgcac aaaacctacc 136680
agccacgaag cttataggcc tctgggatgt caggattcac aatgacagtg ctggatgaga 136740
ggaccgagag gctccgtcca ccgaagtcag agactcgggc tcctttgatg gccatcacgg 136800
gctgccgaga gccgtcaaac ttgtcagcct gcaaatcaaa cgcacgcaca catcactgac 136860
aagaagaatg tacaggatgg ttttatggag aagagtcagt caatgtctgt ggactctaag 136920
acagacctcc cactcgggaa ggagcattgc actacaagaa gctgcaataa ccgatcatct 136980
cacacagcga aggtcttcaa atacttactg gatagcacaa ctccctgagc taaagcccca 137040
ccctcaggac tcggctcagt gcaaggactc acatcttctc cccacagagt tgtggtcacc 137100
accttccctg acatgtccat caaatagata tttctcttag caacttctct gttgttcgac 137160
ttcactgtga ttttaatcga atcttcatag ctcttgcaga ttccaatgat gtctgaaaca 137220
aagaacactt tgtaagagct cccatcaagg ctcctcttta aaacacggca gggacgaaag 137280
gcaagcacgc tagtcacgca tcaccccaaa cactggagac aaaaatcacc actctttgcc 137340
ctcaaccctg gacgcaccta ctagtgcgtc tttagccttg ctctctaggt caccgatccc 137400
tgtgaaatca aactgaactg tgggtaagtg atggccatct tcacagggaa ggacagaagt 137460
ctcattattg aaggtcatct catagtcatt tttaacagcg gagaactgtt tgttagcgat 137520
cttcagggcg ccctttgaga agtaatacac ctgcaaaaga ggccaagtca gggcaagcta 137580
ctcagtccat caaagcccgc cccacaatgc agccttccaa actgtgctca tggctctcac 137640
agttcagcct gtcagctctg actcaacacc gtcttcttac cttgttcact tcaataaggg 137700
gaaagaactt gtccacttgc tcattgaaag cagtagctct gatttcaccc tgcagaagca 137760
agggagagca cattagaact gcgctgctag gccctcgctc tcaacagcga gagcaggcca 137820
ttttgacagt tagacaccat cctcggagca acagtccaag tgtaaagaga ccctcacagg 137880
gctgcagaca ttgcagaatc ccacatatac agttacattt tcaagctatc agctctggta 137940
aaacaaaagc agctcagcca cccgagccta cagttgtaag ttaacacata aaacgaggga 138000
gcctcgagat gatctggaag acaaaggtgt ttcctgtgcc aacctggcca ccctagttta 138060
atcccggaac cctcgggatg gagaagacaa tcgccccacc aagttattct ccagcctttg 138120
cacacgtgtg catgcataca cacgaaaata attcttacat cttatcaaaa catttttaga 138180
aggaatagct taatattccg ataatgaaac ctaatattct gggtcccgag tgatgggctg 138240
gaagcccaca ggaaggcgtg ctgaactcca atgattcagc actcttcctc acgcccgcaa 138300
cctaagtgac ggcttacttc acagtcagga gctggtgcca aaaatgttcc aacaagtcat 138360
gctttcaagc tgactgcact gttacttttc tgtcaggcaa tatgttacag atggataaga 138420
aacttaacta aatggctaaa accttaccca gacaagctgc aggaaattag tttctgatac 138480
tgaatctgcc atcacagtta agatatctgc tgtgctacac cgtgacaaga ggaagaagag 138540
ggggagagag ccccaaagct ttgcccttcc cggtatcatg gcttatttta cgtgtgtggg 138600
tgttttacca gcatgtatgt gtgagcatca ctgagtgtct gatgcctgag gtgaccagga 138660
```

-continued gaggtactgg atcactgaca cgggagtcac agatggttat gtgctactct gttggtgctg 138720
agaattgagc ccaagtcctc tcaaagaaca gcgagtgctc ttaaatgctg agcagtctct 138780
ctggcccctg cattttgctt taagtaaagc ctagtgagta taaatgatca gaagccctcc 138840
ccgcagacta gttaaagctg agtagctgct gctccttctg ctggaggcaa acccgccctg 138900
ctcggcaggt atcaccccag ggcttcaact gtgcccctag caatgtaatt agagcgctgc 138960
agtctctgca gacggagact atttacagtc caccaatctg tattgctaca gacgcgtccc 139020
tttaggagca ctttatctca tgtctgaccc tgtgccccag atagcatcaa aggtctccaa 139080
cagaaggaaa gccacaatga ccgccatgtt cctcggagct gagccccacc cgnnnnnnnn 139140
nnnnnnnnnn nnnnnnnnnn nnnnnnnnnn nnnnnnnnnn nnnnnnnnnn nnnnnnnnnn 139200
nnnnnnnnnn nnnnnnnnnn nnnnnnnnnn nntttttatt aattatgtat agatatagat 139260
atctctatat atgaatgagt atcctgtagt tatcttcaga cacaccagaa gagggcatca 139320
aatcccattt acaggtggtg gtgagccatc atgtaattgc tgggaattaa actcaggacc 139380
tctagaagag caatcagtgc tcttaacccc tgagcccccct cccttttttt tttttttttt 139440
ggcagcttat ttttaattgt tttaaatcac gtatatgttt ctgtatgtag ctatgttcac 139500
ataagcgcag gcactcatag aggtcagaga tgtaagatgc ctttggagct ggacttaaac 139560
atggttgtga gccatctgat atgagcacca agtggacttg ggtcctctgg accgccttgc 139620
tgccttccac ctagaattac agtatatgca attagctgct cagccacccc ctcagtcctc 139680
cttagtactt tcaacatagt gtaaatcgga gagcactcct tggtgcaaag attctgtgtg 139740
ttctatcatt ctctacaccc aggcttcatt gggacgtgtg atgccagcga tgattcattg 139800
gcgtgaagta tgagttagag tcagacaatc agtgctctct gctctgagtg ggtctccctg 139860
cccctgtgtc tctgagacag gggaggattc tcctgttgga tcacatagtg catagagccc 139920
tgtgtgcaca gcgctctcaa ccatttgttg ccatttcaaa tacagtgact tcagagtctt 139980
ccttgaaata acagatttct ccattttgtt tgttcccttc tttcgtcaca aagacctgag 140040
gatgagatgt ttttgaagga actttctagt agttactcgg tggaaaagga caatgatgct 140100
cccctcttct acagagaaga aggaaacagg aaattccaag aaaaggagta cacagatgct 140160
gcagtgctgt actctaaggt aacgtgcgtc caaccagcag ttgaacaagg cggaagatag 140220
aggcaaagtg cagactcata accagtccat tgttttgctt tggttagttg ggttggttgg 140280
tttgtttgtt tgtttgtttc ttcttcttta ttagtcggat tggatttggg aaaaatgtag 140340
tagaattcta ttgttgatta tattcacaaa caaaagactg tttatatgtc ctgaattttg 140400
gcaagattct tcccatattc cttcagaccc atagcagcag caagcttagt ggccctttgc 140460
caggtattct cactgagctg tacagcattt gtctgaagaa ctgatgaaca ttttagctta 140520
tgctcctatg ttagtaaata gctaggtttt tagctagcca ccttgctagc ttacaactag 140580
aatgcctctg gctgagtttg gtggcacttg cctttagttc cagcactcag gaggcagaag 140640
caggtgaatc tctgagttca aggcagcctg gtctacataa caagttccag cctggccagg 140700
gatatgtagt aagactctgt ctcaataaag taaacagcca gaatgactta aatattgcta 140760
aaaaagaaag aaagaaagaa agaaagaaag aaagaaagaa agaaagaaag aaagaaagaa 140820
agaaagaaga aaatgagtgg atttgccata gcctagtcaa actagatttt cttggttata 140880
tgttaacata ctactattaa caacaacaaa tactttacac taaccatgac aagctatatt 140940
tttaaattat tattttatat gtatggtgtg ggaagctgtt gcagagtggc agttggctac 141000

-continued

```
tgctggccac cacacataca taggcagtga aggttctttt gccaagacaa gttaaccaat 141060
cagatgtgag acacgcctct cctaggccta tgtaagcagc accagttctg ggctcagggt 141120
ctcttcgcct ctacaatcaa gctctcccaa taaacgtgtg cagaaggatc ctgttgcagc 141180
gtcgttcttc ctggccagtt gagcgcgcac aagagtatgg gttttcacct acatttatgt 141240
gaactgcatg tgcacttggt acccagggag cccagaagag ggcatcatat cccctggaac 141300
tagagtcaca ggttatgtat gggttctagg aatcaaaccc atgtcctctg gaagaacagc 141360
cagtgttctg gatttaactg ctgagtcatc tctccagccc caccatgatg gatttaactg 141420
ctgagtcatc tctccagccc caccaagctg gatttaactg ctgagtcatc tctccagccc 141480
caccacgctg gatttaactg ctgagtcatc tctccagccc caccacgctg gatttaactg 141540
ctgagtcatc tctccagccc caccacgctg gatttggaag cagaactgag gctttgaaca 141600
ctgtgttatt ctaactcttg cttccttgga accctgagaa aattccttct attggctttt 141660
cagagatctg tatgggctta aaacaagaat atgtccaact cttgatctct gattttatat 141720
attaaaagaa tagagtgagc ctaggagttt ggcacactcc tatgttccaa gcttcaggaa 141780
gggaagaagg tcaggagttg aaggctagtc agtcttagct ttgtgacaag tttgaggcta 141840
acgtgagctc tatgagaccc tgtctaggag aggagaaaga aaggggtaaa gtgaggtgtg 141900
gctccacgct accacttgcc taacacgcat gacgcccaag gtttccgttc ccagccctgg 141960
ggttcagagt attgtgcaca ccctgtatct ttaaaagtca atagtcaacc cttggaatta 142020
actttccgaa aaatattaaa gctacatcat ccactctaca aacttgtaaa agcccttctt 142080
tgtaatggtg taagaaagta tttggcttca gttttatggc ctttgcatcc taaatgttac 142140
cccatggaaa gttgcttaat gaaaacaggt aaaaataaga caggagggac tgcaaagatg 142200
ctcaggctca cgagtgctta ctgcccttgc agagaccatg gcaggcagtg ggtctcccta 142260
ctgcagggaa tccaaaaccc tcttttggcc tctgcaggca accacattaa cacatgcaca 142320
catacacata attttaaaaa taaaataaat cttttaaaat gagctctaga acgagtttga 142380
catcagtcta ggctacacaa gaccttgtct caagaagaaa gaaatgaagg tttgctgtgg 142440
atggagaggg agatgcactt cctattccat gaagctgcta ttttggtgat tatggtactt 142500
tgcaatttta tagagagctg ctattttctt tcttttaaag taatgcttgt tgttttgact 142560
gtaaaagtaa taaatgttac tttggaaaat atagagaagt ataaagagta aaaaaaaaag 142620
tcataaccag tgaagtaccg ttaacatttc tgcttctatc cggccagcca gagtttttcc 142680
tgtgagaatg tgtttttctt ttacaaaatt gggataatgc tgcacttact gttttgtagc 142740
ccactctttc ccttcacgat ttattgtacc cattttctca cagtattaaa ttttcagctc 142800
caagtaattt tccatagcta actctgtgtt ctgttacaga gaagaaatgt acttaattta 142860
agatctaata ttggcataat atttggcatt atgatgctat aataagcatc tttctgtata 142920
aatattttta tgtacagcca gtgttttgtt tgggatgaat tagcacaaga gtaaagtgtg 142980
gggtcaagcc tctgagtgac gctgaattgt tctcaggaaa ggactagtta acatccattc 143040
tgaaagaatg tgggaatgct catttcttaa gcaacactgg ttattattac atactattat 143100
tttgttagta ttatacattt atttaggggg ataggaaata tgctcatata gttcaatttc 143160
aagagttgca aaaatatatg gtgtggtttc ttttcctgtc ccctagttta gtctcacttc 143220
cagccccata atctaccttg ttaaatatac tgtatataag gcatatgtag gtgaataaaa 143280
aacagcctag tatggtggcg ttaacctcgg gttacttgag aactgctctt gcagagaaca 143340
tgactttggc tccgaaagcc ttcctggaat tccagctcca agggatgcag tgcctctggc 143400
```

-continued atccttgggt acgtcactca tgtgcacaca tacacatttg gtttttaatc ttaggaactc 143460
caagtgggcc aatgagatgg ctccatgtat aaaggcagtt atgcaaaggt ctggatgaca 143520
tgagttcagt cttcagattc tgcaagataa caggagagga ccaacccctg cgagttgtcc 143580
tctgacctca gtacacatgt catggtacgt gtgtagtatg cacatgcaca gaagtcccag 143640
cactcgggag gcagaggcag gaggatctct gagttttagg ccagcctggt ctacaaaacg 143700
atttacagtt atataaagaa actctgtttt gaaaaacaaa acaggggttg gggatttagc 143760
tcagtggtag agcgcttgcc tagcaagcgc aaggccctgg gttcagtcct caactctgga 143820
agagagagag agagagggag agggaaaggg agagggagag ggaggagagg gaaaggaagg 143880
aaggaaggaa ggaaggaagg aaggaaggaa gaaagaaaga aagaaagaaa gggaaagaaa 143940
gaaagaaaga aagagagaaa gaaagaaagg gaaagaaaga aaggggaagg aagaaagaaa 144000
gaaagacaaa gcaaagcaaa actaaataaa atacatacaa tatattaaat tttaagactt 144060
gagggcatag atcagtgtta taatgcttac ctagcatgcg taaaactctt ggcttctaaa 144120
cctagcaccc taccgcaaaa tatttgctct gtcttgctaa attatattgc tagttgtcag 144180
actactgtgt actttcacta gcaacataat gagaatgttc actatcccac tcctctgtca 144240
agtaatctgt tcttggtttt atttttcttt gccaaattga tgggtgaaca agtatttcag 144300
ctagcctaga acacacagag aactctcttt atgaactcaa gtttcttatc cttttatgat 144360
ctccagaggt ttgtttttgt gggtttatta gtgtttttg tttggttggt tgtttgtttg 144420
tttggttggt tggttggttt tgctttactt tttcttattc attttttat ttctttattt 144480 ttttgttttt aatttaatgg actggttcca tgtggccaag gatagcctca actttgtagc 144540
agaaactggc tttgaacttc tggtcttcct tcatctacct cccaagtgat gggattaagg 144600
cacgtgccac cacatctaac aatatctggg tttctttatt ggagtttgaa agggattcct 144660
ccagcattac tttgactctt catagtttct tccagagtta ttacactttc atttgttaca 144720
ttaagagttt gatccagggc tggagagatg gctcagtggc taagagcacc aactgctctt 144780
ccagaggtcc tgagttcaat tcccagcaac cacatggtgg ctcacaatcg tctgtaatgg 144840
gatctgatgc cctcttctgg tgtgtctgaa gacagctaca gtgtaatcat ataaataaaa 144900
taaataattc tttaaaaaaa aagagtttga tccatttaca ctggacttct tgaggcagca 144960
ggatcataaa ttcaaggtga gcctgggtga actggcagaa gtggcagaag ctgtgtctca 145020
cactgctgta ttcatttcct cattgatctt cagaggtttg ctaacgggaa gtaagtggaa 145080
cagaaggttc agtattcttt ttttcccaat tctattcagt ctttagtagt agatccctca 145140
ttatctgaga tgcagagtcc cctttattcc tgtgaccatc tcgttgtttt tcagggagtg 145200
tctcattcaa ggcctaacac tgaggacatt tcactgtgct atgccaatcg ctctgcagcg 145260
ctcttccatc tgggtcagta tgaagtgagt attgaagaac ctggtgtcct gcctgtggct 145320
gcagtggaaa atgagctcct ctctgttctt ctgcacacat tgaaatcaac tagcttgcaa 145380
acactgacat ccacccagac ccattctctc ttctgactca tgtcacctct cataggtgac 145440
cacaaacaat atgtagttga caagaagtag ctatgtcatt gtccacagtg catggatttg 145500
ttccaatagg ccagcacttc tgtgtccata tcagctagat gtgctgctga tagtatttta 145560
gattccaaaa tgtgtccaga tattacctcc ttcgtttgtt tcttctaaat aagccaggca 145620
caaagacttg aaagatggct tgatggctct tccagaggct gggtttgatt cccagcccca 145680
acatagcagc tcacaatagg ctataacgtc atttccaagg ggtctgactt cctgttctgg 145740

-continued cctctacagg cagaaagcac agacatacat gcaggcaaaa cacataaaca taattgaaag 145800
aagatattaa ataatagccc acgcttgagc ttattcctct gatgatacag ctctcctgaa 145860
gtcatcatgg gcagtgtaaa agtaaaggtg ccccgccctg cccaggggca tcagtgaggt 145920
agctgactgt gagtggcttt cttctcatcc cctaactgct gcaacatcat caactgtgga 145980
gcattatatc cgtggatttt aagttaggaa atgacaaaga ttagatctat ggccaggcac 146040
tagtgcacgc ctttaatccc agcactcagg aagcagaagt aggtggatct ctgtcagttt 146100
gagtttacag agagtgtcta ggcagccagg gctatataga gaaattctat ctggaaagaa 146160
taaacaaatc agatctgtat ttcaggaaga tgcctatgag ctgtttgaca tgtgtgatag 146220
aggtccttaa ggacaggaaa gtattccaca tgtgtgcatt ttacagaaat tggttataca 146280
ctggagttaa ggactgttgg aatagttgaa tgttcacact cagtgttctt caaatcaaat 146340
agaagaacaa gaatctatct gggcatggtg atgcacaact gtattcctaa catgtagaag 146400
actgaggcat gctatgtgtt tgtggctaac ctgggctaca tagtcaatat tggacagtca 146460
gagctgctac taaaacctaa aaaacaaaaa tctaataatc tgggatttta tattttcctt 146520
tttttaaaaa aagagtgggc agaatgtctc tgattttgtt cagatggcca cagaacctag 146580
aaaaactgct gctgctgctg ctgctgcata gcacacagct aatatttgac tatacgtata 146640
taaattttgt tgtatacttt agctgtgctg tcaactttgg aaaaaaagta tcccagttta 146700 tcatttttaaa ttggcactgt acagaaatta acagccatat tagtctagac acattaaact 146760
tcatttttcc atttatacag aagcaatgta ctgtattaaa tattcagtct tatctacagg 146820
ggtttgatta cagaaactat caaagtattc tctaaatgat gaaaaaagat tcaagaatct 146880
gactgtagat ccaaaggaca agtggagaaa aacttaggaa gaattttccc tttatcccct 146940
ccctatattg atcatctctt ttacttctaa taatagtggc catttattga acatacccag 147000
gagttccttt catcacttta gatatataat ttatctcatc ctaaaatgac ctgttgatga 147060
gtcatctctc tttcagatga gaaacaaaga cattgaaaaa tctaacttgc ctgcataaga 147120
tcacacctag cctcttactc actccatgaa tattcctttt ttttttttcc tttgagacag 147180
aatctcacta tgtagttctg gttgtcctag aactcaatat atagaccagg ctagcctcaa 147240
actcacagag atctgatagc ctctgcctgc cgagtgctag ggttaaatgg atgtgtcacc 147300
aagcccagca aaatttacct tcttaatttt ctaagacgtt tctcctctta aaaaatggaa 147360
ctattgagcc agtcatggtg agacaggctt aatctttaat ctcagcactt aggaggcaaa 147420
gacaggccta tgggttcggg gcagcctgat ctatagagag agttctatgg gttaaagttt 147480
agggttaaag ttttgagaca aaactttgtg tcaaaaacaa acaaacaaag ccagactgct 147540
taataagaca aatcagacat aatattataa acaagtatta gtgtcactca attaaaaagt 147600
cactcaggag gtgagatcaa tccccagcat aatgagggga ggaggggaga gaaggaaatg 147660
aatgggaggg gaggaggaag gaagagagaa aaaggaaaga tctcaaagca gaacacagga 147720
tgtaatttaa ggcctaagct ctcgactgaa gttgtccact tttaatgacc cttttcatgc 147780
tcatggtttt ctgtcttcgg tacatagtga agagtggaaa ccaagggtca tcctggaatt 147840
tccttttgtt ttcaggcatg tcttaaagac atagtggaag caggtatgca tgggtatcct 147900
gaaagactgc agcccaagat gatggtgcgt aagacagaat gcctggtgaa cctggggaga 147960
ctccaggagg caagacagac catcagtgat ctcgaaagca gcctcactgc caagccaacc 148020
ctggtgcttt cctcttacca gattctgcaa aggaatgtcc agcatctgaa aataaagatc 148080
caagaaaagg agactctccc agaacccatc cctgcagctc tcaccaatgc cttcgaggat 148140

-continued atagccctgg gggaagagaa cacacagatt tctggggcct ccctctctgt cagcttatgc 148200
acacaccctt tgaaaggccg ccatctagtt gccacaaaag acattctccc aggagaactg 148260
ctggtgaagg aagatgcttt tgtaagtgtc cttatcccag gagaaatgcc acgacctcat 148320
cattgccttg agaacaagtg ggataccaga gttaccagtg gagacctcta ctgtcaccga 148380
tgtctgaagc acactttggc cacagtacct tgtggcagct gcagctatgc caagtattgc 148440
agccaggaat gtatgcagca ggcatgggac ctctaccata gcacagagtg ttctcttggg 148500
gggctgctcc tcacactcgg ggtcttctgc catgttgccc tgagaatgac tcttttagcc 148560
agatttgaag atgttgatag agttgtaagg atgctttgtg acgaggttgg tagcacagac 148620
acctgtttac ctgaaagcaa gaatctggtc aaggcatttg attacacaag tcagggagag 148680
agtgaagaga agagcaagat aggtgaaccc ccaattcctg gatgcaatgt caatggaaag 148740
tatggaagta attataatgc tatcttcagc cttttgcccc atactgaaaa gcatagccca 148800
gaacacagat tcatctgtgc catcagtgtc tccgcactgt gcagacaact caaagctgac 148860
agcgtgcagg cccaaacctt aaagtcccct aagctgaaag cagtgacccc agggctgtgt 148920
gcagatttga ctgtttgggg agcagccatg ctgcgacaca tgctacagct gcagtgtaat 148980
gcccaggcaa taacatccat atgtcacaca ggtaagtcag aaatggtttt tacttacatt 149040
attggtattt caagagctaa tgtttaagga gaaaaacact ataaaggaag cctggcatca 149100
aataaatcag tgacctaaaa ggaaaacaca gccgtcttat atatcattat gctattgaga 149160
agctttgagc acatttctgt gaacccagag cttgggaggt ggagatagga tgattaggag 149220
tctaagacag ctttagctat acagcacgtt tgaggtcagc ctgaactaca tgagaacttg 149280
tctcttaaaa acttgagcca gagccaggtg gtggtggcac atgcatttaa ttctagtact 149340
caagaggcaa aggcaggcag atccctgaat ccagcctcgt ctatatagtg agatccccac 149400
caggctacat agtaagatcc tgtttcaaat aaataaatat aacaaaaaca gcaataataa 149460
caatagcaac aaattaattt tttagatgta tttatttatt ttatgtatga gtacaccatt 149520 gctttttca gacacaccag aagagggcat tggatcccat tacagatggt tgtgagccac 149580
catgtatgtg gttgctggga attgaactca acacctctgg aagagcagtc ggtgctctta 149640
gccactgagc catctctcca gtccattaat taaaaattta aaactagagt atttttaaac 149700
atttattcat tttgtgtgtg gtatacatac tataatacag gttcataagt caattctctt 149760
ctaccatgtg tgtcttggag atcaaactca ggttcttagg catgggagca agtatttact 149820
tcctgaacca tctccctagc catttctagt attcttttct tttgtcttga aagatttatt 149880
tattatatgt aagtacactg tagctgcctt caaataccgg aaaggggaat caggtcttgt 149940
tagagatgat tgtgagtcac catgtggttg ctgggatttg aactcaggcc ctccagaaga 150000
gcagtcagtg ctcttaactg ctgagctatc tccagcccca tttttagtat tcttattaag 150060
tggtttccat tttatccaaa gatgccttta agggcctggg aagatggctc agtgggcatt 150120
gaacttggtg tgtgagcatg aagaccagag ttcagatccc tagcacccag gcagatgctg 150180
aatgatggtg gcctgcctga gattccagga caacggagac agacaggggc cctagctaac 150240
catactacac actagctgag ctgtgtgctc aagagagcag ccctggctta ctgtgcagga 150300
tggagagtga tcatctccac aggcaagcac acacctgagc acacagacat gcacaaagga 150360
aagaaaagtc cttttaaggt ggtggtggtg ttgttgtttg ggggtctttt gttttgtttt 150420
tttctccccc tccctcattg tgatggcaca ttcctttaat ctcacatctg ggacaaagag 150480

-continued

```
gccggaggat ctttgtgaac tggaggtcag cctgttctac atagcaagcc catttcagcc 150540
aggacgacat agatataccc tgtctcaaac agacaaaaat tatttatttt atatatttga 150600
atgttttgcc tgcatgtatg tctatgcaca ttatgtctgg tgcccatgaa agccagaaga 150660
gggcatcaga tctctcagaa ctggaatttc agacacttat caagtactgc ctgagtgcta 150720
ggaatcaaac caaggtcttc tggaagagca gcaagtagtc tttttttttt ttaatatttt 150780
tttattacat attttcctca attacatttc caatgctatc ccaaaagtcc cccataccct 150840
cccccccccc ccccgagcag caagtattct tcattgctgg gccatctccc catctccttt 150900
tctagttaat taagctgaaa gggagggagg tagatgttgc ccaaacttag gatttattga 150960
cagattaata ctctgttagc ctaactacac tatagaagct tattctttag actttcacat 151020
tacactgtcc agattttgcc atcctttttg ngtgtatatg tctacagatc ttaattcagc 151080
tgccaattta tacagtgttt ataggtattc tttgtgacgt ggatctttta cccatcttaa 151140
agcagtagga tttgaaagct gacatttatg tggcctatgg tcctgttaaa tcacatttca 151200
agttagtctc tgtggtacac attttggggt ctatctgcgg ttccgcatct cacacttttc 151260
cctctcaggg tgtccagaag ctgctgcaca ctgggctgga aggatgaagt ggagtccaga 151320
gtgagtggaa ttctgcagca tcccggtcca gctgggagtg aatgctgggg tcaggaggag 151380
atgggtgaga gggccttctc caagggcctt cttagtgtta cagctctagg caaaggcctt 151440
ctctgacaat cttagcctgt gcatagtttt ttattcgaga tgagcttgta tgcatacact 151500
ttattggcag taaatcagag gttatccact cttagggaag gagataggaa tacccaaggt 151560
ggacagaggt cattggctga aggataacgt actgagatgc tcattagcac ggggaggcat 151620
cccaggaatc tcaggtgctt gctgactggg tttcttaggg ggttgagagg gtagcagtga 151680
tttcaccaag gttatgtatg gcagagggta taggggtttc aggctcccca gacaaagaag 151740
gagaaggaga agccctgctg ataagggaag tcccccattt tgagccactt cagaaggcta 151800
tcaagacact gatagacttt gtccttaatt agcagggccc aacaagtgtc tgttttcttt 151860
tctgccttca ttggctcttt gagccactgc tacaaaatat ccaaatctgg gccaggaagc 151920
tggctcggct agtaaaggtg tttgcctcta agcctgaagg cctgagtttt cacttgattt 151980
ggtttggttt ttgttttttt gagacaaggt ttctcagcat agccctgggt attctggaac 152040
tcactctgta gatcaggctc aacttgaatt cagagatctg cctgcttcta catcccgagt 152100
gcttagatta aagttgtgcg ccaacactgc ccacctaaaa aaaatatgag gggctggtga 152160
gatggctcag tgggtaagag cacccgactg ctcttccgaa ggtccgaagt tcaaatccca 152220
gcaaccacat ggtggctcac aaccacctgt gatgagatct gatgccctct tctggtgcat 152280
ctgaagacag ctacgggtgt acttacatat aataataaat aaatcttaaa aaaaaaaaaa 152340
aagaacacta ttcacaaggt acaacaacag tgtactagga aactttaaaa tagcccatca 152400
ttcattctag gggaaaaatc tttttaaact ttagtgtgta agaaagagag aggggctgta 152460
gaaaggccac agcacgtgta tccaggttag gagtcaactt ttcagaagcg gagtctcccc 152520
ttctacctgt ttttgaggca gtctcttgtt tctgccctac actttgtaca tgaacttcaa 152580
gatggttgtt ctatttctgc ctctcatgtt gccctatgca tgctgagctt actgatgcca 152640
gccaccacat aagcatggca ccagcactga gccaagggca ggcatctggc tcacatggag 152700
agttacccat caagccatct tgctagcccc agaaaatgta tttttgacag gtgtggtggt 152760
gcacatattt aatcccagca ctcaggaggc agaggcaggc agatctctgt gtctgaagcc 152820
agcccagttt acaaatcaag tcccagaata gccaaggcta catagagaaa ccctgttttg 152880
```

-continued aaaaacaaac atccttctgt gttccagtca caatgactgc tgtaacaata atatgaggat 152940
ttgggcgtgt caaaaatcac aagtagcaag gtgtaatggg caggccttta gtctcagcac 153000
ttgggaggca gaggcaggag gatctctgtg agtttagcac agccagggct gttacacaga 153060
gaaaccctgt ctcaaaaaaa ccaagcaaaa atagaattac aagttaacca gggtattggt 153120
gttaatatga aatagcagaa ctcaagatag ctaatgaaac aaaggattct attttataaa 153180
ggagacattc catactgaaa tatatgcaga gcctgatgct tgcctagcaa ctgaactaca 153240
cnnnnnnnnn nnnnnnnnnn nnnnnnnnnn nnnnnnnnnn nnnnnnnnnn nnnnnnnnnn 153300
nnnnnnnnnn nnnnnnnnnn nnnnnnnnnn nnnnnnnnnn ngcctgggca agagtaagca 153360
aaccgtcagg ctcagaggca ggatggcagt gatgtgtttt ggggcacaag gcccccttc 153420
attaaagcac caaatcttgt actaaaaaca gccctctgct ctcgatctgc agagatacga 153480
gagaggcaca catagcttcc gggcccttgc cctctgctct cccggtcagt tcctggactc 153540
ctgggagaag cttgaagctc aagaactggc cgctgttgcc tttgtgctga cgccagaacc 153600
agcagctatt cagcagctgc ggctcttggg caagcttgga agtagctcgt tccttctcct 153660
tctgcagggg aaagacaagg agatggcact gagctgggta gccaggatgt gggaagtaaa 153720
ttgtgtctat gtgggtgagg gaagtgccgt gtgtgtgtgt gtgtgtgtgt gtgtgtgtgt 153780
gtgtgtgtgt gtgtgacaga gacagaaagg gagagtgcat gttcttgtgt gttcctgtga 153840
gtcagtgctc cctttggctc ctcctgccaa aaagcatgct gtgttctcag agtcaagctt 153900
ggccaggctc gcccacccca ccaaagccca ggatctgcca ccccattaag aatgcggggt 153960
taggaaataa aaaacagggt tcttgtccaa gagaattttt attattattt tttctctctt 154020
aattggattc agcatttctt actcctcagt atcctctctg gtagggaatt caggtctgtc 154080
tatgcagagc acaagagact gtgcttgcca gaaacccttg ggccaacagc cctattccct 154140
gactgggctt gcctgcaggc tgccttctgg gctgacccct gagtctggcc ctctgacctc 154200
tgcccgtcct ggggtcatcc aggaggagca ggaccactgt gatacagggt tcctgagatg 154260
gctactgaaa caccctcatc tgctaaggcc actagatttt tttcccactg ccagactact 154320
cagggccctc agtaggtcac tggccaaaga gcctagatgt taaaactgca gctaaagcct 154380
ctcctgaggc cagagctcag agcctccctg gcctgcacaa agtgctaaga aggacattgt 154440
ccatccaacc cattggacta acactgtaga cgctgccttg tctgccagct tgaaaacccc 154500
agaaacctct tccccagctc cgcctagctt gcctccagca ccctgacatc cacttctctc 154560
gctaatgtct gcagcttcta cagtaggggt gacggggtgc tccggggtgc cagacaggcg 154620
tgtgttgcat ataaaaacga ggtgatgttc taagtatcta agaatgttgg tcccctgaag 154680
tgattcttgc tgcttctctt ccttcccgac tcttcccact gacacctttg cccccagcaa 154740
gcccagggac tattgttgct ggctggggtt ctgaacaaaa ttgccgcagt tttttgtttt 154800
ttttttcttt gctagaagtt accgatacag tccttaattg agcaaatata ggttcccgta 154860
tagtttataa acatgataag acatacagtt tggtaaggag tgggttgggg gacctgtgca 154920
tttatatatt tatatatata tatatattat gtgggtgtgt gggcagagtg aggatatata 154980
taagtggaca taggtataaa actgcacctt ctgtgtgact ctcattgcga gtacagttct 155040
aaatgtcatc cactggcgat ctctcctttg gtgattggtt cttggacccc agcaggtctg 155100
ccgggggctg cctgagacgt caggaatgag aggcattacc cccatggata gggactgagg 155160
gtggcatagg gttggacagg gcaggttaac taagtgatct cagacaagag ccaagagtgc 155220

-continued

```
tctgagattg ctggttgccc cagctggctc tgggagagcc ttgttctgag tcctgctcct 155280
tccaaaacca gcagggtcct tcagcccttc tctccaaatg accaggcttc cgcagagccc 155340
agcttcttca aggggcgcat gtcccgacac cactaatgac tcactttgcg tgcctttgac 155400
cactgtgctg gagtggatac ggtccagagg cgctcggtca ggacagccga gtgagacgtg 155460
atacccttcc cgtctacggc tgtacatttt gggcttataa tccaccagga agggtccaga 155520
cggtggctga aggcttcagc agccttttcc tgaaacccag cagatcttcc acttaggaaa 155580
aaaaaaagaa agaaagaaag aaaagaagaa aaaaattctg ttccttgctg gacatgtggc 155640
agtgctgggt gacggagccc tgggtcctca gcggagagtg actgccagcc ccagtatcca 155700
ggccaggagt ggggccccaa gggccgtgcc tgaggatgcc tgctgcaccc cactgggggc 155760
acggatgggg gtcctgcgag cacacttgcc cttcctcttg ggtcgtgcgg tgggcatgat 155820
gtcaaagctg aacttgtgct gatagtcggg ggcatagtcc tgcagttcgg taagctcttt 155880
cccagagctc accttagaga tctggttccg gttcctgtgg ctggtgcagt tcttgcctgc 155940
cttcttgtaa cctgacctgg agccaggcgg atggccatgt gggtggcctt tgtccctgga 156000
ggccccatgg gacggatggt gctccttgcg ggcagccctg tcagaggtgg taagcgtgtg 156060
agacttgatc tggtgaggag acactggtcc tgtgcagttc cggaagtcct ccaccctcag 156120
cagcttcaga tcctggcctt gccgcagctc gggggtcgcg caggggacag cagagctaga 156180
gccacggaac cttcgcagcc attcccacag ggaacgtgcc cggcagccac agtcccaagc 156240
attcccattg aggcgaagga actccaaggc caccaggggg gccagacagt caccctgcag 156300
ctcagtgagg ctgttgttga agagaaagag ggtggttagc ctgtggaggt catggaaagc 156360
cttgtggtga acccactgta gctggttctc atgcagcagc aaccggtcca ggttcaccag 156420
gccccggaag atgccttggc ccaggctcca tagcttgtta ccatggagaa acaagtgact 156480
gagattgacc aggtccacaa agatgtcatc ttggaggtac tcgatatggt tgtcctgcaa 156540
gtagagatac tgcaggctgt gcaggccacc aaagatgcct gcgggcaggg cgctcagtcc 156600
acacttatag aggtagaggg cgtgaagctt caccaggcct tggaaggtct cgggtgccag 156660
cgttcgcagc tgtcggttgt ctccaaggtc tagctcctcc agatgcacaa agccctcgaa 156720
ggtgttggga gcaatgaaag tgatgttgtt ggagtagatc cagagggtga ccatggcggg 156780
gctgaagtgg ccctgctgga ggaaggtgat gcgattgttc tgcaggaaga tgcgctcact 156840
gtcctctggg atgccctccg ggatggcagc aaagttgtgt gcctggcagc tgacagtcat 156900
gggcgcaggg tagcacacac agtctcgagg acaaccacca cccagaggta gctctccagc 156960
gagcagcaac agcagcaatt ccacacagca ccctggtggg gagagacaga acagcagtga 157020
ggggctgccc agaggaggtg gagatagatg gggaacagag ggtggaatgg gggactggca 157080
aatgactctg ttggctcaca gaggttctgt cctctgtatt gtatgcaggg gtcccttgga 157140
cagggcattt ggggccaagg cccacattat ctcctcacct ctttagctct gtccctaaag 157200
tctctaattc catccgaaca cttcttcaga ctgtcagccc caccgcaggg tggaacacac 157260
ttgtgaacac aggcgagtcg gcctccggct ctgggtccgg ctctgccact cgctcactgt 157320
tagctgcctt agcaaggaat gactctaaca aagcaaatct ggagtcctga atgatcactt 157380
tatttaaata attcctcaaa ataaagaaag cattgagtcc atggtaccaa agcatgcctc 157440
aataagcgcc tctttcacac tgtggtacaa aaacttcaaa cctacaactc ctccatggct 157500
gtttcctcat gagttaaaca cagttcacag ggctgtgtgt acagacaagg cacatttctg 157560
tgaggggctg tgagtgacac cagggctgac gcacgaggct tcccttgggg ttcacagtac 157620
```

-continued tgccagatcg aggctgcatg ctcctctccc ccattcacac cccccctcc tgtgctggag 157680
attgccaggc tgtggctgta aaaccgggcc ttgcctcttg actgtccaga gcatttcctc 157740
tgtagcttcc ctctaattgg gcattaatta ggcattcgtt aatggatcct taaaataatt 157800
attttcggat gtgtccagcc tgtggtcggg taataggcct atgctcatta tggaagccgc 157860
ctcattatgg acgattgtca ttacctgcct ttttccaggg tcacagctgc cccaagtggc 157920
ccagcaggcg cgtcaggaag atggggacag gctccaggcc tacgggcgcc caccctgaag 157980
ggccaggcag ccacgaccta tgtcgcctca gttggcctct tgccccttct tttccagctt 158040
gttcagctgg gactcttggg agagccaggg cccctggggg aatatgagct gagctgaatc 158100
ttcttgctgc tagctgtgct cagagcaagt ggaaggagca gggaccttct gaccaggctt 158160
cccacttggg gtcccaggcc cagggactgc ccaggccccg gcagagtagg ttgccacctt 158220
gacttctgac gccccccccc cattcccaac agaaacagca tcgtaagttg acagctccca 158280
gctgttggga gttatgggct cccagagagt ggcagctgct tctcgtccct gtaatcaccc 158340
ggcttcagct agaatgtttc tagcacataa aaatcatcgc atataattta gtttttgcat 158400
aattgggttc agttgtgatt tcagagcaat tatgacctca gcagcagggg tggcacagca 158460
taggacccct ttctgggccg ggccatgccc tgcaggccct ctgcagtgct ttctgcccac 158520
cggcccttag acagcatgca ggctataacc atctctgcct caatttcctg ctccaaaacg 158580
tgtctagatg ttactctgtc gatcttcctc ctcagcatcc tgggtgtggc ctccagcctg 158640
ccagcctctg tcctagggat cctgtgctgc agagggaggc acagtcggag ggaggggagc 158700
ctgccctgtg ccaccagcac tcacactggc tgcacagtcc acagacccac agctccaacc 158760
tccctgcttg gcttgcaccc tctcttccag gaaggccatt cttgccagaa cctttcccaa 158820
cggtcccctg ggaaagcctg gactctaggt tcaaggacat tcatgatgct tgccccacat 158880
tttatgctgg atgagacaca gcagagcctt cttcactggg gggtcctgtg aaaatgaaag 158940
cttttcttcc ccggcctgca gctgcaggca ggtaggggtt gcagtgggct tatcactaat 159000
accattcgac atttgtacag ctcatcggag tttacagagg gcttttgttg taccctcaac 159060
ttcccctgtg ttctcccacc tactgtggct gctctgtctc tgtgcacccc aaaagaatct 159120
ggaagtccct tggggagatt acccccctta catagggggcc tccaaggaat acaggctaca 159180
gctctattta ggaaaaaaaa aatcaaactg aaccaaacct caggtgtgga cttagtaacc 159240
agtttataaa cataccgtgg caagtggagg aggcaggcgg cagaacggca tgaaggtagg 159300
actggggttt tccctctaaa agggcaatgg ggggacaaag ggactctagc caagacctga 159360
tgcagaacca ggctcagttc ccctgttatc tcaaggctat catcactagg aggcctaagg 159420
caatggacca caaggacctt gtccttgtag gacagtcact tcctgcagtg aagtgctctt 159480
ctggaagcat actaatagga tgtaggctca ggacagctgg tctctgtcct ttagtatttt 159540
tccacatgcc agggatgtta accttccaag cctccatctc ttctaatggg ggggggtgt 159600
tgaggggctc agccactctg catccatgtc tttgaaagcc agtggtatta ctccaggacc 159660
ctgagcaagc tgtcctagtc agccctggcc acttctggac tccttgcctg agtcagtagg 159720
tgccaatcct aggattgtca ccagcaggtt tcttcctagg gaggcaagca ctgtatcacc 159780
atggcgcctt ctatgccccc tctatgaggc ccttgggagc cccgccccac tgattgcctg 159840
attaatgtac caacaatgag gatggagcct ttgccatgca ttttaacatt gcaaattagc 159900
aggaatccaa gtctctgtgg aggggccctg cacctcttct gccagactca tcaagcgcct 159960

-continued cttgggcagg gctgccttct acttgagggg gcggaaggga gaagacccag ttccactctc 160020
cttcccctcc aggaggtgcc cttcatcgtg ttctgcttcg ttactctcaa gcctccggcc 160080
tcccacgcac gtgagctccc aaggggctct acagcctccg tcattccttc ttccattcat 160140
acttgccccc tagtctagga gagccatgga agacagtgtg ggaagggctt gacaatgagc 160200
atcatgcccc atttgcatat gcggtggcaa taccctggtg ggtaccagga gagtataggg 160260
gaaattaaga gaggggccta aggaaagcct ctgctatccc tgggctacca gtcagcattg 160320
cttggtcact gatcccctct gtaacaccag cccttctgca acctgccaga gtttttgacc 160380
tttgaactag ggctgagaag ggtctgctct gttcagctgc cttggctggg aggggaatct 160440
gctcagacct cagcacacac tcaacagaag gcatgcaagc aagggagcta gcagtggcct 160500
tgggtcagct ggcaagcccc aaactcttcc tgccaagctg agcatgaaaa gccacctcac 160560
catggtccca tgggaccaga cctggtagga taggtggcaa ggctaaggca gcggaatagc 160620
atgtgcaaag gcactggggt gggaaagggc ctgtgcttct cacccccctct aatggtgcag 160680
agcctccaag gaatactgta acctcagctc agctgggctc gggtggccag agagcttggc 160740
accagaacca gcatcaacag ggcctgtctg ctaaacccag acctcacaag ccagtttagt 160800
aggggccctg tagcaccctg gccaccagaa ctaacgagga agatctgacg ctgggaatat 160860
gtctttaatg aaaagccctt ccggaagcca catttgcaca gaagaaaatg aggtgcccag 160920
agcatcagtg ggctggttgc agctggagaa cacagcaggg ggacaggtcc taccaagcta 160980
ccctgccttc aggctggggc tctagccagc tccctgatgc ctggagtagg taaagcagcc 161040
tcgaaatggg ctgggtcagc tttttcaggc tccaaagggt caggacagct gctgcagctt 161100
agcacccaag gggctgccc ctctacccct aagtagaggc atccccatgg cccctgggca 161160
ggtcagtggg tctctctgaa gctttgtagg ctgcttcttg gccatgtagc caatctctct 161220
ggccttcagt cctccctccc tgcccccagc ctggccagct gctcttctct gagcaatcga 161280
tgttaaccga atgctctctt gctgtgggga tggcggcctc aggccaggcc agctgcactc 161340
ctggggctgc tggcgcctca ggccacttgg cacttgtgcc acttgtgttc taaacacagg 161400
ctccttcctg gctcggccct gaagacaaga aagctggcca gggaacagct gggctcccat 161460
ctcagcctcc actgctgtgc agagcggccg gcagcctcct atccatggct gtgagtagaa 161520
cagggctgtg gagccagagg cctaagttga atcctggctg ctccttttaa tgcttgcagg 161580
agcctcgttt tcctcacctg caaaatgggg cagtcattgg aagctcagcc agtcctccag 161640
cccacagata ctggtaccca cctgcccttc ccacatctcc atctgtctaa ctgaaaccat 161700
ccaaaccaag ctcttctctt cctctccggc ctcctccgtt cacaacttct ccatcttggg 161760
taaagatggt ccctttacat cagctgcctg ggaggaacac ctcagaatca ccgtggctca 161820
ctctggggaa attctgctgg ctagatttta gaatgtatcc agtatctatc cacttatcat 161880
actcgctatt gctaccattc acccagtagc ctcctggatg ccctcccccc cccccgcaa 161940
gccctgcctc ctcaccccta cacctccttc aacaggaact agggtagtcc agggaaagtg 162000
agtcaggaag ggctgctcct tagtctgcat cctccagagt gcccatctaa ctagaagctg 162060
ccccaggtct ttctcccagc ccagaggccc tgcctctccc tggctacaca gaccttgctg 162120
ccgtccctcc cacatgccag ccctcagcct ccctcctgcc tttgtccatg ctgttccatc 162180
tacctggacc ggttcccagt gtgtctgcag ggctgcttcc cagagaagcc actcttgagc 162240
agcgatttgc aaggagcttc tttcctggga cattttactc tacagcacgc gacctcttgg 162300
acagcacgac ataagtcact tgtttccttt atgtccgctg ccactttgtt ctgatgagtg 162360

-continued

```
tgctccctgc acacagtagg tgctcattaa cagttctggg ggagggaatt accttctcaa 162420
gtctctggag aattgaatga tgacactcag gaagccctag gctcaagcct ggggcctgga 162480
tcatagtagg tgctcgataa atgttggttg taattagtcc tgggagactc agagccttca 162540
ggagaacaga cacctgaact tggctcacat caagactcct taggcccatc aaggaagtga 162600
ccgtttgttg gatgagcact ctgagaagga cccaatacca gtcctttcct gggcaagggg 162660
aaatagactg ggactgggga gtttcccaag gtatgggatt ttcagcacta aactggaata 162720
atgctaaaga aaaaaaaaag ttagtcactc taaaaggggc caggaccaaa acctttcaaa 162780
cagaaatgtc tgggtttatg aagagaggaa gccagatatg gtggggcaca tctttaatcc 162840
aggtgcttgg gaggcaaaga cagatggagc tctgtgagtt tgaggccagc ctattctaca 162900
aagtgagttc taggacagcc aaggctacat agagaaaccc acttgacttg ccacccaaat 162960
taaaaatctt agtgggggag cagtcaagga ggaaacacac acacacacac acacacacac 163020
acacacacac acgttagtat aatatcatac tatggctctg tgcctgcagt ccaggaatga 163080
gggctgaact cagagtgtta gtgtgtgcta gtggatattt gagctctgta tttatgtgca 163140
tgtctgtgta gatgtgtacc tgaggtgttt atgtgtacac aggtgttggc ctgttgcata 163200
tggatggaga catggttgtg tttgctaggc atttgcatgt gtctgagttc atgcacataa 163260
actcacatct acctctggag actgagagtg acaacccagg gcccttttat cctgcagcac 163320
cccaggccca gcaccccgac ccagcatccc aggcccagca ctccagaccc agcaccccag 163380
gcccagcatc ccacgcccag catcccaggc ccagcacccc agacccagca tcccaggccc 163440
agcaccccag acccagcacc ccaggcccag catcccaggc ccagcacccc gacccagcat 163500
cccaggccca gcaccccagg tccaagcact caatgcccag caccccgacc cagcatccca 163560
ggcccagcac cccaggccca gcatccaagg cccagcatcc cagggacagc accccaggcc 163620
cagcatccca ggcccagcat cccagggaca gcaccccagg cccagcatcc caggtccagc 163680
atcccaggga cagcacccca ggcccagtat cccagggaca gcaccccagg cccagtatcc 163740
cagggacagc accccaggcc cagtatccca gggacagcac cccaggcaca gtatcccaca 163800
tggaggcagc acatactgaa gatagggaat gtctctgagg cctcttatct tggtccttac 163860
cctcattgct ttcagcacct gctctcctca cactcggaat caaacaccct gtgcaggttc 163920
tcccagtacc aggattcccc tcagctgagg aatgggtagc taccattttg gcttttgtct 163980
gtctggggtt ggcagcccca tgctaattgg actgacagtt tctcctgaga gcaatttggg 164040
cagcacatcc tgcccattag gcctaacctt gcctgcaggg gtgtgctgta ggggcaggga 164100
tggagcctac cctgtatagc tctgtattga ggcactcccc caagctatga cccatgccag 164160
tgggagtcat ttcacctagg caactccaga tgggcacaaa aatctctcca ataagggtag 164220
gtatgggaat aggtaaggag agcatagtga gcctggctgg gcacctgaga cctgagcagc 164280
ctgcacggga gattgtgtca ctgtggttcc agactgccaa gacatcttgg ctttcacccc 164340
aactcaggat ggtccagaat ccagagctct taagagagca gatgctgaga ggcacttaac 164400
ccagggctaa gacccttcct tggacggttt cttggctttc tactctgtcc tctgtcccag 164460
tctgtcatcc ccatctgtgc ctaacagctc tctgtggaaa acatgaggcg tatgagctct 164520
ctacttctcc cagcatccca tgcccgcacc ccagctcact gtgtgccctc atgttactca 164580
aatcttctgc taggtttgag ggccccaggt tgaggctgtg ggtttccctc catctgtccc 164640
tccctttttac caccaccact aatcctcttc ctcctcttcc tcctcttcct cctcctcctc 164700
```

-continued tttctncncn nnnnnnnnnn nnnnnnnnnn nnnnnnnnnn nnnnnnnnnn nnnnnnnnnn 164760
nnnnnnnnnn nnnnnnnnnn nnnnnnnnnn nnnnnnnnnn nnnnnnnnna caaaggacgc 164820
aaattgaact tacagaggaa acacaaatga gctgtaatga cagaaaagga atactatttc 164880
ccttgtgatc agaaagctat agattaaacc ccagcccttt ttgcctttgt ttttcatatt 164940
tagtggttct ggggactgaa cccaaggaag gacagctgct tggaatgttg gagacctctc 165000
aggcattgct tatgctaagc tgacaaaggc tttctgaatg catatggtag tatctattca 165060
tcttaagatg cctataacca tgggtggagc aattctctaa gagtctgtct gaacttctta 165120
agcatgtgct caaaaacaca cataaagatt gtttactgaa gcagtatttg caacagtgaa 165180
acaaaaccaa acaacaacaa aaagtactta atagctcatc agtaggaaaa agaacaacaa 165240
attgggacac atttatacta ttctcgttct atcacacgac tattaagaag attaaggtgt 165300
gaggatgaaa agcccctgca gaacaacgca cacaatgaaa ttgaatagag aataaagaaa 165360
aaaatatata gtgtatttat gtaaaacata cataaacaca taaaaagaat agaaaactct 165420
ttgactgtat atctttgaaa agaaccagca gagtgctatg gtttataaat gaaaagttcc 165480
cccaaaattc ctgagttgga ggttcaatgc agagttcata ctcttaggaa gtaactaaat 165540
caggaatgct ctgatctaat caatggattg accaactgat agattaataa tctgaaggca 165600
acacttccag gaggcagaaa caaggtgagg cctaactgga ggaagtttgt caccagaggc 165660
atgtccttgg agaggctacc tcatccttga tccttccctt tctccgcttc ctggctgtaa 165720
aagtatttat ttgactgatg taactgtcat cttggaggct tactggctcc atcagctaac 165780
ctaggcctag ccctggaagc ttctagcttc catacaatct aatccaagcc tagaatgttc 165840
cagcctttag gacttgctgc tgagatcacc gtttcctgtt ctttctgaac tctagctggc 165900
tgattcagtc cccctgttcc gggctcaaac tcctctcccc gatgatttta ttcacaatct 165960
gtcttttctc ttggcctctg aattgctctg cttggtctca aactaactct agcaatcttt 166020
tctaatctct tgtctccttc acactctctt gcttgttctg tctttactgt gtctagtttg 166080
ttctctcttc catccttctc tgtaaagctc tcccggtaaa cctgcctcct cctccccctc 166140
tgtgccgctc tactctccct ctcagctcta ctgcactgct ctccacagct ctcctgtatc 166200
ctgtgctgca ctctcttctc cggtaccacc tgtgtctccc ttacgtagct tccctttcct 166260
ctctcttctc ctgagggttg ggcagatcct atcctgtcaa acctttctct gattcttcac 166320
tttgtctgcc actcaattag acatcacttt caagcaggag tgcctcctct acaaaccaac 166380
tttaccttca ttgtttcaaa ttaaaggtga gtactaaggg tgtgtctctt tttcagccag 166440
tgagagtaaa gatgtgtgct aataaggctg agccaactct agctagaaat agtttctttt 166500
tctccataaa taacagaatc ttagggttca caatacgatc aaatatcctg agacagctgg 166560
ctgccatgtg gtgaagagaa tgcagagagt taaggatgtg ctcttgaggt ttcagatggg 166620
aataagcatt ttcttgggag ttggattaga gtcattcctg tgacactgtg acaaaggact 166680
cgactacatt ttgccatgcc ttgagactgt ggagggctga gcgatggatt aatacactgg 166740
agtgaatttt aaggcagcca aggctgtggt tggactgtta ctagctacgt ttagctggat 166800
ttatattaag aattgggaac aaaaaagcag agtagaaagg acagttttgg cagaaggagg 166860
tttcttcata tacaacttag tttttatagt tagcttttta tgttgctatg accaaaatac 166920
cttatggaaa ctgaagaata aaaattttta ctgaactctt cttcacccca gaacccgacc 166980
cctcccatct agagattgtt cccggaacac tcctgaactc ttcaccccag aatgctttcc 167040
tgaactcctc accctagagt tcgaaccctc ccaactaaaa actgttccaa gaacattttt 167100

-continued gagataaggg cctcctaaaa caacctcaaa atgaaccggg tacattgcca aataatagga 167160
catgacccct tagttacgta gattcccttg gcagaacccc ttgtcccttg acagaacccc 167220
ctagtgatgt aaacttgtac tttccctgcc cagctctccc cccttgagtt ttactatata 167280
agcctatgaa aaatttggct ggtcgtcgat tctcctctac accactaggt gcatgagttt 167340
cgaccccaga gctctggtct atgttccatg tgctttcttg ctgttgttct attaaatctt 167400
gccttctaca ttttgagtac ggtctcagtg tcttcttggg tccgcggctg tcccggggct 167460
tgagtgcttg agtgagggtc tcccttcggg ggtctttcat tttggtgcat tggccgggaa 167520
acagcgcgac cacccagagg tcctagaccc acttagaggt aaggttcttt gttctgtttt 167580
ggtctgatgt ttgtgttctg tttctaagtt tggtgcgatc gcagtttcgg ttttgcggat 167640
gctcagtgag accgcgctcc gagagggaac gcggggtgga taaggataga cgtgtccagg 167700
tgtccaccgt ccgttcaccc tgggagacgt cccaggaaaa acaggggagg accagggacg 167760
cctggtggac ccctttggag gccaagagac catttggggt tgcgagatcg tgggtttgag 167820
tcccacctcg tgcccagttg cgagatcgtg ggttcgagtc ccacctcgcg ttttgttgcg 167880
agaccgtggg ttcaagtccc acctcgcgtt tggtcacgag atcgtgggtt cgagtcccac 167940
ctcgtgcaga gggtctcaat cggccggcct tagaaaggcc atctgattct ttgagttgct 168000
tgtggtcgac gcagagtcgc cgccgtttct ggtttctttt ttgtcttagt ctcgtgtccg 168060
ctcttgttgt gtctactgtt tttctagaaa tgggacaatc tgtgtccact cccctttctc 168120
tgactctgga gcattggaag gaggtgcggg tcagagccca caaccagtcg gtggaagtca 168180
gaaagggtcc gtggcagacc ttttgcgcct ccgagtggcc aacgtttaga gtaggctggc 168240
cacctgaggg tgcttttgac ttgtcactaa tcgctgccgt caggcgaatt gtttttcagg 168300
aggaaggggg tcaccctgat cagatcccct acattgtgac ctggcagaat ctcgtccaat 168360
tcccacctcc gtgggtcaag ccttggaccc caaactcttc gaaactgacg gtcgcggttg 168420
cccagtctga tgcagccgga aagtctggcc catcagcacc ccccaagatc tatccagaga 168480
ttgacgacct cctctggata gactcccaac ctccccctta ccccctgccc caacagccac 168540
ctgcagctgc cccaccacag ggaccaatag cgagaggggc tcagggaccg gcgggggaga 168600
ctcggagtcg ccgaggccga agccccgggg aggaaggggg gccagactca acagttgcct 168660
tgccactcag agcacatgtg agagggccag caccaggacc taatgatctc attcctttac 168720
agtactggcc tttttcctct tctgatttat ataattgaaa aactaaccac cctcccttct 168780
cagagaaccc ctctggactt actgggctcc ttgagtcact tatgttctcc catcaaccca 168840
cttgggatga ttgtcagcag cttttgcagg ttctttttac aacagaagaa agaaaaagaa 168900
tcctcataga ggcgagaaaa aatgttctgg gagaggacgg cacacccact gccctcccta 168960
acctcgtgga cgaggctttc cccttgaacc gccccaactg ggactacaac accgcggaag 169020
gtaggggacg cctccttgtc tatcgccgga ctctagtggc aggtctcaga ggagccgcta 169080
gacggcccac caatttggct aaggtaagag aggtcttgca ggggcagact gaaccaccct 169140
cagtcttcct tgagcgtcta atggaggcat ataggagata cacccctttt gacccccttgt 169200 cagaggggca gagagccgct gtagccatgg ccttcattgg tcagtccgct cccgacatta 169260
agaaaaagct gcaaaggctg gaggggctcc aagatcatac gctccaagat ttagtaaaag 169320
aagcagaaaa agtctatcat aagagggaaa cagaagaaga gaggcaggag agagagaaga 169380
aagaaataga ggagagggaa aatagacggg atcgccgtca ggagagaaat ctgagtaaaa 169440

-continued ttttggccgc agttgtgaat gatagacagt caggaaaagg taaaataggg ctcctgggca 169500
acagggcagt gaaaccgcaa ggtggcaaaa agataccact ggaaaaagac caatgcgcct 169560
attgcaaaga gaaaggacac tgggctagag attgccctaa aaagcgggag cgatccaagg 169620
tcctaaccct agaagatgat tagggaagtc ggggctcaga ccccctccct gagcctaggg 169680
taactttgtc cgtggagggg actcccgtca acttcctgat agacaccgga gcagaacatt 169740
cagtactcac taacccccta ggcaagctag gctccaaaaa gaccatggta attggagcca 169800
ctggtagtaa attttacccc tggacgacca aacgagctct tcagatagac aaaaatatag 169860
tgacccactc ctttctggtg atacctgagt gccctgctcc cctcttgggg cgcgatctgc 169920
taaccaaact aaaggctcaa gtccaattta cttcagaagg cccacaagta agctggggaa 169980
aggcccctgt tgcctgcctt gtcctcaaca cagaaaaaga gtaccggttg catgaagaac 170040
aacccaaaaa tgcagtctct tcaggttggc taactgcgtt ccccaatgtc tgggcagaac 170100
aagcaggaat ggggttggct aaacaagtgc ctccggttgt ggtagaactt aaagctgatg 170160 ccaccccat ttcggtaaaa caatacccca tgagcaagga agctagaaaa ggcatccggc 170220
ctcatatcca gaggttgctg ggccaaggag ttttagtggc ctgtcagtcc ccctggaata 170280
caccacttct gccggttcaa aaaccaggga ccaatgacta tcgcccggta caagacctcc 170340
gggaggttaa caaaagggtc ctggacattc accccacagt cccgaacccg tacaatttat 170400
taagctctct cccacctgag agaacatggt atacagtcct agacttaaaa gatgccttct 170460
tttgcctgcg tttgcaccct aagagtcagc tcctgtttgc ttttaaatgg agggacccag 170520
agggcggaca gactggtcaa ctaacttgga ctaggctacc acaggggttc aaaaattccc 170580
ccaccctgtt tgacgaggcc ctccatcggg atcttgcgcc ttttcgcgct cgaaaccctc 170640
agcttaccct actacagtat gtagatgatc tcttggtcgc ggcggcctcg aaggagctgt 170700
gtcaccaggg aactgagagg ctcctcacag aactgagtga cttggggtat cgagtttcgg 170760
ctaaaaaggc acaaatctgt caaactgagg taaccttcct ggggtatacc ctccgagggg 170820
gcaaaagatg gctcacagag gcccggaaaa agactgttat gatgatccca tcgccaacta 170880
ccccacggca ggtacgtgag tttctgggga ctgctggctt ttgtagactc tggattccag 170940
gctttgcaac cctagcagca cctctatatc ctttgactaa ggaaggggtt cctttcaagt 171000
ggaaagaaga acaccaaaga gcttttgagg ctatcaagtc gtctctaatg actgccccca 171060
cgctagcatt accagacttg actaagcctt tcgtcctata tgtggacgag agagcgggtg 171120
tagccagggg agtattgaca caagcactgg gaccctgaaa aagacctgta gcctatttgt 171180
caaaaaaatt agatcctgtt gctagtggat ggcccacatg tctgaaagct attgcagcag 171240
tagccctgct gatcaaagat gctgacaaac tgacaatggg acagcaggtg accgttgtag 171300
cccctcatgc cttagaaagt atcgtgcgac agccacctga cagataagat gacaaatgcc 171360
cgaatgacac actatcagag cctgctgcta aatgagcgtg taacctttgc gccccctgcc 171420
atcctcaacc cagctaccct tctccctcta acaaatgatt ccgtcccagt acatcaatgt 171480
atggacatcc tcgctgaaga aactgggacc agaagtgacc tgactgacca accctggcct 171540
agagctccca gttggtacac ggacggcagc agtttcctga tagaggggaa gcaaaaggct 171600
ggagctgcgg tggtagacgg gaaaaaggta atttgggcaa gcgctttgcc tgaaggaaca 171660
tcggcacaaa aggctgaact tatagcgctt atacaagccc tccgagaggc taaaggtaag 171720
atcgttaata tctacactga cagccgatat gcttttgcta ccgcacacat ccatggggcc 171780
atctacaggc agcgagggct attgacctcg gctggtaaag acattaaaaa caaagaaaaa 171840

-continued attctggccc tgttagaagc catacatgca cctaaaaagg tagccatcat ccactgcccc 171900
ggccacccaa aaaggagaaa acttggtggc caagggcaac cgaatggcag acttagtggc 171960
aaaacaagtt gctcaagggg ccatgatctt aactgaaaaa ggtgatccgc ccaaaagccc 172020
tgaggatggg aggtataaca taaaagagct atggtagacc agtgatcccc tcccatactt 172080
tttttgaaag aaaaatagaa ttaactcccg aagaaggaat aaaatttgta aaaggactac 172140
accaattcac ccacctggga gttgaaaaaa tgatgagact aattaaaaat tcccgatacc 172200
aagtccccaa cctgaagtca gtggctcaaa agattataga ctcctgcaaa ccatgtgcat 172260
tcactaatgc aactaaagcc tacagagaac ctggaaagag acaacgggga gaccatcctg 172320
gagtgtattg ggaggtagac tttactgaag ttaaacctga aatgtatggt aacaagtatc 172380
tgttagtatt tgtagacacc ttttcaggat gggttgaggc atttcccact aaaacagaga 172440
ctgcccagat tgtggccaag aagatccttg aagaaatcct gccaagattt gaaatcccta 172500
aggtaatcgg gtccgacaat ggaccagcct ttgttgccca ggtaagtcag ggcttggcca 172560
ctcagttggg catcgattgg aaattacact gtgcttaccg ccctcaaagc tcaggacagg 172620
tagagaagat aaataggacc ttaaaagaga ccttgactaa attagccatt gagaccggca 172680
gaaaagactg ggtggctctc cttcctcttg cgctcaaaca cccctggtcg tttcgggctc 172740
actccttttg aagttctgta tggaggacct ccccccttaa tggaagctgg tggaacatta 172800
gtttccgact ctgaccctgt cttaccctcc tctttgctta ttcatttaaa ggccctaaaa 172860
gtgattagga cccagatttg ggaccaactg aaagcagcct ataccccagg gaccaccgca 172920
gtaccccacg ggttccgagt tggagacaaa gtcttggtca gacggcatcg aaccggtagc 172980
cttgagccac ggtggaaggg accctatttg gtgttactga caacccctac tgcggtaaaa 173040
gttgacggaa tcgcctcctg gatccacgcc tcccacgtca agagggccgc cagtcaagat 173100
gaagaaaacc acgacgacaa ttggacagtg gcagtcactg acaatcctct taagcttcgt 173160
ctgcgccgca ggcgccactc tagacctagg gaaccttaac cctcatgctc caattcaaca 173220
gtcctgggag gtgcttaatg aaaaggaaaa cattgtatgg gcaaccactg cagtccatcc 173280
cctctggatt tggtggcctg atctcacgcc tgacatctgt aagttagcgg caggatcccc 173340
caattgggac ctctcagatc atactgatct tagcaaccca ccccctgagg agcggtgtgt 173400
cccaaatggg atagggagca catatgggtg ttcggggcag ttctaccgag ctaatcttag 173460
agctgcacat ttttatgttt gccctggtca gggtcagagc aaaaggcttc aacaaaaatg 173520
cggggggcca tcagattact tttgtggtaa atggacatgt gaaacgacag gagatgctta 173580
ctggaagccc tcctctaaat gggacctaat cacggtaaaa cgaggtagtg gctatgataa 173640
gtcaaacgaa ggagaaagaa accoctataa atatcaagag agtgggtgcg cttttaaaaa 173700
cagagcaccc tcaggaccat gcaaagataa atactgtaac cccctacgta taaggttcac 173760
cgagaacgga aaacaacacc gtctaagttg gcttaaagga aataggtggg gttggcgagt 173820
atacattcca ctaagagatc ctgggttcat tttcacgatc agattgacag tgagagaccc 173880
ggcagtgaca ctcgtagggc ccaacaaggt ccttataaaa caggggcccc ccagtcgtac 173940
tggctccccc aaaggtcccg actgtaccag ctccaccaac tccacagccc aacacagtgg 174000
taccctccct aggaactaat actctcctca taaagcctac cttggcttcc ccaccgcccc 174060
taggaacaga ggaccgtctg gtcagtctag tccaaggagc ttttttagtt ctaaatagaa 174120
ctaaccctaa tatgactcaa tcatgctggt tatgctatgc ctctagcccc ccttattata 174180

-continued aaggaatagc tcagatcagg acttataata ctacttcaga tcattctcaa tgcctttggg 174240
gaaaaaacag aaagttgact ctagcagcag tttcaggaag agggctttgt ctgggccggg 174300
tacctcagga taaagggcac ctctgtaatc agacccagaa catccagtct agcaaaagcg 174360
gtcagtatct ggtgcctccc ctagacacag tgtgggcttg caataccggt ctcactcctt 174420
gtgtgtctat gtctgttttt aatagttcca aagatttctg cattttggtt cagcttattc 174480
ccagactctt gtatcatgat aatagttctt ttttagataa atttgaacat cgggtccgct 174540
gaaaaagaga acccgttacc ttaactttgg cagttctatt aggattggga gtagcagctg 174600
gagtaggtac aggaaccgct gccttaatta agaccccccc aatactatga agaactacgt 174660
gcagttatgg atattgatct tagaactata gaacagtcta taaccaaatt agaagaatct 174720
ttaacttccc tgtccgaagt ggtgctgcaa aatagaaggg aattagactt attattcctt 174780
aaaaaaagag gactctgtgc tgccttaaaa gaagaatgtt gtttttatgt tgaccattca 174840
ggagtaatca aagattctat ggctaaactt agagaacgcc tagatatacg taaaagagaa 174900
agaaaaagcc aacaaagatg gtttgaaagc tggtttaata agtccccttg gctcaccact 174960
ctcctctcca ctatagcagg acctttaatt acacttatgc ttttgcttac ttttgggccc 175020
tgcatcctta ataagttagt agcttttatt agaaaaagga taaacgcagt ccaggttatg 175080
gtactaaggc aacaatatcg ggtccttcag gaggttgaaa actcgctcta agattagagc 175140
tatctcctaa aagaagtggg gaatgaagaa taaaaatttt tactgaactc ttcttcaccc 175200
cagaacccga cccctcccat ctagagattg ttcccggaac actcctgaac tcttcacccc 175260
agaatgcatt cctgaactcc tcaccctaga gttcgaaccc tcccaactaa aaactgttcc 175320
tagaacattt ttgagataag ggcctcctaa aacaaccgca aaatgaaccg ggtacattgc 175380
caaataatag gacatgaccc cttagttacg tagattccct tggcagaacc ccttgtcccc 175440
tgacagaacc ccctagtgat gtaaacttgt actttccctg cccagctctc ccccccttgag 175500 ttttactata taagcctgta aaaaatttgg ctggtcgtcg attctcctct acaccactag 175560
gtgcatgagt ttcgacccca gagctctggt ctatgttcca tgtgctttct tgctgttgtt 175620
ctattaaatc ttgccttcta cattttgagt acggtctcag tgtcttcttg ggtccgcggc 175680
tgtcccgggg cttgagtgct tgagtgaggg tctcccttcg gggtctttc aaaactactt 175740 cagaggaaaa atgtattctg cctcatgggt tcagggggtt tccctcagca aattcaggga 175800
agacaagatg gaacagctca acctgctggc aggagggtgt gggaaaggac aagtgttcat 175860
tgtgtggtgg acaggaaaca gagagctgcc tacagtctta caggcctacc accactgacc 175920
tacctctgtc cgtcaggccc tacatcttaa aggatctaca gtttattaaa agaacactac 175980
cagataggaa ccaagtatca aaccaccagt ttgtagggga taaaaataca aggaacacat 176040
ctcaatagga gtgtgttcca ggatgtggac aaggagaaca cagttgttta aaagcttaac 176100
gctggccagg agagctgcac acctttaatt ccatcactcg taagagggaa gcaggttcat 176160
ctctgtgagt tcaaggcaag cctgggctat acaattctag attagccaga gctacatcgt 176220
aggagcctgt ttcaaaacaa acaaaaccaa accataaaaa agcatttctg aggctttggg 176280
tttaatcccc atgacctcaa atagccaaac agctctcctc agtccaaacc aaactgcaaa 176340
attggagcta gtgagatggc tcaacatatg aaagtccttc ccaaaaatat tgacaactgt 176400
agcttatctc tggggacaca cataatggga gaggaccaat ttctacaagt taccctctga 176460
cctccacaca tatgcctccc acaaataaga aaatatatat aataaaaaga aagaagtcta 176520
cagctgcaca tggtcatgca tgcctataat ccagcactcc agaggctgag gcaggaggat 176580

-continued tattagtttg agatcgcata gcaagcagta ggctagacag ggctacatag tgtaaacctg 176640
ccttaaaaca caaaaatcaa ttaagcaaca ataacagtaa caaccacaac aaaaacccaa 176700
aagagtactt tgtagtaagg acaataccaa aaatgttcct ttaaggacag ttctggaatc 176760
agcaatagcc ttccgagtgc tcagggatgt ataaatactt agaaaacttc ccctggagaa 176820
atgagcacca gggtacactg ctctcagagc tgcccagaaa gttgtttatc ctggattcat 176880
ttcagccttc ctaactgctc aggcattcag aggtcacttc tgtagtagcc aatgtctaaa 176940
aaggctaaac tactgctcag catggctgtg gtacttggca ttatcatttt gtgactggtt 177000
ttgtagttat gcagaattca agagttatag catcatgaaa gtttccacca agttcctgat 177060
ccagtcacct cttaaaggtt ggatgcacca agtgcctttg gggtgataaa ttatattcaa 177120
ataatggtat tccaccctaa tccccaaaga cttctggcca tctcataatg taaaatgctg 177180
agccatcgca ccagcccatg gccttgaact cttgatggtc ctgtctcagc ctgtgtttgg 177240
attataaatc tgttggtgag gtattccttt gctgataata caagcaaatt cttcaagctt 177300
ccatcctaga ctgaagacca gcagctctcc aggagtcctc aatgcagact ggcccagctg 177360
ggacattgag cctcatggac tcagccgcta ctagattcgc aacctattca gacaagccac 177420
tgttggacta cccagacaat actatgtaag ccaatcccat tttaatacac atattcatct 177480
gggtgtgtgg cacacacctc tactcccagc acgcaagagg cagaggcagg cagatctctg 177540
atttcgaggc ctggtctata gagtgaattc caggccagcc agggctacac agagaaaacc 177600
tgtttcaaca aaaccaaaac cgtaaattca ttctatcagc tctatttcct tagagaattc 177660
taatacatgt gggtaccagg ggttgaactc aaagtcttca tgtttacgta gcaagtttcc 177720
ttctgctagc ctagtgaagc tgaggcaggt acagccggtt ctttactgct ccttgcaaat 177780
ggtcctcctg agctttcctt tgagagccta caaagaactc tttttttctt taggtctcca 177840
ggttttggtc ttaagaggtt ctggacttgg atctgtagct gtcatatcac agacattcaa 177900
catctggcaa atgtcttgac aaaggagatc acttgtgttt gctgcagtgt cccttctggc 177960
tgtgagattt tgctcctcac cactgcagga ctgcagatct attctgcctt tttagttgac 178020
ttttcattcc tgagaactgg ggaaaactga ctttgtattt gggctttgaa tttgtccatt 178080
tgtcaatcca tcacaccaga cctaaccaac tgccaagagt tctgctgact tttgttttct 178140
ctagggtggt cactttgctg ggctcatcct catccttggc ctgcagttta tccccaggaa 178200
agaaaatggc taacgactgc taagaagcag tctttccttc cagaaatttt agtctatcta 178260
gaccttgctg cagtctgaag tctttaaaat gtgtttgtta tggtagaata ttttgagttg 178320
ccttaggagt attgcttgct gtcacctatc atattctatc aggaagcaga cgtcccattt 178380
accaaatgtg aagaaatatg gcatcaatac ccactgcaaa aagtgtaaat aaataataaa 178440
aaaatagatt tattacagag tgcaagggaa aagaaaaaaa tcagccagtt tcagaattgt 178500
aactggacaa atgttggtac agttcatgaa gaggttctac aaaatggctg ggggtgggaa 178560
cataatgagt tagtttgctt tttttttct ctttccttcc ctttcctttc cttacaaggt 178620
ctcatgtagt ctatggtctc aaactcacca ctgtaaatca ccttgaactt ctgatccttc 178680
tgcacgctgg caatgtaagc atgtgccacc aggcctggct cacacatttg gtttttcaat 178740
acagaatagc tctgtgatga ttaacttcaa tcatcaactt gacataacca agaatcgtct 178800
gaggaagagt ctcagtgact gggtgggcta agggcatgct cataagggat tatcctgatt 178860
gttaattgac atggaaagat caagtccatt gtgagcagca acacgccctg aacagaagtc 178920

-continued ttctgaagta taagaggaga aagcttgatg agagcaagca ggcaagcaag ccaggatcca 178980
cgtgtttatt ctctgtctgt tcttgaccgt agatgtgatg gctgtcttgg cttcctggga 179040
aacatgaact gcaccctgga attgcaaggc aaacaaacct tttcctcttc caagttgctt 179100
tatgctaaga tattttatcg cagcaataga aatgaaactt agaacaggcc cataactgcc 179160
agctttggaa ctgaacctaa ggctgttata attcactagg atagggacca ctggaagtga 179220
atctgatttt gatggtaaaa tcatgtgttt gtttctggat atgatagatt tatcaatttg 179280
agactcagaa aagaagttag gacttgaatt ccgttttaga gacattccag agaaaactga 179340
tgtcattgtt ctgaatgtaa gtgcctcagc tgaaaataca aagagtacag ggaagaaagc 179400
ccaggctaga atctgaagga actcctctat tttttgtttg cttgtttgtt tggttggttt 179460
tttgagacag ggtttctctg tgtagccctg actgtcctgg aactcacttt gtagaccagg 179520
ctggcctcga actaagaaat ctgcctgcct ctgcttccca agtgctggga ttaaaggcgt 179580
gtgccaccac accaggctag gaactcgtct attacacatt aacacccctc tttaattaac 179640
tgttcctgcc aatgtaccaa atagtcaatt gattcctgtt tatttaccac atgtttctgt 179700
tagtaaacca gaataactta tctagccaaa gtctgcctat tagccatatt ttcatcagtt 179760
cccaaccatt tttggaattc tgtgagggga atccacagat gctgtagacc gctttagaca 179820
tttttcagct tttttcaagt tgcaggtcat gattcagtgg gtcatgaaat taatttagtg 179880
ggttctgatt agcatttcaa aatgaggcaa gcagagggca tattgtcaca gcacagcaca 179940
tgcggtaagc agccacacac tcttgcttgg aggcttagtc agtttctggc tctaaacgcc 180000
ccaggtttgt ttctctatcc taggcctctc tcttaaattc caaacatagt tagacattac 180060
cattggggca cgtgcaactc aaacacggag tgtgactcct ttccccatct gcggttccca 180120
gatttggcaa tgtcaccctc ctcccttctc cctagggtca gttttacctc tcacactcca 180180
caacacaaca cctctcatct caagaattgc cattagggct ggtgagatgg ctcagaggtt 180240
aagagcaccg actgctcttc tgaaggttct gagttcaaat cccagcaacc acatggtggc 180300
tcacaaccat ctgtaatggg atctgattac ctcttctggt gtgtctgaag acagctacag 180360
tgtactcaca tatattaaat aaataaatct aaaaaaaaaa aaaaaaagaa ttgccattaa 180420
atgtacctca gagtccaaat gcttcttcct cccctgacta cactcacgct ggcctgagtc 180480
cattttctta ttgaggttac tgcttctctg cttctaccct ggctccttct gctgcctatc 180540
cttgacacag cagacaagca gttctttaaa gcagggctca ggaccagtga gactgatcgg 180600
ctctggtggc acttcctgcc atgactgatg atctaaggtt aagcctagaa cccacgaggt 180660
agaagcaaag gacctactct ccaaagccgt cctctgacca ccatgtgtaa actgcacatg 180720
tacatgcatg cacatggtac acacacatac acagaagtaa aaagagattt aaattgaaaa 180780
tcattaaaaa gaaaaatcag ggctcagcaa actttccgtg tagaaaacta gagtacttag 180840
gctttgaaag ccaagaagtg gatattaatt atagttattc attatagcag agatttctaa 180900 aacctttga caaaactaaa aaatataaca gagtgtattt tttttgtaat gtaagtttac 180960
taatggcagc agtgggatta gtttcttttt tagattattg ttattatttt tattaattat 181020
tagtgttttt gtgtttattc atattccaca gcatgtgtgt ggaattggat ttctgcttcc 181080
acctttgtgt gggtcctaga gattgaactc aagtcatcaa gcttgcacag taggtggtca 181140
ggcttacaca gtaggtggtc aggcttgtat ctttggaagg caagcatttt acttcctgtg 181200
ccagctcact ggccttcttt gtttaaaaaa agaaaaaaaa agtccttttt tgtttaatta 181260
gggttcatgg ccagtgctct ttatcttaaa atcaactgca aacttttatc tggtaaaaag 181320

-continued

```
ccatccttag ctgtggtcct aggagaaaaa catacagttg gatggcttta tcctgcaggc 181380
ttagtttgat catctctctt tgaagatata atcagctcac atcacactca agcctctgcc 181440
aacgagtttt ctacttctgt tcaacaaact acccaagctg agcagctcca aacaacagcc 181500
agttatgatc ctcacagtcc ggtgggtcag aagcctaagc gggcgtggct acctcgctgc 181560
tattgcctga ccctgctcgg tgcatccaca ttcacatcct ttcctggtga gtgtggttct 181620
ttgactggtt ttgttccaat ttttagtata tgtgctgctg aaacaatctt tttgcctctg 181680
cctccagact gcagggatta atgttcttga ctgccacaga gcactaatat ttactgaaca 181740
tgtgatcatg tggtgctcag cactcttgca cccaaggctc ggggaacatg gaggaagagg 181800
gggtggaaag attccaagaa ccagaggaag aagaaagtca gaggtgagac tgcatctcct 181860
agaaatgtca gggacatttc tagacctctg aagtctcaag aacaaggcct gaaagtctta 181920
tttatatagg ttaacctgaa aggggaaaaa attcttacag gggtccaacg ttagacaaag 181980
aactctaagc aactaaggaa tgttgggggg ggggtagtct tccccaggga acactcctct 182040
acccttcaag ccccacccaa gctggttatc caaaacaaac tggtcagtcc tgaagccata 182100
tacgcacaag taacatcata tggatgggca gattgcattt aggaatacac acatacacac 182160
acacaactta aaaagagagg ccatgaattt aagagagagc aaagcaaagt gggaaggggt 182220
acatgggaag gttggaggca gnnnnnnnnn nnnnnnnnnn nnnnnnnnnn nnnnnnnnnn 182280
nnnnnnnnnn nnnnnnnnnn nnnnnnnnnn nnnnnnnnnn nnnnnnnnnn nnnnnnnnnn 182340
nagagagaga gcctattatg tcgttggttg cttctaatca ttagaaaacc actctcttag 182400
gctgagtcag aactagccta gctgagacac tgtccaccca ctgtcccaga gcaaggccat 182460
cgctgtccca gatttgcctt tgggggccct tgaaatgaaa gtcaccagca ggctccggaa 182520
gctgcctcat gctaatcagt tgaggttgtg aaaatagccc tgcagtggtt cctgggcctg 182580
cagctgggcc agagccacta aggggagtct ggtcctttgg agcagagtta acagtcatca 182640
gtgctttttt tttttttta aatgttccct gctttaggct cagtgctgtg cgctacttct 182700
aatccttgca ataggctgca agacaggcaa gaatatcatc cctgttttgc cctcaggcaa 182760
attctgaagt ctggcaaatg aaagatgtgg gatttgaaca cagacttgtt tggccaaaga 182820
attctcactc tacttctgcc tgtgccacct tcctctcatg cacggggagg ggaggggagc 182880
ccacctccca tgctcagggg ctaggaagtg gggagaagat ggatgtcctc aaagcagggt 182940
gagaatgaag tagaagccag cttcaaatct aaactaagca atgttttatt tccatttccc 183000
tgaacataaa gttcagttac atttggttta aaaaaaaaaa tccctacaca actggttctt 183060
gagaaatgtc aagtgctaca attcagtgga tgtggatgaa acaatcaaaa tgttgaacac 183120
ccccaaacag atacaaacct tcatcaaagt ctcttccaaa ggctgggtct gaaaagagcg 183180
actcatgttc cagcccagtt ggctccttct catgtgagct ccgacttcca aagactgctt 183240
gcaccaggag gaaatataat agatgtcctt tttaaggggg gtggggtctg tctgacaacc 183300
tcccacagtg actgtggata cagcccagtt agtagagttc tcgcctagca agcgtgcggc 183360
cctgggcttg agatctagca ccctaaggca tagtggtaca tgcccatgac cacagcactt 183420
gggacgtaga ggcagaagga tcagttcaag gtcagatgag gggtggggag gcattccttt 183480
aatgccagca tttgagaggc agaaacagat gaatttgtga gttcaaggcc agcctggtct 183540
acagactgag ttccaagaca gccaaggcta cacagagaaa ccctgtcttg tcaggaaaaa 183600
agatagtggg agagaattca aggttatctt ggactgcata agactttgat tccaaaataa 183660
```

-continued

```
acaaaaatgg agcatgaatg cttgcaactg tggacaatat tgggttcata catattctgt 183720
tttgtcacct acataccaat tatacaaatc agattcagct gggcccactg gtgcatgttt 183780
gttcccagca tctgggaggt agagatgggc agagctctat gactttaagg ctagcctggt 183840
ctacaaagta agttctagga cagccaaccc tacagagaga tacactactt ctaaatcaat 183900
caatcaatcc atcagtcaat catgggctgg agagatagct cagtgatcaa tagtgccatt 183960
cttccagagg acctgggttt gattcccagc acccacatgg cagctcacag atgtctgtaa 184020
ctccaatccc aagggacatg acaacttcta ctggtctctt tggtcaacag gcatgcacgc 184080
agcatacaat atatatatgg gtaaaatgct atatatataa aaatcagatt cacaaatcaa 184140
gtacagaaag agatcaacta taatgaaaca accataacac atactgtttt aaaagctacc 184200
tttcctgtct gacatctgac ttcttgcgtg acccagtgcc tccacaatga gacaagcaga 184260
tggtgtagtc cctgtgaccc aggattaggc aaccactgcc cctgggaagc cattcctagt 184320
aacaggatca aatcccacag tgctccactg taccccgcca gaggacgtga agcctccctt 184380
ccccggctgt ctgtgcagca ccgcccagat gcttggtgtc actgagtgac catcggagcc 184440
caactgagga gtgcctcagt gctcctcagg gcagtgtgca attgaaactt gcatgtgatt 184500
tctggaattt gtcatttgat atttccagac tccagctgac cttggataac agcacagagg 184560
gcagaactgc agaggaaaag gggcactact gtgactgtta tcccctgcat gattatagaa 184620
gggtctgtgc tttctcttac aaatcattgc ggcctctctt cacttccctc ctttgaagtc 184680
gaaaaaaata gatgcatcct cacagtacag gatggcaggt acgaggcggg ttccgggact 184740
gaggcaggac tcatcatgca gcctctttcc ctcaactaca ccgccgcccc tgcagagttc 184800
cctctgatca aatcagtttc aggcctggaa agaaacggcc actcaggctg gggatgtggt 184860
tccattagag gcctgcatgc acgaagctct ggatttgatc ttcagcacgg gcataagccc 184920
agtatggtag tatctgttta gcatggtgtg gaggtatacc tatctctgca cagggagacc 184980
agaagttcag agttatcctt gcacttacag taagttcaaa gctagcttgg gcaacatgaa 185040
gttttgtctt aacaaaacga aacaagaggg gccggggaga tgcttcgctg tgctgagtca 185100
tttgctgcca agtttgatga cctgagtttg gtcccttgag cttatggtgg aaggagagaa 185160
atgacgcttg aactccacgc acatgccaca gcccacgcat gaatgtgtat acacacacac 185220
actaagtgga taaatgttaa aaataaataa atcaaaggaa tggccactca aaatctacca 185280
tcgttgggaa gggaggggaa aaggcaggcg agggagatag ataaccctga tatgaacacg 185340
gaaagagcca gtgtgccacc aaagctgccc agtgtgccac caaagctgcc cagtgtgcca 185400
ccaaagctgc ccagtgtgcc accaaagctg cccagacttg attacagatt tggccaggga 185460
cacaggaggc cagcaggagc agccaggttc cacctcagag gtggagccac aaacctggaa 185520
atgaaacgtc tttccctttc ttcagaccac agcagtgaca gctgtcctgc agagtctgga 185580
gggctggcag ggctcatcca ctctagtgtg cctgtggcca gaacaggcct cagtcacagg 185640
tgcttttcca aggtcttagt gtctaattaa ggttagcagc caaattggag agagaagggt 185700
gctggacttt actctgctgt aaggactttg ggcattgttc cattccgtga tcaaatacca 185760
ctggctctgc caaccaccat gtcagtgggt cttcagaggt agaagaactc atccttttttt 185820
gagaggtttg gtctggtcct tgtctaatgc aaaatgcctg gggcaccagg ttaatgtcaa 185880
ctcaaaggca agtgctggtc cagcatgtgt ggaatcctaa gttcaatacc catcagagcc 185940
ccaagcccta gaggacagac atgctttaaa aaaaagtcat gctttaaaaa aattctgttg 186000
agggggctgg agaaatagct cagcagttaa gagcactagc tgctctttca gaggacccag 186060
```

-continued attccgttcc taacattttc atggtggctc aaagctgtct ataattcaag tcctagaggg 186120
gaatctgttg ccctctctgg ttttctcagg caccaagaac acatgtggtg caaacataca 186180
cgcaggcaaa acactcatac atatgaaaca ttttttataa acctgctcgg atgtggtggc 186240
tcatgccagc gatgctctca gcactcagat ggcagaggca gggggatttt gtgttgagcc 186300
cagcctgagc tatagaatga gatgctgtct caaaaagaaa aaaaaaacaa aaaaaaacaa 186360
aaaacaaaaa caaatctgtg ggcttaatca ttcctagcca gaaggagctg gctccagcaa 186420
caatggatcc ctagagctct gctttgcccc ctggtctgga gagcttgctc tagaaaggaa 186480
ttctccatag accacatttc tattttgggg accactctgg gcctgcacat ggaaaaatgg 186540
agagttgagg tttacatggt catttttttt gttgttacag taatgagagc tttgaaatga 186600
tcacaaaagg aaaataggaa aatatgcctc ctaaaaagag ccgaggcaaa ttattatagc 186660
aaccgaatcc taaaaggaat gttcaagtaa aaaaaaaaaa atatggctca tgcgaagttg 186720
ttatggcaac tgacatttaa aagtaacagg atttgggcaa gtttctttct ccaccctctc 186780
tgcaaagtct tgcaggaact tcatgctaaa attatgcttt aattttaatt agccaaatag 186840
gtcataaata tagcttattc ccaaatcctt agaatttcta ccctgcaagg agctgaacta 186900
ctaatgagga aatatttcca caaaaaccca cttaccatta agaacccccca tccgatattt 186960
ttctaatata atttatcaat ttaaacacat tgcataatgt gccactctgt agcattccat 187020
taaaatgata aatagcaata gtggtgaggg gtgggggggca aaaaccagga gattaaacat 187080
atccaaagca gtgtagctat atttaaatac ctcaatccat tgtagaggaa aacacactgt 187140
tctcatccgc agatacagtc tagactcaga gcagcatatc cttgactgta agggtattaa 187200
taggacagac gaagggggc aataagaaat gacaggaaac ttcagaagaa ataaaatttc 187260
tattaggctt tgttataaga ttacatcaaa gcagttcata tgttttaatc tggggaggaa 187320
aaaaagcaac tacttggggt ttgcgcctgg gggctgcctc tgtgtactga accagacagt 187380
ttgcataatg aacaatttc attcaatcag gatctcagca gagatagctc ctactcaaag 187440
gaacccggca caggctcata gtttttatct cccagctcca cctgctggag aaaccttgta 187500
ttgcagggag agaaagcagt cgggaggcat tgtcctagtg gctgtgtacc taaagttaca 187560
gacctgactt taaacagttt ctctctggag gttgaaaggg gctctgtaag ataccagagt 187620
ggattgctct caaagactct cggactcctg ttacaggcaa gtaaggtcct agcagatggt 187680
agcatggatc tccggccctt ctcactgctt tcttgaatca gggatttaga aattgctatt 187740
tgcataccag gaggactgaa gtttggctcc cggtgaccag aggacaaggt cattgtttaa 187800
aaccacccaa actcatttcc gacttggttg gtcaaatttt caagtttccc agcagtctaa 187860
ggattcataa aataaggcag aggcagagaa acggagggtg tgtgtgtgtg tgtgtgtgtg 187920
tacccaaaat ggaactgcat tttcatgcac aatagaaaac ttaaagactg aaccaatcat 187980
tttggaaaac tggcacagct gacattggct agaggaagga acggccaggg cgagccagct 188040
gcaccaagac ccagggctga ggcctaatcc gcctttatcc gagggtttag tgaggctccc 188100
gccgctcacc aatcccggct ggagccgcag aagagctctc ttcacttggc tcagtcccag 188160
cacagtcgca ctatgctctc ccgtggggag gccgctccgg gagggggagc gacatcaagc 188220
tttgtgaaac tgttttcgaa aacctgggat gatcatttaa atgtttaaaa tatgcacatg 188280
gtaattcaaa actaattacc ctgagcacat ttgaaacatt tatgccatca tcttggatcc 188340
tgcctactga ttgtgcgctg cagctcactc tggtgtttct ataaactgct tcagcgattt 188400

-continued taacttccag gctaaatcag gcagccacag gcgctgcctc cagccctggg ttggtggaga 188460
gacccccatc cctgacttcc aggcgaggag gcggcccgtt tctccagaga gccgtttgtc 188520
agggtcttgt agttctggct gccgaattat tgctcttatc cgtgttcata attctcatct 188580
gcattattta atttaggcta gaatgacctc tttccctccc gagtcttcct ccctcattcc 188640
catttcctct tcttcaattc gtggccccca ttttctgatt ggtccaaata tatagacaaa 188700
tatccttgat cgtcccaccc cacttggcta catcttcatc tgggagccaa tgtggtgagt 188760
tttctgggtt tgcaaggtgg tcaggtccac cagtcatcct aaggtgtgtg agagaggtag 188820
accaacatga gcggcgcaca gccgccatca ctgagagagc acgtgccctg cagctcaggc 188880
acaggcatgc acacaccggc agacatgtgc acatgcgctt tccccagcaa accctgcttg 188940
cagagtaatt aggcctaggc agttcctgaa gcaaattcat ttcccccttt tccagaataa 189000
aatgagttct cttcctttgg gggtgctaaa ccagcatgcc agtggctaga agcctgagat 189060
gggtgatgtg gctgaaacca tttctgcagc caagcctgtg ggcagaagct aaccttgggc 189120
tggggagctg cagtcggaag aggcacaatt ctgggatcaa gaaatgagca ctggtttata 189180
ggtacactcc cagaaataga cagatgaggg ctgcctcctt attagcgctt tgaagatgcc 189240
catggcgggt ttttagacat ttaggaatat aaaagtaggt tggattccca cagtcagctg 189300
aagtttgaca gagtgatatt accgggttta actagagcca ttaagagact cttcattatc 189360
ccacaccacc gccacccaag ttatcacatg agccataatg caagagaatt ttcattccat 189420
caacaagaga gggagccggt ctatctttgt ccaaaggaaa tgagcagccc agcgtgaagc 189480
ttgtgaggaa ttgagtgtac aacactccaa taacatcccc tgcaggattg cctctgcgat 189540
ttagtcggtg aagcaggggt aactgcgctc gagcagtctg cctgtgtacc tggcttgcaa 189600
gaacaccagc tcgaggaaca ccaaaaaggc cgattaatga caaaggacac tcatagaggc 189660
ccgaattcca cagggcttaa gtattaagcc ccaaagaaat caaggtctag gccattctcc 189720
tggcgctcag caatctcatt tattatttct ctacaaagat ccaacactca atttcccagg 189780
tatcccctgt atctgactca cattctcctg ctcagtaagc catcctggtt tgaaacgggc 189840
ctcccctcct cctgcctatg catgctttgc gtcttcacaa cgacagctgg taatttgcaa 189900 gacccctcc actggactct ctcaccccac atacttggaa ctactccttg gaactacttg 189960
tttatcaagt gttctgttgg tgagccttct cttgcattaa agctgtgaga aggaaccaca 190020
gtttctattt cctttacatt tcttgtagcg tctcacatgg gagacaccca ggttagatat 190080
actgagggtc ctggtagttt tagagttgga gttagatgac ccagcaacat gccttccccc 190140
accacgcacc aagcaaaaat tgcacccacc cttccctcag atgttcctgg catcttataa 190200
ctcgcccaaa gccagattta ttgctcctgc tgtaaagtgt atcttctcta agcctcactt 190260
aaaagctacc acttggcaga agatcaagtc agaagtgcag gctagcaggt gacggtgagg 190320
acagggcggg atggggcggg tagggtggag cgaataattg aagctccaag agttaccagc 190380
tcaatattta acctaactgg taatttgctg tgacaattac gccatgaagg gaacgctgcg 190440
actatgcaag aatgttgctc tctaattaag agggctctgc atttcctagt cacccgcact 190500
ttaataacac acagaatgag ccttggctcc gggagctaaa ggttccatta ggagcacggg 190560
cagcatatgg ctgtgcacat aggccgtgag tgatgcagcc cagttaagcc cgctaacacc 190620
ttcaattcgt cctcagatag agcccagaga gcgcggctca ggccctcacg ccacgagccc 190680
catttgactg acaggcatct tcccggaaag cctgcgcgtg cctacactgc aaatggacct 190740
gcttcccaca gcccggcttt caaccaggaa ggcttggcgt gggtctgatc cttcaagagt 190800

-continued

```
aactttaata aggattttct cacagaaaga aaagtccatg ggaacaaatc ctcctcttaa 190860
gagcgtgaga caggaatggg gacacaagcc aacaccccaa ttgctaggct aactctgata 190920
tgagacaaaa gaatattaat atcttggcta tgaaggagga tggtgccatc ttctgaattg 190980
atgggagttt tgaggcatgg ctaagctggg caaaccattt tctttttttt ctcttcttaa 191040
ttagtggttc atttatggag ggcttgctgc ccggagagcc catcagaaga gagctcgctt 191100
tatggagatg tagcttataa aactactcag attttaaaca aacagtgcag gaggccagag 191160
gtagaagtgg tgggggtggg gtggggcaag agaacaattg catctgcaga aggctagccc 191220
tgcaccccaa gcctatgttt agggttgatc agcttcccga ggcaagccca gaagcctcta 191280
aaattttagg ccaatagaaa tgacctctgc accacggctg actgaagcta taaataagcc 191340
tcgagttgag cagtggtgtc aacggagaga gcagaggaaa gtccaatcag agcttcattt 191400
ttttttttta aagtccactt gcttgggact cacctgaagg cagggcattg agtagagcct 191460
tggctccctg cagcgagagg ctccagtttt cccaggcacc agcccatcgg ttggttacct 191520
aaccaccgaa agggaactgc acagcacaca agttaaatat aggctgggtt atctgcattt 191580
tacaagctct gagcaagcta tctgaagaag ctgtcatttt taatgacggc acaaacttcc 191640
aattaccgac tgggtaatcc actagggagc aggtagtttt ggaagaacag ttcaccatta 191700
ttaaaagttt acacaatcac ttttgagttg actataagta tttcacacga ggcaggtggg 191760
attagggact ttttgggtgg tttactcgag gctgcaacca acaatgagtg ttttctcaag 191820
aattatacat tgagatttgt caactgctgg ggagtagtgg agggtcctgg taatgcagaa 191880
aggttatgaa atggccaggt aaggttgggt gcttccaagt ctcaaatata ctcctaaggc 191940
cagctccaag tcataagctc aaacaagtct tcaaggggcc tggagagtta agacaaataa 192000
ggatcactta ggctacccac ggacaagcac ttctcataca aggaccggct acctccaaca 192060
ccatcttccc aacatggctt ctatgttgct tcaacaacca gggcagggtg aattaggggt 192120
gggtctctcc aatgtggact caaatcatga ctacagcntg gggttttttt tttttttttt 192180
tttttttttt tntttggttt ttcgagacag ggtttctcca tatagccctg gctgtcctgg 192240
aactcacttt gtagaccagg ctggcctcgg actcagaaac ccgcctgcct ctgcctctgc 192300
ctcctgagtg ctggaattaa aggtgtatgc taccacgccc ggccgagtcc gtcttgataa 192360
tgaagttccc agtgacctgg atgtcaactg aagttggatt ttactgtgat gactactgag 192420
tccggctcag aattttgggg ggacaaggta ccttgattta actgggcact acacgactgt 192480
aacccccaca ttgggagagg cagaggcaga ggcagaggca gaaagttggt tggaggctag 192540
gcaaggctac acagcaagaa gctgtctcaa aaccaaagac atctttcttg atccaaatcc 192600
tgtcggaggg tgtgaggcct tgggggccag aacaaggtgg tcaaggaaga ccactgactc 192660
tgtcctttgc tccattactt aatcagaatc gccatcacag atatagctag gagattttaa 192720
gccttggtgg ctgcaatctg catttaagag ctaagtggga taaactcagg ggtgggccca 192780
atgcctccct ccccaccctc cctgcatccc tccatttacc tgtttccagg gatctgctta 192840
atttacctgc cagcctttgg tgggacacag gcttagtggc ttagcgctgc tcggggcacc 192900
agagaccctc acagaagcac ctgaatgtac tttcagcgct gcagagcacg cacggctcag 192960
gcccatcaga agaacccagg cttatgctaa ggagccagaa agtagaagca gctggcaaga 193020
gtgattcagc cccataaatt tacacatccg tacagccaaa cccacttgaa gtgatccaga 193080
gccactttta ttgaaatag a aaagatgcct attctggagt gctaagtggt acaggagggt 193140
```

-continued gggtatataa gagataatcc catgttgtct ttgatgtggt gctagggaga taacccagga 193200
cctcacgcct gcctgcaagg tagccaccaa gccacaccca caacctctat ttatacacac 193260
actaagtgtg gaggtatgga taaaaaaaaa tgtcccaaga cctcacgaat ctgcaaacat 193320
ggtgcctggt tggtggcacc gtttggggag gcagtggacc atttggtctt gcaggaggaa 193380
gttatgtcac tgggtatggg ctttgagagt ttgtagcttt gctccccttc cagttaactc 193440
tgctctcgta aggttcctgc caccatgttt cctctgccat tatggacacc tggtcctcta 193500
gaactgtaag ccacttactc tcaggtctct ttcagtcctg gagtcttatc atagcaatga 193560
aaagtaactt gtgtggcagc cagctaagca agggctgtgg ccgactgctt gggattatgg 193620
ttgtgtctgt ctgtctgtct gtcattccat ttatatagtc ctgagaattg aaccacttta 193680
ccactgacat gtctcagtcc tcttggtatc atatattcac ttaagacaag atctcattaa 193740
gtcattcaga ctggttttga gcttgcaatc ctcctgcctc tgcctcaagg cgataggatc 193800
cctagggtac tcgaccagac tgggagtagc aggttctgtt ctcttagctt tctacagtga 193860
ttgtggatta tttgtgtata aagatctgat ggcccgaccg actcccttcc ctttaagtga 193920
acatcaacag tatttagcat caacttaata aactcatttg gtaaagccat ctccccacct 193980
cttgaacaaa tgaaaatcaa acagcagtac ctgttctcct agagcagcgg ctctcagcct 194040
tccggccttt taatacagtt cctcgtgttg cggtgacccc cccccccccc agccgtagaa 194100
ttatttcatt gcttaaccag agttaactgg aagggttaat aataaaacca gtctgggaga 194160
ctaaggttac ccaaccacgc taggaaggag aggaaagggc cactcgcaca aacctgtctt 194220
tgagatgaag aacaatcaac ataacaggga cagagcagtc cttgtaacaa gtgcaaagga 194280
gagagagagg ctgagtttct acttctataa ataaaccctt ggcaggcgga tcactaaagg 194340
aacacaagtc aatataaacc tttagacatg gggctgccaa acttcacttt tcgacagtat 194400
attaattatg tagtcaatag ccatgggttt cattagcgta ttaaatacca cgatcaatat 194460
tatttatact tttcgaagac aagccactca gggaaaaaat ggtgggggga ggaggaggaa 194520
caatttgacc ctgtagttca aaaaaagtca gaacagcaca ctagagatta gcaagggttt 194580
aatggaaggc ataaaacact ggaaatatgg acagaaatca gatccctgcc ttcatttttc 194640
tgccttttac aaagagactg gagggaattc agaaactatt taaaataaag gcaaaatgat 194700
tagagcccct ccctcccctc agctgcttaa cactggggtt gtggtggacg caaaataagc 194760
attgagctct aagtgataga tgagaatcag aacaggaaca gtgtttttga ggcaaaatat 194820
gtccaagaga attcaaagaa ctgtgggcca gaatctactt aggcagtcct ctgggacccg 194880
aatccctcac aggcgttaac agtggaacca atttccaagg cagccctgct ggtgatctga 194940
tttttgagta gggaaatctg ttaaacatcg tcccacgagg gagcccagct ctttcactcc 195000
ccacgggttt ctacatgcag ctgtgctaga tctgctgaag tggccggtga ggaggtgtgg 195060
ggattggttc agcgacctca gaggacattc ttgttcacta gccctcgtgc actggggcga 195120
tgaccgaatg ctgtgagcag gagatatcaa aggccggcta ctggactgaa aactagatca 195180
ccatctctaa cctgcaattt gtcaatctca gacagcaatg aagactgtga ttttctagtc 195240
aacgctttgt aagcaaggtc agatagaggc tccataaaaa ttgttcaggg ttcaggcaga 195300
gaatcaagtg taactcaatc cctatctcct gagattaggg aagggaagga aggctgtgtc 195360
tactaaacca gtgagcctca agcaaagcct gtctgttctc agcaaggtga gccacccacc 195420
aaagatgcca acagctaagg gccagggatg tagtgcaggg tgctgtgata tcaacagctg 195480
ggagacagaa acaggaggat caggacttca aggtagtttg ggctataaaa tataagcttg 195540

-continued aagctaccca cttgaagact gtccccaaca aaacaaacaa gctgggtatg gtggtcgatg 195600
cttgtatttc tagtgtatga gacgaaggaa gaaagctcaa gcccgagacc tgcttgggtt 195660
acatagggaa gatggtgcct caaaaacagg acagccgagg agcagacaga cagggcagac 195720
agggtgcatc gatctaaatc cacatacctg gatttaaagt aatatctggg agactggtct 195780
gtgagggccg ttccagagat ttaataaaga cccaccctga ctgagtatgg gcaacaccca 195840
tgggtggccc aggggtccag actgaataaa gggaaaatgg gaggaagttc agctggtagt 195900
gtttccaagt attaggacca cagcctggcc cctggcatgt gctggccagc tagtctagct 195960
ccagtatcaa gcttcaggcc agcggcaggg cactggacag ttcccacaca cgacacacac 196020
acacacagag cactagcatt cacctcctgg tctcttcttg acaacagata aaatgtaact 196080
ggctgccaca gtgagagtcc cctaccttcc tcaccgttaa ggatggtaca aactgtgagc 196140
cagcagcagc catttctcca gtaacttgct ttccacagat actgttatag cactaagaaa 196200
agcaactgaa acatggggtg ctgtgacccc ttggcaccac aaagccatgg caagctgaag 196260
tgcacacatc acaggccagg cctgaagatg ctgggggact gcaatgctgc ctggattctg 196320
gcagagatgt gcagcagatg ccaagaggtg ggctgcagca accagagata attaatatga 196380
ttaggaacac actgagcagg catgctcttg ccgaatgaaa agcctcgcag tgtaatgact 196440
gttttcttcc tcgatcacgg tctccacgtt tcagagttgg cttggtgtta ggctgccgcg 196500
taaacatcaa tccaaccccg aggggccaga tcatcggtgt tcctgggctc aatcgccttt 196560
ccttttgtgt tttcattcat ttaaagatgc attccagggt tgcaaacatt agtgagaatc 196620
atctccaggc ctcagtctaa tctctgagtc tgtaatgagt taacatcttt ccctagtgaa 196680
tatttattat gaaggctaat taattgcttt ccagttacaa gaatccttta cagtcaaaga 196740
aagtaggatc cacaaagata tactgtttat tcaaacaaag caaaggaaac aaagcttctt 196800
tcttaaattc tatttaacat agctttaata aaggtacaca ggtccgcctg gcaaccgaac 196860
ggtaactgat gcaaactgaa gccatgctct gtagcagcct ggatgtccca gtgccacctc 196920
tgtctgcagg ctttgtcgga tttactaaga ttctgttatc ttcaaacagg gattgtgtct 196980
caagtaactg accccactat gtggataatg aagtaaatta tgcaatttgg gggtttgctt 197040
ttccccaagg ggacagcaag ccagtgctta tcagccgtcc tcagaggaga caattctgat 197100
taatatcaga gtcatctgac tcagtctatt aaacctatca aaccctgaag gaaggatatt 197160
cagatattaa cgataggcct ttgattaata attctacctt gttgccattc taagcattaa 197220
caaccatgca gtaactctgc aaaacagacc ctttgattcc aggcagacgc accctctgaa 197280
cacctgggtt ctcccctact cttctccccc caggaggaac tcaagacaaa aaggtgccac 197340
cactggaaaa gcacactcca ggttacataa tttgcctcat tatccagagt ggggttaatg 197400
acttgtgaca taatttctgt ttgaagataa caaaatttca tgaaatccga caaagccgga 197460
aggcaggagg aggggactgc tgccacacta ccggtggctg agaactggag cggaaggttc 197520
acacacagcc ctctgagctc actgtctttg cttatcagtg agtcccaaga ggggcccaga 197580
tgggttgcca gcctccccta gaggatcttc attgtggagc tgtcccatgg ggcgggaagg 197640
aagccattct atttctgttc ttctctcttc cgttctggcc accagtggta cttgctccca 197700
tcacatgttc ttcctgatgt tcgcgatcag ccgtctgcca tagtctctga agtccacggg 197760
cttcacgtcc atcacagtgg ccttaattcg agattcatcc tttagaaaag agagaagctg 197820
tttgtgagtg gcagagcctg gcgtgcagcg gaagagagaa ctttctttgc ttcagtggct 197880

-continued

```
tcaatgagtc cagcaggaag aaggaaagtt tacaagtctc agagagaaag tgctgtgact 197940
tcctggagtt gggccagatc ctcttccaca gaccctttcc ccatcctagg tgccctgtgc 198000
tcagacctag catcctcccg gagaagcctc tgtctttcta tgggtgcagt gggggcccag 198060
agcagacagg taactcaccc taaagcatca ctttcatcta gaggagctct gtggtagtag 198120
ggactgaggc ttctgctcca gctctgggca aggttacttc tctgctcttc accattcctg 198180
tccatcccag gaagacagaa aatccctaca ctctcccttg atctacccga ctttctgaca 198240
ccagcctacc tatgttcatt taatacaaca actaaaatat ctattcacag gcactaagct 198300
ggtgataacg cagaatgcac aaactctgcg gctgcagggg agacggcaga gttcctcctc 198360
cacttgtctc cttgaactaa acagtgtctt tgaggcagaa cagggtgaca cctagggaca 198420
cacaagtcta gctgggggcc ttcatgcttc catgtgctta gtaattaatt actacatgca 198480
ccgctgttta caagtatggt taggagcccg actgcctggg ttggcctctc gcctctgcca 198540
ctccatggct ttaggttcag agtcattctc tgcatgcctc tgcctgtctc tccgttggta 198600
aagcttgcaa caacagctcc aacacagaaa gtgctgtgag ggtcgacagt ggatagatgg 198660
ctagatagat ggggcaggac ggactgtcca gtaagcaggg ttcatcatgg ctatgcagct 198720
ctggacatca ggattagttt aaacacttgt caggtggggc acttttacca gcacgtgcta 198780
tttgtttaat attctgagtt ttagaaccta aactgtggga aacaagagtc cacacataac 198840
annnnnnnnn nnnnnnnnnn nnnnnnnnnn nnnnnnnnnn nnnnnnnnnn nnnnnnnnnn 198900
nnnnnnnnnn nnnnnnnnnn nnnnnnnnnn nnnnnnnnnn ngccttgaac ttgcttctgc 198960
ctcctgctgg ggttacaggc ttgagccacc atgacagctt tagcaatagc tttgtaaatc 199020
cacagtgtca agctggatat gatggcacat gcttgcaata ctaacctcca aagattccct 199080
gaactcgagt tggtgaaata gtccaccagg taaaagagct tgctgcccaa gcctgaatct 199140
gattccctgg tcacatgctt taaggaaaga acttgccgaa gatgtcctct gagtgccacg 199200
tgtaccgatg catgcttgca gccacccaca cacccacaca agtgcactgt ctcacacagt 199260
gagaacagca agtgaacaaa caaacaagcc gggggggggg ggattgtgac cagaataatt 199320
gaggggggt gtaaagctct tggcaggtgg ctggctcctg gtaacactcc ataagtgggg 199380
aagttccaca tgtaaggtca tgtgatcgag tacatctggg cctccaacag tccttgnnga 199440
agaaacagat gcagtctgtc atatctaaac cattgttgtc gtatctctgg gtagtctttc 199500
ttttctcctt cctttctttt ttctctccct ttctctttta aaaaattatt tatttattat 199560
tatatctaag tacactgtag ctgtcttcaa acacaccaga agagggtgtc tgtcagatct 199620
cattatggat ggttgtgagc catcatgtgg ttgctgggat ttgaactcag gaccttcaga 199680
agaacagtca gtgctcttaa ccgctgagcc atctctccat cccccaaccc ctttctcttt 199740
tgagttaggt tttgtgtagc cctgggtggc gttaccttaa ctacactggc tttgaacttg 199800
caatgatact ctgcctgatc tgtcttaatc attttgagat agggactcac tacatagcct 199860
ttgctggtct ggaactaaca gagatctgcc tgtttctgcc ttgcaaatgc tgggaataaa 199920
gttatgtacc accacacctg gagtttaagg gttttttgtt tgtttgtttt tcgagacagg 199980
gtttctctgg gtagtcctgg ctgtcctgga actcgctctg tagaccaggc tggccttgaa 200040
ctcagaaatc cgcctgcctc tgcctcccaa gtgctgggat taaaggcgtg tgccaccacg 200100
cccagtttaa gggttttttt ttgtttgttt tttcctgaga cagggtttct ctgtgtagct 200160
ctggatgttc tggaactcac tctgtagagc aggttagcct tgaactcaga aatctgactg 200220
cctctgcctc ccaagtgctg ggattaaagg cgtgtgccat cactgcccag tgattttttt 200280
```

-continued tttttaatg tgtgtatttg tatgggtgtg tgggtgcttg tggaagccag gtgtcagatc 200340
cccagagcgg aagtgttctt aaccgctgaa ccatctctct tccctcttcc ctaactctga 200400
ttttaaaggc accaaactct taggtaggag actatacaca cacacacaca cacacacaca 200460
cacacccgta cacacccgta cacaccacat gaccatgcct gagcacacaa gtggttttat 200520
tgctggtctg gcctgtgtat gagctggaac caaaaccttt gtcgggagat ccgcagtctg 200580
cagtttgagc acaggctctc tggtttctgt tctctgtcct gtgtcgcatc ttgactagag 200640
gcagagaagc atctgcaagg ctgtgaccac gctggctggt gctctgccat ctacattttc 200700
aacaggaaat ctcaggagag tatttccttt taagaacgcc agacttttgt gcctgggcca 200760
cttctctact tcccagaaca ttgtgtgcca agtggcaagt tattaaccaa gtgctttgga 200820
aaattaaact ccttggtttg cagagtagca tgggagcatt gagagggtgt atgcctaaag 200880
gcctggttct gctgctggca gagctgacac ttggctaaag ggctggcatt tctgagatga 200940
gcctcactag atccgcgtct cagagtctgc aggagaaatc agagagggga gaaggtccag 201000
tggcctgttc aggatgatct tcctctgcat ttaagggcgg ctggtttgcc cacgtagccc 201060
cagaaccaaa cgagcctcgg acgaagcccc ctaaaggcag taggagagac tgagccttgg 201120
ctcttcagca ggggtgggga caagagcaag aggcgggatc tcgcccggcc ctttagagac 201180
acgtgcggtt gtttccgtgt ctgggagatc acatgacccg catcagctga cccgtcacgg 201240
tggagctcag cgctggtgct tcgcgctccc cgccctgctg cgccccggag cgcaggaccc 201300
tgcggagggg taagaaaacc cccaggcttt ctttcctttg tcgctggttc gcgcagtcac 201360
ctgcacccta ccccccgctc ctcgttcatc ccagtcttcc cggcctggca ccccggaagc 201420
cactgcgagg agggccgtgg ccaggctcag ccttgcgctg cccccaggcg gccaggacca 201480
aatggcccag gggagcagaa ggcggaaagt ggttcttaca gcagggtccg agggctggtc 201540
cccttcctca ggacctgaca tggaggagct gctccggagc gtggagagag atctgaacat 201600
tgatgcccgg cagctggccc tggcgccggg gggcactcat gtagtggccc tagtgtccac 201660
gcgttggctg gctagtctcc gggagcgccg actgggaccc tgtccccggg ctgagggcct 201720
gggtgaagca gaagtcagga ctttactgca acgttcggta cagaggctgc ccccaggctg 201780
gactcgagtg gaggtgcatg ggctgcggaa acggagactg tcctacccgc tgggtggagg 201840
cgtgcccttt gaggaggggt cctgtagccc tgaaactctc actcggttca tgcaggaggt 201900
ggctgcccag aattaccgga acctgtggcg ccatgcatac cacacttatg gacagcctta 201960
cagccacagc actgcccccct cagctctacc tgccctagac tctatacgac aagctctcca 202020
gagggtgtat ggatgcacct tcttgccagt gggtgaatcc atcccatgtc tatcaaatgt 202080
cagggatggg ccctgcccct ctcggggcag ccctgcctgc cccagccttt tgcgagctga 202140
ggctttgctg gagtcgcccg agatgctcta tgtggtacac ccttatgtgc aattctccct 202200
gcatgatgta gttaccttca gccctgccaa gctgaccaac agccaagcca aggtgctctt 202260
tcttctcttc cgtgttctga gggccatgga tgcctgtcac cgccaggggc tggcctgtgg 202320
ggctctgtct ttgcaccaca ttgctgtaga cgagaagcta tgcagtgagc tccggctgga 202380
cctgagcgct tacgagatgc cttccgagga tgaaaaccag gagggctctg aagagaaaaa 202440
tgggacaggc attaagtctg aaaaagaggg ggaagggaga actgagtgtc ccacctgcca 202500
gaaagaactt cggggccttg tgctagactg ggtccatggc cgaatcagca acttccacta 202560
cctcatgcag ctgaatcggt tggcaggtcg acggcagggg gatcccaact atcacccagt 202620

-continued gctgccctgg gtggtggact ttaccacacc ttatgggcgc ttccgagacc ttcgtaaatc 202680
caagttccga ctcaacaagg gagataagca attggacttc acctatgaga tgacccggca 202740
ggcatttgtt gcaggtggtg caggaagtgg ggagccaccc catgttcctc accacatctc 202800
tgacgtgctc tctgacatca cgtactatgt atacaaggcc cgtcgcacac cgcgctcggt 202860
gctctgtgga catgtccgag cgcagtggga accccacgag tatcctgcca ccatggagcg 202920
gatgcagacc tggacaccgg atgagtgcat acccgagttc tacacggacc cctctatctt 202980
ttgctctatc caccctgaca tgcccgacct ggatgtgccg gcctggtgca gttctaacca 203040
ggaatttgtg gctgcccatc gagccctcct ggagagctgg gaggtgtccc aagacctgca 203100
tcactggatt gatcttacct ttggctacaa actccagggc aaagaagctg tgaaggagaa 203160
gaatgtgtgt ctgcacctgg tggacgctca cacccatctg accagctatg gcgtggtaca 203220
gctatttgat cagccacacc cccaacgcct ggctggatct cctgccctgg cccctgaacc 203280
tccactcatc ccccggctgt tggtccagcc tattcgggag gccacaggcc aggaggacat 203340
ttcaggacaa cttataaatg gtgcgggcag gcttgtcgta gaggccactc catgtgagac 203400
tggctggact agagataggc ctgggacagg agaagatgat ttagaacagg ctacagaagc 203460
tctggattcc atctccctcc ccgggaaagc aggtgaccag ccaggctctt cctccagtca 203520
agcatcacct ggcctgttgt ctttttctgc accctcgggg tctcgaccag gccgtaggag 203580
caaagctgcc gggttggacc ctggggaggg tgaagagggc aagattgtcc ttccagaggg 203640
cttcagtccc atacaggcct tggaagagct ggagaaagtg ggtaacttcc tggccaaagg 203700
cctagggagc cagttggagg agcctgaaaa gcctcacgcc cagccacctg tgcacctgca 203760
gagcctcttc catcgagaca tgcaggtcct gggtgtcctg ttggctgaga tggtgtttgc 203820
caccagggtc cggatactgc agcctgatgc acctttgtgg gtacgctttg aggctgttcg 203880
gggtctctgc atacgccact ccaaggacat ccccgtgtct ctgcagcctg tgctagacac 203940
actcctacag ctgagcggac ccaaaagtcc catggtgtcg aagaagggca agctagaccc 204000
actgtttgag tataggccgg tttcccaggg attacccccca cccagcccag cccagctcct 204060
cagccccttc agctccgtgg tccccttccc tccatacttc ccagcactgc acaagttcat 204120
tcttttatat caggcccggc gtgtggagga tgaggtccag ggtcgggagc tggcgtttgc 204180
tctgtggcag cagctgggtg cggtgttaaa tgacatcact cccgagggct tagagatcct 204240
cctgcctttc gtgctgtcgc tcatgtctga ggagcacacg gctgtgtaca cagcctggta 204300
cctatttgaa cccgttgcca aggccctggg ccccaaaaat gccaacaagt acctcctgaa 204360
gcctctcatc ggtgcctatg agagcccctg ccgcctgcat ggccgcttct acctgtacac 204420
cgactgtttt gtggcccagt tggtggtgcg gctgggcttg caggccttcc tcacccacct 204480
gctgccccat gtcctccagg tactggctgg ggtggaggct tcccaggagg agggcaaagg 204540
cctggtcggg accactgagg atgaggaaag tgagctcccg gtgtccgggc ctggctcctg 204600
tgcctttggg gaagagattc agatggatgg gcagccggct gcttcctcag gactggggct 204660
cccagactac aggtcgggcg tcagcttcca tgaccaggcc gacctgccgg acacggagga 204720
cttccaagct ggactctacg tggctgaatc tccacagccc caggaggctg aggccgtgag 204780
cctgggccag ctgagtgata agagcagtac cagcgaagcc tcccagggcg aggagagggg 204840
tggggatgat ggcggtgccc ctgcggacaa gaacagcgtc aagtcagggg acagcagcca 204900
ggacttgaag cagagcgaag gctctgagga agaggaggag gaggaaggct gtgtggtgtt 204960
ggaggaggac caggaggatg aagtcacggg aacatccgag ctcactctgt ctgacacgat 205020

-continued gctgtccatg gagacggtgg tggctcctgg tgatgggaga gacagagaag aggaagagga 205080
gccgctgaca gagcagacag aaggcaaaga acaaaagatc ctccttggtg agcccgtggg 205140
ctgagggggc atgggtcagg tgcttttcct tcaggctctc atatgctggg tgtgggtcca 205200
accagatcca ctgtagcacg cacagccaca gtcagacaca gtgcatggaa tgtggaagtg 205260
ctgtgtgtga gtggaaagtg gggcttagat ttagctttca ggagacagaa agctccttta 205320
aaagccatac cttgggctga ggctgggagt ggagttgagt ggtagagcac ttgtctggta 205380
tactcgaggg ccctgggtgt cttatctcta gccccagaag aagtattaag aaataaaagc 205440
aagtggtggt tgagatgtga atggagccag aactggccgg aacagtcggg tggaagtggg 205500
aagagtgttc cagacaggga acagtgtgtg tgtacctctg aggctctcat ggttccatca 205560
gagaggcagg gaaaggctaa aatggttttc ttaagagagt ccagaagggc tgggcttggt 205620
ggtgcaggcc tttaatccca gcactcagga ggcagaggca ggcggatttt tgagttcgag 205680
gccagcctgg tctacaaagt gagttccagg acagccaggg ctatacagag aaaccctgtc 205740
tcgaaaaaaa aaaaaaaaaa aaagagtgta gaagggtgga agccagggac aagtctgtac 205800
aagaaggaac ttgggagcat tgccgaaagg atgacctctc tgcaggtcct gcccgaggag 205860
ccagtttctg gggaccttga ccatggctag gtgaatggac ccaggatggg atggtcaggc 205920
ttgctagcag agccacagcc gagttggctg ggtggggtgg ggtggggtgg gaagggtgag 205980
ttatctgatg agctcaggac cttttcctgc cctgcagata cagcctgcaa gatggtccgc 206040
tggctgtctg ccaagcttgg ccccacagta gcctctcgcc atgtggcccg gaacctgctg 206100
cgcctgctga catcttgtta tgttggtaag gtctgtggtt agtgctggag accaggttcc 206160
ccagccaggc ttctgcccat ccttagccct ctctaggcga ctccttccct aacttcccag 206220
cactccctga gcagggcctg ggtctcaccc attaagctgg gttttcttgg gtaagtgggg 206280
aagagcccag tattgaatga atagaagcca ccccacagtc tcagaaggcc ggcttccctc 206340
ctgccctcca ctggcttctc aacgctgctg cccttccttg gtagggccca ctcgacagca 206400
gttcaccgtc agcagtgatg acacccctcc actgaatgcc ggcaacatct accagaagag 206460
gccagtccta ggtgacatcg tgtcggggcc tgtgctcagc tgcctcctcc acattgccta 206520
cctgtatgga gaacccgttc tcacctacca gtacctgccc tacatcagct acctggtcag 206580
tccctggttc gtcaaacccc ggcttggggg tgggggcaag gatccaagga ccagccccag 206640
gtcttggggg ttccaggagg tctgtggggt gacctgtccc tccctcatct attctgtggt 206700
tctaggtagc cccagggagc aactcaaacc ccagccgact gaacagccgc aaggaggccg 206760
ggctgctggc agcggtgaca ctgacgcaga aaatcatcgt atacctctct gacacgaccc 206820
tcatggacat tctgccccgc attagccacg aggtcttgct gcctgtgctt ggcttcctca 206880
cctccttcgt cacagggtag gcccctgctg cttgggagag ccacctggct gagggggccc 206940
ccaggaaggg ctaggaagct cagggagaag cagataccgg cctgagtcat ggttctgatg 207000
ttgggggtag tggcacaggt ctttcattcc agcacccaga ggagggcaag tttctgtgag 207060
tctgagacta gcctggtcta cagagagagc tccaggctat ctaaggctcc atagtaagac 207120
tctgacttaa gaaaagagtc gtggttcatt ctgggttgtg ggtgtggctt ggtgatggga 207180
cactttccca gcatgcagga ggagctatgc ttgagttcca gcccttcaga aaaacaaaaa 207240
tgggggctgg aaagaatagc tcagggttta agagcactgg ttgctcttcc agaggatcca 207300
ggttagattc ccagctgcca catggtagct cataaccatc cggcagttct atggaacctg 207360

-continued ccaccctcct tcggtctctg tgggcactgc aaacatgtgc acagacatac atgcaggcag 207420
aaaaaacacc catacacata aaattagacc aaaaaagttc atgttctctc ctacctgtag 207480
ctctgactaa gctacactgc ttccctgtgc ctcagtttcc tcccctggtc tggactgatc 207540
agccttacat gcagctcctg ttatttgaag ttcctggtaa attggtcaag tccttcaggg 207600
aagggctggg aactcttgca ctttgattct aggttcccca gtggggccca ggcccggact 207660
gtcctatgcg tgaaaaccat cagtctcatc gccctcatct gcttgcgcat cgggcaggag 207720
atggtccagc agcacctgag tgagccagtg gccaccttct tccaagtctt ctctcatctg 207780
catgagcttc ggcagcaggt aggcaggcag cttctgggct gggtgggcca ggccaggcca 207840
ggccaggcca gggcagtgga cccactgaat ctgtggtctt cctacccgca ggatctgcca 207900
ctggatccta agggctgtac tgagggccag ctgccagagg cgaccttctc tgatgggcag 207960
cgacgaccag tggaccccac cctgctggaa gagctgcaga aggtgttcac cctggaaatg 208020
gcgtacacaa tctacgtacc tttctcctgc ctgttgggta ttgcccatca cgttcctttg 208080
cacagagttg gtgactacat ctcttccctg gggtgggccc cgatgctttc acctccagag 208140
tcagcaatgg aatcttttta tttttatttt gacatggggt ctcatttagc ccaggctgac 208200
ctttaactcc agctccttcc agcttccacc gtctcctgtt ggcattgtag tcatgtggca 208260
ttgctcaggc ttcttncatg ttcttatttt taaatgacct gtgtgtgtgt gtgatatctg 208320
tgtgagtgtg gaggtgacag aataacagtt ggggggtcag cagatgcctt gcctgatgag 208380
catctctcta gatccagttt ttggttttgt gggcttttat gtgtgtgttt gtttgtctgt 208440
ttttgtagac agggtctctc tgtgtagcct ggccatcctg gaactcattc agtagaccaa 208500
gctggccttg agctcacaga gattcacctg cctctgcctc ccagtgctgg gattaaaggc 208560
gtgtaccact cctgcctggc tttgtttttg ttaaccacca tcctcctgcc tcagcatctg 208620
cctcccctgt gctgggatta caggtgtgtg ctatcacacc cagctaacag tggatttaaa 208680
cgtaggaatt ttaggatcag agtgaccaga tttggtccta gggcccaatt tccacagtga 208740
ttatctatct tagttaggat ctctgttgaa aatcatggtg gaacatcatt accaaatgca 208800
acttggggag gaaaaggttt attttgtctg acaactctca ggtcaccaag ggaagtcagg 208860
gcaggaactc gaggcagaag ctgaagcaaa agccatggaa gaactctggc ttgttcctca 208920
tggcttgctc agtctggtgt accccctccc cacccacctc cccacaatgg tttctctgct 208980
tatgcctggc tgtcctagaa ctcactctgt agactaggct ggcctcaaac tcaagagatc 209040
cccctgcctc tgcatctcaa gtgctaagat taaaggcggg tgccatcacc cctgccccag 209100
gggtggcact acccactgta aattggtccc ttcccatatc agttgttaaa taagaaaact 209160
cctccatagg ccaatctggt gggggaattt tctcagttga gggtttctct tctcaaatga 209220
ctgtagctga tgccaaattg ataaaacaaa tctcaaacca ccaccaccaa caacaataaa 209280
accaaacaaa ccaaacaact aaccaagaca gtgacttata aagagaatct gaacattttc 209340
cagcaggaaa ggctcaggag ctggccattc aagtctgggg aacagaatgt aggggaatat 209400
gatggtctcc agaagctacc tgcaaaggaa tgaacagctt gctgggtttt gtggcttccc 209460
ttatgggatg ggcgctgtac tgggcttctc tctgagtagg atgggccacc ctgtagttgg 209520
gaatattttg ctcctacaga attgtaagtt cccagaggca ggacacatct gtcttattct 209580
tcattgtgtg tctgatgcta gaatggtgcc tggcatacac gtgtgtgtct ctatagagac 209640
agcactcatg tctacgtatc gataaaggaa gctgttttgg ggggaggaaa caggcttaca 209700
gacgagaact taataaccca gagtagccca gtcagtacct tgccttggct tctgttgttt 209760

-continued ctaagctctg ggtagatagc taccttgcca tcttccctga tcttagaact ttccccactc 209820
ccctgtaggt gacatcatcc ggaaaatcat ccccaaccat gagttggtcg gggagctggc 209880
agggctctat ctggaaagca tgagcccgag ctctcgaaac ccagccagca tggaacccac 209940
catggctagt gccggccctg aatgggaccc tcagagtggg agctgtctcc aggacgatgg 210000
ccactcaggg acctttggga gtgtcctggt tggaaatcgc atccagatcc ctgactctca 210060
gccccagagt cctgggccac tgggctccct ctctggagtg ggtagtagcg gaggcctcag 210120
caacaggaat gaagacaacg ccctgaagcg ggagctgcct cggagtgccc atgggctgag 210180
cgggaactgg ctggcgtact ggcagtacga gatcggtgtg agccagcagg atgcccactt 210240
ccacttccac cagatccgcc tgcagagctt cccagggcac acgggggccg tcaaatgcgt 210300
ggccgccctg agcagtgaag acttctttct gagtggcagc aaggaccgga ctgtgcgcct 210360
ctggccgctg tacaactatg ggacgggcac caatgagacg gcttcccgcc tcatctatgc 210420
ccagcaccgc aaaagcgtct tctacgtggg ccagcttgag gccccgcagt atgtggtgag 210480
ctgtgatggg gcagtgcacg tctgggaccc cttcacaggt gagcgggccc aggtgaggcc 210540
tgttcgacgg ctgctttact gtgccttagc caggcctctg ggaacgggac ctagtgcgaa 210600
acgtacaatg gcgtattttg acggggaaga ttcagtgagg caggaagaga agaagagtca 210660
ggacttagaa tctgtgggac ccaagtttga atccactccc ccaacttacc agcaatcggc 210720
tcagttgctg caggcgtctg ccttctacct gtaagaacca aaaatttaga agattccacg 210780
agtatggctt tggcttcttg tacgacgtca cctgtcgtcg ttgtaaagag aagtatcgag 210840
tggaggaggg tcagggcaga cggaggtcgc agctagttag agcatgctat gtgaagagag 210900
cagactgttc tggggctgga cccttgactt cactgtggaa gcagcaagat gagaaagccc 210960
tgagattgtg ttttctgagg gtcactgggg aatgggatgc aggtgtgggg tgagttggag 211020
tttgaagtag ccagggctct ttgatagcca ctaagtcccc agatgtgtcc tttttcagga 211080
aagacccttc gcacagtgga tccttcagac agccgggtgc ccctgacggc tgtggctgtc 211140
atgcctgccc cacacaccag catcaccatg gccagctccg actccactct gcgctttgtg 211200
gactgcagga agccaggctt gcaggtcagg aggggtgcag ttcctgggct actgggggtc 211260
tctaggtacc agtcaggaaa gacactcagg ggactccacc aggaacgctg cagtgacagg 211320
cagccctgtg tgggtggggc gctggcacgg atggggcttt tctcttccgg ggatggagtg 211380
ggagggtcag gcctactggt ttcgtgggcc tgaatggggt gagctgcagt agggtgggtg 211440
gcagtgatgg atggcgacgg gcacttgaac acaatctcct cctatagcat gagttccgac 211500
tgggtggagg gctgaaccct gggcttgttc gctcgttggc cgtcagcccc agtggccgga 211560
gtgttgtggc tggcttctcc tcgggcttca tggtgctcct agatacccgc acgggcctgg 211620
ttctacgagg ctggccagcc catgaagggg acattctaca gatcaaggtg actgactgcc 211680
tgaggtccta tcctttcatt tctacttagg gcctggtctg ggagaggaca ggtttatgct 211740
ggtgtccctt ataactactc ggggacattc agtggggtgg gaaaatggcc ctcgtaggcc 211800
agctcaggaa ccagctgcac aggaggcagg ctaggggcag gaatcagggc tagaactgac 211860
cctgatgctc cacagcgatg ttctaatgag taacccttgt ccatatttgt cttgcttgga 211920
ggatcagggg tcacgccctg tccgtgaccc agttcaggtt aaataaagcc aggaggctgt 211980
ttactgcctg gagaccactg agcagagtcc atgccccctg ctgggctgtc ctgatggggg 212040
gcaggaacag gcgcaggcct gcgcatcgtg ttcctgcctc ctatattcaa tcatagacct 212100

-continued cagagctcag caggttctgg gaggggagaa atagggctgc ttgtgggagg atttctccct 212160
gcagtgggaa ctctcctccc ccgccgtcca gatggaggtg aaagacaggc actgttgctt 212220
acagggaagg caggctgccc ccagctctat ccaggacccc aggggaccct gggtctcagt 212280
gtctctaaat cccaacattc taagaaagtg tcaggatggc tctggggtca tcctgggtgt 212340
tagtcccagc tctcggagtc ttctctgagc accagttctt ttcctatggg aagtaaggac 212400
atgccaggtg ttctttgaga ggacctgagt ttggttctca gcactgtcta gctctggctc 212460
cagggggttc aacacccttt atggcttctg tggacacata ttcttatgtg gcctgcacgc 212520
acacacacga acacaaataa aaataaatgt taaaagaaga cagcggcacc ttgtacctca 212580
catgttagta cgattggatg tggcagtgcc tcacagaatc tgtgggactt tatttattta 212640
tttatttttt ggtcttaaaa ttttaaaaga ttggtttagg agtggtggta cacaccatta 212700
atcgcaacac tcaggagcag aggcaggtgg atctctatgg gtttgaggcc agcctggtct 212760
acagagcaag tttcagggca gccaaggtta cacagagaaa ctctttctca aaaaataaaa 212820
acaaaatatt taaaagattt acttacttct tatttgagct aggatctccc tattagccct 212880
ggctgtcctg gaactcactg tatagaccag gctggcacct taaactcacg aagatcctcc 212940
tgcttctgcc tcctaagtgc tgagattaaa gtagtgttat accatgcccc actattttct 213000
ttatagattt ggtgttttgc ctgcttgtgt atatatgcac taccttcatg cagtgctaat 213060
aggggtcaga ggcgagtatc agctcttcct ggaactagag ttatggaagg ttgggagtca 213120
ccatgctggg actgggtcat ttgcaagagt tacaagtact tctgagccat ctccagcccc 213180
ctagagtttt tttcccccct ggctgtcctg aagtagaatc tgttcttgtt ttgttttgtt 213240
tttcgagaca gggtttctct acataggcct ggctgtcctg gaactcactc tgtagaccag 213300
gctggcctcg aactcagaaa tccgcctgcc tctggctctc agaatactgg aattaaaggt 213360
gtgcgccacc acgcctggct cagaatctgt ttttaaatga gagtaatagt tacaggtttt 213420
ttgttttgtt tttttctttt cttttttgt ttttgtttt tggctcattt gttttatttg 213480
ttttgagaca ggtctcactc tgaaccccta ggtggcctgg agcttgctat gtagaacaca 213540
ctgactttaa acttgttttc tgagtgctgg atttatgggc ttgtgctatt ttgcccagcc 213600
tctgatggtt gttaataaca atattattta gcttttcttt tggagatagg ctctcactgt 213660
atatcaccca gacagtggct ggtctggaaa tcactgtgta ggccaggctg accttgaatt 213720
cacagagatc tgcctcccga gttcagaaat taaaagcact ctgggatggt tttggagttt 213780
ggtgagtacc caagcctcca ttgatgctat ctgtccctcc cgctctctgc aggctgtaga 213840
gggcagcgtg ctcatcagct cctcttccga ccattccttg actgtttgga aggagctgga 213900
acagaagccc acgcaccact acaagtcagc gtccgaccca atccacacct ttgacctgta 213960
cggcagcgag gtggtcaccg gcactgtagc caacaagatt ggtgtctgtt ccctgcttga 214020
gccaccctct caggccacca caaagctcag ttccgagaac ttccgtggca cgctcactag 214080
tctggctttg ctgcccacga aacgccacct cctgctgggc tcggacaatg gcatcatccg 214140
cctcctggca tagggccagc caggagttgg ctgagggcag ggcgagatga catctctcag 214200
ggcccgctcc tcattcttga tctcgaagcc gattcttcta ggcaagcccc aggctctggc 214260
tacccacatg gcctgctgtc tgggattgca cagctcctga atctccaaag ccttgaagtg 214320
gcttcatgaa actcgggaga tactgttcct aaccagcaag aattggggca aggaaagcac 214380
tgtgatcccc attgctcccc agttctgcct tctggattca catggggaca gggcagctcc 214440
aggaaatgaa aggagttggg cctttgctca gccagcttcc tctagccacg ctctccttag 214500

-continued

```
ctctgtttct cccttgggta ggaaactgct cctgtctagg gttctgatgg tactgggact 214560
ccaggctcag gagggctggc caggacctac gactttcagg gcttggtctg gggttttagc 214620
attcattcag ccaggtcttc agtatgggac cagaaaaaag gggatgtgag aacagggcta 214680
gggaaggggt tatatgggcc cagctggtcc aggaatgaat ccatgccttg ccttggtacc 214740
cctaaccaca gcgtttgtgc cttcagccgg ggaggcagcc cttgggacca gcatccctag 214800
ggacaggagg cagcgggaat catctctgta tctcgggttc tgcccagggg atgggcagac 214860
tctgccatct cttgagtgtt cgtttggaga agcctgagat gtggccccctg ctgccttctc 214920
actagttgca gtctatgtaa ataaggtcaa taaattcttt ggaagagcca cggagctgag 214980
tgaggctgtg ttgtgttttg ctttgcctag gctgggctca ggcagctctg cctcagcctc 215040
ccaaggagct ggggaactgg tatatgtcac tgtatatgtc actgtgcctg gcttatggct 215100
tggcttggct ttttttcaga tggtctcaag tgcctcaggt tggccttgat cttgggatga 215160
ccttcctgct tgaaacagag tagtgggctt ataggcatga cccaccaggt ccaattttta 215220
ttttttaaag gcattgattt ttatacgtgt atggttgttt tgcccacttg tacatatgca 215280
caccatactt gtgtctggtc cctgcggagg tcagaagagg gcatcgggat cacctggaac 215340
cgaagttaat gaatggttat gagccacatc tcgatgctga agattgaacc tggatccttt 215400
gcaagagcag ccagtgttct tacccactga gccatctcta agccccacac ccagcttctt 215460
ttgatacaag gtctggtagc tcaaacttga tatgcagccg aggaggttga cctggtattc 215520
cctacctacc ctcttctctc taccttccaa gtgctgatat tatacatagg catggatagt 215580
catgcccacc agtttgcctt gatggcacca gagtcaggaa agtccaaacc tggtagttgc 215640
aaacacagca agagggtaga ggcagccatt gtcctctggc tgccttggat acagagcttc 215700
tgggttgggt ggccttgggt cagttttccg aatggttcac ccttggggaa agggaacact 215760
gctgaagagg tgggaccctg ggagggccgg cctccagctg ggtctctcca gccctcgcct 215820
tggaacctag gctggaggga gccaaccagg atcctggact tgctacagtt aggtgaacag 215880
gctcctgcag cctccccttc ccttgggtag ctgtggtggt ggtggtggtg gtggtggtgg 215940
tggtggtggt ggtggtggtg gtgggggggg gggngnngnt                       215980
```

```
<210> SEQ ID NO 17
<211> LENGTH: 473
<212> TYPE: PRT
<213> ORGANISM: Mus sp.

<400> SEQUENCE: 17

Met Lys Arg Ala Ser Ser Gly Gly Ser Arg Leu Leu Ala Trp Val Leu
  1               5                  10                  15

Trp Leu Gln Ala Trp Arg Val Ala Thr Pro Cys Pro Gly Ala Cys Val
             20                  25                  30

Cys Tyr Asn Glu Pro Lys Val Thr Thr Ser Cys Pro Gln Gln Gly Leu
         35                  40                  45

Gln Ala Val Pro Thr Gly Ile Pro Ala Ser Ser Gln Arg Ile Phe Leu
     50                  55                  60

His Gly Asn Arg Ile Ser His Val Pro Ala Ala Ser Phe Gln Ser Cys
 65                  70                  75                  80

Arg Asn Leu Thr Ile Leu Trp Leu His Ser Asn Ala Leu Ala Arg Ile
                 85                  90                  95

Asp Ala Ala Ala Phe Thr Gly Leu Thr Leu Leu Glu Gln Leu Asp Leu
            100                 105                 110
```

-continued

Ser Asp Asn Ala Gln Leu His Val Val Asp Pro Thr Thr Phe His Gly
115 120 125

Leu Gly His Leu His Thr Leu His Leu Asp Arg Cys Gly Leu Arg Glu
130 135 140

Leu Gly Pro Gly Leu Phe Arg Gly Leu Ala Ala Leu Gln Tyr Leu Tyr
145 150 155 160

Leu Gln Asp Asn Asn Leu Gln Ala Leu Pro Asp Asn Thr Phe Arg Asp
165 170 175

Leu Gly Asn Leu Thr His Leu Phe Leu His Gly Asn Arg Ile Pro Ser
180 185 190

Val Pro Glu His Ala Phe Arg Gly Leu His Ser Leu Asp Arg Leu Leu
195 200 205

Leu His Gln Asn His Val Ala Arg Val His Pro His Ala Phe Arg Asp
210 215 220

Leu Gly Arg Leu Met Thr Leu Tyr Leu Phe Ala Asn Asn Leu Ser Met
225 230 235 240

Leu Pro Ala Glu Val Leu Met Pro Leu Arg Ser Leu Gln Tyr Leu Arg
245 250 255

Leu Asn Asp Asn Pro Trp Val Cys Asp Cys Arg Ala Arg Pro Leu Trp
260 265 270

Ala Trp Leu Gln Lys Phe Arg Gly Ser Ser Ser Glu Val Pro Cys Asn
275 280 285

Leu Pro Gln Arg Leu Ala Asp Arg Asp Leu Lys Arg Leu Ala Ala Ser
290 295 300

Asp Leu Glu Gly Cys Ala Val Ala Ser Gly Pro Phe Arg Pro Ile Gln
305 310 315 320

Thr Ser Gln Leu Thr Asp Glu Glu Leu Leu Ser Leu Pro Lys Cys Cys
325 330 335

Gln Pro Asp Ala Ala Asp Lys Ala Ser Val Leu Glu Pro Gly Arg Pro
340 345 350

Ala Ser Ala Gly Asn Ala Leu Lys Gly Arg Val Pro Pro Gly Asp Thr
355 360 365

Pro Pro Gly Asn Gly Ser Gly Pro Arg His Ile Asn Asp Ser Pro Phe
370 375 380

Gly Thr Leu Pro Ser Ser Ala Glu Pro Pro Leu Thr Ala Leu Arg Pro
385 390 395 400

Gly Gly Ser Glu Pro Pro Gly Leu Pro Thr Thr Gly Pro Arg Arg Arg
405 410 415

Pro Gly Cys Ser Arg Lys Asn Arg Thr Arg Ser His Cys Arg Leu Gly
420 425 430

Gln Ala Gly Ser Gly Ala Ser Gly Thr Gly Asp Ala Glu Gly Ser Gly
435 440 445

Ala Leu Pro Ala Leu Ala Cys Ser Leu Ala Pro Leu Gly Leu Ala Leu
450 455 460

Val Leu Trp Thr Val Leu Gly Pro Cys
465 470

<210> SEQ ID NO 18
<211> LENGTH: 283
<212> TYPE: PRT
<213> ORGANISM: Artificial Sequence
<220> FEATURE:
<223> OTHER INFORMATION: Description of Artificial Sequence: Consensus
sequence
<220> FEATURE:

-continued

<221> NAME/KEY: MOD_RES
<222> LOCATION: (3)..(4)
<223> OTHER INFORMATION: Variable amino acid or not present
<220> FEATURE:
<221> NAME/KEY: MOD_RES
<222> LOCATION: (6)
<223> OTHER INFORMATION: Variable amino acid or not present
<220> FEATURE:
<221> NAME/KEY: MOD_RES
<222> LOCATION: (9)..(10)
<223> OTHER INFORMATION: Variable amino acid or not present
<220> FEATURE:
<221> NAME/KEY: MOD_RES
<222> LOCATION: (12)..(13)
<223> OTHER INFORMATION: Variable amino acid or not present
<220> FEATURE:
<221> NAME/KEY: MOD_RES
<222> LOCATION: (15)
<223> OTHER INFORMATION: Variable amino acid or not present
<220> FEATURE:
<221> NAME/KEY: MOD_RES
<222> LOCATION: (18)..(25)
<223> OTHER INFORMATION: Variable amino acid or not present
<220> FEATURE:
<221> NAME/KEY: MOD_RES
<222> LOCATION: (27)..(29)
<223> OTHER INFORMATION: Variable amino acid or not present
<220> FEATURE:
<221> NAME/KEY: MOD_RES
<222> LOCATION: (31)..(34)
<223> OTHER INFORMATION: Variable amino acid or not present
<220> FEATURE:
<221> NAME/KEY: MOD_RES
<222> LOCATION: (36)
<223> OTHER INFORMATION: Variable amino acid or not present
<220> FEATURE:
<221> NAME/KEY: MOD_RES
<222> LOCATION: (39)..(40)
<223> OTHER INFORMATION: Variable amino acid or not present
<220> FEATURE:
<221> NAME/KEY: MOD_RES
<222> LOCATION: (42)
<223> OTHER INFORMATION: Variable amino acid or not present
<220> FEATURE:
<221> NAME/KEY: MOD_RES
<222> LOCATION: (44)..(50)
<223> OTHER INFORMATION: Variable amino acid or not present
<220> FEATURE:
<221> NAME/KEY: MOD_RES
<222> LOCATION: (52)..(59)
<223> OTHER INFORMATION: Variable amino acid or not present
<220> FEATURE:
<221> NAME/KEY: MOD_RES
<222> LOCATION: (62)..(63)
<223> OTHER INFORMATION: Variable amino acid or not present
<220> FEATURE:
<221> NAME/KEY: MOD_RES
<222> LOCATION: (66)..(69)
<223> OTHER INFORMATION: Variable amino acidor not present
<220> FEATURE:
<221> NAME/KEY: MOD_RES
<222> LOCATION: (71)..(74)
<223> OTHER INFORMATION: Variable amino acid or not present
<220> FEATURE:
<221> NAME/KEY: MOD_RES
<222> LOCATION: (76)..(80)
<223> OTHER INFORMATION: Variable amino acid or not present
<220> FEATURE:
<221> NAME/KEY: MOD_RES
<222> LOCATION: (83)
<223> OTHER INFORMATION: Variable amino acid or not present
<220> FEATURE:
<221> NAME/KEY: MOD_RES
<222> LOCATION: (87)
<223> OTHER INFORMATION: Variable amino acid or not present
<220> FEATURE:
<221> NAME/KEY: MOD_RES
<222> LOCATION: (90)..(91)
<223> OTHER INFORMATION: Variable amino acid or not present -continued
<220> FEATURE:
<221> NAME/KEY: MOD_RES
<222> LOCATION: (93)..(96)
<223> OTHER INFORMATION: Variable amino acid or not present
<220> FEATURE:
<221> NAME/KEY: MOD_RES
<222> LOCATION: (98)
<223> OTHER INFORMATION: Variable amino acid or not present
<220> FEATURE:
<221> NAME/KEY: MOD_RES
<222> LOCATION: (101)
<223> OTHER INFORMATION: Variable amino acid or not present
<220> FEATURE:
<221> NAME/KEY: MOD_RES
<222> LOCATION: (104)..(105)
<223> OTHER INFORMATION: Variable amino acid or not present
<220> FEATURE:
<221> NAME/KEY: MOD_RES
<222> LOCATION: (107)..(108)
<223> OTHER INFORMATION: Variable amino acid or not present
<220> FEATURE:
<221> NAME/KEY: MOD_RES
<222> LOCATION: (110)
<223> OTHER INFORMATION: Variable amino acid or not present
<220> FEATURE:
<221> NAME/KEY: MOD_RES
<222> LOCATION: (112)..(113)
<223> OTHER INFORMATION: Variable amino acid or not present
<220> FEATURE:
<221> NAME/KEY: MOD_RES
<222> LOCATION: (115)
<223> OTHER INFORMATION: Variable amino acid or not present
<220> FEATURE:
<221> NAME/KEY: MOD_RES
<222> LOCATION: (117)..(118)
<223> OTHER INFORMATION: Variable amino acid or not present
<220> FEATURE:
<221> NAME/KEY: MOD_RES
<222> LOCATION: (120)..(123)
<223> OTHER INFORMATION: Variable amino acid or not present
<220> FEATURE:
<221> NAME/KEY: MOD_RES
<222> LOCATION: (125)
<223> OTHER INFORMATION: Variable amino acid or not present
<220> FEATURE:
<221> NAME/KEY: MOD_RES
<222> LOCATION: (128)..(129)
<223> OTHER INFORMATION: Variable amino acid or not present
<220> FEATURE:
<221> NAME/KEY: MOD_RES
<222> LOCATION: (137)
<223> OTHER INFORMATION: Variable amino acid or not present
<220> FEATURE:
<221> NAME/KEY: MOD_RES
<222> LOCATION: (139)..(142)
<223> OTHER INFORMATION: Variable amino acid or not present
<220> FEATURE:
<221> NAME/KEY: MOD_RES
<222> LOCATION: (144)
<223> OTHER INFORMATION: Variable amino acid or not present
<220> FEATURE:
<221> NAME/KEY: MOD_RES
<222> LOCATION: (146)..(147)
<223> OTHER INFORMATION: Variable amino acid or not present
<220> FEATURE:
<221> NAME/KEY: MOD_RES
<222> LOCATION: (149)
<223> OTHER INFORMATION: Variable amino acid or not present
<220> FEATURE:
<221> NAME/KEY: MOD_RES
<222> LOCATION: (152)
<223> OTHER INFORMATION: Variable amino acid or not present
<220> FEATURE:
<221> NAME/KEY: MOD_RES
<222> LOCATION: (155)
<223> OTHER INFORMATION: Variable amino acid or not present
<220> FEATURE:
<221> NAME/KEY: MOD_RES
<222> LOCATION: (163)..(171)

-continued

<223> OTHER INFORMATION: Variable amino acid or not present
<220> FEATURE:
<221> NAME/KEY: MOD_RES
<222> LOCATION: (176)..(177)
<223> OTHER INFORMATION: Variable amino acid or not present
<220> FEATURE:
<221> NAME/KEY: MOD_RES
<222> LOCATION: (185)
<223> OTHER INFORMATION: Variable amino acid or not present
<220> FEATURE:
<221> NAME/KEY: MOD_RES
<222> LOCATION: (187)..(190)
<223> OTHER INFORMATION: Variable amino acid or not present
<220> FEATURE:
<221> NAME/KEY: MOD_RES
<222> LOCATION: (193)..(194)
<223> OTHER INFORMATION: Variable amino acid or not present
<220> FEATURE:
<221> NAME/KEY: MOD_RES
<222> LOCATION: (197)..(198)
<223> OTHER INFORMATION: Variable amino acid or not present
<220> FEATURE:
<221> NAME/KEY: MOD_RES
<222> LOCATION: (200)
<223> OTHER INFORMATION: Variable amino acid or not present
<220> FEATURE:
<221> NAME/KEY: MOD_RES
<222> LOCATION: (203)..(204)
<223> OTHER INFORMATION: Variable amino acid or not present
<220> FEATURE:
<221> NAME/KEY: MOD_RES
<222> LOCATION: (206)
<223> OTHER INFORMATION: Variable amino acid or not present
<220> FEATURE:
<221> NAME/KEY: MOD_RES
<222> LOCATION: (209)
<223> OTHER INFORMATION: Variable amino acid or not present
<220> FEATURE:
<221> NAME/KEY: MOD_RES
<222> LOCATION: (211)
<223> OTHER INFORMATION: Variable amino acid or not present
<220> FEATURE:
<221> NAME/KEY: MOD_RES
<222> LOCATION: (213)..(214)
<223> OTHER INFORMATION: Variable amino acid or not present
<220> FEATURE:
<221> NAME/KEY: MOD_RES
<222> LOCATION: (216)..(219)
<223> OTHER INFORMATION: Variable amino acid or not present
<220> FEATURE:
<221> NAME/KEY: MOD_RES
<222> LOCATION: (221)..(222)
<223> OTHER INFORMATION: Variable amino acid or not present
<220> FEATURE:
<221> NAME/KEY: MOD_RES
<222> LOCATION: (224)..(225)
<223> OTHER INFORMATION: Variable amino acid or not present
<220> FEATURE:
<221> NAME/KEY: MOD_RES
<222> LOCATION: (227)..(228)
<223> OTHER INFORMATION: Variable amino acid or not present
<220> FEATURE:
<221> NAME/KEY: MOD_RES
<222> LOCATION: (233)
<223> OTHER INFORMATION: Variable amino acid or not present
<220> FEATURE:
<221> NAME/KEY: MOD_RES
<222> LOCATION: (235)
<223> OTHER INFORMATION: Variable amino acid or not present
<220> FEATURE:
<221> NAME/KEY: MOD_RES
<222> LOCATION: (237)
<223> OTHER INFORMATION: Variable amino acid or not present
<220> FEATURE:
<221> NAME/KEY: MOD_RES
<222> LOCATION: (239)
<223> OTHER INFORMATION: Variable amino acid or not present
<220> FEATURE:
<221> NAME/KEY: MOD_RES -continued
<222> LOCATION: (242)
<223> OTHER INFORMATION: Variable amino acid or not present
<220> FEATURE:
<221> NAME/KEY: MOD_RES
<222> LOCATION: (244)
<223> OTHER INFORMATION: Variable amino acid or not present
<220> FEATURE:
<221> NAME/KEY: MOD_RES
<222> LOCATION: (247)
<223> OTHER INFORMATION: Variable amino acid or not present
<220> FEATURE:
<221> NAME/KEY: MOD_RES
<222> LOCATION: (249)..(252)
<223> OTHER INFORMATION: Variable amino acid or not present
<220> FEATURE:
<221> NAME/KEY: MOD_RES
<222> LOCATION: (254)
<223> OTHER INFORMATION: Variable amino acid or not present
<220> FEATURE:
<221> NAME/KEY: MOD_RES
<222> LOCATION: (258)
<223> OTHER INFORMATION: Variable amino acid or not present
<220> FEATURE:
<221> NAME/KEY: MOD_RES
<222> LOCATION: (260)
<223> OTHER INFORMATION: Variable amino acid or not present
<220> FEATURE:
<221> NAME/KEY: MOD_RES
<222> LOCATION: (262)..(263)
<223> OTHER INFORMATION: Variable amino acid or not present
<220> FEATURE:
<221> NAME/KEY: MOD_RES
<222> LOCATION: (265)..(270)
<223> OTHER INFORMATION: Variable amino acid or not present
<220> FEATURE:
<221> NAME/KEY: MOD_RES
<222> LOCATION: (273)..(274)
<223> OTHER INFORMATION: Variable amino acid or not present
<220> FEATURE:
<221> NAME/KEY: MOD_RES
<222> LOCATION: (276)..(278)
<223> OTHER INFORMATION: Variable amino acid or not present
<220> FEATURE:
<221> NAME/KEY: MOD_RES
<222> LOCATION: (280)..(282)
<223> OTHER INFORMATION: Variable amino acid or not present

<400> SEQUENCE: 18

```
Cys Pro Xaa Xaa Cys Xaa Cys Tyr Xaa Xaa Pro Xaa Xaa Thr Xaa Ser
  1               5                  10                  15

Cys Xaa Xaa Xaa Xaa Xaa Xaa Xaa Xaa Pro Xaa Xaa Xaa Pro Xaa Xaa
             20                  25                  30

Xaa Xaa Arg Xaa Phe Leu Xaa Xaa Asn Xaa Ile Xaa Xaa Xaa Xaa Xaa
         35                  40                  45

Xaa Xaa Phe Xaa Xaa Xaa Xaa Xaa Xaa Xaa Xaa Leu Trp Xaa Xaa Ser
     50                  55                  60

Asn Xaa Xaa Xaa Xaa Ile Xaa Xaa Xaa Xaa Phe Xaa Xaa Xaa Xaa Xaa
 65                  70                  75                  80

Leu Glu Xaa Leu Asp Leu Xaa Asp Asn Xaa Xaa Leu Xaa Xaa Xaa Xaa
                 85                  90                  95

Pro Xaa Thr Phe Xaa Gly Leu Xaa Xaa Leu Xaa Xaa Leu Xaa Leu Xaa
            100                 105                 110

Xaa Cys Xaa Leu Xaa Xaa Leu Xaa Xaa Xaa Xaa Phe Xaa Gly Leu Xaa
        115                 120                 125

Xaa Leu Gln Tyr Leu Tyr Leu Gln Xaa Asn Xaa Xaa Xaa Xaa Leu Xaa
    130                 135                 140

Asp Xaa Xaa Phe Xaa Asp Leu Xaa Asn Leu Xaa His Leu Phe Leu His
145                 150                 155                 160
```

-continued

```
Gly Asn Xaa Xaa Xaa Xaa Xaa Xaa Xaa Xaa Xaa Phe Arg Gly Leu Xaa
                165                 170                 175

Xaa Leu Asp Arg Leu Leu Leu His Xaa Asn Xaa Xaa Xaa Xaa Val His
            180                 185                 190

Xaa Xaa Ala Phe Xaa Xaa Leu Xaa Arg Leu Xaa Xaa Leu Xaa Leu Phe
        195                 200                 205

Xaa Asn Xaa Leu Xaa Xaa Leu Xaa Xaa Xaa Xaa Leu Xaa Xaa Leu Xaa
    210                 215                 220

Xaa Leu Xaa Xaa Leu Arg Leu Asn Xaa Asn Xaa Trp Xaa Cys Xaa Cys
225                 230                 235                 240

Arg Xaa Arg Xaa Leu Trp Xaa Trp Xaa Xaa Xaa Xaa Arg Xaa Ser Ser
                245                 250                 255

Ser Xaa Val Xaa Cys Xaa Xaa Pro Xaa Xaa Xaa Xaa Xaa Xaa Asp Leu
            260                 265                 270

Xaa Xaa Leu Xaa Xaa Xaa Asp Xaa Xaa Xaa Cys
        275                 280
```

<210> SEQ ID NO 19
<211> LENGTH: 50
<212> TYPE: PRT
<213> ORGANISM: Artificial Sequence
<220> FEATURE:
<223> OTHER INFORMATION: Description of Artificial Sequence: Consensus
sequence
<220> FEATURE:
<221> NAME/KEY: MOD_RES
<222> LOCATION: (2)
<223> OTHER INFORMATION: Variable amino acid or not present
<220> FEATURE:
<221> NAME/KEY: MOD_RES
<222> LOCATION: (4)
<223> OTHER INFORMATION: Variable amino acid or not present
<220> FEATURE:
<221> NAME/KEY: MOD_RES
<222> LOCATION: (6)
<223> OTHER INFORMATION: Variable amino acid or not present
<220> FEATURE:
<221> NAME/KEY: MOD_RES
<222> LOCATION: (11)
<223> OTHER INFORMATION: Variable amino acid or not present
<220> FEATURE:
<221> NAME/KEY: MOD_RES
<222> LOCATION: (14)
<223> OTHER INFORMATION: Variable amino acid or not present
<220> FEATURE:
<221> NAME/KEY: MOD_RES
<222> LOCATION: (16)..(19)
<223> OTHER INFORMATION: Variable amino acid or not present
<220> FEATURE:
<221> NAME/KEY: MOD_RES
<222> LOCATION: (21)
<223> OTHER INFORMATION: Variable amino acid or not present
<220> FEATURE:
<221> NAME/KEY: MOD_RES
<222> LOCATION: (25)
<223> OTHER INFORMATION: Variable amino acid or not present
<220> FEATURE:
<221> NAME/KEY: MOD_RES
<222> LOCATION: (27)
<223> OTHER INFORMATION: Variable amino acid or not present
<220> FEATURE:
<221> NAME/KEY: MOD_RES
<222> LOCATION: (29)..(30)
<223> OTHER INFORMATION: Variable amino acid or not present
<220> FEATURE:
<221> NAME/KEY: MOD_RES
<222> LOCATION: (32)..(37)
<223> OTHER INFORMATION: Variable amino acid or not present
<220> FEATURE:
<221> NAME/KEY: MOD_RES
<222> LOCATION: (40)..(41)

-continued

```
<223> OTHER INFORMATION: Variable amino acid or not present
<220> FEATURE:
<221> NAME/KEY: MOD_RES
<222> LOCATION: (43)..(45)
<223> OTHER INFORMATION: Variable amino acid or not present
<220> FEATURE:
<221> NAME/KEY: MOD_RES
<222> LOCATION: (47)..(49)
<223> OTHER INFORMATION: Variable amino acid or not present

<400> SEQUENCE: 19

Asn Xaa Trp Xaa Cys Xaa Cys Arg Ala Arg Xaa Leu Trp Xaa Trp Xaa
  1               5                  10                  15

Xaa Xaa Xaa Arg Xaa Ser Ser Ser Xaa Val Xaa Cys Xaa Xaa Pro Xaa
             20                  25                  30

Xaa Xaa Xaa Xaa Xaa Asp Leu Xaa Xaa Leu Xaa Xaa Xaa Asp Xaa Xaa
         35                  40                  45

Xaa Cys
     50
```